United States Patent
Shen et al.

(10) Patent No.: US 10,160,762 B2
(45) Date of Patent: Dec. 25, 2018

(54) 6-ALKYL DIHYDROPYRAZOLOPYRIMIDINONE COMPOUNDS AS PDE2 INHIBITORS

(71) Applicants: Merck Sharp & Dohme Corp., Rahway, NJ (US); MSD R & D (China) Co., LTD., Shanghai (CN)

(72) Inventors: Dong-Ming Shen, Edison, NJ (US); Michael P. Dwyer, Scotch Plains, NJ (US); Christopher J. Sinz, South San Francisco, CA (US); Deping Wang, Furlong, PA (US); Shawn J. Stachel, Perkasie, PA (US); Daniel V. Paone, Lansdale, PA (US); Ashley Forster, Harleysville, PA (US); Richard Berger, Harleysville, PA (US); Yili Chen, Hillsborough, NJ (US); Yimin Qian, Plainsboro, NJ (US); Shimin Xu, Beijing (CN); Chunmei Hu, Beijing (CN); William D. Shipe, Chalfont, PA (US); Jianmin Fu, Beijing (CN); Zhigang Guo, Beijing (CN); Haitang Li, Beijing (CN); Yingjian Bo, Beijing (CN)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/574,411

(22) PCT Filed: May 24, 2016

(86) PCT No.: PCT/US2016/033861
§ 371 (c)(1),
(2) Date: Nov. 15, 2017

(87) PCT Pub. No.: WO2016/196071
PCT Pub. Date: Dec. 8, 2016

(65) Prior Publication Data
US 2018/0134712 A1     May 17, 2018

(30) Foreign Application Priority Data

May 29, 2015   (WO) ................ PCT/CN2015/080267

(51) Int. Cl.
| | | |
|---|---|---|
| *C07D 487/04* | (2006.01) |
| *A61K 31/519* | (2006.01) |
| *A61P 25/14* | (2006.01) |
| *A61P 25/28* | (2006.01) |
| *A61P 25/18* | (2006.01) |
| *A61P 25/00* | (2006.01) |
| *A61P 25/16* | (2006.01) |

(52) U.S. Cl.
CPC .......... *C07D 487/04* (2013.01); *A61K 31/519* (2013.01); *A61P 25/00* (2018.01); *A61P 25/14* (2018.01); *A61P 25/16* (2018.01); *A61P 25/18* (2018.01); *A61P 25/28* (2018.01)

(58) Field of Classification Search
None
See application file for complete search history.

(56) References Cited

U.S. PATENT DOCUMENTS

| | | | |
|---|---|---|---|
| 3,211,731 A | 10/1965 | Schmidt et al. | |
| 5,294,612 A * | 3/1994 | Bacon .................. | C07D 487/04 514/234.2 |
| 6,573,263 B2 | 6/2003 | Niewohner et al. | |
| 8,598,155 B2 | 12/2013 | Helal et al. | |
| 8,680,116 B2 | 3/2014 | DeLeon et al. | |
| 2007/0135457 A1 | 6/2007 | Beyer et al. | |
| 2012/0214791 A1 | 8/2012 | Helal et al. | |

(Continued)

FOREIGN PATENT DOCUMENTS

| | | |
|---|---|---|
| CA | 52524898 | 3/2012 |
| EP | 1097706 A1 | 5/2001 |

(Continued)

OTHER PUBLICATIONS

Dumaitre, B. et al., J..Med. Chem. (1996), 39(8), 1635-44.*
Ahlstrom et al., Inactivation of Atrial Natriuretic Factor-Stimulated, Biochemical Pharmacology, 2000, 1133-1139, 59.
Arulomozhi et al., Migraine: Current Therapeutic Targets and Future Avenues, Current Vascular Pharmacology, 2006, 117-128, 4.
Beavo et al., Cyclic GMP as Substrate and Regulator of Cyclic Nucleotide Phosphodiesterases (PDEs), Rev. Physio Biochem Pharm, 1999, 67-104, 135.

(Continued)

*Primary Examiner* — Heidi Reese
(74) *Attorney, Agent, or Firm* — Sylvia A. Ayler; John C. Todaro

(57) ABSTRACT

The present invention is directed to 6-alkyl dihydropyrazolopyrimidinone compounds of formula (I) which are useful as therapeutic agents for the treatment of central nervous system disorders associated with phosphodiesterase 2 (PDE2). The present invention also relates to the use of such compounds for treating neurological and psychiatric disorders, such as schizophrenia, psychosis, Parkinson's disease, Parkinson's disease dementia (PDD), or Huntington's disease, and those associated with striatal hypo-function or basal ganglia dysfunction.

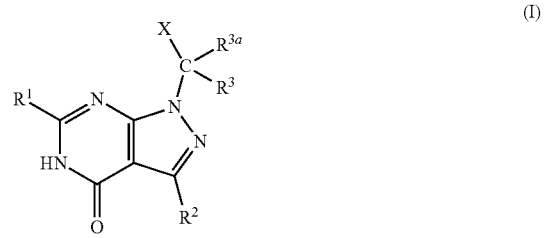

(I)

17 Claims, No Drawings

(56) References Cited

U.S. PATENT DOCUMENTS

2013/0018063 A1 1/2013 Li et al.
2016/0264536 A1 9/2016 Seto et al.

FOREIGN PATENT DOCUMENTS

| EP | 1097707 A1 | 5/2001 |
|---|---|---|
| WO | 2000021926 | 4/2000 |
| WO | WO2005061497 | 12/2003 |
| WO | WO2005041957 | 10/2004 |
| WO | WO2006024640 | 3/2006 |
| WO | WO2006072615 | 7/2006 |
| WO | WO2009016498 | 2/2009 |
| WO | WO20100900737 | 8/2010 |
| WO | WO2010136493 | 12/2010 |
| WO | WO2012114222 | 8/2012 |
| WO | WO2013034758 | 9/2012 |
| WO | WO2013034761 | 9/2012 |
| WO | WO2012168817 | 12/2012 |
| WO | WO201300924 | 1/2013 |
| WO | WO2013034755 | 3/2013 |
| WO | WO2013098373 | 7/2013 |
| WO | 2013161913 | 10/2013 |
| WO | WO2014010732 | 1/2014 |
| WO | WO2014019979 | 2/2014 |
| WO | WO2014139983 | 9/2014 |
| WO | WO2015012328 | 1/2015 |
| WO | WO2005063723 | 7/2017 |

OTHER PUBLICATIONS

Bernard et al., PDE2 Is a Novel Target for Attenuating Tumor Formation in a Mouse Model of UVB-Induced Skin Carcinogenesis, Plos One, 2014, 1-8, 9.
Boess et al., Inhibition of phosphodiesterase 2 increases neuronal cGMP, synaptic plasticity and memory, Neuropharmacology, 2004, 1081-92, 47.
Brandon et al., Potential CNS Applications for, Annual Reports in Medicinal Chemistry, 2007, 3-11, 42.
Bubb et al., Inhibition of Phosphodiesterase 2 Augments cGMP and, Circulation, 2014, 496-507, 268.
Cote et al., Comparative Involvement of Cyclic Nucleotide, Endocrinology, 1999, 3594-3601, 140.
Demaria et al., Highlights of the Year in JACC 2013, j. aMER. cOLL. cARD, 2014, 570-602, 63, (6).
Dickinson et al., Activation of cGMP-stimulated phosphodiesterase by nitroprusside limits, Biochem J., 1997, 371-377, 323.
Ding et al., Protective effects of phosphodiesterase 2 inhibitor on depression- and -Anxiety-Like Behaviors: Involvement of antioxidant and anti-apotoic Mechanisms, Behaviorual Brain Research, 2014, 150-158, 268.
Domek-Lopacinska et al., The Effect of Selective Inhibition of Cyclic GMP Hydrolyzing Phosphodiesterases 2 and 5 on Learning and Memory Processes and Nitric Oxide Synthase Activity, Brain Research, 2008, 68-77, 1216.
Ducrot et al., CoMFA and CoMSIA 3D-Quantitative Structure-Activity Relationship Model on Benzodiaepine Derivatives, Inhibitors of Phosphodiesterase IV, J. of Computer Aided Molecular Designs, 2001, 767-785, 15.
Duran et al., The NO cascade, eNOS Location, and Microvascular Permeability, Cardiovascular Research, 2010, 254-261, 87.
Favot et al., VEGF-Induced HUVEC Migration and Proliferation, Schattauer GmbH Stuttgart, 2003, 3443-343, 90.
Gergega et al., Systematic Effect of Benzo-Annelation on Oxo-Hydroxy Tautomerism of Heterocyclic, J. Phys. Chem A., 2007, 4934-4943, 111.
Giuliano et al., Correction to Tautomerism in 4-Hydroxypyrimidine, S-Methyl-2-thiouracil, and 2-Thiouracil, The Journal of Physical Chemistry A, 2011, 8178-8179, 115.
Giuliano et al., Tautomerism in 4-Hydroxypyrimidine, S-Methyl-2-thiouracil, and 2-Thiouracil, J. Phys. Chem. A, 2010, 12725-12730, 114.

Haynes et al., Erythro-9-(2-Hydroxy-3-Nonyl) Adenine Inhibits Cyclic-3',5' Guanosine Monophosphate—Stimulated Phosphodiesterase to Reverse Hypoxic Pulmonary Vasoconstriction in the Perfused Rat Lung, The J. of Pharmacology, 1996, 752-757, 276.
Herring et al., NO-cGMP Pathway Increases the Hyperpolarisation-Activated Current ,I, and Heart Rate During Adrenergic Stimulation, Cardiovascular Research, 2001, 446-453, 52.
Hiramoto et al., Role of Phosphodiesterase 2 in Growth and Invasion of HUman Maligant Melanoma, Cellular Signaling, 2014, 1807-1817, 26.
Huang et al., A Fluroescence Polarization Assay for Cyclic Nucleotide Phosphodiesterases, J. of Biomolecular Screening, 2002, pp. 215-222, 7.
Jorgensen et al., Selective Inhibitors of PDE2, PDE9, and PDE10: Modulators of Activity of the Central Nervous System, Annual Reports in Medicinal Chemistry, 2013, pp. 37-55, 48.
Keravis et al., Cyclic Nucleotide Hydrolysis in Bovine Aortic Endothelial Cells in Culture: Differential Regulation in Cobblestone and Spindle Phenotypes, J. Vasc. Res, 2000, 235-249, 37.
Kheifets et al., Structure and Amide-Amide Tautomerism of 4-Hydroxypyrimidines. Determination of the Tautomeric Composition by 13C NMR Spectroscopy, Russ. J. of Organic Chemistry, 2000, 1373-1387, 36, 9.
Lieberman et al., Effectiveness of Antipsychotic Drugs in Patients with Chronic Schizophrenia, New England J. of Medicine, Sep. 22, 2005, pp. 1209-1223, 353, US.
Lopez et al., Solution and solid state (CPMAS) NMR Studies of the Tautomerism of Six-Membered Heterocyclic Compounds Related to 2-Pyridones, Spectroscopy, 2000, pp. 121-126, 14.
Markwalder, Synthesis and Biological Evaluation of 1-Aryl-4,5-dihydro-1H-pyrazolo[3,4-d] pyrimidin-4-one Inhibitors of Cyclin-Dependent Kinases, J. Med. Chem, 2004, 5894-5911, 47.
Masood et al., Anxiolytic Effects of Phosphodiesterase-2 Inhibitors Associated with Increased cGMP Signaling, J. of Pharmacology, 2009, 690-699, 331.
Masood et al., Reversal of Oxidative Stress-Induced Anxiety by Inhibition of Phosphodiesterase-2 in Mice, J. of Pharmacology and Experimental Therapeutics, 2008, 369-379, 326.
Michie et al., Rapid Regulation of PDE-2 and PDE-4 Cyclic AMP Phosphodiesterase Activity Folloiwng Ligation of the T Cell Antigen Receptor on Thymocytes: Analysis Using theSelctive Inhibitors Erythro-9-(2-Hydroxy-3Nonyl)-Adenine (EHNA) and Rolipram, Cell Signal, 1996, 97-110, 8.
Morita et al., Characterization of Phosphodiesterase 2A in Human Malignant Melanoma PMP Cells, Oncology Reports, 2013, 1275-1284, 29.
Netherton et al., Vascular Endothelial Cell Cyclic Nucleotide phosphodiesterases and Regulated Cell Migration: IMplications in Angiogenesis, Molecular Pharmacology, 2005, 263-272, 67.
P. C. Tfelt-Hansen et al., One Hundred Years of Migraine Research: Major Clinical and, Headache, 2011, 752-778, 51.
Plummer et al., Discovery of Poten, Selective, Bioavailable Phosphodiesterase 2 (PDE2) Inhibitors Active in an Osteoarthritis Pain Model, Part I: Transformation of Selective Pyrazolodiazepinone Phosphodiesterase 4 (PDE4) Inhibitors into Selective PDE2 Inhibitors, Biorganic & Medicinal Chemistry Letters, 2013, 3438-3442, 23.
Plummer et al., Discovery of potent selective bioavailable phosphodiesterase, Biooorganic & Medicinal Chemistry Letters, 2013, 3443-3447, 23.
Reierson et al., Repeated antidepressant therapy increases cyclic GMP signaling, Neurosci Letter, 2009, 149-153, 466 (3).
Rivet-Bastide et al., cGMP-stimulated Cyclic Nucleotide Phosphodiesterase Regulates the Basal, J. Clin. Invest, 1997, 2710-2718, 99.
Sadhu et al., Differential Expression of the Cyclic GMP-Stimulated Phosphodiesterase PDE2A in HUman Venous and Capillary Endothelial Cells, J. of Histochemistry & Cytochemistry, 1999, 895-905, 47.
Sanchez et al., Gas-Phase Tautomeric Equilibrium of 4-Hydroxypyrimidine, J. Am. Chem Soc., 2007, 6287-6290, 129.
Savai et al., Targeting Cancer with Phosphodiesterase Inhibitors, Expert Opinion, 2010, 117-131, 19.

(56) References Cited

OTHER PUBLICATIONS

Surapisitchat et al., Differential Regulation of Endothelial Cell Permeability by cGMP via Phosphodiesterases 2 and 3, Circulation Research, 2007, 811-818, 101.
Suvrana et al., Hydrolysis of N-Methyl-D-aspartate Receptor-Stimulated cAMP, J. of Pharmacology, 2002, 249-256, 302.
Taylor et al., Synthesis of Pyrazolo[3,4 d) pyrimidine Analogues of the Potent Anti-tumor AgentN-(4-[2-(2-Amino-4(3H)-Oxo 7H-Pyrrolo[2,3-d)Pyrimidin-5-yl_ethyl]-L-glutamic Acid (LY231514), Tetrahedron, 1992, pp. 8089, 48.
Van Staveren et al., The effects of phosphodiesterase inhibition on cyclic GMP and cyclic, Brain Research, 2001, 275-286, 888.
Vandecasteele, Cyclic GMP regulation of the L-type Ca2+ channel current, J. of Physiology, 2001, 329-340, 533.
Velardez et al., Role of Phosphodiesterase and Protein Kinase G on Nitric Oxide-Induced Inhibition of Prolactin Relase from the Rat Anterior Pituitary, Europe J. of Endocrinology, 2000, 279-284, 143.
Wakabayashi et al., Involvement of Phosphodiesterase Isozymes in Osteoblastic, J. of Bone and Mineral Research, 2002, 249-253, 17.
Zhang et al., A Facile One-pot Synthesis of 1-Arylpyrazolo[3,4-d] Pyrimidin-4-ones, Molecules, 2011, 3079-3086, 15.

\* cited by examiner

6-ALKYL DIHYDROPYRAZOLOPYRIMIDINONE COMPOUNDS AS PDE2 INHIBITORS

CROSS REFERENCE TO RELATED APPLICATIONS

This application is the National Stage of International Application No. PCT/US2016/033861 filed on May 24, 2016, which claims the benefit under International Application PCT/CN2015/080267 filed on May 29, 2015.

FIELD OF THE INVENTION

The invention relates generally to compounds which act as inhibitors of the phosphodiesterase (PDE) 2 enzyme, compositions and therapeutic uses thereof.

BACKGROUND OF THE INVENTION

Schizophrenia is a debilitating disorder affecting the psychic and motor functions of the brain. It is typically diagnosed in individuals in their early to mid-twenties and symptoms include hallucinations and delusions or at the other extreme, anhedonia or social withdrawal. Across the spectrum, the symptoms are indicative of cognitive impairment and functional disabilities. Notwithstanding improvements in antipsychotic treatments, current therapies, including typical (haloperidol) and atypical (clozapine or olanzapine) antipsychotics, have been less than acceptable and result in an extremely high rate of noncompliance or discontinuation of medication. Dissatisfaction with therapy is attributed to lack of efficacy or intolerable and unacceptable side effects. The side effects have been associated with significant metabolic, extrapyramidal, prolactic and cardiac adverse events. See, Lieberman et al., N. Engl. J. Med. (2005) 353:1209-1223.

While multiple pathways are believed to be involved with the pathogenesis of schizophrenia leading to psychosis and cognition deficits, much attention has focused on the role of glutamate/NMDA dysfunction associated with cyclic guanosine monophosphate (cGMP) levels and the dopaminergic receptors associated with cyclic adenosine monophosphate (cAMP). These ubiquitous secondary messengers are responsible for altering the function of many intracellular proteins. Cyclic AMP is thought to regulate the activity of cAMP-dependent protein kinase (PKA), which in turn phosphorylates and regulates many types of proteins including ion channels, enzymes and transcription factors. Similarly, cGMP is also responsible for downstream regulation of kinases and ion channels.

One pathway for affecting the levels of cyclic nucleotides, such as cAMP and cGMP, is to alter or regulate the enzymes that degrade these secondary messengers, known as 3', 5'-cyclic nucleotide specific phosphodiesterases (PDEs). The PDE superfamily includes twenty-one genes that encode for eleven families of PDEs. These families are further subdivided based on catalytic domain homology and substrate specificity and include the 1) cAMP specific, PDE4A-D, 7A and 7B, and 8A and 8B, 2) cGMP specific, PDE 5A, 6A-C, and 9A, and 3) those that are dual substrate, PDE 1A-C, 2A, 3A and 3B, 10A, and 11A. The homology between the families, ranging from 20% to 45%, suggests that it may be possible to develop selective inhibitors for each of these families.

PDE2 is highly expressed in the brain, but is also found in many other tissues as well, and therefore has a broad array of function and utility (J. A. Beavo, et al., Rev. Physio. Biochem. Pharm., 135, 67 (1999)). Amongst others, PDE2 has been shown to have therapeutic potential in neuronal development, learning, and memory (W. C. G. van Staveren, et al., Brain Res., 888, 275 (2001) and J. O'Donnell, et al., J. Pharm. Exp. Ther., 302, 249 (2002)); prolactin and aldosterone secretion (M. O. Velardez, et al., Eur. J. Endo., 143, 279 (2000) and N. Gallo-Payet, et al., Endo., 140, 3594 (1999)); bone cell differentiation, growth, and bone resorption (C. Allardt-Lamberg, et al., Biochem. Pharm., 59, 1133 (2000) and S. Wakabayashi, et al., J. Bone, Miner. Res., 17, 249 (2002); immunological response (M. D. Houslay, et al., Cell. Signal., 8, 97 (1996); vascular angiogenesis (T. Keravis, et al., J. Vasc. Res., 37, 235 (2000); inflammatory cell transit (S. L. Wolda, et al., J. Histochem. Cytochem., 47, 895 (1999); cardiac contraction (R. Fischmeister, et al., J. Clin. Invest., 99, 2710 (1997), P. Donzeau-Gouge, et al., J. Physiol., 533, 329 (2001), and D. J. Paterson, et Al., Card. Res., 52, 446 (2001); platelet aggregation (R. J. Haslam, et Al., Biochem. J., 323, 371 (1997); female sexual arousal disorder (C. P. Wayman, et al., EP Patent Publications EP10977707 and EP1097706); osteoarthritis pain (M. Plummer et. al., Bioorganic & Medicinal Chemistry Letters, 23(11), 3438-3442 and 3443-3447(2013)); malignant melanoma (H. Morita, et al., Oncology Reports, 29, 1275-1284, 2013; Hiramoto, et al., Cell. Signal., 26(9), 1807-1817, 2014; and J. J. Bernard, et al., PloS ONE 9(10): e109862, 2014); heart failure (A. N. DeMaria, et al., J. Amer. Coll. Card. 63 (6), 570-602, 2014); pulmonary hypertension (K. J, Bubb, et al., Circulation, 130, 496-508, 2014); depression and anxiety (L. Ding, et al., Behav. Brain Res. 268, 150-158, 2014); and hypoxic pulmonary vasoconstriction (J. Haynes, et. al., J. Pharm. Exp. Ther., 276, 752 (1996). See also US2007135457, WO00/21926, U.S. Pat. No. 3,211,731, WO2015060368, and J. Markwalder, et al., J. Med. CHem. 2004, 47, 5894-5911.

Inhibition of PDE2 (e.g., PDE2A) has been shown to enhance cognitive function across multiple preclinical models of cognitive performance that reflect improvements in recognition memory, social interactions and working memory, which are all deficient in schizophrenia (Boess et al., *Inhibition of Phosphodiesterase 2 Increases Neuronal cGMP, Synaptic Plasticity and Memory Performance*, Neuropharmacology, 47(7): 1081-92, 2004). PDE2A inhibition was also shown to improve cognitive deficits that develop in aging and Alzheimer's disease (Domek-Lopacinska and Strosznajder, *The Effect of Selective Inhibition of Cyclic GMP Hydrolyzing Phosphodiesterases 2 and 5 on Learning and Memory Processes and Nitric Oxide Synthetase Activity in Brain During Aging*, Brain Research, 1216:68-77, 2008). The role of PDE2 inhibition in cognitive disorders was also shown in Brandon et al., *Potential CNS Applications for Phosphodiesterase Enzyme Inhibitors*, Annual Reports in Medicinal Chemistry 42: 4-5, 2007 (compound BAY 60-7550 was reported to have significant potency at other PDE isoforms, had high clearance and limited brain penetration). See also Jorgenson, et al, Annual Reports in Medicinal Chemistry 48: 37-55, 2013. "Selective Inhibitors of PDE2, PDE9, and PDE10: Modulators of Activity of the Central Nervous System".

PDE2 inhibitors have also been shown to have efficacy in preclinical models of anxiety and depression (Masood et al., Anxiolytic Effects of Phosphodiesterase-2 Inhibitors Associated with Increased cGMP Signaling, JPET 331(2):690-699, 2009; Masood et al., Reversal of Oxidative Stress-Induced Anxiety by Inhibition of Phosphodiesterase-2 in Mice, JPET 326(2):369-379, 2008; Reierson et al., Repeated Antidepressant Therapy Increases Cyclic GMP Signaling in Rat Hippocampus, Neurosci. Lett., 466(3):149-53, 2009). See also Ducrot et al., CoMFA and CoMSIA 3D-quantitative structure-activity relationship model on benzodiazepine derivatives, inhibitors of phosphodieserase IV, J Computer-Aided Molecular Design, 15: 767785, 2001; US20120214791; WO2012168817; WO2013034755; WO2013034758; WO2013034761; WO2005041957; WO2005061497; WO2006024640; WO2013161913; WO2010136493; WO 2013098373; WO 2009016498; U.S. Pat. Nos. 6,573,263; 8,598,155; and 8,680,116; WO2015012328; WO2014139983; WO2014019979; WO2014010732; WO2013000924; WO2012114222; WO2006072615; WO2005063723; M. Plummer et al., Bioorg Med Chem Lett 23(11), 3438, 2013; and M. Plummer et al., Bioorg Med Chem Lett 23(11), 3443, 2013.

An increase in vascular permeability has been shown to be attributable to increased activity of PDE2. PDE2 and PDE3 in the endothelium can act as a sensor or switch to detect normal versus pathological concentrations of cGMP and thus regulate endothelial permeability accordingly with potential relevance to migraine. See Surapisitchat et al., *Differential Regulation of Endothelial Cell Permeability by cGMP via Phosphodieserase 2 and 3*, Circulation Research, 2007; 101, pgs.: 811-818 and Duran et al., *The NO Cascade, eNOS Location and Microvascular Permeability*, Cardiovascular Res. (2010) 87, 254-261. Cerebral vasodilation is considered a major cause of migraine. See P. C. Tfelt-Hansen and P. J. Koehler, *One hundred years of migraine research: major clinical and scientific observations from 1910 to 2010*, Headache, 2011. 51(5), 752-578 and D. K. Arulmozhi et al., *Migraine: current therapeutic targets and future avenues*, Current Vascular Pharmacology, 2006, 4(2), 117-128. Therefore, PDE2 inhibition may have utility as a treatment or prophylactic for migraine.

The need for new and improved PDE2 modulators believed to be useful for treating diseases or disorders associated with PDE2 such as Alzheimer's disease, cognitive impairment associated with schizophrenia, depression, migraines, Parkinson's disease, Parkinson's disease dementia (PDD) and the like continues to exist. Inhibitors of PDE2 are not only believed to be useful in treating schizophrenia but also a wide variety of conditions or disorders that would benefit from increasing levels of cAMP and/or cGMP within neurons, including a variety neurological, psychotic, anxiety and/or movement disorders. Accordingly, agents that inhibit PDE2 and PDE2A would be desirable as therapeutics for neurological and psychiatric disorders.

SUMMARY OF THE INVENTION

The present invention is directed to 6-alkyl dihydropyrazolopyrimidinone compounds which may be useful as therapeutic agents for the treatment of central nervous system and/or peripheral disorders associated with phosphodiesterase 2 (PDE2). The present invention also relates to the use of such compounds for treating neurological and psychiatric disorders, such as schizophrenia, psychosis, Alzheimer's, cognitive impairment, anxiety, depression, migraines, or Huntington's disease, Parkinson's disease, Parkinson's disease dementia (PDD), and other diseases associated with striatal hypofunction or basal ganglia dysfunction.

DETAILED DESCRIPTION OF THE INVENTION

The present invention is directed to 6-alkyl dihydropyrazolopyrimidinone compounds of formula I:

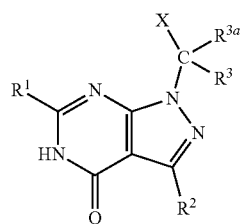

or a pharmaceutically acceptable salt thereof, wherein:

X represents $C_{3-6}$cycloalkyl, $C_{3-10}$heterocyclyl, or $ZC_{6-10}$aryl, said heterocyclyl and aryl optionally substituted with 1 to 3 groups of $R^a$;

Z represents a bond, —$(CH2)_n$-, —C(O)NH—, —CH(OH)—, —$C(CH_3)OH$—, —$(CH_2)_nNH$—, or —$(CH_2)_nNCH_3$—;

$R^1$ represents $C_{1-6}$alkyl, $(CH_2)_{1-4}OR$, $C_{1-4}$haloalkyl, $C(O)C_{6-10}$aryl, —$(CH_2)_nC_{6-10}$aryl, $(CH_2)_nC_{3-10}$heterocyclyl or $(CH_2)_nC_{3-10}$cycloalkyl wherein when $R^1$ is a heterocyclyl it is attached to the pyrazolopyrimidinyl ring through a carbon atom, and wherein said alkyl, aryl, heterocyclyl and cycloalkyl are optionally substituted with 1 to 3 groups of $R^a$;

$R^2$ represents halo, $C_{1-6}$alkyl, $(CH_2)_nOR$, $C_{1-4}$haloalkyl, C(O)OR, C=O, $(CH_2)_nC_{3-10}$heterocyclyl, O—$(CH_2)_nC_{3-10}$heterocyclyl, $C(O)NH(CH_2CF_3)$, $NR_2$, $NHSO_2R$, C(O)R, C(O)—N-linked morpholinyl, $NHC(O)CH_3$, $(CH_2)_nC(CF_3)OH$, $CF_2CH_2OH$, said alkyl and heterocyclyl optionally substituted with 1 to 3 groups of $R^a$, $R^3$ and $R^{3a}$ independently represent hydrogen, $C_{1-6}$alkyl, or $C_{3-6}$ cycloalkyl, or $R^3$ and $R^{3a}$ can combine with the carbon atom to which they are attached to form a $C_{3-6}$cycloalkyl, or $C_{4-10}$heterocycloalkyl, said alkyl, cycloalkyl, and heterocycloalkyl optionally substituted with 1 to 3 groups of $R^a$, or $R^3$ or $R^{3a}$ can combine with X and the carbon atom to which they are attached to form a $C_{6-10}$aryl, said aryl optionally substituted with 1 to 3 groups of $R^a$, R represents hydrogen or $C_{1-6}$alkyl, said alkyl optionally substituted with 1 to 3 groups of $R^a$, $R^a$ is selected from the group consisting of halo, CN, $C_{1-6}$alkyl, $(CH_2)_nOR$, $(CH_2)_nC_{1-4}$haloalkyl, O—$C_{1-4}$haloalkyl, $SCF_3$, $SF_5$, $C_{6-10}$aryl, $C(O)N(CH_3)_2$, =NOH, —NHOH, $SO_2R$, $NR_2$, $OC(O)CH_3$, $NHC(O)CH_3$, $OCH_2C_{6-10}$aryl, and $C_{3-6}$cycloalkyl, said cycloalkyl optionally substituted with 1 to 3 groups selected from $C_{1-6}$alkyl and $C_{1-4}$haloalkyl;

n represents 0, 1, 2, 3, or 4.

Another embodiment of the invention of formula I is realized when X is an optionally substituted $C_{3-6}$cycloalkyl. A subembodiment of this aspect of the invention of formula I is realized when the cycloalkyl is selected from the group consisting of optionally substituted cyclopropyl, cyclobutyl, cyclopentyl and cyclohexyl.

Another embodiment of the invention of formula I is realized when X is optionally substituted $C_{4-10}$heterocyclyl. A subembodiment of this aspect of the invention of formula I is realized when the heterocyclyl is selected from the group consisting of optionally substituted thiophenyl, pyrazolyl, pyridazinyl, triazolyl, thiazolyl, and pyridyl.

Another embodiment of the invention of formula I is realized when X is $ZC_{6-10}$aryl, wherein Z is a bond. A subembodiment of this aspect of the invention of formula I is realized when Z is a bond and the aryl is optionally substituted phenyl.

Another embodiment of the invention of formula I is realized when X is $ZC_{6-10}$aryl, Z is —(C(O)NH—, —$(CH_2)_n$NH—, or —$(CH_2)_n$NCH$_3$— and the aryl is optionally substituted phenyl.

Another embodiment of the invention of formula I is realized when X is $ZC_{6-10}$aryl, Z is —CH(OH)—, and the aryl is optionally substituted phenyl.

Another embodiment of the invention of formula I is realized when X is $ZC_{6-10}$aryl, Z is —$(CH_2)_n$—, or —C(CH$_3$)OH—, and the aryl is optionally substituted phenyl.

An embodiment of the invention of formula I is realized when $R^1$ is optionally substituted $C_{1-6}$alkyl, or $(CH_2)_n$OR. A subembodiment of this aspect of the invention is realized when the alkyl of $R^1$ is selected from the group consisting of CH$_3$, $(CH_2)_2$CH$_3$, CH$_2$(CH$_3$)$_2$, CH$_2$C(CH$_3$)$_3$, $(CH_2)_n$OCH$_3$, CH$_2$CH$_3$, CH(CH$_3$)$_2$, CH(CH$_3$)OH, and $(CH_2)_2$OCH$_2$CH$_3$. Another subembodiment of this aspect of the invention is realized when $R^1$ is CH$_3$. Another subembodiment of this aspect of the invention is realized when $R^1$ is $(CH_2)_2$CH$_3$. Another subembodiment of this aspect of the invention is realized when $R^1$ is CH$_2$CH$_3$. Another subembodiment of this aspect of the invention is realized when $R^1$ is CH(CH$_3$)$_2$.

An embodiment of the invention of formula I is realized when $R^1$ is $C_{1-4}$haloalkyl. A subembodiment of this aspect of the invention is realized when the haloalkyl of $R^1$ is selected from the group consisting CHF$_2$, CF$_3$, and CH$_2$F.

An embodiment of the invention of formula I is realized when $R^1$ is optionally substituted C(O)$C_{6-10}$aryl or $(CH_2)_n$$C_{6-10}$aryl. A subembodiment of this aspect of the invention is realized when $R^1$ is selected from the group consisting of optionally substituted C(O)phenyl, and CH$_2$phenyl.

An embodiment of the invention of formula I is realized when $R^1$ is optionally substituted $(CH_2)_n$$C_{3-10}$heterocyclyl. A subembodiment of this aspect of the invention is realized when the heterocyclyl of $R^1$ is selected from the group consisting of optionally substituted pyrazolyl, tetrahydrofuranyl, tetrahydropyranyl, oxetanyl, oxazolyl, pyridyl, quinoxalinyl, and furanyl. Another subembodiment of this aspect of the invention is realized when the heterocyclyl of $R^1$ is selected from the group consisting of optionally substituted tetrahydrofuranyl and furanyl.

Another embodiment of the invention of formula I is realized when $R^1$ is optionally substituted $(CH_2)_n$$C_{3-10}$cycloalkyl. A subembodiment of this aspect of the invention is realized when the cycloalkyl of $R^1$ is selected from the group consisting of optionally substituted cyclopropyl, cyclobutyl, cyclopentyl, and cyclohexyl. Another subembodiment of this aspect of the invention is realized when the cycloalkyl of $R^1$ is optionally substituted cyclopropyl.

Another embodiment of the invention of formula I is realized when $R^2$ is $C_{1-6}$alkyl or $(CH_2)_n$OR. A subembodiment of this aspect of the invention is realized when the alkyl of $R^2$ is selected from the group consisting of optionally substituted CH$_2$OH, CH$_3$, CH$_2$CN, CH(CH$_3$)OH, C(CH$_3$)$_2$OH, CH$_2$NHC(O)CH$_3$, CH$_2$C(CH$_3$)OH, CH$_2$OC(O)CH$_3$, CH$_2$SO$_2$CH$_3$, CH=NOH, and CH$_2$OCH$_2$phenyl. A subembodiment of this aspect of the invention is realized when the alkyl of $R^2$ is CH$_2$OH. A subembodiment of this aspect of the invention is realized when the alkyl of $R^2$ is CH$_3$.

Another embodiment of the invention of formula I is realized when $R^2$ is $C_{1-4}$haloalkyl. A subembodiment of this aspect of the invention is realized when the haloalkyl of $R^2$ is selected from the group consisting of CH$_2$F, CHF$_2$, $(CH_2)$nCF$_3$, CF$_2$CH$_2$OH, and CH(CF$_3$)OH. A subembodiment of this aspect of the invention is realized when the haloalkyl of $R^2$ is CF$_3$, CH$_2$F or CHF$_2$.

Another embodiment of the invention of formula I is realized when $R^2$ is optionally substituted $(CH_2)_n$$C_{4-10}$heterocyclyl. A subembodiment of this aspect of the invention is realized when the heterocyclyl of $R^2$ is selected from the group consisting of oxetanyl, tetrahydrofuranyl, furanyl, oxadiazolyl, and pyrazolyl.

Another embodiment of the invention of formula I is realized when $R^2$ is selected from the group consisting of C(O)NR$_2$, C(O)—N-linked morpholinyl, C(O)NH(CH$_2$CF$_3$), NR$_2$, NHSO$_2$R, C(O)R, and NHC(O)CH$_3$.

Still another embodiment of the invention is realized when both $R^3$ and $R^{3a}$ are hydrogen.

Another embodiment of the invention is realized when $R^3$ and $R^{3a}$ independently represents hydrogen, CH$_3$, CH(CH$_3$)$_2$, CH$_2$CH$_3$, CH$_2$OCH$_3$, C(CH$_3$)$_3$, CH$_2$CF$_3$, and optionally substituted cyclopropyl, cyclobutyl, cyclopentyl and cyclohexyl. A subembodiment of this aspect of the invention is realized when one of $R^3$ and $R^{3a}$ is hydrogen and the other is selected from the group consisting of CH$_3$, CH(CH$_3$)$_2$, CH$_2$CH$_3$, CH$_2$OCH$_3$, C(CH$_3$)$_3$, CH$_2$CF$_3$, and optionally substituted cyclopropyl, cyclobutyl, cyclopentyl and cyclohexyl. Another subembodiment of this aspect of the invention is realized when one of $R^3$ and $R^{3a}$ is hydrogen and the other is CH$_3$. Another subembodiment of this aspect of the invention is realized when one of $R^3$ and $R^{3a}$ is hydrogen and the other is CH(CH$_3$)$_2$. Another subembodiment of this aspect of the invention is realized when one of $R^3$ and $R^{3a}$ is hydrogen and the other is optionally substituted cyclopropyl or cyclobutyl.

Another embodiment of the invention is realized when $R^3$ and $R^{3a}$ combine with the carbon atom to which they are attached to form an optionally substituted $C_{3-6}$cycloalkyl or $C_{3-6}$heterocycloalkyl selected from oxetanyl, cyclopropyl, cyclobutyl, cyclopentyl and cyclohexyl. A subembodiment of this aspect of the invention is realized when $R^3$ and $R^{3a}$ combine to form an optionally substituted cyclopropyl or cyclobutyl.

Another embodiment of the invention is realized when $R^3$ and $R^{3a}$ combine with X and the carbon atom to which they are attached to form a $C_{6-10}$aryl, said aryl optionally substituted with 1 to 3 groups of $R^a$. A subembodiment of this aspect of the invention is realized when $R^3$ and $R^{3a}$, X and the carbon atom to which they are attached to form optionally substituted dihydroindenyl.

Another embodiment of the invention of formula I is realized when $R^a$ is selected from OH, halo, $(CH_2)_n$CH$_3$, CH(CH$_3$)$_2$, C(CH$_3$)$_3$, $(CH_2)_n$OCH$_3$, OC(CH$_3$)$_2$, CH$_2$F, CHF$_2$, $(CH_2)_n$CF$_3$, C(CH$_3$)F$_2$, OCHF$_2$, OCF$_3$, SCF$_3$, SF$_5$, CH$_2$NH$_2$, $(CH_2)_n$N(CH$_3$)$_2$, CF$_2$CF$_3$, cyclobutyl, cyclopropyl, phenyl, naphthyl, pyrimidinyl, pyridyl.

Another embodiment of the invention of formula I is realized when n is 0. Another embodiment of the invention of formula I is realized when n is 1. Another embodiment of the invention of formula I is realized when n is 2. Another embodiment of the invention of formula I is realized when n is 3. Still another embodiment of the invention of formula I is realized when n of $R^a$ is 0-1, 0-2, or 0-3.

Another embodiment of the invention of formula I is represented by structural formula Ia:

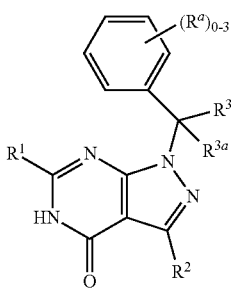

wherein $R^1$, $R^2$, $R^3$, $R^{3a}$ and $R^a$ are as originally described.

An aspect of the invention of formula Ia is realized when $R^2$ is optionally substituted $C_{1\text{-}6}$alkyl or $(CH_2)_nOR$. A subembodiment of this aspect of the invention of formula Ia is realized when $R^2$ is selected from the group consisting of optionally substituted $CH_2OH$, $CH_3$, $CH_2CN$, $CH(CH_3)OH$, $CH(CH_3)CH_2OH$, $C(CH_3)_2OH$, $CH_2NHC(O)CH_3$, $CH_2C(CH_3)OH$, $CH_2OC(O)CH_3$, $CH_2SO_2CH_3$, $CH_2NHOH$, and $CH_2OCH_2$phenyl. A subembodiment of this aspect of the invention of formula Ia is realized when $R^2$ is $CH_2OH$. A subembodiment of this aspect of the invention of formula Ia is realized when $R^2$ is $CH_3$.

Another embodiment of the invention of formula Ia is realized when $R^2$ is $C_{1\text{-}4}$haloalkyl. A subembodiment of this aspect of the invention of formula Ia is realized when the haloalkyl of $R^2$ is selected from the group consisting of $CH_2F$, $CHF_2$, $(CH_2)_nCF_3$, $CF_2CH_2OH$, and $CH(CF_3)OH$. A subembodiment of this aspect of the invention of formula Ia is realized when the haloalkyl of $R^2$ is $CH_2F$ or $CHF_2$.

Another embodiment of the invention of formula Ia is realized when $R^2$ is selected from the group consisting of $CH_2$oxetanyl, tetrahydrofuranyl, furanyl, oxadiazolyl, pyrazolyl, $C(O)NR_2$, $C(O)NH(CH_2CF_3)$, $NR_2$, $NHSO_2R$, $C(O)R$, and $NHC(O)CH_3$.

Another aspect of the invention of formula Ia is realized when $R^3$ and $R^{3a}$ independently represents hydrogen, $CH_3$, $CH(CH_3)_2$, $CH_2CH_3$, $CH_2OCH_3$, $C(CH_3)_3$, $CH_2CF_3$, and optionally substituted cyclopropyl, cyclobutyl, cyclopentyl and cyclohexyl. A subembodiment of this aspect of the invention of formula Ia is realized when one of $R^3$ and $R^{3a}$ is hydrogen and the other is selected from the group consisting of $CH_3$, $CH(CH_3)_2$, $CH_2CH_3$, $C(CH_3)_3$, $CH_2CF_3$, cyclopropyl, cyclobutyl, cyclopentyl and cyclohexyl. Another subembodiment of this aspect of the invention of formula Ia is realized when one of $R^3$ and $R^{3a}$ is hydrogen and the other is $CH_3$. Another subembodiment of this aspect of the invention of formula Ia is realized when one of $R^3$ and $R^{3a}$ is hydrogen and the other is $CH(CH_3)_2$. Another subembodiment of this aspect of the invention of formula Ia is realized when one of $R^3$ and $R^{3a}$ is hydrogen and the other is optionally substituted cyclopropyl.

Still another embodiment of the invention of formula Ia is realized when $R^3$ and $R^{3a}$ combine with the carbon atom to which they are attached to form an optionally substituted $C_{3\text{-}6}$cycloalkyl or $C_{3\text{-}6}$heterocycloalkyl selected from oxetanyl, cyclopropyl, cyclobutyl, cyclopentyl and cyclohexyl. A subembodiment of this aspect of the invention of formula Ia is realized when $R^3$ and $R^{3a}$ combine to form an optionally substituted cyclopropyl or cyclobutyl.

Another embodiment of the invention of formula Ia is realized when the $R^a$ on the phenyl ring of formula Ia is selected from fluorine, chlorine, iodine, bromine, $CH_3$, $CH(CH_3)_2$, $C(CH_3)_3$, $(CH_2)_nOCH_3$, $OC(CH_3)_2$, $C(CH_3)F_2$, $CF_2CF_3$, $CH_2F$, $CHF_2$, $CF_3$, $OCHF_2$, $OCF_3$, $SF_5$, and optionally substituted cyclopropyl.

Still another embodiment of the invention of formula Ia is realized two adjacent $R^a$ groups on the phenyl of formula Ia together with the atoms to which they are attached combine to form a cyclic ring, said ring optionally interrupted by 1 to 2 heteroatoms selected from N, S, and O. A subembodiment of this aspect of the invention is realized when a bicyclic ring results, namely optionally substituted benzodioxolyl.

Another embodiment of the invention of formula Ia is realized when $R^2$ is $CH_2OH$, $CH_2F$, $CHF_2$ or $CH_3$, one of $R^3$ and $R^{3a}$ is hydrogen and the other is selected from the group consisting of $CH_3$, $CH(CH_3)_2$, $CH_2CH_3$, $C(CH_3)_3$, $CH_2CF_3$, and cyclopropyl, or $R^3$ and $R^{3a}$ combine with the carbon atom to which they are attached to form an optionally substituted $C_{3\text{-}6}$cycloalkyl selected from cyclopropyl, cyclobutyl, cyclopentyl and cyclohexyl, and the $R^a$ on the phenyl ring of formula Ia is selected from fluorine, Iodine, $CH_3$, $CH(CH_3)_2$, $C(CH_3)_3$, $(CH_2)_nOCH_3$, $OC(CH_3)_2$, $C(CH_3)F_2$, $CF_2CF_3$, $CH_2F$, $CHF_2$, $CF_3$, $OCHF_2$, $OCF_3$, $SF_5$, and cyclopropyl.

Still another embodiment of the invention is realized when it is represented by structural formula Ib:

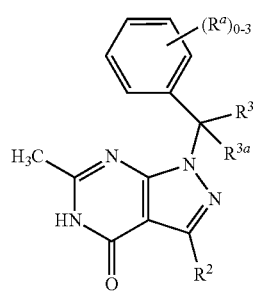

or a pharmaceutically acceptable salt thereof wherein $R^2$, $R^3$, $R^{3a}$ and $R^a$ are as originally described.

An aspect of the invention of formula Ib is realized when $R^2$ is optionally substituted $C_{1\text{-}6}$alkyl or $(CH_2)_nOR$. A subembodiment of this aspect of the invention of formula Ib is realized when $R^2$ is selected from the group consisting of optionally substituted $CH_2OH$, $CH_3$, $CH_2CN$, $CH(CH_3)OH$, $CH(CH_3)CH_2OH$, $C(CH_3)_2OH$, $CH_2NHC(O)CH_3$, $CH_2C(CH_3)OH$, $CH_2OC(O)CH_3$, $CH_2SO_2CH_3$, $CH=NOH$, and $CH_2OCH_2$phenyl. A subembodiment of this aspect of the invention of formula Ib is realized when $R^2$ is $CH_2OH$. A subembodiment of this aspect of the invention of formula Ib is realized when $R^2$ is $CH_3$.

Another embodiment of the invention of formula Ib is realized when $R^2$ is $C_{1\text{-}4}$haloalkyl. A subembodiment of this aspect of the invention of formula Ib is realized when the haloalkyl of $R^2$ is selected from the group consisting of $CH_2F$, $CHF_2$, $(CH_2)nCF_3$, $CF_2CH_2OH$, and $CH(CF_3)OH$. A subembodiment of this aspect of the invention of formula Ib is realized when the haloalkyl of $R^2$ is $CH_2F$ or $CHF_2$.

Another embodiment of the invention of formula Ib is realized when $R^2$ is selected from the group consisting of $CH_2$oxetanyl, tetrahydrofuranyl, furanyl, oxadiazolyl, pyrazolyl, $C(O)NR_2$, $C(O)$—N-linked morpholinyl, $C(O)NH(CH_2CF_3)$, $NR_2$, $NHSO_2R$, $C(O)R$, and $NHC(O)CH_3$.

Another aspect of the invention of formula Ib is realized when $R^3$ and $R^{3a}$ independently represents hydrogen $CH_3$, $CH(CH_3)_2$, $CH_2CH_3$, $CH_2OCH_3$, $C(CH_3)_3$, $CH_2CF_3$, and optionally substituted cyclopropyl, cyclobutyl, cyclopentyl and cyclohexyl. A subembodiment of this aspect of the invention of formula Ib is realized when one of $R^3$ and $R^{3a}$ is hydrogen and the other is selected from the group consisting of $CH_3$, $CH(CH_3)_2$, $CH_2CH_3$, $C(CH_3)_3$, $CH_2CF_3$, cyclopropyl, cyclobutyl, cyclopentyl and cyclohexyl. Another subembodiment of this aspect of the invention of formula Ib is realized when one of $R^3$ and $R^{3a}$ is hydrogen and the other is $CH_3$. Another subembodiment of this aspect of the invention of formula Ib is realized when one of $R^3$ and $R^{3a}$ is hydrogen and the other is $CH(CH_3)_2$. Another subembodiment of this aspect of the invention of formula Ib is realized when one of $R^3$ and $R^{3a}$ is hydrogen and the other is optionally substituted cyclopropyl.

Still another embodiment of the invention of formula Ib is realized when $R^3$ and $R^{3a}$ combine with the carbon atom to which they are attached to form an optionally substituted $C_{3-6}$cycloalkyl or $C_{3-6}$heterocycloalkyl selected from oxetanyl, cyclopropyl, cyclobutyl, cyclopentyl and cyclohexyl. A subembodiment of this aspect of the invention of formula Ib is realized when $R^3$ and $R^{3a}$ combine to form an optionally substituted cyclopropyl or cyclobutyl.

Another embodiment of the invention of formula Ib is realized when the $R^a$ on the phenyl ring of formula Ib is selected from fluorine, chlorine, iodine, bromine, $CH_3$, $CH(CH_3)_2$, $C(CH_3)_3$, $(CH_2)_nOCH_3$, $OC(CH_3)_2$, $C(CH_3)F_2$, $CF_2CF_3$, $CH_2F$, $CHF_2$, $CF_3$, $OCHF_2$, $OCF_3$, $SF_5$, and optionally substituted cyclopropyl.

Still another embodiment of the invention of formula Ib is realized two adjacent $R^a$ groups on the phenyl of formula Ib together with the atoms to which they are attached combine to form a cyclic ring, said ring optionally interrupted by 1 to 2 heteroatoms selected from N, S, and O. A subembodiment of this aspect of the invention is realized when a bicyclic ring results, namely optionally substituted benzodioxolyl.

Another embodiment of the invention of formula Ib is realized when $R^2$ is $CH_2OH$, $CH_2F$, $CHF_2$ or $CH_3$, one of $R^3$ and $R^{3a}$ is hydrogen and the other is selected from the group consisting of $CH_3$, $CH(CH_3)_2$, $CH_2CH_3$, $C(CH_3)_3$, $CH_2CF_3$, and cyclopropyl, or $R^3$ and $R^{3a}$ combine with the carbon atom to which they are attached to form an optionally substituted $C_{3-6}$cycloalkyl selected from cyclopropyl, cyclobutyl, cyclopentyl and cyclohexyl, and the $R^a$ on the phenyl ring of formula Ib is selected from fluorine, Iodine, $CH_3$, $CH(CH_3)_2$, $C(CH_3)_3$, $(CH_2)_nOCH_3$, $OC(CH_3)_2$, $C(CH_3)F_2$, $CF_2CF_3$, $CH_2F$, $CHF_2$, $CF_3$, $OCHF_2$, $OCF_3$, $SF_5$, and cyclopropyl.

The invention is also directed to a method for the treatment of central nervous system disorders associated with phosphodiesterase 2 (PDE2) using the compounds of Formula I. More specifically, the present invention relates to the use of such compounds for treating neurological and psychiatric disorders, such as schizophrenia, psychosis, Alzheimer's, cognitive impairment, anxiety, depression, migraines, Parkinson's disease, Parkinson's disease dementia (PDD), or Huntington's disease, and those associated with striatal hypofunction or basal ganglia dysfunction using the compounds of formula I.

Examples of compounds of the invention can be found throughout the specification as illustrated by Examples 1 through 351.

The invention also encompasses pharmaceutical compositions containing a compound of formula I, and methods for treatment or prevention of phosphodiesterase mediated diseases using compounds of formula I.

Where a variable occurs more than once in any formula of the invention, or in a substituent thereof, the individual occurrences of that variable are independent of each other, unless otherwise specified. Also, combinations of substituents and/or variables are permissible only if such combinations result in stable compounds and valency permits.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. $C_0$ alkyl means a bond.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

As used herein, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

The term heterocyclyl, heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocyclyl, heterocycle or heterocyclic includes heteroaryl moieties. Examples of such heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyl, benzoxazolyl, chromanyl, cinnolinyl, dihydrobenzofuryl, dihydroisobenzofuranyl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyrazolopyridinyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, thienyl, and triazolyl. The term "heteroaryl", as used herein except where noted, represents a stable 5- to 7-membered monocyclic- or stable 9- to 10-membered fused bicyclic heterocyclic ring system which contains an aromatic ring, any ring of which may be saturated, such as piperidinyl, partially saturated, or unsaturated, such as pyridinyl, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure.

When a heterocyclyl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo. The term "haloalkyl" means an alkyl, as defined above, wherein one or more of the bonding positions on the alkyl moiety typically occupied by hydrogen atoms are instead occupied by a halo group, perhaloalkyl (or "fully halogenated" alkyl) means that all bonding positions not participating in bonding the alkyl substituent to a substrate are occupied by a halogen, for example, where the alkyl is selected to be methyl, the term perfluoroalkyl means —$CF_3$.

It should be appreciated by any one skilled in the art that the compounds of this invention can exist in several tautomeric forms as shown below:

it is intended that the invention embrace both both solvated and unsolvated forms. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates and the like. "Hydrate" is a solvate wherein the solvent molecule is $H_2O$.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of the compound bound to PDE2 enzyme, crystalline products or crystalline intermediates that are derivatized, if necessary, with a reagent containing an asymmetric center of known absolute configuration.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of the invention. The present invention includes all stereoisomers of formulae (I) and pharmaceutically acceptable salts thereof.

The compounds of the present invention may contain one or more stereogenic centers and can thus occur as racemates, racemic mixtures, single enantiomers, diastereomeric mixtures and individual diastereomers. Additional asymmetric centers may be present depending upon the nature of the

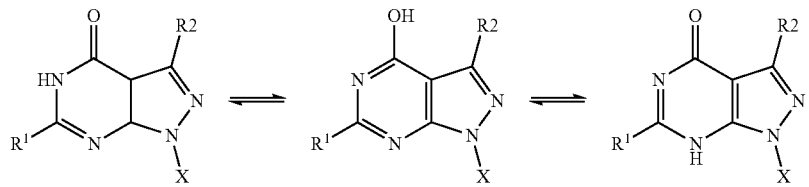

Previous researchers have studied similar compounds and found that one of these tautomers can exist as the predominant form depending on structures and conditions. See B. M. Giuliano, et al. J. Phys. Chem. A, 114, 12725-12730, 2010; B. M. Giuliano, et al. J. Phys. Chem. A, 115, 8178-8179, 2011; A. Gerega, et al. J. Phys. Chem. A, 111, 4934-4943, 2007; R. Sanchez, et al., J. Amer. Chem. Soc., 129(19), 6287-6290, 2007; C. Lopez, et al., Spectroscopy 14, 121-126, 2000; and G. M. Kheifets, et al., Russ. J. Org. Chem., 36(9), 1373-1387, 2000. For brevity and simplicity, we have represented the compounds of the present invention using Formula I and Ia and they are intended to represent all possible tautomeric forms for these compounds without regard to what actually is the predominant tautomeric form in existence for a particular compound.

One or more compounds of the invention may exist in unsolvated as well as solvated forms with pharmaceutically acceptable solvents such as water, ethanol, and the like, and various substituents on the molecule. Each such asymmetric center will independently produce two optical isomers and it is intended that all of the possible optical isomers and diastereomers in mixtures and as pure or partially purified compounds are included within the ambit of this invention. Any formulas, structures or names of compounds described in this specification that do not specify a particular stereochemistry are meant to encompass any and all existing isomers as described above and mixtures thereof in any proportion. When stereochemistry is specified, the invention is meant to encompass that particular isomer in pure form or as part of a mixture with other isomers in any proportion.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

In the compounds of the invention the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formulas I, Ia and Ib. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically enriched compounds within generic formulas I, Ia and Ib can be prepared without undue experimentation by conventional techniques well known to those skilled in the art or by processes analogous to those described in the Schemes and Examples herein using appropriate isotopically enriched reagents and/or intermediates.

The term "substantially pure" means that the isolated material is at least 90% pure, and preferably 95% pure, and even more preferably 99% pure as assayed by analytical techniques known in the art.

For purposes of this specification, the following abbreviations have the indicated meanings:

Ac=acetyl
ACN=acetonitrile
AcO=acetate
BOC=t-butyloxycarbonyl
CBZ=carbobenzoxy
CDI=carbonyldiimidazole
DCC=1,3-dicyclohexylcarbodiimide
DCE=1,2-dichloroethane
DI=de-ionized
DIBAL=diisobutyl aluminum hydride
DIPEA or DIEA=N,N-diisoproylethylamine, also known as Hunig's base
DMA=dimethylacetamide
DMAP=4-(dimethylamino)pyridine
DMF=dimethylformamide
DMP=Dess-Martin periodinane
DPPA=Diphenylphosphoryl azide
DPPP=1,3-bis(diphenylphosphino)propane
Dtbbpy=4,4'-di-tert-butyl-2,2'-dipyridyl
EDC or EDCI=1-(3-dimethylaminopropyl)-3-ethylcarbodiimide hydrochloride
EDTA=ethylenediaminetetraacetic acid, tetrasodium salt
EtOAc or EA=ethyl acetate
FAB=fast atom bombardment
FMOC=9-fluorenylmethoxycarbonyl
HMPA=hexamethylphosphoramide
HATU=O-(7-Azabenzotriazol-1-yl)N,N,N',N'-tetramethyluronium hexafluorophosphate
HOAt=1-Hydroxy-7-azabenzotriazole
HOBt=1-hydroxybenzotriazole
HRMS=high resolution mass spectrometry
IBCF=isobutyl chloroformate
KHMDS=potassium hexamethyldisilazane
LC-MS=Liquid chromatography-mass spectrometry
LDA=lithium diisopropylamide
LiHMDS=lithium hexamethyldisilazane
MCPBA=metachloroperbenzoic acid
MMPP=magnesium monoperoxyphthlate hexahydrate
Ms=methanesulfonyl=mesyl
MsO=methanesulfonate=mesylate
MTBE=Methyl t-butyl ether
NBS=N-bromosuccinimide
NMM=4-methylmorpholine
NMP=N-methylpyrrolidinone
NMR=Nuclear magnetic resonance
PCC=pyridinium chlorochromate
PDC=pyridinium dichromate
Ph=phenyl
PPTS=pyridinium p-toluene sulfonate
pTSA=p-toluene sulfonic acid
PyH.Br$_3$=pyridine hydrobromide perbromide
r.t./RT=room temperature
rac.=racemic
T3P=2,4,6-Tripropyl-1,3,5,2,4,6-trioxatriphosphinane 2,4,6-trioxide
TBAF=tetrabutylammonium fluoride
TFA=trifluoroacetic acid
TfO=trifluoromethanesulfonate=triflate
THF=tetrahydrofuran
TLC=thin layer chromatography
TMSCl=trimethylsilyl chloride All patents, patent applications and publications cited herein, whether supra or infra, are hereby incorporated by reference in their entirety and are deemed representative of the prevailing state of the art.

It will be understood that, as used herein, references to the compounds of present invention are meant to also include the pharmaceutically acceptable salts, and also salts that are not pharmaceutically acceptable when they are used as precursors to the free compounds or in other synthetic manipulations. The compounds of the present invention may be administered in the form of a pharmaceutically acceptable salt. The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, cupric, cuprous, ferric, ferrous, lithium, magnesium, manganic, manganous, potassium, sodium, zinc and the like salts. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylamino-ethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments are citric, hydrobromic, hydrochloric, maleic, phosphoric, sulfuric, fumaric, and tartaric acids. It will be understood that, as used herein, references to the compounds of the present invention are meant to also include the pharmaceutically acceptable salts.

Exemplifying the invention are the specific compounds disclosed in the Examples and herein. The subject compounds may be useful in a method of treating a neurological or psychiatric disorder associated with PDE2 function or activity in a patient such as a mammal in need of such inhibition comprising the administration of an effective amount of the compound. In addition to primates, especially humans, a variety of other mammals can be treated according to the method of the present invention. The subject compounds may be useful in a method of inhibiting PDE2 activity in a patient such as a mammal in need of such inhibition comprising the administration of an effective amount of the compound. The subject compounds also may be useful for treating a neurological or psychiatric disorder associated with striatal hypofunction or basal ganglia dysfunction in a mammalian patient in need thereof. In addition to primates, especially humans, a variety of other mammals can be treated according to the method of the present invention.

The present invention is directed to a compound of the present invention or a pharmaceutically acceptable salt thereof for use in medicine. The present invention is further directed to a use of a compound of the present invention or a pharmaceutically acceptable salt thereof for the manufacture of a medicament for treating a neurological or psychiatric disorder associated with PDE2 function in a mammalian patient in need thereof. The present invention is further directed to a use of a compound of the present invention or a pharmaceutically acceptable salt thereof for the manufacture of a medicament for treating a neurological or psychiatric disorder associated with striatal hypofunction or basal ganglia dysfunction in a mammalian patient in need thereof.

Treating" or "treatment of" a disease state includes: 1 inhibiting the disease state, i.e., arresting the development of the disease state or its clinical symptoms; 2) or relieving the disease state, i.e., causing temporary or permanent regression of the disease state or its clinical symptoms.

The invention is also directed to use of the compounds to prevent the disease state.

The subject treated in the present methods is generally a mammal, in particular, a human being, male or female, in whom therapy is desired. The term "therapeutically effective amount" means the amount of the subject compound that will elicit the biological or medical response of a tissue, system, animal or human that is being sought by the researcher, veterinarian, medical doctor or other clinician. It is recognized that one skilled in the art may affect the neurological and psychiatric disorders by treating a patient presently afflicted with the disorders or by prophylactically treating a patient afflicted with such disorders with an effective amount of the compound of the present invention.

Applicants propose that inhibitors of PDE2, including PDE2A, will provide therapeutic benefit to those individuals suffering from psychiatric and cognitive disorders. The unique and exclusive distribution of PDE2A in the medium spiny projection neurons of the striatum, which form the principle site for cortical and dopaminergic input within basal ganglia, suggests that it may be possible and desirable to identify inhibitors of PDE2 to enhance cellular signaling. Without wishing to be bound by any theory, applicants believe that inhibition of PDE2A in the striatum will result in increased cAMP/cGMP signaling and striatal output, which has the potential to restore behavioral inhibition that is impaired in cognitive disease such as schizophrenia. Regulation and integration of glutamatergic and dopaminergic inputs will enhance cognitive behavior, while suppressing or reducing unwanted behavior. Thus, in one embodiment, compounds of the invention provide a method for treating or ameliorating diseases or conditions in which striatal hypofunction is a prominent feature or ones in which basal ganglia dysfunction plays a role, such as, Parkinson's disease, Parkinson's disease dementia (PDD), Huntington's disease, schizophrenia, obsessive-compulsive disorders, addiction and psychosis. Other conditions for which the inhibitors described herein may have a desirable and useful effect include those requiring a reduction in activity and reduced response to psychomotor stimulants or where it would be desirable to reduce conditional avoidance responses, which is often predictive of clinical antipsychotic activity.

In another embodiment the compounds of this invention there is provided a method for treating or ameliorating diseases or conditions in neuronal development, learning, and memory, prolactin and aldosterone secretion, bone cell differentiation, growth, and bone resorption, immunological response, vascular angiogenesis, inflammatory cell transit, cardiac contraction, platelet aggregation, female sexual arousal disorder, and hypoxic pulmonary vasoconstriction.

As used herein, the term "selective PDE2 inhibitor" refers to an organic molecule that effectively inhibits an enzyme from the PDE2 family to a greater extent than enzymes from the PDE 1, and 3-11 families. In one embodiment, a selective PDE2 inhibitor is an organic molecule having a Ki for inhibition of PDE2 that is less than or about one-tenth that for a substance that is an inhibitor for another PDE enzyme. In other words, the organic molecule inhibits PDE2 activity to the same degree at a concentration of about one-tenth or less than the concentration required for any other PDE enzyme. Preferably, a selective PDE2 inhibitor is an organic molecule, having a Ki for inhibition of PDE2 that is less than or about one-hundredth that for a substance that is an inhibitor for another PDE enzyme. In other words, the organic molecule inhibits PDE2 activity to the same degree at a concentration of about one-hundredth or less than the concentration required for any other PDE enzyme. Preferably, a selective PDE2 inhibitor is an organic molecule, having a Ki for inhibition of PDE2 that is less than or about five-hundredth that for a substance that is an inhibitor for another PDE enzyme. In other words, the organic molecule inhibits PDE2 activity to the same degree at a concentration of about five-hundredth or less than the concentration required for any other PDE enzyme. A "selective PDE2 inhibitor" can be identified, for example, by comparing the ability of an organic molecule to inhibit PDE2 activity to its ability to inhibit PDE enzymes from the other PDE families. For example, an organic molecule may be assayed for its ability to inhibit PDE2 activity, as well as PDE1A, PDE1B, PDE1C, PDE3A, PDE3B, PDE4A, PDE4B, PDE4C, PDE4D, PDE5A, PDE6A, PDE6B, PDE6C, PDE7A, PDE7B, PDE8A, PDE8B, PDE9A, PDE10 and/or PDE11A.

Phosphodiesterase enzymes including PDE2 have been implicated in a wide range of biological functions. This has suggested a potential role for these enzymes in a variety of disease processes in humans or other species. The compounds of the present invention may have utility in treating a variety of neurological and psychiatric disorders.

In a specific embodiment, compounds of the present invention provide a method for treating schizophrenia or psychosis comprising administering to a patient in need thereof an effective amount of a compound of the present invention. The Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorders. As used herein, the term "schizophrenia or psychosis" includes the diagnosis and classification of these mental disorders as described in DSM-IV-TR and the term is intended to include similar disorders described in other sources. Disorders and conditions encompassed herein include, but are not limited to, conditions or diseases such as schizophrenia or psychosis, including schizophrenia (paranoid, disorganized, catatonic, undifferentiated, or residual type), schizophreniform disorder, schizoaffective disorder, for example of the delusional type or the depressive type, delusional disorder, psychotic disorder, brief psychotic disorder, shared psychotic disorder, psychotic disorder due to a general medical condition and substance-induced or drug-induced (for example psychosis induced by alcohol, amphetamine, *cannabis*, cocaine, hallucinogens, inhalants, opioids, phencyclidine, ketamine and other dissociative anaesthetics, and other psychostimulants), psychosispsychotic disorder, psychosis associated with affective disorders, brief reactive psychosis, schizoaffective psychosis, "schizophrenia-spectrum" disorders such as schizoid or schizotypal personality disorders, personality disorder of the paranoid type, personality disorder of the schizoid type, illness associated with psychosis (such as major depression, manic depressive (bipolar) disorder, Alzheimer's disease and post-traumatic stress syndrome), including both the positive and the negative symptoms of schizophrenia and other psychoses.

In another specific embodiment, the compounds of the present invention provide a method for treating cognitive disorders comprising administering to a patient in need thereof an effective amount of a compound of the present invention. The DSM-IV-TR also provides a diagnostic tool that includes cognitive disorders including dementia, delirium, amnestic disorders and age-related cognitive decline. As used herein, the term "cognitive disorders" includes the diagnosis and classification of these disorders as described in DSM-IV-TR and the term is intended to include similar disorders described in other sources. Disorders and conditions encompassed herein include, but are not limited to, disorders that comprise as a symptom a deficiency in attention and/or cognition, such as dementia (associated with Alzheimer's disease, ischemia, multi-infarct dementia, trauma, intracranial tumors, cerebral trauma, vascular problems or stroke, alcoholic dementia or other drug-related dementia, AIDS, HIV disease, Parkinson's disease, Parkinson's disease dementia (PDD), Huntington's disease, Pick's disease, Creutzfeldt Jacob disease, perinatal hypoxia, other general medical conditions or substance abuse), Alzheimer's disease, multi-infarct dementia, AIDS-related dementia, and Fronto temporal dementia, delirium, amnestic disorders or age related cognitive decline.

In another specific embodiment, compounds of the present invention provide a method for treating anxiety disorders comprising administering to a patient in need thereof an effective amount of a compound of the present invention. The DSM-IV-TR also provides a diagnostic tool that includes anxiety disorders as generalized anxiety disorder, obsessive-compulsive disorder and panic attack. As used herein, the term "anxiety disorders" includes the diagnosis and classification of these mental disorders as described in DSM-IV-TR and the term is intended to include similar disorders described in other sources. Disorders and conditions encompassed herein include, but are not limited to, anxiety disorders such as, acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition.

In another specific embodiment, compounds of the present invention provide a method for treating substance-related disorders and addictive behaviors comprising administering to a patient in need thereof an effective amount of a compound of the present invention. The DSM-IV-TR also provides a diagnostic tool that includes persisting dementia, persisting amnestic disorder, psychotic disorder or anxiety disorder induced by substance abuse, and tolerance of, dependence on or withdrawal from substances of abuse. As used herein, the term "substance-related disorders and addictive behaviors" includes the diagnosis and classification of these mental disorders as described in DSM-IV-TR and the term is intended to include similar disorders described in other sources. Disorders and conditions encompassed herein include, but are not limited to, substance-related disorders and addictive behaviors, such as substance-induced delirium, persisting dementia, persisting amnestic disorder, psychotic disorder or anxiety disorder, drug addiction, tolerance, and dependence or withdrawal from substances including alcohol, amphetamines, cannabis, cocaine, hallucinogens, inhalants, nicotine, opioids, phencyclidine, sedatives, hypnotics or anxiolytics.

In another specific embodiment, compounds of the present invention provide a method for treating obesity or eating disorders associated with excessive food intake, and complications associated therewith, comprising administering to a patient in need thereof an effective amount of a compound of the present invention. At present, obesity is included in the tenth edition of the International Classification of Diseases and Related Health Problems (ICD-10) (1992 World Health Organization) as a general medical condition. The DSM-IV-TR also provides a diagnostic tool that includes obesity in the presence of psychological factors affecting medical condition. As used herein, the term "obesity or eating disorders associated with excessive food intake" includes the diagnosis and classification of these medical conditions and disorders described in ICD-2 and DSM-IV-TR and the term is intended to include similar disorders described in other sources. Disorders and conditions encompassed herein include, but are not limited to, obesity, bulimia nervosa and compulsive eating disorders.

In another specific embodiment, compounds of the present invention provide a method for treating mood and depressive disorders comprising administering to a patient in need thereof an effective amount of a compound of the present invention. As used herein, the term "mood and depressive disorders" includes the diagnosis and classification of these medical conditions and disorders described in the DSM-IV-TR and the term is intended to include similar disorders described in other sources. Disorders and conditions encompassed herein include, but are not limited to, bipolar disorders, mood disorders including depressive disorders, major depressive episode of the mild, moderate or severe type, a manic or mixed mood episode, a hypomanic mood episode, a depressive episode with atypical features, a depressive episode with melancholic features, a depressive episode with catatonic features, a mood episode with postpartum onset, post-stroke depression; major depressive disorder, dysthymic disorder, minor depressive disorder, premenstrual dysphoric disorder, post-psychotic depressive disorder of schizophrenia, a major depressive disorder superimposed on a psychotic disorder such as delusional disorder or schizophrenia, a bipolar disorder, for example, bipolar I disorder, bipolar II disorder, cyclothymic disorder, depression including unipolar depression, seasonal depression and post-partum depression, premenstrual syndrome (PMS) and premenstrual dysphoric disorder, mood disorders due to a general medical condition, and substance-induced mood disorders.

In another specific embodiment, compounds of the present invention provide a method for treating pain comprising administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In other specific embodiments, compounds of the invention provide methods for treating other types of cognitive, learning and mental related disorders including, but not limited to, learning disorders, such as a reading disorder, a mathematics disorder, or a disorder of written expression, attention-deficit/hyperactivity disorder, age-related cognitive decline, pervasive developmental disorder including autistic disorder, attention disorders such as attention-deficit hyperactivity disorder (ADHD) and conduct disorder; an NMDA receptor-related disorder, such as autism, depression, benign forgetfulness, childhood learning disorders and closed head injury; a neurodegenerative disorder or condition, such as neurodegeneration associated with cerebral trauma, stroke, cerebral infarct, epileptic seizure, neurotoxin poisoning, or hypoglycemia-induced neurodegeneration; multi-system atrophy; movement disorders, such as akinesias and akinetic-rigid syndromes (including, Parkinson's disease, Parkinson's disease dementia (PDD), drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Huntington's disease, dyskinesia associated with dopamine agonist therapy, Gilles de la Tourette's syndrome, epilepsy, muscular spasms and disorders associated with muscular spasticity or weakness including tremors; dyskinesias, including tremor (such as, rest tremor, postural tremor, intention tremor and essential tremor), restless leg syndrome, chorea (such as Sydenham's chorea, Huntington's disease, benign hereditary chorea, neuroacanthocytosis, symptomatic chorea, drug-induced chorea and hemibalism), myoclonus (including, generalised myoclonus and focal myoclonus), tics (including, simple tics, complex tics and symptomatic tics), dystonia (including, generalised, iodiopathic, drug-induced, symptomatic, paroxymal, and focal (such as blepharospasm, oromandibular, spasmodic, spasmodic torticollis, axial dystonia, hemiplegic and dystonic writer's cramp)); urinary incontinence; neuronal damage (including ocular damage, retinopathy or macular degeneration of the eye, tinnitus, hearing impairment and loss, and brain edema); emesis; and sleep disorders, including insomnia and narcolepsy.

Of the disorders above, the treatment of schizophrenia, bipolar disorder, depression, including unipolar depression, seasonal depression and post-partum depression, premenstrual syndrome (PMS) and premenstrual dysphoric disorder, learning disorders, pervasive developmental disorders, including autistic disorder, attention disorders including Attention-Deficit/Hyperactivity Disorder, autism, tic disorders including Tourette's disorder, anxiety disorders including phobia and post-traumatic stress disorder, cognitive disorders associated with dementia, AIDS dementia, Alzheimer's, Parkinson's, Huntington's disease, spasticity, myoclonus, muscle spasm, tinnitus and hearing impairment and loss are of particular importance.

Angiogenesis is the physiological process through which new blood vessels form, and agents that inhibit this process have been shown to be effective treatments for some cancers. As initiation of angiogenesis involves migration and proliferation of vascular endothelial cells, and agents that elevate cAMP inhibit these processes, PDE2 inhibition may have utility as a treatment for cancer. See Savai, et al, *Targeting cancer with phosphodiesterase inhibitors*, Expert Opin. Investig. Drugs (2010) 19(1):117-131. PDE2 has been shown to be expressed in human vascular endothelial cells (VECs) and inhibition of PDE2 by treatment with selective inhibitors inhibited VEGF promoted migration of VECs. See Netherton and Maurice, *Vascular Endothelial Cell Cyclic Nucleotide Phosphodiesterases and Regulated Cell Migration: Implications in Angiogenesis*, Mol Pharmacol (2005) 67:263-272 and Favot, et al, *VEGF-induced HUVEC migration and proliferation are decreased by PDE2 and PDE4 inhibitors*. Thromb Haemost (2003) 90:334-343. Reduction of PDE2 activity with either small molecule inhibitors or PDE2A siRNA suppressed cell growth and invasion in a human malignant melanoma PMP cell line. See Hiramoto, et al, *Role of phosphodiesterase 2 in growth and invasion of human malignant melanoma cells*, Cellular Signalling (2014), 26:1807-1817. Reduction of PDE2 activity with a small molecule inhibitor attenuated tumor formation in a mouse model of ultraviolet light B-induced tumorigenesis. See Bernard, et al, *PDE2 is a Novel Target for Attenuating Tumor Formation in a Mouse Model of UVB-Induced Skin Carcinogenesis*, PLoS ONE (2014), 9(10):e109862. Thus, in another specific embodiment, compounds of the invention provide methods for treating, preventing, controlling, and/or reducing, attenuating cancers, such as malignant melanomas, skin cancer, and the like.

The subject compounds may be further useful in a method for the prevention, treatment, control, amelioration, or reduction of risk of the diseases, disorders and conditions noted herein. The subject compounds are further useful in a method for the prevention, treatment, control, amelioration, or reduction of risk of the aforementioned diseases, disorders and conditions in combination with other agents. The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefore, contemporaneously or sequentially with a compound of the present invention. When a compound of the present invention is used contemporaneously with one or more other drugs, a pharmaceutical composition in unit dosage form containing such other drugs and the compound of the present invention may be desirable. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. Accordingly, the pharmaceutical compositions of the present invention include those that also contain one or more other active ingredients, in addition to a compound of the present invention. The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Accordingly, the subject compounds may be used alone or in combination with other agents which are known to be beneficial in the subject indications or other drugs that affect receptors or enzymes that either increase the efficacy, safety, convenience, or reduce unwanted side effects or toxicity of the compounds of the present invention. The subject compound and the other agent may be co-administered, either in concomitant therapy or in a fixed combination.

In one embodiment, the subject compound may be employed in combination with anti-Alzheimer's agents, including AChEi's (such as Aricept (donepezil)) and Exelon (rivastigmine)) and NMDA blocker Namenda (memantine), beta-secretase inhibitors, gamma-secretase inhibitors, HMG-CoA reductase inhibitors, NSAID's including ibuprofen, vitamin E, and anti-amyloid antibodies.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, atypical antipsychotics, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MAO-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In another embodiment, the subject compound may be employed in combination with an antidepressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, t-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

The compounds of the present invention may be administered by oral, parenteral (e.g., intramuscular, intraperitoneal, intravenous, ICV, intracistemal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans. The terms "administration of" and or "administering a" compound should be understood to mean providing a compound of the invention or a prodrug of a compound of the invention to the individual in need of treatment.

The term "composition" as used herein is intended to encompass a product comprising specified ingredients in predetermined amounts or proportions, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. Accordingly, the pharmaceutical compositions of the present invention encompass any composition made by mixing a compound of the present invention and a pharmaceutically acceptable carrier.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredients are mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions, oily suspensions, dispersible powders or granules, oil-in-water emulsions, and sterile injectable aqueous or oleagenous suspension may be prepared by standard methods known in the art. By "pharmaceutically acceptable" it is meant the carrier, diluent or excipient must be compatible with the other ingredients of the formulation and not deleterious to the recipient thereof.

The subject compounds are further useful in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.001 to 10 mg/kg of body weight daily are administered to the patient, e.g., humans and elderly humans. The dosage range will generally be about 0.5 mg to 1.0 g per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 50 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day.

Several methods, schemes, and examples for preparing representative compounds of this invention are illustrated below and can be found in further detail in U.S. Pat. No. 7,144,913, which is incorporated by reference herein in its entirety. Starting materials and the requisite intermediates are in some cases commercially available, or can be prepared according to literature procedures or as illustrated herein. The compounds of this invention may be prepared by employing reactions as shown in the following schemes, in addition to other standard manipulations that are known in the literature or exemplified in the experimental procedures. Substituent numbering as shown in the schemes does not necessarily correlate to that used in the claims and often, for clarity, a single substituent is shown attached to the compound where multiple substituents are allowed under the definitions hereinabove. The compounds of this invention are prepared by employing reactions as shown in the schemes and examples herein, in addition to other standard manipulations such as ester hydrolysis, cleavage of protecting groups, etc., as may be known in the literature or exemplified in the experimental procedures. Starting materials are made according to procedures known in the art or as illustrated herein.

In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood.

The representative examples of the compounds of the invention are illustrated in the following non-limiting schemes and Examples.

General

Starting materials used were obtained from commercial sources or prepared in other examples, unless otherwisely noted.

The progress of reactions was often monitored by TLC or LC-MS. The LC-MS was recorded using one of the following methods.

Method A: XBridge C18: 4.6×50 mm, 3.5 um, 1.0 uL injection, 1.50 mL/min flow rate, 90-900 amu scan range, 190-400 nm UV range, 10-95% (over 2.2 min) gradient with MeCN and water (5 μM NH$_4$HCO$_3$), hold 1 min; 3.6 minute total run time.

Method B: Supelco Ascentis Express C18, 3×50 mm, 2.7 um column. 2.0 uL injection, 1.25 ml/min flow rate, 170-900 amu scan range, 200-400 nm UV range, 10-99% (over 2.0 min) gradient with MeCN (0.05% TFA) and water (0.05%); 3 minute total run time.

Method C: Supelco Ascentis Express C18, 3×100 mm, 2.7 um column. 2.0 uL injection, 1.00 ml/min flow rate, 170-900 amu scan range, 200-400 nm UV range, 10-99% (over 4.0 min) gradient with MeCN (0.05% TFA) and water (0.05%); 5 minute total run time.

Method D: Waters Acquity UPLC, HSS C18 1.8 um, 2.1×50 mm, MeCN and water with 0.1% trifluoroacetic acid, 1 mL/min flow rate, gradient 5%-100% MeCN over 1.4 min.

Method E: Waters Acquity UPLC, HSS C18 1.8 um, 2.1×50 mm, MeCN and water with 0.1% formic acid, 1 mL/min flow rate, gradient 5%-100% MeCN over 1.4 min.

Method F: Shimadzu: 3.0×50 mm, 2.2 um, 1.0 uL injection, 1.00 mL/min flow rate, 90-900 amu scan range, 190-400 nm UV range, 5-100% (over 2.2 min) gradient with MeCN (0.05% TFA) and water (0.05% TFA), hold 1 min; 3.6 minute total run time.

Method G: Titan C18: 2.1×50 mm, 1.9 um, 1.0 uL injection, 0.80 mL/min flow rate, 90-900 amu scan range, 190-400 nm UV range, 5-100% (over 2.1 min) gradient with MeCN (0.05% TFA) and water (0.05% TFA), hold 0.5 min; 3.0 minute total run time.

Method H: ZORBAX Eclipse Plus C18: 3.0×50 mm, 1.8 um, 1.0 uL injection, 1.00 mL/min flow rate, 90-900 amu scan range, 190-400 nm UV range, 5-100% (over 2.1 min) gradient with MeCN (0.1% FA) and water (0.1% FA), hold 0.5 min; 3.0 minute total run time.

NMR was recorded at room temperature unless noted otherwise on Varian Inova 400 or 500 MHz spectrometers with the solvent peak used as the reference or on Bruker 300 or 400 MHz spectrometers with the TMS peak used as internal reference.

The methods used for the preparation of the compounds of this invention are illustrated by the following schemes. Unless specified otherwise, all starting materials used are commercially available.

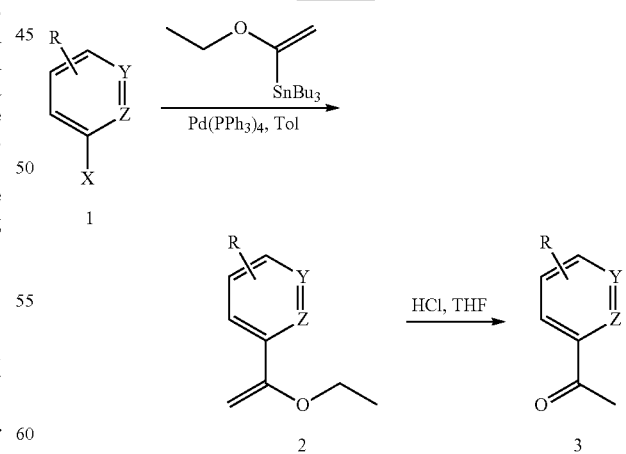

Scheme 1.

Scheme 1 illustrates a synthetic procedure to the preparation of ketones such as 3 from precursors such as 1. Palladium-catalyzed stannylation of 1 furnishes intermediate 2 which can then be hydrolyzed under acidic conditions to afford ketone 3.

Scheme 2.

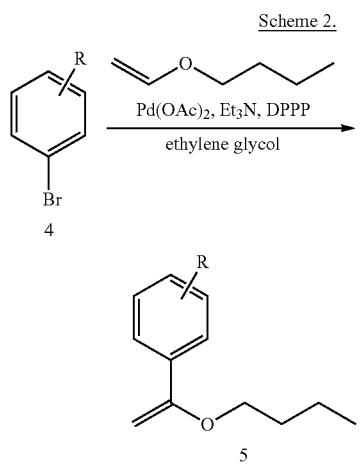

Scheme 2 illustrates a synthetic procedure to the preparation of ketones such as 6 from precursors such as 4. Palladium-catalyzed Heck reaction of bromide 4 furnishes intermediate 5 which can then be hydrolyzed under acidic conditions to afford ketone 6.

Scheme 3.

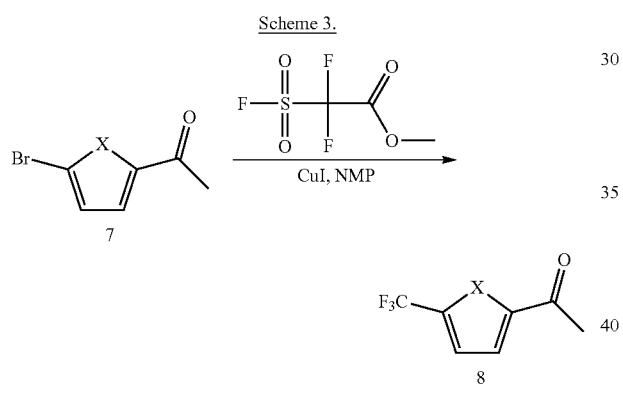

Scheme 3 illustrates a synthetic procedure to the preparation of ketones such as 8 from precursors such as 7. Copper-catalyzed trifluoromethylation of bromide 7 furnishes ketone 8.

Scheme 4.

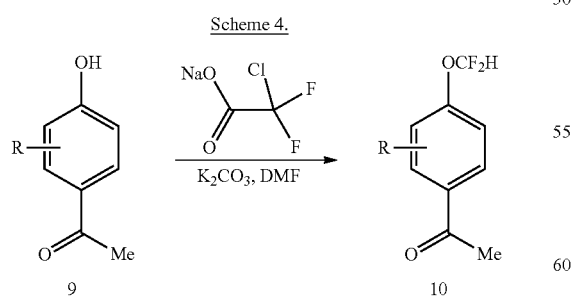

Scheme 4 illustrates a synthetic procedure to the preparation of ketones such as 10 from precursors such as 9. Base-catalyzed difluoromethylation of phenol 9 furnishes ketone 10.

Scheme 5.

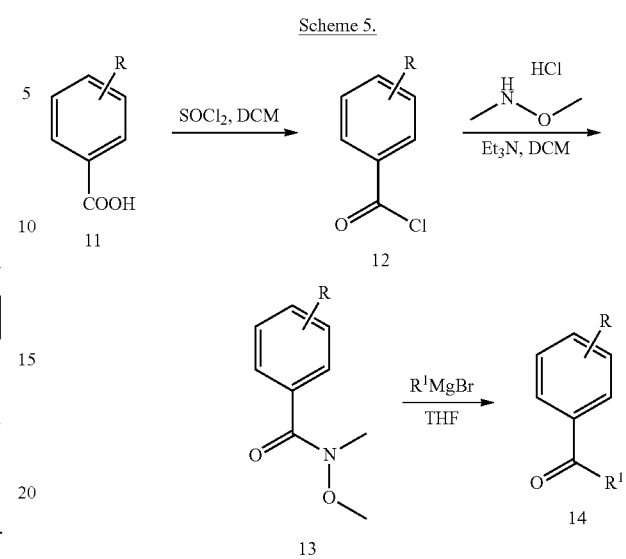

Scheme 5 illustrates a synthetic procedure to the preparation of ketones such as 14 from precursors such as 11. Treatment of acid 11 with thionyl chloride affords the intermediate acid chloride 12 which can be reacted with the requisite amine to afford amide 13. Treatment of 13 with a Grignard reagent affords ketone 14.

Scheme 6.

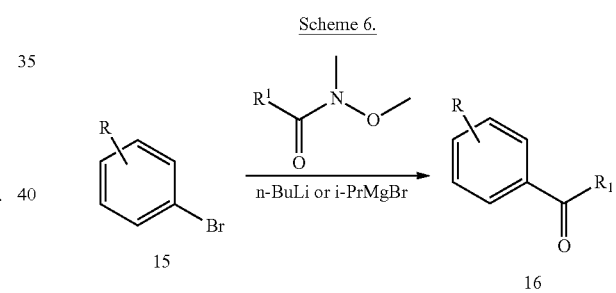

Scheme 6 illustrates a synthetic procedure to the preparation of ketones such as 16 from precursors such as 15. Treatment of bromide 15 with either n-BuLi or i-PrMgBr followed by the Weinreb amide affords ketone 16.

Scheme 7.

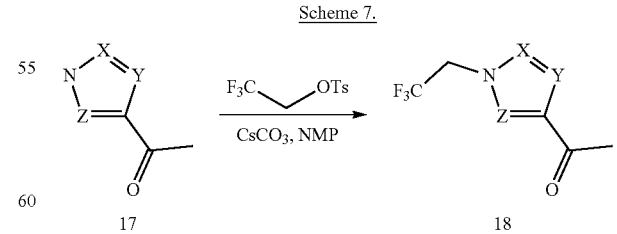

Scheme 7 illustrates a synthetic procedure to the preparation of ketones such as 18 from precursors such as 17. Treatment of nitrogen heterocycle 17 with trifluoroethyl tosylate in the presence of base affords ketone 18.

Scheme 8.

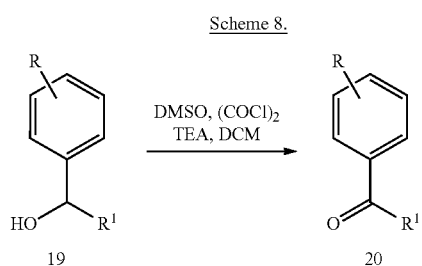

Scheme 8 illustrates a synthetic procedure to the preparation of ketones such as 20 from precursors such as 19. Swern oxidation of 19 affords ketone 20.

Scheme 9.

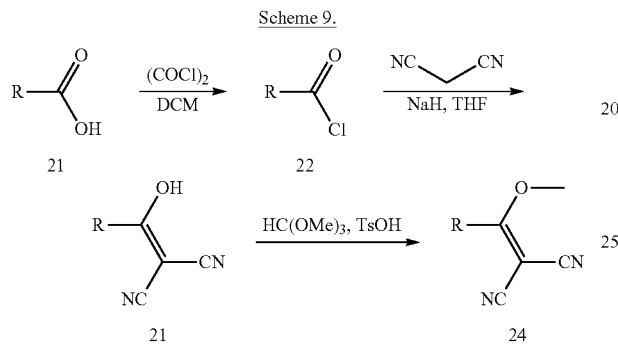

Scheme 9 illustrates one procedure for the syntheses of alkylidenes such as 24 from acids 21. Treatment of acid 21 with oxalyl chloride affords acid chloride 22 which is reacted with malononitrile in the presence of NaH to provide 23. Intermediate 23 is methylated using HC(OMe)$_3$ and TsOH to afford alkylidene 24.

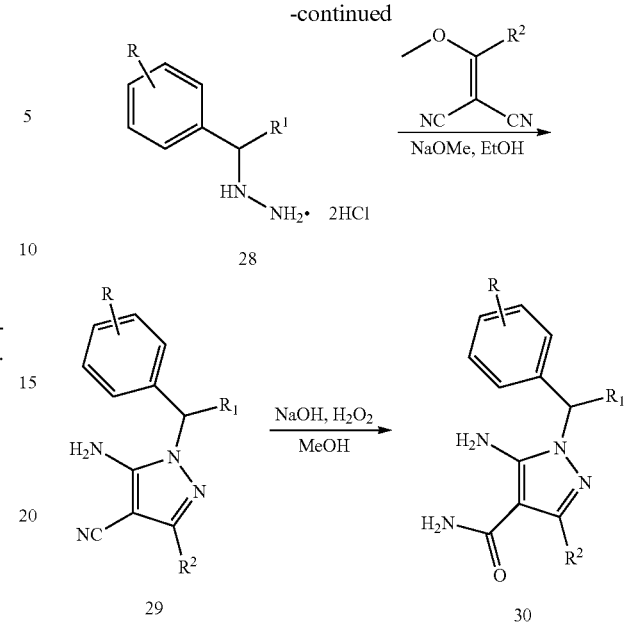

Scheme 10 illustrates a synthetic sequence for the syntheses of 5-aminopyrazole-4-carboxamides such as 30. Condensation of ketone 25 with tert-butyl hydrazinecarboxylate in THF and heptane affords hydrazone 6 which is reduced with sodium cyanoborohydride in methanol to afford 26. Deprotection of Boc protected hydrazine 26 is carried out using hydrogen chloride which is followed by cyclization with a substituted alkylidene to afford the 5-aminopyrazole-4-carbonitrile 29. Treatment with sodium hydroxide and hydrogen peroxide yields aminopyrazole-4-carboxamide 30.

Scheme 10.

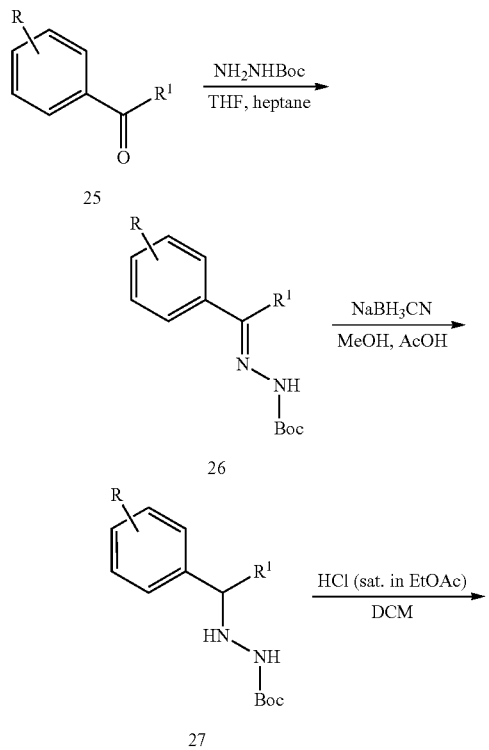

Scheme 11.

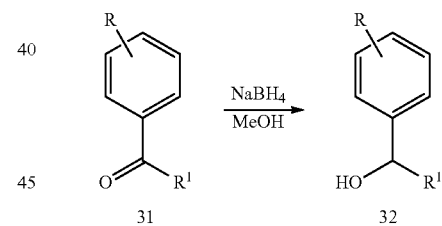

Scheme 11 illustrates a synthetic procedure to the preparation of alcohols such as 32 from ketone precursors such as 31 using a reducing agent such as sodium borohydride.

Scheme 12.

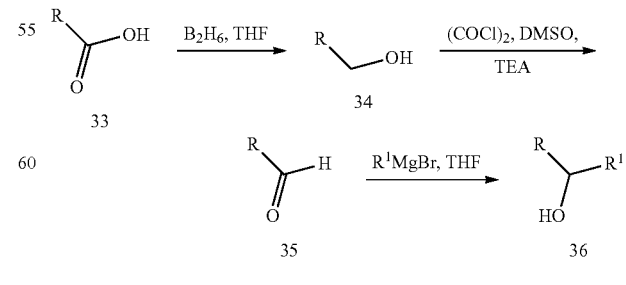

Scheme 12 illustrates a synthetic procedure to the preparation of alcohols such as 36 from acid precursors such as 33. Borane reduction of acid 33 followed by Swern oxidation of the intermediate alcohol 34 can yield aldehyde 35. Grignard addition to 35 furnishes alcohol 36.

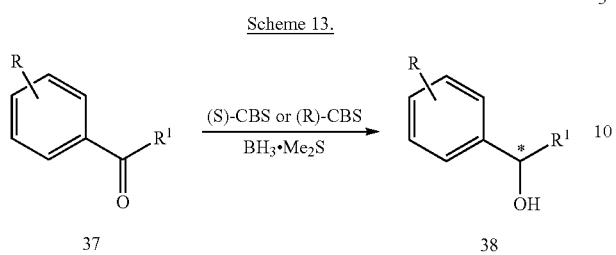

Scheme 13.

Scheme 13 illustrates a synthetic procedure for the preparation of chiral alcohols such as 38 using either (S)-(−)-2-methyl CBS oxazaborolidine or (R)-(+)-2-methyl CBS oxazaborolidine in the presence of borane on ketone precursors such as 37.

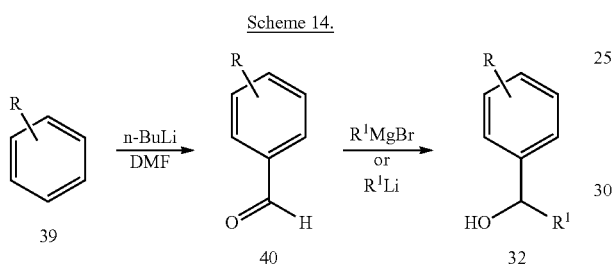

Scheme 14.

Scheme 14 illustrates a synthetic procedure to the preparation of alcohols such as 32 from substituted benzene precursors such as 39. Formylation of 39 followed by either Grignard or organolithium addition furnishes alcohol 32.

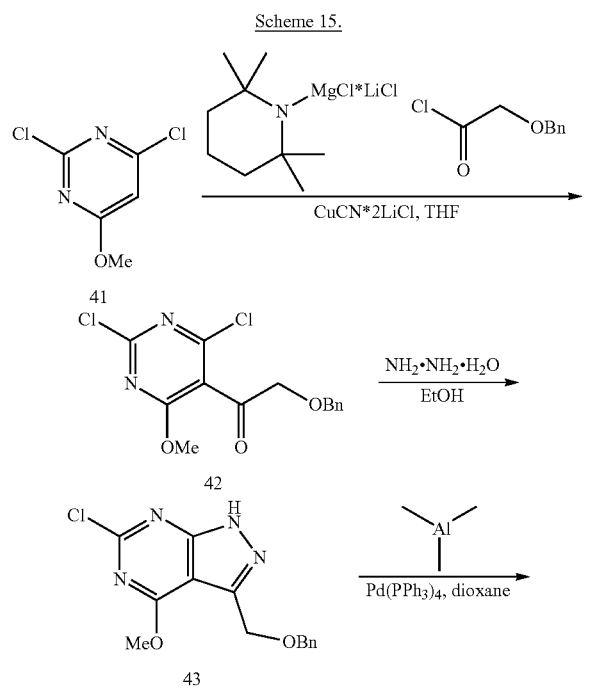

Scheme 15.

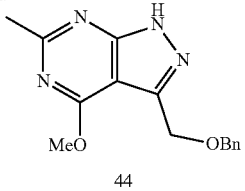

Scheme 15 illustrates a synthetic procedure to the preparation of pyrazolopyrimdine intermediate 44 from the dichloropyrimidine 41. Cuprate formation followed by quenching with benzoyloxy acetyl chloride may yield 42. Treatment with hydrazine followed by Pd-catalyzed methylation furnishes pyrazolopyrimidine 44.

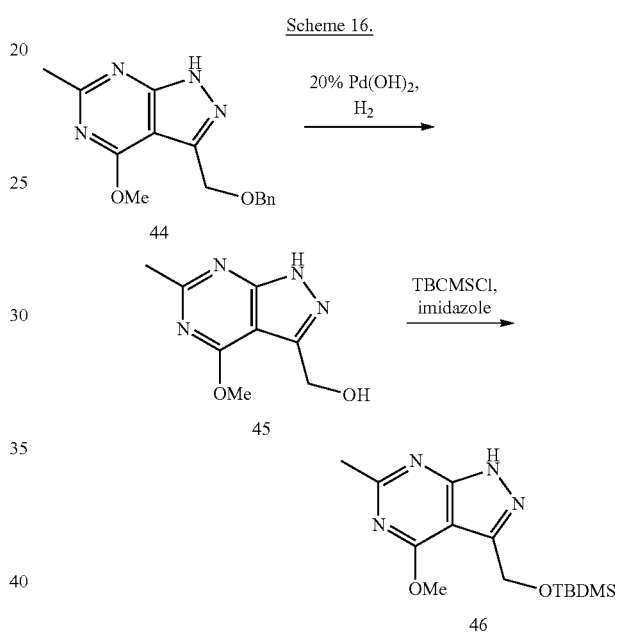

Scheme 16.

Scheme 16 illustrates a synthetic procedure to the preparation of pyrazolopyrimidine intermediate 46 from the corresponding benzyl adduct 44. Debenzylation using Pearlman's catalyst in the presence of hydrogen affords the intermediate alcohol followed by silyl ether introductions furnishes pyrazolopyrimidine 46.

Scheme 17.

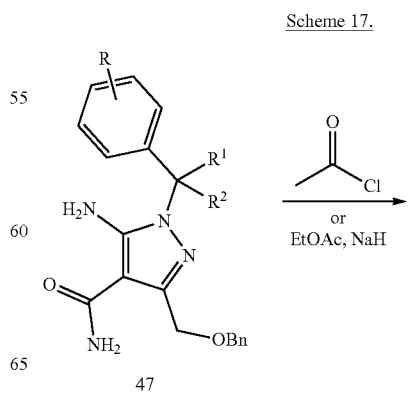

Scheme 18 illustrates a procedure for the syntheses of 3,6-disubstituted pyrazolopyrimidinones such as 51 by treatment of 5-aminopyrazole-4-carboxamide 50 with various acid chlorides.

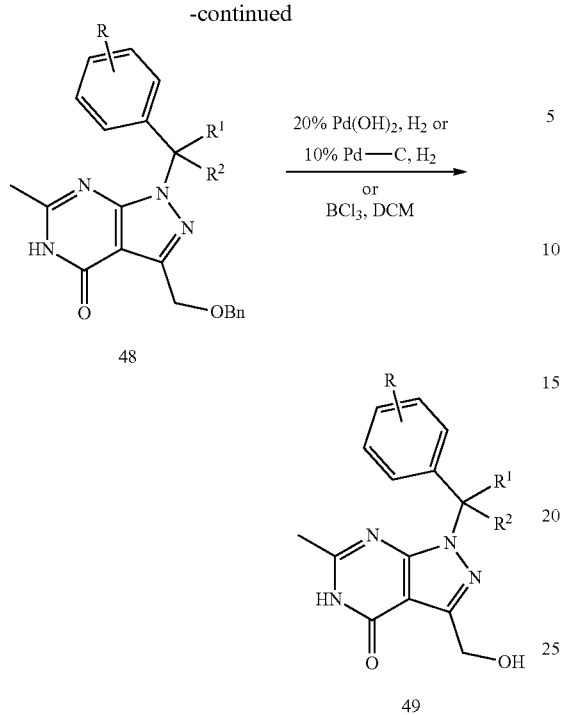

Scheme 17 illustrates one procedure for the syntheses of 3-(hydroxymethyl)-6-methyl-pyrazolopyrimidinone such as 49. Cyclization of 5-aminopyrazole-4-carboxamide 47 with acetyl chloride or ethyl acetate in the presence of sodium hydride affords 3-(benzyloxymethyl)-6-methyl-pyrazolopyrimidinone 48. The benzyl deprotection can be achieved using one of three methods shown relying either on hydrogenolysis in the presence of a $H_2$ and a palladium catalyst or with $BCl_3$ to furnish hydroxymethyl pyrazolopyrimidinone 49.

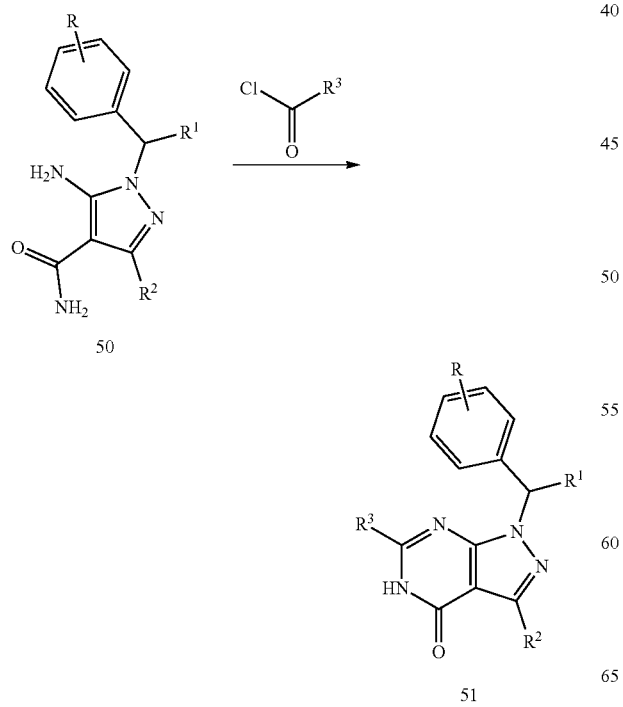

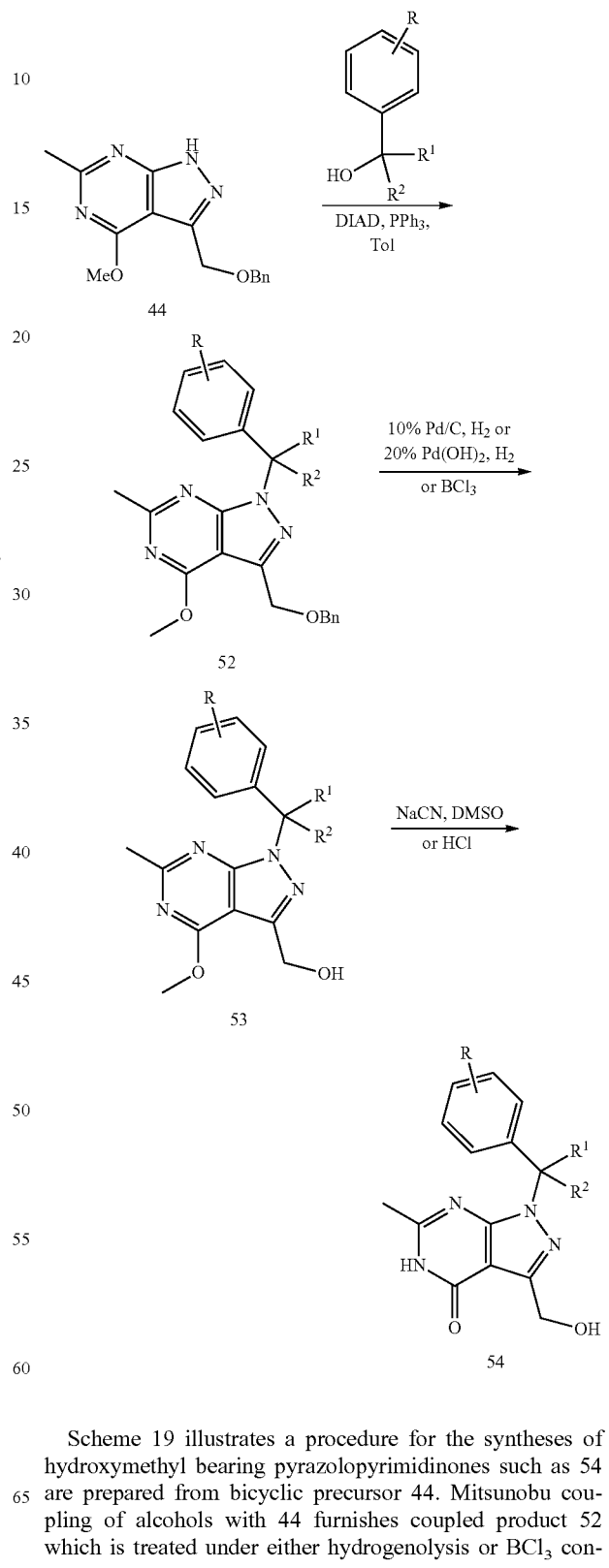

Scheme 19 illustrates a procedure for the syntheses of hydroxymethyl bearing pyrazolopyrimidinones such as 54 are prepared from bicyclic precursor 44. Mitsunobu coupling of alcohols with 44 furnishes coupled product 52 which is treated under either hydrogenolysis or $BCl_3$ conditions to afford 53. Methoxy deprotection can be achieved with either NaCN or HCl to afford hydroxymethyl pyrazolopyrimidinone 54.

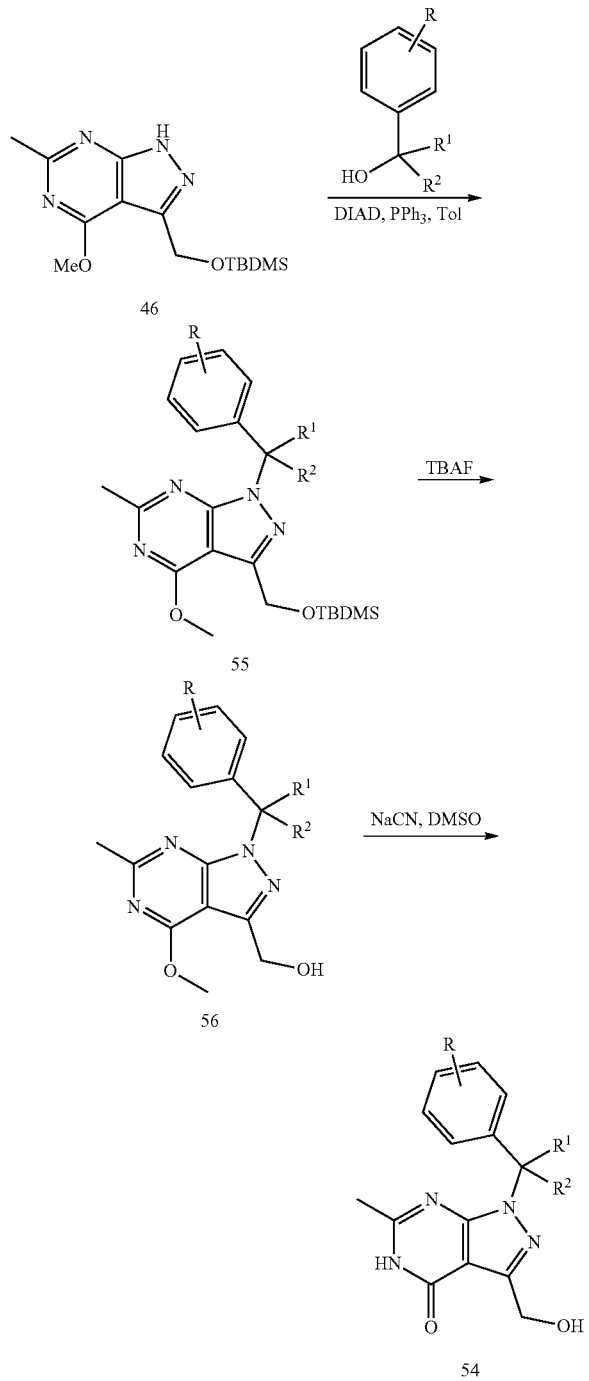

Scheme 20.

Scheme 21.

Scheme 20 illustrates a procedure for the syntheses of hydroxymethyl bearing pyrazolopyrimidinones such as 54 are prepared from bicyclic precursor 46. Mitsunobu coupling of alcohols with 46 furnishes coupled product 55 which can be treated with TBAF to furnish alcohol 56. Sodium cyanide exposure furnishes hydroxymethyl pyrazolopyrimidone 54.

Scheme 21 illustrates a procedure for the syntheses of chiral hydroxymethyl bearing pyrazolopyrimidinones such as 59 which are prepared using chiral, non-racemic secondary alcohols. Mitsunobu coupling of alcohols with 46 furnishes coupled product 57 which can be treated with TBAF to furnish alcohol 58. Sodium cyanide exposure furnishes hydroxymethyl pyrazolopyrimidinone 59.

Scheme 22.

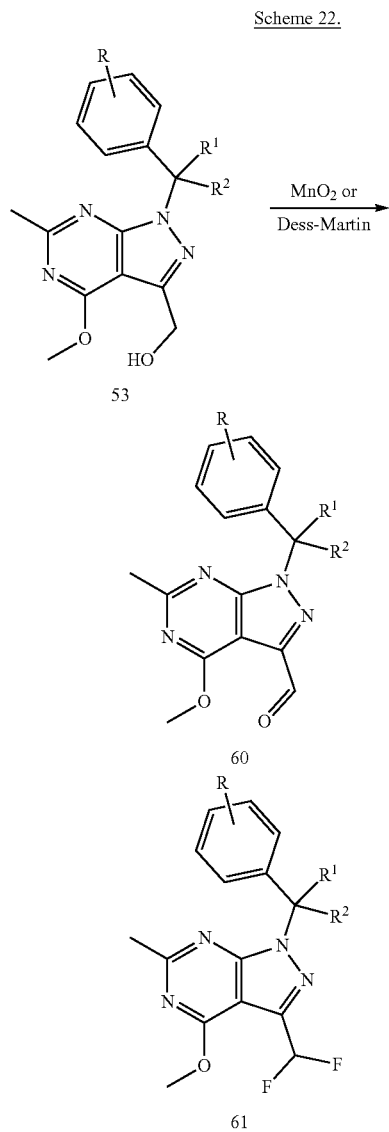

Scheme 23.

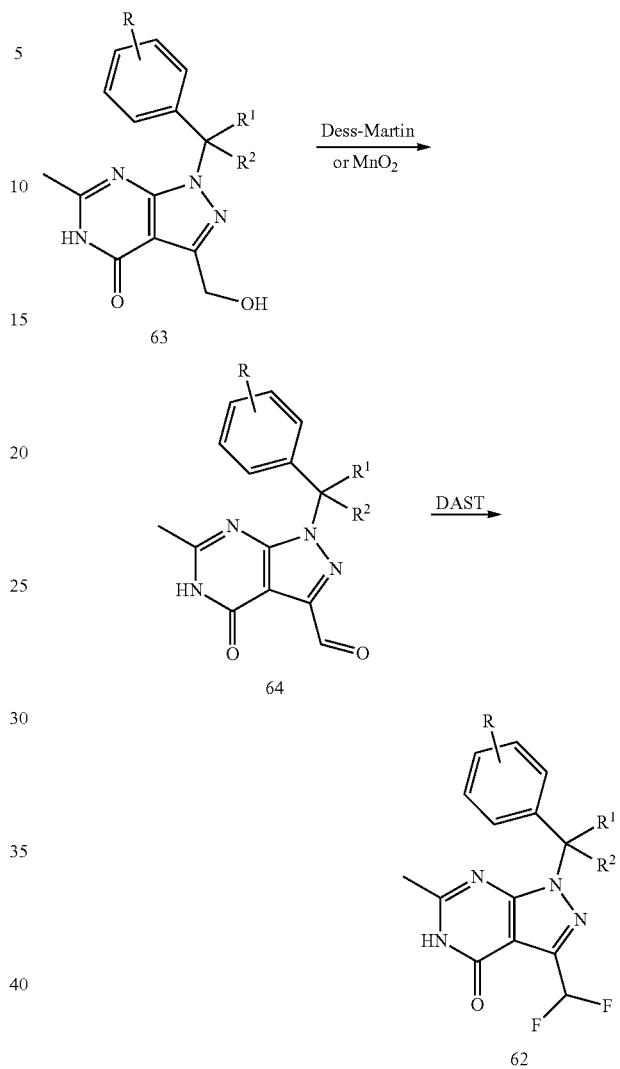

Scheme 23 illustrates a procedure for the syntheses difluoromethyl bearing pyrazolopyrimidinones such as 62 are prepared from hydroxymethyl pyrazolopyrimidones such as 63. Oxidation of 63 with Dess-Martin reagent yields the intermediate aldehyde 64 which can be treated with DAST to furnish difluoromethyl pyrazolopyrimidinone 62.

Scheme 24.

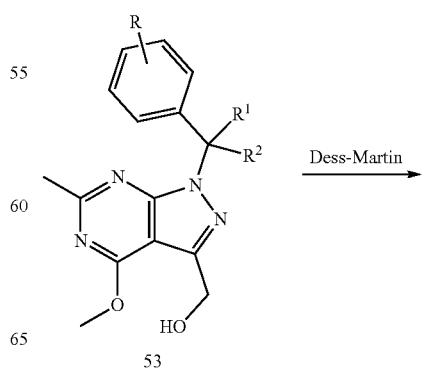

Scheme 22 illustrates a procedure for the syntheses difluoromethyl bearing pyrazolopyrimidinones such as 62, prepared from hydroxymethyl precursors such as 53. Oxidation of 53 with either manganese dioxide or Dess-Martin reagent yields the intermediate aldehyde 60 which can be treated with DAST to furnish 61. Deprotection with either sodium cyanide or hydrochloric acid furnishes the difluoromethyl pyrazolopyrimidinone 62.

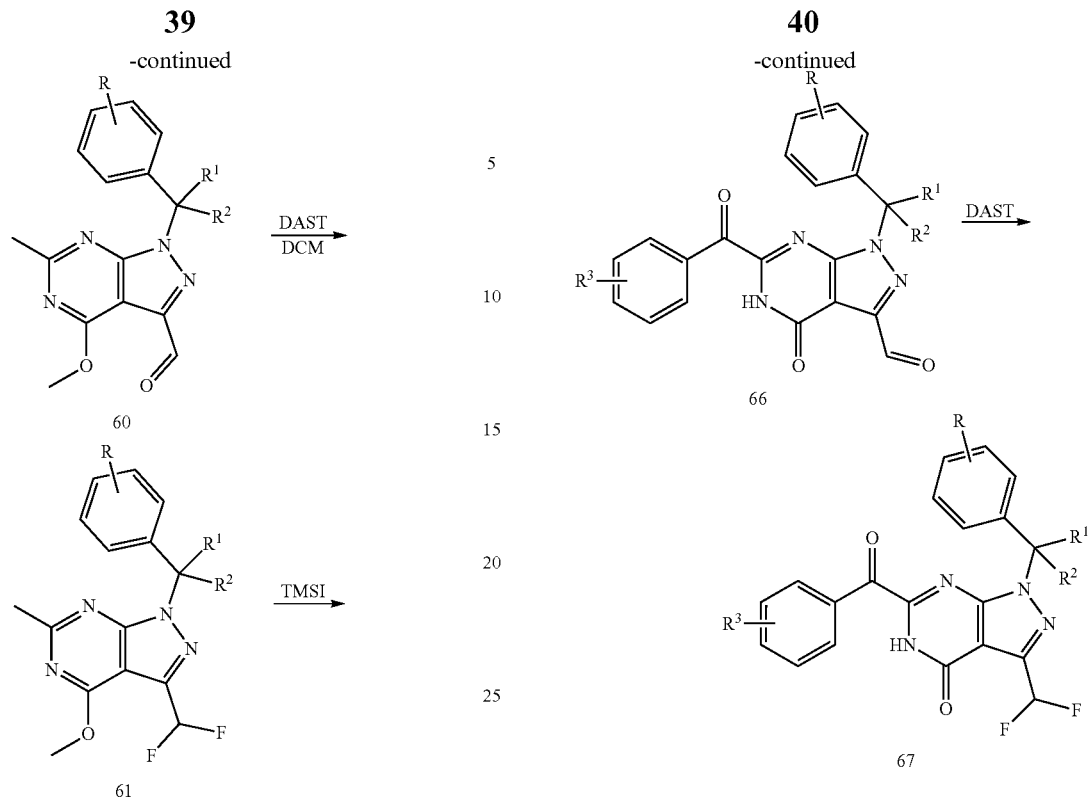

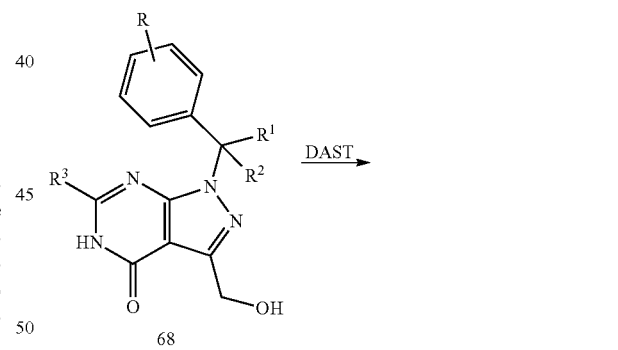

Scheme 25 illustrates a procedure for the syntheses difluoromethyl bearing pyrazolopyrimidinones such as 67, prepared from hydroxymethyl precursors such as 65. Bis-oxidation of 65 with manganese dioxide followed by treatment with DAST furnishes difluoro compound 67.

Scheme 26.

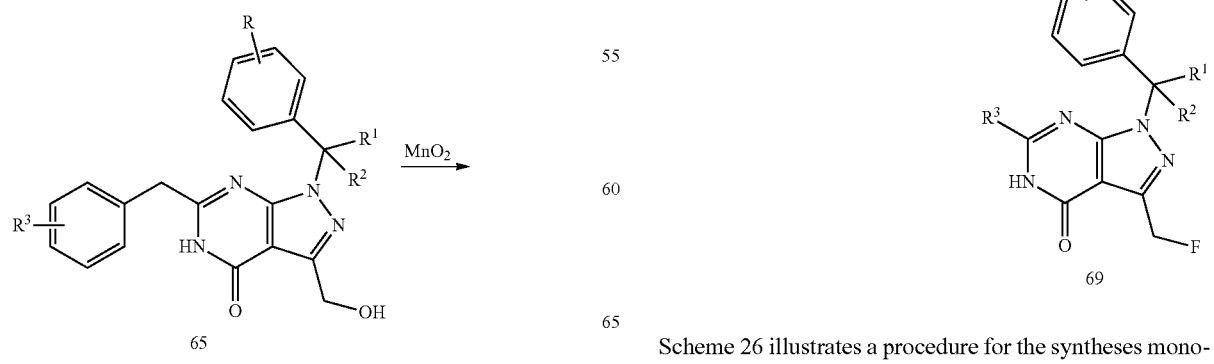

Scheme 24 illustrates a procedure for the syntheses difluoromethyl bearing pyrazolopyrimidinones such as 62 are prepared from hydroxymethyl precursors such as 53. Oxidation of 53 with Dess-Martin reagent yields the intermediate aldehyde 61 which can be treated with DAST to furnish 61. Deprotection with TMSI furnishes the difluoromethyl pyrazolopyrimidinone 62.

Scheme 25.

Scheme 26 illustrates a procedure for the syntheses monofluoro bearing pyrazolopyrimidinones such as 69 which can be prepared from hydroxymethyl pyrazolopyrimidinones such as 68 by treatment with DAST.

Scheme 27.

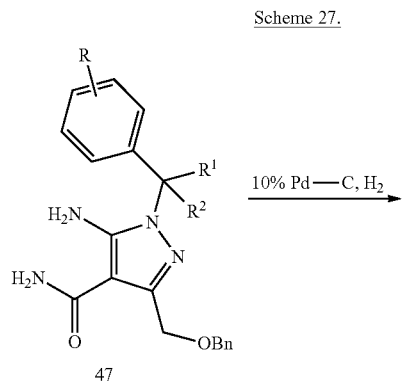

Scheme 28.

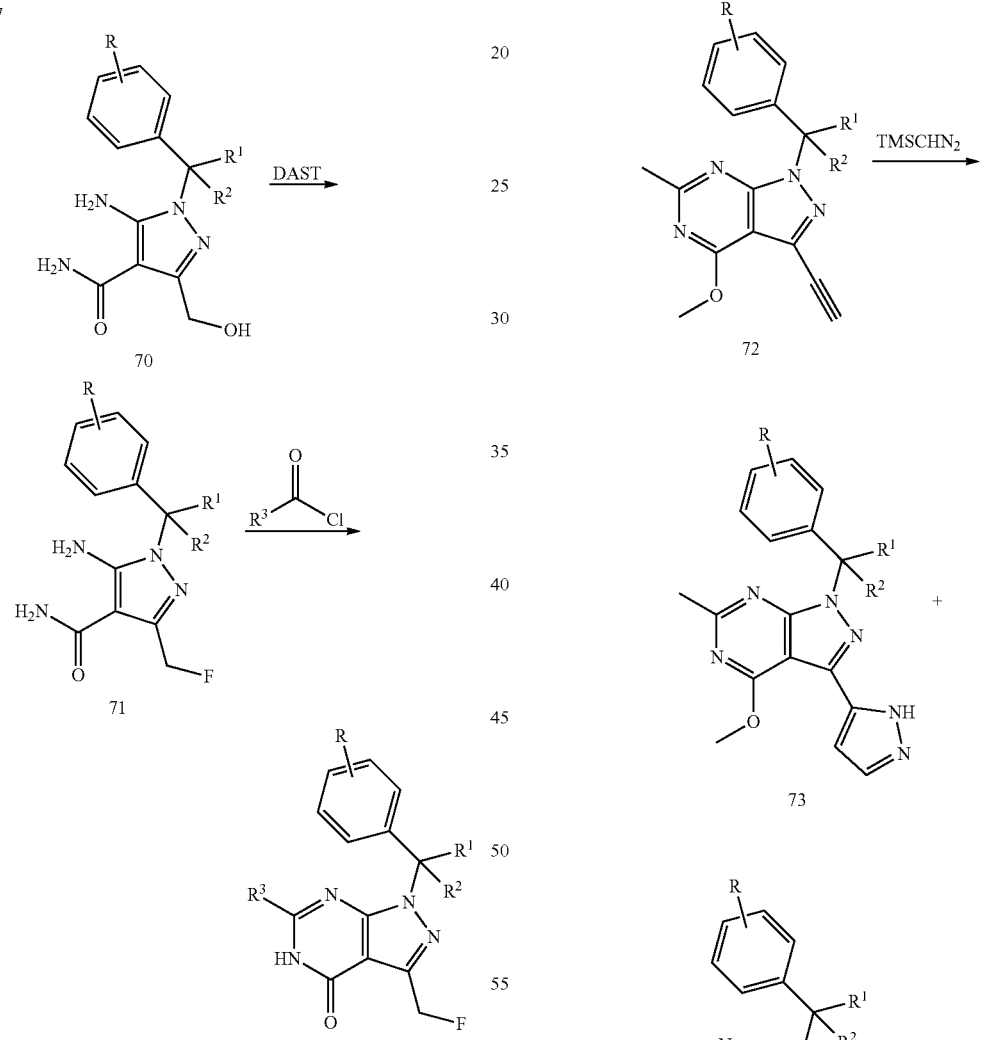

Scheme 27 illustrates a procedure for the syntheses of fluoromethyl pyrazolopyrimidinones such as 69 which can be prepared from a 5-aminopyrazole-4-carboxamide 47. Treatment under hydrogenolysis conditions followed by DAST treatment should furnish the mono fluoro adduct 71. Cyclization with acid chlorides yields the fluoromethyl pyrazolopyrimidinone 69.

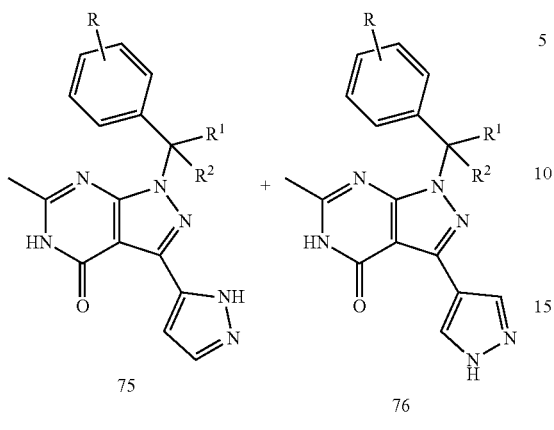

Scheme 28 illustrates a procedure for the syntheses of pyrazole bearing pyrazolopyrimidinones such as 75 and 76. Treatment of aldehyde 60 under Gilbert-Seyferth alkynylation conditions furnishes alkyne 72, which when treated with trimethylsilyl diazomethane, furnishes a separable mixture of two regioisomeric pyrazole adducts 73 and 74. Separate treatment with sodium cyanide in DMSO furnishes 75 and 76.

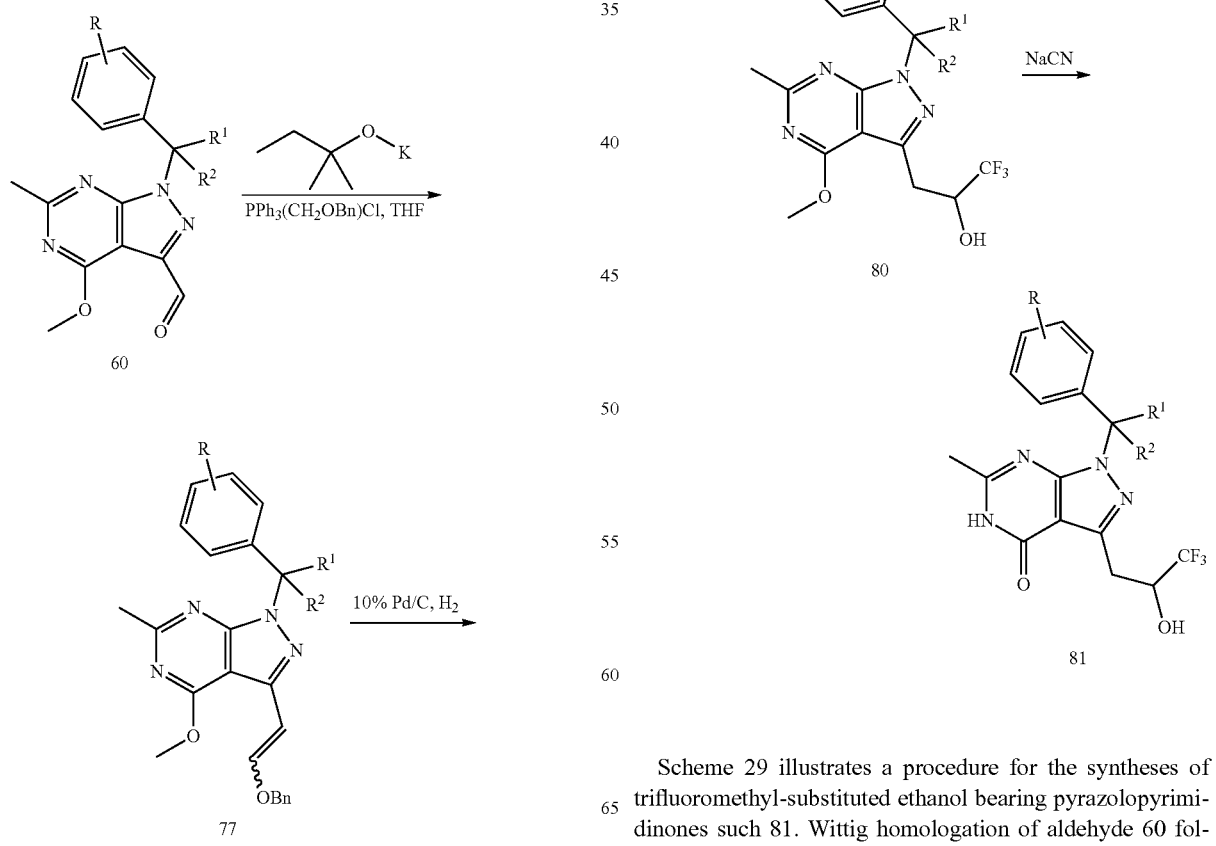

Scheme 29 illustrates a procedure for the syntheses of trifluoromethyl-substituted ethanol bearing pyrazolopyrimidinones such 81. Wittig homologation of aldehyde 60 followed by hydrogenolysis using 10% Pd/C in the presence of H₂ furnishes alcohol 78. Treatment with IBX followed by fluoride-promoted CF₃ addition and deprotection using sodium cyanide affords 81.

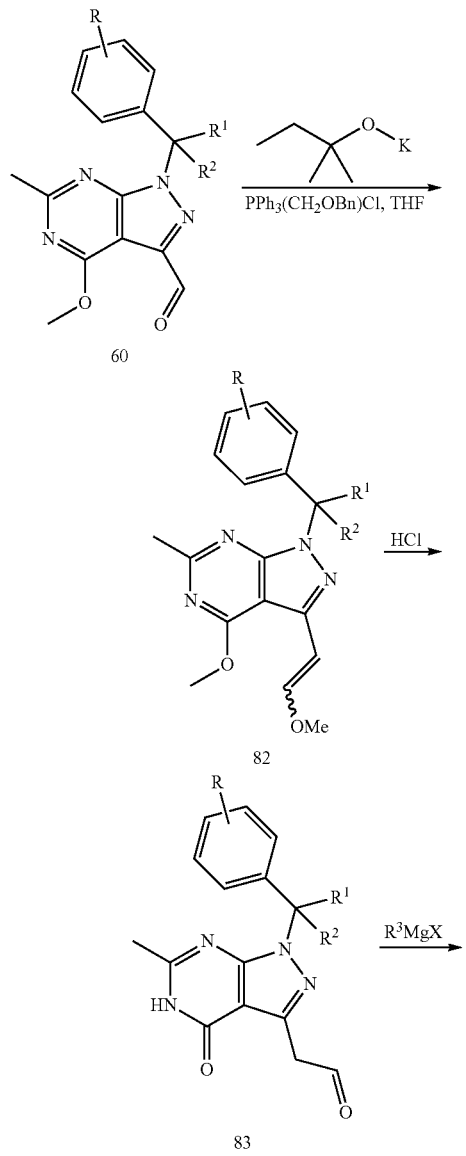

Scheme 30 illustrates a procedure for the syntheses of substituted-ethanol bearing pyrazolopyrimidinones such 84. Wittig homologation of aldehyde 60 followed by hydrolysis with 3M HCl furnishes aldehyde 83. Treatment with a Grignard reagent can afford alcohol 84.

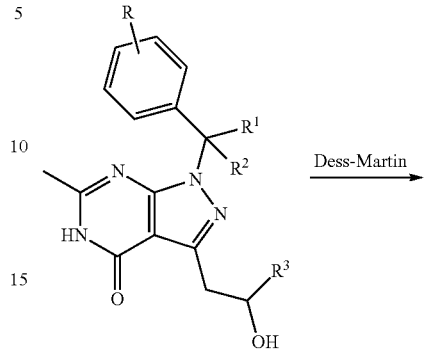

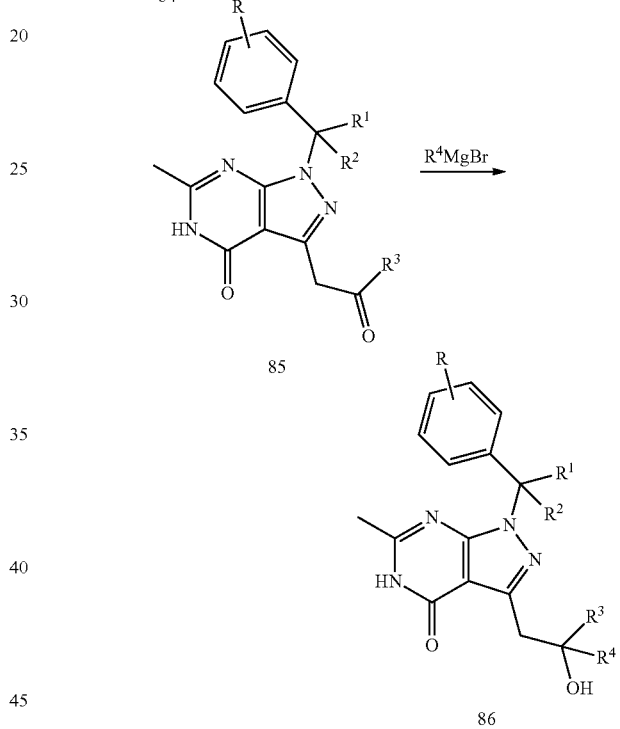

Scheme 31 illustrates a procedure for the syntheses of substituted alcohol bearing pyrazolopyrimidinones such 86. Oxidation of secondary alcohol 84 using Dess-Martin reagent followed by Grignard addition to the intermediate aldehyde 85 furnishes tertiary alcohol 86.

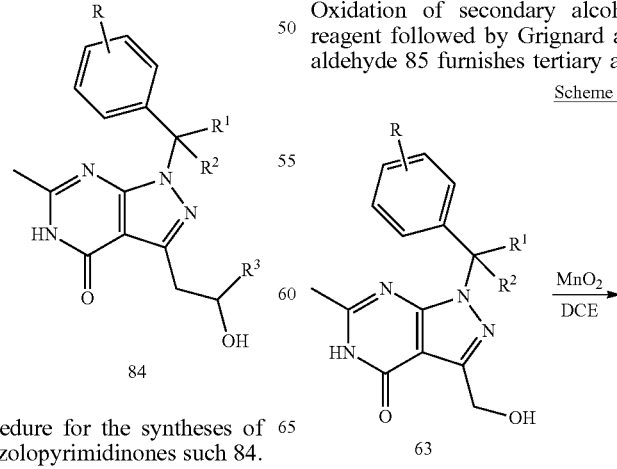

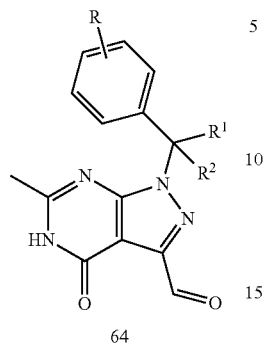

Scheme 32 illustrates a procedure for the syntheses of pyrazolopyrimidinones bearing carboxaldehydes such as 64 by manganese dioxide oxidation of alcohol 64.

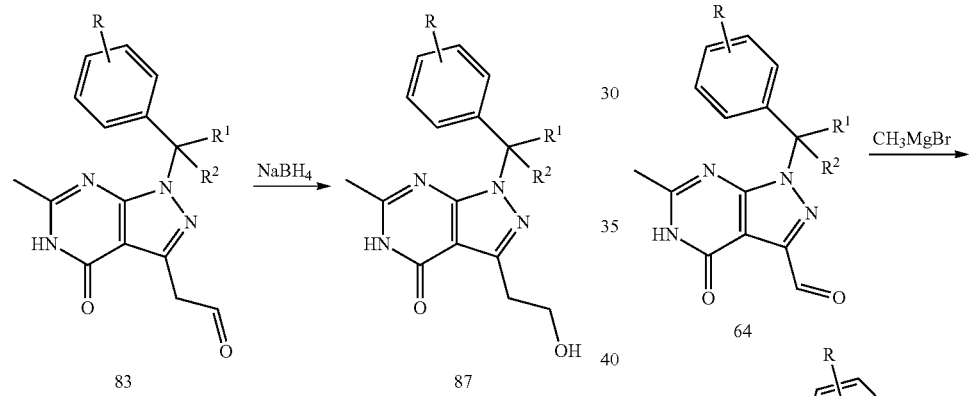

Scheme 33 illustrates a procedure for the syntheses of pyrazolopyrimidinones bearing ethanol substitution by reduction of aldehyde 83 with sodium borohydride to furnish 87.

Scheme 34.

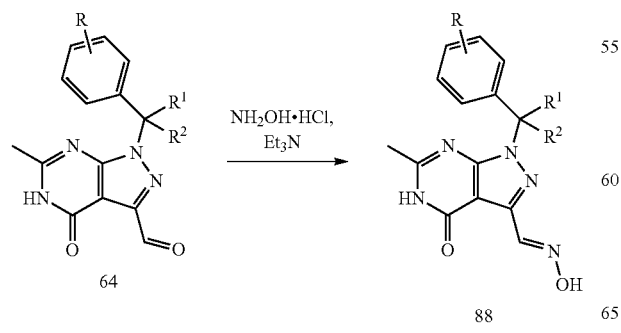

Scheme 34 illustrates procedures for the syntheses of pyrazolopyrimidinones bearing either oxime or cyano functionality by treatment of aldehyde 64 with hydroxylamine hydrochloride and base with or without 2,4,6-Tripropyl-1,3,5,2,4,6-trioxatriphosphinane 2,4,6-trioxide T3P to afford oxime 88 or nitrile 89.

Scheme 35.

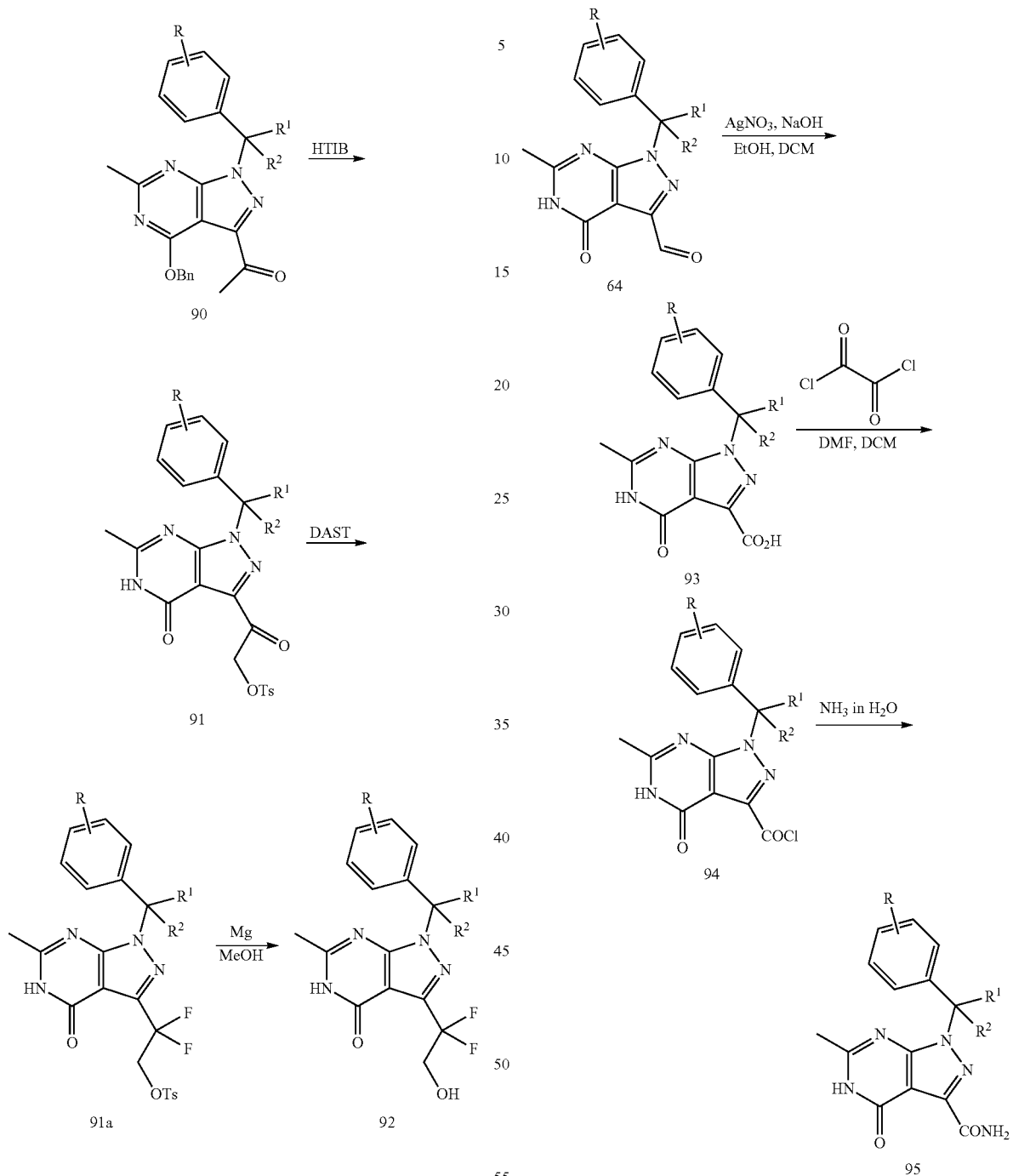

Scheme 35 illustrates a procedure for the syntheses of pyrazolopyrimidinones bearing a difluoroethanol moiety such as found in 92 from aldehyde 64. Grignard addition to aldehyde 64 followed by Dess-Martin oxidation should furnish ketone 89. Treatment with silver carbonate and benzyl bromide should yield the benzyl-protected adduct 90 coupled, and exposure to hydroxy(tosyloxy)iodobenzene should yield tosylate 91. Exposure of 91 to DAST will furnish difluoro adduct 91a followed by treatment with magnesium metal in the presence of MeOH to afford alcohol 92.

Scheme 36 illustrates procedures for the syntheses of pyrazolopyrimidinones bearing a primary amide moiety such as in 95 from aldehyde 64. Oxidation of aldehyde 64 can be accomplished with silver nitrate to yield acid 93 which can be converted to acid chloride 94 using oxalyl chloride with catalytic DMF. Treatment of 94 with ammonia in water will afford amide 95.

Scheme 37.

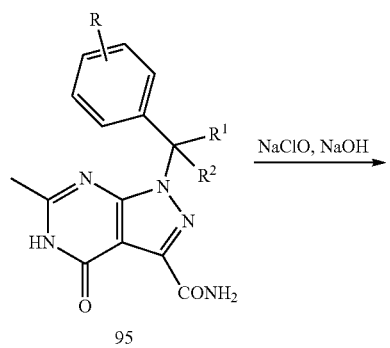

Scheme 37 illustrates a procedure for the syntheses of pyrazolopyrimidinones bearing an amino group by treatment of amide 95 with sodium hypochlorite in the presence of base to furnish amine 96.

Scheme 38.

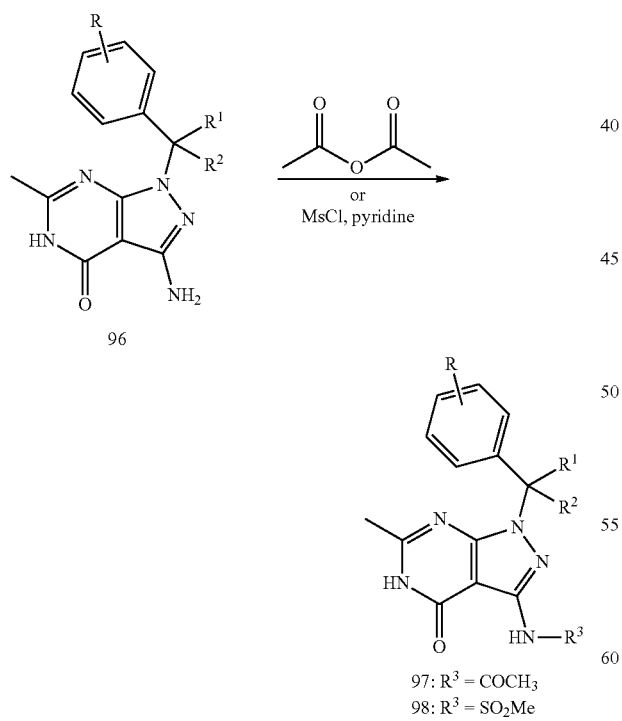

97: R³ = COCH₃
98: R³ = SO₂Me

Scheme 38 illustrates procedures for the syntheses of pyrazolopyrimidinones bearing either a N-acetyl group or N-sulfonamide. Treatment of amine 96 with acetic anhydride furnishes 97 while mesyl chloride in the presence of triethylamine affords sulfonamide 98.

Scheme 39.

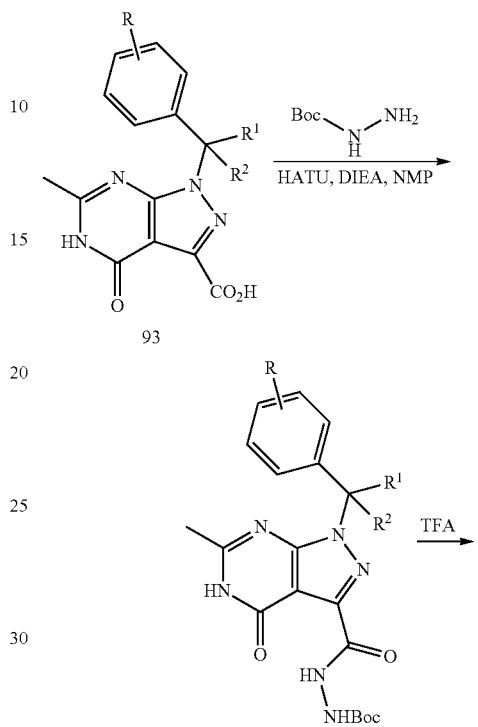

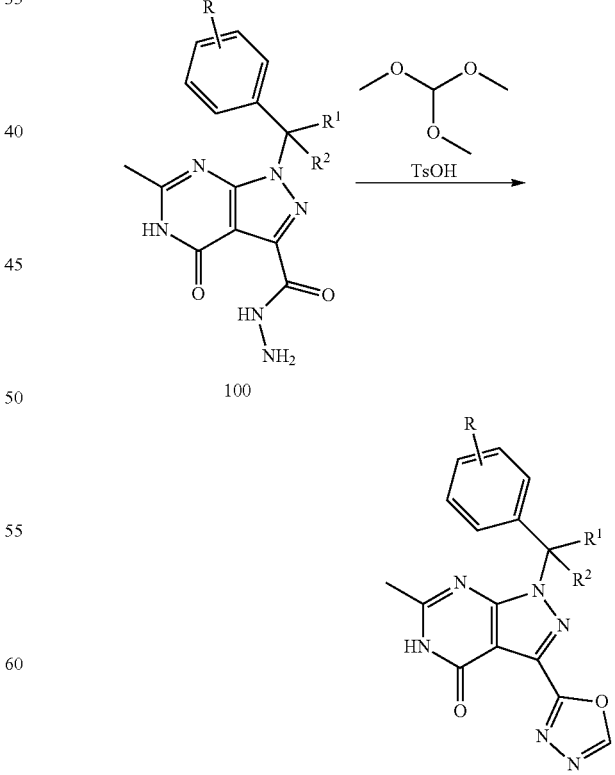

Scheme 39 illustrates procedures for the syntheses of oxadiazole-substituted pyrazolopyrimidinone derivatives such as 101 from acid precursors such as 93. HATU-mediated coupling of acid 93 with tert-butyl hydrazinecarboxylate furnishes 99 which can be treated with TFA to afford hydrazide 100. Cyclization of hydrazide 100 with trimethyl orthoformate in the presence of acid furnishes oxadiazole 101.

Scheme 40.

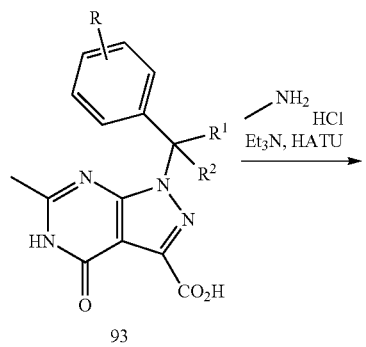

93

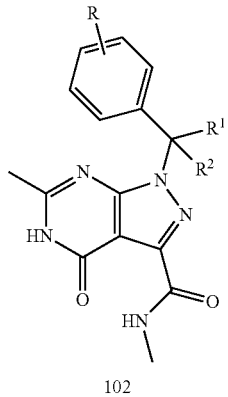

102

Scheme 40 illustrates procedures for the syntheses of pyrazolopyrimidones bearing an amide by treatment of acid 93 with an amine hydrochloride, base, and coupling agent such as HATU to furnish 102.

Scheme 41.

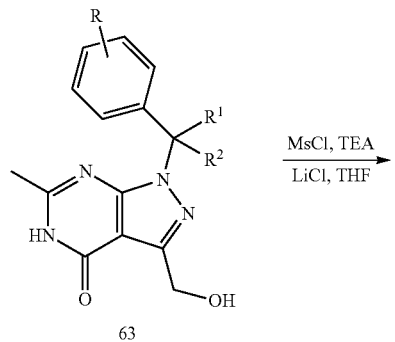

63

-continued

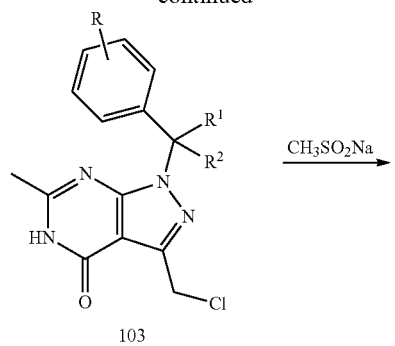

103

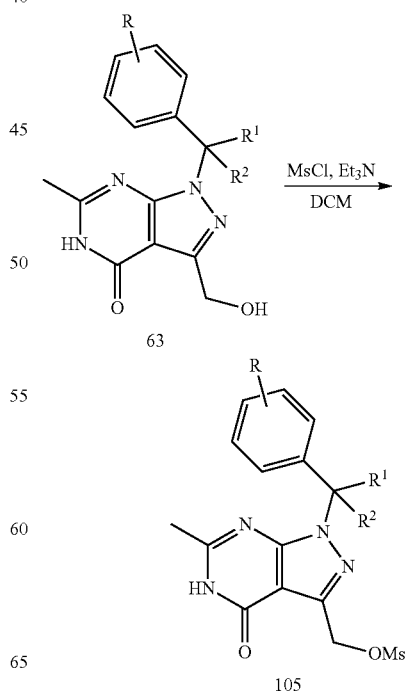

104

Scheme 41 illustrates procedures for the syntheses of pyrazolopyrimidinones bearing a methyl sulfone moiety. Treatment of alcohol 63 with mesyl chloride with base in the presence of lithium chloride can afford primary chloride 103. Exposure of 103 to sodium methanesulfinate furnishes methyl sulfone derivative 104.

Scheme 42.

63

105

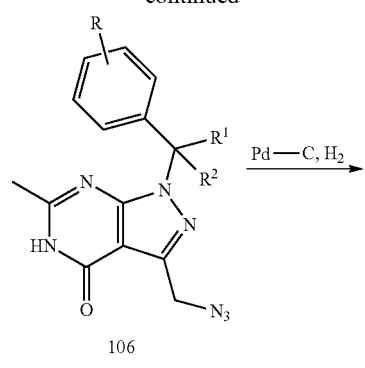

106

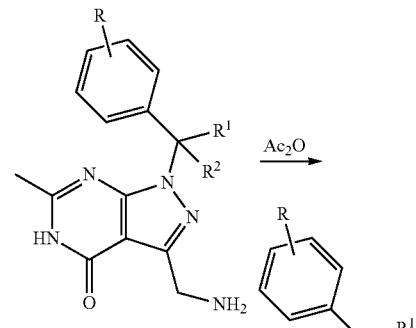

107

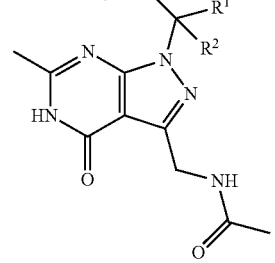

108

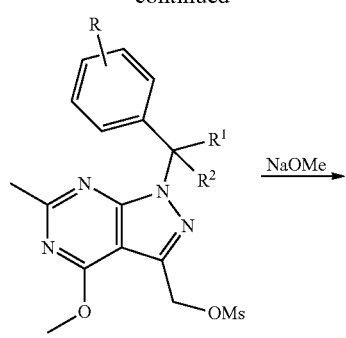

109

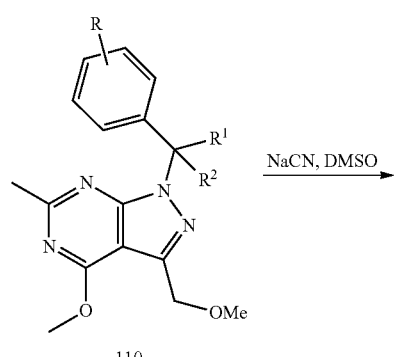

110

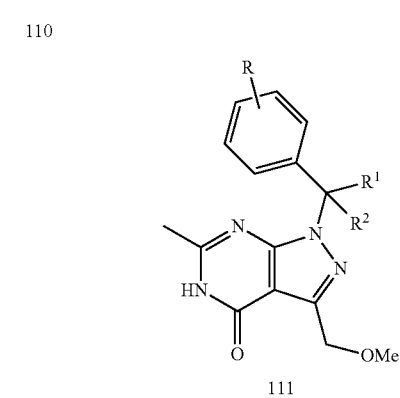

111

Scheme 42 illustrates procedures for the syntheses of methylamine-based pyrazolopyrimidinone derivatives from methanol precursors such as 63. Treatment of alcohol 63 with mesyl chloride followed by exposure to sodium azide can afford primary azide 106. Hydrogenolysis with 10% palladium on carbon in the presence of hydrogen can yield amine 107 which can be treated with acetic anhydride to furnish acetate 108.

Scheme 43 illustrates procedures for the syntheses of methoxymethyl pyrazolopyrimidinone derivatives such as 111 from methanol precursors such as 53. Treatment of alcohol 64 with mesyl chloride in the presence of base should afford mesylate 109 which can be treated with sodium methoxide to furnish methoxy intermediate 110. Treatment with sodium cyanide furnishes 111.

Scheme 43.

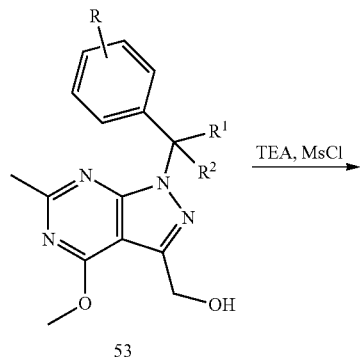

53

Scheme 44.

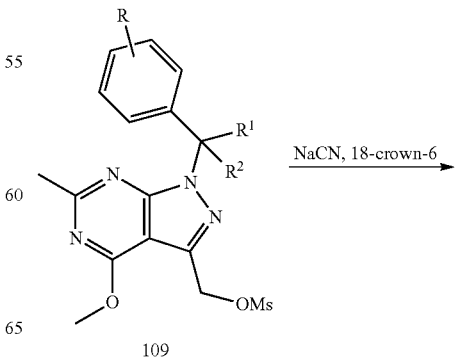

109

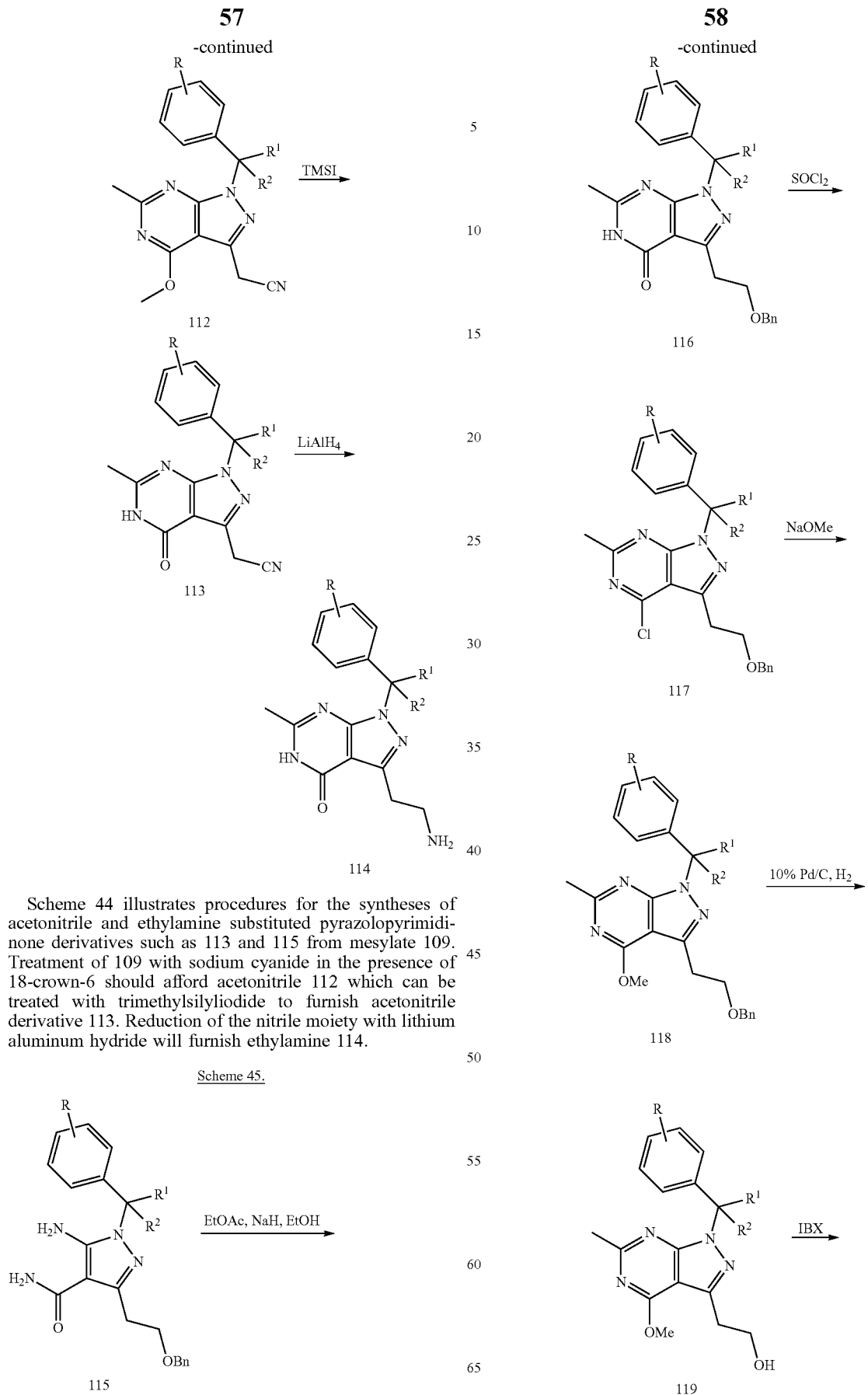

Scheme 44 illustrates procedures for the syntheses of acetonitrile and ethylamine substituted pyrazolopyrimidinone derivatives such as 113 and 115 from mesylate 109. Treatment of 109 with sodium cyanide in the presence of 18-crown-6 should afford acetonitrile 112 which can be treated with trimethylsilyliodide to furnish acetonitrile derivative 113. Reduction of the nitrile moiety with lithium aluminum hydride will furnish ethylamine 114.

Scheme 45.

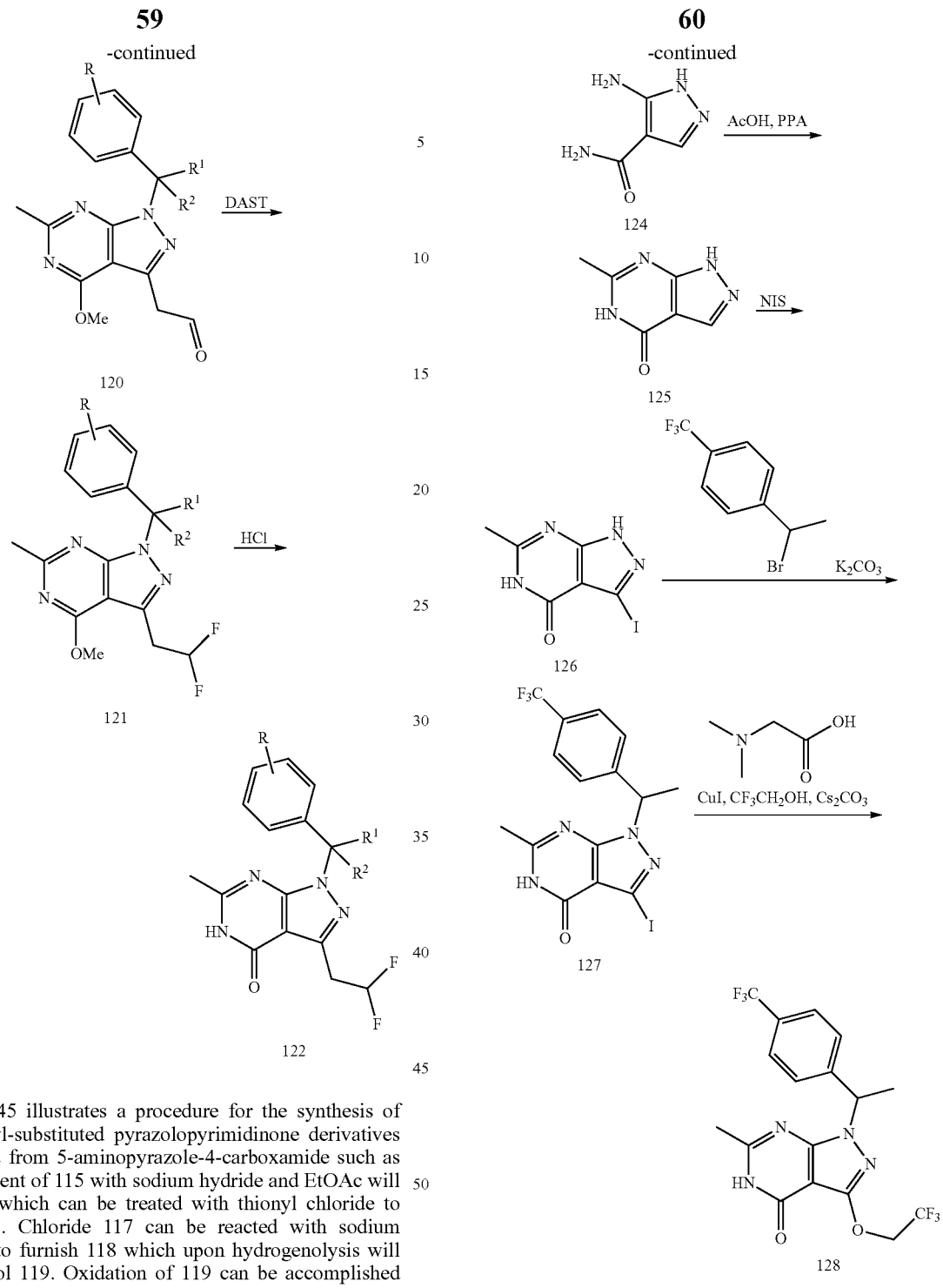

Scheme 45 illustrates a procedure for the synthesis of difluoroethyl-substituted pyrazolopyrimidinone derivatives such as 122 from 5-aminopyrazole-4-carboxamide such as 115. Treatment of 115 with sodium hydride and EtOAc will afford 116 which can be treated with thionyl chloride to furnish 117. Chloride 117 can be reacted with sodium methoxide to furnish 118 which upon hydrogenolysis will yield ethanol 119. Oxidation of 119 can be accomplished with IBX followed by DAST treatment to furnish 121, which can be treated with hydrochloric acid to afford difluoro adduct 122.

Scheme 46.

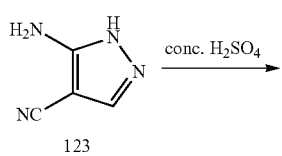

123

Scheme 46 illustrates a procedure for the synthesis of O-linked trifluoroethanol derivatives such as 128 from amino nitrile precursors such as 123. Treatment of 123 with sulfuric acid will afford from 5-aminopyrazole-4-carboxamide 124 which can be cyclized with polyphosphoric acid in acetic acid to yield 125. Iodination can be accomplished with NIS to afford 126 which can be treated with a secondary bromide in the presence of potassium carbonate to furnish 127. Iodide 127 can be coupled with trifluoroethanol in the presence of a copper salt to furnish trifluoroethanol ether 128.

Scheme 47.

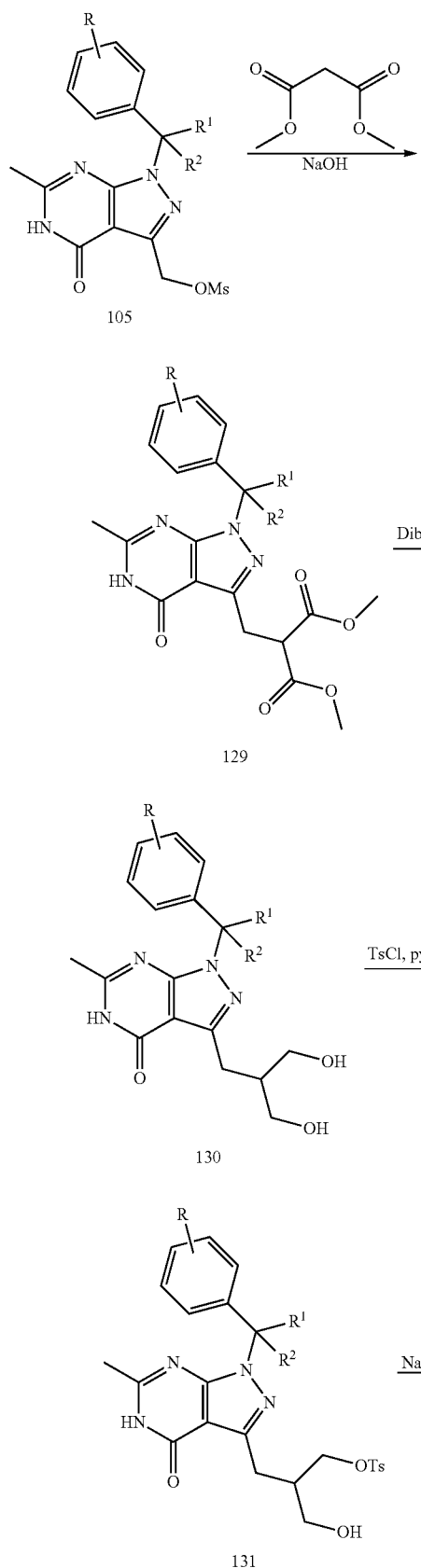

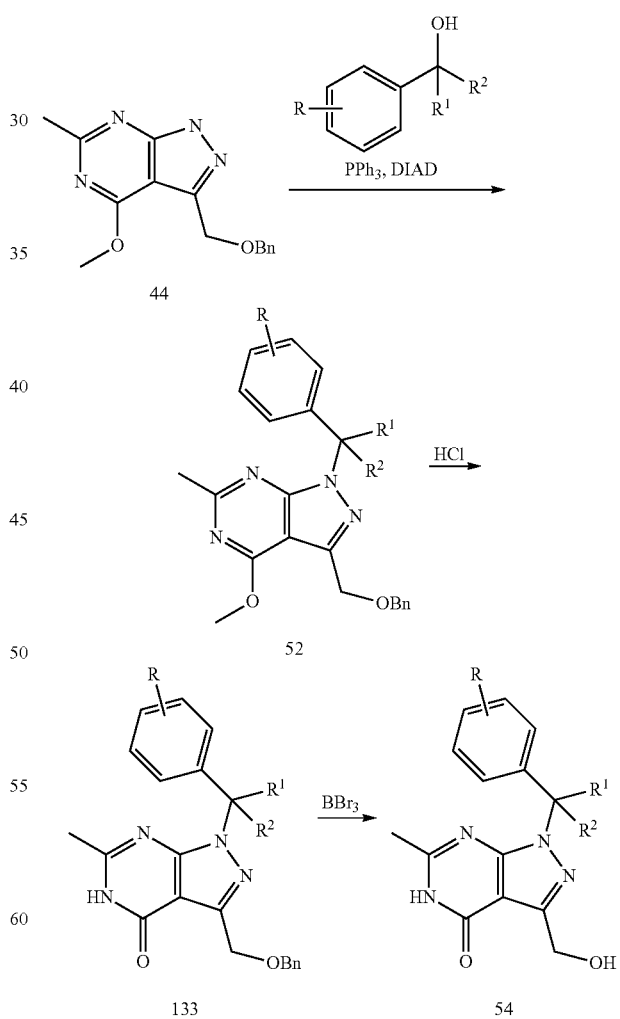

Scheme 47 illustrates a procedure for the synthesis of oxetanemethyl pyrazolopyrimidinone derivatives such as 132 from mesylate precursors such as 105. Treatment of 105 with dimethylmalonate in the presence of sodium hydroxide will afford 129 which can be treated with diisobutylaluminum hydride to furnish diol 130. Selective tosylate installation on 130 will yield 131 which can be treated with sodium hydride to furnish oxetane 132.

Scheme 48.

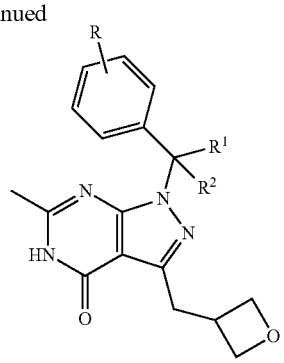

Scheme 48 illustrates procedures for the syntheses of hydroxymethyl substituted pyrazolopyrimidinone derivatives such as 54. Mitsunobu coupling of 44 with a secondary alcohol will afford 52 which can be treated with hydrochloric acid to furnish 133. Deprotection can be achieved by treatment with boron tribromide to afford alcohol 54.

tives such as 136. Acylation of 47 with acetyl chloride will afford 134 which can be treated under hydrogenolyis conditions to afford alcohol 135. Cyclization with acetyl chloride furnishes acetate 136.

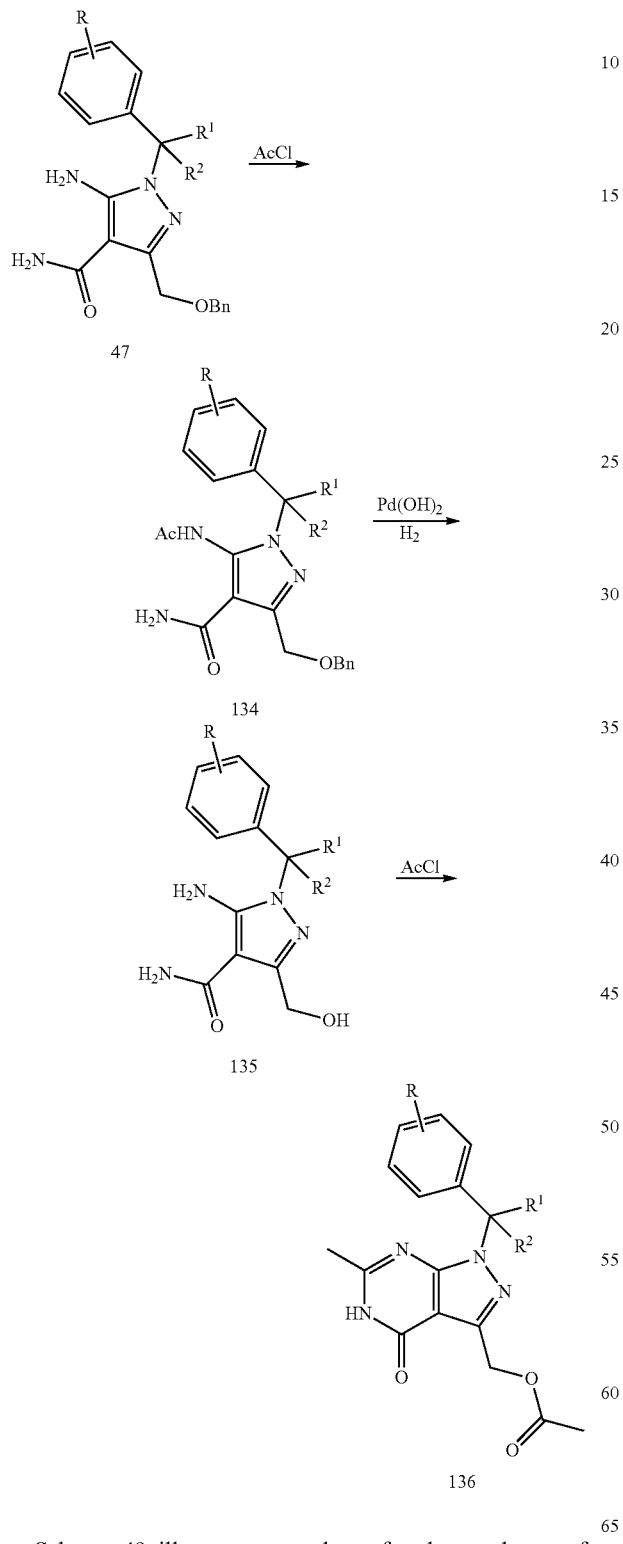

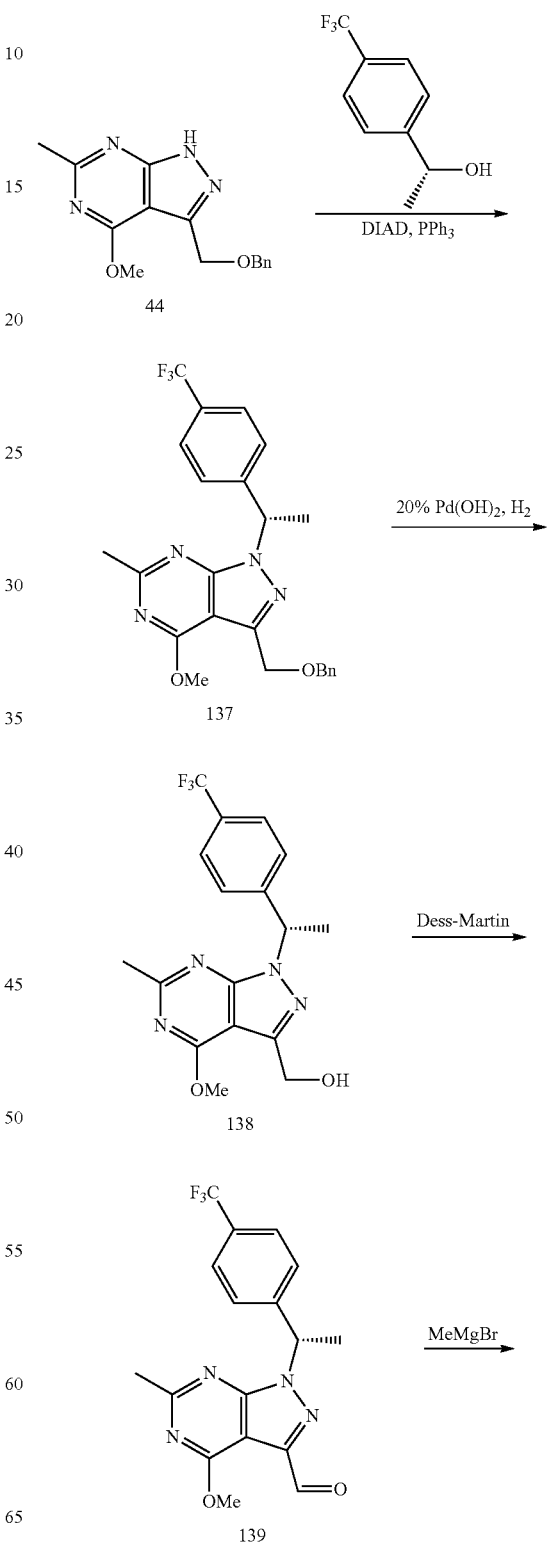

Scheme 49 illustrates procedures for the syntheses of acetoxymethyl substituted pyrazolopyrimidinone deriva-

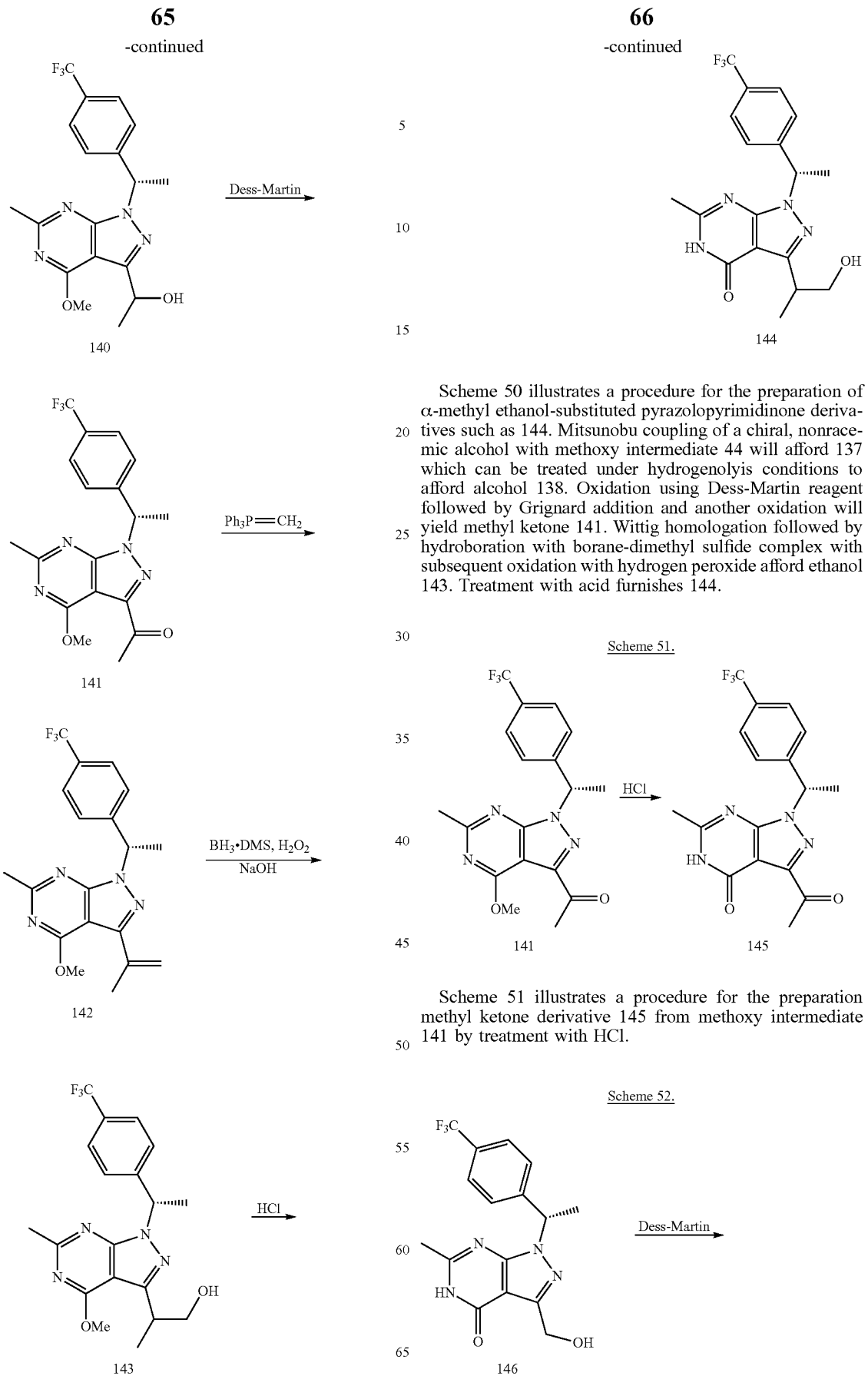

Scheme 50 illustrates a procedure for the preparation of α-methyl ethanol-substituted pyrazolopyrimidinone derivatives such as 144. Mitsunobu coupling of a chiral, nonracemic alcohol with methoxy intermediate 44 will afford 137 which can be treated under hydrogenolyis conditions to afford alcohol 138. Oxidation using Dess-Martin reagent followed by Grignard addition and another oxidation will yield methyl ketone 141. Wittig homologation followed by hydroboration with borane-dimethyl sulfide complex with subsequent oxidation with hydrogen peroxide afford ethanol 143. Treatment with acid furnishes 144.

Scheme 51.

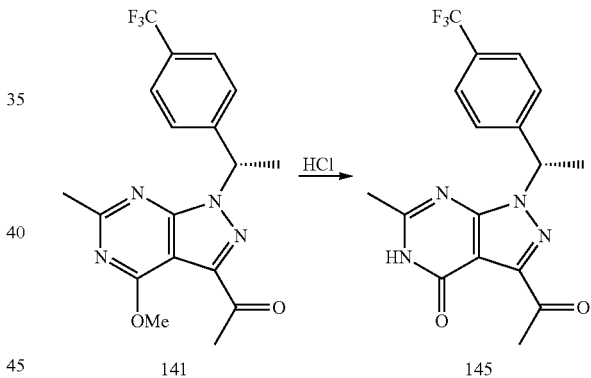

Scheme 51 illustrates a procedure for the preparation methyl ketone derivative 145 from methoxy intermediate 141 by treatment with HCl.

Scheme 52.

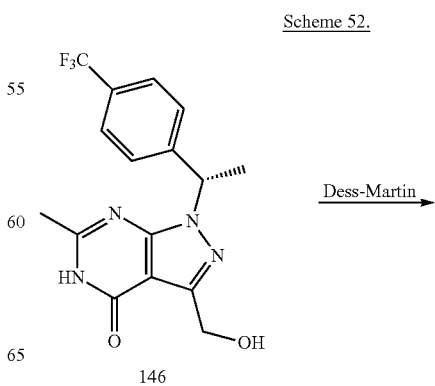

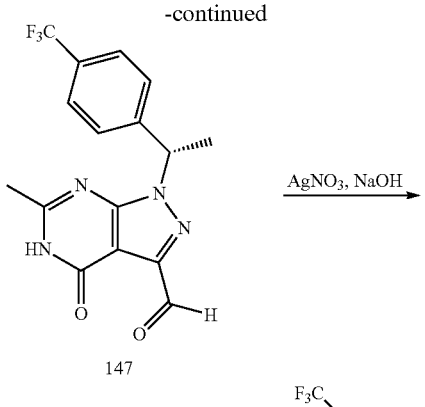

147

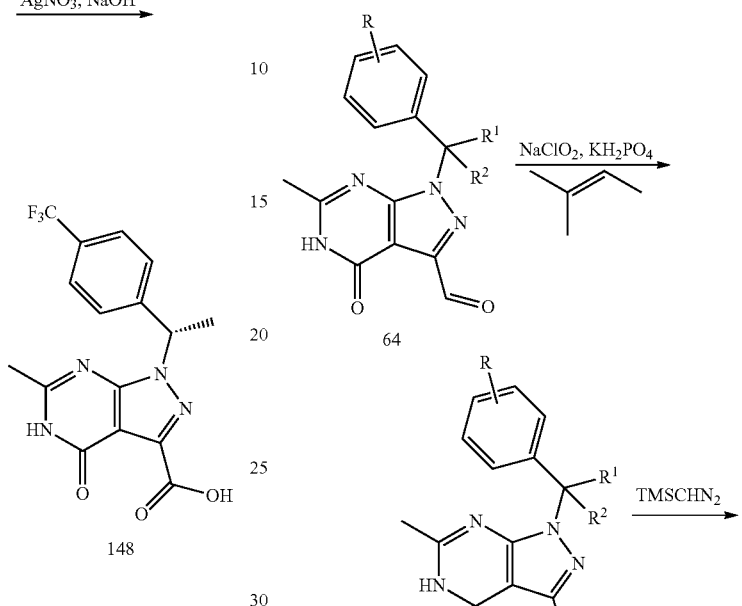

Scheme 52 illustrates a procedure for the chiral acid derivative 148 from an alcohol precursor. Treatment of alcohol 146 under Dess-Martin conditions can furnish the intermediate aldehyde 147 which can be further oxidized with silver nitrate in the presence of base to afford acid 148.

Scheme 53 illustrates a procedure for the bromo derivative 150 from a pyrazole precursor 149. Treatment of 149 with the secondary bromide under basic conditions furnishes 150.

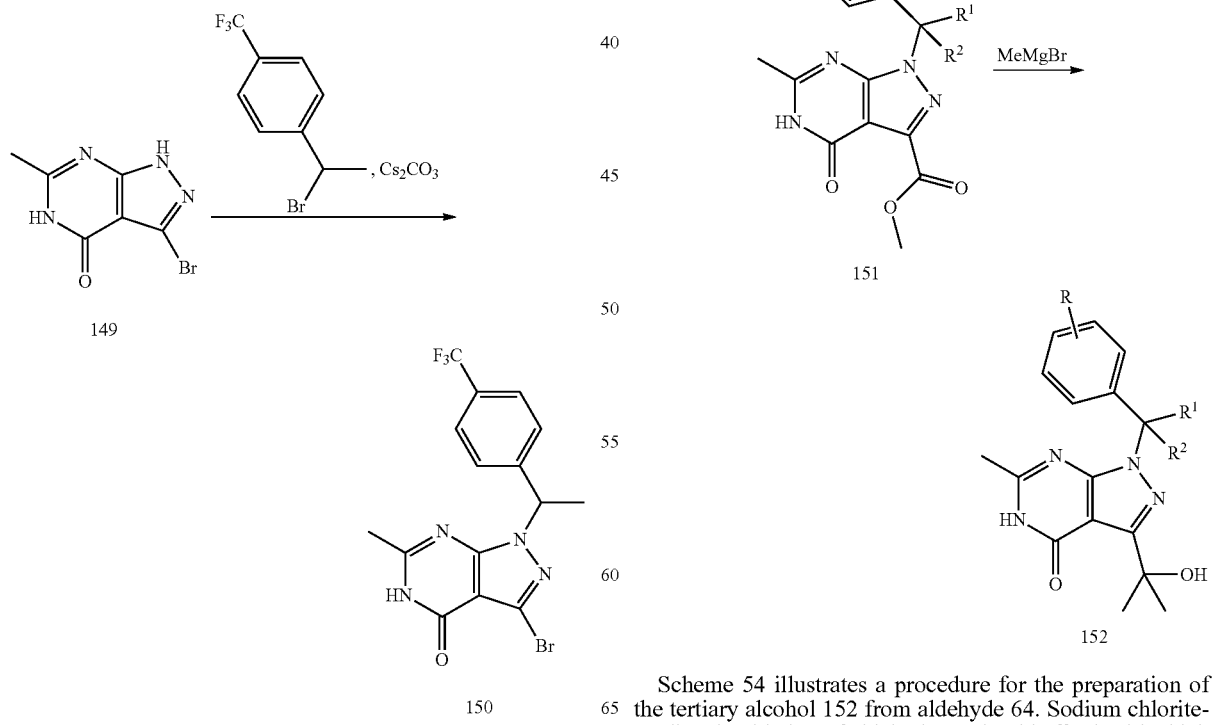

Scheme 54 illustrates a procedure for the preparation of the tertiary alcohol 152 from aldehyde 64. Sodium chlorite-mediated oxidation of aldehyde 64 should afford acid which upon treatment with trimethylsilyldiazomethane will furnish methyl ester 151. Treatment of 151 with excess methylmagnesium bromide furnishes tertiary alcohol 152.

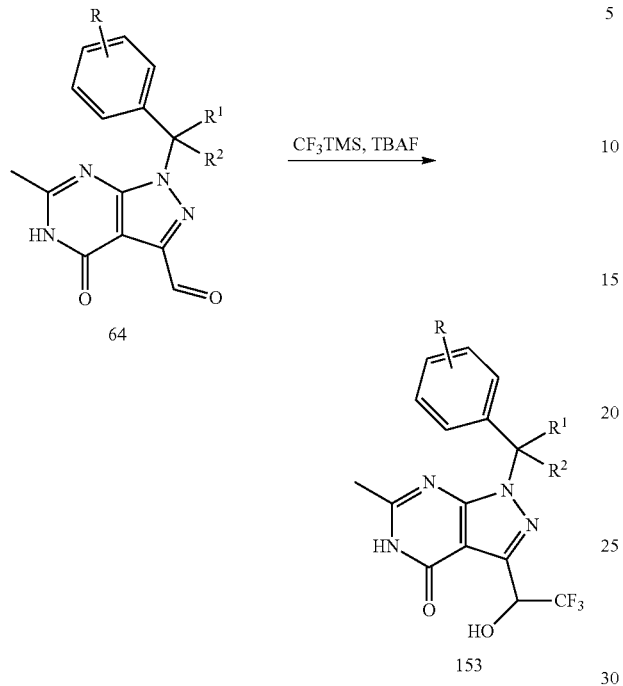

Scheme 55 illustrates a procedure for the preparation of the trifluoromethyl-substituted secondary alcohol derivative 153 from aldehyde 64. Reaction of aldehyde 64 with trifluoromethyltrimethyl silane in the presence of TBAF should afford alcohol 153.

Scheme 56 illustrates a procedure for the preparation of the hydroxy-substituted pyrazolopyrimidinone derivatives such as 155 from ketone 141. Baeyer-Villager oxidation of 141 with MCPBA in the presence of trifluoroacetic acid will furnish acetate 154 which can be subjected to hydrochloric acid to afford pyrazolopyrimidinone 155.

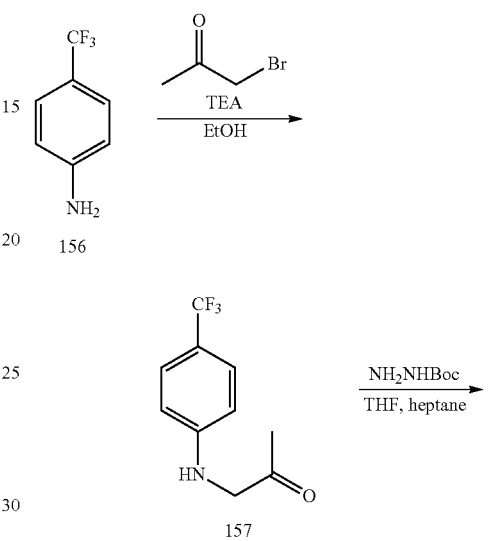

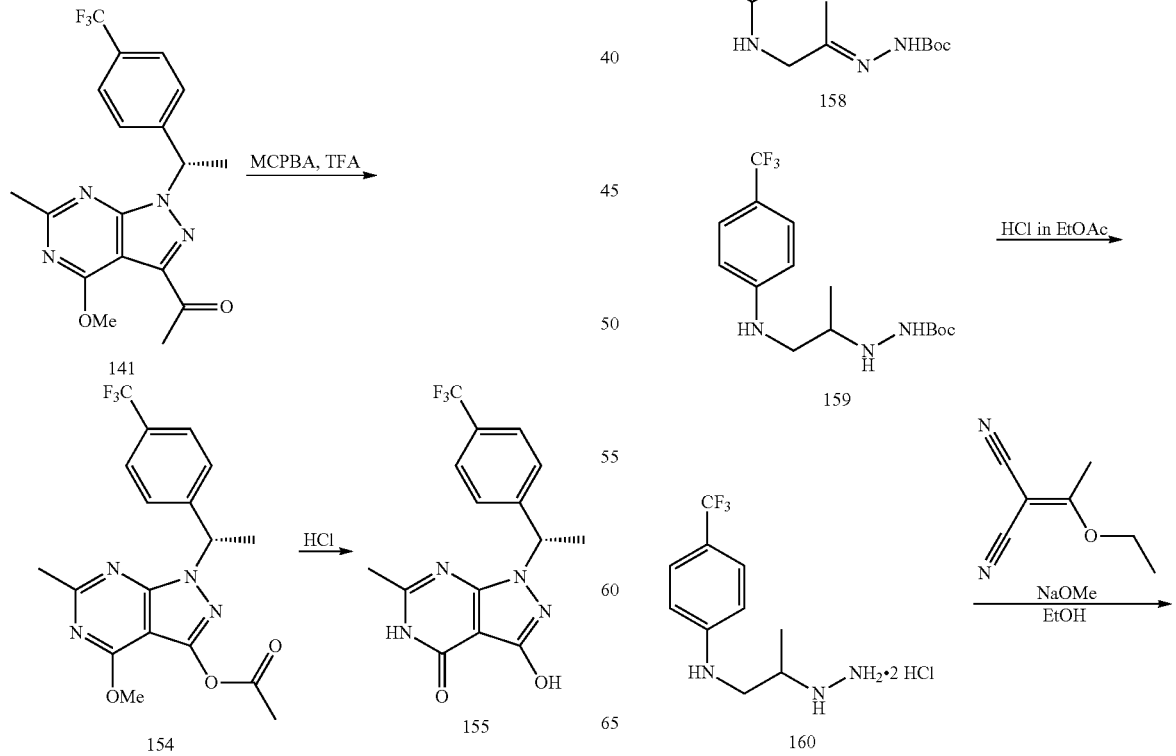

-continued

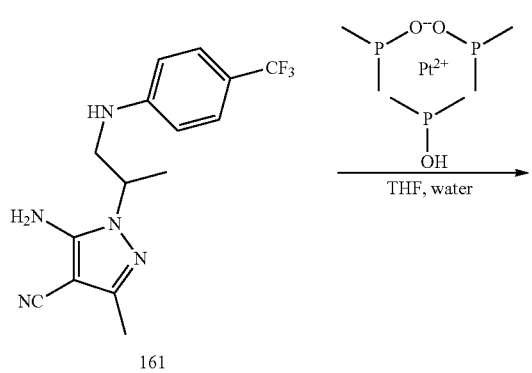

161

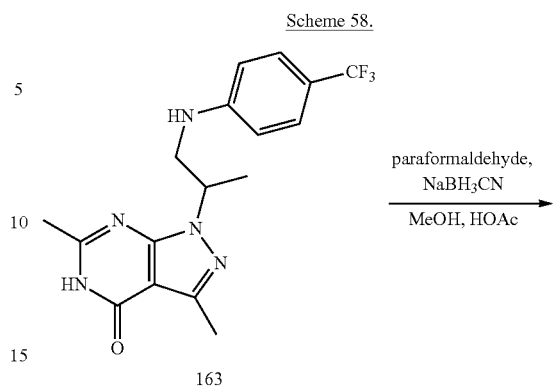

Scheme 58.

163 paraformaldehyde,
NaBH₃CN
──────────────→
MeOH, HOAc

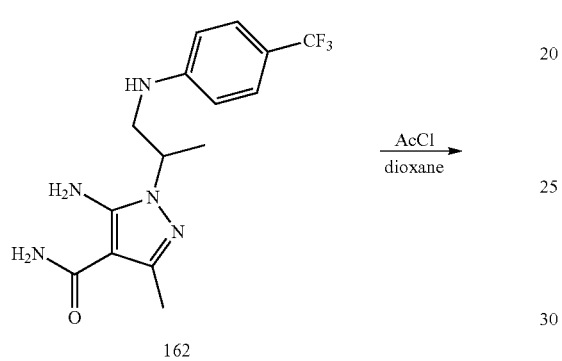

162

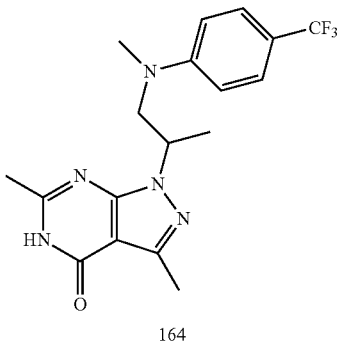

164

Scheme 58 illustrates a procedure for the preparation of an N-methyl pyrazolopyrimidinone derivative 164 from the corresponding amino precursor 163 by reaction with paraformaldehyde in the presence of sodium cyanoborohydride.

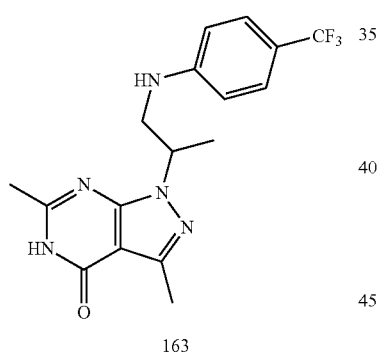

163

Scheme 59.

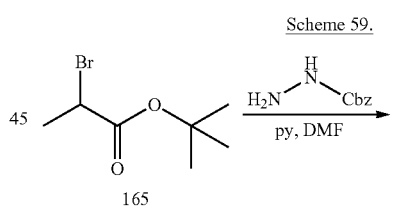

165

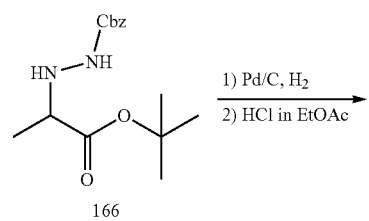

166

1) Pd/C, H₂
2) HCl in EtOAc

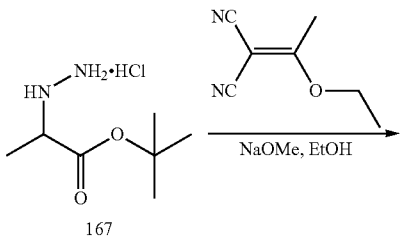

167

NaOMe, EtOH

Scheme 57 illustrates a procedure for the preparation of the ethyl amino-substituted pyrazolopyrimidinone derivatives such as 163 from aniline 156. N-alkylation of aniline 156 under basic conditions will afford 157 which can be condensed with tert-butyl hydrazine carboxylate to furnish hydrazone 158. Treatment of 158 with sodium cyanoborohydride under acidic conditions will yield protected hydrazine 159 which can be treated with hydrochloric acid to furnish 160 as the dihydrochloride salt. Cyclization of 160 with a substituted alkylidene under basic conditions will afford 161 which upon subjection to platinum-mediated reduction will furnish 5-aminopyrazole-4-carboxamide 162. Treatment of 162 with acetyl chloride will furnish pyrazolopyrimidinone 163.

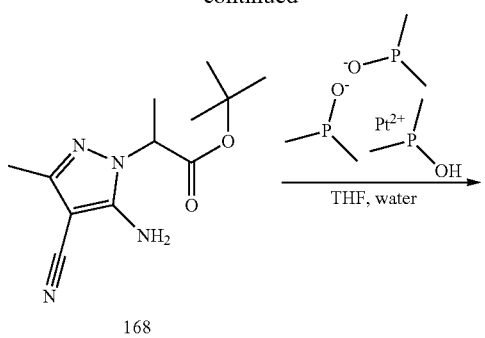

168

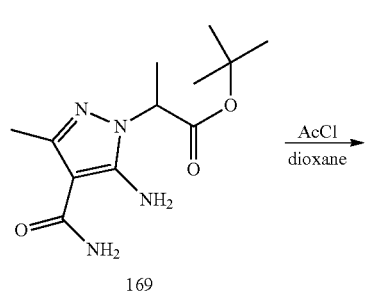

169

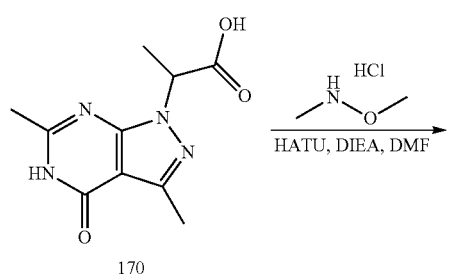

170

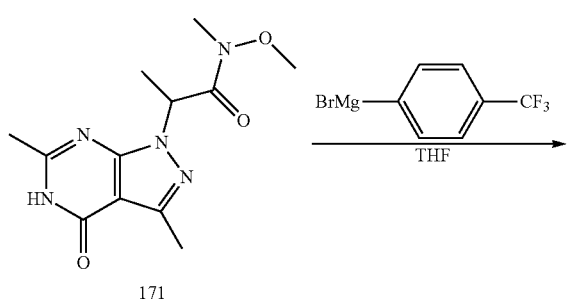

171

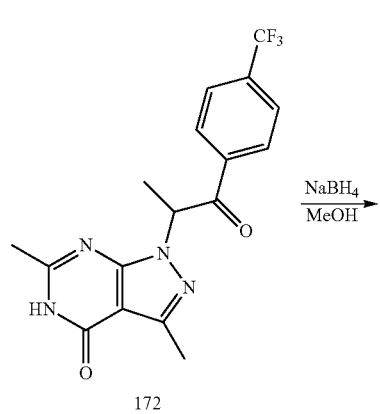

172

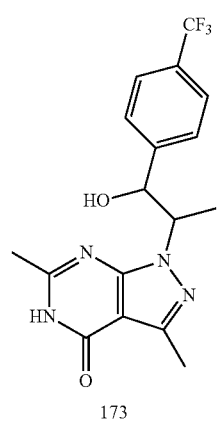

173

Scheme 59 illustrates a procedure for the preparation of the ethyl alcohol-substituted pyrazolopyrimidinone derivatives such as 173 from bromoester 165. N-alkylation of 165 followed by hydrogenolysis and acid treatment will afford 167. Cyclization of 167 with a substituted alkylidene under basic conditions will afford 168 which can be subjected to platinum-mediated reduction to furnish 5-aminopyrazole-4-carboxamide 169. Cyclization with acetyl chloride with t-butyl ester deprotection will yield 170 which can be converted to the Weinreb amide 171. Aryl Grignard addition to 171 will afford 172 which can be treated with sodium borohydride to furnish pyrazolopyrimidinone 173.

Scheme 60.

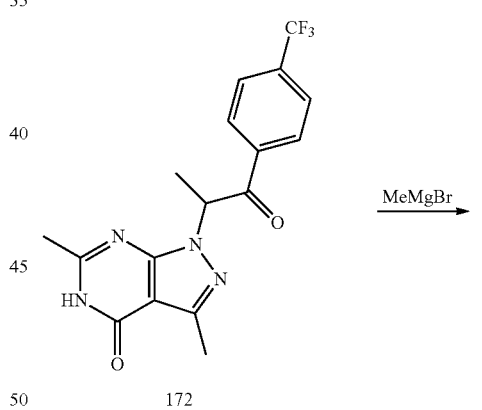

172

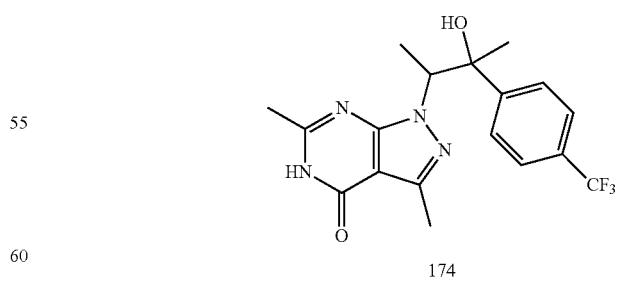

174

Scheme 60 illustrates a procedure for the preparation of a tertiary alcohol substituted pyrazolopyrimidinone derivative 174 from the corresponding ketone precursor 172 by reaction with methyl magnesium bromide.

Scheme 61.

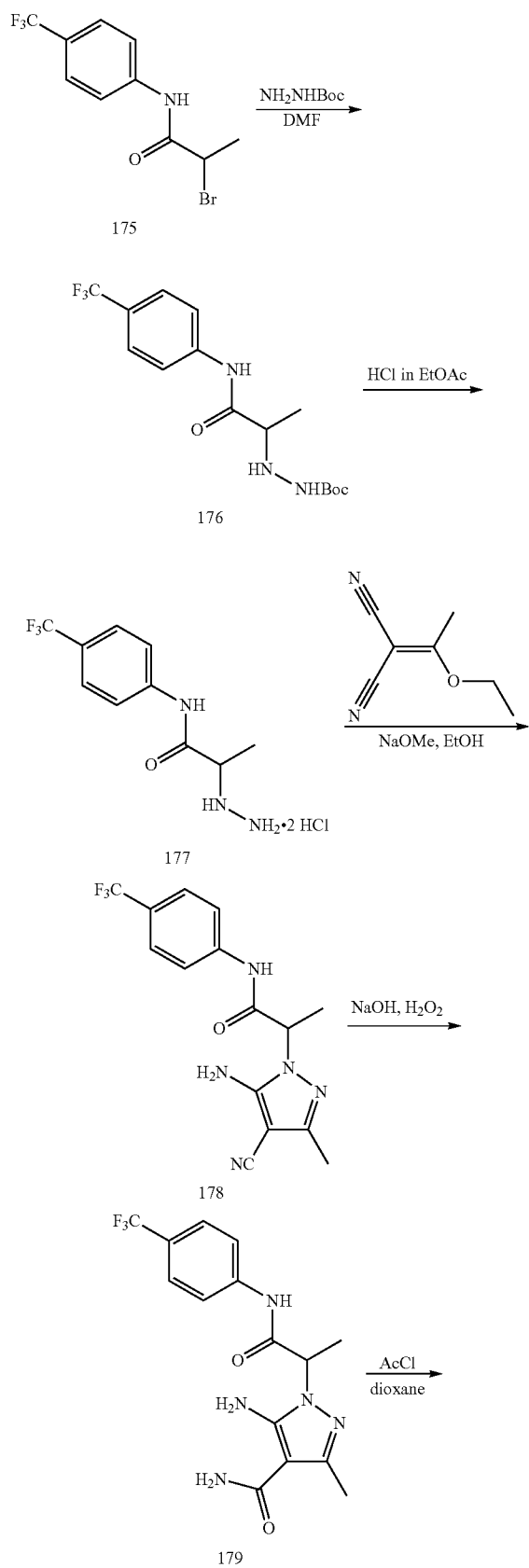

Scheme 61 illustrates a procedure for the preparation of α-methyl amide-substituted pyrazolopyrimidinone derivatives such as 180 from secondary bromide 175. N-alkylation of bromide 175 with tert-butyl hydrazine carboxylate will furnish hydrazine 176. Treatment of 176 with hydrochloric acid will furnish 177 as the dihydrochloride salt which can be cyclized with an alkylidene under basic conditions to afford 178. Basic hydrolysis of nitrile 178 will afford 5-aminopyrazole-4-carboxamide 179 which can be treated with acetyl chloride to furnish pyrazolopyrimidinone 180.

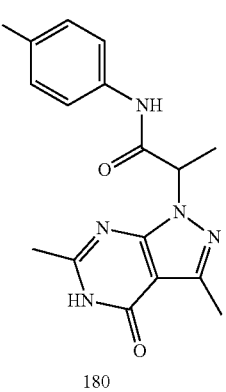

Scheme 62.

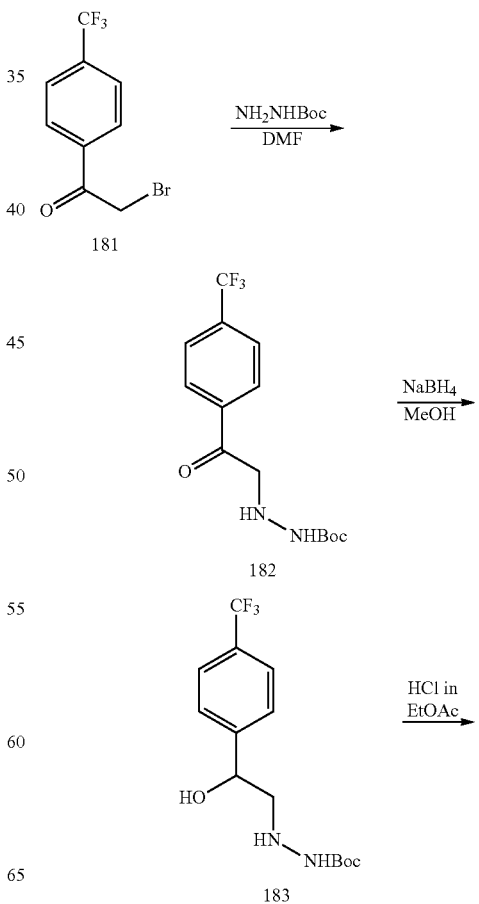

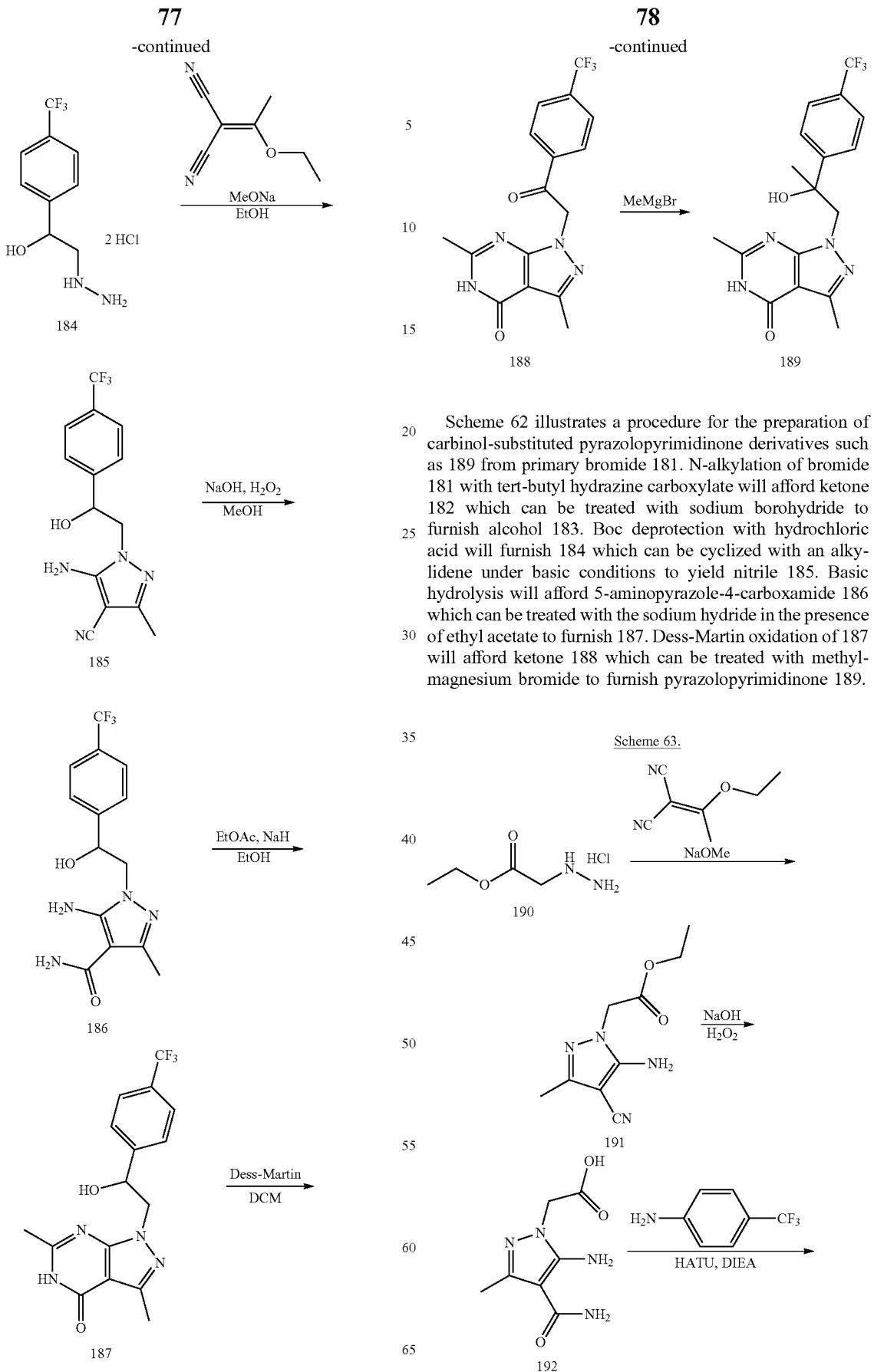

Scheme 62 illustrates a procedure for the preparation of carbinol-substituted pyrazolopyrimidinone derivatives such as 189 from primary bromide 181. N-alkylation of bromide 181 with tert-butyl hydrazine carboxylate will afford ketone 182 which can be treated with sodium borohydride to furnish alcohol 183. Boc deprotection with hydrochloric acid will furnish 184 which can be cyclized with an alkylidene under basic conditions to yield nitrile 185. Basic hydrolysis will afford 5-aminopyrazole-4-carboxamide 186 which can be treated with the sodium hydride in the presence of ethyl acetate to furnish 187. Dess-Martin oxidation of 187 will afford ketone 188 which can be treated with methylmagnesium bromide to furnish pyrazolopyrimidinone 189.

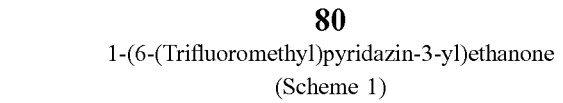

Step 1.
3-(1-Ethoxyvinyl)-6-(trifluoromethyl)pyridazine

To a solution of 3-chloro-6-(trifluoromethyl)pyridazine (0.30 g, 1.6 mmol) in toluene (3 mL) were added tributyl (1-ethoxyvinyl)stannane (1.2 g, 3.3 mmol) and Pd(PPh$_3$)$_4$ (1.90 g, 1.64 mmol) at RT. The mixture was purged with nitrogen for 3 times and stirred at 120° C. for 16 h under nitrogen. The mixture was cooled to RT and filtered. The filter cake was washed with ethyl acetate (20 mL) and the resultant filtrate was diluted with sat. aq. KF solution (30 mL). The layers were separated and the aqueous layer was extracted with ethyl acetate (3×10 mL). The organic layers were combined, dried over Na$_2$SO$_4$, filtered, and concentrated under reduced pressure. The residue was purified by silica gel column chromatography (5% ethyl acetate in petroleum ether) to afford the title compound as an oil. MS=219.0 (+ESI).

Step 2.
1-(6-(Trifluoromethyl)pyridazin-3-yl)ethanone

To a solution of 3-(1-ethoxyvinyl)-6-(trifluoromethyl) pyridazine (0.25 g, 1.2 mmol) in THF (1 mL) was added hydrochloric acid (6.0 M, 2.0 mL) at RT. The reaction solution was stirred at RT for 1 h. The resulting mixture was diluted with water (10 mL) and extracted with ethyl acetate (3×10 mL). The organic layers were combined, dried over Na$_2$SO$_4$, filtered, and concentrated under reduced pressure to afford the title crude compound as an oil. MS=190.0 (+EI, GC-MS).

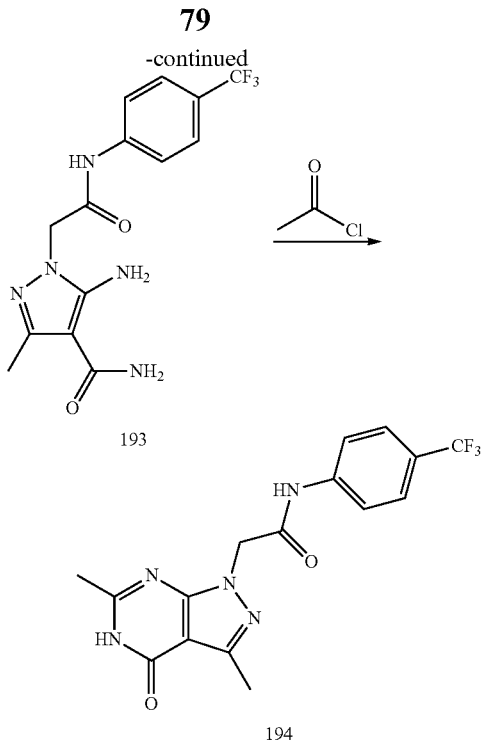

Scheme 63 illustrates a procedure for the preparation of carboxamide-substituted pyrazolopyrimidinone derivatives such as 194 from hydrazine precursors such as 190. Cyclization of hydrazine 190 with an alkylidene under basic conditions will afford nitrile 191 which can be treated under basic conditions to afford 5-aminopyrazole-4-carboxamide 192. HATU-mediated coupling with 4-trifluoromethylaniline will afford 193 which can be cyclized with acetyl chloride to furnish pyrazolopyrimidinone 194.

PREPARATORY EXAMPLE 1

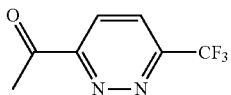

TABLE 1

The following compounds were prepared using procedures similar to those described in Preparatory Example 1 using appropriate starting materials.

| Prep. Ex# | Structure | IUPAC Name | GCMS or $^1$H NMR |
|---|---|---|---|
| 2 | 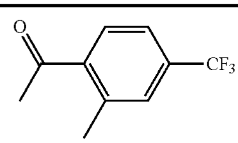 | 1-(2-methyl-4-(trifluoromethyl)phenyl)ethanone | $^1$H NMR (300 MHz, CDCl$_3$) δ: 7.74 (d, J = 7.8 Hz, 1H), 7.53 (d, J = 7.8 Hz, 1H), 7.51 (s, 1H), 2.60 (s, 3H), 2.56 (s, 3H). |
| 3 | 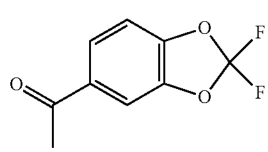 | 1-(2,2-difluorobenzo[d][1,3]dioxol-5-yl)ethanone | $^1$H NMR (300 MHz, CDCl$_3$) δ: 7.76 (d, J = 8.4 Hz, 1H), 7.69 (s, 1H), 7.14 (d, J = 8.4 Hz, 1H), 2.60 (s, 3H). |
| 4 | 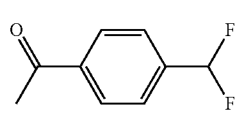 | 1-(4-(difluoromethyl)phenyl)ethanone | $^1$H NMR (300 MHz, DMSO-d$_6$) δ: 8.08 (d, J = 8.4 Hz, 2H), 7.72 (d, J = 8.4 Hz, 2H), 7.14 (t, J = 55.5 Hz, 1H), 2.62 (s, 3H). |

TABLE 1-continued

The following compounds were prepared using procedures similar to those described in Preparatory Example 1 using appropriate starting materials.

| Prep. Ex# | Structure | IUPAC Name | GCMS or $^1$H NMR |
|---|---|---|---|
| 5 | 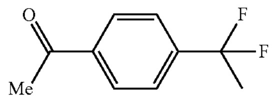 | 1-(4-(1,1-difluoroethyl)phenyl)ethanone | MS = 184.0 (+EI) |
| 6 | 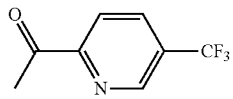 | 1-(5-(trifluoromethyl)pyridin-2-yl)ethanone | $^1$H NMR (400 MHz, CDCl$_3$) δ: 8.98 (s, 1H), 8.18 (d, J = 8.4 Hz, 1H), 8.11 (dd, J = 8.4 Hz, 1.8 Hz, 1H), 2.79 (s, 3H). |

PREPARATORY EXAMPLE 7

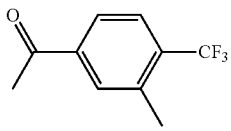

1-(3-Methyl-4-(trifluoromethyl)phenyl)ethanone (Scheme 2)

Step 1. 4-(1-Butoxyvinyl)-2-methyl-1-(trifluoromethyl)benzene

Diacetoxypalladium (3.7 mg, 0.02 mmol), 1,3-bis(diphenylphosphino)propane (14 mg, 0.03 mmol), 1-(vinyloxy)butane (0.67 g, 6.7 mmol) and triethylamine (0.70 mL, 5.0 mmol) were added to a solution of 4-bromo-2-methyl-1-(trifluoromethyl)benzene (0.40 g, 1.7 mmol) in ethylene glycol (2 mL) at RT. The mixture was purged with nitrogen 3 times and stirred at 145° C. for 3 h under nitrogen. The mixture was cooled to RT, diluted with brine (50 mL), and the mixture was extracted with CH$_2$Cl$_2$ (3×50 mL). The organic layers were combined, dried over Na$_2$SO$_4$, filtered, and concentrated under reduced pressure to afford the title compound as a liquid. The title compound was used directly in the next step without purification. MS=259.0 (+ESI).

Step 2. 1-(3-Methyl-4-(trifluoromethyl)phenyl)ethanone

To a solution of 4-(1-butoxyvinyl)-2-methyl-1-(trifluoromethyl)benzene (0.30 g, 1.2 mmol) in THF (2 mL) at RT was added hydrochloric acid (6 M, 2.0 mL). The reaction mixture was stirred for 2 h at RT. The resulting mixture was diluted with brine (50 mL), extracted with CH$_2$Cl$_2$ (3×50 mL), and the organic layers were combined. The organic layer was dried over Na$_2$SO$_4$, filtered, and concentrated under reduced pressure. The residue was purified by silica gel column chromatography (5% ethyl acetate in petroleum ether) to afford the title compound as a liquid. $^1$H NMR (400 MHz, CDCl$_3$) δ: 7.88 (s, 1H), 7.85 (d, J=8.0 Hz, 1H), 7.73 (d, J=8.0 Hz, 1H), 2.65 (s, 3H), 2.58 (s, 3H).

TABLE 2

The following compounds were prepared using procedures similar to those described in Preparatory Example 7 using appropriate starting materials.

| Prep Ex# | Structure | IUPAC Name | GCMS or $^1$H NMR |
|---|---|---|---|
| 8 | 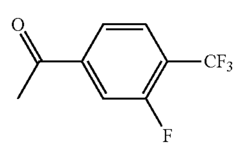 | 1-(3-fluoro-4-(trifluoromethyl)phenyl)ethanone | $^1$H NMR (300 MHz, CDCl$_3$) δ: 7.87-7.72 (m, 3H), 2.65 (s, 3H). |
| 9 | 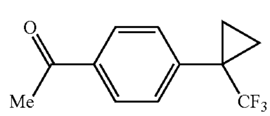 | 1-(4-(1-(trifluoromethyl)cyclopropyl)phenyl)ethanone | $^1$H NMR (300 MHz, DMSO-d$_6$) δ: 7.98-7.94 (m, 2H), 7.61 (d, J = 8.1 Hz, 2H), 2.59 (s, 3H), 1.42-1.38 (m, 2H), 1.20-1.16 (m, 2H). |

PREPARATORY EXAMPLE 10

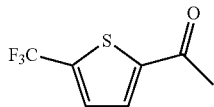

1-(5-(Trifluoromethyl)thiophen-2-yl)ethanone
(Scheme 3)

To a stirred solution of 1-(5-bromothiophen-2-yl)ethanone (2.00 g, 9.8 mmol) in N-methyl-2-pyrrolidinone (8 mL) were added copper(I) iodide (0.46 g, 2.4 mmol) and methyl 2,2-difluoro-2-(fluorosulfonyl)acetate (5.62 g, 29.3 mmol) at RT. The reaction mixture was purged with nitrogen for 3 times and stirred under nitrogen atmosphere at 135° C. for 16 h. The resulting mixture was cooled to RT, diluted with water (100 mL) and extracted with ethyl acetate (3×30 mL). The organic layers were combined, washed with brine (1×60 mL), and dried over $Na_2SO_4$. The organic layer filtered and concentrated under reduced pressure. The residue was purified by silica gel column chromatography (0-20% ethyl acetate in petroleum ether) to afford the title compound as an oil. MS=194.8 (+ESI)

PREPARATORY EXAMPLE 11

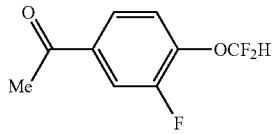

1-(4-(Difluoromethoxy)-3-fluorophenyl)ethanone
(Scheme 4)

Sodium 2-chloro-2,2-difluoroacetate (1.20 g, 7.8 mmol) was added to a mixture of 1-(3-fluoro-4-hydroxy-phenyl)ethanone (1.00 g, 6.5 mmol) and potassium carbonate (1.1 g, 7.8 mmol) in DMF at RT. The reaction mixture was purged with nitrogen for 3 times and stirred under nitrogen atmosphere at 120° C. for 16 h. The resulting mixture was cooled, diluted with water (20 mL), and extracted with ethyl acetate (3×20 mL). The organic layers were combined, washed with brine (20 mL), and dried over $Na_2SO_4$. The organic layer was filtered and concentrated under reduced pressure. The residue was purified by silica gel column chromatography (0-10% ethyl acetate in petroleum ether) to afford the title compound as an oil. MS=204.4 (+ESI)

PREPARATORY EXAMPLE 12

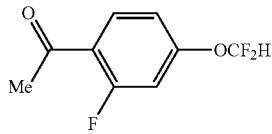

1-(4-(Difluoromethoxy)-2-fluorophenyl)ethanone
(Scheme 4)

The title compound was prepared using procedures similar to those described in Preparatory Example 11 using 1-(2-fluoro-4-hydroxyphenyl)ethanone to afford a solid. $^1$H NMR (300 MHz, $CDCl_3$) δ: 7.97-7.91 (m, 1H), 7.00-6.90 (m, 2H), 6.59 (t, J=72.6 Hz, 1H), 2.62 (s, 3H).

PREPARATORY EXAMPLE 13

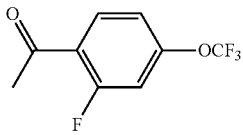

1-(2-Fluoro-4-(trifluoromethoxy)phenyl)ethanone
(Scheme 5)

Step 1. 2-Fluoro-4-(trifluoromethoxy)benzoyl chloride

Thionyl chloride (0.29 mL, 4.0 mmol) was added to a solution of 2-fluoro-4-(trifluoromethoxy)benzoic acid (0.50 g, 2.0 mmol) in $CH_2Cl_2$ (10 mL) under $N_2$ at RT. The mixture was stirred at 40° C. for 2 h and the mixture was cooled to RT. The mixture was concentrated under reduced pressure to afford the title compound as an oil which was used directly for the next step without purification.

Step 2. 2-Fluoro-N-methoxy-N-methyl-4-(trifluoromethoxy)benzamide

To a mixture of N,O-dimethylhydroxylamine hydrochloride (0.36 g, 3.7 mmol) and 2-fluoro-4-(trifluoromethoxy)benzoyl chloride (0.45 g, 1.9 mmol) in $CH_2Cl_2$ (10 mL) was added triethylamine (0.80 mL, 5.6 mmol) at RT. The reaction mixture was stirred at RT for 2 h. The resulting mixture was diluted with water (20 mL) and extracted with ethyl acetate (3×20 mL). The organic layers were combined, washed with brine (50 mL) and dried over $Na_2SO_4$. The organic layer was filtered and concentrated under reduced pressure. The residue was purified by silica gel column chromatography (0-33% ethyl acetate in hexanes) to afford the title compound as a liquid. MS=267.9 (+ESI)

Step 3.
1-(2-Fluoro-4-(trifluoromethoxy)phenyl)ethanone

To a solution of 2-fluoro-N-methoxy-N-methyl-4-(trifluoromethoxy)benzamide (0.35 g, 1.3 mmol) in THF (5 mL) was added dropwise methylmagnesium bromide (1 M in THF, 3.9 mL, 3.9 mmol) under nitrogen atmosphere at 0° C. The reaction mixture was stirred under nitrogen atmosphere for 2 h at RT. The resulting mixture was diluted with water (30 mL) and extracted with ethyl ether (3×20 mL). The organic layers were combined, washed with brine (50 mL), and dried over $Na_2SO_4$. The organic layer was filtered and concentrated under reduced pressure. The crude title compound was obtained as a liquid and was used directly for the next step without purification. $^1$H NMR (400 MHz, $CDCl_3$) δ: 7.99-7.94 (m, 1H), 7.10 (d, J=8.8 Hz, 1H), 7.03 (d, J=11.2 Hz, 1H), 2.65 (s, 3H).

TABLE 3

The following compounds were prepared using procedures similar to those described in Preparatory Example 13 using appropriate starting materials.

| Prep. Ex#. | Structure | IUPAC Name | GCMS or ¹H NMR |
|---|---|---|---|
| 14 | 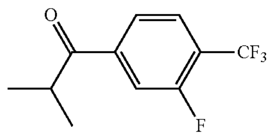 [SMILES: CC(C)C(=O)c1ccc(C(F)(F)F)c(F)c1] | 1-(3-fluoro-4-(trifluoromethyl)phenyl)-2-methylpropan-1-one | ¹H NMR (300 MHz, CDCl₃) δ: 7.82-7.70 (m, 3H), 3.55-3.42 (m, 1H), 1.24 (d, J = 6.6 Hz, 6H). |
| 15 | 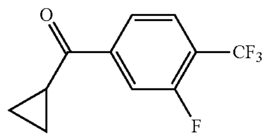 [SMILES: O=C(c1ccc(C(F)(F)F)c(F)c1)C1CC1] | cyclopropyl(3-fluoro-4-(trifluoromethyl)phenyl)methanone | ¹H NMR (400 MHz, CDCl₃) δ: 7.91-7.89 (m, 1H), 7.83-7.74 (m, 2H), 2.67-2.60 (m, 1H), 1.38-1.33 (m, 2H), 1.32-1.27 (m, 2H). |
| 16 | 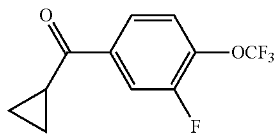 [SMILES: O=C(c1ccc(OC(F)(F)F)c(F)c1)C1CC1] | cyclopropyl(3-fluoro-4-(trifluoromethoxy)phenyl)methanone | ¹H NMR (400 MHz, CDCl₃) δ: 7.88-7.85 (m, 2H), 7.46-7.42 (m, 1H), 2.65-2.59 (m, 1H), 1.32-1.24 (m, 2H), 1.19-1.12 (m, 2H). |
| 17 | 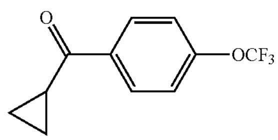 | cyclopropyl(4-(trifluoromethoxy)phenyl)methanone | ¹H NMR (300 MHz, CDCl₃) δ: 8.11 (d, J = 8.1 Hz, 2H), 7.74 (d, J = 8.1 Hz, 2H), 2.71-2.63 (m, 1H), 1.35-1.28 (m, 2H), 1.17-1.03 (m, 2H). |
| 18 | 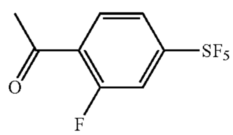 | 1-(2-fluoro-4-(pentafluorothio)phenyl)ethanone | ¹H NMR (300 MHz, CDCl₃) δ: 8.02-7.98 (m, 1H), 7.67-6.57 (m, 2H), 2.70 (s, 3H). |
| 19 | 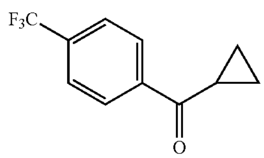 [SMILES: O=C(c1ccc(C(F)(F)F)cc1)C1CC1] | cyclopropyl(4-(trifluoromethyl)phenyl)methanone | ¹H NMR (300 MHz, CDCl₃) δ: 8.11 (d, J = 8.1 Hz, 2H), 7.74 (d, J = 8.1 Hz, 2H), 2.71-2.63 (m, 1H), 1.31-1.22 (m, 2H), 1.19-1.02 (m, 2H). |

PREPARATORY EXAMPLE 20

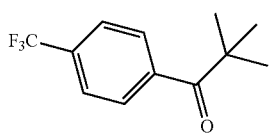 [SMILES: CC(C)(C)C(=O)c1ccc(C(F)(F)F)cc1]

2,2-Dimethyl-1-(4-(trifluoromethyl)phenyl)propan-1-one (Scheme 6)

To a stirred solution of 1-bromo-4-(trifluoromethyl)benzene (3.0 g, 13.3 mmol) in THF (20 mL) was added dropwise n-butyllithium (2.5 M in hexane, 5.9 mL, 14.7 mmol) under nitrogen atmosphere at −78° C. The reaction solution was stirred at −78° C. for 30 min whereupon N-methoxy-N-methylpivalamide (2.9 g, 20.0 mmol) was added. The reaction mixture and stirred for additional 1 h at −78° C. and was quenched with water (10 mL) and extracted with ethyl ether (3×20 mL). The organic layers were combined, dried over Na₂SO₄, filtered, and concentrated under reduced pressure. The residue was purified by silica gel column chromatography (0-33% ethyl acetate in petroleum ether) to afford the title compound as an oil. ¹H NMR (300 MHz, CDCl₃) δ: 7.73 (d, J=8.4 Hz, 2H), 7.67 (d, J=8.4 Hz, 2H), 1.34 (s, 9H).

PREPARATORY EXAMPLE 21

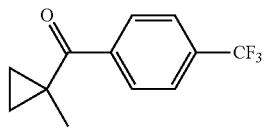 [SMILES: CC1(C(=O)c2ccc(C(F)(F)F)cc2)CC1]

(1-Methylcyclopropyl)(4-(trifluoromethyl)phenyl)methanone (Scheme 6)

The title compound was prepared using procedures similar to those described in Preparatory Example 20 using 1-bromo-4-(trifluoromethyl)benzene and N,O-dimethyl-N-(1 methylcyclopropyl)hydroxylamine to afford an oil. ¹H NMR (400 MHz, CDCl$_3$) δ: 7.86 (d, J=8.0 Hz, 2H), 7.72 (d, J=8.0 Hz, 2H), 1.45 (s, 3H), 1.37-1.33 (m, 2H), 0.91-0.83 (m, 2H).

PREPARATORY EXAMPLE 22

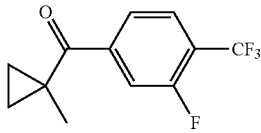 [SMILES: CC1(C(=O)c2ccc(C(F)(F)F)c(F)c2)CC1]

(3-Fluoro-4-(trifluoromethyl)phenyl)(1-methylcyclopropyl)methanone (Scheme 6)

To a solution of 4-bromo-2-fluoro-1-(trifluoromethyl) benzene (0.34 g, 1.4 mmol) in THF (5 mL) was added dropwise isopropylmagnesium bromide (0.48 mL, 1.40 mmol) at −78° C. and the solution was stirred for 1 h. A solution of N-methoxy-N,1-dimethylcyclopropanecarboxamide (0.20 g, 1.4 mmol) in THF (5 mL) was added to the solution dropwise at −78° C. The mixture was stirred for 16 h while slowly warming it to RT. Sat. aq. NH$_4$Cl (5 mL) was added to quench the reaction. The resulting solution was extracted with EtOAc (3×5 mL). The organic layers were combined, dried over Na$_2$SO$_4$, filtered, and concentrated under reduced pressure. The residue was purified by silica gel column chromatography (0-10% ethyl acetate in petroleum ether) to afford the title compound as an oil. MS=246.0 (+EI)

PREPARATORY EXAMPLE 23

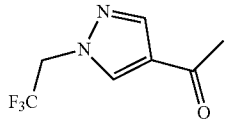

1-(1-(222-Trifluoroethyl)-1H-pyrazol-4-yl)ethanone (Scheme 7)

To a mixture of 1-(1H-pyrazol-4-yl)ethanone (0.30 g, 2.5 mmol) and 2,2,2-trifluoroethyl 4-methylbenzenesulfonate (0.62 g, 2.5 mmol) in NMP (7.0 mL) was added Cs$_2$CO$_3$ (0.50 g, 2.5 mmol) at RT. The reaction mixture was stirred at 60° C. for 18 h. The reaction mixture was cooled to RT, diluted with water (30 mL) and extracted with ethyl acetate (2×40 mL). The combined organic layers were washed with brine (2×40 mL), dried over Na$_2$SO$_4$, filtered, and concentrated under reduced pressure. The residue was purified by silica gel column chromatography (0-50% ethyl acetate in hexanes) to afford the title compound as an oil. $^1$H NMR (400 MHz, CDCl$_3$) δ: 8.01 (s, 1H), 7.98 (s, 1H), 4.74 (q, J=8.4 Hz, 2H), 2.47 (s, 3H).

PREPARATORY EXAMPLE 24

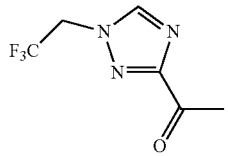

1-(1-(2,2,2-Trifluoroethyl)-1H-1,2,4-triazol-3-yl)ethanone (Scheme 7)

The title compound was prepared using procedures similar to those described in Preparatory Example 23 using 1-(1H-1,2,4-triazol-3-yl)ethanone in acetonitrile to afford the title compound as a solid. $^1$H NMR (400 MHz, DMSO-d$_6$) δ: 8.85 (s, 1H), 5.49-5.42 (m, 2H), 2.57 (s, 3H).

PREPARATORY EXAMPLE 25

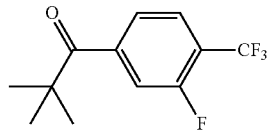

1-(3-Fluoro-4-(trifluoromethyl)phenyl)-2,2-dimethylpropan-1-one (Scheme 8)

To a solution of dimethyl sulfoxide (1.7 mL, 24.0 mmol) in CH$_2$Cl$_2$ (20 mL) was added dropwise oxalyl chloride (1.0 mL, 12.0 mmol) under nitrogen atmosphere at −78° C. The reaction solution was stirred at −78° C. for 30 min. Then to the reaction mixture was added 1-(3-fluoro-4-(trifluoromethyl)phenyl)-2,2-dimethylpropan-1-ol (1.50 g, 6.0 mmol) and the mixture was stirred for additional 40 min at −78° C. The resulting mixture was quenched with triethylamine (6.7 mL, 48.0 mmol), extracted with CH$_2$Cl$_2$ (3×30 mL) and the organic layers were combined. The organic layer was dried over Na$_2$SO$_4$, filtered, and concentrated under reduced pressure. The residue was purified by silica gel column chromatography (0-20% ethyl acetate in petroleum ether) to afford the title compound as an oil. $^1$H NMR (400 MHz, CDCl$_3$) δ: 7.70-7.66 (m, 1H), 7.52-7.45 (m, 2H), 1.36 (s, 9H).

TABLE 4

The following compounds were prepared using the known procedures listed in the table employing the appropriate starting materials

| Prep. Ex# | Structure | IUPAC Name | Literature |
| --- | --- | --- | --- |
| 26 | Cl–[thiophene]–C(=O)CH$_3$ | 1-(5-chlorothiophen-2-yl)ethan-1-one | Syn. Comm., 2008, 38, 255. |

TABLE 4-continued

The following compounds were prepared using the known procedures listed in the table employing the appropriate starting materials

| Prep. Ex# | Structure | IUPAC Name | Literature |
|---|---|---|---|
| 27 | 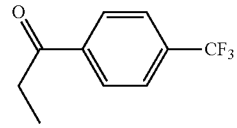 | 1-(4-(trifluoromethyl)phenyl)-propan-1-one | *J. Med. Chem.* 1995, 38, 3918. |
| 28 | 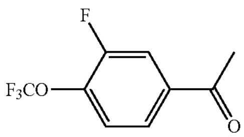 | 1-(3-fluoro-4-(trifluoromethoxy)-phenyl)ethan-1-one | US2014/329796A1, 2014 |
| 29 | 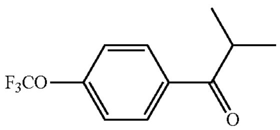 [SMILES: CC(C)C(=O)c1ccc(OC(F)(F)F)cc1] | 2-methyl-1-(4-(trifluoromethyl)-phenyl)propan-1-one | *Org. Lett.*, 2008, 10, 2067. |
| 30 | 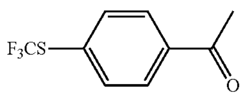 | 1-(4-((trifluoromethyl)thio)-phenyl)ethan-1-one | *Tett. Lett.* 2014, 55, 4909. |
| 31 | 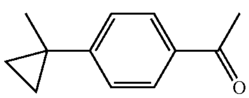 | 1-(4-(1-methylcyclopropyl)phenyl)ethan-1-one | *Bull. Chem. Soc. Jpn*, 1991, 64, 2954. |
| 32 | 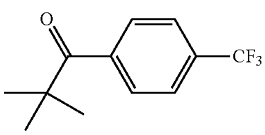 [SMILES: CC(C)(C)C(=O)c1ccc(C(F)(F)F)cc1] | 2,2-dimethyl-1-(4-(trifluoro-methyl)phenyl)propan-1-one | *Tetrahedron* 2012, 68, 6557. |
| 33 | 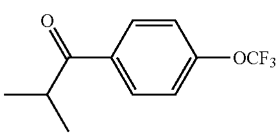 [SMILES: CC(C)C(=O)c1ccc(OC(F)(F)F)cc1] | 2-methyl-1-(4-(trifluoro-methoxy)phenyl)propan-1-one | US4318866A1, 1982 |
| 34 | 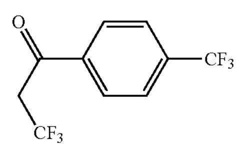 [SMILES: O=C(CC(F)(F)F)c1ccc(C(F)(F)F)cc1] | 3,3,3-trifluoro-1-(4-(trifluoro-methyl)phenyl)propan-1-one | *J. Org. Chem.* 2014, 79, 5145. |
| 35 | 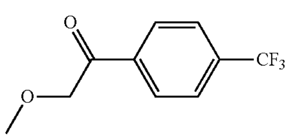 | 2-methoxy-1-(4-(trifluoro-methyl)phenyl)ethan-1-one | *Org. Biomol. Chem.* 2007, 5, 2690. |
| 36 | 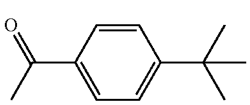 | 1-(4-(tert-butyl)phenyl)ethan-1-one | *Tetrahedron* 2014, 70, 4760. |
| 37 | 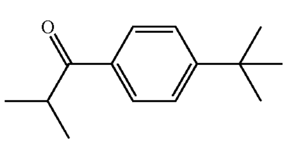 | 1-(4-(tert-butyl)phenyl)-2-methylpropan-1-one | *Chem. Comm.* 2012, 48, 7034. |

TABLE 4-continued

The following compounds were prepared using the known procedures listed in the table employing the appropriate starting materials

| Prep. Ex# | Structure | IUPAC Name | Literature |
|---|---|---|---|
| 38 | 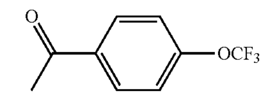 | 1-(4-(trifluoromethoxy)-phenyl)ethan-1-one | WO2011/137024 2011. |
| 39 | 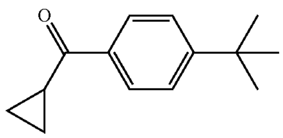 | (4-(tert-butyl)phenyl)-(cyclopropyl)methanone | J. Org. Chem. 2007, 72, 144. |
| 40 | 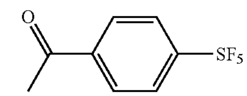 | 1-(4-(pentafluoro-l6-sulfanyl)phenyl)ethan-1-one | WO2013/61205 A2, 2013 |
| 41 | 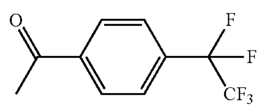 | 1-(4-(perfluoroethyl)-phenyl)ethan-1-one | J. Am. Chem. Soc. 2013, 135, 12587. |
| 42 | 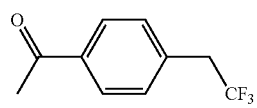 | 1-(4-(2,2,2-trifluoroethyl)-phenyl)ethan-1-one | J. Org. Chem. 1997, 62, 7758. |

PREPARATORY EXAMPLE 43

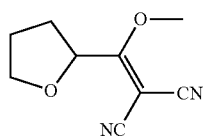

2-(Methoxy(tetrahydrofuran-2-yl)methylene)malononitrile (Scheme 9)

Step 1. Tetrahydrofuran-2-carbonyl chloride

To a solution of tetrahydrofuran-2-carboxylic acid (1.50 g, 12.9 mmol) in $CH_2Cl_2$ (5 mL) at 0° C. was added oxalyl chloride (1.7 mL, 19.4 mmol) at 0° C. followed by a drop of DMF. The resulting mixture was stirred at RT for 2 h whereupon the mixture was concentrated under reduced pressure to afford the title compound as a liquid. The title compound was used without purification for the next transformation.

Step 2. 2-(Hydroxy(tetrahydrofuran-2-yl)methylene)malononitrile

To a mixture of sodium hydride (1.07 g, 26.8 mmol) in THF (10 mL) was added malononitrile (0.884 g, 13.4 mmol) in THF (5 mL) at 0° C. The mixture was stirred at RT for 1 h whereupon a solution of tetrahydrofuran-2-carbonyl chloride (1.80 g, 13.4 mmol) in THF (10 mL) was added dropwise. The mixture was stirred at RT for 16 h, quenched with water (10 mL), and treated with 3 M HCl (~10 mL) until the solution pH~3 was obtained. The mixture was extracted with ethyl acetate (3×40 mL) and the organic layers were combined. The organic layer was washed with water (2×50 mL), brine (50 mL), and dried over $Na_2SO_4$. The organic layer was filtered and concentrated under reduced pressure to afford the title compound as an oil. The title compound was carried onto the next step without purification. $^1H$ NMR (400 MHz, DMSO-$d_6$) δ: 12.97 (br, 1H), 4.55-4.50 (m, 1H), 3.90-3.82 (m, 1H), 3.75-3.70 (m, 1H), 2.15-2.10 (m, 1H), 1.90-1.75 (m, 3H).

Step 3. 2-(Methoxy(tetrahydrofuran-2-yl)methylene)malononitrile

To the mixture of 2-(hydroxy(tetrahydrofuran-2-yl)methylene)malononitrile (2.90 g, 17.7 mmol) in trimethyl orthoformate (31 mL) at RT was added 4-methylbenzenesulfonic acid (1.52 g, 8.8 mmol). The mixture was stirred at 110° C. for 16 h, cooled to RT, and concentrated under reduced pressure. The residue was purified by silica gel column chromatography (15% ethyl acetate in petroleum ether) to afford the title compound as a solid. $^1H$ NMR (400 MHz, $CDCl_3$) δ: 4.88-4.84 (m, 1H), 4.29 (s, 3H), 4.11-4.06 (m, 1H), 3.97-3.90 (m, 1H), 2.42-2.33 (m, 1H), 2.11-1.89 (m, 3H).

TABLE 5

The following compounds were prepared using procedures similar to those described in Preparatory Example 43 using appropriate starting materials.

| Prep. Ex#. | Structure | IUPAC Name | $^1$H NMR |
|---|---|---|---|
| 44 | (furan structure) | 2-(furan-2-yl(methoxy)methylene)malononitrile | $^1$H NMR (300 MHz, CDCl$_3$) δ: 7.76 (dd, J = 1.7 Hz, 0.8 Hz, 1H), 7.42 (dd, J = 3.6 Hz, 0.6 Hz, 1H), 6.67 (dd, J = 3.6 Hz, 1.8 Hz, 1H), 4.25 (s, 3H). |
| 45 | (F$_3$C structure) | 2-(3,3,3-trifluoro-1-methoxypropylidene)malononitrile | $^1$H NMR (300 MHz, CDCl$_3$) δ: 4.35 (s, 3H), 3.47 (q, J = 9.3 Hz, 2H). |
| 46 | (BnO structure) | 2-(3-(benzyloxy)-1-methoxypropylidene)malononitrile | $^1$HNMR (400 MHz, CDCl$_3$) δ: 7.42-7.31 (m, 5H), 4.56 (s, 2H), 4.20 (s, 3H), 3.79 (t J = 6.0 Hz, 2H), 2.96 (t, J = 6.0 Hz, 2H). |

TABLE 6

The following compounds were prepared using known procedures similar to those described in Preparatory Example 43 using appropriate starting materials.

| Prep. Ex#. | Structure | IUPAC Name | Reference |
|---|---|---|---|
| 47 | (structure) | 2-(1-ethoxyethylidene)malononitrile | *Tetrahedron*, 2006, 62, 6222-6227 |
| 48 | (structure) | 2-(2-(benzyloxy)-1-methoxyethylidene)malononitrile | WO2009/62118 A2, 2009 |
| 49 | (F$_3$C structure) | 2-(1-ethoxy-2,2,2-trifluoroethylidene)malononitrile | US5294612 A1, 1994 |

PREPARATORY EXAMPLE 50

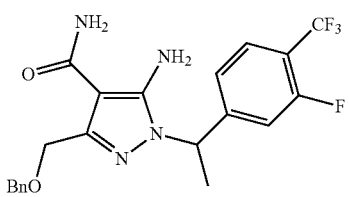 [SMILES: CC(c1ccc(C(F)(F)F)c(F)c1)n1nc(COCc2ccccc2)c(C(N)=O)c1N]

5-Amino-3-(benzyloxymethyl)-1-(1-(3-fluoro-4-(trifluoromethyl)phenyl)ethyl)-1H-pyrazole-4-carboxamide (Scheme 10)

Step 1. tert-Butyl 2-(1-(3-fluoro-4-(trifluoromethyl)phenyl)ethylidene)hydrazinecarboxylate tert-Butyl hydrazinecarboxylate (0.705 g, 5.3 mmol) and 1-(3-fluoro-4-(trifluoromethyl)phenyl)ethanone (1.10 g, 5.34 mmol) were dissolved in THF (2 mL) and heptane (6 mL) at RT. The resulting mixture was heated to 75° C., stirred at this temperature for 16 h, and then cooled to RT. The mixture was concentrated under reduced pressure to afford the title compound as a solid which was used in the next step without purification. $^1$H NMR (400 MHz, CDCl$_3$) δ: 7.81-7.79 (br, 1H), 7.71-7.57 (m, 3H), 2.21 (s, 3H), 1.58 (s, 9H).

Step 2. tert-Butyl 2-(1-(3-fluoro-4-(trifluoromethyl)phenyl)ethyl)hydrazinecarboxylate To a solution of tert-butyl 2-(1-(3-fluoro-4-(trifluoromethyl)phenyl)ethylidene)hydrazinecarboxylate (1.7 g, 5.31 mmol) in methyl alcohol (6 mL) and glacial acetic acid (6 mL) was added sodium cyanoborohydride (0.33 g, 5.3 mmol) at 0° C. under nitrogen. The resulting solution was slowly warmed to RT and continued to stir for 2 h whereupon the mixture was concentrated. The residue was partitioned between sat. aq. NaHCO$_3$ (10 mL) and CH$_2$Cl$_2$ (10 mL), layers were separated, and the aqueous layer was extracted with CH$_2$Cl$_2$ (10 mL). The organic layers were combined, dried over Na$_2$SO$_4$, filtered and concentrated under reduced pressure to afford the title compound as a solid. The title compound was used directly in the next step without purification. $^1$H NMR (300 MHz, CDCl$_3$) δ: 7.61-7.51 (m, 1H), 7.28-7.19 (m, 2H), 4.32-4.20 (m, 1H), 1.44 (s, 9H), 1.32 (d, J=6.6 Hz, 3H).

Step 3. (1-(3-Fluoro-4-(trifluoromethyl)phenyl)ethyl)hydrazine dihydrochloride

To a solution of tert-butyl 2-(1-(3-fluoro-4-(trifluoromethyl)phenyl)ethyl)hydrazinecarboxylate (1.7 g, 5.3 mmol)

in dichloromethane (20 mL) was added HCl (saturated in ethyl acetate) (20 mL, 5.3 mmol) at 0° C. The solution was slowly warmed to RT and stirred for additional 16 h at RT. The solution was concentrated under reduced pressure to afford the title compound as a solid which was used in the next step without purification. $^1$H NMR (300 MHz, CDCl$_3$) δ: 7.88-7.78 (m, 1H), 7.60-7.50 (m, 1H), 7.48-7.39 (m, 1H), 4.31-4.27 (m, 1H), 1.34 (d, J=6.3 Hz, 3H).

Step 4. 5-Amino-3-((benzyloxy)methyl)-1-(1-(3-fluoro-4-(trifluoromethyl)phenyl)ethyl)-1H-pyrazole-4-carbonitrile To a solution of (1-(3-fluoro-4-(trifluoromethyl)phenyl)ethyl)hydrazine dihydrochloride (0.52 g, 1.78 mmol) in EtOH (15 mL) was added a solution of 2-(2-(benzyloxy)-1-methoxy-ethylidene)malononitrile (0.40 g, 1.8 mmol) in EtOH (4 mL) at 0° C. A 30% solution of NaOMe in MeOH (0.7 mL, 3.7 mmol) was added dropwise to the solution which was allowed to gradually warm to RT and stir for an additional 16 h. The mixture was concentrated under reduced pressure whereupon the resultant residue was partitioned between EtOAc (10 mL) and sat. aq. NaHCO$_3$ (5 mL). The layers were separated and the aqueous layer was extracted with EtOAc (3×5 mL). The organic layers were combined, dried over Na$_2$SO$_4$, filtered and concentrated under reduced pressure. The residue was purified by silica gel chromatography (0-50% ethyl acetate in petroleum ether) to afford the title compound as an oil. $^1$H NMR (300 MHz, CDCl$_3$) δ: 7.63-7.55 (m, 1H), 7.46-7.27 (m, 5H), 7.09-7.01 (m, 2H), 5.22 (q, J=7.2 Hz, 1H), 4.64 (s, 2H), 4.54 (s, 2H), 1.88 (d, J=6.9 Hz, 3H).

Step 5. 5-Amino-3-((benzyloxy)methyl)-1-(1-(3-fluoro-4-(trifluoromethyl)phenyl)ethyl)-1H-pyrazole-4-carboxamide To a solution of 5-amino-3-((benzyloxy)methyl)-1-(1-(3-fluoro-4-(trifluoromethyl)phenyl)ethyl)-1H-pyrazole-4-carbonitrile (0.37 g, 0.90 mmol) in MeOH (8 mL) was added NaOH (0.5 mL, 0.9 mmol) and H$_2$O$_2$ (0.36 mL, 3.6 mmol) at 0° C. The solution was slowly warmed to RT, stirred for 16 h, and was concentrated under reduced pressure. The residue was partitioned between water (5 mL) and EtOAc (10 mL) and the layers were separated. The aqueous layer was extracted with EtOAc (5 mL) and the organic layers were combined. The organic layer was dried over Na$_2$SO$_4$, filtered, and concentrated under reduced pressure to afford the title compound as a solid. The title compound was used in the next step without purification. MS=437.1 (+ESI).

TABLE 7

The following compounds were prepared using procedures similar to those described in Preparatory Example 50 using appropriate starting materials.

| Prep Ex# | Structure | IUPAC Name | Exact Mass [M + H]$^+$ |
|---|---|---|---|
| 51 | (structure) | 5-amino-3-(benzyloxymethyl)-1-(1-(3-fluoro-4-(trifluoromethyl)phenyl)ethyl)-1H-pyrazole-4-carboxamide | Calc'd 437.2, found 437.1 |
| 52 | (structure) | 5-amino-3-(benzyloxymethyl)-1-(1-(3-fluoro-4-(trifluoromethoxy)phenyl)ethyl)-1H-pyrazole-4-carboxamide | Calc'd 453.1, found 453.2 |
| 53 | (structure) | 5-amino-3-(benzyloxymethyl)-1-(1-p-tolylethyl)-1H-pyrazole-4-carboxamide | Calc'd 365.2, found 365.3 |
| 54 | (structure) | 5-amino-3-(benzyloxymethyl)-1-(1-(4-(trifluoromethoxy)phenyl)ethyl)-1H-pyrazole-4-carboxamide | Calc'd 435.2, found 435.1 |

TABLE 7-continued

The following compounds were prepared using procedures similar to those described in
Preparatory Example 50 using appropriate starting materials.

| Prep Ex# | Structure | IUPAC Name | Exact Mass [M + H]+ |
|---|---|---|---|
| 55 | 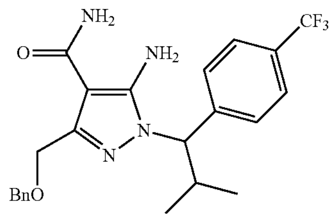 [SMILES: CC(C)C(c1ccc(C(F)(F)F)cc1)n1nc(COCc2ccccc2)c(C(N)=O)c1N] | 5-amino-3-(benzyloxymethyl)-1-(2-methyl-1-(4-(trifluoromethyl)phenyl)propyl)-1H-pyrazole-4-carboxamide | Calc'd 447.2, found 447.4 |
| 56 | 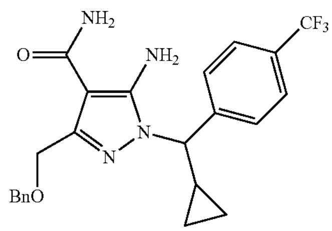 [SMILES: NC(=O)c1c(COCc2ccccc2)nn(C(c2ccc(C(F)(F)F)cc2)C2CC2)c1N] | 5-amino-3-(benzyloxymethyl)-1-(cyclopropyl(4-(trifluoromethyl)phenyl)methyl)-1H-pyrazole-4-carboxamide | Calc'd 445.2, found 445.2 |
| 57 | 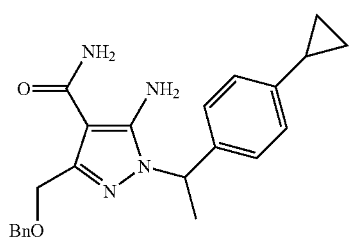 [SMILES: CC(c1ccc(C2CC2)cc1)n1nc(COCc2ccccc2)c(C(N)=O)c1N] | 5-amino-3-(benzyloxymethyl)-1-(1-(4-cyclopropylphenyl)ethyl)-1H-pyrazole-4-carboxamide | Calc'd 391.2, found 391.3 |
| 58 | 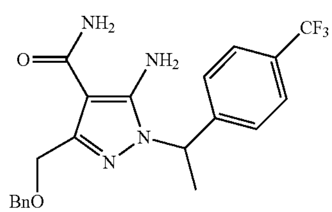 [SMILES: CC(c1ccc(C(F)(F)F)cc1)n1nc(COCc2ccccc2)c(C(N)=O)c1N] | 5-amino-3-(benzyloxymethyl)-1-(1-(4-(trifluoromethyl)phenyl)ethyl)-1H-pyrazole-4-carboxamide | Calc'd 419.2, found 419.2 |
| 59 | 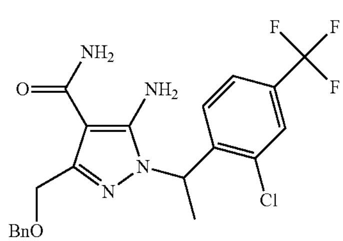 [SMILES: CC(c1ccc(C(F)(F)F)cc1Cl)n1nc(COCc2ccccc2)c(C(N)=O)c1N] | 5-amino-3-(benzyloxymethyl)-1-(1-(2-chloro-4-(trifluoromethyl)phenyl)ethyl)-1H-pyrazole-4-carboxamide | Calc'd 453.1, found 453.1 |
| 60 | 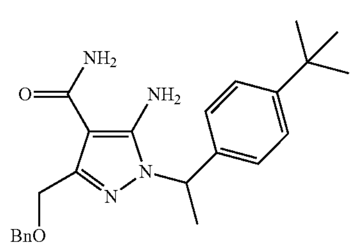 [SMILES: CC(c1ccc(C(C)(C)C)cc1)n1nc(COCc2ccccc2)c(C(N)=O)c1N] | 5-amino-3-(benzyloxymethyl)-1-(1-(4-tert-butylphenyl)ethyl)-1H-pyrazole-4-carboxamide | Calc'd 407.2, found 407.2 |

TABLE 7-continued

The following compounds were prepared using procedures similar to those described in Preparatory Example 50 using appropriate starting materials.

| Prep Ex# | Structure | IUPAC Name | Exact Mass [M + H]+ |
|---|---|---|---|
| 61 | 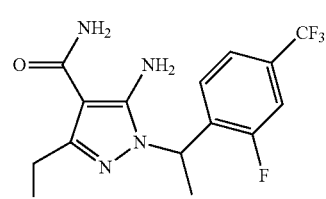 | 5-amino-3-(benzyloxymethyl)-1-(1-(2-fluoro-4-(trifluoromethyl)phenyl)ethyl)-1H-pyrazole-4-carboxamide | Calc'd 437.2, found 437.3 |
| 62 | 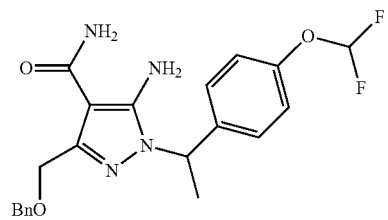 [SMILES: CC(c1ccc(OC(F)F)cc1)n1nc(COCc2ccccc2)c(C(N)=O)c1N] | 5-amino-3-(benzyloxymethyl)-1-(1-(4-(difluoromethoxy)phenyl)ethyl)-1H-pyrazole-4-carboxamide | Calc'd 417.2, found 417.3 |
| 63 | 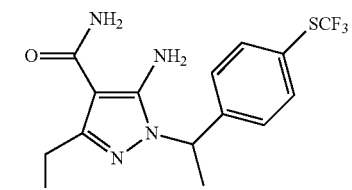 | 5-amino-3-(benzyloxymethyl)-1-(1-(4-(trifluoromethylthio)phenyl)ethyl)-1H-pyrazole-4-carboxamide | Calc'd 451.1, found 451.1 |
| 64 | 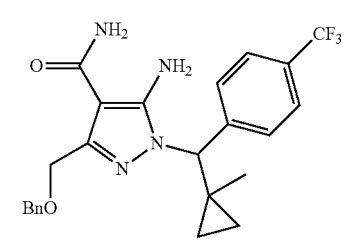 [SMILES: CC1(C(c2ccc(C(F)(F)F)cc2)n2nc(COCc3ccccc3)c(C(N)=O)c2N)CC1] | 5-amino-3-(benzyloxymethyl)-1-((1-methylcyclopropyl)(4-(trifluoromethyl)phenyl)methyl)-1H-pyrazole-4-carboxamide | Calc'd 459.1, found 459.2 |
| 65 | 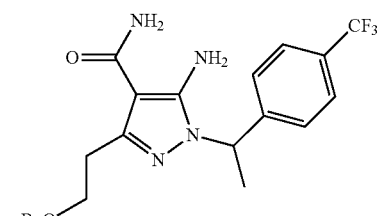 | 5-amino-3-(2-(benzyloxy)ethyl)-1-(1-(4-(trifluoromethyl)phenyl)ethyl)-1H-pyrazole-4-carboxamide | Calc'd 433.2, found 433.1 |
| 66 | 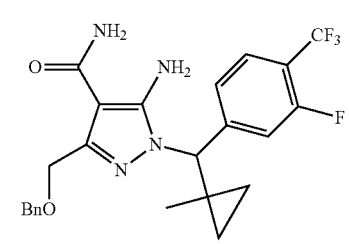 [SMILES: CC1(C(c2ccc(C(F)(F)F)c(F)c2)n2nc(COCc3ccccc3)c(C(N)=O)c2N)CC1] | 5-amino-3-(benzyloxymethyl)-1-((3-fluoro-4-(trifluoromethyl)phenyl)(1-methylcyclopropyl)methyl)-1H-pyrazole-4-carboxamide | Calc'd 477.2, found 477.4 |

TABLE 7-continued

The following compounds were prepared using procedures similar to those described in Preparatory Example 50 using appropriate starting materials.

| Prep Ex# | Structure | IUPAC Name | Exact Mass [M + H]+ |
|---|---|---|---|
| 67 | 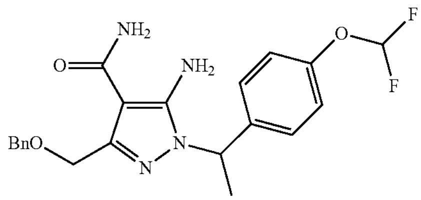 [SMILES: CC(c1ccc(OC(F)F)cc1)n1nc(COCc2ccccc2)c(C(N)=O)c1N] | 5-amino-3-(benzyloxymethyl)-1-(1-(4-(difluoromethoxy)phenyl)ethyl)-1H-pyrazole-4-carboxamide | Calc'd 417.2, found 417.3 |
| 68 | 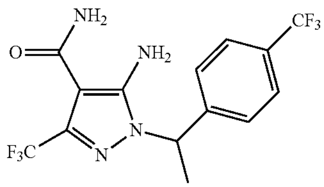 [SMILES: CC(c1ccc(C(F)(F)F)cc1)n1nc(C(F)(F)F)c(C(N)=O)c1N] | 5-amino-3-(trifluoromethyl)-1-(1-(4-(trifluoromethyl)phenyl)ethyl)-1H-pyrazole-4-carboxamide | Calc'd 367.1, found 367.2 |
| 69 | 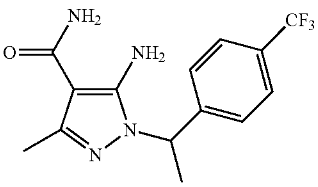 [SMILES: Cc1nn(C(C)c2ccc(C(F)(F)F)cc2)c(N)c1C(N)=O] | 5-amino-3-methyl-1-(1-(4-(trifluoromethyl)phenyl)ethyl)-1H-pyrazole-4-carboxamide | Calc'd 313.1, found 313.3 |
| 70 | 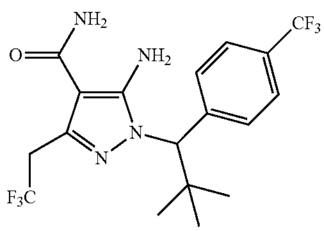 [SMILES: CC(C)(C)C(c1ccc(C(F)(F)F)cc1)n1nc(CC(F)(F)F)c(C(N)=O)c1N] | 5-amino-1-(2,2-dimethyl-1-(4-(trifluoromethyl)phenyl)propyl)-3-(2,2,2-trifluoroethyl)-1H-pyrazole-4-carboxamide | Calc'd 423.2, found 423.2 |
| 71 | 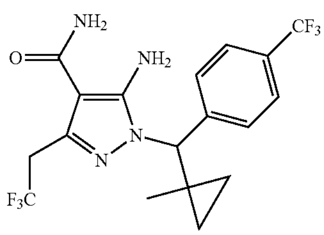 [SMILES: CC1(C(c2ccc(C(F)(F)F)cc2)n2nc(CC(F)(F)F)c(C(N)=O)c2N)CC1] | 5-amino-1-((1-methylcyclopropyl)(4-(trifluoromethyl)phenyl)methyl)-3-(2,2,2-trifluoroethyl)-1H-pyrazole-4-carboxamide | Calc'd 421.2, found 421.1 |
| 72 | 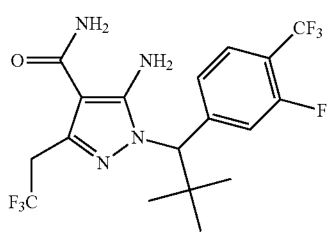 [SMILES: CC(C)(C)C(c1ccc(C(F)(F)F)c(F)c1)n1nc(CC(F)(F)F)c(C(N)=O)c1N] | 5-amino-1-(1-(3-fluoro-4-(trifluoromethyl)phenyl)-2,2-dimethylpropyl)-3-(2,2,2-trifluoroethyl)-1H-pyrazole-4-carboxamide | Calc'd 441.1, found 441.1 |
| 73 | 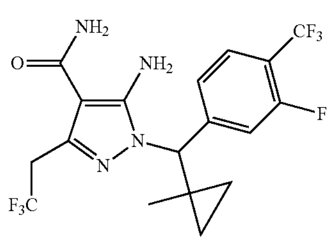 [SMILES: CC1(C(c2ccc(C(F)(F)F)c(F)c2)n2nc(CC(F)(F)F)c(C(N)=O)c2N)CC1] | 5-amino-1-((3-fluoro-4-(trifluoromethyl)phenyl)(1-methylcyclopropyl)methyl)-3-(2,2,2-trifluoroethyl)-1H-pyrazole-4-carboxamide | Calc'd 439.1, found 439.3 |

TABLE 7-continued

The following compounds were prepared using procedures similar to those described in Preparatory Example 50 using appropriate starting materials.

| Prep Ex# | Structure | IUPAC Name | Exact Mass [M + H]⁺ |
|---|---|---|---|
| 74 | 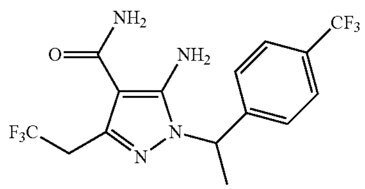 [SMILES: CC(c1ccc(C(F)(F)F)cc1)n1nc(CC(F)(F)F)c(C(N)=O)c1N] | 5-amino-3-(2,2,2-trifluoroethyl)-1-(1-(4-(trifluoromethyl)phenyl)ethyl)-1H-pyrazole-4-carboxamide | Calc'd 381.1, found 381.1 |
| 75 | 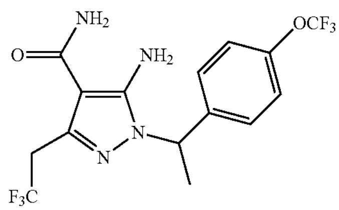 [SMILES: CC(c1ccc(OC(F)(F)F)cc1)n1nc(CC(F)(F)F)c(C(N)=O)c1N] | 5-amino-3-(2,2,2-trifluoroethyl)-1-(1-(4-(trifluoromethoxy)phenyl)ethyl)-1H-pyrazole-4-carboxamide | Calc'd 397.1, found 397.1 |
| 76 | 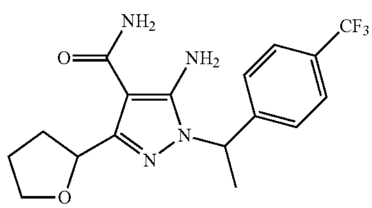 [SMILES: CC(c1ccc(C(F)(F)F)cc1)n1nc(C2CCCO2)c(C(N)=O)c1N] | 5-amino-3-(tetrahydrofuran-2-yl)-1-(1-(4-(trifluoromethyl)phenyl)ethyl)-1H-pyrazole-4-carboxamide | Calc'd 369.1, found 368.7 |
| 77 | 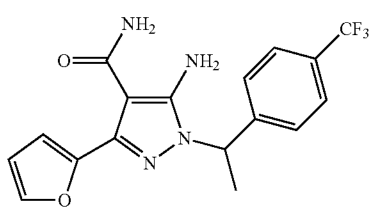 [SMILES: CC(c1ccc(C(F)(F)F)cc1)n1nc(-c2ccco2)c(C(N)=O)c1N] | 5-amino-3-(furan-2-yl)-1-(1-(4-(trifluoromethyl)phenyl)ethyl)-1H-pyrazole-4-carboxamide | Calc'd 365.1, found 365.2 |
| 78 | 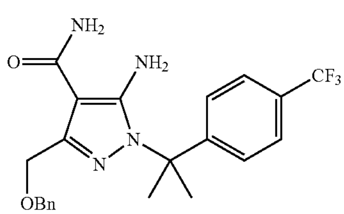 [SMILES: CC(C)(c1ccc(C(F)(F)F)cc1)n1nc(COCc2ccccc2)c(C(N)=O)c1N] | 5-amino-3-((benzyloxy)methyl)-1-(2-(4-(trifluoromethyl)phenyl)propan-2-yl)-1H-pyrazole-4-carboxamide | Calc'd 433.4, found 433.4 |
| 79 | 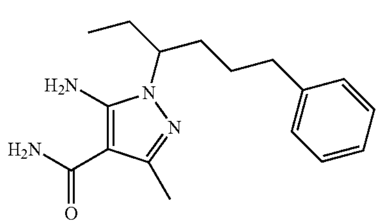 [SMILES: CCC(CCCc1ccccc1)n1nc(C)c(C(N)=O)c1N] | 5-amino-3-methyl-1-(6-phenylhexan-3-yl)-1H-pyrazole-4-carboxamide | Calc'd 301.2, found 301.2 |

TABLE 7-continued

The following compounds were prepared using procedures similar to those described in Preparatory Example 50 using appropriate starting materials.

| Prep Ex# | Structure | IUPAC Name | Exact Mass [M + H]+ |
|---|---|---|---|
| 80 | 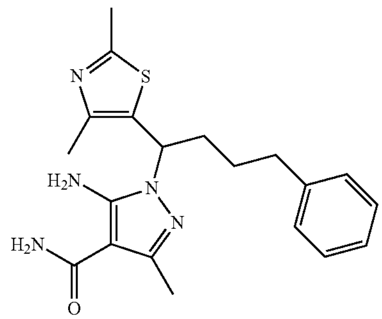 [SMILES: Cc1nc(C)c(C(CCCc2ccccc2)n2nc(C)c(C(N)=O)c2N)s1] | 5-amino-1-(1-(2,4-dimethylthiazol-5-yl)-4-phenylbutyl)-3-methyl-1H-pyrazole-4-carboxamide | Calc'd 384.2, found 384.1 |
| 81 | 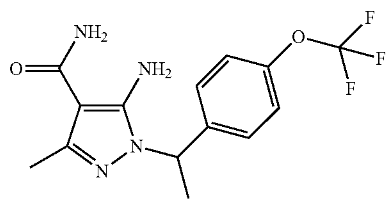 [SMILES: Cc1nn(C(C)c2ccc(OC(F)(F)F)cc2)c(N)c1C(N)=O] | 5-amino-3-methyl-1-(1-(4-(trifluoromethoxy)phenyl)ethyl)-1H-pyrazole-4-carboxamide | Calc'd 329.1, found 329.1 |

PREPARATORY EXAMPLE 82

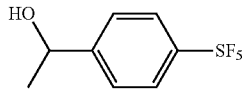

1-(4-(Pentafluorothio)phenyl)ethanol (Scheme 11)

To a solution of 1-(4-(pentafluorothio)phenyl)ethanone (0.50 g, 2.0 mmol) in MeOH (8.0 mL) was added NaBH$_4$ (11 g, 3.1 mmol) in portions at 0° C. The reaction mixture was stirred for 1 h at 0° C. whereupon the resulting solution was quenched with 2M aqueous hydrochloric acid (4 mL). The mixture was diluted with brine (10 mL) and extracted with EtOAc (3×10 mL). The organic layers were combined, dried over Na$_2$SO$_4$, filtered, and concentrated under reduced pressure to afford the title compound as a liquid. $^1$H NMR (400 MHz, CD$_3$OD) δ: 7.79 (d, J=8.8 Hz, 2H), 7.56 (d, J=8.4 Hz, 2H), 4.94-4.91 (m, 1H), 1.46 (d, J=6.4 Hz, 3H).

TABLE 8

The following compounds were prepared using procedures similar to those described in Preparatory Example 62 using appropriate starting materials.

| Prep Ex# | Structure | IUPAC Name | $^1$H NMR or Exact Mass [M + H]+ |
|---|---|---|---|
| 83 | 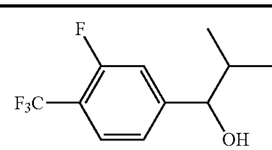 | 1-(3-fluoro-4-(trifluoromethyl)phenyl)-2-methylpropan-1-ol | $^1$H NMR (400 MHz, CDCl$_3$) δ: 7.60-7.50 (m, 1H), 7.20-7.10 (m, 2H), 4.51 (d, J = 6.0 Hz, 1H), 1.97 (heptet, J = 6.8 Hz, 1H), 0.97 (d, J = 6.8 Hz, 3H), 0.90 (d, J = 6.8 Hz, 3H) |
| 84 | 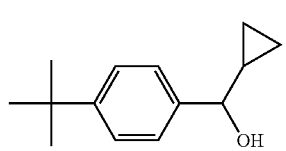 | (4-(tert-butyl)phenyl)(-cyclopropyl)methanol | $^1$H NMR (300 MHz, CDCl$_3$) δ: 7.42-7.30 (m 4H) 3.98 (d, J = 8.4 Hz, 1H), 1.32 (s, 9H), 1.29-1.10 (m, 1H), 0.70-0.22 (m, 4H). |
| 85 | 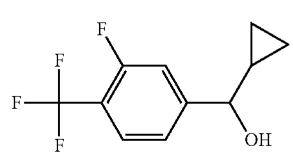 [SMILES: OC(c1ccc(C(F)(F)F)c(F)c1)C1CC1] | cyclopropyl(3-fluoro-4-(trifluoromethyl)phenyl)methanol | $^1$H NMR (400 MHz, CDCl$_3$) δ: 7.63-7.53 (m, 1H) 7.38-7.20 (m, 2H), 4.09-4.00 (m, 1H) 2.00-1.85 (br, 1H), 1.20-1.03 (m, 1H), 1.70-1.50 (m, 2H), 1.50-1.40 (m, 2H). |

TABLE 8-continued

The following compounds were prepared using procedures similar to those described in Preparatory Example 62 using appropriate starting materials.

| Prep Ex# | Structure | IUPAC Name | $^1$H NMR or Exact Mass [M + H]$^+$ |
|---|---|---|---|
| 86 | 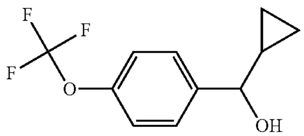 [SMILES: OC(c1ccc(OC(F)(F)F)cc1)C1CC1] | cyclopropyl(4-(trifluoromethoxy)phenyl)methanol | $^1$H NMR (300 MHz, CDCl$_3$) δ: 7.46 (d, J = 8.7 Hz, 2H), 7.20 (d, J = 8.1 Hz, 2H), 4.02 (d, J = 8.7 Hz, 1H), 1.80-1.50 (br, 1H), 1.21-1.09 (m, 1H), 0.69-0.50 (m, 2H), 0.50-0.29 (m, 2H). |
| 87 | 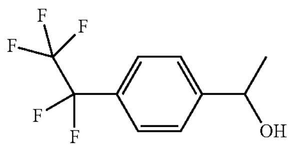 [SMILES: CC(O)c1ccc(C(F)(F)C(F)(F)F)cc1] | 1-(4-(perfluoroethyl)phenyl)ethan-1-ol | $^1$H NMR (400 MHz, CDCl$_3$) δ: 7.61 (d, J = 8.4 Hz, 2H), 7.54 (d, J = 8.4 Hz, 2H), 5.01 (q, J = 6.8 Hz, 1H), 1.90-1.70 (br, 1H), 1.54 (d, J = 6.4 Hz, 3H) |
| 88 | 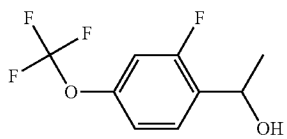 | 1-(2-fluoro-4-(trifluoromethoxy)phenyl)ethan-1-ol | $^1$H NMR (400 MHz, CDCl$_3$) δ: 7.58-7.49 (m, 1H), 7.04 (d, J = 8.4 Hz, 1H), 6.91-6.83 (m, 1H), 5.19 (q, J = 6.8 Hz, 1H), 1.90-1.60 (br, 1H), 1.51 (d, J = 6.4 Hz, 3H) |
| 89 | 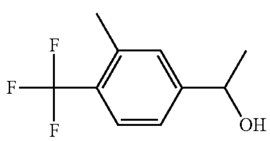 | 1-(3-methyl-4-(trifluoromethyl)phenyl)ethan-1-ol | $^1$H NMR (400 MHz, CDCl$_3$) δ: 7.61 (d, J = 8.0 Hz, 1H), 7.31 (d, J = 8.4 Hz, 1H), 7.30 (s, 1H), 4.94 (q, J = 6.4 Hz, 1H), 2.51 (s, 3H), 1.89-1.70 (br, 1H), 1.52 (d, J = 6.4 Hz, 3H). |
| 90 | 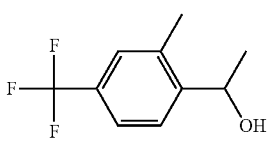 | 1-(2-methyl-4-(trifluoromethyl)phenyl)ethan-1-ol | $^1$H NMR (300 MHz, CDCl$_3$) δ: 7.66 (d, J = 8.1 Hz, 1H), 7.49 (d, J = 8.1 Hz, 1H), 7.38 (s, 1H), 5.17 (q, J = 6.3 Hz, 1H), 2.39 (s, 3H), 1.69-1.52 (br, 1H), 1.42 (d, J = 6.6 Hz, 3H) |
| 91 | 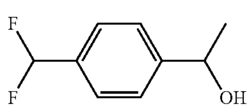 | 1-(4-(difluoromethyl)phenyl)ethan-1-ol | $^1$H NMR (300 MHz, DMSO-d$_6$) δ: 7.47 (d, J = 8.7 Hz, 2H), 7.43 (d, J = 8.4 Hz, 2H), 6.96 (t, J = 56.1 Hz, 1H), 4.81-4.65 (m, 1H), 1.28 (d, J = 6.3 Hz, 3H). |
| 92 | 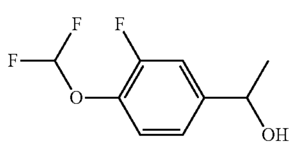 | 1-(4-(difluoromethoxy)-3-fluorophenyl)ethan-1-ol | $^1$H NMR (300 MHz, CDCl$_3$) δ: 7.29-7.07 (m, 3H), 6.53 (t, J = 73.5 Hz, 1H), 4.89 (q, J = 6.3 Hz, 1H), 1.48 (d, J = 6.6 Hz, 3H) |
| 93 | 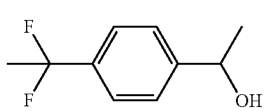 | 1-(4-(1,1-difluoroethyl)phenyl)ethan-1-ol | $^1$H NMR (400 MHz, DMSO-d$_6$) δ: 7.51 (d, J = 8.4 Hz, 2H), 7.45 (d, J = 8.4 Hz, 2H), 4.82-4.69 (m, 1H), 1.96 (t, J = 18.8 Hz, 3H), 1.33 (d, J = 6.4 Hz, 3H). |
| 94 | 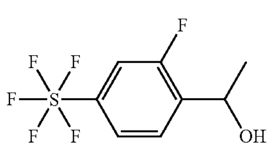 [SMILES: CC(O)c1ccc(S(F)(F)(F)(F)F)cc1F] | 1-(2-fluoro-4-(pentafluorosulfanyl)phenyl)ethan-1-ol | $^1$H NMR (300 MHz, CDCl$_3$) δ: 7.70-7.52 (m, 2H), 7.50-7.40 (m, 1H), 5.23 (q, J = 6.6 Hz, 1H), 1.52 (d, J = 6.6 Hz, 3H) |
| 95 | 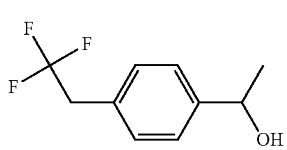 | 1-(4-(2,2,2-trifluoroethyl)phenyl)ethan-1-ol | $^1$H NMR (400 MHz, CDCl$_3$) δ: 7.39 (d, J = 5.6 Hz, 2H), 7.29 (d, J = 6.0 Hz, 2H), 4.95-4.85 (m, 1H), 3.38 (q, J = 10.8 Hz, 2H), 1.54 (d, J = 9.6 Hz, 3H). |

TABLE 8-continued

The following compounds were prepared using procedures similar to those described in Preparatory Example 62 using appropriate starting materials.

| Prep Ex# | Structure | IUPAC Name | ¹H NMR or Exact Mass [M + H]⁺ |
|---|---|---|---|
| 96 | 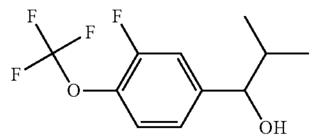 [SMILES: CC(C)C(O)c1ccc(OC(F)(F)F)c(F)c1] | 1-(3-fluoro-4-(trifluoromethoxy)phenyl)-2-methylpropan-1-ol | ¹H NMR (400 MHz, CDCl₃) δ: 7.31-7.21 (m, 2H), 7.13-7.10 (m, 1H), 4.44 (d, J = 6.4 Hz, 1H), 1.99-1.90 (m, 1H), 0.98 (d, J = 6.8 Hz, 3H), 0.87 (d, J = 6.8 Hz, 3H). |
| 97 | 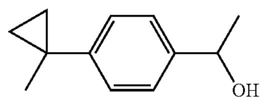 | 1-(4-(1-methylcyclopropyl)phenyl)ethan-1-ol | ¹H NMR (400 MHz, CDCl₃) δ: 7.32 (d, J = 8.0 Hz, 2H), 7.26 (d, J = 8.4 Hz, 2H), 4.89 (q, J = 6.4 Hz, 1H), 1.88-1.72 (br, 1H), 1.51 (d, J = 6.4 Hz, 3H), 1.45 (s, 3H), 0.92-0.83 (m, 2H), 0.79-0.70 (m, 2H). |
| 98 | 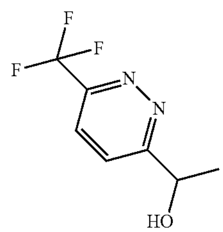 | 1-(6-(trifluoromethyl)pyridazin-3-yl)ethan-1-ol | ¹H NMR (400 MHz, CDCl₃) δ: 7.87 (d, J = 8.8 Hz, 1H), 7.85 (d, J = 9.2 Hz, 1H), 5.32 (q, J = 6.8 Hz, 1H), 1.68 (d, J = 6.4 Hz, 3H). |
| 99 | 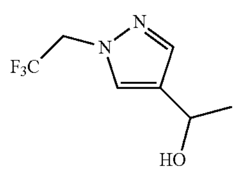 | 1-(1-(2,2,2-trifluoroethyl)-1H-pyrazol-4-yl)ethan-1-ol | ¹H NMR (400 MHz, CDCl₃) δ: 7.55 (s, 1H), 7.46 (s, 1H), 4.91 (q, J = 6.4 Hz, 1H), 4.67 (q, J = 4.4 Hz, 2H), 2.15-2.01 (br, 1H), 1.53 (d, J = 6.0 Hz, 3H). |
| 100 | 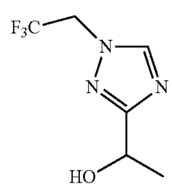 | 1-(1-(2,2,2-Trifluoroethyl)-1H-1,2,4-triazol-3-yl)ethanol | ¹H NMR (400 MHz, CDCl₃) δ: 8.19 (s, 1H), 5.01 (q, J = 6.8 Hz, 1H), 4.79-4.73 (m, 2H), 2.70 (br, 1H), 1.61 (d, J = 6.4 Hz, 3H) |
| 101 | 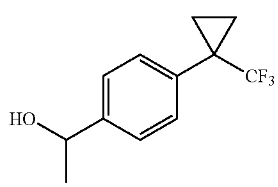 [SMILES: CC(O)c1ccc(C2(C(F)(F)F)CC2)cc1] | 1-(4-(1-(Trifluoromethyl)cyclopropyl)phenyl)ethanol | ¹H NMR (400 MHz, CDCl₃) δ: 7.44 (d, J = 8.4 Hz, 2H), 7.34 (d, J = 8.4 Hz, 2H), 4.90 (q, J = 6.4 Hz, 1H), 1.49 (d, J = 6.4 Hz, 3H), 1.41-1.33 (m, 2H), 1.05-0.97 (m, 2H). |

PREPARATORY EXAMPLE 102

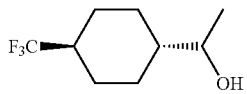

(R)- and (S)-1-((Trans)-4-(trifluoromethyl)cyclohexyl)ethan-1-ol (Scheme 12)

Step 1.
((Trans)-4-(Trifluoromethyl)cyclohexyl)methanol

To a solution of (1R,4R)-4-(trifluoromethyl)cyclohexanecarboxylic acid (0.50 g, 2.6 mmol) in THF (3 mL) at −20° C. was added a 1 M solution of B₂H₆ in THF (2.6 mL, 2.6 mmol) dropwise. The reaction mixture was allowed to warm to RT and was stirred for 2 h. The mixture was cooled to 0° C. whereupon the mixture was quenched with water (10 mL) and extracted with ethyl acetate (3×20 mL). The organic layers were combined and washed with brine (2×20 mL). The organic layer was dried over Na₂SO₄, filtered, and concentrated under reduced pressure to afford the title compound as an oil. ¹H NMR (400 MHz, DMSO-d₆) δ 3.48 (d, J=6.0 Hz, 2H), 2.07-1.84 (m, 5H), 1.59-1.22 (m, 3H), 1.18-0.98 (m, 2H)

Step 2.
(Trans)-4-(Trifluoromethyl)cyclohexanecarbaldehyde

The title compound was prepared using procedures similar to those described in Preparatory Example 25 using ((trans)-4-(trifluoromethyl)cyclohexyl)methanol to afford a liquid. ¹H NMR (400 MHz, DMSO-d₆) δ 9.65 (s, 1H), 2.14-1.78 (m, 5H), 1.48-1.22 (m, 3H), 1.18-0.92 (m, 2H).

Step 3. (R)- or (S)-1-((trans)-4-(Trifluoromethyl)cyclohexyl)ethanol

To a solution of (trans)-4-(trifluoromethyl)cyclohexanecarbaldehyde (0.140 g, 0.8 mmol) in THF (5 mL) at 0° C. under N$_2$ was added dropwise a 1 M solution of MeMgBr in THF (0.9 mL, 0.9 mmol) dropwise. The reaction solution was stirred at 0° C. for 2 where upon the mixture was quenched with sat. aq. NH$_4$Cl (10 mL) and water (10 mL). The mixture was extracted with EtOAc (3×15 mL) and the organic layers were combined and washed with brine (2×15 mL). The organic layer was dried over Na$_2$SO$_4$, filtered, and concentrated under reduced pressure. The residue was purified by silica gel column chromatography (0-20% EtOAc in petroleum ether) to afford the title compound as an oil. $^1$H NMR (400 MHz, DMSO-d$_6$) δ 3.65-3.52 (m, 1H), 2.13-1.86 (m, 5H), 1.38-1.22 (m, 3H), 1.19 (d, J=4.0 Hz, 3H), 1.15-0.92 (m, 2H).

TABLE 9

The following compounds were prepared using procedure from Step 3 of Preparatory Example 102 using appropriate starting materials.

| Prep Ex #. | Structure | IUPAC Name | $^1$H NMR or Exact Mass [M + H]$^+$ |
|---|---|---|---|
| 103 | 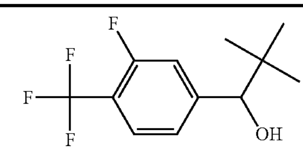 | 1-(3-fluoro-4-(trifluoromethyl)phenyl)-2,2-dimethylpropan-1-ol | $^1$H NMR (400 MHz, CDCl$_3$) δ: 7.60-7.50 (m, 1H), 7.21-7.13 (m, 2H), 0.95 (s, 9H). |
| 104 | 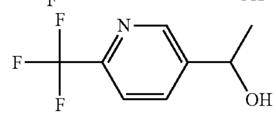 | 1-(6-(trifluoromethyl)pyridin-3-yl)ethan-1-ol | MS = 192.1 (+ESI) |

PREPARATORY EXAMPLE 105

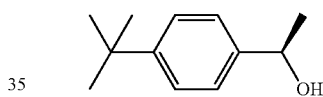

(R)-1-(4-tert-Butylphenyl)ethanol (Scheme 13)

To a solution of 1-(4-tert-butylphenyl)ethanone (0.50 g, 2.8 mmol) in CH$_2$Cl$_2$ (15 mL) at RT was added (S)-(−)-2-methyl CBS oxazaborolidine solution (1 M in THF, 0.6 mL, 0.6 mmol) dropwise to the mixture. BH$_3$ DMS (0.30 mL, 2.84 mmol, 10 M) was added dropwise to the solution over 1 h at RT and the solution was stirred for 16 h. The reaction mixture was diluted with brine (25 mL) and extracted with ethyl acetate (3×25 mL). The organic layers were combined and were concentrated under reduced pressure. The residue was purified by silica gel column chromatography (0-30% EtOAc in petroleum ether) to afford the title compound as a solid. $^1$H NMR (300 MHz, CD$_3$OD) δ: 7.37 (d, J=8.4 Hz, 2H), 7.28 (d, J=8.1 Hz, 2H), 4.80 (q, J=6.6 Hz, 1H), 1.43 (d, J=6.3 Hz, 3H), 1.31 (s, 9H).

TABLE 10

The following compounds were prepared using procedures similar to those described in Preparatory Example 105 using appropriate starting materials.

| Prep. Ex. # | Structure | IUPAC Name | $^1$H NMR or Exact Mass [M + H]$^+$ |
|---|---|---|---|
| 106 | 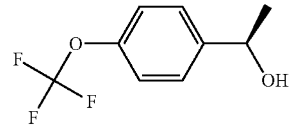 | (R)-1-(4-(trifluoromethoxy)phenyl)ethan-1-ol | $^1$H NMR (400 MHz, CDCl$_3$) δ: 7.40 (d, J = 7.2 Hz, 2H), 7.19 (d, J = 7.2 Hz, 2H), 4.92 (q, J = 6.4 Hz, 1H), 1.92-1.83 (br, 1H), 1.49 (d, J = 6.4 Hz, 3H). |

TABLE 10-continued

The following compounds were prepared using procedures similar to those described in Preparatory Example 105 using appropriate starting materials.

| Prep. Ex. # | Structure | IUPAC Name | $^1$H NMR or Exact Mass [M + H]$^+$ |
|---|---|---|---|
| 107 | 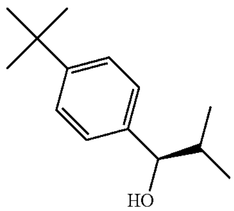 | (R)-1-(4-(tert-butyl)phenyl)-2-methylpropan-1-ol | $^1$H NMR (300 MHz, CDCl$_3$) δ: 7.34 (d, J = 8.4 Hz, 2H), 7.22 (d, J = 9.0 Hz, 2H), 4.31 (d, J = 7.2 Hz, 1H), 2.03-1.87 (m, 1H), 1.30 (s, 9H), 0.99 (d, J = 6.9 Hz, 3H), 0.79 (d, J = 6.6 Hz, 3H). |
| 108 | 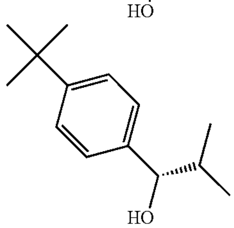 | (S)-1-(4-(tert-butyl)phenyl)-2-methylpropan-1-ol | $^1$H NMR (300 MHz, CDCl$_3$) δ: 7.34 (d, J = 8.4 Hz, 2H), 7.22 (d, J = 9.0 Hz, 2H), 4.31 (d, J = 7.2 Hz, 1H), 2.03-1.87 (m, 1H), 1.30 (s, 9H), 0.99 (d, J = 6.9 Hz, 3H), 0.79 (d, J = 6.6 Hz, 3H). |

PREPARATORY EXAMPLE 109

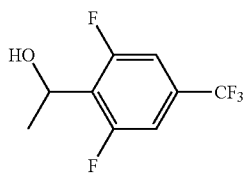

1-(2,6-Difluoro-4-(trifluoromethyl)phenyl)ethanol
(Scheme 14)

Step 1.
2,6-Difluoro-4-(trifluoromethyl)benzaldehyde

To a solution of 1,3-difluoro-5-(trifluoromethyl)benzene (1.50 g, 8.24 mmol) in Et$_2$O (70 mL) at −78° C. under N$_2$ was added 2M n-BuLi in pentane (4.5 mL, 9.9 mmol) dropwise. The mixture was stirred at −78° C. for 1 h whereupon a solution of DMF (3.19 mL, 41.2 mmol) in Et$_2$O (5 mL) was added to the mixture dropwise. The reaction mixture was stirred at −78° C. for another 1 h whereupon sat. aq. NH$_4$Cl solution (50 mL) was added to the mixture which was extracted with Et$_2$O (3×50 mL). The organic layers were combined, dried over Na$_2$SO$_4$, filtered, and concentrated under reduced pressure to afford the title compound as an oil. $^1$H NMR (400 MHz, CDCl$_3$) δ: 8.92 (s, 1H), 7.36-7.13 (m, 2H).

Step 2.
1-(2,6-Difluoro-4-(trifluoromethyl)phenyl)ethanol

The title compound was prepared using procedures similar to those described in step 3 of Preparatory Example 102 using 2,6-difluoro-4-(trifluoromethyl)benzaldehyde to afford an oil. $^1$H NMR (400 MHz, CDCl$_3$) δ: 7.26-7.12 (m, 2H), 5.30 (q, J=6.8 Hz, 1H), 1.67 (s, J=6.8 Hz, 3H).

TABLE 11

The following compounds were prepared according the literature as listed below in the table.

| Prep Ex# | Structure | IUPAC Name | CAS# or literature reference |
|---|---|---|---|
| 110 | 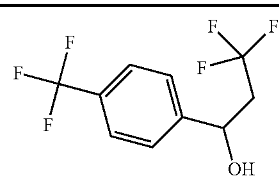 | 3,3,3-trifluoro-1-(4-(trifluoromethyl)phenyl)propan-1-ol | *Synlett* 2014, 25, 1307 |
| 111 | 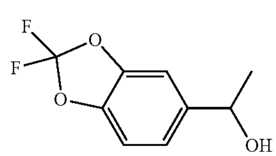 | 1-(2,2-difluorobenzo[d][1,3]dioxol-5-yl)ethan-1-ol | US20050209274 A1 |

TABLE 11-continued

The following compounds were prepared according the literature as listed below in the table.

| Prep Ex# | Structure | IUPAC Name | CAS# or literature reference |
|---|---|---|---|
| 112 | 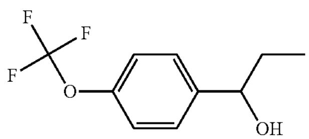 | 1-(4-(trifluoromethoxy)phenyl)propan-1-ol | J. Med. Chem. 2011, 54(6), 5639-5669. |
| 113 | 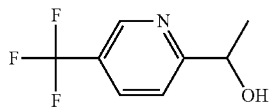 | 1-(5-(trifluoromethyl)pyridin-2-yl)ethan-1-ol | WO 2011137024 A1 |
| 114 | 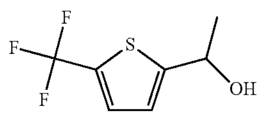 | 1-(5-(trifluoromethyl)thiophen-2-yl)ethan-1-ol | WO 2013147183 A1 |

PREPARATORY EXAMPLE 115

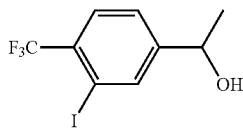

1-(3-Iodo-4-(trifluoromethyl)phenyl)ethanol (Scheme 12)

Step 1. 3-Iodo-4-(trifluoromethyl)benzaldehyde

To a solution of (3-iodo-4-(trifluoromethyl)phenyl)methanol (2.2 g, 7.28 mmol) in DCM (40 mL) was added Dess-Martin periodinane (4.63 g, 10.93 mmol) at RT. The mixture was stirred for 2 h, diluted with water, and extracted with DCM (3×100 mL). The organic layers were combined, dried over $Na_2SO_4$, filtered, and concentrated under reduced pressure. The residue was purified by silica gel column chromatography (0-50% EtOAc in hexanes) to afford the title compound as a white solid. $^1$H NMR (CDCl$_3$, 500 MHz) δ: 10.19 (s, 1H), 8.21 (s, 1H), 7.99 (d, J=6.5 Hz, 1H), 7.73 (d, J=6.5 Hz, 1H).

Step 2. 1-(3-Iodo-4-(trifluoromethyl)phenyl)ethanol

To a suspension of 3-iodo-4-(trifluoromethyl)benzaldehyde (1.3 g, 4.3 mmol) in anhydrous THF (20 mL) at 0° C. under $N_2$ was added a solution of methylmagnesium bromide (3M in ether, 2.89 ml, 8.67 mmol) dropwise. The resulting mixture was allowed to warm to RT and stir for 2 h. Sat. aq. NH$_4$Cl (15 mL) was added to the mixture which was extracted with EtOAc (3×100 mL) and the organic layers were combined. The organic layer was dried over $Na_2SO_4$, filtered, and concentrated under reduced pressure. The residue was purified by silica gel column chromatography (0-100% EtOAc in hexanes) to afford the title compound as an oil. $^1$H NMR (CDCl$_3$, 500 MHz) δ: 8.09 (s, 1H), 7.92 (d, J=7.1 Hz, 1H), 7.08 (d, J=7.1 Hz, 1H), 5.12 (m, 1H), 2.19 (br s, 1H), 1.43 (d, J=7.5 Hz, 3H).

PREPARATORY EXAMPLE 116

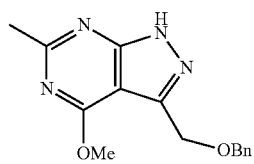 [SMILES: COc1nc(C)nc2[nH]nc(COCc3ccccc3)c12]

3-((Benzyloxy)methyl)-4-methoxy-6-methyl-1H-pyrazolo[3,4-d]pyrimidine (Scheme 15)

Step 1. 2-(Benzyloxy)-1-(2,4-dichloro-6-methoxypyrimidin-5-yl)ethanone

To a solution of 2,4-dichloro-6-methoxypyrimidine (13.3 g, 74.3 mmol) in THF (400 mL) at −30° C. was added 2,2,6,6-tetramethylpiperidinylmagnesium chloride lithium chloride complex (18.0 g, 74.3 mmol). The reaction mixture was purged with $N_2$ three times and the mixture was stirred under nitrogen atmosphere for 2 h at −30° C. A 1 M solution of CuCN.2LiCl in THF (74 mL, 74.3 mmol) was added dropwise to the mixture at −30° C. and was stirred at this temperature for 30 min. 2-(Benzyloxy)acetyl chloride (27.4 g, 0.15 mol) was added dropwise to the mixture which was allowed to gradually warm to RT and stir for 16 h. The resulting solution was quenched with 20% aqueous NaHCO$_3$ (50 mL), diluted with water (500 mL), and extracted with EtOAc (3×500 mL). The combined organic layers were washed with brine (1×300 mL), dried over $Na_2SO_4$, filtered, and concentrated under reduced pressure. The residue was purified by silica gel column chromatography (0-10% of EtOAc in hexanes) to afford the title compound as a liquid. $^1$H NMR (400 MHz, DMSO-d$_6$) δ: 7.41-7.30 (m, 5H), 4.58 (s, 2H), 4.54 (s, 2H), 4.00 (s, 3H).

Step 2. 3-(Benzyloxymethyl)-6-chloro-4-methoxy-1H-pyrazolo[3,4-d]pyrimidine

To a solution of 2-(benzyloxy)-1-(2,4-dichloro-6-methoxypyrimidin-5-yl)ethanone (3.50 g, 10.7 mmol) in EtOH (40 mL) at RT was added hydrazine hydrate (0.546 g, 10.7 mmol) followed by Et$_3$N (1.30 g, 12.8 mmol). The reaction solution heated to 40° C., stirred for 16 h, and cooled to RT. The mixture was diluted with brine (100 mL) and extracted with EtOAc (3×100 mL). The organic layers were combined and washed with water (100 mL). The organic layer was dried over Na$_2$SO$_4$, filtered, and concentrated under reduced pressure. The residue was purified by silica gel column chromatography (0-33% EtOAc in hexanes) to afford the title compound as a solid. MS=305.2, 307.2 (+ESI).

Step 3. 3-(Benzyloxymethyl)-4-methoxy-6-methyl-1H-pyrazolo[3,4-d]pyrimidine

To a solution of 3-((benzyloxy)methyl)-6-chloro-4-methoxy-1H-pyrazolo[3,4-d]pyrimidine (0.80 g, 2.6 mmol) in dioxane (15 mL) at RT was added a 1M solution of AlMe$_3$ in THF (7.9 mL, 7.9 mmol) at RT. Pd(PPh$_3$)$_4$ (0.61 g, 0.5 mmol) was added to the mixture which was purged with nitrogen three times. The mixture was heated to 70° C., stirred under N$_2$ for 16 h, and recooled to RT. The mixture was quenched with 20% aqueous K$_2$CO$_3$ (15 mL), diluted with water (70 mL) and extracted with EtOAc (3×100 mL). The organic layers were combined, washed with brine (100 mL), dried over Na$_2$SO$_4$, filtered, and concentrated under reduced pressure. The residue was purified by silica gel column chromatography (0-20% ethyl acetate in petroleum ether) to afford the title compound as a solid. MS=285.1 (+ESI).

PREPARATORY EXAMPLE 117

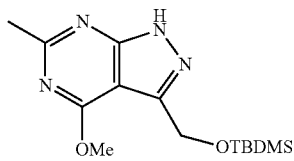 [SMILES: COc1nc(C)nc2[nH]nc(CO[Si](C)(C)C(C)(C)C)c12]

3-(((tert-Butyldimethylsilyl)oxy)methyl)-4-methoxy-6-methyl-1H-pyrazolo[3,4-d]pyrimidine (Scheme 16)

Step 1. (4-Methoxy-6-methyl-1H-pyrazolo[3,4-d]pyrimidin-3-yl)methanol

To a 500-mL round-bottom flask charged with 3-((benzyloxy)methyl)-4-methoxy-6-methyl-1H-pyrazolo[3,4-d]pyrimidine (2.0 g, 7.0 mmol) from Preparatory Example 116 in MeOH/THF (70 mL/70 mL) at RT was added 20% Pd(OH)$_2$ (1.5 g, 2.1 mmol) to afford a heterogeneous mixture. The resulting mixture was degassed under house vacuum and filled with N$_2$ and this protocol was repeated three additional times. The resulting mixture was degassed under house vacuum and filled with H$_2$ instead and this protocol was repeated three additional times. The mixture was heated to 55° C. and was stirred under a H$_2$ balloon for 2 days. The mixture was cooled to RT, purged with N$_2$ and was filtered through a pad of Celite™ which was washed with MeOH (5×30 mL). The resulting filtrate was concentrated under reduced pressure to afford the title compound as a solid. MS=195.1 (M+1)

Step 2. 3-(((tert-Butyldimethylsilyl)oxy)methyl)-4-methoxy-6-methyl-1H-pyrazolo[3,4-d]pyrimidine To a round bottom flask charged with (4-methoxy-6-methyl-1H-pyrazolo[3,4-d]pyrimidin-3-yl)methanol (1.30 g, 6.7 mmol) from in DMF (22 mL) at RT was added imidazole (1.4 g, 20.1 mmol) followed by TBDMSCl (3.0 g, 20.1 mmol) to afford a light yellow, homogenous solution. The resulting mixture was stirred for 12 h at RT whereupon the mixture was treated with brine (1×30 mL) and was extracted with EtOAc (3×150 mL). The organic layers were combined, washed with brine (1×40 mL), dried over Na$_2$SO$_4$, filtered, and concentrated under reduced pressure. The crude solid was diluted with hexanes (50 mL), stirred vigorously for 15 min, stopped, and the solvent was decanted off the solid. This protocol was repeated two additional times whereupon the remaining solid was placed under high vacuum to afford the title compound as a solid. MS=309.2 (M+1)

EXAMPLE 1

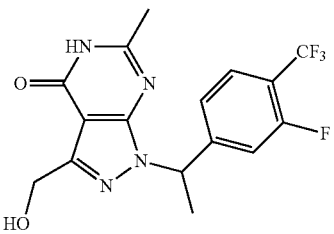 [SMILES: Cc1nc2c(c(CO)nn2C(C)c2ccc(C(F)(F)F)c(F)c2)c(=O)[nH]1]

1-(1-(3-Fluoro-4-(trifluoromethyl)phenyl)ethyl)-3-(hydroxymethyl)-6-methyl-1H-pyrazolo[3,4-d]pyrimidin-4(5H)-one (Scheme 17)

Step 1. 3-((Benzyloxy)methyl)-1-(1-(3-fluoro-4-(trifluoromethyl)phenyl)ethyl)-6-methyl-1H-pyrazolo[3,4-d]pyrimidin-4(5H)-one To a solution of 5-amino-3-((benzyloxy)methyl)-1-(1-(3-fluoro-4-(trifluoromethyl)phenyl)ethyl)-1H-pyrazole-4-carboxamide (0.13 g, 0.30 mmol) in 1,4-dioxane (2 mL) at RT was added AcCl (0.032 mL, 0.40 mmol) dropwise. The resulting solution was heated to 100° C., stirred for 48 h, and was cooled to RT. The mixture was partitioned between water (2 mL) and EtOAc (10 mL) and the layers were separated. The aqueous layer was extracted with EtOAc (3×5 mL) and the organic layers were combined. The organic layer was washed with brine, dried over Na₂SO₄, filtered, and concentrated under reduced pressure. The residue was purified by silica gel column chromatography (0-40% EtOAc in petroleum ether) to afford the title compound as an oil. MS=461.0 (+ESI).

Step 2. 1-(1-(3-Fluoro-4-(trifluoromethyl)phenyl) ethyl)-3-(hydroxymethyl)-6-methyl-1H-pyrazolo[3,4-d]pyrimidin-4(5H)-one To a solution of 3-((benzyloxy)methyl)-1-(1-(3-fluoro-4-(trifluoromethyl)phenyl)ethyl)-6-methyl-1H-pyrazolo[3,4-d]pyrimidin-4(5H)-one (40 mg, 0.09 mmol) in EtOH (3 mL) at RT was added 20% palladium hydroxide on carbon (30.5 mg, 0.043 mmol) at RT. The reaction mixture was evacuated, filled with H₂, and was stirred under a H₂ balloon for 24 h. The resulting solution was purged to N₂, filtered, and concentrated under reduced pressure. The residue was purified by preparative HPLC (Gemini, 40-45% acetonitrile in water (0.05% NH₄HCO₃)) to afford the title compound (Example 1) as a solid. MS=371.0 (+ESI). ¹H NMR (300 MHz, DMSO-d₆): δ 12.30-12.10 (br, 1H), 7.81-7.69 (m, 1H), 7.42 (d, J=12.0 Hz, 1H), 7.25 (d, J=8.1 Hz, 1H), 6.09 (q, J=5.3 Hz, 1H), 5.19 (t, J=6.0 Hz, 1H), 4.66 (d, J=5.7 Hz, 2H), 2.35 (s, 3H), 1.83 (d, J=6.9 Hz, 3H).

EXAMPLE 2

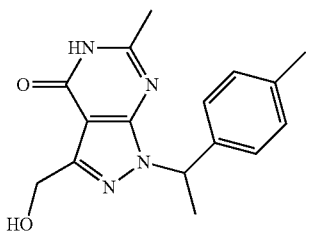 [SMILES: Cc1ccc(C(C)n2nc(CO)c3c(=O)[nH]c(C)nc32)cc1]

3-(Hydroxymethyl)-6-methyl-1-(1-p-tolylethyl)-1H-pyrazolo[3, 4-d]pyrimidin-4(5H)-one (Scheme 17)

Step 1. 3-((Benzyloxy)methyl)-6-methyl-1-(1-(p-tolyl)ethyl)-1,5-dihydro-4H-pyrazolo[3,4-d]pyrimidin-4-one The title compound was prepared using procedures similar to those described in step 1 of Example 1 using 5-amino-3-((benzyloxy)methyl)-1-(1-(p-tolyl)ethyl)-1H-pyrazole-4-carboxamide to afford a solid. MS=389.2 (+ESI).

Step 2. 3-(Hydroxymethyl)-6-methyl-1-(1-p-tolyl-ethyl)-1H-pyrazolo[3,4-d]pyrimidin-4(5H)-one To a mixture of 3-(benzyloxymethyl)-1-(1-(4-cyclopropylphenyl)ethyl)-6-methyl-1H-pyrazolo[3,4-d]pyrimidin-4 (5H)-one (0.12 g, 0.30 mmol) in MeOH (1 mL) at RT was added 10% Pd/C (10.2 mg, 0.05 mmol). The reaction was stirred under a hydrogen balloon for 3 h and was filtered through a pad of Celite™ which was washed with MeOH (3×2 mL). The filtrate was concentrated under vacuum and the residue was purified by preparative HPLC (X Bridge RP C¹⁸, 30-70% ACN in water (0.1% TFA)) to afford the title compound (Example 2) as a solid. ¹H NMR (300 MHz, CD₃OD) δ: 7.22 (d, J=7.8 Hz, 2H), 7.01 (d, J=7.8 Hz, 2H), 6.18-5.95 (m, 1H), 4.82 (s, 2H), 2.47 (s, 3H), 1.99-1.72 (m, 4H), 1.00-0.84 (m, 2H), 0.69-0.56 (m, 2H); MS=299.2 (+ESI).

EXAMPLE 3

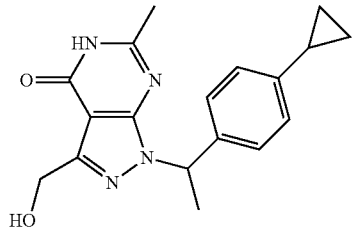 [SMILES: Cc1nc2c(c(CO)nn2C(C)c2ccc(C3CC3)cc2)c(=O)[nH]1]

1-(1-(4-Cyclopropylphenl)ethyl)-3-(hydroxymethyl)-6-methyl-1H-pyrazolo[3,4-d]pyrimidin-4(5H)-one (Scheme 17)

Step 1. 3-(Benzyloxymethyl)-1-(1-(4-cyclopropyl-phenyl)ethyl)-6-methyl-1H-pyrazolo[3,4-d]pyrimi-din-4(5H)-one The title compound was prepared using procedures similar to those described in step 1 of Example 1 using 5-amino-3-((benzyloxy)methyl)-1-(1-(4-cyclopropylphenyl)ethyl)-1H-pyrazole-4-carboxamide to afford a solid. MS=415.3 (+ESI).

Step 2. 1-(Cyclopropyl(4-(trifluoromethyl)phenyl) methyl)-3-(hydroxymethyl)-6-methyl-1H-pyrazolo [3,4-d]pyrimidin-4(5H)-one To a mixture of 3-((benzyloxy)methyl)-1-(1-(4-cyclopropylphenyl)ethyl)-6-methyl-1H-pyrazolo[3,4-d]pyrimidin-4 (5H)-one (0.12 g, 0.30 mmol) in CH₂Cl₂ (1 mL) at 0° C. was added a solution of boron trichloride (1 M in CH₂Cl₂, 0.6 mL, 0.6 mmol). The reaction was stirred for 3 h at 0° C. whereupon the mixture was quenched with MeOH (10 mL). The mixture was concentrated under vacuum and the residue was purified by preparative HPLC (X Bridge RP C18, 30-70% ACN in water (0.1% TFA)) to afford the title compound (Example 3) as a solid. ¹H NMR (300 MHz, CD₃OD) δ: 7.22 (d, J=7.8 Hz, 2H), 7.01 (d, J=7.8 Hz, 2H), 6.18-5.95 (m, 1H), 4.82 (s, 2H), 2.47 (s, 3H), 1.99-1.72 (m, 4H), 1.00-0.84 (m, 2H), 0.69-0.56 (m, 2H); MS (+ESI) m/z=325.2.

TABLE 12

The following compounds were prepared using procedures similar to those described in Examples 1, 2, and 3 using appropriate starting materials and the listed deprotection conditions. Where an "*" appears in any structure in a table it is intended to indicate a single stereoisomer where the absolute stereochemistry has not been determined.
Deprotection conditions: A: 20% Pd(OH)$_2$/H$_2$; B: 10% Pd/C/H$_2$; C: BCl$_3$

| Ex # | Structure | IUPAC Name | Exact Mass [M + H]$^+$ or [M + Na]$^+$ | DC |
|---|---|---|---|---|
| 4 | 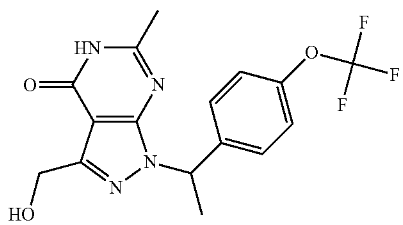 [SMILES: Cc1nc2c(c(CO)nn2C(C)c2ccc(OC(F)(F)F)cc2)c(=O)[nH]1] | 3-(Hydroxymethyl)-6-methyl-1-(1-(4-(trifluoromethoxy)phenypethyl)-1H-pyrazolo[3,4-d]pyrimidin-4(5H)-one | Calc'd 369.1, found 369.0 | B |
| 5 | 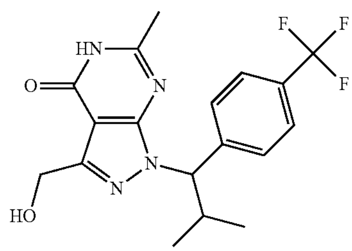 [SMILES: Cc1nc2c(c(CO)nn2C(c2ccc(C(F)(F)F)cc2)C(C)C)c(=O)[nH]1] | 3-(Hydroxymethyl)-6-methyl-1-(2-methyl-1-(4-(trifluoromethyl)phenyl)propyl)-1H-pyrazolo[3,4-d]pyrimidin-4(5H)-one | Calc'd 381.2, found 381.2 | B |
| 6 | 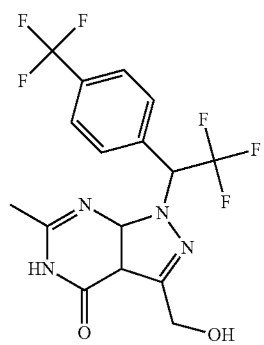 [SMILES: CC1=NC2C(C(=O)N1)C(CO)=NN2C(c1ccc(C(F)(F)F)cc1)C(F)(F)F] | 3-(Hydroxymethyl)-6-methyl-1-(2,2,2-trifluoro-1-(4-(trifluoromethyl)phenyl)ethyl)-1H-pyrazolo[3,4-d]pyrimidin-4(5H)-one | Calc'd 407.1, found 407.2 | B |
| 7 | 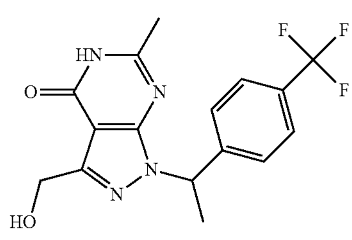 [SMILES: Cc1nc2c(c(CO)nn2C(C)c2ccc(C(F)(F)F)cc2)c(=O)[nH]1] | 3-(Hydroxymethyl)-6-methyl-1-(1-(4-(trifluoromethyl)phenyl)ethyl)-1H-pyrazolo[3,4-d]pyrimidin-4(5H)-one | Calc'd 353.1, found 353.2 | A |
| 8 | 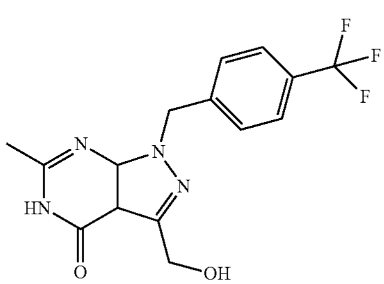 [SMILES: CC1=NC2C(C(=O)N1)C(CO)=NN2Cc1ccc(C(F)(F)F)cc1] | 3-(Hydroxymethyl)-6-methyl-1-[4-(trifluoromethyl)benzyl]-1,5-dihydro-4H-pyrazolo[3,4-d]pyrimidin-4-one | Calc'd 339.1, found 339.3 | A |

TABLE 12-continued

The following compounds were prepared using procedures similar to those described in Examples 1, 2, and 3 using appropriate starting materials and the listed deprotection conditions. Where an "*" appears in any structure in a table it is intended to indicate a single stereoisomer where the absolute stereochemistry has not been determined.
Deprotection conditions: A: 20% Pd(OH)$_2$/H$_2$; B: 10% Pd/C/H$_2$; C: BCl$_3$

| Ex # | Structure | IUPAC Name | Exact Mass [M + H]$^+$ or [M + Na]$^+$ | DC |
|---|---|---|---|---|
| 9 | 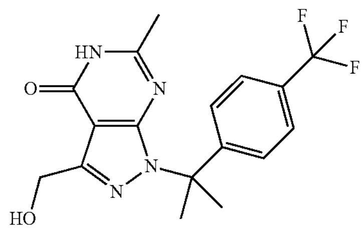 [SMILES: Cc1nc2c(c(CO)nn2C(C)(C)c2ccc(C(F)(F)F)cc2)c(=O)[nH]1] | 3-(Hydroxymethyl)-6-methyl-1-{1-methyl-1-[4-(trifluoromethyl)phenyl]ethyl}-1,5-dihydro-4H-pyrazolo[3,4-d]pyrimidin-4-one | Calc'd 367.1, found 367.3 | A |

DC = Deprotection Conditions

TABLE 13

The following compounds were prepared using procedures similar to those described in Examples 1, 2, and 3 using appropriate starting materials and the deprotection conditions listed. Racemic products were separated using the chiral columns specified in the table. For those pairs of enantiomers, the faster-eluting isomer is always listed first in this table.
Deprotection conditions: A: 20% Pd(OH)$_2$/H$_2$; B: 10% Pd/C/H$_2$; C: BCl$_3$

| Ex # | Structure | IUPAC Name | Exact Mass [M + H]$^+$ or [M + Na]$^+$ | Chiral column | DC |
|---|---|---|---|---|---|
| 10 | 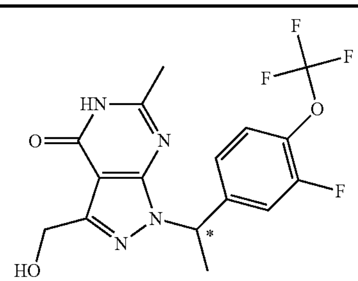 | (R)- or (S)-1-(1-(3-Fluoro-4-(trifluoromethoxy)phenyl)ethyl)-3-(hydroxymethyl)-6-methyl-1H-pyrazolo[3,4-d]pyrimidin-4(5H)-one | Calc'd 387.1, found 387.1 | Chiralpak IA | B |
| 11 | 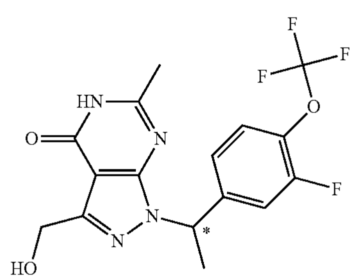 [SMILES: Cc1nc2c(c(CO)nn2C(C)c2ccc(OC(F)(F)F)c(F)c2)c(=O)[nH]1] | (S)- or (R)-1-(1-(3-Fluoro-4-(trifluoromethoxy)phenyl)ethyl)-3-(hydroxymethyl)-6-methyl-1H-pyrazolo[3,4-d]pyrimidin-4(5H)-one | Calc'd 387.1, found 387.1 | Chiralpak IA | B |
| 12 | 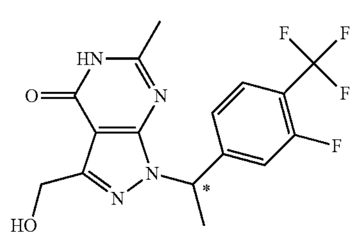 [SMILES: Cc1nc2c(c(CO)nn2C(C)c2ccc(C(F)(F)F)c(F)c2)c(=O)[nH]1] | (R)- or (S)-1-(1-(3-Fluoro-4-(trifluoromethyl)phenyl)ethyl)-3-(hydroxymethyl)-6-methyl-1H-pyrazolo[3,4-d]pyrimidin-4(5H)-one | Calc'd 371.1, found 371.1 | Chiralpak IA | A |

TABLE 13-continued

The following compounds were prepared using procedures similar to those
described in Examples 1, 2, and 3 using appropriate starting materials and the deprotection
conditions listed. Racemic products were separated using the chiral columns specified in the table.
For those pairs of enantiomers, the faster-eluting isomer is always listed first in this table.
Deprotection conditions: A: 20% Pd(OH)$_2$/H$_2$; B: 10% Pd/C/H$_2$; C: BCl$_3$

| Ex # | Structure | IUPAC Name | Exact Mass [M + H]$^+$ or [M + Na]$^+$ | Chiral column | DC |
|---|---|---|---|---|---|
| 13 | 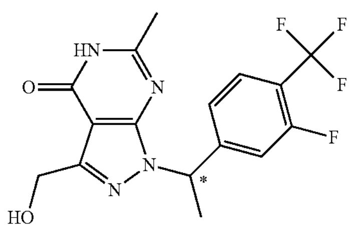 [SMILES: Cc1nc2c(c(CO)nn2C(C)c2ccc(C(F)(F)F)c(F)c2)c(=O)[nH]1] | (S)- or (R)-1-(1-(3-Fluoro-4-(trifluoromethyl)phenyl)ethyl)-3-(hydroxymethyl)-6-methyl-1H-pyrazolo[3,4-d]pyrimidin-4(5H)-one | Calc'd 371.1, found 371.1 | Chiralpak IA | A |
| 14 | 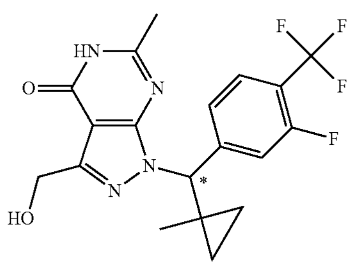 [SMILES: Cc1nc2c(c(CO)nn2C(c2ccc(C(F)(F)F)c(F)c2)C2(C)CC2)c(=O)[nH]1] | (R)- or (S)-1-((3-Fluoro-4-(trifluoromethyl)phenyl)(1-methylcyclopropyl)methyl)-3-(hydroxymethyl)-6-methyl-1H-pyrazolo[3,4-d]pyrimidin-4(5H)-one | Calc'd 411.1, found 411.3 | Chiralpak IA | A |
| 15 | 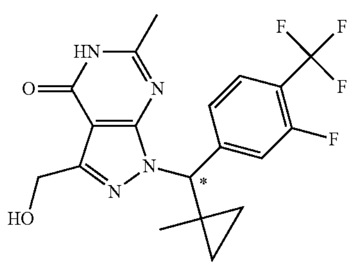 [SMILES: Cc1nc2c(c(CO)nn2C(c2ccc(C(F)(F)F)c(F)c2)C2(C)CC2)c(=O)[nH]1] | (S)- or (R)-1-((3-Fluoro-4-(trifluoromethyl)phenyl)(1-methylcyclopropyl)methyl)-3-(hydroxymethyl)-6-methyl-1H-pyrazolo[3,4-d]pyrimidin-4(5H)-one | Calc'd 411.1, found 411.3 | Chiralpak IA | A |
| 16 | 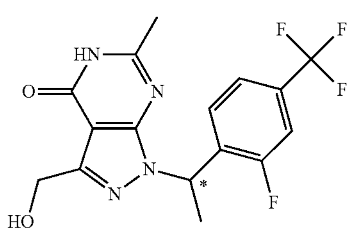 [SMILES: Cc1nc2c(c(CO)nn2C(C)c2ccc(C(F)(F)F)cc2F)c(=O)[nH]1] | (R)- or (S)-1-(1-(2-Fluoro-4-(trifluoromethyl)phenyl)ethyl)-3-(hydroxymethyl)-6-methyl-1H-pyrazolo[3,4-d]pyrimidin-4(5H)-one | Calc'd 371.1, found 371.2 | XSelect CSH Prep18 OBD | A |
| 17 | 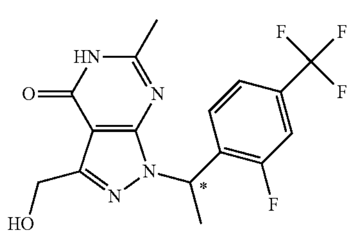 [SMILES: Cc1nc2c(c(CO)nn2C(C)c2ccc(C(F)(F)F)cc2F)c(=O)[nH]1] | (S)- or (R)-1-(1-(2-Fluoro-4-(trifluoromethyl)phenyl)ethyl)-3-(hydroxymethyl)-6-methyl-1H-pyrazolo[3,4-d]pyrimidin-4(5H)-one | Calc'd 371.1, found 371.2 | XSelect CSH Prep18 OBD | A |

TABLE 13-continued

The following compounds were prepared using procedures similar to those described in Examples 1, 2, and 3 using appropriate starting materials and the deprotection conditions listed. Racemic products were separated using the chiral columns specified in the table. For those pairs of enantiomers, the faster-eluting isomer is always listed first in this table.
Deprotection conditions: A: 20% Pd(OH)$_2$/H$_2$; B: 10% Pd/C/H$_2$; C: BCl$_3$

| Ex # | Structure | IUPAC Name | Exact Mass [M + H]$^+$ or [M + Na]$^+$ | Chiral column | DC |
|---|---|---|---|---|---|
| 18 | 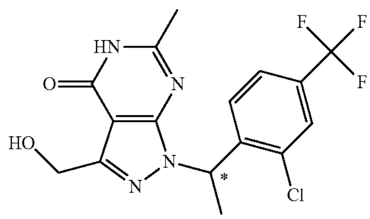 [SMILES: Cc1nc2c(c(CO)nn2C(C)c2ccc(C(F)(F)F)cc2Cl)c(=O)[nH]1] | (R)- or (S)-1-(1-(2-Chloro-4-(trifluoromethyl)phenyl)ethyl)-3-(hydroxymethyl)-6-methyl-1H-pyrazolo[3,4-d]pyrimidin-4(5H)-one | Calc'd 387.1, found 387.1 | Chiralpak IA | C |
| 19 | 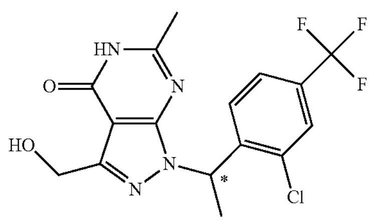 [SMILES: Cc1nc2c(c(CO)nn2C(C)c2ccc(C(F)(F)F)cc2Cl)c(=O)[nH]1] | (S)- or (R)-1-(1-(2-Chloro-4-(trifluoromethyl)phenyl)ethyl)-3-(hydroxymethyl)-6-methyl-1H-pyrazolo[3,4-d]pyrimidin-4(5H)-one | Calc'd 387.1, found 387.1 | Chiralpak IA | C |
| 20 | 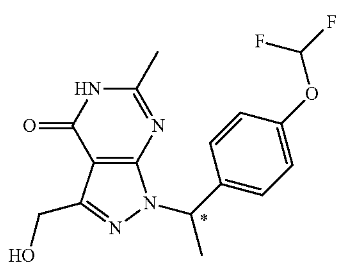 [SMILES: Cc1nc2c(c(CO)nn2C(C)c2ccc(OC(F)F)cc2)c(=O)[nH]1] | (R)- or (S)-1-(1-(4-(Difluoromethoxy)phenyl)ethyl)-3-(hydroxymethyl)-6-methyl-1H-pyrazolo[3,4-d]pyrimidin-4(5H)-one | Calc'd 351.1, found 351.1 | Chiralpak IA | C |
| 21 | 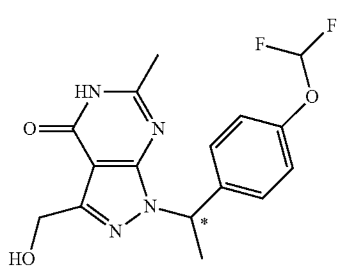 [SMILES: Cc1nc2c(c(CO)nn2C(C)c2ccc(OC(F)F)cc2)c(=O)[nH]1] | (S)- or (R)-1-(1-(4-(Difluoromethoxy)phenyl)ethyl)-3-(hydroxymethyl)-6-methyl-1H-pyrazolo[3,4-d]pyrimidin-4(5H)-one | Calc'd 351.1, found 351.1 | Chiralpak IA | C |
| 22 | 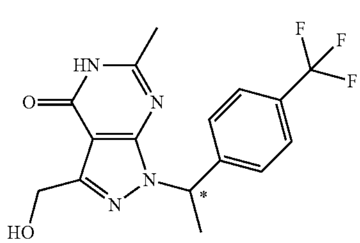 | (R)- or (S)-3-(Hydroxymethyl)-6-methyl-1-(1-(4-(trifluoromethylthio)phenyl)ethyl)-1H-pyrazolo[3,4-d]pyrimidin-4(5H)-one | Calc'd 385.1, found 385.2 | Chiralpak IA | C |

TABLE 13-continued

*The following compounds were prepared using procedures similar to those described in Examples 1, 2, and 3 using appropriate starting materials and the deprotection conditions listed. Racemic products were separated using the chiral columns specified in the table. For those pairs of enantiomers, the faster-eluting isomer is always listed first in this table. Deprotection conditions: A: 20% Pd(OH)$_2$/H$_2$; B: 10% Pd/C/H$_2$; C: BCl$_3$*

| Ex # | Structure | IUPAC Name | Exact Mass [M + H]$^+$ or [M + Na]$^+$ | Chiral column | DC |
|---|---|---|---|---|---|
| 23 | 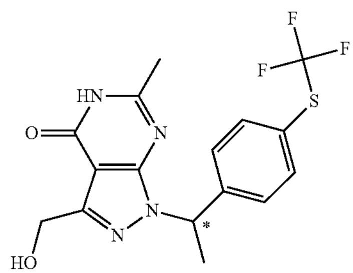 [SMILES: Cc1nc2c(c(CO)nn2C(C)c2ccc(SC(F)(F)F)cc2)c(=O)[nH]1] | (S)- or (R)-3-(Hydroxymethyl)-6-methyl-1-(1-(4-(trifluoromethylthio)phenyl)ethyl)-1H-pyrazolo[3,4-d]pyrimidin-4(5H)-one | Calc'd 385.1, found 385.1 | Chiralpak IA | C |
| 24 | 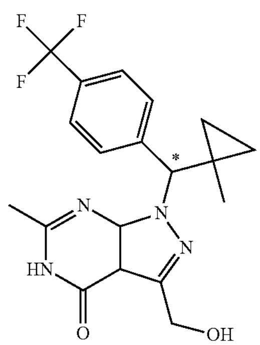 [SMILES: CC1=NC2C(C(=O)N1)C(CO)=NN2C(c1ccc(C(F)(F)F)cc1)C1(C)CC1] | (R)- or (S)-3-(Hydroxymethyl)-6-methyl-1-((1-methylcyclopropyl)(4-(trifluoromethyl)phenyl)methyl)-1H-pyrazolo[3,4-d]pyrimidin-4(5H)-one | Calc'd 393.2, found 393.3 | Chiracel OJ-H | C |
| 25 | 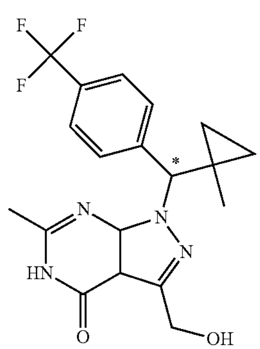 [SMILES: CC1=NC2C(C(=O)N1)C(CO)=NN2C(c1ccc(C(F)(F)F)cc1)C1(C)CC1] | (S)- or (R)-3-(Hydroxymethyl)-6-methyl-1-((1-methylcyclopropyl)(4-(trifluoromethyl)phenyl)methyl)-1H-pyrazolo[3,4-d]pyrimidin-4(5H)-one | Calc'd 393.2, found 393.3 | Chiracel OJ-H | C |
| 26 | 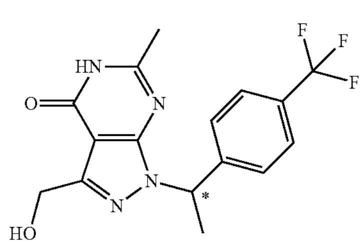 | (R)- or (S)-3-(Hydroxymethyl)-6-methyl-1-{1-[4-(trifluoromethyl)phenyl]ethyl}-1,5-dihydro-4H-pyrazolo[3,4-d]pyrimidin-4-one | Calc'd 353.1, found 353.0 | AD | A |

TABLE 13-continued

The following compounds were prepared using procedures similar to those described in Examples 1, 2, and 3 using appropriate starting materials and the deprotection conditions listed. Racemic products were separated using the chiral columns specified in the table. For those pairs of enantiomers, the faster-eluting isomer is always listed first in this table.
Deprotection conditions: A: 20% Pd(OH)$_2$/H$_2$; B: 10% Pd/C/H$_2$; C: BCl$_3$

| Ex # | Structure | IUPAC Name | Exact Mass [M + H]$^+$ or [M + Na]$^+$ | Chiral column | DC |
|---|---|---|---|---|---|
| 27 | 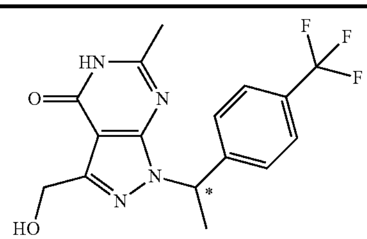 | (S)- or (R)-3-(Hydroxymethyl)-6-methyl-1-{1-[4-(trifluoromethyl)phenyl]ethyl]-1,5-dihydro-4H-pyrazolo[3,4-d]pyrimidin-4-one | Calc'd 353.1, found 353.0 | AD | A |

DC=Deprotection Conditions

EXAMPLE 28

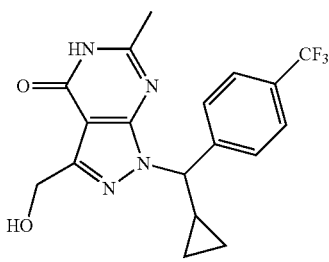 [SMILES: Cc1nc2c(c(CO)nn2C(c2ccc(C(F)(F)F)cc2)C2CC2)c(=O)[nH]1]

1-(Cyclopropyl(4-(trifluoromethyl)phenyl)methyl)-3-(hydroxymethyl)-6-methyl-1H-pyrazolo[3,4-d]pyrimidin-4(5H)-one (Scheme 18)

Step 1. 3-((Benzyloxy)methyl)-1-(cyclopropyl(4-(trifluoromethyl)phenyl)methyl)-6-methyl-1H-pyrazolo[3,4-d]pyrimidin-4(5H)-one To a solution of 5-amino-3-((benzyloxy)methyl)-1-(cyclopropyl(4-(trifluoromethyl)phenyl)methyl)-1H-pyrazole-4-carboxamide (90.0 mg, 0.20 mmol) in EtOH (10 mL) were added EtOAc (0.10 mL, 1.2 mmol) and NaH (0.16 g, 4.1 mmol) at 0° C. The solution was heated to 90° C., stirred for 16 h, and was cooled to RT. The mixture was concentrated under reduced pressure and the resultant residue was dissolved in EtOAc (40 mL). The organic layer was washed with water (1×20 mL), brine (1×10 mL), dried over Na$_2$SO$_4$, filtered and concentrated under reduced pressure. The residue was purified by silica gel column chromatography (0-60% EtOAc in petroleum ether) to obtain the title compound as a solid. MS=469.2 (+ESI).

Step 2. 1-(Cyclopropyl(4-(trifluoromethyl)phenyl) methyl)-3-(hydroxymethyl)-6-methyl-1H-pyrazolo [3,4-d]pyrimidin-4(5H)-one The title compound was prepared using procedures similar to those described in step 2 of Example 1 using 3-((benzyloxy)methyl)-1-(cyclopropyl(4-(trifluoromethyl)phenyl)methyl)-6-methyl-1H-pyrazolo[3,4-d]pyrimidin-4(5H)-one in methanol to afford the title compound (Example 28) as a solid. MS=379.2 (+ESI); $^1$H NMR (300 MHz, DMSO-d$_6$) δ: 12.25-12.15 (br, 1H), 7.72 (d, J=8.4 Hz, 2H), 7.62 (d, J=8.1 Hz, 2H), 5.18 (t, J=6.0 Hz, 1H), 5.10 (d, J=10.2 Hz, 1H), 4.66 (d, J=6.0 Hz, 2H), 2.34 (s, 3H), 1.96-1.79 (m, 1H), 0.79-0.26 (m, 4H).

EXAMPLE 29

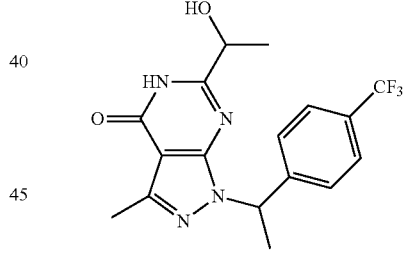

6-(1-Hydroxyethyl)-3-methyl-1-(1-(4-(trifluoromethyl)phenyl)ethyl)-1H-pyrazolo[3,4-d]pyrimidin-4 (5H)-one (Scheme 17)

The title compound was prepared using procedures similar to those described in step 1 of Example 2 using 5-amino-3-methyl-1-(1-(4-(trifluoromethyl)phenyl)ethyl)-1H-pyrazole-4-carboxamide and ethyl 2-hydroxypropanoate to afford the title compound (Example 29) as a solid. MS=367.0 (+ESI). $^1$H NMR (300 MHz, DMSO-d$_6$) δ: 11.50-11.40 (br, 1 H), 7.70 (d, J=8.4 Hz, 2H), 7.50 (d, J=8.4 Hz, 2H), 6.06 (q, J=6.9 Hz, 1H), 5.74-5.68 (br, 1H), 4.56 (q, J=6.9 Hz, 1H), 2.48 (s, 3H), 1.85 (d, J=6.9 Hz, 3H), 1.38 (d, J=6.6 Hz, 3H).

TABLE 14

The following compounds were prepared using procedures similar to those described in Example 29 using appropriate starting materials.

| Ex# | Structure | IUPAC Name | Exact Mass [M + H]+ |
|---|---|---|---|
| 30 | 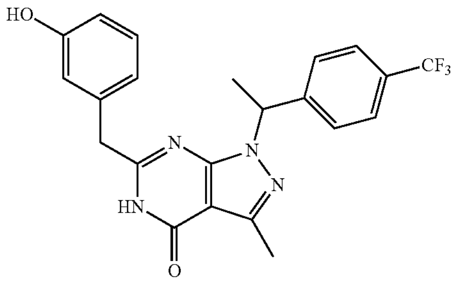 [SMILES: Cc1nn(C(C)c2ccc(C(F)(F)F)cc2)c2nc(Cc3cccc(O)c3)[nH]c(=O)c12] | 6-(3-Hydroxybenzyl)-3-methyl-1-(1-(4-(trifluoromethyl)phenyl)ethyl)-1H-pyrazolo[3,4-d]pyrimidin-4(5H)-one | Calc'd 429.1, found 429.3 |
| 31 | 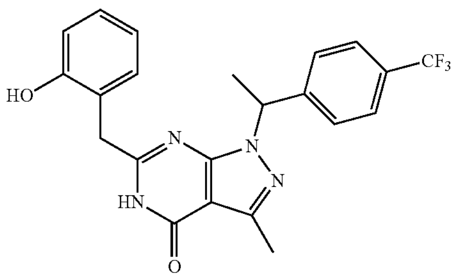 [SMILES: Cc1nn(C(C)c2ccc(C(F)(F)F)cc2)c2nc(Cc3ccccc3O)[nH]c(=O)c12] | 6-(2-Hydroxybenzyl)-3-methyl-1-(1-(4-(trifluoromethyl)phenyl)ethyl)-1H-pyrazolo[3,4-d]pyrimidin-4(5H)-one | Calc'd 429.1, found 429.3 |
| 32 | 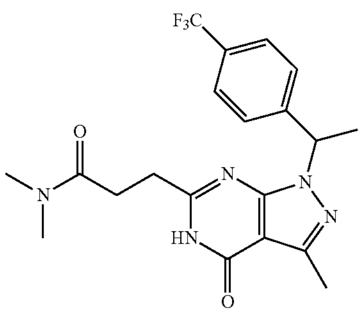 [SMILES: Cc1nn(C(C)c2ccc(C(F)(F)F)cc2)c2nc(CCC(=O)N(C)C)[nH]c(=O)c12] | N,N-Dimethyl-3-(3-methyl-4-oxo-1-(1-(4-(trifluoromethyl)phenyl)ethyl)-4,5-dihydro-1H-pyrazolo[3,4-d]pyrimidin-6-yl)propanamide | Calc'd 422.2, found 422.1 |
| 33 | 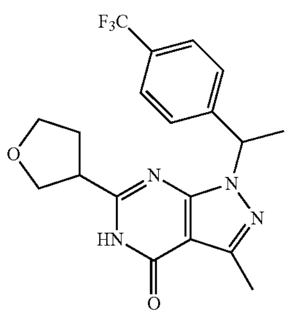 [SMILES: Cc1nn(C(C)c2ccc(C(F)(F)F)cc2)c2nc(C3CCOC3)[nH]c(=O)c12] | 3-Methyl-6-(tetrahydrofuran-3-yl)-1-(1-(4-(trifluoromethyl)phenyl)ethyl)-1H-pyrazolo[3,4-d]pyrimidin-4(5H)-one | Calc'd 393.1, found 393.3 |
| 34 | 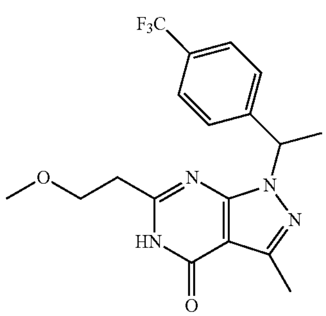 [SMILES: COCCc1nc2c(c(C)nn2C(C)c2ccc(C(F)(F)F)cc2)c(=O)[nH]1] | 6-(2-Methoxyethyl)-3-methyl-1-(1-(4-(trifluoromethyl)phenyl)ethyl)-1H-pyrazolo[3,4-d]pyrimidin-4(5H)-one | Calc'd 381.1, found 381.1 |

TABLE 14-continued

The following compounds were prepared using procedures similar to those described in Example 29 using appropriate starting materials.

| Ex# | Structure | IUPAC Name | Exact Mass [M + H]+ |
|---|---|---|---|
| 35 | 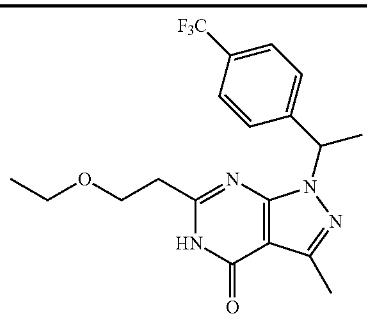 | 6-(2-Ethoxyethyl)-3-methyl-1-(1-(4-(trifluoromethyl)phenyl)ethyl)-1H-pyrazolo[3,4-d]pyrimidin-4(5H)-one | Calc'd 395.2, found 395.2 |

EXAMPLES 36 and 37

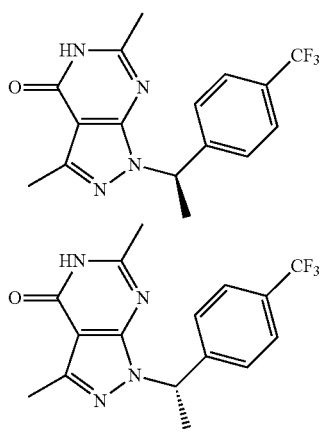

(R)- and (S)-3,6-Dimethyl-1-(1-(4-(trifluoromethyl)phenyl)ethyl)-1, 5-dihydro-4H-pyrazolo[3,4-d]pyrimidin-4-one (Scheme 18)

To a solution of 5-amino-3-methyl-1-(1-(4-(trifluoromethyl)phenyl)ethyl)-1H-pyrazole-4-carboxamide (100 mg, 0.32 mmol) in dioxane (1.6 mL) at RT under $N_2$ was added acetyl chloride (27.6 mg, 0.352 mmol). The resulting mixture was heated to 100° C., stirred for 1.5 h at this temperature, and was cooled to RT. The mixture was concentrated under reduced pressure and the residue was purified by silica gel column chromatography (0-5% MeOH in DCM) to afford the racemic title compound. The enantiopure title compounds were obtained by chiral SFC chromatography (OJ, 10% MeOH (0.2% DEA/$CO_2$)). The faster eluting enantiomer of the title compound (Example 36) was isolated as a solid. $^1$H NMR (CDCl$_3$, 500 MHz) δ: $^1$H NMR (CDCl$_3$, 500 MHz) δ: 11.72 (br s, 1 H); 7.56 (d, J=8.0 Hz, 2 H); 7.48 (d, J=8.0 Hz, 2 H); 6.04 (q, J=7.1 Hz, 1 H); 2.58 (s, 3 H); 2.51 (s, 3 H); 1.95 (d, J=7.1 Hz, 3 H). LC/MS (m/z): 337.1 (M+H)+. The slower eluting enantiomer of the title compound (Example 37) was isolated as a solid. $^1$H NMR (CDCl$_3$, 500 MHz) δ: $^1$H NMR (CDCl$_3$, 500 MHz) δ: 11.72 (br s, 1 H); 7.56 (d, J=8.0 Hz, 2 H); 7.48 (d, J=8.0 Hz, 2 H); 6.04 (q, J=7.1 Hz, 1 H); 2.58 (s, 3 H); 2.51 (s, 3H); 1.95 (d, J=7.1 Hz, 3 H). MS=337.1 (M+H)+.

TABLE 15

The following compounds were prepared using procedures similar to those described in Examples 36 and 37 using the appropriate starting materials.

| Ex# | Structure | IUPAC Name | Exact Mass [M + H]+ |
|---|---|---|---|
| 38 | 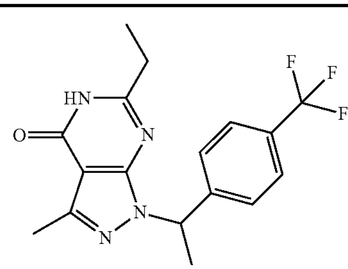 | 6-Ethyl-3-methyl-1-{1-[4-(trifluoromethyl)phenyl]ethyl}-1,5-dihydro-4H-pyrazolo[3,4-d]pyrimidin-4-one | Calc'd 351.1, found 351.1 |

TABLE 15-continued

The following compounds were prepared using procedures similar to those described in Examples 36 and 37 using the appropriate starting materials.

| Ex# | Structure | IUPAC Name | Exact Mass [M + H]+ |
|---|---|---|---|
| 39 | 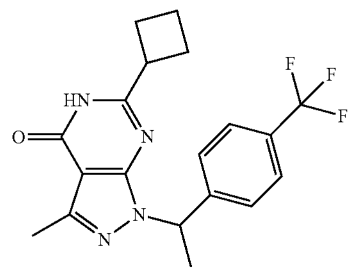 [SMILES: Cc1nn(C(C)c2ccc(C(F)(F)F)cc2)c2nc(C3CCC3)[nH]c(=O)c12] | 6-Cyclobutyl-3-methyl-1-{1-[4-(trifluoromethyl)phenyl]ethyl}-1,5-dihydro-4H-pyrazolo[3,4-d]pyrimidin-4-one | Calc'd 377.2, found 377.1 |
| 40 | 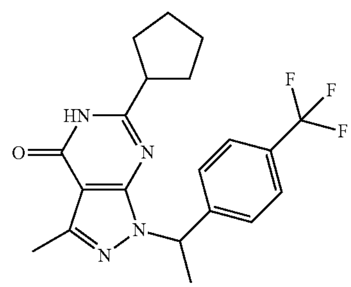 [SMILES: Cc1nn(C(C)c2ccc(C(F)(F)F)cc2)c2nc(C3CCCC3)[nH]c(=O)c12] | 6-Cyclopentyl-3-methyl-1-{1-[4-(trifluoromethyl)phenyl]ethyl}-1,5-dihydro-4H-pyrazolo[3,4-d]pyrimidin-4-one | Calc'd 391.2, found 391.2 |
| 41 | 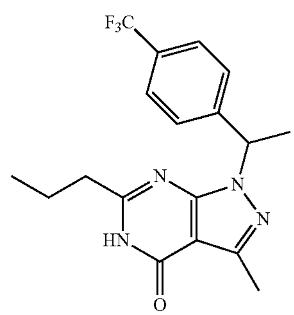 [SMILES: CCCc1nc2c(c(C)nn2C(C)c2ccc(C(F)(F)F)cc2)c(=O)[nH]1] | 3-Methyl-6-propyl-1-{1-[4-(trifluoromethyl)phenyl]ethyl}-1,5-dihydro-4H-pyrazolo[3,4-d]pyrimidin-4-one | Calc'd 365.2, found 365.2 |
| 42 | 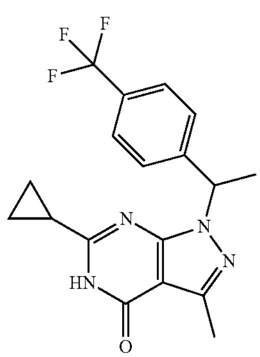 [SMILES: Cc1nn(C(C)c2ccc(C(F)(F)F)cc2)c2nc(C3CC3)[nH]c(=O)c12] | 6-Cyclopropyl-3-methyl-1-{1-[4-(trifluoromethyl)phenyl]ethyl}-1,5-dihydro-4H-pyrazolo[3,4-d]pyrimidin-4-one | Calc'd 363.1, found 363.2 |
| 43 | 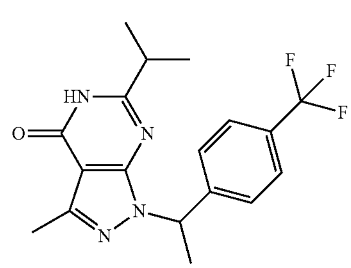 [SMILES: Cc1nn(C(C)c2ccc(C(F)(F)F)cc2)c2nc(C(C)C)[nH]c(=O)c12] | 3-Methyl-6-(1-methylethyl)-1-{1-[4-(trifluoromethyl)phenyl]ethyl}-1,5-dihydro-4H-pyrazolo[3,4-d]pyrimidin-4-one | Calc'd 365.2, found 365.2 |

TABLE 15-continued

The following compounds were prepared using procedures similar to those described in Examples 36 and 37 using the appropriate starting materials.

| Ex# | Structure | IUPAC Name | Exact Mass [M + H]+ |
|---|---|---|---|
| 44 | 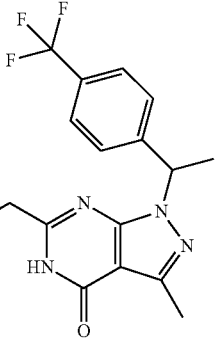 | 6-(3,4-Dimethoxybenzyl)-3-methyl-1-{1-[4-(trifluoromethyl)phenyl]ethyl}-1,5-dihydro-4H-pyrazolo[3,4-d]pyrimidin-4-one | Calc'd 473.2, found 473.1 |
| 45 | 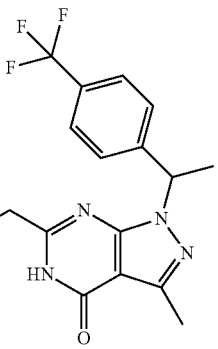 | 6-(3-Methoxybenzyl)-3-methyl-1-{1-[4-(trifluoromethyl)phenyl]ethyl}-1,5-dihydro-4H-pyrazolo[3,4-d]pyrimidin-4-one | Calc'd 443.2, found 443.1 |
| 46 | 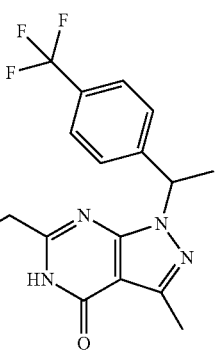 | 6-(4-Methoxybenzyl)-3-methyl-1-{1-[4-(trifluoromethyl)phenyl]ethyl}-1,5-dihydro-4H-pyrazolo[3,4-d]pyrimidin-4-one | Calc'd 443.2, found 443.1 |
| 47 | 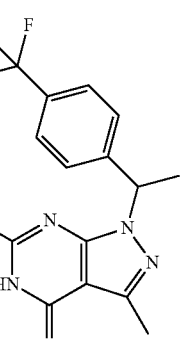 | 6-(3-Methoxyphenyl)-3-methyl-1-{1-[4-(trifluoromethyl)phenyl]ethyl}-1,5-dihydro-4H-pyrazolo[3,4-d]pyrimidin-4-one | Calc'd 429.2, found 429.4 |

TABLE 15-continued

The following compounds were prepared using procedures similar to those described in Examples 36 and 37 using the appropriate starting materials.

| Ex# | Structure | IUPAC Name | Exact Mass [M + H]+ |
|---|---|---|---|
| 48 | 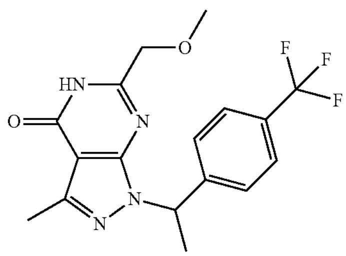 [SMILES: COCc1nc2c(c(C)nn2C(C)c2ccc(C(F)(F)F)cc2)c(=O)[nH]1] | 6-(Methoxymethyl)-3-methyl-1-{1-[4-(trifluoromethyl)phenyl]ethyl}-1,5-dihydro-4H-pyrazolo[3,4-d]pyrimidin-4-one | Calc'd 367.1, found 367.3 |
| 49 | 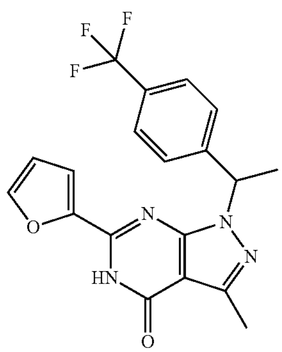 [SMILES: Cc1nn(C(C)c2ccc(C(F)(F)F)cc2)c2nc(-c3ccco3)[nH]c(=O)c12] | 6-Furan-2-yl-3-methyl-1-{1-[4-(trifluoromethyl)phenyl]ethyl}-1,5-dihydro-4H-pyrazolo[3,4-d]pyrimidin-4-one | Calc'd 389.1, found 389.3 |
| 50 | 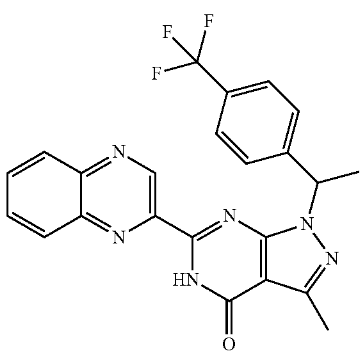 [SMILES: Cc1nn(C(C)c2ccc(C(F)(F)F)cc2)c2nc(-c3cnc4ccccc4n3)[nH]c(=O)c12] | 3-Methyl-6-quinoxalin-2-yl-1-{1-[4-(trifluoromethyl)phenyl]ethyl}-1,5-dihydro-4H-pyrazolo[3,4-d]pyrimidin-4-one | Calc'd 451.1, found 451.3 |
| 51 | 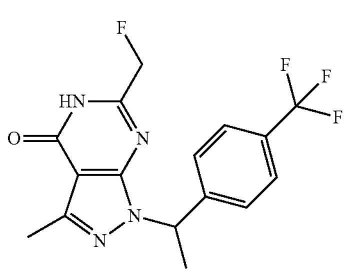 [SMILES: Cc1nn(C(C)c2ccc(C(F)(F)F)cc2)c2nc(CF)[nH]c(=O)c12] | 6-(Fluoromethyl)-3-methyl-1-{1-[4-(trifluoromethyl)phenyl]ethyl}-1,5-dihydro-4H-pyrazolo[3,4-d]pyrimidin-4-one | Calc'd 355.1, found 355.3 |

TABLE 15-continued

The following compounds were prepared using procedures similar to those described in Examples 36 and 37 using the appropriate starting materials.

| Ex# | Structure | IUPAC Name | Exact Mass [M + H]+ |
|---|---|---|---|
| 52 | 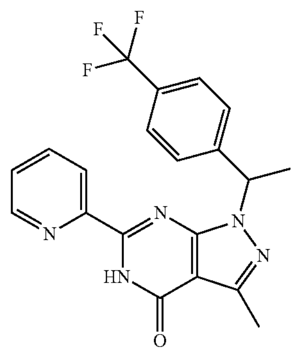 [SMILES: Cc1nn(C(C)c2ccc(C(F)(F)F)cc2)c2nc(-c3ccccn3)[nH]c(=O)c12] | 3-Methyl-6-pyridin-2-yl-1-{1-[4-(trifluoromethyl)phenyl]ethyl}-1,5-dihydro-4H-pyrazolo[3,4-d]pyrimidin-4-one | Calc'd 400.1, found 400.3 |
| 53 | 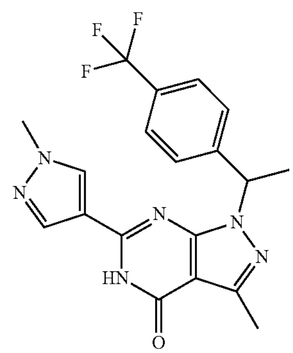 [SMILES: Cc1nn(C(C)c2ccc(C(F)(F)F)cc2)c2nc(-c3cnn(C)c3)[nH]c(=O)c12] | 3-Methyl-6-(1-methyl-1H-pyrazol-4-yl)-1-{1-[4-(trifluoromethyl)phenyl]ethyl}-1,5-dihydro-4H-pyrazolo[3,4-d]pyrimidin-4-one | Calc'd 403.1, found 403.3 |
| 54 | 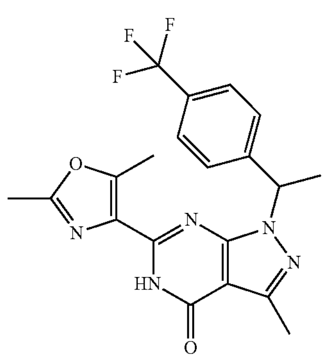 [SMILES: Cc1nc(-c2nc3c(c(C)nn3C(C)c3ccc(C(F)(F)F)cc3)c(=O)[nH]2)c(C)o1] | 6-(2,5-Dimethyl-1,3-oxazol-4-yl)-3-methyl-1-{1-[4-(trifluoromethyl)phenyl]ethyl}-1,5-dihydro-4H-pyrazolo[3,4-d]pyrimidin-4-one | Calc'd 418.1, found 418.3 |
| 55 | 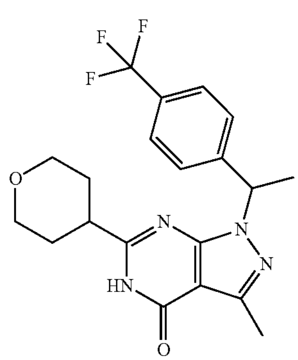 [SMILES: Cc1nn(C(C)c2ccc(C(F)(F)F)cc2)c2nc(C3CCOCC3)[nH]c(=O)c12] | 3-Methyl-6-(tetrahydro-2H-pyran-4-yl)-1-{1-[4-(trifluoromethyl)phenyl]ethyl}-1,5-dihydro-4H-pyrazolo[3,4-d]pyrimidin-4-one | Calc'd 407.2, found 407.4 |

TABLE 16

The following compounds were prepared using procedures similar to those described in Examples 36 and 37 using appropriate starting materials. Racemic products were separated using chiral columns specified in the table. For those pairs of enantiomers, the faster-eluting isomer is always listed first in this table. In the case of stereoisomers, the examples are listed in which they elute from the chiral column.

| Ex# | Structure | IUPAC Name | Exact Mass [M + H]+ | Chiral column |
|---|---|---|---|---|
| 56 | 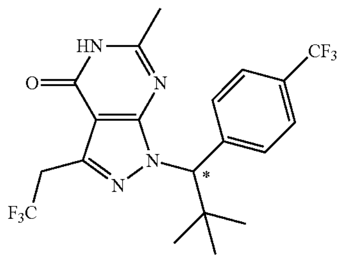 [SMILES: Cc1nc2c(c(CC(F)(F)F)nn2C(c2ccc(C(F)(F)F)cc2)C(C)(C)C)c(=O)[nH]1] | (R)- or (S)-1-(2,2-Dimethyl-1-(4-(trifluoromethyl)phenyl)propyl)-6-methyl-3-(2,2,2-trifluoroethyl)-1H-pyrazolo[3,4-d]pyrimidin-4(5H)-one | Calc'd 447.2, found 447.2 | Chiralpak IA |
| 57 | 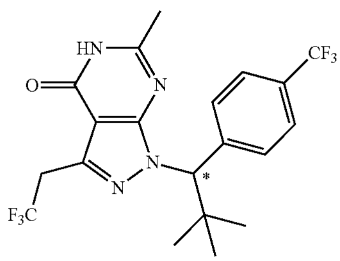 [SMILES: Cc1nc2c(c(CC(F)(F)F)nn2C(c2ccc(C(F)(F)F)cc2)C(C)(C)C)c(=O)[nH]1] | (S)- or (R)-1-(2,2-Dimethyl-1-(4-(trifluoromethyl)phenyl)propyl)-6-methyl-3-(2,2,2-trifluoroethyl)-1H-pyrazolo[3,4-d]pyrimidin-4(5H)-one | Calc'd 447.2, found 447.2 | Chiralpak IA |
| 58 | 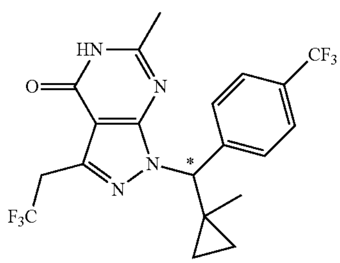 [SMILES: Cc1nc2c(c(CC(F)(F)F)nn2C(c2ccc(C(F)(F)F)cc2)C2(C)CC2)c(=O)[nH]1] | (R)- or (S)-6-Methyl-1-((1-methylcyclopropyl)(4-(trifluoromethyl)phenyl)methyl)-3-(2,2,2-trifluoroethyl)-1H-pyrazolo[3,4-d]pyrimidin-4(5H)-one | Calc'd 445.1, found 445.3 | Chiralpak IA |
| 59 | 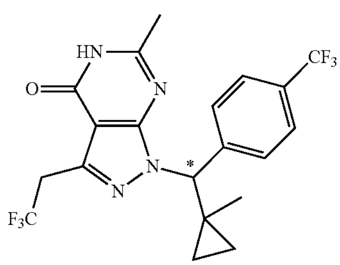 [SMILES: Cc1nc2c(c(CC(F)(F)F)nn2C(c2ccc(C(F)(F)F)cc2)C2(C)CC2)c(=O)[nH]1] | (S)- or (R)-6-Methyl-1-((1-methylcyclopropyl)(4-(trifluoromethyl)phenyl)methyl)-3-(2,2,2-trifluoroethyl)-1H-pyrazolo[3,4-d]pyrimidin-4(5H)-one | Calc'd 445.1, found 445.3 | Chiralpak IA |
| 60 | 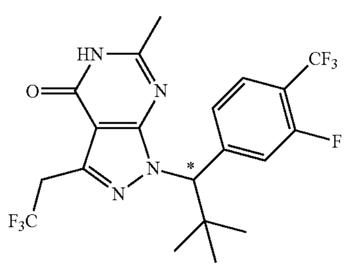 [SMILES: Cc1nc2c(c(CC(F)(F)F)nn2C(c2ccc(C(F)(F)F)c(F)c2)C(C)(C)C)c(=O)[nH]1] | (R)- or (S)-1-(1-(3-Fluoro-4-(trifluoromethyl)phenyl)-2,2-dimethylpropyl)-6-methyl-3-(2,2,2-trifluoroethyl)-1H-pyrazolo[3,4-d]pyrimidin-4(5H)-one | Calc'd 465.1, found 465.3 | Chiralpak IA |

TABLE 16-continued

The following compounds were prepared using procedures similar to those described in Examples 36 and 37 using appropriate starting materials. Racemic products were separated using chiral columns specified in the table. For those pairs of enantiomers, the faster-eluting isomer is always listed first in this table. In the case of stereoisomers, the examples are listed in which they elute from the chiral column.

| Ex# | Structure | IUPAC Name | Exact Mass [M + H]+ | Chiral column |
|---|---|---|---|---|
| 61 | 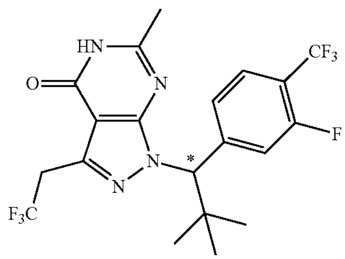 [SMILES: Cc1nc2c(c(CC(F)(F)F)nn2C(c2ccc(C(F)(F)F)c(F)c2)C(C)(C)C)c(=O)[nH]1] | (S)- or (R)-1-(1-(3-Fluoro-4-(trifluoromethyl)phenyl)-2,2-dimethylpropyl)-6-methyl-3-(2,2,2-trifluoroethyl)-1H-pyrazolo[3,4-d]pyrimidin-4(5H)-one | Calc'd 465.1, found 465.3 | Chiralpak IA |
| 62 | 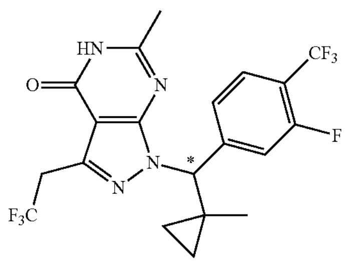 [SMILES: Cc1nc2c(c(CC(F)(F)F)nn2C(c2ccc(C(F)(F)F)c(F)c2)C2(C)CC2)c(=O)[nH]1] | (R)- or (S)-1-((3-Fluoro-4-(trifluoromethyl)phenyl)(1-methylcyclopropyl)methyl)-6-methyl-3-(2,2,2-trifluoroethyl)-1H-pyrazolo[3,4-d]pyrimidin-4(5H)-one | Calc'd 463.1, found 463.3 | Chiralpak IA |
| 63 | 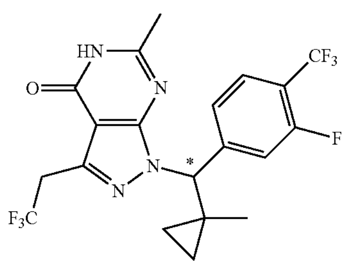 [SMILES: Cc1nc2c(c(CC(F)(F)F)nn2C(c2ccc(C(F)(F)F)c(F)c2)C2(C)CC2)c(=O)[nH]1] | (S)- or (R)-1-((3-Fluoro-4-(trifluoromethyl)phenyl)(1-methylcyclopropyl)methyl)-6-methyl-3-(2,2,2-trifluoroethyl)-1H-pyrazolo[3,4-d]pyrimidin-4(5H)-one | Calc'd 463.1, found 463.3 | Chiralpak IA |
| 64 | 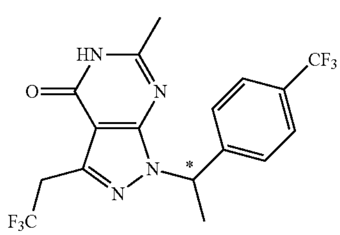 [SMILES: Cc1nc2c(c(CC(F)(F)F)nn2C(C)c2ccc(C(F)(F)F)cc2)c(=O)[nH]1] | (R)- or (S)-6-Methyl-3-(2,2,2-trifluoroethyl)-1-(1-(4-(trifluoromethyl)phenyl)ethyl)-1H-pyrazolo[3,4-d]pyrimidin-4(5H)-one | Calc'd 405.1, found 405.3 | Chiralpak IA |
| 65 | 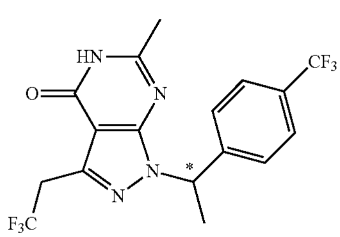 [SMILES: Cc1nc2c(c(CC(F)(F)F)nn2C(C)c2ccc(C(F)(F)F)cc2)c(=O)[nH]1] | (S)- or (R)-6-Methyl-3-(2,2,2-trifluoroethyl)-1-(1-(4-(trifluoromethyl)phenyl)ethyl)-1H-pyrazolo[3,4-d]pyrimidin-4(5H)-one | Calc'd 405.1, found 405.3 | Chiralpak IA |

TABLE 16-continued

The following compounds were prepared using procedures similar to those described in Examples 36 and 37 using appropriate starting materials. Racemic products were separated using chiral columns specified in the table. For those pairs of enantiomers, the faster-eluting isomer is always listed first in this table. In the case of stereoisomers, the examples are listed in which they elute from the chiral column.

| Ex# | Structure | IUPAC Name | Exact Mass [M + H]+ | Chiral column |
|---|---|---|---|---|
| 66 | 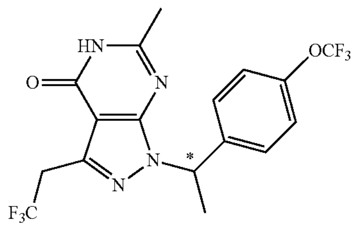 [SMILES: Cc1nc2c(c(CC(F)(F)F)nn2C(C)c2ccc(OC(F)(F)F)cc2)c(=O)[nH]1] | (R)- or (S)-6-Methyl-3-(2,2,2-trifluoroethyl)-1-(1-(4-(trifluoromethoxy)phenyl)ethyl)-1H-pyrazolo[3,4-d]pyrimidin-4(5H)-one | Calc'd 421.1, found 421.3 | Chiralpak IA |
| 67 | 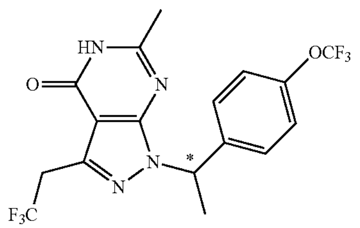 | (S)- or (R)-6-Methyl-3-(2,2,2-trifluoroethyl)-1-(1-(4-(trifluoromethoxy)phenyl)ethyl)-1H-pyrazolo[3,4-d]pyrimidin-4(5H)-one | Calc'd 421.1, found 421.3 | Chiralpak IA |
| 68 | 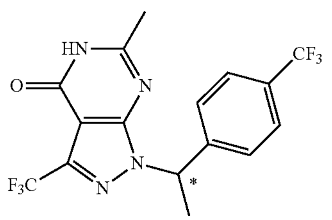 [SMILES: Cc1nc2c(c(C(F)(F)F)nn2C(C)c2ccc(C(F)(F)F)cc2)c(=O)[nH]1] | (R)- or (S)-6-Methyl-3-(trifluoromethyl)-1-(1-(4-(trifluoromethyl)phenyl)ethyl)-1H-pyrazolo[3,4-d]pyrimidin-4(5H)-one | Calc'd 391.1, found 391.2 | LUX Cellulose-4 |
| 69 | 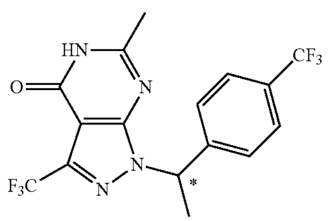 [SMILES: Cc1nc2c(c(C(F)(F)F)nn2C(C)c2ccc(C(F)(F)F)cc2)c(=O)[nH]1] | (S)- or -(R)-6-Methyl-3-(trifluoromethyl)-1-(1-(4-(trifluoromethyl)phenyl)ethyl)-1H-pyrazolo[3,4-d]pyrimidin-4(5H)-one | Calc'd 391.1, found 391.2 | LUX Cellulose-4 |
| 70 | 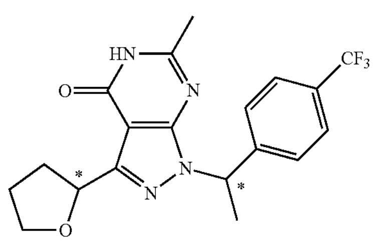 [SMILES: Cc1nc2c(c(C3CCCO3)nn2C(C)c2ccc(C(F)(F)F)cc2)c(=O)[nH]1] | (R, R)- or (R, S) or (S, R) or (S, S)-6-Methyl-3-(-tetrahydrofuran-(trifluoromethyl)phenyl)ethyl)-1H-pyrazolo[3,4-d]pyrimidin-4(5H)-one | Calc'd 393.2, found 393.3 | Chiralpak IB |
| 71 | 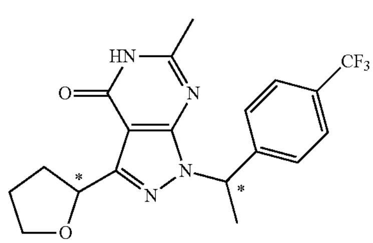 [SMILES: Cc1nc2c(c(C3CCCO3)nn2C(C)c2ccc(C(F)(F)F)cc2)c(=O)[nH]1] | (R, S)- or (R, R)- or (S, R)- or (S, S)-6-Methyl-3-(-tetrahydrofuran-2-yl)-1-(-1-(4-(trifluoromethyl)phenyl)ethyl)-1H-pyrazolo[3,4-d]pyrimidin-4(5H)-one | Calc'd 393.2, found 393.3 | Chiralpak IB |

TABLE 16-continued

The following compounds were prepared using procedures similar to those described in Examples 36 and 37 using appropriate starting materials. Racemic products were separated using chiral columns specified in the table. For those pairs of enantiomers, the faster-eluting isomer is always listed first in this table. In the case of stereoisomers, the examples are listed in which they elute from the chiral column.

| Ex# | Structure | IUPAC Name | Exact Mass [M + H]⁺ | Chiral column |
|---|---|---|---|---|
| 72 | 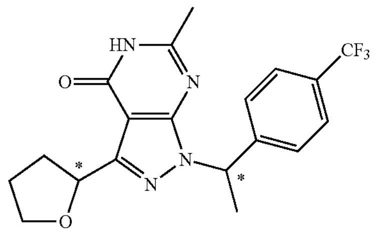 [SMILES: Cc1nc2c(c(C3CCCO3)nn2C(C)c2ccc(C(F)(F)F)cc2)c(=O)[nH]1] | (S, R)- or (S, S)- or (R, S)- or (R, R)-6-Methyl-3-(-tetrahydrofuran-(trifluoromethyl)phenyl)ethyl)-1H-pyrazolo[3,4-d]pyrimidin-4(5H)-one | Calc'd 393.2, found 393.3 | Chiralpak IB |
| 73 | 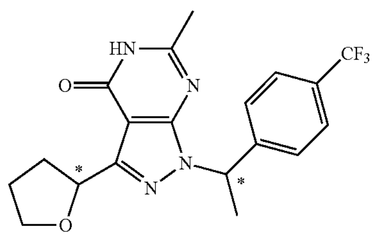 [SMILES: Cc1nc2c(c(C3CCCO3)nn2C(C)c2ccc(C(F)(F)F)cc2)c(=O)[nH]1] | (S, S)- or (S, R)- or (R, R)- or (R, S)-6-Methyl-3-(-tetrahydrofuran-2-yl)-1-(-1-(4-(trifluoromethyl)phenyl)ethyl)-1H-pyrazolo[3,4-d]pyrimidin-4(5H)-one | Calc'd 393.2, found 393.3 | Chiralpak IB |
| 74 | 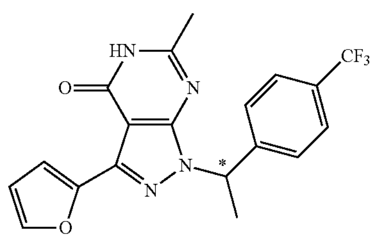 [SMILES: Cc1nc2c(c(-c3ccco3)nn2C(C)c2ccc(C(F)(F)F)cc2)c(=O)[nH]1] | (R)- or (S)-3-(Furan-2-yl)-6-methyl-1-(1-(4-(trifluoromethyl)phenyl)ethyl)-1H-pyrazolo[3,4-d]pyrimidin-4(5H)-one | Calc'd 389.1, found 389.2 | Chiralpak IB |
| 75 | 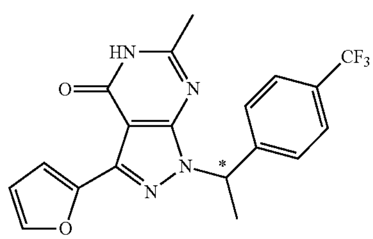 [SMILES: Cc1nc2c(c(-c3ccco3)nn2C(C)c2ccc(C(F)(F)F)cc2)c(=O)[nH]1] | (S)- or (R)-3-(Furan-2-yl)-6-methyl-1-(1-(4-(trifluoromethyl)phenyl)ethyl)-1H-pyrazolo[3,4-d]pyrimidin-4(5H)-one | Calc'd 389.1, found 389.2 | Chiralpak IB |

EXAMPLES 76 and 77

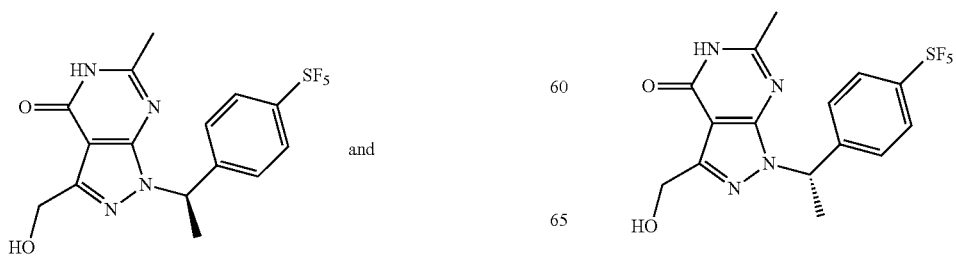

(R)- and (S)-3-(Hydroxymethyl)-6-methyl-1-(1-(4-(pentafluorothio)phenyl)ethyl)-1H-pyrazolo[3,4-d]pyrimidin-4(5H)-one (Scheme 19)

Step 1. 3-(Benzyloxymethyl)-4-methoxy-6-methyl-1-(1-(4-(pentafluorothio)phenyl)ethyl)-1H-pyrazolo[3,4-d]pyrimidine To a stirred mixture of 1-(4-(pentafluorothio)phenyl)ethanol (0.26 g, 1.1 mmol) from Preparatory Example 82 and 3-((benzyloxy)methyl)-4-methoxy-6-methyl-1H-pyrazolo[3,4-d]pyrimidine (0.20 g, 0.7 mmol) from Preparatory Example 116 in toluene (2.0 mL) at RT was added $PPh_3$ (0.55 g, 2.1 mmol) followed by dropwise addition of DIAD (0.4 mL, 2.1 mmol). The reaction mixture was stirred at RT for 16 h and was concentrated under reduced pressure. The residue was purified by silica gel chromatography (0-25% EtOAc in petroleum ether) to afford the title compound as an oil. MS=515.1 (+ESI).

Step 2. (4-Methoxy-6-methyl-1-(1-(4-(pentafluorothio)phenyl)ethyl)-1H-pyrazolo[3,4-d]pyrimidin-3-yl)methanol The title compound was prepared using procedures similar to those described in step 2 of Example 2 using 3-(benzyloxymethyl)-4-methoxy-6-methyl-1-(1-(4-(pentafluorothio)phenyl)ethyl)-1H-pyrazolo[3,4-d]pyrimidine in methanol to afford a solid. MS=425.2 (+ESI).

Step 3. (R)- and (S)-3-(Hydroxymethyl)-6-methyl-1-(1-(4-(pentafluorothio)phenyl)ethyl)-1H-pyrazolo[3,4-d]pyrimidin-4(5H)-one To a solution of (4-methoxy-6-methyl-1-(1-(4-(pentafluorothio)phenyl)ethyl)-1H-pyrazolo[3,4-d]pyrimidin-3-yl)methanol (90 mg, 0.21 mmol) in DMSO (2.0 mL) at RT was added NaCN (31 mg, 0.6 mmol). The reaction mixture was heated to 130° C., stirred for 1 h, and was cooled to RT. The mixture was diluted with water (25 mL) and extracted with EtOAc (3×10 mL). The organic layers were combined, dried over $Na_2SO_4$, filtered, and concentrated under reduced pressure. The residue was purified by preparative HPLC (Xbridge $C^{18}$, 30-70% ACN in water (0.1% TFA)) to afford the racemic title compound. The enantiopure title compounds were obtained by chiral preparative HPLC (Chiralpak IA, 30% EtOH in hexanes). The faster-eluting enantiomer of the title compound (Example 76) was obtained as a solid. MS=410.9 (+ESI). $^1$H NMR (300 MHz, $CD_3OD$) δ: 7.74 (d, J=9.0 Hz, 2H), 7.49 (d, J=8.1 Hz, 2H), 6.10 (q, J=7.2 Hz, 1H), 4.79 (s, 2H), 2.41 (s, 3H), 1.90 (d, J=7.2 Hz, 3H). The slower-eluting enantiomer of the title compound (Example 77) was obtained as a solid. MS=410.9 (+ESI). $^1$H NMR (300 MHz, $CD_3OD$) δ: 7.72 (d, J=8.7 Hz, 2H), 7.49 (d, J=8.4 Hz, 2H), 6.10 (q, J=7.2 Hz, 1H), 4.74 (s, 2H), 2.41 (s, 3H), 1.91 (d, J=7.2 Hz, 3H).

TABLE 17

The following compounds were prepared using procedures similar to those described in Examples 76 and 77 using appropriate starting materials.

| Ex# | Structure | IUPAC Name | Exact Mass [M + H]+ Or [M + Na]+ |
|---|---|---|---|
| 78 | 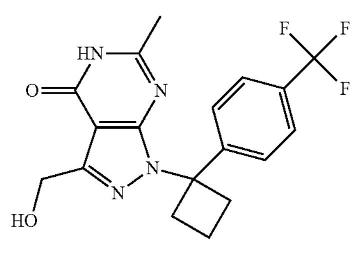 [SMILES: Cc1nc2c(c(CO)nn2C2(c3ccc(C(F)(F)F)cc3)CCC2)c(=O)[nH]1] | 3-(Hydroxymethyl)-6-methyl-1-(1-(4-(trifluoromethyl)phenyl)cyclobutyl)-1H-pyrazolo[3,4-d]pyrimidin-4(5H)-one | Calc'd 379.1, found 379.2 |
| 79 | 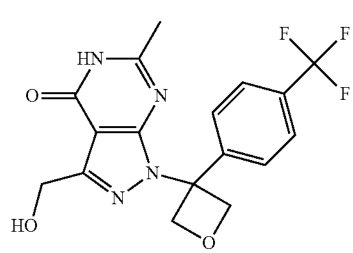 [SMILES: Cc1nc2c(c(CO)nn2C2(c3ccc(C(F)(F)F)cc3)COC2)c(=O)[nH]1] | 3-(Hydroxymethyl)-6-methyl-1-(3-(4-(trifluoromethyl)phenyl)oxetan-3-yl)-1H-pyrazolo[3,4-d]pyrimidin-4(5H)-one | Calc'd 381.1, found 381.2 |

EXAMPLES 80 and 81

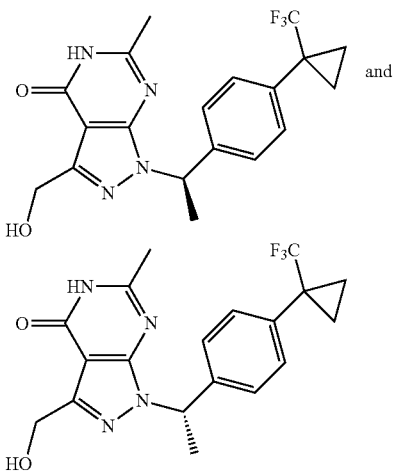

(R)- and (S)-3-(Hydroxymethyl)-6-methyl-1-(1-(4-(1-(trifluoromethyl)cyclopropyl)phenyl)ethyl)-1H-pyrazolo[3,4-d]pyrimidin-4(5H)-one (Scheme 19)

Step 1. 3-(Benzyloxymethyl)-4-methoxy-6-methyl-1-(1-(4-(1-(trifluoromethyl)cyclopropyl)phenyl)ethyl)-1H-pyrazolo[3,4-d]pyrimidine The title compound was prepared using procedures similar to those described in step 1 of Examples 76 and 77 using 1-(4-(1-(trifluoromethyl)cyclopropyl)phenyl)ethanol from Preparatory Example 101 and 3-((benzyloxy)methyl)-4-methoxy-6-methyl-1H-pyrazolo[3,4-d]pyrimidinone from Preparatory Example 123 to afford an oil. MS=497.2 (+ESI).

Step 2. (4-Methoxy-6-methyl-1-(1-(4-(1-(trifluoromethyl)cyclopropyl)phenyl)ethyl)-1H-pyrazolo[3,4-d]pyrimidin-3-yl)methanol The title compound was prepared using procedures similar to those described in step 2 of Example 2 using 3-((benzyloxy)methyl)-4-methoxy-6-methyl-1-(1-(4-(1-(trifluoromethyl)cyclopropyl)phenyl)ethyl)-1H-pyrazolo[3,4-d]pyrimidine to afford an oil. MS=407.1 (+ESI).

Step 3. (R)- and (S)-3-(Hydroxymethyl)-6-methyl-1-(1-(4-(1-(trifluoromethyl)cyclopropyl)phenyl)ethyl)-1H-pyrazolo[3,4-d]pyrimidin-4(5H)-one To a solution of sat. HCl in EtOAc (5 mL, 0.123 mmol) at RT was added (4-methoxy-6-methyl-1-(1-(4-(1-(trifluoromethyl)cyclopropyl)phenyl)ethyl)-1H-pyrazolo[3,4-d]pyrimidin-3-yl)methanol (50 mg, 0.1 mmol). The solution heated 80° C., stirred for 30 min, and was cooled to RT. The mixture was diluted with sat. aq. $NaHCO_3$ (20 mL) and extracted with EtOAc (3×10 mL) combining the organic layers. The organic layer was dried over $Na_2SO_4$, filtered, and concentrated under reduced pressure. The residue was purified by preparative HPLC (X Bridge RP C18, 40-60% ACN in water (0.1% $NH_4HCO_3$)) to afford the racemic title compound as a solid. The enantiopure title compounds were obtained by chiral preparative HPLC (Chiralpak IA, 10% EtOH in hexanes). The faster-eluting enantiomer of the title compound (Example 80) was obtained as a solid. MS=393.1 (+ESI). $^1H$ NMR (400 MHz, $CD_3OD$) δ: 7.43 (d, J=8.4 Hz, 2H), 7.36 (d, J=8.4 Hz, 2H), 6.08 (q, J=7.2 Hz, 1H), 4.89 (s, 2H), 2.47 (s, 3H), 1.93 (d, J=7.2 Hz, 3H), 1.35-1.32 (m, 2H), 1.06-1.02 (m, 2H). The slower-eluting enantiomer of the title compound (Example 81) was obtained as a solid. MS=393.1 (+ESI). $^1H$ NMR (400 MHz, $CD_3OD$) δ: 7.43 (d, J=8.4 Hz, 2H), 7.36 (d, J=8.4 Hz, 2H), 6.08 (q, J=7.2 Hz, 1H), 4.89 (s, 2H), 2.47 (s, 3H), 1.93 (d, J=7.2 Hz, 3H), 1.35-1.32 (m, 2H), 1.06-1.02 (m, 2H).

TABLE 18

The following compounds were prepared using procedures similar to those described in Examples 76, 77, 80, and 81 using appropriate starting materials and the benzyl and methoxy deprotection conditions listed. Racemic products were separated using the chiral columns specified in the table. For those pairs of enantiomers, the faster-eluting isomer is always listed first in this table.
Benzyl deprotection conditions: A: 20% $Pd(OH)_2/H_2$; B: 10% $Pd/C/H_2$; C: $BCl_3$
Methoxy deprotection conditions: D: NaCN; E: HCl in ethyl acetate or dioxane

| Ex #. | Structure | IUPAC Name | Exact Mass [M + H]+ or [M + Na]+ | Chiral Column | Bn and Methoxy DC |
|---|---|---|---|---|---|
| 82 | 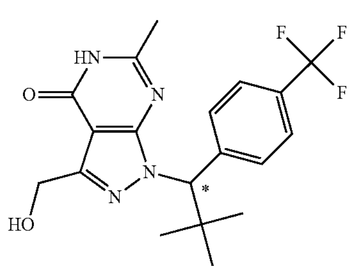 [SMILES: Cc1nc2c(c(CO)nn2C(c2ccc(C(F)(F)F)cc2)C(C)(C)C)c(=O)[nH]1] | (R)- or (S)-1-(2,2-Dimethyl-1-(4-(trifluoromethyl)phenyl)-propyl)-3-(hydroxymethyl)-6-methyl-1H-pyrazolo[3,4-d]pyrimidin-4(5H)-one | Calc'd 395.2, found 395.1 | Chiralpak IA | B, D |

TABLE 18-continued

The following compounds were prepared using procedures similar to those described in Examples 76, 77, 80, and 81 using appropriate starting materials and the benzyl and methoxy deprotection conditions listed. Racemic products were separated using the chiral columns specified in the table. For those pairs of enantiomers, the faster-eluting isomer is always listed first in this table.
Benzyl deprotection conditions: A: 20% Pd(OH)$_2$/H$_2$; B: 10% Pd/C/H$_2$; C: BCl$_3$
Methoxy deprotection conditions: D: NaCN; E: HCl in ethyl acetate or dioxane

| Ex #. | Structure | IUPAC Name | Exact Mass [M + H]$^+$ or [M + Na]$^+$ | Chiral Column | Bn and Methoxy DC |
|---|---|---|---|---|---|
| 83 | 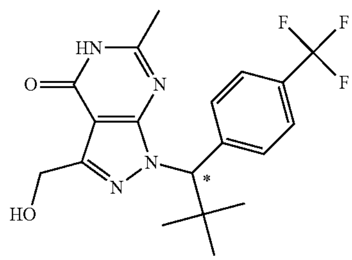 [SMILES: Cc1nc2c(c(CO)nn2C(c2ccc(C(F)(F)F)cc2)C(C)(C)C)c(=O)[nH]1] | (S)- or (R)-1-(2,2-Dimethyl-1-(4-(trifluoromethyl)phenyl)-propyl)-3-(hydroxymethyl)-6-methyl-1H-pyrazolo[3,4-d]pyrimidin-4(5H)-one | Calc'd 395.2, found 395.1 | Chiralpak IA | B, D |
| 84 | 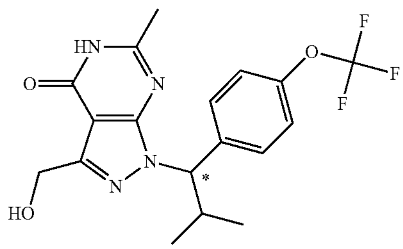 [SMILES: Cc1nc2c(c(CO)nn2C(c2ccc(OC(F)(F)F)cc2)C(C)C)c(=O)[nH]1] | (R)- or (S)-3-(Hydroxymethyl)-6-methyl-1-(2-methyl-1-(4-(trifluoromethoxy)phenyl) propyl)-1H-pyrazolo[3,4-d]pyrimidin-4(5H)-one | Calc'd 397.1, found 396.9 | Chiralpak IA | A, D |
| 85 | 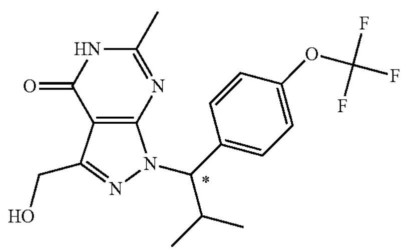 [SMILES: Cc1nc2c(c(CO)nn2C(c2ccc(OC(F)(F)F)cc2)C(C)C)c(=O)[nH]1] | (S)- or (R)-3-(Hydroxymethyl)-6-methyl-1-(2-methyl-1-(4-(trifluoromethoxy)phenyl) propyl)-1H-pyrazolo[3,4-d]pyrimidin-4(5H)-one | Calc'd 397.1, found 396.9 | Chiralpak IA | A, D |
| 86 | 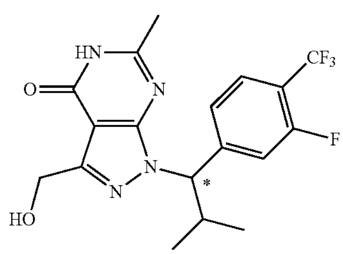 [SMILES: Cc1nc2c(c(CO)nn2C(c2ccc(C(F)(F)F)c(F)c2)C(C)C)c(=O)[nH]1] | (R)- or (S)-1-(1-(3-Fluoro-4-(trifluoromethyl)phenyl)-2-methylpropyl)-3-(hydroxymethyl)-6-methyl-1H-pyrazolo[3,4-d]pyrimidin-4(5H)-one | Calc'd 399.1, found 399.9 | Chiralpak IA | A, D |
| 87 | 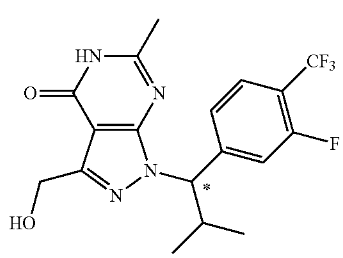 [SMILES: Cc1nc2c(c(CO)nn2C(c2ccc(C(F)(F)F)c(F)c2)C(C)C)c(=O)[nH]1] | (S)- or (R)-1-(1-(3-Fluoro-4-(trifluoromethyl)phenyl)-2-methylpropyl)-3-(hydroxymethyl)-6-methyl-1H-pyrazolo[3,4-d]pyrimidin-4(5H)-one | Calc'd 399.1, found 399.9 | Chiralpak IA | A, D |

TABLE 18-continued

The following compounds were prepared using procedures similar to those described in Examples 76, 77, 80, and 81 using appropriate starting materials and the benzyl and methoxy deprotection conditions listed. Racemic products were separated using the chiral columns specified in the table. For those pairs of enantiomers, the faster-eluting isomer is always listed first in this table.
Benzyl deprotection conditions: A: 20% Pd(OH)$_2$/H$_2$; B: 10% Pd/C/H$_2$; C: BCl$_3$
Methoxy deprotection conditions: D: NaCN; E: HCl in ethyl acetate or dioxane

| Ex #. | Structure | IUPAC Name | Exact Mass [M + H]$^+$ or [M + Na]$^+$ | Chiral Column | Bn and Methoxy DC |
|---|---|---|---|---|---|
| 88 | 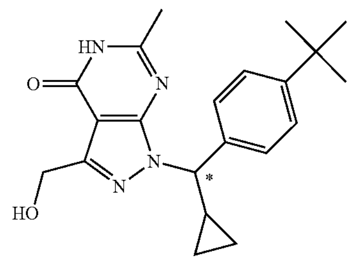 [SMILES: Cc1nc2c(c(CO)nn2C(c2ccc(C(C)(C)C)cc2)C2CC2)c(=O)[nH]1] | (R)- or (S)-1-((4-tert-Butylphenyl)(cyclopropyl)methyl)-3-(hydroxymethyl)-6-methyl-1H-pyrazolo[3,4-d]pyrimidin-4(5H)-one | Calc'd 367.2, found 367.2 | Lux Cellulose-4 | B, D |
| 89 | 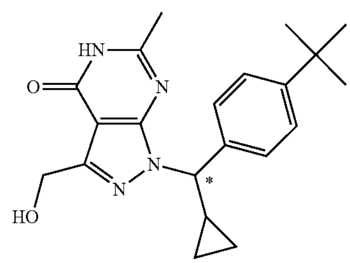 [SMILES: Cc1nc2c(c(CO)nn2C(c2ccc(C(C)(C)C)cc2)C2CC2)c(=O)[nH]1] | (S)- or (R)-1-((4-tert-Butylphenyl)(cyclopropyl)methyl)-3-(hydroxymethyl)-6-methyl-1H-pyrazolo[3,4-d]pyrimidin-4(5H)-one | Calc'd 367.2, found 367.2 | Lux Cellulose-4 | B, D |
| 90 | 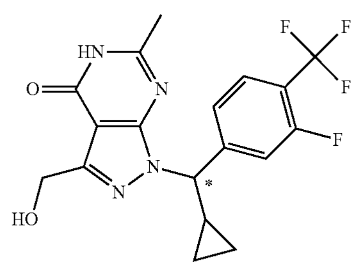 [SMILES: Cc1nc2c(c(CO)nn2C(c2ccc(C(F)(F)F)c(F)c2)C2CC2)c(=O)[nH]1] | (R)- or (S)-1-(Cyclopropyl(3-fluoro-4-(trifluoromethyl)phenyl)methyl)-3-(hydroxymethyl)-6-methyl-1H-pyrazolo[3,4-d]pyrimidin-4(5H)-one | Calc'd 397.1, found 397.2 | Chiralpak IA | B, D |
| 91 | 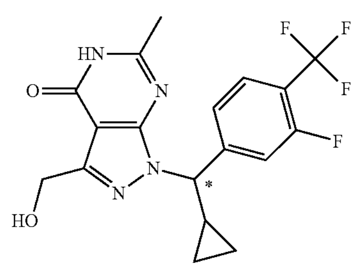 [SMILES: Cc1nc2c(c(CO)nn2C(c2ccc(C(F)(F)F)c(F)c2)C2CC2)c(=O)[nH]1] | (S)- or (R)-1-(Cyclopropyl(3-fluoro-4-(trifluoromethyl)phenyl)methyl)-3-(hydroxymethyl)-6-methyl-1H-pyrazolo[3,4-d]pyrimidin-4(5H)-one | Calc'd 397.1, found 397.1 | Chiralpak IA | B, D |
| 92 | 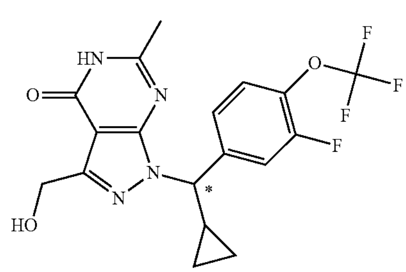 [SMILES: Cc1nc2c(c(CO)nn2C(c2ccc(OC(F)(F)F)c(F)c2)C2CC2)c(=O)[nH]1] | (R)- or (S)-1-(Cyclopropyl(3-fluoro-4-(trifluoromethoxy)phenyl)methyl)-3-(hydroxymethyl)-6-methyl-1H-pyrazolo[3,4-d]pyrimidin-4(5H)-one | Calc'd 413.1, found 413.1 | Chiralpak IA | B, D |

TABLE 18-continued

The following compounds were prepared using procedures similar to those described in Examples 76, 77, 80, and 81 using appropriate starting materials and the benzyl and methoxy deprotection conditions listed. Racemic products were separated using the chiral columns specified in the table. For those pairs of enantiomers, the faster-eluting isomer is always listed first in this table.
Benzyl deprotection conditions: A: 20% Pd(OH)$_2$/H$_2$; B: 10% Pd/C/H$_2$; C: BCl$_3$
Methoxy deprotection conditions: D: NaCN; E: HCl in ethyl acetate or dioxane

| Ex #. | Structure | IUPAC Name | Exact Mass [M + H]$^+$ or [M + Na]$^+$ | Chiral Column | Bn and Methoxy DC |
|---|---|---|---|---|---|
| 93 | 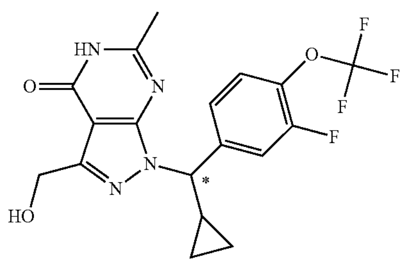 [SMILES: Cc1nc2c(c(CO)nn2C(c2ccc(OC(F)(F)F)c(F)c2)C2CC2)c(=O)[nH]1] | (S)- or (R)-1-(Cyclopropyl(3-fluoro-4-(trifluoromethoxy)phenyl)methyl)-3-(hydroxymethyl)-6-methyl-1H-pyrazolo[3,4-d]pyrimidin-4(5H)-one | Calc'd 413.1, found 413.1 | Chiralpak IA | B, D |
| 94 | 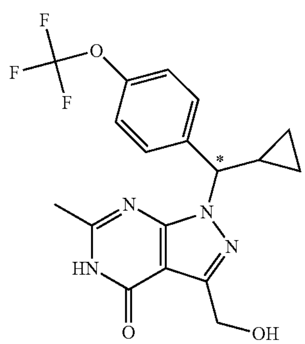 [SMILES: Cc1nc2c(c(CO)nn2C(c2ccc(OC(F)(F)F)cc2)C2CC2)c(=O)[nH]1] | (R)- or (S)-1-(Cyclopropyl(4-(trifluoromethoxy)phenyl)methyl)-3-(hydroxymethyl)-6-methyl-1H-pyrazolo[3,4-d]pyrimidin-4(5H)-one | Calc'd 395.1, found 395.0 | Chiralpak IA | A, D |
| 95 | 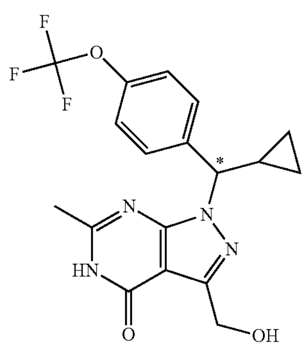 [SMILES: Cc1nc2c(c(CO)nn2C(c2ccc(OC(F)(F)F)cc2)C2CC2)c(=O)[nH]1] | (S)- or (R)-1-(Cyclopropyl(4-(trifluoromethoxy)phenyl)methyl)-3-(hydroxymethyl)-6-methyl-1H-pyrazolo[3,4-d]pyrimidin-4(5H)-one | Calc'd 395.1, found 395.0 | Chiralpak IA | A, D |
| 96 | 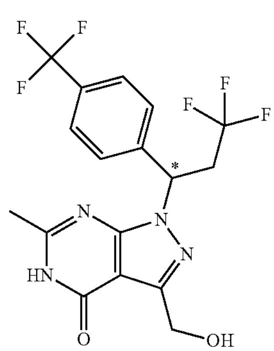 [SMILES: Cc1nc2c(c(CO)nn2C(CC(F)(F)F)c2ccc(C(F)(F)F)cc2)c(=O)[nH]1] | (R)- or (S)-3-(Hydroxymethyl)-6-methyl-1-(3,3,3-trifluoro-1-(4-(trifluoromethyl)phenyl)propyl)-1H-pyrazolo[3,4-d]pyrimidin-4(5H)-one | Calc'd 421.1, found 421.1 | Chiralpak AS-H | A, D |

TABLE 18-continued

The following compounds were prepared using procedures similar to those described in Examples 76, 77, 80, and 81 using appropriate starting materials and the benzyl and methoxy deprotection conditions listed. Racemic products were separated using the chiral columns specified in the table. For those pairs of enantiomers, the faster-eluting isomer is always listed first in this table.
Benzyl deprotection conditions: A: 20% Pd(OH)$_2$/H$_2$; B: 10% Pd/C/H$_2$; C: BCl$_3$
Methoxy deprotection conditions: D: NaCN; E: HCl in ethyl acetate or dioxane

| Ex #. | Structure | IUPAC Name | Exact Mass [M + H]$^+$ or [M + Na]$^+$ | Chiral Column | Bn and Methoxy DC |
|---|---|---|---|---|---|
| 97 | 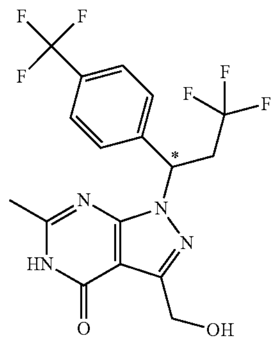 [SMILES: Cc1nc2c(c(CO)nn2C(CC(F)(F)F)c2ccc(C(F)(F)F)cc2)c(=O)[nH]1] | (S)- or (R)-3-(Hydroxymethyl)-6-methyl-1-(3,3,3-trifluoro-1-(4-(trifluoromethyl)phenyl)propyl)-1H-pyrazolo[3,4-d]pyrimidin-4(5H)-one | Calc'd 421.1, found 421.1 | Chiralpak AS-H | A, D |
| 98 | 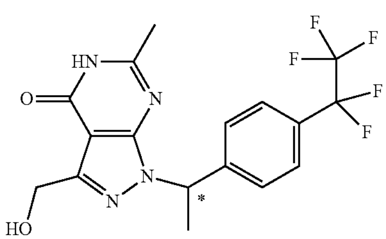 [SMILES: Cc1nc2c(c(CO)nn2C(C)c2ccc(C(F)(F)C(F)(F)F)cc2)c(=O)[nH]1] | (R)- or (S)-3-(Hydroxymethyl)-6-methyl-1-(1-(4-(perfluoroethyl)phenyl)ethyl)-1H-pyrazolo[3,4-d]pyrimidin-4(5H)-one | Calc'd 403.1, found 403.1 | Chiralpak IC | B, E |
| 99 | 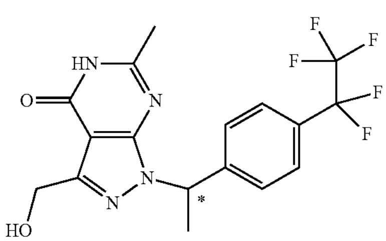 [SMILES: Cc1nc2c(c(CO)nn2C(C)c2ccc(C(F)(F)C(F)(F)F)cc2)c(=O)[nH]1] | (S)- or (R)-3-(Hydroxymethyl)-6-methyl-1-(1-(4-(perfluoroethyl)phenyl)ethyl)-1H-pyrazolo[3,4-d]pyrimidin-4(5H)-one | Calc'd 403.1, found 403.1 | Chiralpak IC | B, E |
| 100 | 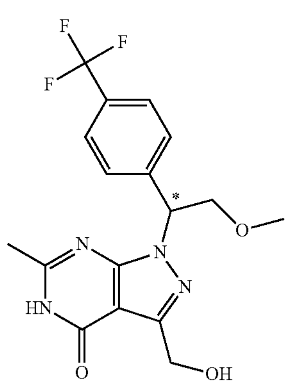 | (R)- or (S)-3-(Hydroxymethyl)-1-(2-methoxy-1-(4-(trifluoromethyl)phenyl)ethyl)-6-methyl-1H-pyrazolo[3,4-d]pyrimidin-4(5H)-one | Calc'd 383.1, found 383.2 | Chiralpak IA | A, E |

TABLE 18-continued

The following compounds were prepared using procedures similar to those described in Examples 76, 77, 80, and 81 using appropriate starting materials and the benzyl and methoxy deprotection conditions listed. Racemic products were separated using the chiral columns specified in the table. For those pairs of enantiomers, the faster-eluting isomer is always listed first in this table.

Benzyl deprotection conditions: A: 20% Pd(OH)$_2$/H$_2$; B: 10% Pd/C/H$_2$; C: BCl$_3$
Methoxy deprotection conditions: D: NaCN; E: HCl in ethyl acetate or dioxane

| Ex #. | Structure | IUPAC Name | Exact Mass [M + H]$^+$ or [M + Na]$^+$ | Chiral Column | Bn and Methoxy DC |
|---|---|---|---|---|---|
| 101 | 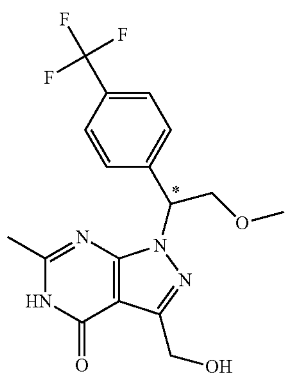 | (S)- or (R)-3-(Hydroxymethyl)-1-(2-methoxy-1-(4-(trifluoromethyl)phenyl)ethyl)-6-methyl-1H-pyrazolo[3,4-d]pyrimidin-4(5H)-one | Calc'd 383.1, found 383.2 | Chiralpak IA | A, E |
| 102 | 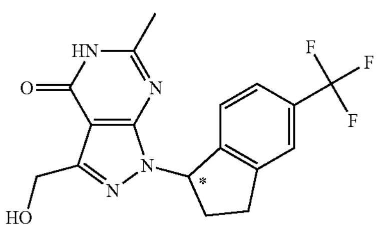 [SMILES: Cc1nc2c(c(CO)nn2C2CCc3cc(C(F)(F)F)ccc32)c(=O)[nH]1] | (R)- or (S)-3-(Hydroxymethyl)-6-methyl-1-(5-(trifluoromethyl)-2,3-dihydro-1H-inden-1-yl)-1H-pyrazolo[3,4-d]pyrimidin-4(5H)-one | Calc'd 365.1, found 365.0 | Chiralpak IC | A, E |
| 103 | 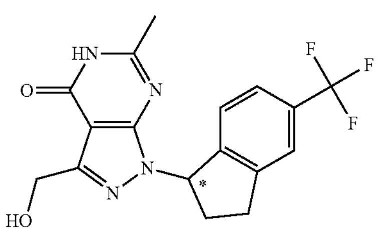 [SMILES: Cc1nc2c(c(CO)nn2C2CCc3cc(C(F)(F)F)ccc32)c(=O)[nH]1] | (S)- or (R)-3-(Hydroxymethyl)-6-methyl-1-(5-(trifluoromethyl)-2,3-dihydro-1H-inden-1-yl)-1H-pyrazolo[3,4-d]pyrimidin-4(5H)-one | Calc'd 365.1, found 365.0 | Chiralpak IC | A, E |
| 104 | 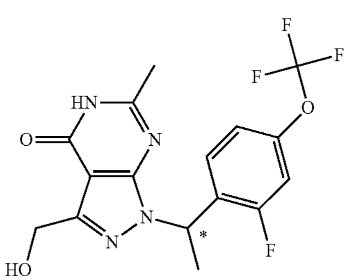 [SMILES: Cc1nc2c(c(CO)nn2C(C)c2ccc(OC(F)(F)F)cc2F)c(=O)[nH]1] | (R)- or (S)-1-(1-(2-Fluoro-4-(trifluoromethoxy)phenyl)ethyl)-3-(hydroxymethyl)-6-methyl-1H-pyrazolo[3,4-d]pyrimidin-4(5H)-one | Calc'd 387.1, found 386.9 | Phenomenex Lux 5u Cellulose-4, AXIA | A, E |

TABLE 18-continued

*The following compounds were prepared using procedures similar to those described in Examples 76, 77, 80, and 81 using appropriate starting materials and the benzyl and methoxy deprotection conditions listed. Racemic products were separated using the chiral columns specified in the table. For those pairs of enantiomers, the faster-eluting isomer is always listed first in this table.*

*Benzyl deprotection conditions: A: 20% Pd(OH)$_2$/H$_2$; B: 10% Pd/C/H$_2$; C: BCl$_3$*
*Methoxy deprotection conditions: D: NaCN; E: HCl in ethyl acetate or dioxane*

| Ex #. | Structure | IUPAC Name | Exact Mass [M + H]$^+$ or [M + Na]$^+$ | Chiral Column | Bn and Methoxy DC |
|---|---|---|---|---|---|
| 105 | 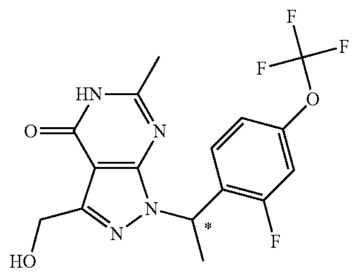 [SMILES: Cc1nc2c(c(CO)nn2C(C)c2ccc(OC(F)(F)F)cc2F)c(=O)[nH]1] | (S)- or (R)-1-(1-(2-Fluoro-4-(trifluoromethoxy)phenyl)ethyl)-3-(hydroxymethyl)-6-methyl-1H-pyrazolo[3,4-d]pyrimidin-4(5H)-one | Calc'd 387.1, found 386.9 | Phenomenex Lux 5u Cellulose-4, AXIA | A, E |
| 106 | 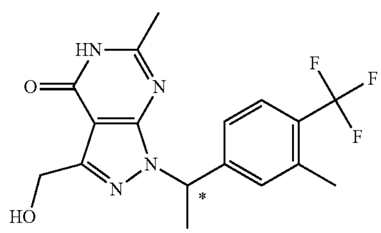 [SMILES: Cc1nc2c(c(CO)nn2C(C)c2ccc(C(F)(F)F)c(C)c2)c(=O)[nH]1] | (R)- or (S)-3-(Hydroxymethyl)-6-methyl-1-(1-(3-methyl-4-(trifluoromethyl)phenyl)ethyl)-1H-pyrazolo[3,4-d]pyrimidin-4(5H)-one | Calc'd 367.1, found 367.1 | Chiralpak IA | B, E |
| 107 | 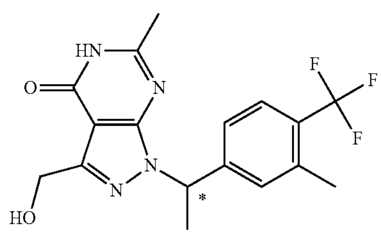 [SMILES: Cc1nc2c(c(CO)nn2C(C)c2ccc(C(F)(F)F)c(C)c2)c(=O)[nH]1] | (S)- or (R)-3-(Hydroxymethyl)-6-methyl-1-(1-(3-methyl-4-(trifluoromethyl)phenyl)ethyl)-1H-pyrazolo[3,4-d]pyrimidin-4(5H)-one | Calc'd 367.1, found 367.1 | Chiralpak IA | B, E |
| 108 | 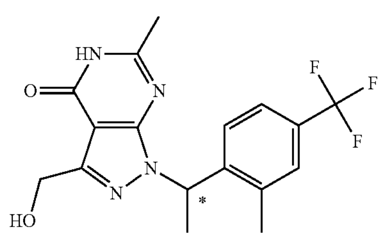 [SMILES: Cc1nc2c(c(CO)nn2C(C)c2ccc(C(F)(F)F)cc2C)c(=O)[nH]1] | (R)- or (S)-3-(Hydroxymethyl)-6-methyl-1-(1-(2-methyl-4-(trifluoromethyl)phenyl)ethyl)-1H-pyrazolo[3,4-d]pyrimidin-4(5H)-one | Calc'd 367.1, found 366.9 | Chiralpak IA | B, E |
| 109 | 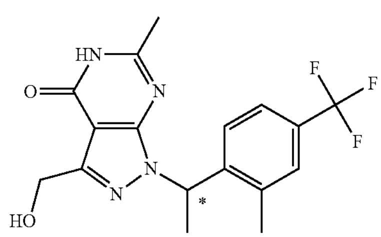 [SMILES: Cc1nc2c(c(CO)nn2C(C)c2ccc(C(F)(F)F)cc2C)c(=O)[nH]1] | (S)- or (R)-3-(Hydroxymethyl)-6-methyl-1-(1-(2-methyl-4-(trifluoromethyl)phenyl)ethyl)-1H-pyrazolo[3,4-d]pyrimidin-4(5H)-one | Calc'd 367.1, found 367.1 | Chiralpak IA | B, E |

TABLE 18-continued

The following compounds were prepared using procedures similar to those described in Examples 76, 77, 80, and 81 using appropriate starting materials and the benzyl and methoxy deprotection conditions listed. Racemic products were separated using the chiral columns specified in the table. For those pairs of enantiomers, the faster-eluting isomer is always listed first in this table.
Benzyl deprotection conditions: A: 20% Pd(OH)$_2$/H$_2$; B: 10% Pd/C/H$_2$; C: BCl$_3$
Methoxy deprotection conditions: D: NaCN; E: HCl in ethyl acetate or dioxane

| Ex #. | Structure | IUPAC Name | Exact Mass [M + H]$^+$ or [M + Na]$^+$ | Chiral Column | Bn and Methoxy DC |
|---|---|---|---|---|---|
| 110 | 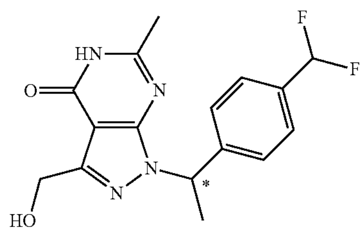 [SMILES: Cc1nc2c(c(CO)nn2C(C)c2ccc(C(F)F)cc2)c(=O)[nH]1] | (R)- or (S)-1-(1-(4-(Difluoromethyl)phenyl)ethyl)-3-(hydroxymethyl)-6-methyl-1H-pyrazolo[3,4-d]pyrimidin-4(5H)-one | Calc'd 335.1, found 335.1 | Chiralpak IA | A, D |
| 111 | 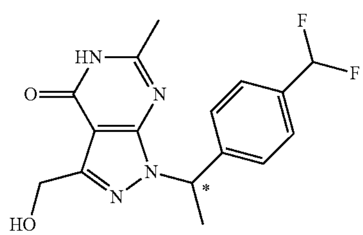 [SMILES: Cc1nc2c(c(CO)nn2C(C)c2ccc(C(F)F)cc2)c(=O)[nH]1] | (S)- or (R)-1-(1-(4-(Difluoromethyl)phenyl)ethyl)-3-(hydroxymethyl)-6-methyl-1H-pyrazolo[3,4-d]pyrimidin-4(5H)-one | Calc'd 335.1, found 335.1 | Chiralpak IA | A, D |
| 112 | 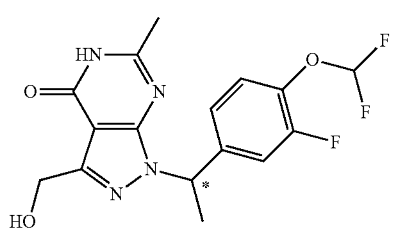 [SMILES: Cc1nc2c(c(CO)nn2C(C)c2ccc(OC(F)F)c(F)c2)c(=O)[nH]1] | (R)- or (S)-1-(1-(4-(Difluoromethoxy)-3-fluorophenyl)ethyl)-3-(hydroxymethyl)-6-methyl-1H-pyrazolo[3,4-d]pyrimidin-4(5H)-one | Calc'd 369.1, found 369.2 | Chiralpak IA | A, E |
| 113 | 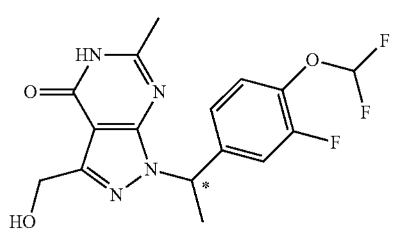 [SMILES: Cc1nc2c(c(CO)nn2C(C)c2ccc(OC(F)F)c(F)c2)c(=O)[nH]1] | (S)- or (R)-1-(1-(4-(Difluoromethoxy)-3-fluorophenyl)ethyl)-3-(hydroxymethyl)-6-methyl-1H-pyrazolo[3,4-d]pyrimidin-4(5H)-one | Calc'd 369.1, found 369.1 | Chiralpak IA | A, E |
| 114 | 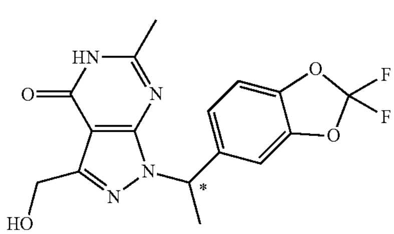 [SMILES: Cc1nc2c(c(CO)nn2C(C)c2ccc3c(c2)OC(F)(F)O3)c(=O)[nH]1] | (R)- or (S)-1-(1-(2,2-Difluorobenzo[d][1,3]dioxol-5-yl)ethyl)-3-(hydroxymethyl)-6-methyl-1H-pyrazolo[3,4-d]pyrimidin-4(5H)-one | Calc'd 365.1, found 365.2 | Chiralpak IC | A, D |

TABLE 18-continued

The following compounds were prepared using procedures similar to those described in Examples 76, 77, 80, and 81 using appropriate starting materials and the benzyl and methoxy deprotection conditions listed. Racemic products were separated using the chiral columns specified in the table. For those pairs of enantiomers, the faster-eluting isomer is always listed first in this table.
Benzyl deprotection conditions: A: 20% Pd(OH)$_2$/H$_2$; B: 10% Pd/C/H$_2$; C: BCl$_3$
Methoxy deprotection conditions: D: NaCN; E: HCl in ethyl acetate or dioxane

| Ex #. | Structure | IUPAC Name | Exact Mass [M + H]$^+$ or [M + Na]$^+$ | Chiral Column | Bn and Methoxy DC |
|---|---|---|---|---|---|
| 115 | 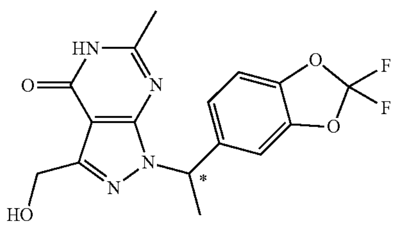 [SMILES: Cc1nc2c(c(CO)nn2C(C)c2ccc3c(c2)OC(F)(F)O3)c(=O)[nH]1] | (S)- or (R)-1-(1-(2,2-Difluorobenzo[d][1,3]dioxol-5-yl)ethyl)-3-(hydroxymethyl)-6-methyl-1H-pyrazolo[3,4-d]pyrimidin-4(5H)-one | Calc'd 365.1, found 365.2 | Chiralpak IC | A, D |
| 116 | 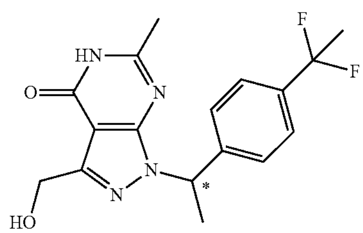 [SMILES: Cc1nc2c(c(CO)nn2C(C)c2ccc(C(C)(F)F)cc2)c(=O)[nH]1] | (R)- or (S)-1-(1-(4-(1,1-Difluoroethyl)phenyl)ethyl)-3-(hydroxymethyl)-6-methyl-1H-pyrazolo[3,4-d]pyrimidin-4(5H)-one | Calc'd 349.1, found 349.2 | Chiralpak IA | A, D |
| 117 | 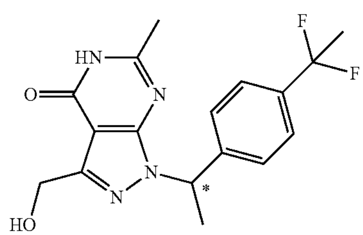 | (S)- or (R)-1-(1-(4-(1,1-Difluoroethyl)phenyl)ethyl)-3-(hydroxymethyl)-6-methyl-1H-pyrazolo[3,4-d]pyrimidin-4(5H)-one | Calc'd 349.1, found 349.2 | Chiralpak IA | A, D |
| 118 | 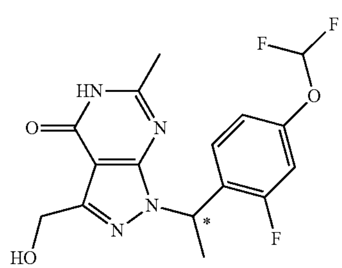 [SMILES: Cc1nc2c(c(CO)nn2C(C)c2ccc(OC(F)F)cc2F)c(=O)[nH]1] | (R)- or (S)-1-(1-(4-(Difluoromethoxy)-2-fluorophenyl)ethyl)-3-(hydroxymethyl)-6-methyl-1H-pyrazolo[3,4-d]pyrimidin-4(5H)-one | Calc'd 369.1, found 369.2 | Chiralpak IC | A, D |
| 119 | 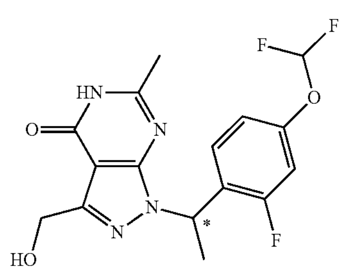 [SMILES: Cc1nc2c(c(CO)nn2C(C)c2ccc(OC(F)F)cc2F)c(=O)[nH]1] | (S)- or (R)-1-(1-(4-(Difluoromethoxy)-2-fluorophenyl)ethyl)-3-(hydroxymethyl)-6-methyl-1H-pyrazolo[3,4-d]pyrimidin-4(5H)-one | Calc'd 369.1, found 369.2 | Chiralpak IC | A, D |

TABLE 18-continued

The following compounds were prepared using procedures similar to those described in Examples 76, 77, 80, and 81 using appropriate starting materials and the benzyl and methoxy deprotection conditions listed. Racemic products were separated using the chiral columns specified in the table. For those pairs of enantiomers, the faster-eluting isomer is always listed first in this table.
Benzyl deprotection conditions: A: 20% Pd(OH)$_2$/H$_2$; B: 10% Pd/C/H$_2$; C: BCl$_3$
Methoxy deprotection conditions: D: NaCN; E: HCl in ethyl acetate or dioxane

| Ex #. | Structure | IUPAC Name | Exact Mass [M + H]$^+$ or [M + Na]$^+$ | Chiral Column | Bn and Methoxy DC |
|---|---|---|---|---|---|
| 120 | 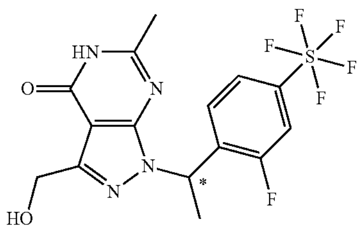 [SMILES: Cc1nc2c(c(CO)nn2C(C)c2ccc(S(F)(F)(F)(F)F)cc2F)c(=O)[nH]1] | (R)- or (S)-3-(Hydroxymethyl)-6-methyl-1-(1-(4-(pentafluorothio)phenyl)ethyl)-1H-pyrazolo[3,4-d]pyrimidin-4(5H)-one | Calc'd 429.1, found 429.2 | Phenomenex Lux 5u Cellulose-4, AXIA Packed | A, E |
| 121 | 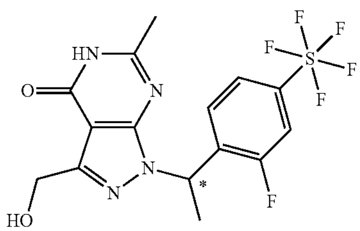 [SMILES: Cc1nc2c(c(CO)nn2C(C)c2ccc(S(F)(F)(F)(F)F)cc2F)c(=O)[nH]1] | (S)- or (R)-3-(Hydroxymethyl)-6-methyl-1-(1-(4-(pentafluorothio)phenyl)ethyl)-1H-pyrazolo[3,4-d]pyrimidin-4(5H)-one | Calc'd 429.1, found 429.2 Packed | Phenomenex Lux 5u Cellulose-4, AXIA | A, E |
| 122 | 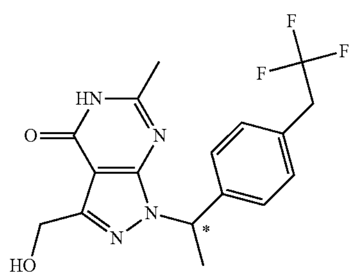 [SMILES: Cc1nc2c(c(CO)nn2C(C)c2ccc(CC(F)(F)F)cc2)c(=O)[nH]1] | (R)- or (S)-3-(Hydroxymethyl)-6-methyl-1-(1-(4-(2,2,2-trifluoroethyl)phenyl)ethyl)-1H-pyrazolo[3,4-d]pyrimidin-4(5H)-one | Calc'd 367.1, found 367.0 | Chiralpak IC | A, E |
| 123 | 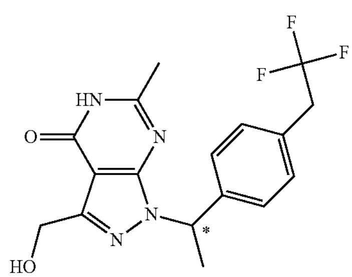 [SMILES: Cc1nc2c(c(CO)nn2C(C)c2ccc(CC(F)(F)F)cc2)c(=O)[nH]1] | (S) or (R)-3-(Hydroxymethyl)-6-methyl-1-(1-(4-(2,2,2-trifluoroethyl)phenyl)ethyl)-1H-pyrazolo[3,4-d]pyrimidin-4(5H)-one | Calc'd 367.1, found 367.0 | Chiralpak IC | A, E |
| 124 | 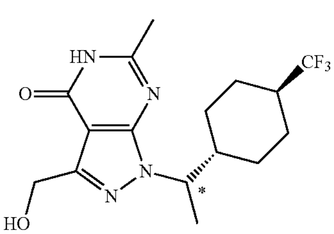 [SMILES: Cc1nc2c(c(CO)nn2C(C)[C@H]2CC[C@H](C(F)(F)F)CC2)c(=O)[nH]1] | (R)- or (S)-3-(Hydroxymethyl)-6-methyl-1-((trans)-4-(trifluoromethyl)cyclohexyl)ethyl)-1H-pyrazolo[3,4-d]-pyrimidin-4(5H)-one | Calc'd 359.1, found 359.0 | Chiralpak AS-H | A, D |

TABLE 18-continued

The following compounds were prepared using procedures similar to those described in Examples 76, 77, 80, and 81 using appropriate starting materials and the benzyl and methoxy deprotection conditions listed. Racemic products were separated using the chiral columns specified in the table. For those pairs of enantiomers, the faster-eluting isomer is always listed first in this table.
Benzyl deprotection conditions: A: 20% Pd(OH)$_2$/H$_2$; B: 10% Pd/C/H$_2$; C: BCl$_3$
Methoxy deprotection conditions: D: NaCN; E: HCl in ethyl acetate or dioxane

| Ex #. | Structure | IUPAC Name | Exact Mass [M + H]$^+$ or [M + Na]$^+$ | Chiral Column | Bn and Methoxy DC |
|---|---|---|---|---|---|
| 125 | 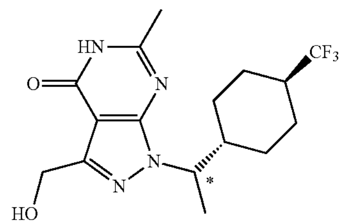 [SMILES: Cc1nc2c(c(CO)nn2C(C)[C@H]2CC[C@H](C(F)(F)F)CC2)c(=O)[nH]1] | (S)- or (R)-3-(Hydroxymethyl)-6-methyl-1-((trans)-4-(trifluoromethyl)cyclohexyl)ethyl)-1H-pyrazolo[3,4-d]pyrimidin-4(5H)-one | Calc'd 359.1, found 359.0 | Chiralpak AS-H | A, D |
| 126 | 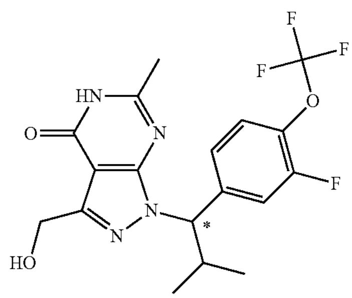 [SMILES: Cc1nc2c(c(CO)nn2C(c2ccc(OC(F)(F)F)c(F)c2)C(C)C)c(=O)[nH]1] | (R)- or (S)-1-(1-(3-Fluoro-4-(trifluoromethoxy)phenyl)-2-methylpropyl)-3-(hydroxylmethyl)-6-methyl-1H-pyrazolo-[3,4-d]pyrimidin-4(5H)-one | Calc'd 415.1, found 415.1 | Chiralpak IA-3 | A, D |
| 127 | 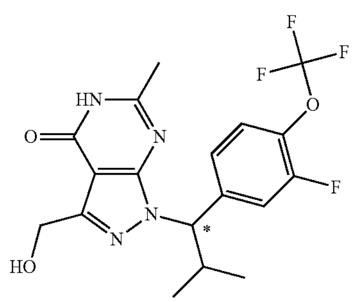 [SMILES: Cc1nc2c(c(CO)nn2C(c2ccc(OC(F)(F)F)c(F)c2)C(C)C)c(=O)[nH]1] | (S)- or (R)-1-(1-(3-Fluoro-4-(trifluoromethoxy)phenyl)-2-methylpropyl)-3-(hydroxymethyl)-6-methyl-1H-pyrazolo[3,4-d]pyrimidin-4(5H)-one | Calc'd 415.1, found 415.1 | Chiralpak IA-3 | A, D |
| 128 | 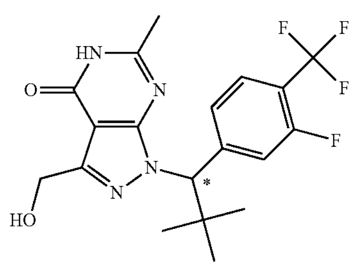 [SMILES: Cc1nc2c(c(CO)nn2C(c2ccc(C(F)(F)F)c(F)c2)C(C)(C)C)c(=O)[nH]1] | (R)- or (S)-1-(1-(3-Fluoro-4-(trifluoromethyl)phenyl)-2,2-dimethylpropyl)-3-(hydroxyl-methyl)-6-methyl-1H-pyrazolo-[3,4-d]pyrimidin-4(5H)-one | Calc'd 413.2, found 413.0 | Chiralpak IA-3 | B, D |
| 129 | 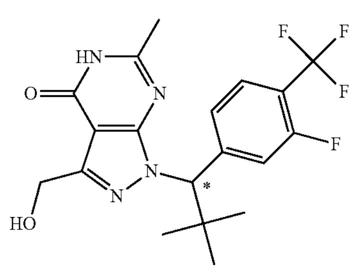 [SMILES: Cc1nc2c(c(CO)nn2C(c2ccc(C(F)(F)F)c(F)c2)C(C)(C)C)c(=O)[nH]1] | (S)- or (R)-1-(1-(3-Fluoro-4-(trifluoromethyl)phenyl)-2,2-dimethylpropyl)-3-(hydroxyl-methyl)-6-methyl-1H-pyrazolo-[3,4-d]pyrimidin-4(5H)-one | Calc'd 413.2, found 413.0 | Chiralpak IA-3 | B, D |

TABLE 18-continued

The following compounds were prepared using procedures similar to those described in Examples 76, 77, 80, and 81 using appropriate starting materials and the benzyl and methoxy deprotection conditions listed. Racemic products were separated using the chiral columns specified in the table. For those pairs of enantiomers, the faster-eluting isomer is always listed first in this table.
Benzyl deprotection conditions: A: 20% Pd(OH)$_2$/H$_2$; B: 10% Pd/C/H$_2$; C: BCl$_3$
Methoxy deprotection conditions: D: NaCN; E: HCl in ethyl acetate or dioxane

| Ex #. | Structure | IUPAC Name | Exact Mass [M + H]$^+$ or [M + Na]$^+$ | Chiral Column | Bn and Methoxy DC |
|---|---|---|---|---|---|
| 130 | 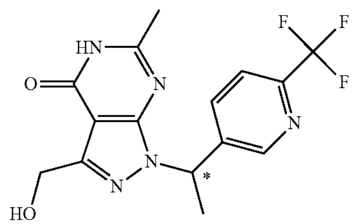 [SMILES: Cc1nc2c(c(CO)nn2C(C)c2ccc(C(F)(F)F)nc2)c(=O)[nH]1] | (R)- or (S)-3-(Hydroxymethyl)-6-methyl-1-(1-(6-(trifluoromethyl)pyridin-3-yl)ethyl)-1H-pyrazolo[3,4-d]pyrimidin-4(5H)-one | Calc'd 354.1, found 354.1 | Phenomenex Lux 5u Cellulose-4, AXIA Packed | C, D |
| 131 | 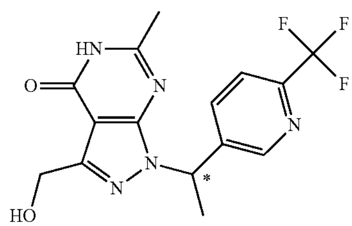 [SMILES: Cc1nc2c(c(CO)nn2C(C)c2ccc(C(F)(F)F)nc2)c(=O)[nH]1] | (S)- or (R)-3-(Hydroxymethyl)-6-methyl-1-(1-(6-(trifluoromethyl)pyridin-3-yl)ethyl)-1H-pyrazolo[3,4-d]pyrimidin-4(5H)-one | Calc'd 354.1, found 354.2 | Phenomenex Lux 5u Cellulose-4, AXIA Packed | C, D |
| 132 | 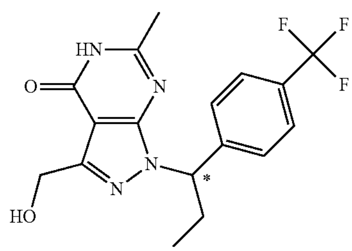 [SMILES: CCC(c1ccc(C(F)(F)F)cc1)n1nc(CO)c2c(=O)[nH]c(C)nc21] | (R)- or (S)-3-(Hydroxymethyl)-6-methyl-1-(1-(4-(trifluoromethyl)phenyl)propyl)-1H-pyrazolo[3,4-d]pyrimidin-4(5H)-one | Calc'd 367.1, found 367.0 | Chiralpak AS-H | B, E |
| 133 | 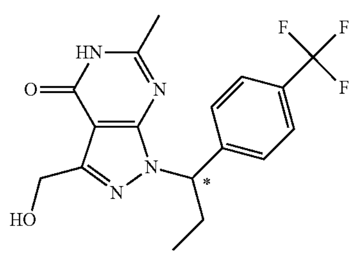 [SMILES: CCC(c1ccc(C(F)(F)F)cc1)n1nc(CO)c2c(=O)[nH]c(C)nc21] | (S)- or (R)-3-(Hydroxymethyl)-6-methyl-1-(1-(4-(trifluoromethyl)phenyl)propyl)-1H-pyrazolo[3,4-d]pyrimidin-4(5H)-one | Calc'd 367.1, found 367.0 | Chiralpak AS-H | B, E |
| 134 | 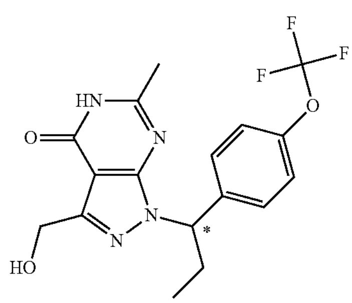 [SMILES: CCC(c1ccc(OC(F)(F)F)cc1)n1nc(CO)c2c(=O)[nH]c(C)nc21] | (R)- or (S)-3-(Hydroxymethyl)-6-methyl-1-(1-(4-(trifluoromethoxy)phenyl)propyl)-1H-pyrazolo[3,4-d]pyrimidin-4(5H)-one | Calc'd 383.1, found 383.0 | Chiralpak IA | B, E |

TABLE 18-continued

The following compounds were prepared using procedures similar to those described in Examples 76, 77, 80, and 81 using appropriate starting materials and the benzyl and methoxy deprotection conditions listed. Racemic products were separated using the chiral columns specified in the table. For those pairs of enantiomers, the faster-eluting isomer is always listed first in this table.
Benzyl deprotection conditions: A: 20% Pd(OH)$_2$/H$_2$; B: 10% Pd/C/H$_2$; C: BCl$_3$
Methoxy deprotection conditions: D: NaCN; E: HCl in ethyl acetate or dioxane

| Ex #. | Structure | IUPAC Name | Exact Mass [M + H]$^+$ or [M + Na]$^+$ | Chiral Column | Bn and Methoxy DC |
|---|---|---|---|---|---|
| 135 | 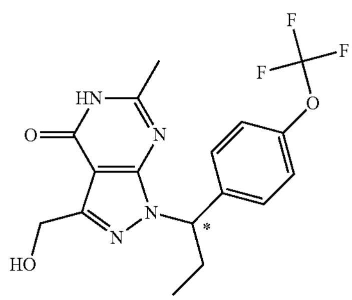 [SMILES: CCC(c1ccc(OC(F)(F)F)cc1)n1nc(CO)c2c(=O)[nH]c(C)nc21] | (S)- or (R)-3-(Hydroxymethyl)-6-methyl-1-(1-(4-(trifluoromethoxy)phenyl)propyl)-1H-pyrazolo[3,4-d]pyrimidin-4(5H)-one | Calc'd 383.1, found 383.0 | Chiralpak IA | B, E |
| 136 | 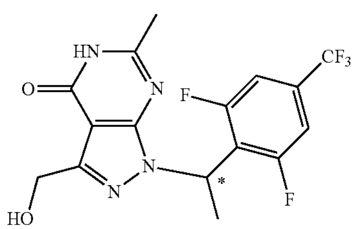 [SMILES: Cc1nc2c(c(CO)nn2C(C)c2c(F)cc(C(F)(F)F)cc2F)c(=O)[nH]1] | (R) and (S)-1-(1-(2,6-Difluoro-4-(trifluoromethyl)phenyl)-ethyl)-3-(hydroxymethyl)-6-methyl-1H-pyrazolo[3,4-d]pyrimidin-4(5H)-one | Calc'd 389.1, found 389.0 | Chiracel-OJ | B, E |
| 137 | 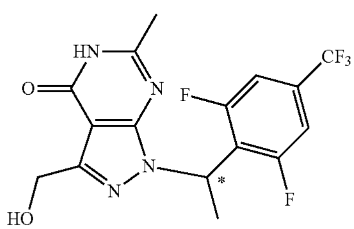 [SMILES: Cc1nc2c(c(CO)nn2C(C)c2c(F)cc(C(F)(F)F)cc2F)c(=O)[nH]1] | (S) and (R)-1-(1-(2,6-Difluoro-4-(trifluoromethyl)phenyl)-ethyl)-3-(hydroxymethyl)-6-methyl-1H-pyrazolo[3,4-d]pyrimidin-4(5H)-one | Calc'd 389.1, found 389.0 | Chiracel-OJ | B, E |
| 138 | 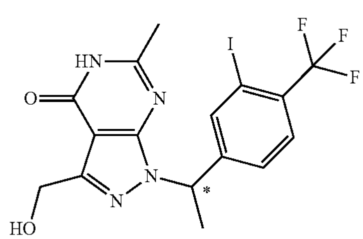 [SMILES: Cc1nc2c(c(CO)nn2C(C)c2ccc(C(F)(F)F)c(I)c2)c(=O)[nH]1] | (R)- or (S)-3-(Hydroxymethyl)-1-(1-(3-iodo-4-(trifluoromethyl-)phenyl)ethyl)-6-methyl-1,5-dihydro-4H-pyrazolo[3,4-d]pyrimidin-4-one | Calc'd 479.0, found: 479.0 | Chiralpak AS-H | C, D |
| 139 | 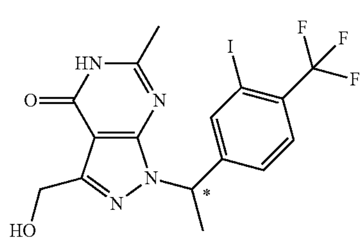 [SMILES: Cc1nc2c(c(CO)nn2C(C)c2ccc(C(F)(F)F)c(I)c2)c(=O)[nH]1] | (S)- or (R)-3-(Hydroxymethyl)-1-(1-(3-iodo-4-(trifluoromethyl-)phenyl)ethyl)-6-methyl-1,5-dihydro-4H-pyrazolo[3,4-d]pyrimidin-4-one | Calc'd 479.0, found: 479.0 | Chiralpak AS-H | C, D |

TABLE 18-continued

The following compounds were prepared using procedures similar to those described in Examples 76, 77, 80, and 81 using appropriate starting materials and the benzyl and methoxy deprotection conditions listed. Racemic products were separated using the chiral columns specified in the table. For those pairs of enantiomers, the faster-eluting isomer is always listed first in this table.
Benzyl deprotection conditions: A: 20% Pd(OH)$_2$/H$_2$; B: 10% Pd/C/H$_2$; C: BCl$_3$
Methoxy deprotection conditions: D: NaCN; E: HCl in ethyl acetate or dioxane

| Ex #. | Structure | IUPAC Name | Exact Mass [M + H]$^+$ or [M + Na]$^+$ | Chiral Column | Bn and Methoxy DC |
|---|---|---|---|---|---|
| 140 | 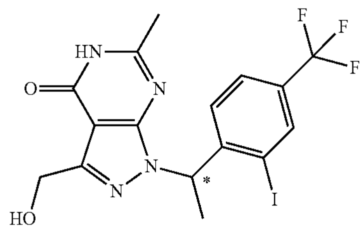 [SMILES: Cc1nc2c(c(CO)nn2C(C)c2ccc(C(F)(F)F)cc2I)c(=O)[nH]1] | (R)- or (S)-3-(Hydroxymethyl)-1-(1-(2-iodo-4-(trifluoromethyl-)phenyl)ethyl)-6-methyl-1,5-dihydro-4H-pyrazolo[3,4-d]pyrimidin-4-one | Calc'd 479.0, found 479.0 | Chiralpak AS-H | C, D |
| 141 | 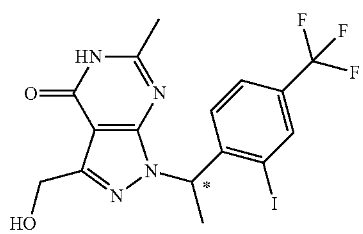 [SMILES: Cc1nc2c(c(CO)nn2C(C)c2ccc(C(F)(F)F)cc2I)c(=O)[nH]1] | (S)- or (R)-3-(Hydroxymethyl)-1-(1-(2-iodo-4-(trifluoromethyl-)phenyl)ethyl)-6-methyl-1,5-dihydro-4H-pyrazolo[3,4-d]pyrimidin-4-one | Calc'd 479.0, found 479.0 | Chiralpak AS-H | C, D |

DC=Deprotection Conditions

EXAMPLE 142

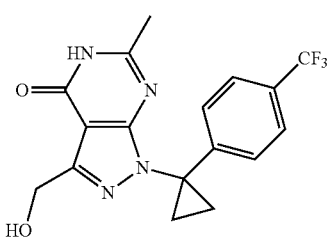 [SMILES: Cc1nc2c(c(CO)nn2C2(c3ccc(C(F)(F)F)cc3)CC2)c(=O)[nH]1]

3-(Hydroxymethyl)-6-methyl-1-(1-(4-(trifluoromethyl)phenyl)cyclopropyl)-1H-pyrazolo[3,4-d]pyrimidin-4(5H)-one (Scheme 20)

Step 1. 3-((tert-Butyldimethylsilyloxy)methyl)-4-methoxy-6-methyl-1-(1-(4-(trifluoromethyl)phenyl)cyclopropyl)-1H-pyrazolo[3,4-d]pyrimidine The title compound was prepared using procedures similar to those described in step 1 of Examples 76 and 77 using 3-(((tert-butyldimethylsilyl)oxy)methyl)-4-methoxy-6-methyl-1H-pyrazolo[3,4-d]pyrimidine from Preparatory Example 117 and 1-(4-(trifluoromethyl)phenyl)cyclopropanol to afford an oil. MS=493.1 (+ESI).

Step 2. (4-Methoxy-6-methyl-1-(1-(4-(trifluoromethyl)phenyl)cyclopropyl)-1H-pyrazolo[3,4-d]pyrimidin-3-yl)methanol To a solution of 3-(((tert-butyldimethylsilyl)oxy)methyl)-4-methoxy-6-methyl-1-(1-(4-(trifluoromethyl)phenyl)cyclopropyl)-1H-pyrazolo[3,4-d]pyrimidine (0.10 g, 0.20 mmol) in THF (2 mL) at RT was added a TBAF solution (1 M in THF, 0.4 mL, 0.4 mmol) dropwise. The reaction mixture was stirred at RT for 3 h, concentrated under reduced pressure, and the residue was diluted with water (5 mL). The mixture was extracted with EtOAc (3×5 mL) and the organic layers were combined and concentrated under reduced pressure. The residue was purified by preparative HPLC (X Bridge C18, 40-75% ACN in water (0.05% NH$_4$HCO$_3$)) to afford the title compound as an oil. MS=379.0 (+ESI).

Step 3. 3-(Hydroxymethyl)-6-methyl-1-(1-(4-(trifluoromethyl)phenyl)cyclopropyl)-1H-pyrazolo[3,4-d]pyrimidin-4(5H)-one The title compound was prepared using procedures similar to those described in step 3 of Examples 76 and 77 using (4-methoxy-6-methyl-1-(1-(4-(trifluoromethyl)phenyl)cyclopropyl)-1H-pyrazolo[3,4-d]pyrimidin-3-yl)methanol to afford the title compound (Example 142) as a solid. MS=365.2 (+ESI). $^1$H NMR (400 MHz, DMSO-d$_6$) δ: 12.26 (br s, 1H), 7.62 (d, J=8.4 Hz, 2H), 7.00 (d, J=8.4 Hz, 2H), 5.21 (t, J=5.6 Hz, 1H), 4.67 (d, J=5.6 Hz, 2H), 2.33 (s, 3H), 1.81 (d, J=4.4 Hz, 2H), 1.75 (d, J=4.4 Hz, 2H).

TABLE 19

The following compounds were prepared using procedures similar to those described in Example 142 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 143 | 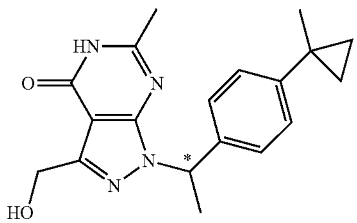 [SMILES: Cc1nc2c(c(CO)nn2C(C)c2ccc(C3(C)CC3)cc2)c(=O)[nH]1] | (R)- or (S)-3-(Hydroxymethyl)-6-methyl-1-(1-(4-(1-methylcyclopropyl)phenyl)ethyl)-1H-pyrazolo[3,4-d]pyrimidin-4(5H)-one | Calc'd 339.2, found 339.1 | Chiralpak IA |
| 144 | 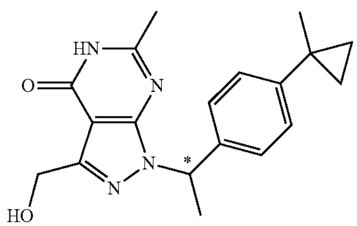 [SMILES: Cc1nc2c(c(CO)nn2C(C)c2ccc(C3(C)CC3)cc2)c(=O)[nH]1] | (S)- or (R)-3-(Hydroxymethyl)-6-methyl-1-(1-(4-(1-methylcyclopropyl)phenyl)ethyl)-1H-pyrazolo[3,4-d]pyrimidin-4(5H)-one | Calc'd 339.2, found 339.1 | Chiralpak IA |
| 145 | 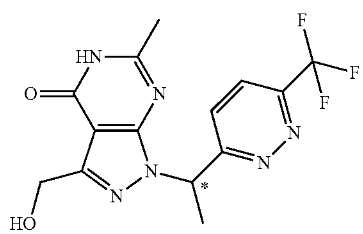 [SMILES: Cc1nc2c(c(CO)nn2C(C)c2ccc(C(F)(F)F)nn2)c(=O)[nH]1] | (R)- or (S)-3-(Hydroxymethyl)-6-methyl-1-(1-(6-(trifluoromethyl)pyridazin-3-yl)ethyl)-1H-pyrazolo[3,4-d]pyrimidin-4(5H)-one | Calc'd 355.1, found 355.0 | Chiralpak IB |
| 146 | 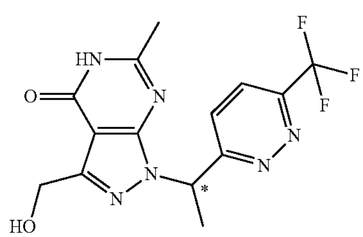 [SMILES: Cc1nc2c(c(CO)nn2C(C)c2ccc(C(F)(F)F)nn2)c(=O)[nH]1] | (S)- or (R)-3-(Hydroxymethyl)-6-methyl-1-(1-(6-(trifluoromethyl)pyridazin-3-yl)ethyl)-1H-pyrazolo[3,4-d]pyrimidin-4(5H)-one | Calc'd 355.1, found 355.0 | Chiralpak IB |
| 147 | 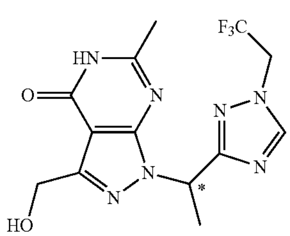 [SMILES: Cc1nc2c(c(CO)nn2C(C)c2ncn(CC(F)(F)F)n2)c(=O)[nH]1] | (R)- and (S)-3-(Hydroxymethyl)-6-methyl-1-(1-(1-(2,2,2-trifluoroethyl)-1H-1,2,4-triazol-3-yl)ethyl)-1H-pyrazolo[3,4-d]pyrimidin-4(5H)-one | Calc'd 358.1, found 358.2 | Phenomenex Lux Cellulose-4, AXIA |
| 148 | 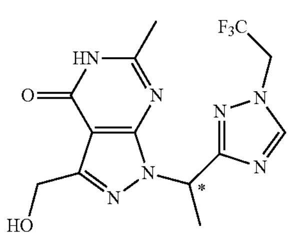 [SMILES: Cc1nc2c(c(CO)nn2C(C)c2ncn(CC(F)(F)F)n2)c(=O)[nH]1] | (S)- and (R)-3-(Hydroxymethyl)-6-methyl-1-(1-(1-(2,2,2-trifluoroethyl)-1H-1,2,4-triazol-3-yl)ethyl)-1H-pyrazolo[3,4-d]pyrimidin-4(5H)-one | Calc'd 358.1, found 358.2 | Phenomenex Lux Cellulose-4, AXIA |

TABLE 19-continued

The following compounds were prepared using procedures similar to those described in Example 142 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 149 | 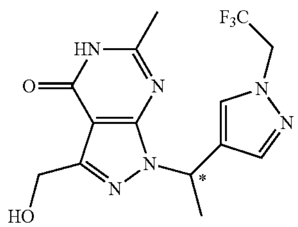 [SMILES: Cc1nc2c(c(CO)nn2C(C)c2cnn(CC(F)(F)F)c2)c(=O)[nH]1] | (R)- or (S)-3-(Hydroxymethyl)-6-methyl-1-(1-(1-(2,2,2-trifluoroethyl)-1H-pyrazol-4-yl)ethyl)-1H-pyrazolo[3,4-d]pyrimidin-4(5H)-one | Calc'd 357.1, found 357.1 | Phenomenex Lux Cellulose-4, AXIA |
| 150 | 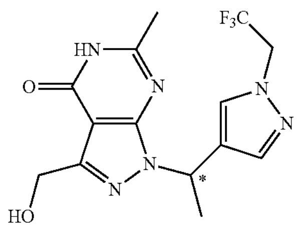 [SMILES: Cc1nc2c(c(CO)nn2C(C)c2cnn(CC(F)(F)F)c2)c(=O)[nH]1] | (S)- or (R)-3-(Hydroxymethyl)-6-methyl-1-(1-(1-(2,2,2-trifluoroethyl)-1H-pyrazol-4-yl)ethyl)-1H-pyrazolo[3,4-d]pyrimidin-4(5H)-one | Calc'd 356.1, found 357.0 | Phenomenex Lux Cellulose-4, AXIA |
| 151 | 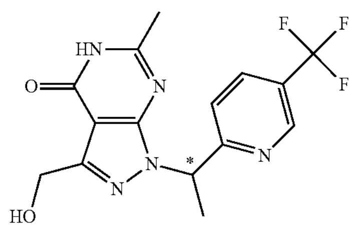 [SMILES: Cc1nc2c(c(CO)nn2C(C)c2ccc(C(F)(F)F)cn2)c(=O)[nH]1] | (R)- or (S)-3-(Hydroxymethyl)-6-methyl-1-(1-(5-(trifluoromethyl)pyridin-2-yl)ethyl)-1H-pyrazolo[3,4-d]pyrimidin-4(5H)-one | Calc'd 354.1, found 354.1 | Lux Chiralpak IA-3 |
| 152 | 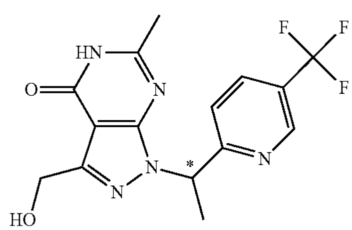 [SMILES: Cc1nc2c(c(CO)nn2C(C)c2ccc(C(F)(F)F)cn2)c(=O)[nH]1] | (S)- or (R)-3-(Hydroxymethyl)-6-methyl-1-(1-(5-(trifluoromethyl)pyridin-2-yl)ethyl)-1H-pyrazolo[3,4-d]pyrimidin-4(5H)-one | Calc'd 354.1, found 354.1 | Lux Chiralpak IA-3 |
| 153 | 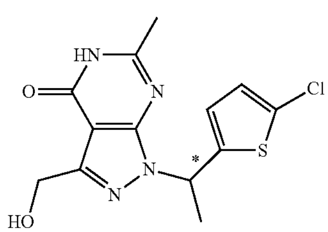 [SMILES: Cc1nc2c(c(CO)nn2C(C)c2ccc(Cl)s2)c(=O)[nH]1] | (R)- or (S)-1-(1-(5-Chlorothiophen-2-yl)ethyl)-3-(hydroxymethyl)-6-methyl-1H-pyrazolo[3,4-d]pyrimidin-4(5H)-one | Calc'd 325.1, found 325.1 | Chiralpak IA |
| 154 | 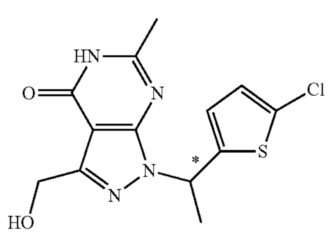 [SMILES: Cc1nc2c(c(CO)nn2C(C)c2ccc(Cl)s2)c(=O)[nH]1] | (S)- or (R)-1-(1-(5-Chlorothiophen-2-yl)ethyl)-3-(hydroxymethyl)-6-methyl-1H-pyrazolo[3,4-d]pyrimidin-4(5H)-one | Calc'd 325.1, found 325.1 | Chiralpak IA |

TABLE 19-continued

The following compounds were prepared using procedures similar to those described in Example 142 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 155 | 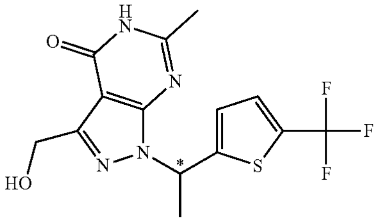 [SMILES: Cc1nc2c(c(CO)nn2C(C)c2ccc(C(F)(F)F)s2)c(=O)[nH]1] | (R)- or (S)-3-(Hydroxymethyl)-6-methyl-1-(1-(5-(trifluoromethyl)thiophen-2-yl)ethyl)-1H-pyrazolo[3,4-d]pyrimidin-4(5H)-one | Calc'd 359.1, found 359.1 | Chiralpak IA |
| 156 | 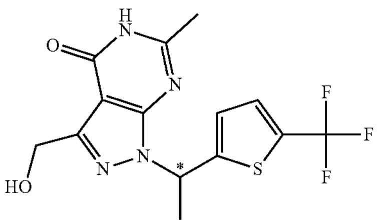 [SMILES: Cc1nc2c(c(CO)nn2C(C)c2ccc(C(F)(F)F)s2)c(=O)[nH]1] | (S)- or (R)-3-(Hydroxymethyl)-6-methyl-1-(1-(5-(trifluoromethyl)thiophen-2-yl)ethyl)-1H-pyrazolo[3,4-d]pyrimidin-4(5H)-one | Calc'd 359.1, found 359.1 | Chiralpak IA |

EXAMPLE 157

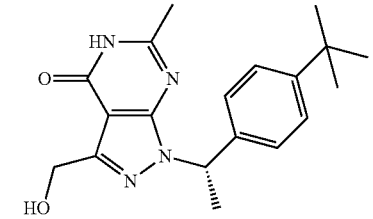 [SMILES: Cc1nc2c(c(CO)nn2[C@@H](C)c2ccc(C(C)(C)C)cc2)c(=O)[nH]1]

(S)-1-(1-(4-tert-Butylphenyl)ethyl)-3-(hydroxymethyl)-6-methyl-1H-pyrazolo[3,4-d]pyrimidin-4(5H)-one (Scheme 21)

Step 1. (S)-3-(Benzyloxymethyl)-1-(1-(4-tert-butylphenyl)ethyl)-4-methoxy-6-methyl-1H-pyrazolo[3,4-d]pyrimidine The title compound was prepared using procedures similar to those described in step 1 of Examples 76 and 77 using (R)-1-(4-(tert-butyl)phenyl)ethanol from Preparatory Example 105 and 3-((benzyloxy)methyl)-4-methoxy-6-methyl-1H-pyrazolo[3,4-d]pyrimidine from Preparatory Example 116 to afford an oil. MS=445.3 (+ESI).

Step 2. (S)-(1-(1-(4-tert-Butylphenyl)ethyl)-4-methoxy-6-methyl-1H-pyrazolo[3,4-d]pyrimidin-3-yl)methanol The title compound was prepared using procedures similar to those described in step 2 of Example 2 using (S)-3-((benzyloxy)methyl)-1-(1-(4-(tert-butyl)phenyl)ethyl)-4-methoxy-6-methyl-1H-pyrazolo[3,4-d]pyrimidine to afford a liquid. MS=355.2 (+ESI).

Step 3. (S)-1-(1-(4-tert-Butylphenyl)ethyl)-3-(hydroxymethyl)-6-methyl-1H-pyrazolo[3,4-d]pyrimidin-4(5H)-one The title compound was prepared using procedures similar to those described in step 3 of Examples 76 and 77 using (S)-(1-(1-(4-(tert-butyl)phenyl)ethyl)-4-methoxy-6-methyl-1H-pyrazolo[3,4-d]pyrimidin-3-yl)methanol to afford the title compound (Example 149) as a solid. MS=341.2 (+ESI). $^1$H NMR (300 MHz, DMSO-$d_6$) δ: 12.15 (s, 1H), 7.33 (d, J=8.1 Hz, 2H), 7.21 (d, J=8.4 Hz, 2H), 5.95 (q, J=6.0 Hz, 1H), 5.15 (br s, 1H), 4.64 (s, 2H), 2.37 (s, 3H), 1.81 (d, J=6.9 Hz, 3H), 1.23 (s, 9H).

TABLE 20

The following compounds in were prepared using procedures similar to those described in Example 157 using appropriate starting materials.

| Ex #. | Structure | IUPAC Name | Exact Mass [M + H]+ or [M + Na]+ |
|---|---|---|---|
| 158 | 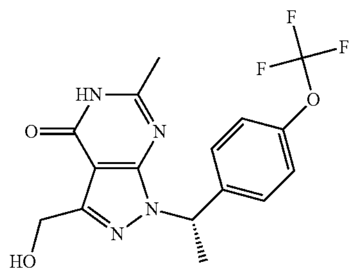 [SMILES: Cc1nc2c(c(CO)nn2[C@@H](C)c2ccc(OC(F)(F)F)cc2)c(=O)[nH]1] | (S)-3-(Hydroxymethyl)-6-methyl-1-(1-(4-(trifluoromethoxy)phenyl)ethyl)-1H-pyrazolo[3,4-d]pyrimidin-4(5H)-one | Calc'd 369.1, found 369.1 |
| 159 | 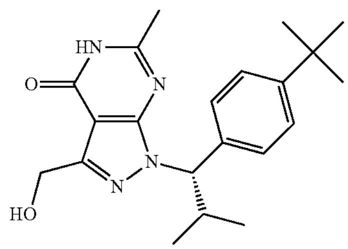 [SMILES: Cc1nc2c(c(CO)nn2[C@H](c2ccc(C(C)(C)C)cc2)C(C)C)c(=O)[nH]1] | (S)-1-(1-(4-tert-Butylphenyl)-2-methylpropyl)-3-(hydroxymethyl)-6-methyl-1H-pyrazolo[3,4-d]pyrimidin-4(5H)-one | Calc'd 369.2, found 369.2 |
| 160 | 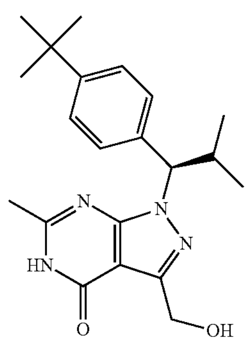 [SMILES: Cc1nc2c(c(CO)nn2[C@@H](c2ccc(C(C)(C)C)cc2)C(C)C)c(=O)[nH]1] | (R)-1-(1-(4-tert-Butylphenyl)-2-methylpropyl)-3-(hydroxymethyl)-6-methyl-1H-pyrazolo[3,4-d]pyrimidin-4(5H)-one | Calc'd 369.2, found 369.3 |

EXAMPLES 161 and 162

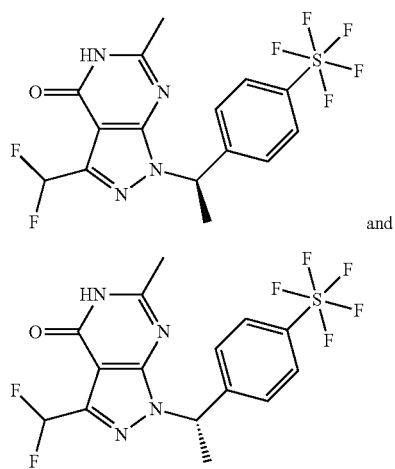

and (R)- and (S)-3-(Difluoromethyl)-6-methyl-1-(1-(4-(pentafluorothio)phenyl)ethyl)-1H-pyrazolo[3,4-d]pyrimidin-4(5H)-one (Scheme 22)

Step 1. 4-Methoxy-6-methyl-1-(1-(4-(pentafluorothio)phenyl)ethyl)-1H-pyrazolo[3,4-d]pyrimidine-3-carbaldehyde To a stirred mixture of 3-(hydroxymethyl)-6-methyl-1-(1-(4-(pentafluorothio)phenyl)ethyl)-1H-pyrazolo[3,4-d]pyrimidin-4(5H)-one (0.27 g, 0.64 mmol) in DCE (4 mL) at RT was added MnO₂ (0.55 g, 6.4 mmol). The mixture was heated to 50° C., stirred for 4 h, and was recooled to RT. The mixture was filtered through a Celite™ pad which was washed with 1,2-dichloroethane (2×3 mL). The filtrate was concentrated under reduced pressure to afford the title compound as an oil which was used directly without purification. MS=423.3 (+ESI).

Step 2. 3-(Difluoromethyl)-4-methoxy-6-methyl-1-(1-(4-(pentafluorothio)phenyl)ethyl)-1H-pyrazolo[3,4-d]pyrimidine To a stirred mixture of 4-methoxy-6-methyl-1-(1-(4-(pentafluorothio)phenyl)ethyl)-1H-pyrazolo[3,4-d]pyrimidine- 3-carbaldehyde (0.29 g, 0.7 mmol) in $CH_2Cl_2$ (3 mL) at 0° C. was added DAST (0.5 mL, 3.4 mmol) dropwise. The mixture was allowed to warm to RT and stir for 16 h. The mixture was cooled to 0° C., diluted with $CH_2Cl_2$ (15 mL), and the mixture was washed with sat. aq. $NaHCO_3$ (2×10 mL). The organic layer was dried over $Na_2SO_4$, filtered, and concentrated under reduced pressure. The residue was purified by silica gel column chromatography (0-70% EtOAc in petroleum ether) to afford the title compound as an oil. MS=445.3 (+ESI).

Step 3. (R)- and (S)-3-(Difluoromethyl)-6-methyl-1-(1-(4-(pentafluorothio)phenyl)ethyl)-1H-pyrazolo[3,4-d]pyrimidin-4(5H)-one The racemic title compound was prepared using procedures similar to those described in step 3 of Examples 76 and 77 using 3-(difluoromethyl)-4-methoxy-6-methyl-1-(1-(4-(pentafluoro-thio)phenyl)ethyl)-1H-pyrazolo[3,4-d]pyrimidine. The enantiopure title compounds were obtained by chiral preparative HPLC (Chiralpak IC, 5% EtOH in hexanes) The faster-eluting enantiomer of the title compound (Example 161) was obtained as a solid. MS=431.2 (+ESI). $^1$H NMR (400 MHz, $CDCl_3$) δ: 11.22 (s, 1H), 7.71 (d, J=8.4 Hz, 2H), 7.52-7.48 (m, 2H), 6.92 (t, J=53.8 Hz, 1H), 6.11 (q, J=7.2 Hz, 1H), 2.54 (s, 3H), 1.97 (d, J=7.2 Hz, 3H). The slower-eluting enantiomer of the title compound (Example 162) was obtained as a solid. MS=431.2 (+ESI). $^1$H NMR (400 MHz, $CDCl_3$) δ: 11.08 (s, 1H), 7.71 (d, J=8.8 Hz, 2H), 7.52-7.48 (m, 2H), 6.92 (t, J=53.8 Hz, 1H), 6.10 (q, J=7.2 Hz, 1H), 2.54 (s, 3H), 1.97 (d, J=7.2 Hz, 3H).

TABLE 21

The following compounds were prepared using procedures similar to those described in Examples 161 and 162 using the appropriate starting materials except using NaCN deprotection from step 3 of Examples 76 and 77.

| Ex # | Structure | IUPAC Name | Exact Mass [M + H]+ |
|---|---|---|---|
| 163 | 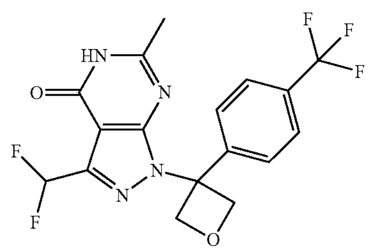 [SMILES: Cc1nc2c(c(C(F)F)nn2C2(c3ccc(C(F)(F)F)cc3)COC2)c(=O)[nH]1] | 3-(Difluoromethyl)-6-methyl-1-(3-(4-(trifluoromethyl)phenyl)oxetan-3-yl)-1H-pyrazolo[3,4-d]pyrimidin-4(5H)-one | Calc'd 401.1, found 401.2 |
| 164 | 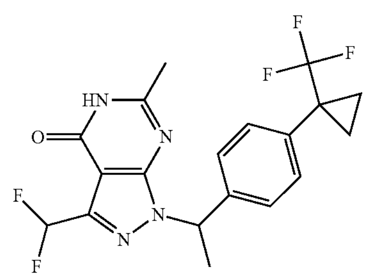 [SMILES: Cc1nc2c(c(C(F)F)nn2C(C)c2ccc(C3(C(F)(F)F)CC3)cc2)c(=O)[nH]1] | 3-(Difluoromethyl)-6-methyl-1-(1-(4-(1-(trifluoromethyl)cyclopropyl)phenyl)ethyl)-1H-pyrazolo[3,4-d]pyrimidin-4(5H)-one | Calc'd 413.1, found 413.0 |
| 165 | 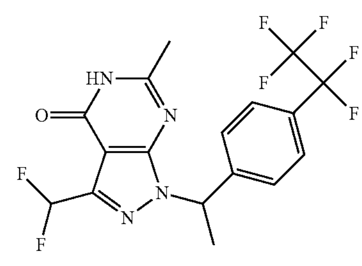 [SMILES: Cc1nc2c(c(C(F)F)nn2C(C)c2ccc(C(F)(F)C(F)(F)F)cc2)c(=O)[nH]1] | 3-(Difluoromethyl)-6-methyl-1-(1-(4-(perfluoroethyl)phenyl)ethyl)-1H-pyrazolo[3,4-d]pyrimidin-4(5H)-one | Calc'd 423.1, found 423.0 |
| 166 | 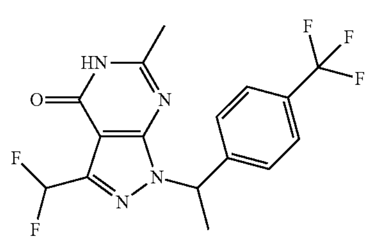 [SMILES: Cc1nc2c(c(C(F)F)nn2C(C)c2ccc(C(F)(F)F)cc2)c(=O)[nH]1] | 3-(Difluoromethyl)-6-methyl-1-{1-[4-(trifluoromethyl)phenyl]ethyl}-1,5-dihydro-4H-pyrazolo[3,4-d]pyrimidin-4-one | Calc'd 373.1, found 373.1 |

TABLE 22

The following compounds were prepared using procedures similar to those described in Examples 161 and 162 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 167 | 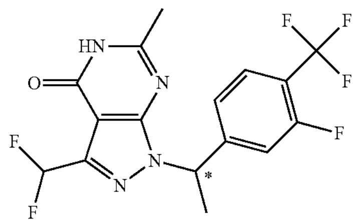 [SMILES: Cc1nc2c(c(C(F)F)nn2C(C)c2ccc(C(F)(F)F)c(F)c2)c(=O)[nH]1] | (R)- or (S)-3-(Difluoromethyl)-1-(1-(3-fluoro-4-(trifluoromethyl)phenyl)ethyl)-6-methyl-1H-pyrazolo[3,4-d]pyrimidin-4(5H)-one | Calc'd 391.1, found 391.2 | Chiralpak IA-3 |
| 168 | 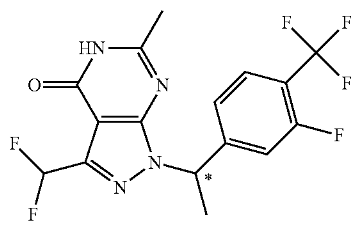 [SMILES: Cc1nc2c(c(C(F)F)nn2C(C)c2ccc(C(F)(F)F)c(F)c2)c(=O)[nH]1] | (S)- or (R)-3-(Difluoromethyl)-1-(1-(3-fluoro-4-(trifluoromethyl)phenyl)ethyl)-6-methyl-1H-pyrazolo[3,4-d]pyrimidin-4(5H)-one | Calc'd 391.1, found 391.2 | Chiralpak IA-3 |
| 169 | 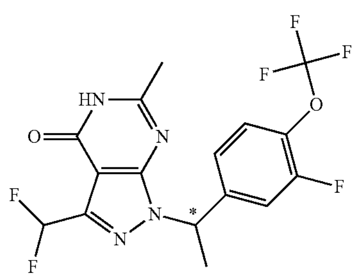 [SMILES: Cc1nc2c(c(C(F)F)nn2C(C)c2ccc(OC(F)(F)F)c(F)c2)c(=O)[nH]1] | (R)- or (S)-3-(Difluoromethyl)-1-(1-(3-fluoro-4-(trifluoromethoxy)phenyl)ethyl)-6-methyl-1H-pyrazolo[3,4-d]pyrimidin-4(5H)-one | Calc'd 407.1, found 407.1 | Chiralpak IC |
| 170 | 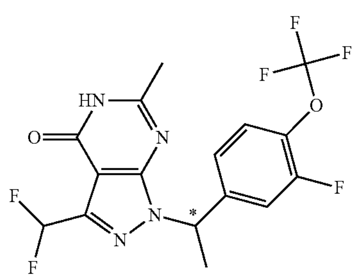 [SMILES: Cc1nc2c(c(C(F)F)nn2C(C)c2ccc(OC(F)(F)F)c(F)c2)c(=O)[nH]1] | (S)- or (R)-3-(Difluoromethyl)-1-(1-(3-fluoro-4-(trifluoromethoxy)phenyl)ethyl)-6-methyl-1H-pyrazolo[3,4-d]pyrimidin-4(5H)-one | Calc'd 407.1, found 407.2 | Chiralpak IC |
| 171 | 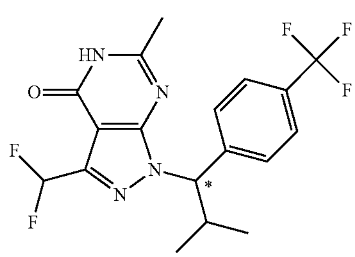 [SMILES: Cc1nc2c(c(C(F)F)nn2C(c2ccc(C(F)(F)F)cc2)C(C)C)c(=O)[nH]1] | (R)- or (S)-3-(Difluoromethyl)-6-methyl-1-(2-methyl-1-(4-(trifluoromethyl)phenyl)propyl)-1H-pyrazolo[3,4-d]pyrimidin-4(5H)-one | Calc'd 401.1, found 401.2 | Chiralpak IC |

TABLE 22-continued

The following compounds were prepared using procedures similar to those described in Examples 161 and 162 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 172 | 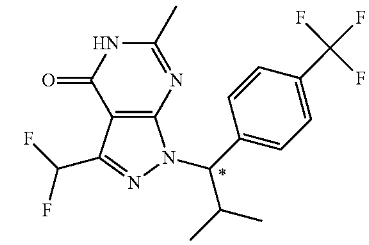 [SMILES: Cc1nc2c(c(C(F)F)nn2C(c2ccc(C(F)(F)F)cc2)C(C)C)c(=O)[nH]1] | (S)- or (R)-3-(Difluoromethyl)-6-methyl-1-(2-methyl-1-(4-(trifluoromethyl)phenyl)propyl)-1H-pyrazolo[3,4-d]pyrimidin-4(5H)-one | Calc'd 401.1, found 401.2 | Chiralpak IC |
| 173 | 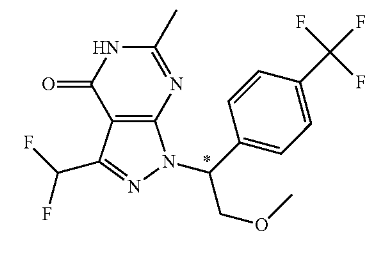 [SMILES: COCC(c1ccc(C(F)(F)F)cc1)n1nc(C(F)F)c2c(=O)[nH]c(C)nc21] | (R)- or (S)-3-(Difluoromethyl)-1-(2-methoxy-1-(4-(trifluoromethyl)phenyl)ethyl)-6-methyl-1H-pyrazolo[3,4-d]pyrimidin-4(5H)-one | Calc'd 403.1, found 403.2. | Chiralpak AS-H |
| 174 | 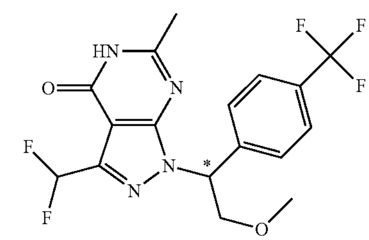 [SMILES: COCC(c1ccc(C(F)(F)F)cc1)n1nc(C(F)F)c2c(=O)[nH]c(C)nc21] | (S)- or (R)-3-(Difluoromethyl)-1-(2-methoxy-1-(4-(trifluoromethyl)phenyl)ethyl)-6-methyl-1H-pyrazolo[3,4-d]pyrimidin-4(5H)-one | Calc'd 403.1, found 403.2. | Chiralpak AS-H |

EXAMPLES 175 and 176

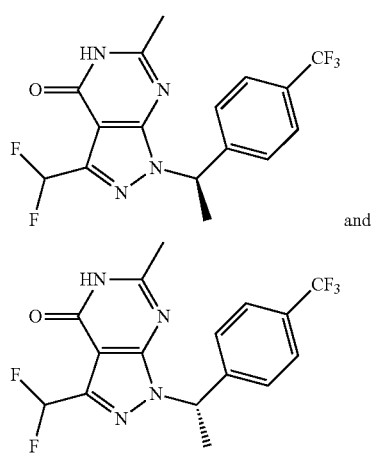

(R)- and (S)-3-(Difluoromethyl)-6-methyl-1-(1-(4-(trifluoromethyl)phenyl)ethyl)-1H-pyrazolo[3,4-d]pyrimidin-4(5H)-one (Scheme 23)

Step 1. 6-Methyl-4-oxo-1-(1-(4-(trifluoromethyl)phenyl)ethyl)-4,5-dihydro-1H-pyrazolo[3,4-d]pyrimidine-3-carbaldehyde To the solution of 3-(hydroxymethyl)-6-methyl-1-(1-(4-(trifluoromethyl)phenyl)ethyl)-1H-pyrazolo[3,4-d]pyrimidin-4(5H)-one (0.60 g, 1.7 mmol) in CH$_2$Cl$_2$ (10 mL) at RT was added Dess-Martin periodinane (0.94 g, 2.2 mmol). The resulting mixture was stirred at RT for 2 h whereupon sat. aq. NaHCO$_3$ (100 mL) was added and extracted with ethyl acetate (3×100 mL). The combined organic layers were washed with brine (200 mL), dried with anhydrous sodium sulfate, and filtered. The filtrate was concentrated under reduced pressure. The residue was purified by silica gel column chromatography (50% ethyl acetate in petroleum ether) to afford the title compound as a solid. MS=351.1 (+ESI).

Step 2. (R)- and (S)-3-(Difluoromethyl)-6-methyl-1-(1-(4-(trifluoromethyl)phenyl)ethyl)-1H-pyrazolo[3,4-d]pyrimidin-4(5H)-one The racemic title compound was prepared using procedures similar to those described in step 2 of Examples 161 and 162 using 6-methyl-4-oxo-1-(1-(4-(trifluoromethyl)phenyl)ethyl)-4,5-dihydro-1H-pyrazolo[3,4-d]pyrimidine-3-carbaldehyde to afford a solid. The enantiopure title compounds were obtained by chiral preparative HPLC (Lux CHIRAL PAK IA-3, 10% EtOH in hexanes). The faster-eluting enantiomer of the title compound (Example 175) was obtained as a solid. MS=373.1 (+ESI). $^1$H NMR (400 MHz, DMSO-$d_6$) δ: 12.40 (br s, 1H), 7.73 (d, J=8.0 Hz, 2H), 7.49 (d, J=8.0 Hz, 2H), 7.17 (t, J=53.2 Hz, 1H), 6.18 (q, J=7.2 Hz, 1H), 2.38 (s, 3H), 1.88 (d, J=7.2 Hz, 3H). The slower-eluting enantiomer of the title compound (Example 176) was obtained as a solid. MS=373.1 (+ESI). $^1$H NMR (400 MHz, DMSO-$d_6$) δ: 12.40 (br s, 1H), 7.73 (d, J=8.4 Hz, 2H), 7.49 (d, J=8.0 Hz, 2H), 7.17 (t, J=53.2 Hz, 1H), 6.18 (q, J=7.2 Hz, 1H), 2.38 (s, 3H), 1.88 (d, J=7.2 Hz, 3H).

TABLE 23

The following compounds were prepared using procedures similar to those described in Examples 175 and 176 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 177 | 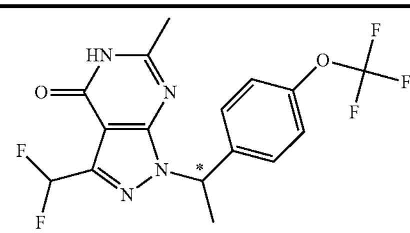 | (R)- or (S)-3-(Difluoromethyl)-6-methyl-1-(1-(4-(trifluoromethoxy)phenyl)ethyl)-1H-pyrazolo[3,4-d]pyrimidin-4(5H)-one | Calc'd 389.1, found 389.2 | Chiralpak IA |
| 178 | 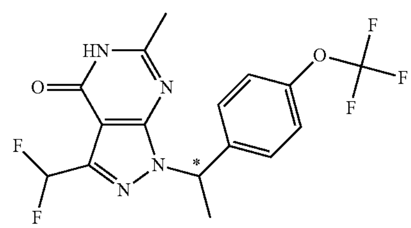 | (S)- or (R)-3-(Difluoromethyl)-6-methyl-1-(1-(4-(trifluoromethoxy)phenyl)ethyl)-1H-pyrazolo[3,4-d]pyrimidin-4(5H)-one | Calc'd 389.1, found 389.2 | Chiralpak IA |
| 179 | 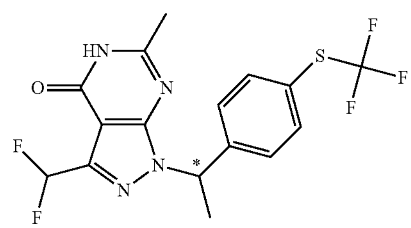 [SMILES: Cc1nc2c(c(C(F)F)nn2C(C)c2ccc(SC(F)(F)F)cc2)c(=O)[nH]1] | (R)- or (S)-3-(Difluoromethyl)-6-methyl-1-(1-(4-(trifluoromethylthio)phenyl)ethyl)-1H-pyrazolo[3,4-d]pyrimidin-4(5H)-one | Calc'd 405.1, found 405.1 | Chiralpak IA |
| 180 | 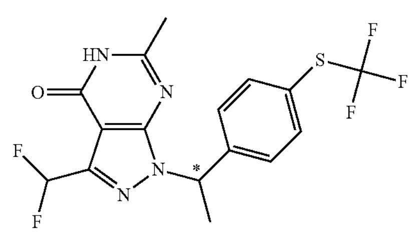 [SMILES: Cc1nc2c(c(C(F)F)nn2C(C)c2ccc(SC(F)(F)F)cc2)c(=O)[nH]1] | (S)- or (R)-3-(Difluoromethyl)-6-methyl-1-(1-(4-(trifluoromethylthio)phenyl)ethyl)-1H-pyrazolo[3,4-d]pyrimidin-4(5H)-one | Calc'd 405.1, found 405.1 | Chiralpak IA |
| 181 | 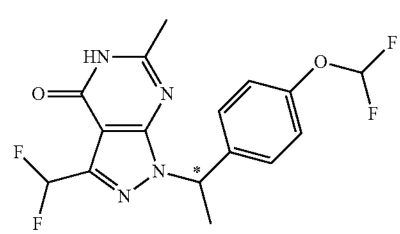 [SMILES: Cc1nc2c(c(C(F)F)nn2C(C)c2ccc(OC(F)F)cc2)c(=O)[nH]1] | (R)- or (S)-1-(1-(4-(Difluoromethoxy)phenyl)ethyl)-3-(difluoromethyl)-6-methyl-1H-pyrazolo[3,4-d]pyrimidin-4(5H)-one | Calc'd 371.1, found 371.2 | Chiralpak IC |

TABLE 23-continued

The following compounds were prepared using procedures similar to those described in Examples 175 and 176 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 182 | 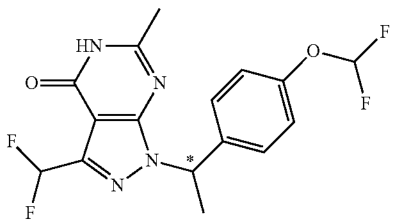 [SMILES: Cc1nc2c(c(C(F)F)nn2C(C)c2ccc(OC(F)F)cc2)c(=O)[nH]1] | (S)- or (R)-1-(1-(4-(Difluoromethoxy)phenyl)ethyl)-3-(difluoromethyl)-6-methyl-1H-pyrazolo[3,4-d]pyrimidin-4(5H)-one | Calc'd 371.1, found 371.2 | Chiralpak IC |
| 183 | 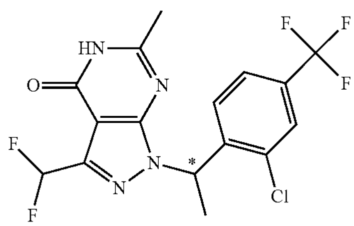 [SMILES: Cc1nc2c(c(C(F)F)nn2C(C)c2ccc(C(F)(F)F)cc2Cl)c(=O)[nH]1] | (R)- or (S)-1-(1-(2-Chloro-4-(trifluoromethyl)phenyl)ethyl)-3-(difluoromethyl)-6-methyl-1H-pyrazolo[3,4-d]pyrimidin-4(5H)-one | Calc'd 407.1, found 407.1, 409.1 | Chiralpak IC |
| 184 | 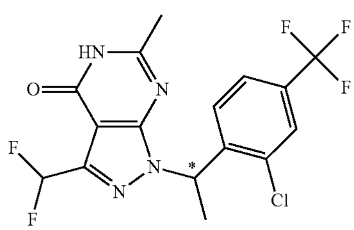 [SMILES: Cc1nc2c(c(C(F)F)nn2C(C)c2ccc(C(F)(F)F)cc2Cl)c(=O)[nH]1] | (S)- or (R)-1-(1-(2-Chloro-4-(trifluoro-methyl)phenyl)-ethyl)-3-(difluoromethyl)-6-methyl-1H-pyrazolo[3,4-d]pyrimidin-4(5H)-one | Calc'd 407.1, found 407.1, 409.1 | Chiralpak IC |
| 185 | 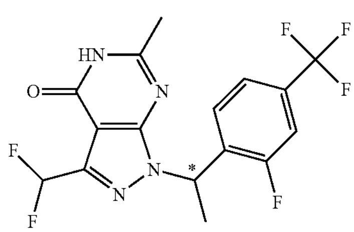 | (R)- or (S)-3-(Difluoro-methyl)-1-(1-(2-fluoro-4-(trifluoro-methyl)phenyl)-ethyl)-6-methyl-1H-pyrazolo[3,4-d]pyrimidin-4(5H)-one | Calc'd 391.1, found 391.0 | Chiralpak IC |
| 186 | 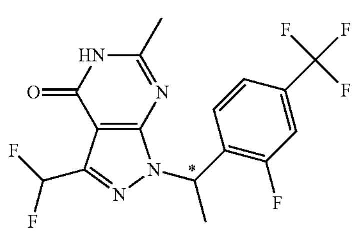 [SMILES: Cc1nc2c(c(C(F)F)nn2C(C)c2ccc(C(F)(F)F)cc2F)c(=O)[nH]1] | (S)- or (R)-3-(Difluoro-methyl)-1-(1-(2-fluoro-4-(trifluoromethyl)phenyl)ethyl)-6-methyl-1H-pyrazolo[3,4-d]pyrimidin-4(5H)-one | Calc'd 391.1, found 391.1 | Chiralpak IC |
| 187 | 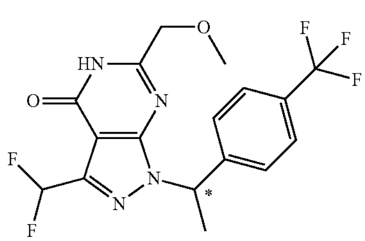 [SMILES: COCc1nc2c(c(C(F)F)nn2C(C)c2ccc(C(F)(F)F)cc2)c(=O)[nH]1] | (R)- or (S)-3-(Difluoromethyl)-6-(methoxymethyl)-1-{1-[4-(trifluoromethyl)phenyl]ethyl}-1,5-dihydro-4H-pyrazolo-[3,4-d]pyrimidin-4-one | Calc'd 403.1, found 403.0 | AD-H |

TABLE 23-continued

The following compounds were prepared using procedures similar to those described in Examples 175 and 176 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 188 | 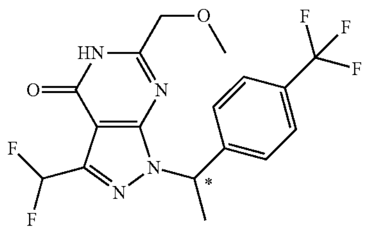 [SMILES: COCc1nc2c(c(C(F)F)nn2C(C)c2ccc(C(F)(F)F)cc2)c(=O)[nH]1] | (S)- or (R)-3-(Difluoro-methyl)-6-(methoxymethyl)-1-{1-[4-(trifluoromethyl)phenyl]ethyl}-1,5-dihydro-4H-pyrazolo-[3,4-d]pyrimidin-4-one | Calc'd 403.1, found: 403.0 | AD-H |
| 189 | 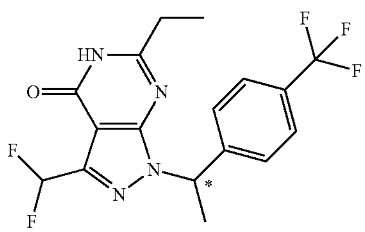 [SMILES: CCc1nc2c(c(C(F)F)nn2C(C)c2ccc(C(F)(F)F)cc2)c(=O)[nH]1] | (R)- or (S)-3-(Difluoromethyl)-6-ethyl-1-(1-(4-(trifluoromethyl)phenyl)ethyl)-1,5-dihydro-4H-pyrazolo[3,4-d]pyrimidin-4-one | Calc'd 387.1, found 386.9 | AD-H |
| 190 | 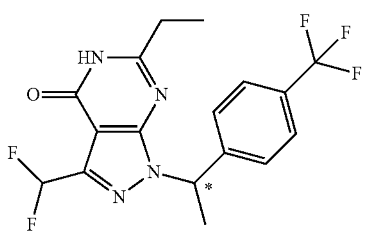 [SMILES: CCc1nc2c(c(C(F)F)nn2C(C)c2ccc(C(F)(F)F)cc2)c(=O)[nH]1] | (S)- or (R)-3-(Difluoromethyl)-6-ethyl-1-(1-(4-(trifluoromethyl)-phenyl)ethyl)-1,5-dihydro-4H-pyrazolo[3,4-d]pyrimidin-4-one | Calc'd 387.1, found 386.9 | AD-H |
| 191 | 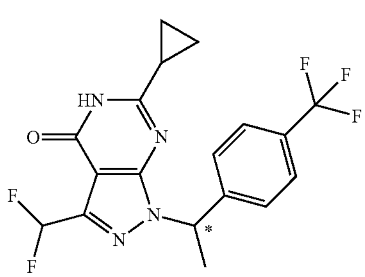 [SMILES: CC(c1ccc(C(F)(F)F)cc1)n1nc(C(F)F)c2c(=O)[nH]c(C3CC3)nc21] | (R)- or (S)-6-Cyclopropyl-3-(difluoromethyl)-1-(1-(4-(trifluoromethyl)phenyl)ethyl)-1,5-dihydro-4H-pyrazolo[3,4-d]pyrimidin-4-one | Calc'd 399.1, found 398.9 | AD-H |
| 192 | 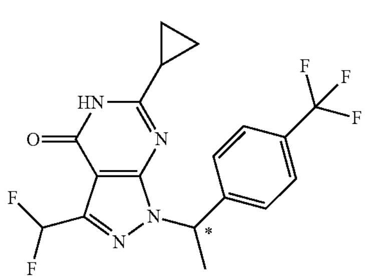 [SMILES: CC(c1ccc(C(F)(F)F)cc1)n1nc(C(F)F)c2c(=O)[nH]c(C3CC3)nc21] | (S)- or (R)-6-Cyclopropyl-3-(difluoromethyl)-1-(1-(4-(trifluoromethyl)phenyl)ethyl)-1,5-dihydro-4H-pyrazolo[3,4-d]pyrimidin-4-one | Calc'd 399.1, found 398.8 | AD-H |

EXAMPLE 193

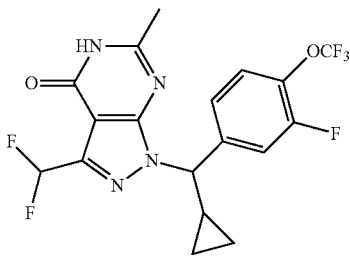 [SMILES: Cc1nc2c(c(C(F)F)nn2C(c2ccc(OC(F)(F)F)c(F)c2)C2CC2)c(=O)[nH]1]

1-(Cyclopropyl(3-fluoro-4-(trifluoromethoxy)phenyl)methyl)-3-(difluoromethyl)-6-methyl-1H-pyrazolo[3,4-d]pyrimidin-4(5H)-one (Scheme 23)

Step 1. 1-(Cyclopropyl(3-fluoro-4-(trifluoromethoxy)phenyl)methyl)-6-methyl-4-oxo-4,5-dihydro-1H-pyrazolo[3,4-d]pyrimidine-3-carbaldehyde The title compound was prepared using procedures similar to those described in step 1 of Examples 161 and 162 using 1-(cyclopropyl(3-fluoro-4-(trifluoromethoxy)phenyl)methyl)-3-(hydroxymethyl)-6-methyl-1H-pyrazolo[3,4-d]pyrimidin-4(5H)-one to afford a solid. MS=411.1 (+ESI).

Step 2. 1-(Cyclopropyl(3-fluoro-4-(trifluoromethoxy)phenyl)methyl)-3-(difluoromethyl)-6-methyl-1H-pyrazolo[3,4-d]pyrimidin-4(5H)-one The title compound was prepared using procedures similar to those described in step 2 of Examples 161 and 162 using 1-(cyclopropyl(3-fluoro-4-(trifluoromethoxy)phenyl)methyl)-6-methyl-4-oxo-4,5-dihydro-1H-pyrazolo[3,4-d]pyrimidine-3-carbaldehyde to afford the title compound (Example 193) as a solid. MS=431.0 (−ESI). $^1$H NMR (400 MHz, DMSO-$d_6$) δ: 12.38 (s, 1H), 7.60-7.56 (m, 2H), 7.34-7.30 (m, 1H), 7.17 (t, J=53.2 Hz, 1H), 5.18 (d, J=10.0 Hz, 1H), 2.38 (s, 3H), 1.94-1.89 (m, 1H), 0.76-0.72 (m, 2H), 0.59-0.55 (m, 1H), 0.38-0.34 (m, 1H).

EXAMPLES 194 and 195

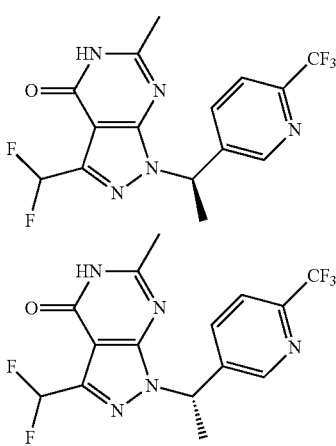

(R)- and (S)-3-(Difluoromethyl)-6-methyl-1-(1-(6-(trifluoromethyl)pyridin-3-yl)ethyl)-1H-pyrazolo[3,4-d]pyrimidin-4(5H)-one (Scheme 24)

Step 1. 3-(Benzyloxymethyl)-4-methoxy-6-methyl-1-(1-(6-(trifluoromethyl)pyridin-3-yl)ethyl)-1H-pyrazolo[3,4-d]pyrimidine The title compound was prepared using procedures similar to those described in step 5 of Examples 76 and 77 using 3-(benzyloxymethyl)-4-methoxy-6-methyl-1H-pyrazolo[3,4-d]pyrimidine from Preparative Example 116 and 1-(6-(trifluoromethyl)pyridin-3-yl)ethanol to afford an oil. MS=458.2 (+ESI).

Step 2. (4-Methoxy-6-methyl-1-(1-(6-(trifluoromethyl)pyridin-3-yl)ethyl)-1H-pyrazolo[3,4-d]pyrimidin-3-yl)methanol The title compound was prepared using procedures similar to those described in step 2 of Example 3 using 3-(benzyloxymethyl)-4-methoxy-6-methyl-1-(1-(6-(trifluoromethyl)pyridin-3-yl)ethyl)-1H-pyrazolo[3,4-d]pyrimidine to afford an oil. MS=368.2 (+ESI).

Step 3. 4-Methoxy-6-methyl-1-(1-(6-(trifluoromethyl)pyridin-3-yl)ethyl)-1H-pyrazolo[3,4-d]pyrimidine-3-carbaldehyde The title compound was prepared using procedures similar to those described in step 1 of Examples 175 and 176 using (4-methoxy-6-methyl-1-(1-(6-(trifluoromethyl)pyridin-3-yl)ethyl)-1H-pyrazolo[3,4-d]pyrimidin-3-yl)methanol to afford an oil which was used for next step directly without purification. MS=366.1 (+ESI).

Step 4. 3-(Difluoromethyl)-4-methoxy-6-methyl-1-(1-(6-(trifluoromethyl)pyridin-3-yl)ethyl)-1H-pyrazolo[3,4-d]pyrimidine The title compound was prepared using procedures similar to those described in step 2 of Examples 161 and 162 using 4-methoxy-6-methyl-1-(1-(6-(trifluoromethyl)pyridin-3-yl)ethyl)-1H-pyrazolo[3,4-d]pyrimidine-3-carbaldehyde to afford a solid. MS=388.1 (+ESI).

Step 5. (R)- and (S)-3-(Difluoromethyl)-6-methyl-1-(1-(6-(trifluoromethyl)pyridin-3-yl)ethyl)-1H-pyrazolo[3,4-d]pyrimidin-4(5H)-one To a stirred mixture of 3-(difluoromethyl)-4-methoxy-6-methyl-1-(1-(6-(trifluoromethyl)pyridine-3-yl)ethyl)-1H-pyrazolo[3,4-d]pyrimidine (50 mg, 0.10 mmol) and NaI (58.1 mg, 0.40 mmol) in $CH_3CN$ (1.5 mL) at RT was added TMSCl (42 mg, 0.40 mmol). The mixture was stirred at RT for 3 h and was diluted with EtOAc (30 mL). The mixture was washed with water (2×20 mL), dried over $Na_2SO_4$ filtered, and concentrated under reduced pressure. The residue was purified by silica gel column chromatography (0-30% EtOAc in hexanes) to afford the racemic title compound as a solid. The enantiopure title compounds were obtained by chiral preparative HPLC (Phenomenex Lux Cellulose-4, AXIA Packed, 5% EtOH in hexanes) The faster-eluting enantiomer of the title compound (Example 194) was obtained as a solid. MS=374.2 (+ESI). $^1$H NMR (400 MHz, CDCl$_3$) δ: 11.14 (br, 1H), 8.83 (s, 1H), 7.97 (d, J=6.8 Hz, 1H), 7.69 (d, J=8.0 Hz, 1H), 6.93 (t, J=53.6 Hz, 1H), 6.20 (q, J=7.2 Hz, 1H), 2.56 (s, 3H), 2.04 (d, J=7.2 Hz, 3H). The slower-eluting enantiomer of the title compound (Example 195) was obtained as a solid. MS=374.2 (+ESI). ¹H NMR (400 MHz, CDCl₃) δ: 11.43 (br, 1H), 8.80 (s, 1H), 7.95 (d, J=7.2 Hz, 1H), 7.66 (d, J=8.4 Hz, 1H), 6.91 (t, J=53.8 Hz, 1H), 6.18 (q, J=7.2 Hz, 1H), 2.55 (s, 3H), 2.02 (d, J=7.2 Hz, 3H).

EXAMPLES 196 and 197

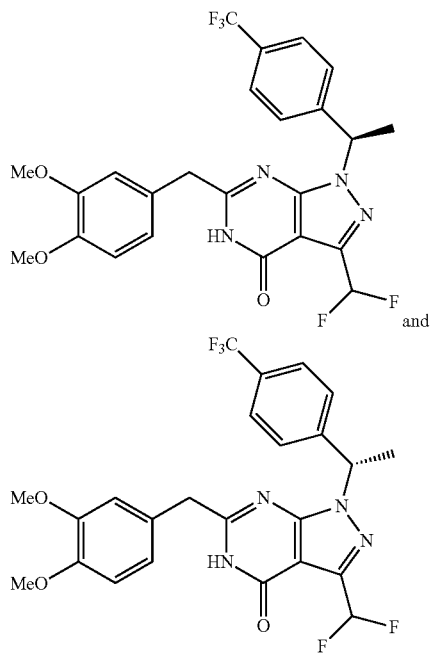

(R)- and (S)-3-(Difluoromethyl)-6-(3,4-dimethoxybenzyl)-1-(1-(4-(trifluoromethyl)phenyl)ethyl)-1H-pyrazolo[3,4-d]pyrimidin-4(5H)-one (Scheme 23)

Step 1. 2-(3,4-Dimethoxyphenyl)acetyl chloride

To the solution of 2-(3,4-dimethoxyphenyl)acetic acid (0.59 g, 3.0 mmol) in CH₂Cl₂ (5 mL) at 0° C. was added thionyl chloride (0.66 mL, 9.0 mmol) dropwise. The mixture was heated to 50° C., stirred for 16 h, and was cooled to RT. The mixture was concentrated under reduced pressure to afford the title compound as a solid which was used in the next step without purification.

Step 2. 3-((Benzyloxy)methyl)-6-(3,4-dimethoxybenzyl)-1-(1-(4-(trifluoromethyl)phenyl)ethyl)-1H-pyrazolo[3,4-d]pyrimidin-4(5H)-one The title compound was prepared using procedures similar to those described in step 1 of Example 1 using 5-amino-3-((benzyloxy)methyl)-1-(1-(4-(trifluoromethyl)phenyl) ethyl)-1H-pyrazole-4-carboxamide and 2-(3,4-dimethoxyphenyl)acetyl chloride to afford a solid. MS=579.3 (+ESI).

Step 3. 6-(3,4-Dimethoxybenzyl)-3-(hydroxymethyl)-1-(1-(4-(trifluoromethyl)phenyl)ethyl)-1H-pyrazolo[3,4-d]pyrimidin-4(5H)-one The title compound was prepared using procedures similar to those described in step 2 of Example 1 using ((ben-zyloxy)methyl)-6-(3,4-dimethoxybenzyl)-1-(1-(4-(trifluoromethyl)phenyl)ethyl)-1H-pyrazolo[3,4-d]pyrimidin-4(5H)-one in methanol to afford a solid. MS=489.2 (+ESI).

Step 4. 6-(3,4-Dimethoxybenzyl)-4-oxo-1-(1-(4-(trifluoromethyl)phenyl)ethyl)-4,5-dihydro-1H-pyrazolo[3,4-d]pyrimidine-3-carbaldehyde The title compound was prepared using procedures similar to those described in step 1 of Examples 175 and 176 using 6-(3,4-dimethoxybenzyl)-3-(hydroxymethyl)-1-(1-(4-(trifluoromethyl)phenyl)ethyl)-1H-pyrazolo[3,4-d]pyrimidin-4(5H)-one to afford a solid. MS=487.1 (+ESI).

Step 5. (R)- and (S)-3-(Difluoromethyl)-6-(3,4-dimethoxybenzyl)-1-(1-(4-(trifluoromethyl)phenyl) ethyl)-1H-pyrazolo[3,4-d]pyrimidin-4(5H)-one The racemic title compound was prepared using procedures similar to those described in step 2 of Examples 161 and 162 using 6-(3,4-dimethoxybenzyl)-4-oxo-1-(1-(4-(trifluoromethyl)phenyl)ethyl)-4,5-dihydro-1H-pyrazolo[3,4-d]pyrimidine-3-carbaldehyde. The enantiopure title compounds were obtained by chiral preparative HPLC (Lux CHIRAL PAK IA-3, 20% EtOH in hexanes). The faster-eluting enantiomer of the title compound (Example 196) was obtained as a solid. MS=509.1 (+ESI); ¹H NMR (400 MHz, DMSO-d₆) δ: 12.59 (br, 1H), 7.69 (d, J=8.4 Hz, 2H), 7.47 (d, J=8.4 Hz, 2H), 7.16 (t, J=13.2 Hz, 1H), 7.00-6.81 (m, 3H), 6.13 (q, J=6.8 Hz, 1H), 3.86 (s, 2H), 3.71 (s, 3H), 3.65 (s, 3H), 1.89 (d, J=7.2 Hz, 3H). The slower-eluting enantiomer of the title compound (Example 197) was obtained as a solid. MS=509.1 (+ESI); ¹H NMR (400 MHz, DMSO-d₆) δ: 12.59 (br, 1H), 7.69 (d, J=8.4 Hz, 2H), 7.47 (d, J=8.4 Hz, 2H), 7.16 (t, J=13.2 Hz, 1H), 7.00-6.81 (m, 3H), 6.13 (q, J=6.8 Hz, 1H), 3.86 (s, 2H), 3.71 (s, 3H), 3.65 (s, 3H), 1.89 (d, J=7.2 Hz, 3H).

EXAMPLE 198

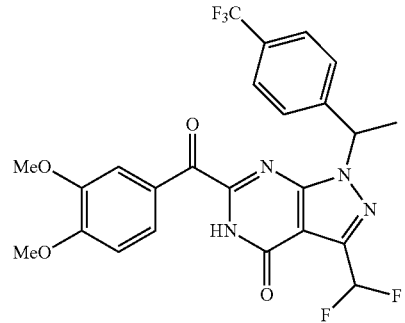 [SMILES: COc1ccc(C(=O)c2nc3c(c(C(F)F)nn3C(C)c3ccc(C(F)(F)F)cc3)c(=O)[nH]2)cc1OC]

3-(Difluoromethyl)-6-(3,4-dimethoxybenzoyl)-1-(1-(4-(trifluoromethyl)phenyl)ethyl)-1H-pyrazolo[3,4-d]pyrimidin-4(5H)-one (Scheme 25)

Step 1. 6-(3,4-Dimethoxybenzoyl)-4-oxo-1-(1-(4-(trifluoromethyl)phenyl)ethyl)-4,5-dihydro-1H-pyrazolo[3,4-d]pyrimidine-3-carbaldehyde The title compound was prepared using procedures similar to those described in step 1 of Examples 161 and 162 using 6-(3,4-dimethoxybenzyl)-3-(hydroxymethyl)-1-(1-(4-(trifluoromethyl)phenyl)ethyl)-1H-pyrazolo[3,4-d]pyrimidin-4(5H)-one as a solid. MS=501.4 (+ESI).

Step 2. 3-(Difluoromethyl)-6-(3,4-dimethoxybenzyl)-1-(1-(4-(trifluoromethyl)phenyl)ethyl)-1H-pyrazolo[3,4-d]pyrimidin-4(5H)-one The title compound was prepared using procedures similar to those described in step 2 of Examples 161 and 162 using 6-(3,4-dimethoxybenzyl)-3-(hydroxymethyl)-1-(1-(4-(trifluoromethyl)phenyl)ethyl)-1H-pyrazolo[3,4-d]pyrimidin-4(5H)-one to afford the title compound (Example 198) as a solid. MS=523.1 (+ESI). $^1$H NMR (300 MHz, DMSO-$d_6$) δ: 13.00-12.90 (br, 1H), 7.75-7.68 (m, 3H), 7.61 (s, 1H), 7.46 (d, J=8.7 Hz, 2H), 7.06 (d, J=8.7 Hz, 2H), 6.16 (q, J=7.2 Hz, 1H), 3.89 (s, 3H), 3.72 (s, 3H), 1.90 (d, J=6.9 Hz, 3H).

EXAMPLES 199 and 200

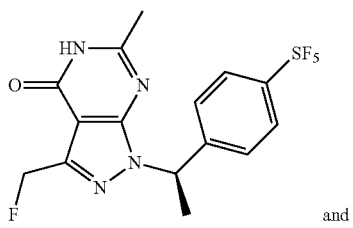

and

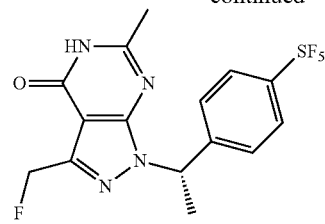

(R)- and (S)-3-(Fluoromethyl)-6-methyl-1-(1-(4-(pentafluorothio)phenyl)ethyl)-1H-pyrazolo[3, 4-d]pyrimidin-4(5H)-one (Scheme 26)

The racemic 3-(fluoromethyl)-6-methyl-1-(1-(4-(pentafluorothio)phenyl)ethyl)-1H-pyrazolo[3,4-d]pyrimidin-4(5H)-one was prepared using procedures similar to those described in step 2 of Examples 161 and 162 using 3-(hydroxymethyl)-6-methyl-1-(1-(4-(pentafluorothio)phenyl)ethyl)-1H-pyrazolo[3,4-d]pyrimidin-4(5H)-one. The enantiopure title compounds were obtained by chiral preparative HPLC (Phenomenex Lux 5u Cellulose-42, 10% EtOH in hexanes) was obtained as a solid. MS=412.9 (+ESI). $^1$H NMR (400 MHz, CD$_3$OD) δ: 7.80 (d, J=8.8 Hz, 2H), 7.53 (d, J=8.8 Hz, 2H), 6.19 (q, J=7.2 Hz, 1H), 5.64 (s, 1H), 5.53 (s, 1H), 2.46 (s, 3H), 1.98 (d, J=6.8 Hz, 3H). The slower-eluting enantiomer of the title compound (Example 200) was obtained as a solid. MS=412.9 (+ESI). $^1$H NMR (400 MHz, CD$_3$OD) δ: 7.80 (d, J=8.8 Hz, 2H), 7.53 (d, J=8.8 Hz, 2H), 6.19 (q, J=7.2 Hz, 1H), 5.64 (s, 1H), 5.53 (s, 1H), 2.46 (s, 3H), 1.98 (d, J=6.8 Hz, 3H)

TABLE 24

The following compounds were prepared using procedures similar to those described in Examples 199 and 200 using appropriate starting materials.

| Ex # | Structure | IUPAC Name | Exact Mass [M + H]+ |
|---|---|---|---|
| 201 | 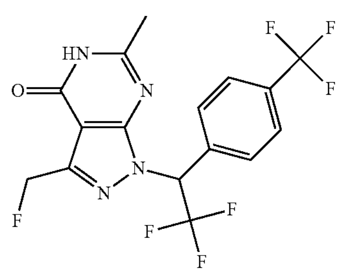 [SMILES: Cc1nc2c(c(CF)nn2C(c2ccc(C(F)(F)F)cc2)C(F)(F)F)c(=O)[nH]1] | 3-(Fluoromethyl)-6-methyl-1-(2,2,2-trifluoro-1-(4-(trifluoromethyl)phenyl)-ethyl)-1H-pyrazolo[3,4-d]pyrimidin-4(5H)-one | Calc'd 409.1, found 409.0 |
| 202 | 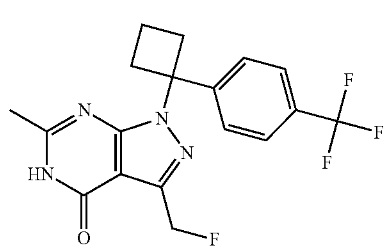 [SMILES: Cc1nc2c(c(CF)nn2C2(c3ccc(C(F)(F)F)cc3)CCC2)c(=O)[nH]1] | 3-(Fluoromethyl)-6-methyl-1-(1-(4-(trifluoromethyl)phenyl)cyclobutyl)-1H-pyrazolo[3,4-d]pyrimidin-4(5H)-one | Calc'd 381.1, found 381.2 |

TABLE 24-continued

The following compounds were prepared using procedures similar to those described in Examples 199 and 200 using appropriate starting materials.

| Ex # | Structure | IUPAC Name | Exact Mass [M + H]+ |
|---|---|---|---|
| 203 | 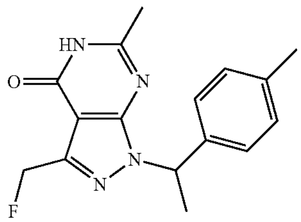 [SMILES: Cc1ccc(C(C)n2nc(CF)c3c(=O)[nH]c(C)nc32)cc1] | 3-(Fluoromethyl)-6-methyl-1-(1-p-tolylethyl)-1H-pyrazolo[3,4-d]pyrimidin-4(5H)-one | Calc'd 301.1, found 301.3 |
| 204 | 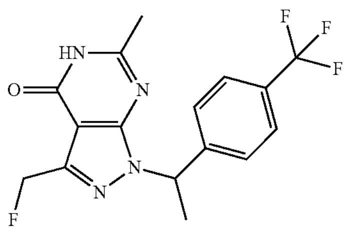 [SMILES: Cc1nc2c(c(CF)nn2C(C)c2ccc(C(F)(F)F)cc2)c(=O)[nH]1] | 3-(Fluoromethyl)-6-methyl-1-{1-[4-(trifluoromethyl)phenyl]ethyl}-1,5-dihydro-4H-pyrazolo[3,4-d]pyrimidin-4-one | Calc'd 355.1, found 355.1 |
| 205 | 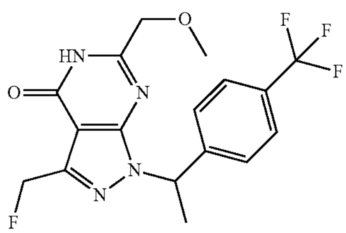 [SMILES: COCc1nc2c(c(CF)nn2C(C)c2ccc(C(F)(F)F)cc2)c(=O)[nH]1] | 3-(Fluoromethyl)-6-(methoxymethyl)-1-{1-[4-(trifluoromethyl)phenyl]ethyl}-1,5-dihydro-4H-pyrazolo[3,4-d]pyrimidin-4-one | Calc'd 385.1, found 384.9 |

TABLE 25

The following compounds were prepared using procedures similar to those described in Examples 184 and 185 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 206 | 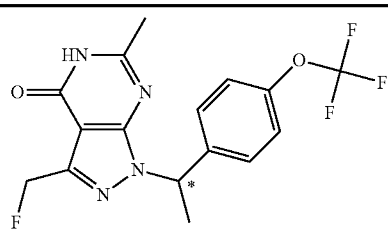 | (R)- or (S)-3-(Fluoromethyl)-6-methyl-1-(1-(4-(trifluoro-methoxy-)phenyl)ethyl)-1H-pyrazolo[3,4-d]pyrimidin-4(5H)-one | Calc'd 371.1, found 371.2 | Chiralpak IA-3 |
| 207 | 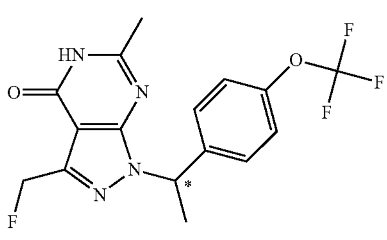 [SMILES: Cc1nc2c(c(CF)nn2C(C)c2ccc(OC(F)(F)F)cc2)c(=O)[nH]1] | (S)- or (R)-3-(Fluoromethyl)-6-methyl-1-(1-(4-(trifluoromethoxy)phenyl)ethyl)-1H-pyrazolo[3,4-d]pyrimidin-4(5H)-one | Calc'd 371.1, found 371.2 | Chiralpak IA-3 |

TABLE 25-continued

The following compounds were prepared using procedures similar to those described in Examples 184 and 185 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 208 | 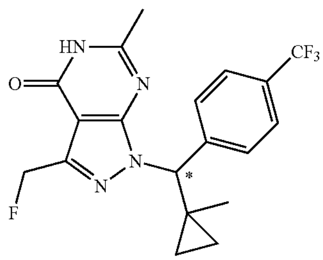 [SMILES: Cc1nc2c(c(CF)nn2C(c2ccc(C(F)(F)F)cc2)C2(C)CC2)c(=O)[nH]1] | (R)- or (S)-3-(Fluoromethyl)-6-methyl-1-((1-methylcyclopropyl)(4-(trifluoromethyl)phenyl)methyl)-1H-pyrazolo[3,4-d]pyrimidin-4(5H)-one | Calc'd 395.1, found 395.3 | Chiralpak IA-3 |
| 209 | 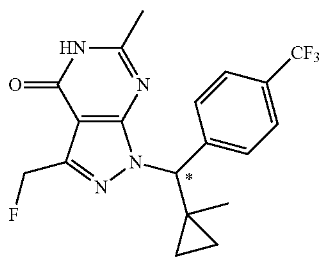 [SMILES: Cc1nc2c(c(CF)nn2C(c2ccc(C(F)(F)F)cc2)C2(C)CC2)c(=O)[nH]1] | (S)- or (R)-3-(Fluoromethyl)-6-methyl-1-((1-(trifluoromethyl)phenyl)methyl)-1H-pyrazolo[3,4-d]pyrimidin-4(5H)-one | Calc'd 395.1, found 395.3 | Chiralpak IA-3 |
| 210 | 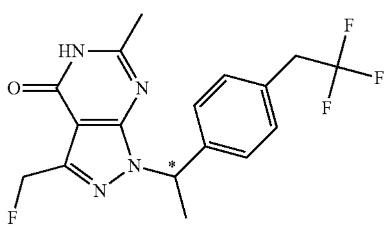 [SMILES: Cc1nc2c(c(CF)nn2C(C)c2ccc(CC(F)(F)F)cc2)c(=O)[nH]1] | (R)- or (S)-3-(Fluoromethyl)-6-methyl-1-(1-(4-(2,2,2-trifluoroethyl)phenyl)ethyl)-1H-pyrazolo[3,4-d]pyrimidin-4(5H)-one | Calc'd 369.1, found 369.1. | Chiralpak IA |
| 211 | 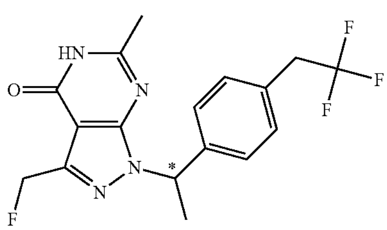 [SMILES: Cc1nc2c(c(CF)nn2C(C)c2ccc(CC(F)(F)F)cc2)c(=O)[nH]1] | (S)- or (R)-3-(Fluoromethyl)-6-methyl-1-(1-(4-(2,2,2-trifluoroethyl)phenyl)ethyl)-1H-pyrazolo[3,4-d]pyrimidin-4(5H)-one | Calc'd 369.1, found 369.1. | Chiralpak IA |
| 212 | 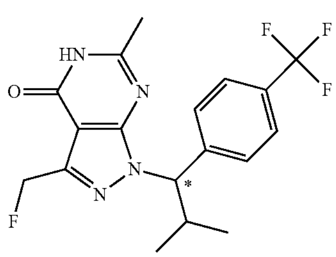 [SMILES: Cc1nc2c(c(CF)nn2C(c2ccc(C(F)(F)F)cc2)C(C)C)c(=O)[nH]1] | (R)- or (S)-3-(Fluoromethyl)-6-methyl-1-(2-methyl-1-(4-(trifluoromethyl)phenyl)propyl)-1H-pyrazolo[3,4-d]pyrimidin-4(5H)-one | Calc'd 383.1, found 383.2. | Chiralpak IA |

TABLE 25-continued

The following compounds were prepared using procedures similar to those described in Examples 184 and 185 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 213 | 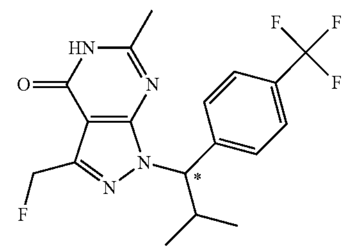 [SMILES: Cc1nc2c(c(CF)nn2C(c2ccc(C(F)(F)F)cc2)C(C)C)c(=O)[nH]1] | (S)- or (R)-3-(Fluoromethyl)-6-methyl-1-(2-methyl-1-(4-(trifluoromethyl)phenyl)propyl)-1H-pyrazolo[3,4-d]pyrimidin-4(5H)-one | Calc'd 383.1, found 383.1. | Chiralpak IA |
| 214 | 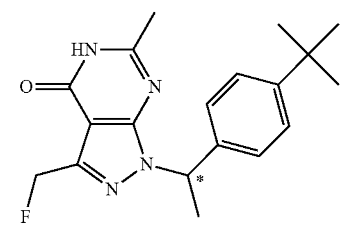 [SMILES: Cc1nc2c(c(CF)nn2C(C)c2ccc(C(C)(C)C)cc2)c(=O)[nH]1] | (R)- or (S)-1-(1-(4-tert-Butylphenyl)ethyl)-3-(fluoromethyl)-6-methyl-1H-pyrazolo[3,4-d]pyrimidin-4(5H)-one | Calc'd 343.2, found 343.3. | Chiralpak IA |
| 215 | 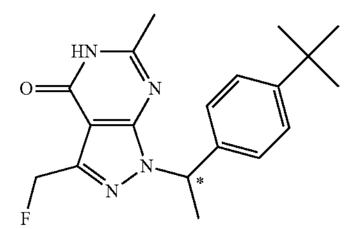 [SMILES: Cc1nc2c(c(CF)nn2C(C)c2ccc(C(C)(C)C)cc2)c(=O)[nH]1] | (S)- or (R)-1-(1-(4-tert-Butylphenyl)ethyl)-3-(fluoromethyl)-6-methyl-1H-pyrazolo[3,4-d]pyrimidin-4(5H)-one | Calc'd 343.2, found 343.3. | Chiralpak IA |
| 216 | 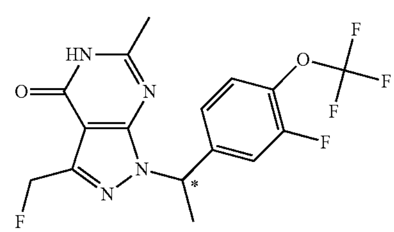 [SMILES: Cc1nc2c(c(CF)nn2C(C)c2ccc(OC(F)(F)F)c(F)c2)c(=O)[nH]1] | (R)- or (S)-1-(1-(3-Fluoro-4-(trifluoromethoxy)phenyl)ethyl)-3-(fluoromethyl)-6-methyl-1H-pyrazolo[3,4-d]pyrimidin-4(5H)-one | Calc'd 389.1, found 389.1 | Chiralpak IA |
| 217 | 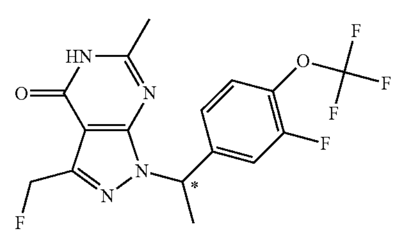 [SMILES: Cc1nc2c(c(CF)nn2C(C)c2ccc(OC(F)(F)F)c(F)c2)c(=O)[nH]1] | (S)- or (R)-1-(1-(3-Fluoro-4-(trifluoromethoxy)phenyl)ethyl)-3-(fluoromethyl)-6-methyl-1H-pyrazolo[3,4-d]pyrimidin-4(5H)-one | Calc'd 389.1, found 389.1 | Chiralpak IA |

TABLE 25-continued

The following compounds were prepared using procedures similar to those described in Examples 184 and 185 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 218 | 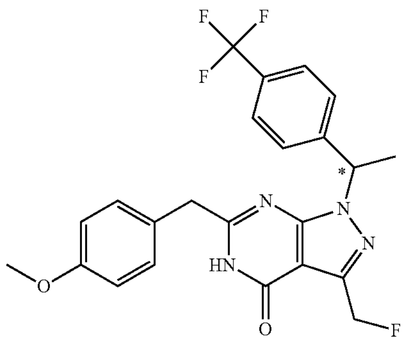 [SMILES: COc1ccc(Cc2nc3c(c(CF)nn3C(C)c3ccc(C(F)(F)F)cc3)c(=O)[nH]2)cc1] | (R)- or (S)-3-(Fluoromethyl)-6-(4-methoxybenzyl)-1-(1-(4-(trifluoromethyl)phenyl)ethyl)-1H-pyrazolo[3,4-d]pyrimidin-4(5H)-one | Calc'd 461.2, found 461.1 | Lux 5u Cellulose-42 |
| 219 | 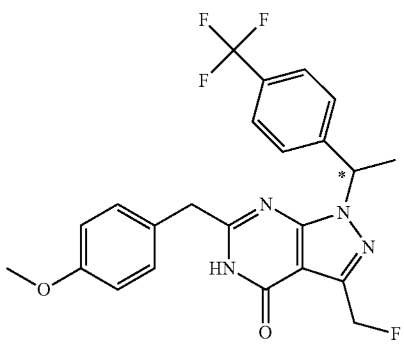 [SMILES: COc1ccc(Cc2nc3c(c(CF)nn3C(C)c3ccc(C(F)(F)F)cc3)c(=O)[nH]2)cc1] | (S)- or (R)-3-(Fluoromethyl)-6-(4-methoxybenzyl)-1-(1-(4-(trifluoromethyl)phenyl)ethyl)-1H-pyrazolo[3,4-d]pyrimidin-4(5H)-one | Calc'd 461.2, found 461.2 | Lux 5u Cellulose-42 |
| 220 | 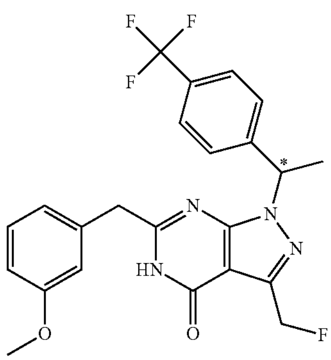 [SMILES: COc1cccc(Cc2nc3c(c(CF)nn3C(C)c3ccc(C(F)(F)F)cc3)c(=O)[nH]2)c1] | (R)- or (S)-3-(Fluoromethyl)-6-(3-methoxybenzyl)-1-(1-(4-(trifluoromethyl)phenyl)ethyl)-1H-pyrazolo[3,4-d]pyrimidin-4(5H)-one | Calc'd 461.2, found 461.1 | Lux 5u Cellulose-42 |
| 221 | 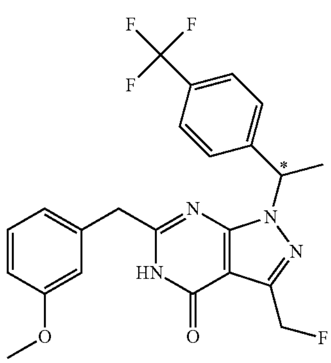 [SMILES: COc1cccc(Cc2nc3c(c(CF)nn3C(C)c3ccc(C(F)(F)F)cc3)c(=O)[nH]2)c1] | (S)- or (R)-3-(Fluoromethyl)-6-(3-methoxybenzyl)-1-(1-(4-(trifluoromethyl)phenyl)ethyl)-1H-pyrazolo[3,4-d]pyrimidin-4(5H)-one | Calc'd 461.2, found 461.1 | Lux 5u Cellulose-42 |

TABLE 25-continued

The following compounds were prepared using procedures similar to those described in Examples 184 and 185 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 222 | 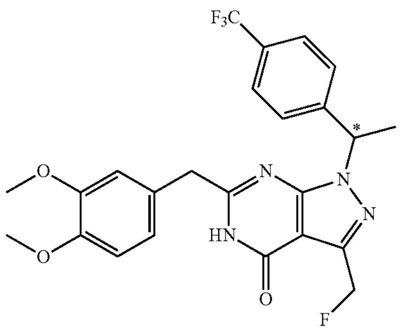 [SMILES: COc1ccc(Cc2nc3c(c(CF)nn3C(C)c3ccc(C(F)(F)F)cc3)c(=O)[nH]2)cc1OC] | (R)- or (S)-6-(3,4-Dimethoxybenzyl)-3-(fluoromethyl)-1-(1-(4-(trifluoromethyl)phenyl)ethyl)-1,5-dihydro-4H-pyrazolo[3,4-d]pyrimidin-4-one | Calc'd 491.2, found 491.2 | AD |
| 223 | 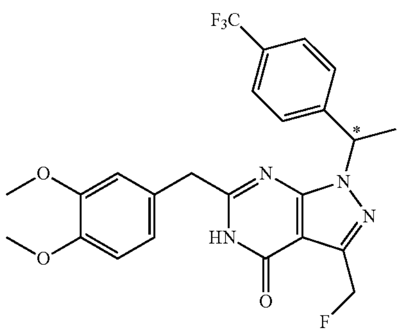 [SMILES: COc1ccc(Cc2nc3c(c(CF)nn3C(C)c3ccc(C(F)(F)F)cc3)c(=O)[nH]2)cc1OC] | (S)- or (R)-6-(3,4-Dimethoxybenzyl)-3-(fluoromethyl)-1-(1-(4-(trifluoromethyl)phenyl)ethyl)-1,5-dihydro-4H-pyrazolo[3,4-d]pyrimidin-4-one | Calc'd 491.2, found 491.2 | AD |
| 224 | 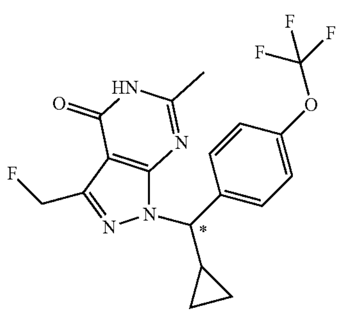 [SMILES: Cc1nc2c(c(CF)nn2C(c2ccc(OC(F)(F)F)cc2)C2CC2)c(=O)[nH]1] | (R)- or (S)-1-(Cyclopropyl(4-(trifluoromethoxy)phenyl)methyl)-3-(fluoromethyl)-6-methyl-1,5-dihydro-4H-pyrazolo[3,4-d]pyrimidin-4-one | Calc'd 397.1, found 396.8 | OJ |
| 225 | 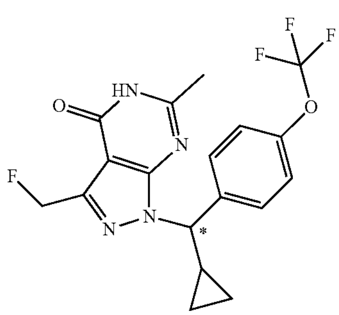 [SMILES: Cc1nc2c(c(CF)nn2C(c2ccc(OC(F)(F)F)cc2)C2CC2)c(=O)[nH]1] | (S)- or (R)-1-(Cyclopropyl(4-(trifluoromethoxy)phenyl)methyl)-3-(fluoromethyl)-6-methyl-1,5-dihydro-4H-pyrazolo[3,4-d]pyrimidin-4-one | Calc'd 397.1, found 396.8 | OJ |

TABLE 25-continued

The following compounds were prepared using procedures similar to those described in Examples 184 and 185 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 226 | 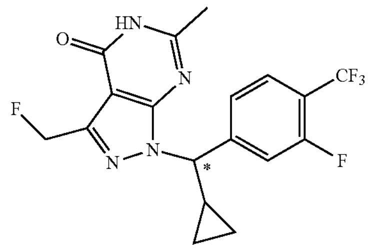 [SMILES: Cc1nc2c(c(CF)nn2C(c2ccc(C(F)(F)F)c(F)c2)C2CC2)c(=O)[nH]1] | (R)- or (S)-1-(Cyclopropyl(3-fluoro-4-(trifluoromethyl)phenyl)methyl)-3-(fluoromethyl)-6-methyl-1,5-dihydro-4H-pyrazolo[3,4-d]pyrimidin-4-one | Calc'd 399.1, found 398.8 | OJ |
| 227 | 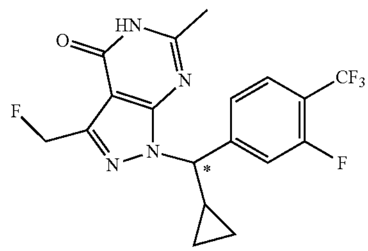 [SMILES: Cc1nc2c(c(CF)nn2C(c2ccc(C(F)(F)F)c(F)c2)C2CC2)c(=O)[nH]1] | (S)- or (R)-1-(Cyclopropyl(3-fluoro-4-(trifluoromethyl)phenyl)methyl)-3-(fluoromethyl)-6-methyl-1,5-dihydro-4H-pyrazolo[3,4-d]pyrimidin-4-one | Calc'd 399.1, found 398.8 | OJ |
| 228 | 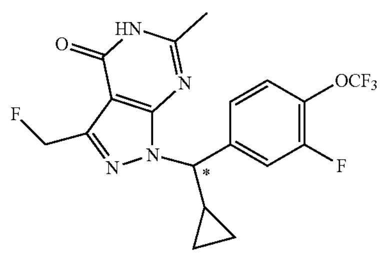 [SMILES: Cc1nc2c(c(CF)nn2C(c2ccc(OC(F)(F)F)c(F)c2)C2CC2)c(=O)[nH]1] | (R)- or (S)-1-(Cyclopropyl(3-fluoro-4-(trifluoromethoxy)phenyl)methyl)-3-(fluoromethyl)-6-methyl-1,5-dihydro-4H-pyrazolo[3,4-d]pyrimidin-4-one | Calc'd 415.1, found 414.8 | OJ |
| 229 | 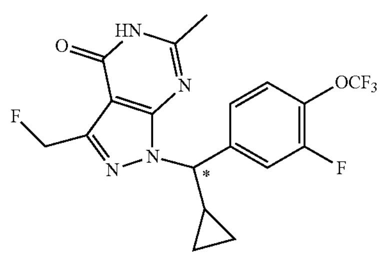 [SMILES: Cc1nc2c(c(CF)nn2C(c2ccc(OC(F)(F)F)c(F)c2)C2CC2)c(=O)[nH]1] | (S)- or (R)-1-(Cyclopropyl(3-fluoro-4-(trifluoromethoxy)phenyl)methyl)-3-(fluoromethyl)-6-methyl-1,5-dihydro-4H-pyrazolo[3,4-d]pyrimidin-4-one | Calc'd 415.1, found 414.8 | OJ |

EXAMPLE 230

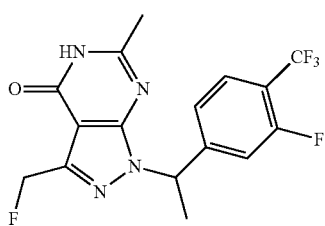 [SMILES: Cc1nc2c(c(CF)nn2C(C)c2ccc(C(F)(F)F)c(F)c2)c(=O)[nH]1]

1-(1-(3-Fluoro-4-(trifluoromethyl)phenyl)ethyl)-3-(fluoromethyl)-6-methyl-1H-pyrazolo[3,4-d]pyrimidin-4(5H)-one (Scheme 27)

Step 1. 5-Amino-1-(1-(3-fluoro-4-(trifluoromethyl)phenyl)ethyl)-3-(hydroxymethyl)-1H-pyrazole-4-carboxamide The title compound was prepared using procedures similar to those described in step 2 of Example 2 using 5-amino-3-(benzyloxymethyl)-1-(1-(3-fluoro-4-(trifluoromethyl)phenyl)ethyl)-1H-pyrazole-4-carboxamide from Preparatory Example 51 to afford a solid. MS=347.1 (+ESI).

Step 2. 5-Amino-1-(cyclopropyl(4-(trifluoromethyl)phenyl)methyl)-3-(fluoromethyl)-1H-pyrazole-4-carboxamide The title compound was prepared using procedures similar to those described in step 2 of Examples 161 and 162 using 5-amino-1-(1-(3-fluoro-4-(trifluoromethyl)phenyl)ethyl)-3-(hydroxymethyl)-1H-pyrazole-4-carboxamide to afford a solid. MS=349.1 (+ESI).

Step 3. 1-(1-(3-Fluoro-4-(trifluoromethyl)phenyl)ethyl)-3-(fluoromethyl)-6-methyl-1H-pyrazolo[3,4-d]pyrimidin-4(5H)-one The title compound was prepared using procedures similar to those described in step 1 of Example 1 using 5-amino-1-(cyclopropyl(4-(trifluoromethyl)phenyl)-methyl)-3-(fluoromethyl)-1H-pyrazole-4-carboxamide to afford the title compound (Example 230) as a solid. MS=371.0 (+ESI); $^1$H NMR (300 MHz, DMSO-$d_6$+$D_2O$): δ: 7.76-7.74 (m, 1H), 7.42 (d, J=12.0 Hz, 1H), 7.27 (d, J=7.8 Hz, 1H), 6.25 (q, J=7.2 Hz, 1H), 5.55 (d, J=48.0 Hz, 2H), 2.37 (s, 3H), 1.86 (d, J=7.2 Hz, 3H).

EXAMPLES 231 and 232

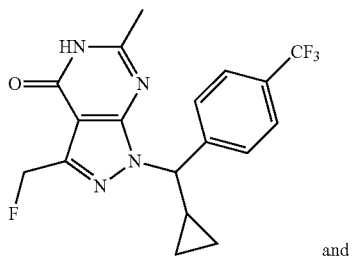

231

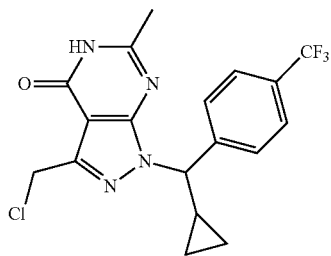

and

232

1-(Cyclopropyl(4-(trifluoromethyl)phenyl)methyl)-3-(fluoromethyl)-6-methyl-1H-pyrazolo[3,4-d]pyrimidin-4(5H)-one and 3-(Chloromethyl)-1-(cyclopropyl(4-(trifluoromethyl)phenyl)methyl)-6-methyl-1H-pyrazolo[3,4-d]pyrimidin-4(5H)-one (Scheme 27)

Step 1. 5-Amino-1-(cyclopropyl(4-(trifluoromethyl)phenyl)methyl)-3-(hydroxymethyl)-1H-pyrazole-4-carboxamide The title compound was prepared using procedures similar to those described in step 2 of Example 2 using 5-amino-3-(benzyloxymethyl)-1-(cyclopropyl(4-(trifluoromethyl)phenyl)methyl)-1H-pyrazole-4-carboxamide from Preparatory Example 56 to afford a solid. MS=355.1 (+ESI).

Step 2. 5-Amino-1-(cyclopropyl(4-(trifluoromethyl)phenyl)methyl)-3-(fluoromethyl)-1H-pyrazole-4-carboxamide The title compound was prepared using procedures similar to those described in step 2 of Examples 161 and 162 using 5-amino-1-(cyclopropyl(4-(trifluoromethyl)phenyl)methyl)-3-(hydroxymethyl)-1H-pyrazole-4-carboxamide to afford a solid. MS=357.1 (+ESI).

Step 3. 1-(Cyclopropyl(4-(trifluoromethyl)phenyl)methyl)-3-(fluoromethyl)-6-methyl-H-pyrazolo-[3,4-d]pyrimidin-4(5H)-one and 3-(Chloromethyl)-1-(cyclopropyl(4-(trifluoromethyl)phenyl)methyl)-6-methyl-1H-pyrazolo[3,4-d]pyrimidin-4(5H)-one The title compounds were prepared using procedures similar to those described in step 1 of Example 1 using 5-amino-1-(cyclopropyl(4-(trifluoromethyl)phenyl)methyl)-3-(fluoromethyl)-1H-pyrazole-4-carboxamide. The title compounds were separated by preparative HPLC (Xbridge RP18, 40-80% acetonitrile in water (0.1% TFA). The faster-eluting compound, 1-(cyclopropyl(4-(trifluoromethyl)phenyl)methyl)-3-(fluoromethyl)-6-methyl-1H-pyrazolo[3,4-d]pyrimidin-4(5H)-one (Example 231) was obtained as a solid. MS=381.1 (+ESI); $^1$H NMR (300 MHz, CDCl$_3$): δ: 11.40 (br, 1H), 7.61-7.55 (m, 4H), 5.66 (d, J=37.5 Hz, 2H), 5.08 (d, J=10.2 Hz, 1H), 2.53 (s, 3H), 2.09-1.97 (m, 1H), 0.92-0.83 (m, 1H), 0.71-0.63 (m, 1H), 0.59-0.50 (m, 1H), 0.49-0.42 (m, 1H). The slower-eluting compound, 3-(chloromethyl)-1-(cyclopropyl(4-(trifluoromethyl)phenyl)methyl)-6-methyl-1H-pyrazolo[3,4-d]pyrimidin-4(5H)-one (Example 232) was obtained as a solid. MS=397.0 (+ESI); $^1$H NMR (300 MHz, DMSO-$d_6$) δ: 12.23 (br, 1H), 7.73 (d, J=8.4 Hz, 2H), 7.61 (d, J=8.4 Hz, 2H), 5.14 (d, J=10.2 Hz, 1H), 4.88 (s, 2H), 2.35 (s, 3H), 1.92-1.86 (m, 1H), 0.78-0.67 (m, 2H), 0.62-0.51 (m, 1H), 0.38-0.33 (m, 1H).

EXAMPLE 233

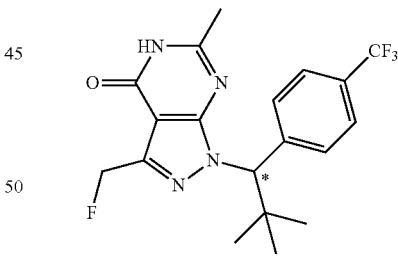

(R)- or (S)-1-(2,2-Dimethyl-1-(4-(trifluoromethyl)phenyl)propyl)-3-(fluoromethyl)-6-methyl-1H-pyrazolo[3,4-d]pyrimidin-4(5H)-one (Scheme 27)

The title compound was prepared using procedures similar to those described in step 2 of Examples 161 and 162 using (R)- or (S)-1-(2,2-dimethyl-1-(4-(trifluoromethyl)phenyl)propyl)-3-(hydroxymethyl)-6-methyl-1H-pyrazolo[3,4-d]pyrimidin-4(5H)-one from Example 82 to afford the title compound (Example 233) as a solid. MS=397.2 (+ESI). $^1$H NMR (400 MHz, CD$_3$OD) δ: 7.95 (d, J=8.0 Hz, 2H), 7.66 (d, J=8.0 Hz, 2H), 5.89 (s, 1H), 5.65 (d, J=48.0 Hz, 2H), 2.48 (s, 3H), 1.07 (s, 9H).

EXAMPLE 234

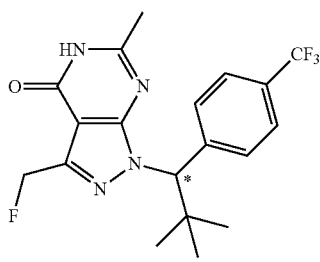 [SMILES: Cc1nc2c(c(CF)nn2C(c2ccc(C(F)(F)F)cc2)C(C)(C)C)c(=O)[nH]1]

(S)- or (R)-1-(2,2-Dimethyl-1-(4-(trifluoromethyl)phenyl)propyl)-3-(fluoromethyl)-6-methyl-1H-pyrazolo[3,4-d]pyrimidin-4(5H)-one (Scheme 27)

The title compound was prepared using procedures similar to those described in step 2 of Examples 161 and 162 using (S)-(2,2-dimethyl-1-(4-(trifluoromethyl)phenyl)propyl)-3-(hydroxymethyl)-6-methyl-1H-pyrazolo[3,4-d]pyrimidin-4(5H)-one prepared from Example 83 to afford the title compound (Example 234) as a solid. MS=397.3 (+ESI); $^1$H NMR (400 MHz, CD$_3$OD) δ: 7.95 (d, J=8.0 Hz, 2 H), 7.66 (d, J=8.0 Hz, 2 H), 5.89 (s, 1 H), 5.65 (d, J=48.0 Hz, 2H), 2.48 (s, 3H), 1.07 (s, 9H).

EXAMPLES 235, 236, 237, and 238

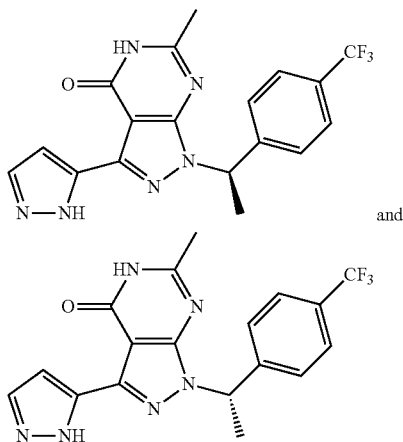

and (R)- and (S)-6-Methyl-3-(1H-pyrazol-5-yl)-1-(1-(4-(trifluoromethyl)phenyl)ethyl)-1H-pyrazolo[3,4-d]pyrimidin-4(5H)-one (Scheme 28)

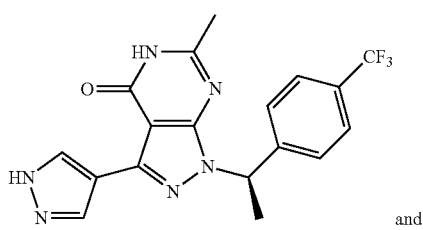

and

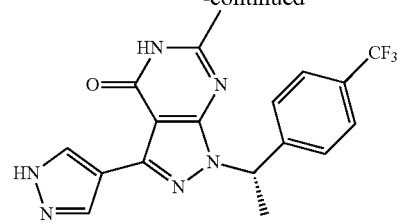

(R)- and (S)-6-Methyl-3-(1H-pyrazol-4-yl)-1-(1-(4-(trifluoromethyl)phenyl)ethyl)-1H-pyrazolo[3,4-d]pyrimidin-4(5H)-one (Scheme 28)

Step 1. 3-(Benzyloxymethyl)-4-methoxy-6-methyl-1-(1-(4-(trifluoromethyl)phenyl)ethyl)-1H-pyrazolo[3,4-d]pyrimidine The title compound was prepared using procedures similar to those described in step 5 of Examples 76 and 77 using 3-(benzyloxymethyl)-4-methoxy-6-methyl-1H-pyrazolo[3,4-d]pyrimidine from Preparatory Example 123 and 1-(4-(trifluoromethyl)phenyl)ethanol to afford an oil. MS=457.4 (+ESI).

Step 2. (4-Methoxy-6-methyl-1-(1-(4-(trifluoromethyl)phenyl)ethyl)-1H-pyrazolo[3,4-d]pyrimidin-3-yl)methanol The title compound was prepared using procedures similar to those described in step 2 of Example 2 using 3-(benzyloxymethyl)-4-methoxy-6-methyl-1-(1-(4-(trifluoromethyl)phenyl)ethyl)-1H-pyrazolo[3,4-d]pyrimidine to afford a solid. MS=367.1 (+ESI).

Step 3. 4-Methoxy-6-methyl-1-(1-(4-(trifluoromethyl)phenyl)ethyl)-1H-pyrazolo[3,4-d]pyrimidine-3-carbaldehyde The title compound was prepared using procedures similar to those described in step 1 of Examples 175 and 176 using (4-methoxy-6-methyl-1-(1-(4-(trifluoromethyl)phenyl)ethyl)-1H-pyrazolo[3,4-d]pyrimidin-3-yl)methanol to afford an oil. MS=365.0 (+ESI).

Step 4. 3-Ethynyl-4-methoxy-6-methyl-1-(1-(4-(trifluoromethyl)phenyl)ethyl)-1H-pyrazolo[3,4-d]pyrimidine Dimethyl (1-diazo-2-oxopropyl)phosphonate (1.65 g, 8.6 mmol) was added dropwise to a solution of 4-methoxy-6-methyl-1-(1-(4-(trifluoromethyl)phenyl)ethyl)-1H-pyrazolo[3,4-d]pyrimidine-3-carbaldehyde (1.20 g, 3.3 mmol) in MeOH (20 mL) at RT followed by addition of potassium carbonate (1.59 g, 11.5 mmol). The mixture was stirred at RT for 16 h and was concentrated and diluted with water (10 mL). The mixture was extracted with EtOAc (3×20 mL) and the organic layers were combined and washed with water (2×5 mL). The organic layer was dried over Na$_2$SO$_4$, filtered and concentrated under reduced pressure. The residue was purified by silica gel column chromatography (0-30% ethyl acetate in petroleum ether) to afford the title compound as a solid. MS=361.0 (+ESI).

Step 5. 4-Methoxy-6-methyl-3-(1H-pyrazol-5-yl)-1-(1-(4-(trifluoromethyl)phenyl)ethyl)-1H-pyrazolo[3,4-d]pyrimidine and 4-methoxy-6-methyl-3-(1H-pyrazol-4-yl)-1-(1-(4-(trifluoromethyl)phenyl)ethyl)-1H-pyrazolo[3,4-d]pyrimidine A solution of trimethylsilyl)diazomethane (2 M in hexanes, 6.2 mL, 12.5 mmol) was added to a solution of 3-ethynyl-4-methoxy-6-methyl-1-(1-(4-(trifluoromethyl)phenyl)ethyl)-1H-pyrazolo[3,4-d]pyrimidine (0.90 g, 2.5 mmol) in THF (7.0 mL) at RT. The solution was stirred at 80° C. for 16 h whereupon the mixture was cooled to RT and quenched with water (10 mL). The reaction mixture was extracted with EtOAc (3×20 mL) and the combined organic layers were dried over $Na_2SO_4$, filtered, and concentrated under reduced pressure. The residue was purified by silica gel column chromatography (0-55% ethyl acetate in petroleum ether) to afford a faster-eluting isomer of the title compound as a solid. MS=403.2 (+ESI) as well as a slower-eluting isomer of the title compound as a solid. MS=403.3 (+ESI).

Step 6. (R)- and (S)-6-Methyl-3-(1H-pyrazol-5-yl)-1-(1-(4-(trifluoromethyl)phenyl)ethyl)-1H-pyrazolo[3,4-d]pyrimidin-4(5H)-one To a solution of 4-methoxy-6-methyl-3-(1H-pyrazol-3-yl)-1-(1-(4-(trifluoromethyl)phenyl)ethyl)-1H-pyrazolo[3,4-d]pyrimidine (60 mg, 0.2 mmol) in DMSO (1.0 mL) at RT was added sodium cyanide (22 mg, 0.5 mmol). The resulting mixture was stirred at 130° C. for 2 h whereupon the mixture was cooled and water (10 mL) was added. The mixture was extracted with EtOAc (3×15 mL) and the combined organic layers were concentrated under reduced pressure. The residue was purified by preparative HPLC (Xbridge C18, 15-75% acetonitrile in water (0.1% $NH_4HCO_3$)) to afford the title racemic compound as a solid. The enantiopure title compounds were obtained by chiral preparative HPLC (Chiracel OJ-H, 15% EtOH in hexanes). The faster-eluting enantiomer of the title compound (Example 235) was obtained as a solid. MS=389.2 (+ESI); $^1$H NMR (400 MHz, $CD_3OD$) δ: 7.75-7.58 (m, 5H), 7.02 (d, J=1.6 Hz, 1H), 6.24 (q, J=7.2 Hz, 1H), 2.50 (s, 3H), 2.03 (d, J=7.2 Hz, 3H); The slower-eluting enantiomer of the title compound (Example 236) was obtained as a solid. MS=389.2 (+ESI); $^1$H NMR (400 MHz, $CD_3OD$) δ: 7.75-7.58 (m, 5H), 7.02 (d, J=1.6 Hz, 1H), 6.24 (q, J=7.2 Hz, 1H), 2.50 (s, 3H), 2.03 (d, J=7.2 Hz, 3H).

Step 7. (R) and (S)-6-Methyl-3-(1H-pyrazol-4-yl)-1-(1-(4-(trifluoromethyl)phenyl)ethyl)-1H-pyrazolo[3,4-d]pyrimidin-4(5H)-one The racemic title compound was prepared using procedures similar to those described above in step 6 of Examples 235, 236, 237 and 238 using 4-methoxy-6-methyl-3-(1H-pyrazol-4-yl)-1-(1-(4-(trifluoromethyl)phenyl)ethyl)-1H-pyrazolo[3,4-d]pyrimidine as a solid. The enantiopure title compounds were obtained by chiral preparative HPLC (Chiracel OJ-H, 10% EtOH in hexanes) The faster-eluting enantiomer of the title compound (Example 237) was obtained as a solid. MS=389.1 (+ESI); $^1$H NMR (400 MHz, $CD_3OD$) δ: 8.66 (s, 1H), 8.31 (s, 1H), 7.65 (d, J=8.4 Hz, 2H), 7.57 (d, J=8.4 Hz, 2H), 6.19 (q, J=7.2 Hz, 1H), 2.46 (s, 3H), 2.01 (d, J=7.2 Hz, 3H). The slower-eluting enantiomer of the title compound (Example 238) was obtained as a solid. MS=389.0 (+ESI). $^1$H NMR (400 MHz, $CD_3OD$) δ: 8.66 (s, 1H), 8.31 (s, 1H), 7.65 (d, J=8.4 Hz, 2H), 7.57 (d, J=8.4 Hz, 2H), 6.19 (q, J=7.2 Hz, 1H), 2.46 (s, 3H), 2.00 (d, J=7.2 Hz, 3H).

EXAMPLES 239, 240, 241, and 242

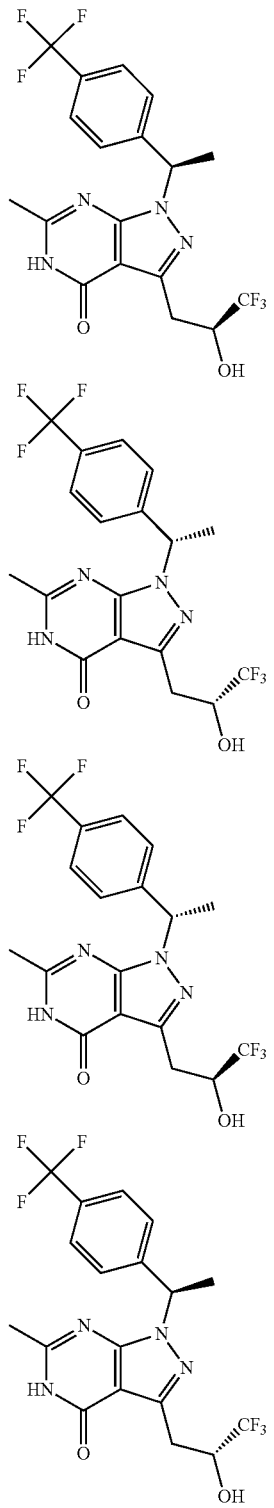

6-Methyl-3-((R)-3,3,3-trifluoro-2-hydroxypropyl)-1-((R)-1-(4-(trifluoromethyl)phenyl)ethyl)-1H-pyrazolo[3,4-d]pyrimidin-4(5H)-one and 6-methyl-3-((S)-3,3,3-trifluoro-2-hydroxypropyl)-1-((S)-1-(4-(trifluoromethyl)phenyl)ethyl)-1H-pyrazolo[3,4-d]pyrimidin-4(5H)-one and 6-methyl-3-((R)-3,33-trifluoro-2-hydroxypropyl)-1-((S)-1-(4-(trifluoromethyl)phenyl)ethyl)-1H-pyrazolo[3,4-d]pyrimidin-4(5H)-one and 6-methyl-3-((S)-3,3,3-trifluoro-2-hydroxypropyl)-1-((R)-1-(4-(trifluoromethyl)phenyl)ethyl)-1H-pyrazolo[3,4-d]pyrimidin-4(5H)-one (Scheme 29)

Step 1. 3-(2-(Benzyloxy)vinyl)-4-methoxy-6-methyl-1-(1-(4-(trifluoromethyl)phenyl)ethyl)-1H-pyrazolo[3,4-d]pyrimidine To a solution of ((benzyloxy)methyl)triphenylphosphonium chloride (1.37 g, 3.3 mmol) in THF (7.0 mL) at −78° C. was added a solution of potassium 2-methylbutan-2-olate (0.5 M in toluene, 1.7 mL, 3.3 mmol) dropwise. The reaction was warmed to −30° C. and stirred for 1 h and was cooled to −78° C. A solution of 4-methoxy-6-methyl-1-(1-(4-(trifluoromethyl)phenyl)ethyl)-1H-pyrazolo[3,4-d]pyrimidine-3-carbaldehyde (0.60 g, 1.1 mmol) from step 3 of Examples 213, 214, 215 and 216 in THF (3 mL) was added to the reaction mixture. The reaction mixture was warmed to RT and stirred for additional 16 h. Sat. aq. NH$_4$Cl (aq, 30 mL) was added and the mixture was concentrated under vacuum. The mixture was extracted with EtOAc (3×20 mL) and the combined organic fractions were washed with water (2×50 mL). The organic layer was dried over Na$_2$SO$_4$, filtered, and concentrated under reduced pressure. The residue was purified by silica gel column chromatography (0-20% methanol in dichloromethane) to afford the title compound as a solid. MS=469.1 (+ESI).

Step 2. 2-(4-Methoxy-6-methyl-1-(1-(4-(trifluoromethyl)phenyl)ethyl)-1H-pyrazolo[3,4-d]pyrimidin-3-yl)ethanol The title compound was prepared using procedures similar to those described in step 2 of Example 2 using (Z)-3-(2-(benzyloxy)vinyl)-4-methoxy-6-methyl-1-(1-(4-(trifluoromethyl)phenyl)ethyl)-1H-pyrazolo[3,4-d]pyrimidine to afford a solid. MS=381.0 (+ESI).

Step 3. 2-(4-Methoxy-6-methyl-1-(1-(4-(trifluoromethyl)phenyl)ethyl)-1H-pyrazolo[3,4-d]pyrimidin-3-yl)acetaldehyde To a solution of 2-(4-methoxy-6-methyl-1-(1-(4-(trifluoromethyl)phenyl)ethyl)-1H-pyrazolo[3,4-d]pyrimidin-3-yl)ethanol (0.26 g, 0.7 mmol) in acetonitrile (1.5 mL) at RT was added 2-iodoxybenzoic acid (1.53 g, 5.5 mmol). The mixture was stirred at 80° C. for 1 h whereupon a solid was formed. The solid was filtered off, then the resultant filtrate was concentrated under reduced pressure to afford the title compound as a solid which was taken onto the next step without purification. MS=379.0 (+ESI).

Step 4. 1,1,1-Trifluoro-3-(4-methoxy-6-methyl-1-(1-(4-(trifluoromethyl)phenyl)ethyl)-1H-pyrazolo[3,4-d]pyrimidin-3-yl)propan-2-ol To a solution of 2-(4-methoxy-6-methyl-1-(1-(4-(trifluoromethyl)phenyl)ethyl)-1H-pyrazolo[3,4-d]pyrimidin-3-yl) acetaldehyde (0.170 g, 0.5 mmol) in THF (3 mL) at 0° C. was added (trifluoromethyl)trimethylsilane (0.4 mL, 2.7 mmol) followed by TBAF solution (1 M in THF, 0.05 mL, 0.05 mmol). The solution was stirred for 1.5 h at RT whereupon the mixture was concentrated under reduced pressure. The mixture was diluted with EtOAc (100 mL) and was washed with water (2×10 mL) and brine (1×10 mL). The organic layer was dried over Na$_2$SO$_4$, filtered, and concentrated under reduced pressure. The residue was taken up in THF (2 mL) and a TBAF solution (1 M in THF, 1 mL, 1 mmol) was added dropwise to the solution. The mixture was stirred at RT for 30 min and was concentrated under vacuum. The mixture was diluted with EtOAc (20 mL) and water (10 mL) and the layers were separated. The aqueous layer was extracted with EtOAc (3×20 mL) and the organic layers were combined washing sequentially with water (2×10 mL) and brine (1×20 mL). The organic layer was dried over Na$_2$SO$_4$, filtered, and concentrated under reduced pressure. The residue was purified by silica gel column chromatography (0-60% ethyl acetate in petroleum ether) to afford the mixture of four stereoisomers of the title compound as a solid. MS=449.0 (+ESI).

Step 5. (R,R)-, (S,S)-, (R,S)- and (S,R)-6-Methyl-3-(3,3,3-trifluoro-2-hydroxypropyl)-1-(1-(4-(trifluoromethyl)phenyl)ethyl)-1H-pyrazolo[3,4-d]pyrimidin-4(5H)-one To a solution of 1,1,1-trifluoro-3-(4-methoxy-6-methyl-1-(1-(4-(trifluoromethyl)phenyl)ethyl)-1H-pyrazolo[3,4-d]pyrimidin-3-yl)propan-2-ol (80 mg, 0.2 mmol) in DMSO (0.5 mL) at RT was added sodium cyanide (17.5 mg, 0.4 mmol) in one portion. The mixture was heated to 130° C., stirred for 1 h, and was cooled to RT. The mixture was extracted with EtOAc (3×60 mL) and the combined organic layer was washed with water (2×10 mL) and brine (10 mL). The organic layer was dried over Na$_2$SO$_4$, filtered, and concentrated under reduced pressure. The residue was purified by preparative HPLC (X Select C18, 40-75% acetonitrile in water (0.05% NH$_4$HCO$_3$)) to afford the mixture of four stereoisomers as a white solid. The individual isomers of the were obtained by chiral preparative HPLC (Chiralpak IA, 10% i-PrOH in hexanes). The first two eluting diastereomers were obtained as a mixture at 5.14 min. The third eluting isomer of the title compound (Example 239) was obtained as a solid. MS=435.2 (+ES); $^1$H NMR (400 MHz, CD$_3$OD) δ: 7.62 (d, J=8.4 Hz, 2H), 7.51 (d, J=8.4 Hz, 2H), 6.12 (q, J=7.2 Hz, 1H), 4.74-4.71 (m, 1H), 3.34-3.17 (m, 2H), 2.45 (s, 3H), 2.04 (d, J=7.2 Hz, 3H). The fourth eluting isomer of the title compound (Example 240) was obtained as a solid. MS=435.3 (+ES); $^1$H NMR (400 MHz, CD$_3$OD) δ: 7.62 (d, J=8.0 Hz, 2H), 7.51 (d, J=8.4 Hz, 2H), 6.12 (q, J=7.2 Hz, 1H), 4.88-4.69 (m, 1H), 3.33-3.15 (m, 2H), 2.43 (s, 3H), 1.95 (d, J=7.2 Hz, 3H). The mixture of the two fastest eluting isomers was repurified by chiral preparative HPLC (CHIRALCEL OJ-H, 10% EtOH in hexanes). The fastest-eluting isomer of the title compound (Example 241) was obtained at as a solid. MS=435.3 (+ES); $^1$H NMR (300 MHz, CD$_3$OD) δ: 7.60 (d, J=8.4 Hz, 2H), 7.51 (d, J=8.4 Hz, 2H), 6.12 (q, J=7.2 Hz, 1H), 4.74-4.69 (m, 1H), 3.33-3.13 (m, 2H), 2.43 (s, 3H), 1.94 (d, J=7.2 Hz, 3H). The second fastest eluting isomer of the title compound (Example 242) was obtained as a solid. MS=435.3 (+ES); $^1$H NMR (300 MHz, CD$_3$OD) δ: 7.60 (d, J=8.4 Hz, 2H), 7.51 (d, J=8.1 Hz, 2H), 6.12 (q, J=7.2 Hz, 1H), 4.74-4.69 (m, 1H), 3.33-3.13 (m, 2H), 2.43 (s, 3H), 1.94 (d, J=7.2 Hz, 3H).

EXAMPLES 243, 244, 245, and 246

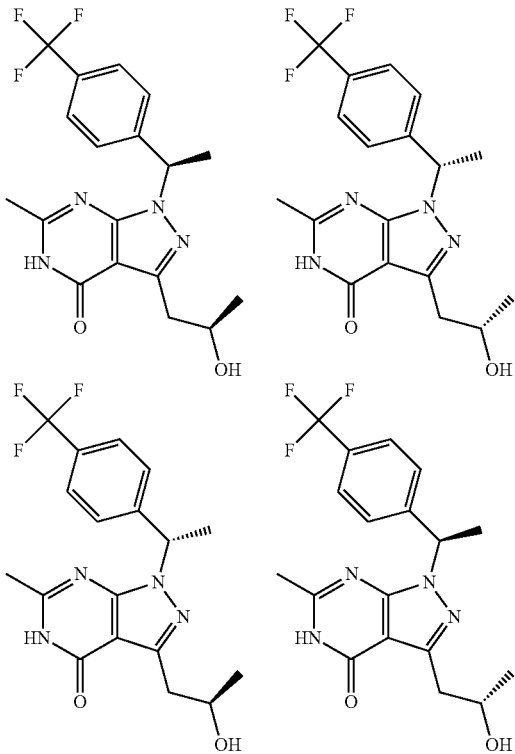

3-((R)-2-Hydroxypropyl)-6-methyl-1-((R)-1-(4-(trifluoromethyl)phenyl)ethyl) 1H-pyrazolo[3,4-d]pyrimidin-4(5H)-one and 3-((S)-2-hydroxypropyl)-6-methyl-1-((S)-1-(4-(trifluoromethyl)phenyl)ethyl)-1H-pyrazolo[3,4-d]pyrimidin-4(5H)-one and 3-((R)-2-hydroxypropyl)-6-methyl-1-((S)-1-(4-(trifluoromethyl)phenyl)ethyl)-1H-pyrazolo[3,4-d]pyrimidin-4(5H)-one and 3-((S)-2-hydroxypropyl)-6-methyl-1-((R)-1-(4-(trifluoromethyl)phenyl)ethyl)-1H-pyrazolo[3,4-d]pyrimidin-4(5H)-one (Scheme 30)

Step 1. 3-(2-Methoxyvinyl)-6-methyl-1-(1-(4-(trifluoromethyl)phenyl)ethyl)-1H-pyrazolo[3,4-d]pyrimidin-4(5H)-one The title compound was prepared using procedures similar to those described in step 1 of Examples 239, 240, 241, and 242 using 6-methyl-4-oxo-1-(1-(4-(trifluoromethyl)phenyl)ethyl)-4,5-dihydro-1H-pyrazolo[3,4-d]pyrimidine-3-carbaldehyde and (methoxymethyl)triphenylphosphonium chloride to afford an oil. MS=379.2 (+ESI).

Step 2. 2-(6-Methyl-4-oxo-1-(1-(4-(trifluoromethyl)phenyl)ethyl)-4,5-dihydro-1H-pyrazolo[3,4-d]pyrimidin-3-yl)acetaldehyde To the solution of 3-(2-methoxyvinyl)-6-methyl-1-(1-(4-(trifluoromethyl)phenyl)ethyl)-1H-pyrazolo[3,4-d]pyrimidin-4(5H)-one (0.40 g, 0.7 mmol) in THF (20 mL) at RT was added 3 N HCl (24.7 mL, 74.0 mmol). The resulting mixture was stirred for 16 h at RT whereupon the reaction mixture was diluted with sat. aq. sodium bicarbonate (100 mL) and extracted with EtOAc (3×100 mL). The organic layers were combined, washed with brine (3×100 mL), dried over Na$_2$SO$_4$, filtered, and concentrated under vacuum. The residue was purified by silica gel column chromatography (5% methanol in DCM) to afford the title compound as a solid. MS=365.1 (+ESI).

Step 3: (R, R)-, (S, S)-, (R, S)-, and (S, R)-3-(2-Hydroxypropyl)-6-methyl-1-(1-(4-(trifluoromethyl)phenyl)ethyl)-1H-pyrazolo[3,4-d]pyrimidin-4(5H)-one To a solution of 2-(6-methyl-4-oxo-1-(1-(4-(trifluoromethyl)phenyl)ethyl)-4,5-dihydro-1H-pyrazolo[3,4-d]pyrimidin-3-yl)acetaldehyde (0.30 g, 0.8 mmol) in THF (5.0 mL) at −78° C. was added MeMgBr (1 M in THF, 2.9 mL, 2.9 mmol) dropwise. The mixture was warmed to RT and stirred 16 h. The reaction was treated with sat. aq. NH$_4$Cl (3 mL) and was concentrated under reduced pressure. The residue was extracted with EtOAc (3×20 mL) and the combined organic fractions were washed with water (2×5 mL) and brine (1×10 mL). The organic layer was dried over Na$_2$SO$_4$, filtered, and concentrated under reduced pressure. The residue was purified by preparative HPLC (X Bridge C18, 35-45% acetonitrile in water (0.05% NH$_4$HCO$_3$)) to afford a mixture of four stereoisomers. The individual stereoisomers of the title compound were obtained by chiral preparative HPLC (Chiralpak IA, 7% EtOH in hexanes). The first-eluting stereoisomer of the title compound (Example 243) was obtained as a solid. MS=381.2 (+ESI); $^1$H NMR (400 MHz, CD$_3$OD) δ: 7.62 (d, J=8.4 Hz, 2H), 7.52 (d, J=8.4 Hz, 2H), 6.13 (q, J=7.2 Hz, 1H), 4.33-4.25 (m, 1H), 3.12-3.02 (m, 2H), 2.44 (s, 3H), 1.95 (d, J=7.2 Hz, 3H), 1.20 (d, J=7.2 Hz, 3H); The second-eluting stereoisomer of the title compound (Example 244) was obtained as a solid. MS=381.2 (+ESI); $^1$H NMR (400 MHz, CD$_3$OD) δ: 7.63 (d, J=8.4 Hz, 2H), 7.52 (d, J=8.4 Hz, 2H), 6.13 (q, J=7.2 Hz, 1H), 4.31-4.26 (m, 1H), 3.13-3.01 (m, 2H), 2.44 (s, 3H), 1.96 (d, J=7.2 Hz, 3H), 1.20 (d, J=7.2 Hz, 3H); The third-eluting stereoisomer of the title compound (Example 245) was obtained as a solid. MS=381.2 (+ESI); $^1$H NMR (400 MHz, CD$_3$OD) δ: 7.50 (d, J=8.4 Hz, 2H), 7.40 (d, J=8.4 Hz, 2H), 6.01 (q, J=7.2 Hz, 1H), 4.20-4.12 (m, 1H), 3.03-2.89 (m, 2H), 2.32 (s, 3H), 1.84 (d, J=7.2 Hz, 3H), 1.08 (d, J=7.2 Hz, 3H); The fourth-eluting stereoisomer of the title compound (Example 246) was obtained as a solid. MS=381.2 (+ESI); $^1$H NMR (400 MHz, CD$_3$OD) δ: 7.50 (d, J=8.4 Hz, 2H), 7.40 (d, J=8.4 Hz, 2H), 6.01 (q, J=7.2 Hz, 1H), 4.21-4.13 (m, 1H), 3.04-2.90 (m, 2H), 2.32 (s, 3H), 1.83 (d, J=7.2 Hz, 3H), 1.09 (d, J=7.2 Hz, 3H).

EXAMPLE 247

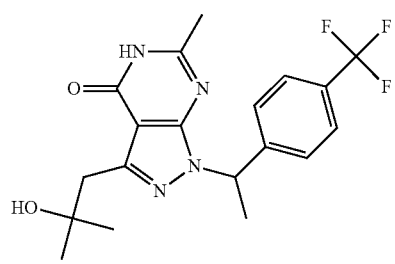 [SMILES: Cc1nc2c(c(CC(C)(C)O)nn2C(C)c2ccc(C(F)(F)F)cc2)c(=O)[nH]1]

3-(2-Hydroxy-2-methylpropyl)-6-methyl-1-(1-(4-(trifluoromethyl)phenyl)ethyl)-1H-pyrazolo[3,4-d]pyrimidin-4(5H)-one (Scheme 31)

Step 1. 6-Methyl-3-(2-oxopropyl)-1-(1-(4-(trifluoromethyl)phenyl)ethyl)-1H-pyrazolo[3,4-d]pyrimidin-4(5H)-one The title compound was prepared using procedures similar to those described in step 1 of Examples 175 and 176 using 3-(2-hydroxypropyl)-6-methyl-1-(1-(4-(trifluoromethyl)phenyl)ethyl)-1H-pyrazolo[3,4-d]pyrimidin-4(5H)-one from Examples 243, 244, 245, and 246 to afford a solid. MS=379.2 (+ESI).

Step 2. 3-(2-Hydroxy-2-methylpropyl)-6-methyl-1-(1-(4-(trifluoromethyl)phenyl)ethyl)-1H-pyrazolo[3,4-d]pyrimidin-4(5H)-one The title compound was prepared using procedures similar to those described in step 3 of Examples 243, 244, 245, and 246 using 6-methyl-3-(2-oxopropyl)-1-(1-(4-(trifluoromethyl)phenyl)ethyl)-1H-pyrazolo[3,4-d]pyrimidin-4(5H)-one to afford the title compound (Example 247) as a solid. MS=395.1 (+ESI); $^1$H NMR (300 MHz, CD$_3$OD): δ 7.63 (d, J=8.4 Hz, 2H), 7.53 (d, J=8.1 Hz, 2H), 6.14 (q, J=7.2 Hz, 1H), 3.10 (s, 2H), 2.45 (s, 3H), 1.96 (d, J=6.9 Hz, 3H), 1.25 (s, 3H), 1.24 (s, 3H).

EXAMPLE 248

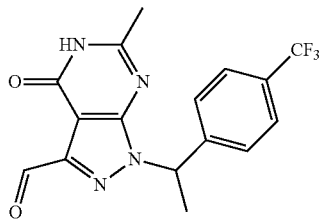 [SMILES: Cc1nc2c(c(C=O)nn2C(C)c2ccc(C(F)(F)F)cc2)c(=O)[nH]1]

6-Methyl-4-oxo-1-(1-(4-(trifluoromethyl)phenyl)ethyl)-4,5-dihydro-1H-pyrazolo[3,4-d]pyrimidine-3-carbaldehyde (Scheme 32)

The title compound was prepared using procedures similar to those described in step 1 of Examples 161 and 162 using 3-(hydroxymethyl)-6-methyl-1-(1-(4-(trifluoromethyl)phenyl)ethyl)-1H-pyrazolo[3,4-d]pyrimidin-4(5H)-one to afford the title compound (Example 248) as a solid. MS=351.1 (+ESI). $^1$H NMR (300 MHz, CDCl$_3$) δ: 10.24 (s, 1H), 7.61-7.53 (m, 4H), 6.21 (q, J=7.2 Hz, 1H), 2.57 (s, 3H), 2.03 (d, J=7.2 Hz, 3H).

EXAMPLES 249 and 250

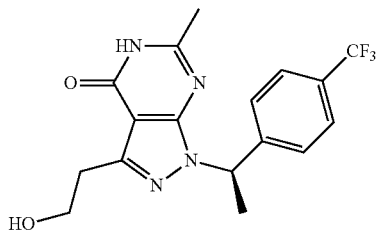

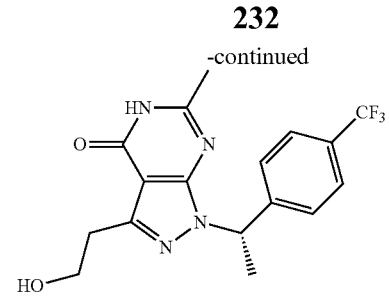

(R)- and (S)-3-(2-Hydroxyethyl)-6-methyl-1-(1-(4-(trifluoromethyl)phenyl)ethyl)-1H-pyrazolo[3,4-d]pyrimidin-4(5H)-one (Scheme 33)

The racemic title compound was prepared using procedures similar to those described in step 1 of Preparatory Example 82 using 6-methyl-4-oxo-1-(1-(4-(trifluoromethyl)phenyl)ethyl)-4,5-dihydro-1H-pyrazolo[3,4-d]pyrimidine-3-carbaldehyde from step 2 of Examples 243, 244, 245, and 246 to afford a solid. The enantiopure title compounds were obtained by chiral preparative HPLC (Chiralpak IA, 20% EtOH in hexanes). The faster-eluting enantiomer of the title compound (Example 249) was obtained as a solid. MS=367.2 (+ESI). $^1$H NMR (400 MHz, DMSO-d$_6$): δ 12.06-11.95 (br, 1H), 7.69 (d, J=8.4 Hz, 2H), 7.47 (d, J=8.0 Hz, 2H), 6.04 (q, J=7.2 Hz, 1H), 4.67 (t, J=5.4 Hz, 1H), 3.75 (m, 2H), 2.97 (t, J=7.2 Hz, 2H), 2.33 (s, 3H), 1.83 (d, J=6.8 Hz, 3H). The slower-eluting enantiomer of the title compound (Example 250) was obtained as a solid. MS=367.2 (+ESI). $^1$H NMR (400 MHz, DMSO-d$_6$) δ: 7.69 (d, J=8.0 Hz, 2H), 7.47 (d, J=8.0 Hz, 2H), 6.04 (q, J=6.8 Hz, 1H), 4.67 (t, J=5.4 Hz, 1H), 3.75 (m, 2H), 2.97 (t, J=7.2 Hz, 2H), 2.33 (s, 3H), 1.83 (d, J=6.8 Hz, 3H).

EXAMPLE 251

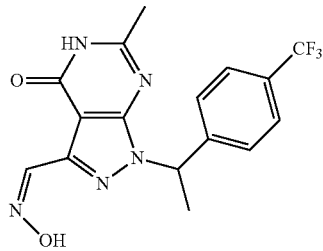 [SMILES: Cc1nc2c(c(/C=N\O)nn2C(C)c2ccc(C(F)(F)F)cc2)c(=O)[nH]1]

(Z)-6-Methyl-4-oxo-1-(1-(4-(trifluoromethyl)phenyl)ethyl)-4,5-dihydro-1H-pyrazolo[3,4-d]pyrimidine-3-carbaldehyde oxime (Scheme 34)

To a solution of 6-methyl-4-oxo-1-(1-(4-(trifluoromethyl)phenyl)ethyl)-4,5-dihydro-1H-pyrazolo[3,4-d]pyrimidine-3-carbaldehyde (20 mg, 0.06 mmol) from Example 248 in ethanol (1 mL) at RT was added hydroxylamine hydrochloride (6.0 mg, 0.09 mmol) followed by Et$_3$N (25 μL, 0.18 mmol). The reaction mixture was stirred for 1 h at reflux, cooled to RT, and concentrated under vacuum. The residue was purified by preparative HPLC (X Bridge RP C18, 35% acetonitrile in water (0.1% TFA)) to afford the title compound (Example 251) as a solid. MS=366.1 (+ESI). $^1$H NMR (300 MHz, DMSO-d$_6$) δ: 11.60 (br, 1H), 8.30 (s, 1H), 7.70 (d, J=8.4 Hz, 2H), 7.50 (d, J=8.4 Hz, 2H), 6.14 (q, J=7.5 Hz, 1H), 2.35 (s, 3H), 1.87 (d, J=6.9 Hz, 3H).

EXAMPLES 252 and 253

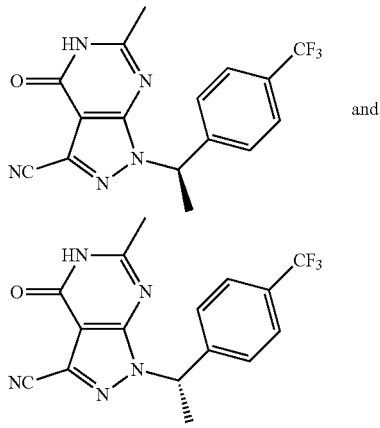

(R)- and (S)-6-Methyl-4-oxo-1-(1-(4-(trifluoromethyl)phenyl)ethyl)-4,5-dihydro-1H-pyrazolo[3,4-d]pyrimidine-3-carbonitrile (Scheme 34)

To a solution of 6-methyl-4-oxo-1-(1-(4-(trifluoromethyl)phenyl)ethyl)-4,5-dihydro-1H-pyrazolo[3,4-d]pyrimidine-3-carbaldehyde (40.0 mg, 0.1 mmol) from Example 248 in DMF (0.5 mL) at RT was added hydroxylamine hydrochloride (11.9 mg, 0.2 mmol) followed by TEA (0.019 mL, 0.1 mmol). 2,4,6-Tripropyl-1,3,5,2,4,6-trioxatriphosphorinane-2,4,6-trioxide (T3P) (43.6 mg, 0.1 mmol) was added to the mixture, which was then heated to 100° C. and stirred for 5 h. The resulting mixture was cooled, diluted with water (3 mL) and extracted with EtOAc (3×5 mL). The combined organic layers were washed with brine (3×15 mL), dried over $Na_2SO_4$, filtered, and concentrated under vacuum. The residue was purified by silica gel column chromatography (50% ethyl acetate in petroleum ether) to afford the racemic title compound. The enantiopure title compounds were obtained by chiral preparative HPLC (Phenomenex 5u Lux Cellulose-4, AXIA Packed; 15% EtOH in hexanes (0.05% TFA)). The faster-eluting enantiomer of the title compound (Example 252) was obtained as a solid. MS=345.9 (−ESI). $^1$H NMR (400 MHz, $CD_3OD$) δ: 7.67 (d, J=8.4 Hz, 2H), 7.57 (d, J=8.4 Hz, 2H), 6.26 (q, J=7.2 Hz, 1H), 2.47 (s, 3H), 1.99 (d, J=7.2 Hz, 3H). The slower-eluting enantiomer of the title compound (Example 253) was obtained as a solid. MS=346.0 (−ESI). $^1$H NMR (400 MHz, $CD_3OD$) δ: 7.66 (d, J=8.4 Hz, 2H), 7.57 (d, J=8.4 Hz, 2H), 6.26 (q, J=7.2 Hz, 1H), 2.47 (s, 3H), 1.99 (d, J=7.2 Hz, 3H).

EXAMPLES 254 and 255

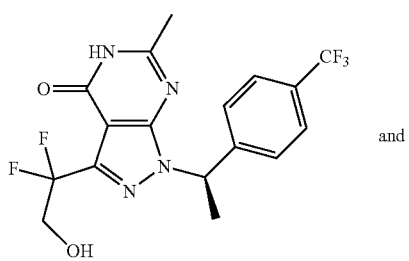

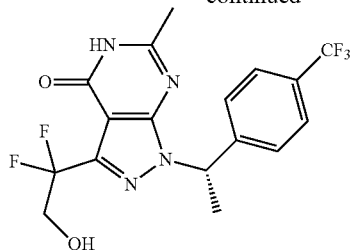

(R)- of (S)-3-(1,1-Difluoro-2-hydroxyethyl)-6-methyl-1-(1-(4-(trifluoromethyl)phenyl)ethyl)-1H-pyrazolo[3,4-d]pyrimidin-4(5H)-one (Scheme 35)

Step 1. 3-(1-Hydroxyethyl)-6-methyl-1-(1-(4-(trifluoromethyl)phenyl)ethyl)-1H-pyrazolo[3,4-d]pyrimidin-4(5H)-one The title compound was prepared using procedures similar to those described in step 3 of Examples 243, 244, 245, and 246 using 6-methyl-4-oxo-1-(1-(4-(trifluoromethyl)phenyl)ethyl)-4,5-dihydro-1H-pyrazolo[3,4-d]pyrimidine-3-carbaldehyde from Example 248 to afford a solid which was used in the next step without purification. MS=367.1 (+ESI).

Step 2. 3-Acetyl-6-methyl-1-(1-(4-(trifluoromethyl)phenyl)ethyl)-1H-pyrazolo[3,4-d]pyrimidin-4(5H)-one To a solution of 3-(1-hydroxyethyl)-6-methyl-1-(1-(4-(trifluoromethyl)phenyl)ethyl)-1H-pyrazolo[3,4-d]pyrimidin-4(5H)-one (0.38 g, 1.0 mmol) in $CH_2Cl_2$ (15 mL) at RT was added Dess-Martin periodinane (0.57 g, 1.3 mmol). The reaction mixture was stirred for 2 h at RT whereupon the resulting mixture was treated with sat. aq. $Na_2CO_3$ (5 mL). The mixture was extracted with $CH_2Cl_2$ (3×10 mL) and the combined organic fractions were washed with water (2×10 mL). The organic layer was dried over $Na_2SO_4$, filtered, and concentrated under vacuum. The residue was purified by silica gel column chromatography (5% ethyl acetate in petroleum ether) to afford the title compound as a solid. MS=365.1 (+ESI).

Step 3. 1-(4-(Benzyloxy)-6-methyl-1-(1-(4-(trifluoromethyl)phenyl)ethyl)-1H-pyrazolo[3,4-d]pyrimidin-3-yl)ethanone To a solution of 3-acetyl-6-methyl-1-(1-(4-(trifluoromethyl)-ethyl)-1H-pyrazolo[3,4-d]pyrimidin-4(5H)-one (0.22 g, 0.6 mmol) in acetonitrile (10 mL) at RT was added silver carbonate (100 mg, 0.4 mmol) followed by (bromomethyl)benzene (0.124 g, 0.7 mmol). The reaction mixture was heated to 55° C. and stirred for 16 h. The resulting mixture was cooled to RT, diluted with brine (50 mL) and extracted with EtOAc (3×50 mL). The combined organic layers were dried over $Na_2SO_4$, filtered, and concentrated under vacuum. The residue was purified by silica gel column chromatography (16% ethyl acetate in petroleum ether) to afford the title compound as a solid. MS=455.2 (+ESI).

Step 4. 2-(6-Methyl-4-oxo-1-(1-(4-(trifluoromethyl)phenyl)ethyl)-4,5-dihydro-1H-pyrazolo[3,4-d]pyrimidin-3-yl)-2-oxoethyl 4-methylbenzenesulfonate To a solution of 1-(4-(benzyloxy)-6-methyl-1-(1-(4-(trifluoromethyl)phenyl)ethyl)-1H-pyrazolo[3,4-d]pyrimidin-3- yl)ethanone (0.13 g, 0.3 mmol) in CH$_3$CN (5 mL) was added [hydroxy(tosyloxy)iodo]benzene (0.22 g, 0.6 mmol) at RT. The reaction mixture was stirred for 16 h at 80° C. The resulting mixture was cooled to RT, diluted with water (10 mL), and extracted with EtOAc (3×20 mL). The combined organic layers was washed with brine (3×20 mL), dried over Na$_2$SO$_4$, filtered, and concentrated under vacuum. The residue was purified by preparative-TLC (CH$_2$Cl$_2$:MeOH=10:1) to afford the title compound as a solid. MS=535.1 (+ESI).

Step 5. 2,2-Difluoro-2-(6-methyl-4-oxo-1-(1-(4-(trifluoromethyl)phenyl)ethyl)-4,5-dihydro-1H-pyrazolo[3,4-d]pyrimidin-3-yl)ethyl 4-methylbenzenesulfonate The title compound was prepared using procedures similar to those described in step 2 of Examples 161 and 162 using 2-(6-methyl-4-oxo-1-(1-(4-(trifluoromethyl)phenyl)ethyl)-4,5-dihydro-1H-pyrazolo[3,4-d]pyrimidin-3-yl)-2-oxoethyl 4-methylbenzenesulfonate to afford an oil. MS=557.1 (+ESI).

Step 6. (R) and (S)-3-(1,1-Difluoro-2-hydroxyethyl)-6-methyl-1-(1-(4-(trifluoromethyl)phenyl)ethyl)-1H-pyrazolo[3,4-d]pyrimidin-4(5H)-one To a solution of 2,2-difluoro-2-(6-methyl-4-oxo-1-(1-(4-(trifluoromethyl)phenyl)ethyl)-4,5-dihydro-1H-pyrazolo[3,4-d]pyrimidin-3-yl)ethyl-4-methylbenzenesulfonate (0.10 g, 0.2 mmol) in MeOH (5 mL) at RT was added magnesium metal (0.44 g, 18 mmol). The reaction mixture was stirred for 4 h at RT. The resulting mixture was cooled to 0° C., quenched with sat. aq. NH$_4$Cl (50 mL) and extracted with CH$_2$Cl$_2$ (3×50 mL). The combined organic layers were washed with brine (200 mL), dried over Na$_2$SO$_4$, filtered, and concentrated under reduced pressure. The residue was purified by silica gel column chromatography (5% methanol in dichloromethane) to afford the racemic title compound. The enantiopure title compounds were obtained by chiral preparative HPLC (Chiralpak IC, 10% EtOH in hexanes). The faster-eluting enantiomer of the title compound (Example 254) was obtained as a solid. MS=403.2 (+ESI). $^1$H NMR (400 MHz, CD$_3$OD): δ 7.64 (d, J=8.0 Hz, 2H), 7.55 (d, J=8.0 Hz, 2H), 6.21 (q, J=7.2 Hz, 1H), 4.30 (td, J=13.6 Hz, 2.0 Hz, 2H), 2.46 (s, 3H), 1.98 (d, J=7.2 Hz, 3H). The slower-eluting enantiomer of the title compound (Example 255) was obtained as a solid. MS=403.2 (+ESI). $^1$H NMR (400 MHz, CD$_3$OD): δ 7.64 (d, J=8.0 Hz, 2H), 7.55 (d, J=8.0 Hz, 2H), 6.21 (q, J=7.2 Hz, 1H), 4.30 (td, J=13.8 Hz, 2.0 Hz, 2H), 2.46 (s, 3H), 1.98 (d, J=7.2 Hz, 3H).

EXAMPLES 256 and 257

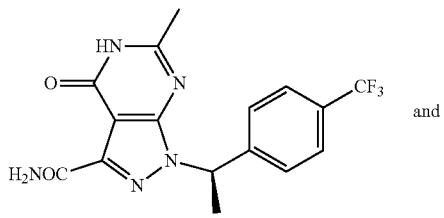

and

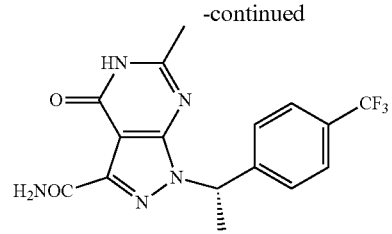

(R)- and (S)-6-Methyl-4-oxo-1-(1-(4-(trifluoromethyl)phenyl)ethyl)-4,5-dihydro-1H-pyrazolo[3,4-d]pyrimidine-3-carboxamide (Scheme 36)

Step 1. 6-Methyl-4-oxo-1-(1-(4-(trifluoromethyl)phenyl)ethyl)-4,5-dihydro-1H-pyrazolo[3,4-d]pyrimidine-3-carboxylic acid To the solution of 6-methyl-4-oxo-1-(1-(4-(trifluoromethyl)phenyl)ethyl)-4,5-dihydro-1H-pyrazolo[3,4-d]pyrimidine-3-carbaldehyde (1.0 g, 2.9 mmol) from Example 226 in EtOH (30 mL) and CH$_2$Cl$_2$ (15 mL) at RT was added a solution of silver nitrate (1.76 g, 11.4 mmol) in water (10 mL). A solution of NaOH (0.913 g, 22.8 mmol) in water (20 mL) was added and the resulting suspension was stirred at RT for 3 h. The mixture was diluted with water (10 mL) and the pH of the resulting mixture was adjusted to 3-4 with 1 M HCl. The mixture was extracted with CH$_2$Cl$_2$ (3×50 mL) and the combined organic layers were washed with brine (3×50 mL). The organic layer was dried over Na$_2$SO$_4$, filtered, and concentrated under vacuum to afford the title compound as an oil which was taken onto the next step without purification. MS=367.0 (+ESI).

Step 2. 6-Methyl-4-oxo-1-(1-(4-(trifluoromethyl)phenyl)ethyl)-4,5-dihydro-1H-pyrazolo[3,4-d]pyrimidine-3-carbonyl chloride The title compound was prepared using procedures similar to those described in step 1 of Preparatory Example 43 using 6-methyl-4-oxo-1-(1-(4-(trifluoromethyl)phenyl)ethyl)-4,5-dihydro-1H-pyrazolo[3,4-d]pyrimidine-3-carboxylic acid to afford an oil that was used in the next step directly without purification.

Step 3: (R)- and (S)-6-Methyl-4-oxo-1-(1-(4-(trifluoromethyl)phenyl)ethyl)-4,5-dihydro-1H-pyrazolo[3,4-d]pyrimidine-3-carboxamide To a solution of ammonia (0.5 M in dioxane, 0.60 mL, 0.3 mmol) at 0° C. was added 6-methyl-4-oxo-1-(1-(4-(trifluoromethyl)phenyl)ethyl)-4,5-dihydro-1H-pyrazolo[3,4-d]pyrimidine-3-carbonyl chloride (50.0 mg, 0.1 mmol) in CH$_2$Cl$_2$ (1.0 mL) and DMF (0.2 mL). The reaction mixture was stirred at RT for 1 h and was concentrated under vacuum. The residue was purified by preparative HPLC (XBridge C18, 30-70% acetonitrile in water (0.05% NH$_4$HCO$_3$)) to afford the title racemic compound as a solid. The enantiopure title compounds were obtained by chiral preparative HPLC (Chiralpak IA, 30% EtOH in hexanes). The faster-eluting enantiomer of the title compound (Example 256) was obtained as a solid. MS=366.1 (+ESI); $^1$H NMR (400 MHz, DMSO-d$_6$): δ 12.68 (br, 1H), 9.49 (br s, 1H), 7.84 (br, 1H), 7.70 (d, J=8.0 Hz, 2H), 7.48 (d, J=8.0 Hz, 2H), 6.20 (q, J=7.2 Hz, 1H), 2.40 (s, 3H), 1.87 (d, J=7.2 Hz, 3H). The slower-eluting enantiomer of the title compound (Example 257) was obtained as a solid. MS=366.1 (+ESI); $^1$H NMR (400 MHz, CD$_3$OD): δ 12.68 (br, 1H), 9.49 (br s, 1H), 7.84 (br, 1H), 7.70 (d, J=8.0 Hz, 2H), 7.48 (d, J=8.0 Hz, 2H), 6.20 (q, J=7.2 Hz, 1H), 2.40 (s, 3H), 1.87 (d, J=7.2 Hz, 3H).

EXAMPLE 258

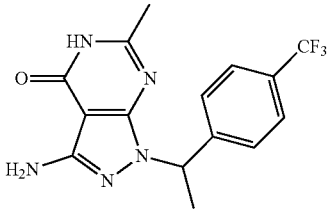 [SMILES: Cc1nc2c(c(N)nn2C(C)c2ccc(C(F)(F)F)cc2)c(=O)[nH]1]

3-Amino-6-methyl-1-(1-(4-(trifluoromethyl)phenyl)ethyl)-H-pyrazolo[3,4-d]pyrimidin-4(5H)-one (Scheme 37)

To the solution of 6-methyl-4-oxo-1-(1-(4-(trifluoromethyl)phenyl)ethyl)-4,5-dihydro-1H-pyrazolo[3,4-d]pyrimidine-3-carboxamide (0.17 g, 0.5 mmol) from Examples 256 and 257 step 3 in 1,4-dioxane (1 mL) and water (0.5 mL) at RT was added solid sodium hypochlorite solution (55 μL, 0.9 mmol) and solid NaOH (37.2 mg, 0.9 mmol). The resulting mixture was heated to 80° C. and stirred for 6 h. The reaction mixture was cooled to RT, diluted with water (50 mL), and extracted with EtOAc (3×100 mL). The combined organic layers were washed with brine (3×50 mL), dried over Na$_2$SO$_4$, filtered, and concentrated under vacuum to afford the title compound (Example 258) as a solid. MS=338.1 (+ESI). $^1$H NMR (400 MHz, DMSO-d$_6$): δ 11.78 (br, 1H), 7.69 (d, J=8.0 Hz, 2H), 7.47 (d, J=8.0 Hz, 2H), 5.90 (q, J=6.8 Hz, 1H), 5.40 (br, 2H), 2.29 (s, 3H), 1.76 (d, J=6.8 Hz, 3H).

Examples 259 and 260

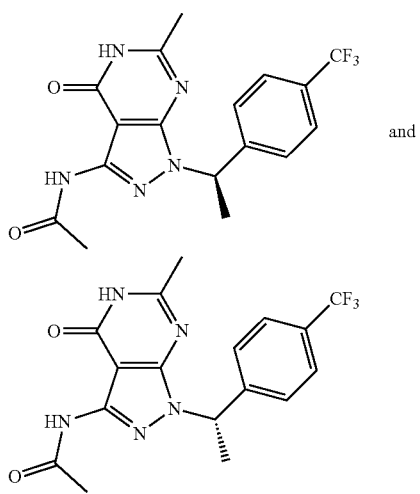

(R)- and (S)—N-(6-Methyl-4-oxo-1-(1-(4-(trifluoromethyl)phenyl)ethyl)-4,5-dihydro-1H-pyrazolo[3,4-d]pyrimidin-3-yl)acetamide (Scheme 38)

A solution of 3-amino-6-methyl-1-(1-(4-(trifluoromethyl)phenyl)ethyl)-1H-pyrazolo[3,4-d]pyrimidin-4(5H)-one (70 mg, 0.2 mmol) from Example 258 in acetic anhydride (0.20 mL, 2.1 mmol) was stirred at RT for 16 h. The reaction mixture was diluted with water (30 mL) and extracted with EtOAc (3×30 mL). The combined organic layers were washed with brine (3×50 mL), dried over Na$_2$SO$_4$, filtered, and concentrated under vacuum. The residue was purified by preparative HPLC (SunFire Prep C18, 20-45% acetonitrile in water (0.1% NH$_4$HCO$_3$)) to afford the title racemic compound. The enantiopure title compounds were obtained by chiral preparative HPLC (Chiralpak IA, 30% EtOH in hexanes). The faster-eluting enantiomer of the title compound (Example 259) was obtained as a solid. MS=380.0 (+ESI); $^1$H NMR (400 MHz, CD$_3$OD): δ 7.62 (d, J=8.4 Hz, 2H), 7.55 (d, J=8.8 Hz, 2H), 6.14 (q, J=7.2 Hz, 1H), 2.44 (s, 3H), 2.28 (s, 3H), 1.94 (d, J=6.8 Hz, 3H). The slower-eluting enantiomer of the title compound (Example 260) was obtained as a solid. MS=380.0 (+ESI); $^1$H NMR (400 MHz, CD$_3$OD): δ 7.62 (d, J=8.4 Hz, 2H), 7.55 (d, J=8.4 Hz, 2H), 6.14 (q, J=7.2 Hz, 1H), 2.44 (s, 3H), 2.20 (s, 3H), 1.94 (d, J=7.2 Hz, 3H).

EXAMPLE 261

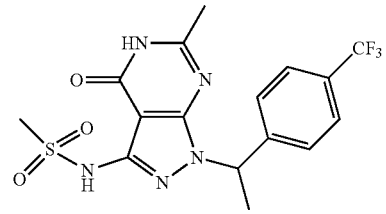 [SMILES: Cc1nc2c(c(NS(C)(=O)=O)nn2C(C)c2ccc(C(F)(F)F)cc2)c(=O)[nH]1]

N-(6-Methyl-4-oxo-1-(1 (4-(trifluoromethyl)phenyl)ethyl)-4,5-dihydro-1H-pyrazolo[3,4-d]pyrimidin-3-yl)methanesulfonamide (Scheme 38)

To a solution of 3-amino-6-methyl-1-(1-(4-(trifluoromethyl)phenyl)ethyl)-1H-pyrazolo[3,4-d]pyrimidin-4(5H)-one (70 mg, 0.2 mmol) from Example 258 in DCM (2 mL) were added MsCl (0.04 mL, 0.5 mmol) and pyridine (0.04 mL, 0.5 mmol) at RT. The mixture was heated to 50° C., stirred for 16 h, and cooled to RT. The mixture was diluted with water (20 mL), extracted with EtOAc (3×20 mL), and the organic layers were combined. The organic layer was washed with brine (3×30 mL), dried over Na$_2$SO$_4$, filtered, and concentrated under vacuum. The residue was purified by preparative HPLC (XBridge C18, 30-40% acetonitrile in water (0.1% NH$_4$HCO$_3$)) to afford the title compound (Example 261) as a solid. MS=416.0 (+ESI); $^1$H NMR (400 MHz, CD$_3$OD): δ 7.62 (d, J=8.4 Hz, 2H), 7.56 (d, J=8.4 Hz, 2H), 6.12 (q, J=7.2 Hz, 1H), 2.54 (s, 3H), 1.94 (d, J=7.2 Hz, 3H), 3.33 (s, 3H).

EXAMPLES 262 and 263

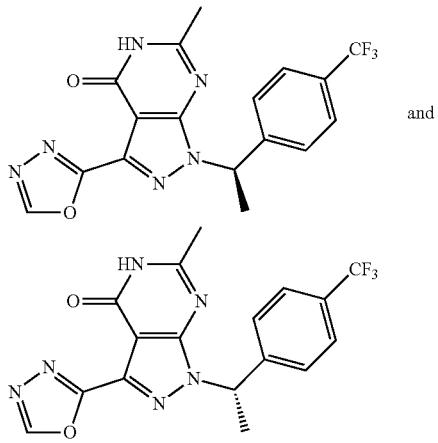

(R)- and (S)-6-Methyl-3-(1,3,4-oxadiazol-2-yl)-1-(1-(4-(trifluoromethyl)phenyl)ethyl)-1H-pyrazolo[3,4-d]pyrimidin-4(5H)-one (Scheme 39)

Step 1. tert-Butyl 2-(6-methyl-4-oxo-1-(1-(4-(trifluoromethyl)phenyl)ethyl)-4,5-dihydro-1H-pyrazolo[3,4-d]pyrimidine-3-carbonyl)hydrazinecarboxylate To a stirred mixture of 6-methyl-4-oxo-1-(1-(4-(trifluoromethyl)phenyl)ethyl)-4,5-dihydro-1H-pyrazolo[3,4-d]pyrimidine-3-carboxylic acid (100 mg, 0.27 mmol) prepared from step 1 of Examples 256 and 257 in NMP (3 ml) under $N_2$ at RT was added tert-butyl hydrazinecarboxylate (46.9 mg, 0.36 mmol) followed by HATU (0.10 g, 0.27 mmol) and DIEA (0.14 ml, 0.82 mmol). The mixture was stirred at RT for 12 h, diluted with EtOAc (30 mL) and the organic layer was washed with brine (3×30 mL). The organic layer was dried over $Na_2SO_4$, filtered, and concentrated under reduced pressure. The residue was purified by silica gel column chromatography (0-60% EtOAc in petroleum ether) to afford the title compound as an oil. MS=481.2 (+ESI).

Step 2. 6-Methyl-4-oxo-1-(1-(4-(trifluoromethyl)phenyl)ethyl)-4,5-dihydro-1H-pyrazolo[3,4-d]pyrimidine-3-carbohydrazide To a stirred mixture of tert-butyl 2-(6-methyl-4-oxo-1-(1-(4-(trifluoromethyl)phenyl)ethyl)-4,5-dihydro-1H-pyrazolo[3,4-d]pyrimidine-3-carbonyl)hydrazinecarboxylate (0.10 g, 0.2 mmol) in $CH_2Cl_2$ (4.0 mL) at RT was added TFA (1.0 mL) dropwise. The reaction mixture was stirred at RT for 2 h. The resulting mixture was concentrated under reduced pressure to give the title compound as an oil and used for next step without purification. MS=381.0 (+ESI).

Step 3. (R)- and (S)-6-Methyl-3-(1,3,4-oxadiazol-2-yl)-1-(1-(4-(trifluoromethyl)phenyl)ethyl)-1H-pyrazolo[3,4-d]pyrimidin-4(5H)-one To a mixture of 6-methyl-4-oxo-1-(1-(4-(trifluoromethyl)phenyl)ethyl)-4,5-dihydro-1H-pyrazolo[3,4-d]pyrimidine-3-carbohydrazide (60 mg, 0.2 mmol) in trimethyl orthoformate (5.2 mL, 47.3 mmol) at RT was added 4-methylbenzenesulfonic acid (5.4 mg, 0.03 mmol). The mixture was stirred at 90° C. for 16 h, cooled to RT, and concentrated under reduced pressure. The residue was purified by preparative HPLC (Xbridge C18, 35% acetonitrile in water (0.05% TFA)) to afford the racemic title compound as a solid. The enantiopure title compounds were obtained by chiral preparative HPLC (Chiralpak IA, 20% EtOH in hexanes). The faster-eluting enantiomer of the title compound (Example 262) was obtained as a solid. MS=391.1 (+ESI). $^1$H NMR (400 MHz, $CD_3OD$) δ: 9.13 (s, 1H), 7.67 (d, J=8.4 Hz, 2H), 7.63 (d, J=8.8 Hz, 2H), 6.31 (q, J=7.2 Hz, 1H), 2.49 (s, 3H), 2.04 (d, J=7.2 Hz, 3H). The slower-eluting enantiomer of the title compound (Example 263) was obtained as a solid. MS=391.1 (+ESI). $^1$H NMR (300 MHz, $CD_3OD$) δ: 9.13 (s, 1H), 7.67 (d, J=8.4 Hz, 2H), 7.63 (d, J=8.8 Hz, 2H), 6.31 (q, J=7.2 Hz, 1H), 2.49 (s, 3H), 2.04 (d, J=7.2 Hz, 3H).

EXAMPLES 264 and 265

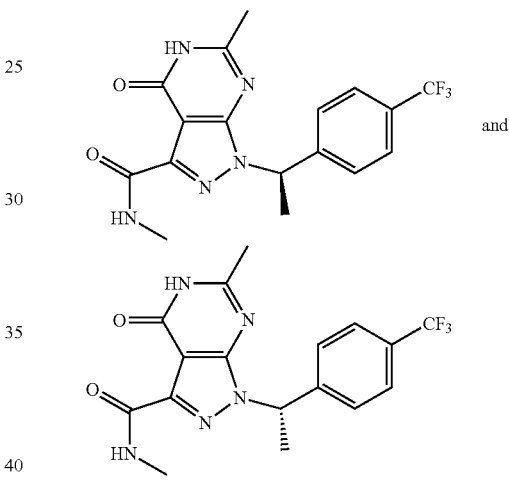

(R)- and (S)—N,6-Dimethyl-4-oxo-1-(1-(4-(trifluoromethyl)phenyl)ethyl)-4,5-dihydro-1H-pyrazolo[3,4-d]pyrimidine-3-carboxamide (Scheme 40)

The racemic title compound was prepared using procedures similar to those described in step 1 of Examples 262 and 263 using 6-methyl-4-oxo-1-(1-(4-(trifluoromethyl)phenyl)ethyl)-4,5-dihydro-1H-pyrazolo[3,4-d]pyrimidine-3-carboxylic acid from step 1 of Examples 256 and 257 and methylamine hydrochloride as a solid. The enantiopure title compounds were obtained by chiral preparative HPLC (Chiralpak IA, 30% EtOH in hexanes). The faster-eluting enantiomer of the title compound (Example 264) was obtained as a solid. MS=380.0 (+ESI). $^1$H NMR (400 MHz, DMSO-$d_6$) δ: 12.71 (br, 1H), 9.97 (d, J=4.8 Hz, 1H), 7.71 (d, J=8.4 Hz, 2H), 7.49 (d, J=8.0 Hz, 2H), 6.21 (q, J=7.2 Hz, 1H), 2.88 (d, J=4.8 Hz, 3H), 2.33 (s, 3H), 1.89 (d, J=7.2 Hz, 3H). The slower-eluting enantiomer of the title compound (Example 265) was obtained as a solid. MS=380.0 (+ESI). $^1$H NMR (400 MHz, DMSO-$d_6$) δ: 12.71 (br, 1H), 9.97 (d, J=4.8 Hz, 1H), 7.71 (d, J=8.4 Hz, 2H), 7.49 (d, J=8.0 Hz, 2H), 6.21 (q, J=6.8 Hz, 1H), 2.88 (d, J=4.4 Hz, 3H), 2.33 (s, 3H), 1.89 (d, J=6.8 Hz, 3H).

TABLE 26

The following compounds were prepared using procedures similar to those described in Examples 264 and 265 using appropriate starting materials. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 266 | 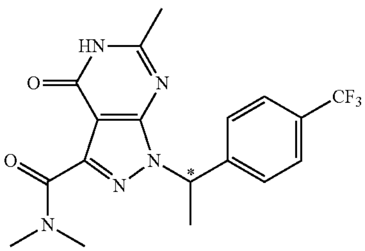 [SMILES: Cc1nc2c(c(C(=O)N(C)C)nn2C(C)c2ccc(C(F)(F)F)cc2)c(=O)[nH]1] | (R)- or (S)-N,N,6-Trimethyl-4-oxo-1-(1-(4-(trifluoromethyl)phenyl)ethyl)-4,5-dihydro-1H-pyrazolo[3,4-d]pyrimidine-3-carboxamide | Calc'd 394.1, found 394.0. | Chiracel OJ-H |
| 267 | 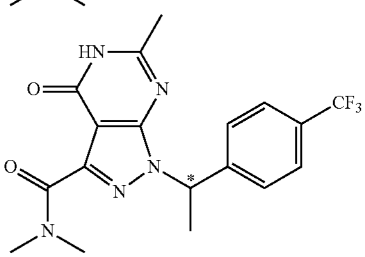 | (S)- or (R)-N,N,6-Trimethyl-4-oxo-1-(1-(4-(trifluoromethyl)phenyl)ethyl)-4,5-dihydro-1H-pyrazolo[3,4-d]pyrimidine-3-carboxamide | Calc'd 394.1, found 394.0. | Chiracel OJ-H |
| 268 | 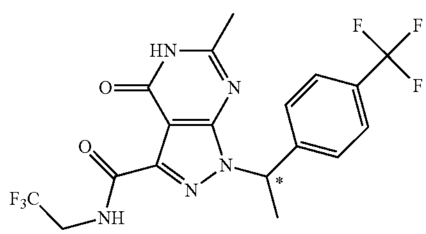 [SMILES: Cc1nc2c(c(C(=O)NCC(F)(F)F)nn2C(C)c2ccc(C(F)(F)F)cc2)c(=O)[nH]1] | (R)- or (S)-6-Methyl-4-oxo-N-(2,2,2-trifluoroethyl)-1-(1-(4-(trifluoromethyl)phenyl)ethyl)-4,5-dihydro-1H-pyrazolo[3,4-d]pyrimidine-3-carboxamide | Calc'd 448.1, found 448.0. | Chiralpak IA |
| 269 | 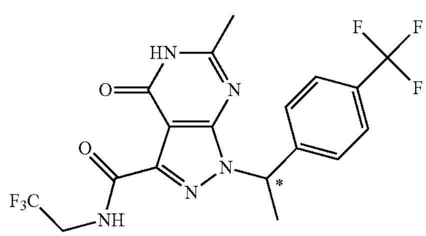 [SMILES: Cc1nc2c(c(C(=O)NCC(F)(F)F)nn2C(C)c2ccc(C(F)(F)F)cc2)c(=O)[nH]1] | (S)- or (R)-6-Methyl-4-oxo-N-(2,2,2-trifluoroethyl)-1-(1-(4-(trifluoromethyl)phenyl)ethyl)-4,5-dihydro-1H-pyrazolo[3,4-d]pyrimidine-3-carboxamide | Calc'd 448.1, found 448.0. | Chiralpak IA |
| 270 | 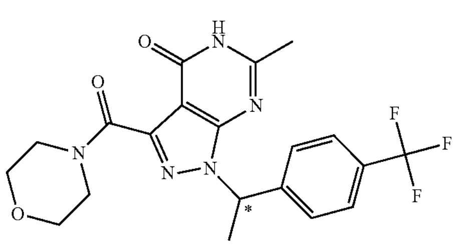 [SMILES: Cc1nc2c(c(C(=O)N3CCOCC3)nn2C(C)c2ccc(C(F)(F)F)cc2)c(=O)[nH]1] | (R)- or (S)-6-Methyl-3-(morpholine-4-carbonyl)-1-(1-(4-(trifluoromethyl)phenyl)ethyl)-1H-pyrazolo[3,4-d]pyrimidin-4(5H)-one | Calc'd 436.2, found 436.0. | Chiralpak IB |
| 271 | 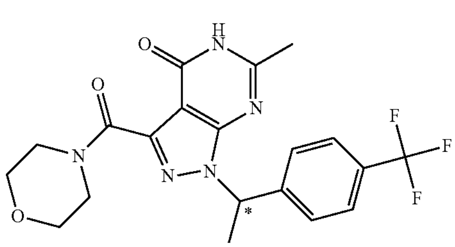 [SMILES: Cc1nc2c(c(C(=O)N3CCOCC3)nn2C(C)c2ccc(C(F)(F)F)cc2)c(=O)[nH]1] | (S)- or (R)-6-Methyl-3-(morpholine-4-carbonyl)-1-(1-(4-(trifluoromethyl)phenyl)ethyl)-1H-pyrazolo[3,4-d]pyrimidin-4(5H)-one | Calc'd 436.2, found 436.1. | Chiralpak IB |

EXAMPLES 272 and 273

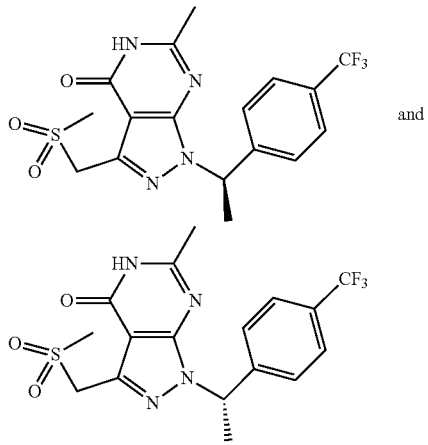

(R)- and (S)-6-Methyl-3-(methylsulfonlmethyl)-1-(1-(4-(trifluoromethyl)phenyl)ethyl)-1H-pyrazolo[3,4-d]pyrimidin-4(5H)-one (Scheme 41)

Step 1. 3-(Chloromethyl)-6-methyl-1-(1-(4-(trifluoromethyl)phenyl)ethyl)-1H-pyrazolo[3,4-d]pyrimidin-4(5H)-one To a solution of 3-(hydroxymethyl)-6-methyl-1-(1-(4-(trifluoromethyl)phenyl)ethyl)-1H-pyrazolo[3,4-d]pyrimidin-4(5H)-one (0.20 g, 0.6 mmol) from Example 7 and TEA (0.16 mL, 1.1 mmol) in THF (4 mL) was added methanesulfonyl chloride (98.0 mg, 0.9 mmol) at 0° C. LiCl (72.2 mg, 1.7 mmol) was added to the mixture which was warmed to RT and stirred for 20 h. The resulting mixture was concentrated under reduced pressure and the residue was diluted with EtOAc (10 mL) and water (10 mL). The layers were separated and the aqueous layer was extracted with EtOAc (3×10 mL). The organic layers were combined and washed with water (2×5 mL) and brine (1×10 mL). The organic layer was dried over anhydrous $Na_2SO_4$, filtered, and concentrated under reduced pressure. The residue was purified by silica gel column chromatography (0-45% ethyl acetate in petroleum ether) to afford the title compound as a solid. MS=371.0 (ESI+).

Step 2. (R)- and (S)-6-Methyl-3-(methylsulfonylmethyl)-1-(1-(4-(trifluoromethyl)phenyl)ethyl)-1H-pyrazolo[3,4-d]pyrimidin-4(5H)-one To a solution of 3-(chloromethyl)-6-methyl-1-(1-(4-(trifluoromethyl)phenyl)ethyl)-1H-pyrazolo[3,4-d]pyrimidin-4(5H)-one (85 mg, 0.2 mmol) in ethanol (4 mL) was added sodium methanesulfinate (23.4 mg, 0.2 mmol) at RT. The reaction solution heated to 80° C. and was stirred for 16 h. The mixture was cooled to RT and was concentrated under vacuum. The residue was diluted with EtOAc (10 mL) and water (10 mL) and the layers were separated. The aqueous layer was extracted with EtOAc (3×10 mL) and the combined organic layers were washed with water (2×5 mL) and brine (10 mL). The organic layer was dried over $Na_2SO_4$, filtered, and concentrated under reduced pressure. The residue was purified by preparative HPLC (Sunfire C18, 40-75% acetonitrile in water (0.1% TFA)) to afford the racemic title compound as a solid. The enantiopure title compounds were obtained by chiral preparative HPLC (Chiralpak IA, 20% EtOH in hexanes). The faster-eluting enantiomer of the title compound (Example 272) was obtained as a solid. MS=415.1 (+ESI). $^1$H NMR (400 MHz, DMSO-$d_6$) δ: 12.25-12.15 (br s, 1H), 7.69 (d, J=8.4 Hz, 2H), 7.49 (d, J=8.4 Hz, 2H), 6.14 (q, J=7.2 Hz, 1H), 4.71 (s, 2H), 3.04 (s, 3H), 2.37 (s, 3H), 1.87 (d, J=6.8 Hz, 3H). The slower-eluting enantiomer of the title compound (Example 273) was obtained as a solid. MS=415.1 (+ESI). $^1$H NMR (400 MHz, DMSO-$d_6$): δ: 12.25-12.15 (br s, 1H), 7.69 (d, J=8.4 Hz, 2H), 7.49 (d, J=8.4 Hz, 2H), 6.14 (q, J=7.2 Hz, 1H), 4.71 (s, 2H), 3.04 (s, 3H), 2.37 (s, 3H), 1.87 (d, J=6.8 Hz, 3H).

EXAMPLES 274 and 275

(R)- and (S)-3-(Aminomethyl)-6-methyl-1-(1-(4-(trifluoromethyl)phenyl)ethyl)-1H-pyrazolo[3,4-d]pyrimidin-4(5H)-one (Scheme 42)

Step 1. (6-Methyl-4-oxo-1-(1-(4-(trifluoromethyl)phenyl)ethyl)-4,5-dihydro-1H-pyrazolo[3,4-d]pyrimidin-3-yl)methyl methanesulfonate The title compound was prepared using procedures similar to those described in Example 261 using 3-(hydroxymethyl)-6-methyl-1-(1-(4-(trifluoromethyl)phenyl)ethyl)-1H-pyrazolo[3,4-d]pyrimidin-4(5H)-one from Example 7 to afford an oil which was used for the next step without purification. MS=431.5 (+ESI).

Step 2. 3-(Azidomethyl)-6-methyl-1-(1-(4-(trifluoromethyl)phenyl)ethyl)-1H-pyrazolo[3,4-d]pyrimidin-4(5H)-one To a solution of (6-methyl-4-oxo-1-(1-(4-(trifluoromethyl)phenyl)ethyl)-4,5-dihydro-1H-pyrazolo[3,4-d]pyrimidin-3-yl)methyl methanesulfonate (0.10 g, 0.2 mmol) in DMF (4 mL) at RT was added sodium azide (76 mg, 1.2 mmol). The reaction mixture was stirred for 1 h at 60° C. The resulting mixture was cooled, diluted with sat. aq. $NaHCO_3$ (20 mL) and extracted with EtOAc (3×20 mL). The combined organic layers were washed with brine (3×50 mL), dried over $Na_2SO_4$, filtered, and concentrated under reduced pressure. The title compound was obtained as an oil which was used in the next step without further purification. MS=378.2 (+ESI).

Step 3. (R)- and (S)-3-(Aminomethyl)-6-methyl-1-(1-(4-(trifluoromethyl)phenyl)ethyl)-1H-pyrazolo[3,4-d]pyrimidin-4(5H)-one To a solution of 3-(azidomethyl)-6-methyl-1-(1-(4-(trifluoromethyl)phenyl)ethyl)-1H-pyrazolo[3,4-d]pyrimidin-4 (5H)-one (0.10 g, 0.3 mmol) in ethanol (1.5 mL) at RT was added 10% palladium on carbon (0.11 g, 0.05 mmol). The reaction mixture was purged with H$_2$ for three times and stirred for 16 h at RT under a H$_2$ balloon. The resulting mixture was purged to nitrogen, filtered through Celite™, and the filtrate was concentrated under reduced pressure. The residue was purified by preparative HPLC (Sunfire shield C18, 40-45% acetonitrile in water (0.05% NH$_4$HCO$_3$)) to afford the title racemic compound as a solid. The enantiopure title compounds were obtained by chiral preparative HPLC (Chiralpak AD-H, 10% EtOH in hexanes (0.1% TFA)). The faster-eluting enantiomer of the title compound (Example 274) was obtained as a solid. MS=352.1 (+ESI). $^1$H NMR (400 MHz, CDCl$_3$): δ 7.64 (d, J=8.4 Hz, 2H), 7.58 (d, J=8.4 Hz, 2H), 6.20 (q, J=7.2 Hz, 1H), 4.44 (s, 2H), 2.49 (s, 3H), 1.98 (d, J=7.2 Hz, 3H). The slower-eluting enantiomer of the title compound (Example 275) was obtained as a solid. MS=352.1 (+ESI). $^1$H NMR (400 MHz, CDCl$_3$): δ 7.64 (d, J=8.4 Hz, 2H), 7.58 (d, J=8.4 Hz, 2H), 6.20 (q, J=7.2 Hz, 1H), 4.44 (s, 2H), 2.49 (s, 3H), 1.98 (d, J=7.2 Hz, 3H).

EXAMPLES 276 and 277

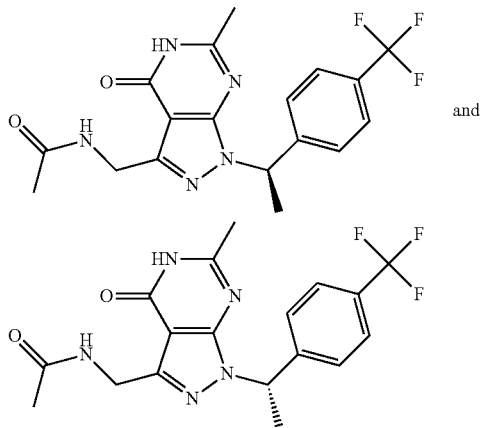

(R)- and (S)-N-((6-Methyl-4-oxo-1-(1-(4-(trifluoromethyl)phenyl)ethyl)-4,5-dihydro-1H-pyrazolo[3,4-d]pyrimidin-3-yl)methyl)acetamide (Scheme 42)

3-(Aminomethyl)-6-methyl-1-(1-(4-(trifluoromethyl)phenyl)ethyl)-1H-pyrazolo[3,4-d]pyrimidin-4(5H)-one (0.15 g, 0.4 mmol) from Examples 274 and 275 was dissolved in acetic anhydride (1.6 mL, 17.1 mmol) and the resulting solution was stirred at RT for 2.5 h. MeOH (20 mL) was added and the mixture was concentrated under vacuum. The residue was treated with sat. aq. NaHCO$_3$ (30 mL) and was stirred for 20 min. The mixture was extracted with EtOAc (3×40 mL) and the combined organic layers were washed with brine (1×20 mL). The organic layer was dried over Na$_2$SO$_4$, filtered, and concentrated under vacuum. The residue was purified by preparative HPLC (X Bridge C18, 10-70% acetonitrile in water (0.05% TFA)) to afford the title racemic compound as a solid. The enantiopure title compounds were obtained by chiral preparative HPLC (Lux Chiralpak IC, 15% EtOH in hexanes). The faster-eluting enantiomer of the title compound (Example 276) was obtained as a solid. MS=394.2 (+ESI); $^1$H NMR (400 MHz, CD$_3$OD): δ 7.51 (d, J=8.4 Hz, 2H), 7.42 (d, J=8.4 Hz, 2H), 6.02 (q, J=7.2 Hz, 1H), 4.54 (s, 2H), 2.33 (s, 3H), 1.89 (s, 3H), 1.83 (d, J=7.2 Hz, 3H). The slower-eluting enantiomer of the title compound (Example 277) was obtained as a solid. MS=394.2 (+ESI); $^1$H NMR (400 MHz, CD$_3$OD): δ 7.51 (d, J=8.4 Hz, 2H), 7.42 (d, J=8.4 Hz, 2H), 6.02 (q, J=7.2 Hz, 1H), 4.54 (s, 2H), 2.33 (s, 3H), 1.89 (s, 3H), 1.83 (d, J=7.2 Hz, 3H).

EXAMPLES 278 and 279

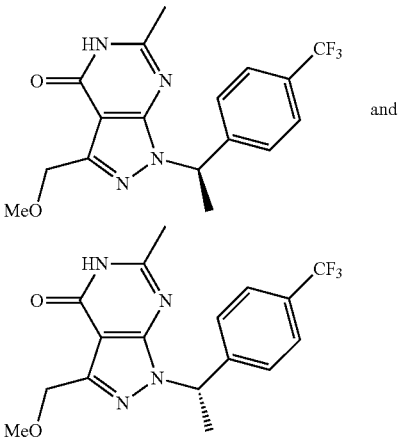

(R)- and (S)-3-(Methoxymethyl)-6-methyl-1-(1-(4-(trifluoromethyl)phenyl)ethyl)-1H-pyrazolo[3,4-d]pyrimidin-4(5H)-one (Scheme 43)

Step 1. (4-Methoxy-6-methyl-1-(1-(4-(trifluoromethyl)phenyl)ethyl)-1H-pyrazolo[3,4-d]pyrimidin-3-yl)methyl methanesulfonate The title compound was prepared using procedures similar to those described in Example 261 using (4-methoxy-6-methyl-1-(1-(4-(trifluoromethyl)phenyl)ethyl)-1H-pyrazolo[3,4-d]pyrimidin-3-yl)methanol to afford an oil that used in the next step without purification. MS=445.1 (+ESI).

Step 2. 4-Methoxy-3-(methoxymethyl)-6-methyl-1-(1-(4-(trifluoromethyl)phenyl)ethyl)-1H-pyrazolo[3,4-d]pyrimidine To a solution of (4-methoxy-6-methyl-1-(1-(4-(trifluoromethyl)phenyl)ethyl)-1H-pyrazolo[3,4-d]pyrimidin-3-yl) methyl methanesulfonate (0.12 g, 0.30 mmol) in MeOH (5 mL) was added sodium methoxide (73 mg, 1.4 mmol) at RT. The reaction mixture was heated to 60° C. and was stirred for 6 h. The resulting mixture was cooled to RT and was concentrated under vacuum. The residue was diluted with water (20 mL) and extracted with EtOAc (3×15 mL). The combined organic layers were dried over Na$_2$SO$_4$, filtered, and concentrated under reduced pressure to afford the title compound was obtained as an oil. The title compound was used in the next step without purification. MS=381.2 (+ESI).

Step 3. (R)- and (S)-3-(Methoxymethyl)-6-methyl-1-(1-(4-(trifluoromethyl)phenyl)ethyl)-1H-pyrazolo[3,4-d]pyrimidin-4(5H)-one To a solution of 4-methoxy-3-(methoxymethyl)-6-methyl-1-(1-(4-(trifluoromethyl)phenyl)ethyl)-1H-pyrazolo[3,4-d]pyrimidine (65 mg, 0.21 mmol) in DMSO (3 mL) was added NaCN (33.5 mg, 0.7 mmol) at RT. The reaction mixture was heated to 130° C. and was stirred for 1 h. The reaction mixture was cooled to RT, diluted with water (15 mL), and extracted with EtOAc (3×10 mL). The combined organic phases were dried over Na$_2$SO$_4$, filtered, and concentrated under reduced pressure. The residue was purified by preparative HPLC (XBridge RP C18, 20-60% acetonitrile in water (0.05% NH$_4$HCO$_3$)) to afford the racemic title compound as a solid. The enantiopure title compounds were obtained by chiral preparative HPLC (Chiralpak IA, 5% EtOH in hexanes). The faster-eluting enantiomer of the title compound (Example 278) was obtained as a solid. MS=367.0 (+ESI). $^1$H NMR (300 MHz, CD$_3$OD): δ 7.62 (d, J=8.4 Hz, 2H), 7.52 (d, J=8.1 Hz, 2H), 6.16 (q, J=7.2 Hz, 1H), 4.71 (s, 2H), 3.43 (s, 3H), 2.44 (s, 3H), 1.96 (d, J=7.2 Hz, 3H). The slower-eluting enantiomer of the title compound (Example 279) was obtained as a solid. MS=367.0 (+ESI). $^1$H NMR (300 MHz, CD$_3$OD): δ 7.62 (d, J=8.4 Hz, 2H), 7.52 (d, J=8.1 Hz, 2H), 6.16 (q, J=7.2 Hz, 1H), 4.71 (s, 2H), 3.43 (s, 3H), 2.44 (s, 3H), 1.96 (d, J=7.2 Hz, 3H).

EXAMPLES 280 and 281

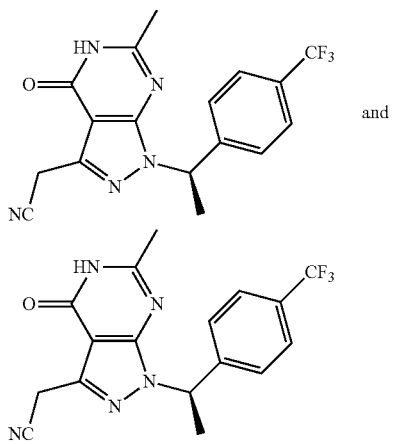

(R)- and (S)-2-(6-Methyl-4-oxo-1-(1-(4-(trifluoromethyl)phenyl)ethyl)-4,5-dihydro-1H-pyrazolo[3,4-d]pyrimidin-3-yl)acetonitrile (Scheme 44)

Step 1. 2-(4-Methoxy-6-methyl-1-(1-(4-(trifluoromethyl)phenyl)ethyl)-1H-pyrazolo[3,4-d]pyrimidin-3-yl)acetonitrile To a mixture of (4-methoxy-6-methyl-1-(1-(4-(trifluoromethyl)phenyl)ethyl)-1H-pyrazolo[3,4-d]pyrimidin-3-yl) methyl methanesulfonate (0.17 g, 0.4 mmol) and sodium cyanide (38 mg, 0.8 mmol) in acetonitrile (4 mL) was added 18-crown-6 (10.1 mg, 0.04 mmol) at RT. The mixture was heated to 65° C., stirred for 2 h, and cooled to RT. The mixture was filtered and the resultant solid washed with EtOAc (10 mL) with the combined filtrate being concentrated under reduced pressure. The residue was purified by silica gel column chromatography (20% ethyl acetate in petroleum ether) to afford the title compound as an oil. MS=376.0 (+ESI).

Step 2. (R)- and (S)-2-(6-Methyl-4-oxo-1-(1-(4-(trifluoromethyl)phenyl)ethyl)-4,5-dihydro-1H-pyrazolo[3,4-d]pyrimidin-3-yl)acetonitrile The racemic title compound was prepared using procedures similar to those described in step 5 of Examples 194 and 195 using 2-(4-methoxy-6-methyl-1-(1-(4-(trifluoromethyl)phenyl)ethyl)-1H-pyrazolo[3,4-d]pyrimidin-3-yl)acetonitrile to afford a solid. The enantiopure title compounds were obtained by chiral preparative HPLC (Chiralpak IA, 20% EtOH in hexanes). The faster-eluting enantiomer of the title compound (Example 280) was obtained as a solid. MS=359.8 (−ESI). $^1$H NMR (400 MHz, DMSO-d$_6$): δ 12.25 (s, 1H), 7.72 (d, J=8.0 Hz, 2H), 7.50 (d, J=8.0 Hz, 2H), 6.10 (q, J=6.8 Hz, 1H), 4.26 (s, 2H), 2.36 (s, 3H), 1.87 (d, J=6.8 Hz, 3H). The slower-eluting enantiomer of the title compound (Example 281) was obtained as a solid. MS=359.8 (−ESI). $^1$H NMR (400 MHz, DMSO-d$_6$): δ 12.25 (s, 1H), 7.72 (d, J=8.0 Hz, 2H), 7.50 (d, J=8.0 Hz, 2H), 6.10 (q, J=6.8 Hz, 1H), 4.26 (s, 2H), 2.36 (s, 3H), 1.87 (d, J=6.8 Hz, 3H).

EXAMPLE 282

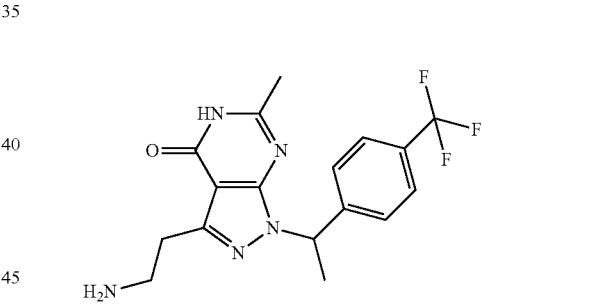

3-(2-Aminoethyl)-6-methyl-1-(1-(4-(trifluoromethyl)phenyl)ethyl)-1H-pyrazolo[3,4-d]pyrimidin-4(5H)-one (Scheme 44)

To a suspension of LiAlH$_4$ (16.8 mg, 0.4 mmol) in diethyl ether (1 mL) was added 2-(6-methyl-4-oxo-1-(1-(4-(trifluoromethyl)phenyl)ethyl)-4,5-dihydro-1H-pyrazolo[3,4-d]pyrimidin-3-yl)acetonitrile (80 mg, 0.2 mmol) under nitrogen at −78° C. The suspension was warmed slowly to RT and stirred for 16 h. MeOH (5 mL) and NaSO$_4$ 10H$_2$O (1.00 g) were carefully added to the suspension which was stirred at RT for additional 2 h. The suspension was filtered and the filtrate was concentrated under reduced pressure. The residue was purified by preparative HPLC (X Bridge C18, 30-70% acetonitrile in water (0.05% TFA)) to afford the title compound (Example 282) as a solid. MS=366.1 (+ESI). $^1$H NMR (300 MHz, CD$_3$OD): δ 7.58 (d, J=8.4 Hz, 2H), 7.48 (d, J=8.4 Hz, 2H), 6.08 (q, J=7.2 Hz, 1H), 3.18-3.02 (m, 4H), 2.40 (s, 3H), 1.89 (d, J=7.2 Hz, 3H).

EXAMPLES 283 and 284

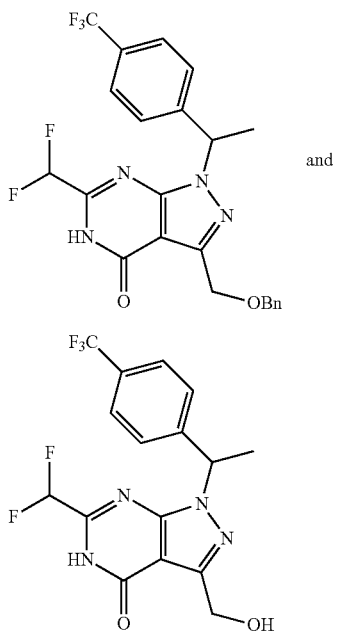

283

284

3-((Benzyloxy)methyl)-6-(difluoromethyl)-1-(1-(4-(trifluoromethyl)phenyl)ethyl) 1H-pyrazolo[3,4-d]pyrimidin-4(5H)-one and 6-(Difluoromethyl)-3-(hydroxymethyl)-1-(1-(4-(trifluoromethyl)phenyl)ethyl)-1H-pyrazolo[3,4-d]pyrimidin-4(5H)-one (Scheme 17)

Step 1. 3-((Benzyloxy)methyl)-6-(difluoromethyl)-1-(1-(4-(trifluoromethyl)phenyl)ethyl)-1H-pyrazolo[3,4-d]pyrimidin-4(5H)-one The title compound, 3-((benzyloxy)methyl)-6-(difluoromethyl)-1-(1-(4-(trifluoromethyl)phenyl)ethyl)-1H-pyrazolo[3,4-d]pyrimidin-4(5H)-one, was prepared using procedures similar to those described in step 1 of Example 28 utilizing 5-amino-3-((benzyloxy)methyl)-1-(1-(4-(trifluoromethyl)phenyl)ethyl)-1H-pyrazole-4-carboxamide from Preparatory Example 58 and ethyl 2,2-difluoroacetate to afford the title compound (Example 283) as an oil. MS=479.2 (+ESI). $^1$H NMR (300 MHz, CDCl$_3$): δ 9.91 (br s, 1H), 7.57 (d, J=8.4 Hz, 2H), 7.51 (d, J=8.4 Hz, 2H), 7.41-7.26 (m, 5H), 6.43 (t, J=53.8 Hz, 1H), 6.06 (q, J=7.2 Hz, 1H), 4.87 (s, 2H), 4.70 (s, 2H), 2.00 (d, J=7.2 Hz, 3H).

Step 2. 6-(Difluoromethyl)-3-(hydroxymethyl)-1-(1-(4-(trifluoromethyl)phenyl)ethyl)-1H-pyrazolo[3,4-d]pyrimidin-4(5H)-one The title compound, 6-(difluoromethyl)-3-(hydroxymethyl)-1-(1-(4-(trifluoromethyl)phenyl)ethyl)-1H-pyrazolo[3,4-d]pyrimidin-4(5H)-one, was prepared using procedures similar to those described in step 2 of Example 1 using 3-((benzyloxy)methyl)-6-(difluoromethyl)-1-(1-(4-(trifluoromethyl)phenyl)ethyl)-1H-pyrazolo[3,4-d]pyrimidin-4(5H)-one to afford the title compound (Example 284) as a solid. MS=389.2 (+ESI). $^1$H NMR (300 MHz, DMSO-d$_6$): δ 13.07 (br s, 1H), 7.71 (d, J=8.4 Hz, 2H), 7.51 (d, J=8.1 Hz, 2H), 6.82 (t, J=53.0 Hz, 1H), 6.14 (q, J=6.9 Hz, 1H), 5.22 (br, 1H), 4.70 (s, 2H), 1.89 (d, J=6.9 Hz, 3H).

EXAMPLES 285 and 286

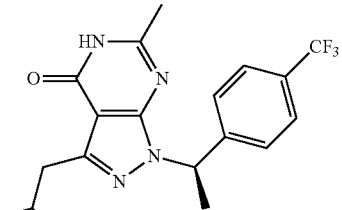

and (R)- and (S)-3-(2,2-Difluoroethyl)-6-methyl-1-(1-(4-(trifluoromethyl)phenyl)ethyl)-1H-pyrazolo[3,4-d]pyrimidin-4(5H)-one (Scheme 45)

Step 1. 3-(2-(Benzyloxy)ethyl)-6-methyl-1-(1-(4-(trifluoromethyl)phenyl)ethyl)-1H-pyrazolo[3,4-d]pyrimidin-4(5H)-one The title compound was prepared using procedures similar to those described in step 1 of Example 28 using 5-amino-3-(2-(benzyloxy)ethyl)-1-(1-(4-(trifluoromethyl)phenyl)ethyl)-1H-pyrazole-4-carboxamide from Preparatory Example 65 to afford an oil. MS=457.1 (+ESI).

Step 2. 3-(2-(Benzyloxy)ethyl)-4-chloro-6-methyl-1-(1-(4-(trifluoromethyl)phenyl)ethyl)-1H-pyrazolo[3,4-d]pyrimidine To a solution of 3-(2-(benzyloxy)ethyl)-6-methyl-1-(1-(4-(trifluoromethyl)phenyl)ethyl)-1H-pyrazolo[3,4-d]pyrimidin-4(5H)-one (2.7 g, 5.9 mmol) in thionyl chloride (12 mL) at RT was added N,N-dimethylformamide (0.046 mL, 0.6 mmol). The reaction solution was heated to 70° C., stirred for 1.5 h at 70° C., and was cooled to RT. The mixture was concentrated under reduced pressure to afford the title compound as an oil which was used directly in the next step without purification. MS=475.1, 477.1 (+ESI).

Step 3. 3-(2-(Benzyloxy)ethyl)-4-methoxy-6-methyl-1-(1-(4-(trifluoromethyl)phenyl)ethyl)-1H-pyrazolo[3,4-d]pyrimidine To a solution of 3-(2-(benzyloxy)ethyl)-4-chloro-6-methyl-1-(1-(4-(trifluoromethyl)phenyl)ethyl)-1H-pyrazolo[3,4-d]pyrimidine (3.0 g, 6.3 mmol) in THF (10 mL) at RT was added sodium methoxide in methanol (30% solution, 4.70 mL, 25.3 mmol). The solution was stirred for 16 h at RT whereupon the mixture was concentrated under reduced pressure. The residue was diluted with ethyl acetate (100 mL) and was washed with water (2×10 mL) and brine (1×10 mL). The organic layer was dried over Na$_2$SO$_4$, filtered, and concentrated under reduced pressure. The residue was purified by silica gel column chromatography (0-30% of ethyl acetate in petroleum ether) to afford the title compound as an oil. MS=471.1 (+ESI).

Step 4. 2-(4-Methoxy-6-methyl-1-(1-(4-(trifluoromethyl)phenyl)ethyl)-1H-pyrazolo[3,4-d]pyrimidin-3-yl)ethanol The title compound was prepared using procedures similar to those described in step 2 of Example 2 using 3-(2-(benzyloxy)ethyl)-4-methoxy-6-methyl-1-(1-(4-(trifluoromethyl)phenyl)ethyl)-1H-pyrazolo[3,4-d]pyrimidine to afford an oil. MS=381.1 (+ESI).

Step 5. 2-(4-Methoxy-6-methyl-1-(1-(4-(trifluoromethyl)phenyl)ethyl)-1H-pyrazolo[3,4-d]pyrimidin-3-yl)acetaldehyde The title compound was prepared using procedures similar to those described in step 3 of Examples 239, 240, 241, and 242 using 2-(4-methoxy-6-methyl-1-(1-(4-(trifluoromethyl)phenyl)ethyl)-1H-pyrazolo[3,4-d]pyrimidin-3-yl)ethanol to afford a solid. MS=379.0 (+ESI).

Step 6. 3-(2,2-Difluoroethyl)-4-methoxy-6-methyl-1-(1-(4-(trifluoromethyl)phenyl)ethyl)-1H-pyrazolo[3,4-d]pyrimidine The title compound was prepared using procedures similar to those described in step 2 of Examples 161 and 162 using 2-(4-methoxy-6-methyl-1-(1-(4-(trifluoromethyl)phenyl)ethyl)-1H-pyrazolo[3,4-d]pyrimidin-3-yl)acetaldehyde to afford a solid. MS=401.1 (+ESI).

Step 7. (R)- and (S)-3-(2,2-Difluoroethyl)-6-methyl-1-(1-(4-(trifluoromethyl)phenyl)ethyl)-1H-pyrazolo[3,4-d]pyrimidin-4(5H)-one The title racemic compound was prepared using procedures similar to those described in step 4 of Examples 80 and 81 using 3-(2,2-difluoroethyl)-4-methoxy-6-methyl-1-(1-(4-(trifluoromethyl)phenyl)ethyl)-1H-pyrazolo[3,4-d]pyrimidine as a solid. The enantiopure title compounds were obtained by chiral preparative HPLC (Chiralpak AD-H, 5% isopropanol in hexanes). The faster-eluting enantiomer of the title compound (Example 285) was obtained as a solid. MS=387.2 (+ESI). $^1$H NMR (400 MHz, DMSO-d$_6$): δ 12.25-12.10 (br s, 1H), 7.70 (d, J=8.4 Hz, 2H), 7.48 (d, J=8.4 Hz, 2H), 6.50 (tt, J=6.4 Hz, 4.8 Hz, 1H), 6.09 (q, J=6.8 Hz, 1H), 3.46 (td, J=16.8 Hz, 4.8 Hz, 2H), 2.35 (s, 3H), 1.85 (d, J=7.2 Hz, 3H). The slower-eluting enantiomer of the title compound (Example 286) was obtained as a solid. MS=387.2 (+ESI). $^1$H NMR (400 MHz, DMSO-d$_6$): δ 12.25-12.10 (br s, 1H), 7.70 (d, J=8.4 Hz, 2H), 7.48 (d, J=8.4 Hz, 2H), 6.50 (tt, J=6.4 Hz, 4.8 Hz, 1H), 6.09 (q, J=6.8 Hz, 1H), 3.46 (td, J=16.8 Hz, 4.8 Hz, 2H), 2.35 (s, 3H), 1.85 (d, J=7.2 Hz, 3H)

EXAMPLES 287 and 288

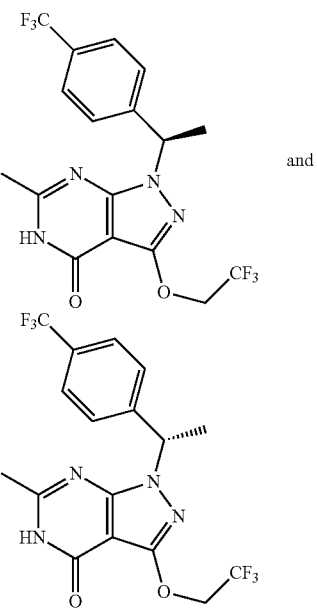

(R)- and (S)-6-Methyl-3-(2,2,2-trifluoroethoxy)-1-(1-(4-(trifluoromethyl)phenyl)ethyl)-1H-pyrazolo[3,4-d]pyrimidin-4(5H)-one (Scheme 46)

Step 1. 5-Amino-1H-pyrazole-4-carboxamide

To a stirred solution of concentrated sulfuric acid (5 mL, 94.0 mmol) at RT was added 5-amino-1H-pyrazole-4-carbonitrile (1.0 g, 9.3 mmol) portion-wise. The reaction mixture was stirred at RT for 3 h and was poured into ice/water (60 mL). The resulting solid was filtered, washed with water (3×2 mL) and dried to afford the title compound. MS=126.9 (+ESI).

Step 2. 6-Methyl-1H-pyrazolo[3,4-d]pyrimidin-4(5H)-one

To a stirred solution of polyphosphoric acid (3.0 mL) and AcOH (3.0 mL) at RT was added 5-amino-1H-pyrazole-4-carboxamide (1.2 g, 6.9 mmol). The mixture was heated to 120° C. and stirred overnight. The reaction solution was cooled to RT and diluted with water (15 mL). 50% aq. NaOH was added to the mixture to attain pH~5 and the resulting solid was filtered off. The solid was washed with water (3×2 mL) and methanol (1 mL) and dried to afford the title compound. MS=151.0 (+ESI).

Step 3. 3-Iodo-6-methyl-1H-pyrazolo[3,4-d]pyrimidin-4(5H)-one

To a suspension of 6-methyl-1H-pyrazolo[3,4-d]pyrimidin-4(5H)-one (0.40 g, 2.7 mmol) in DMF (5 mL) was added NIS (0.78 g, 3.5 mmol) at RT. The mixture was heated to 110° C., stirred for 16 h, and cooled to RT. The mixture was concentrated under reduced pressure whereupon a 5% aqueous acetic acid solution (20 mL) was added. The resulting precipitate was collected by filtration and dried to afford the title compound as a solid. MS=276.8 (+ESI).

Step 4. 3-Iodo-6-methyl-1-(1-(4-(trifluoromethyl)phenyl)ethyl)-1H-pyrazolo[3,4-d]pyrimidin-4(5H)-one To the solution of 3-iodo-6-methyl-1H-pyrazolo[3,4-d]pyrimidin-4(5H)-one (0.20 g, 0.7 mmol) in DMF (3 mL) were added 1-(1-bromoethyl)-4-(trifluoromethyl)benzene (0.22 g, 0.9 mmol) and $K_2CO_3$ (0.15 g, 1.1 mmol) at RT. The resulting mixture was stirred for 16 h and was diluted with water (10 mL) and extracted with EtOAc (3×10 mL). The combined organic layers were washed with brine (3×20 mL), dried over $Na_2SO_4$, filtered, and concentrated under vacuum. The residue was purified by silica gel column chromatography (0-30% of ethyl acetate in petroleum ether) to afford the title compound as a solid. MS=449.0 (+ESI).

Step 5. (R)- and (S)-6-Methyl-3-(2,2,2-trifluoroethoxy)-1-(1-(4-(trifluoromethyl)phenyl)ethyl)-1H-pyrazolo[3,4-d]pyrimidin-4(5H)-one To the solution of 3-iodo-6-methyl-1-(1-(4-(trifluoromethyl)phenyl)ethyl)-1H-pyrazolo[3,4-d]pyrimidin-4(5H)-one (80 mg, 0.2 mmol) in DMF (2.0 mL) in a microwave tube at RT was added 2,2,2-trifluoroethanol (0.13 mL, 1.8 mmol), $Cs_2CO_3$ (0.17 g, 0.5 mmol), and 2-(dimethylamino)acetic acid (5.5 mg, 0.05 mmol). The tube was evacuated and purged with nitrogen three times followed by the addition of copper(I) iodide (6.8 mg, 0.04 mmol) under nitrogen atmosphere. The tube was capped, then subjected to microwave radiation at 130° C. for 30 mins. The reaction mixture was cooled to RT and was diluted with brine (50 mL) and extracted with DCM (3×50 mL). The combined organic layers was dried over anhydrous $Na_2SO_4$, filtered, and concentrated under vacuum. The residue was purified by preparative HPLC (X Bridge C18, 35-65% acetonitrile in water (0.05% $NH_4HCO_3$)) to afford the racemic title compound as a solid. The enantiopure title compounds were obtained by chiral preparative HPLC (Chiralpak IA, 5% EtOH in hexanes). The faster-eluting enantiomer of the title compound (Example 287) was obtained as a solid. MS=421.1 (+ESI). $^1$H NMR (400 MHz, $CD_3OD$): δ 7.64 (d, J=8.0 Hz, 2H), 7.55 (d, J=8.4 Hz, 2H), 6.09 (q, J=7.2 Hz, 1H), 4.96-4.88 (m, 2H), 2.43 (s, 3H), 1.90 (d, J=7.2 Hz, 3H). The slower-eluting enantiomer of the title compound (Example 288) was obtained as a solid. MS=421.1 (+ESI). $^1$H NMR (400 MHz, $CD_3OD$) δ: 7.64 (d, J=8.0 Hz, 2H), 7.55 (d, J=8.4 Hz, 2H), 6.09 (q, J=7.2 Hz, 1H), 4.96-4.88 (m, 2H), 2.43 (s, 3H), 1.90 (d, J=7.2 Hz, 3H).

EXAMPLE 289

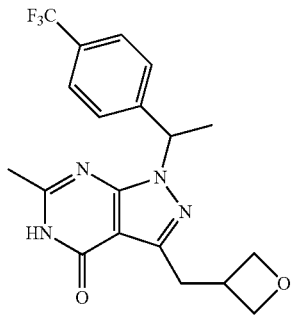 [SMILES: Cc1nc2c(c(CC3COC3)nn2C(C)c2ccc(C(F)(F)F)cc2)c(=O)[nH]1]

6-Methyl-3-(oxetan-3-ylmethyl)-1-(1-(4-(trifluoromethyl)phenyl)ethyl)-1H-pyrazolo[3,4-d]pyrimidin-4(5H)-one (Scheme 47)

Step 1. Dimethyl 2-((6-methyl-4-oxo-1-(1-(4-(trifluoromethyl)phenyl)ethyl)-4,5-dihydro-1H-pyrazolo[3,4-d]pyrimidin-3-yl)methyl)malonate To a mixture of (6-methyl-4-oxo-1-(1-(4-(trifluoromethyl)phenyl)ethyl)-4,5-dihydro-1H-pyrazolo[3,4-d]pyrimidin-3-yl)methyl methanesulfonate (0.38 g, 0.9 mmol) from Examples 262 and 263 in THF (10 mL) at 0° C. was added solid NaOH (25.4 mg, 1.1 mmol) followed by dimethyl malonate (0.15 mL, 1.3 mmol). The reaction mixture was heated to 60° C., stirred for 2 h, and was cooled to RT. The resulting mixture was quenched with water (10 mL) and extracted with EtOAc (3×10 mL). The combined organic layers were washed with water (3×10 mL) and brine (3×10 mL), dried over $Na_2SO_4$, filtered, and concentrated under vacuum. The residue was purified by silica gel column chromatography (0-60% ethyl acetate in petroleum ether) to afford the title compound as an oil. MS=467.3 (+ESI).

Step 2. 3-(3-Hydroxy-2-(hydroxymethyl)propyl)-6-methyl-1-(1-(4-(trifluoromethyl)phenyl)ethyl)-1H-pyrazolo[3,4-d]pyrimidin-4(5H)-one To a solution of dimethyl 2-((6-methyl-4-oxo-1-(1-(4-(trifluoromethyl)phenyl)ethyl)-4,5-dihydro-1H-pyrazolo[3,4-d]pyrimidin-3-yl)methyl)malonate (0.26 g, 0.6 mmol) in THF (10 mL) at 0° C. was added diisobutylaluminum hydride (0.22 mL, 3.3 mmol). The reaction mixture was stirred at 0° C. for 2 h where water (10 mL) was added followed by extraction with EtOAc (3×10 mL). The combined organic layers were washed with water (3×10 mL) and brine (3×10 mL), dried over $Na_2SO_4$, filtered, and concentrated under vacuum. The residue was purified by silica gel column chromatography (0-5% of methanol in dichloromethane) to afford the title compound as an oil. MS=411.3 (+ESI).

Step 3. 3-Hydroxy-2-((6-methyl-4-oxo-1-(1-(4-(trifluoromethyl)phenyl)ethyl)-4,5-dihydro-1H-pyrazolo[3,4-d]pyrimidin-3-yl)methyl)propyl 4-methylbenzenesulfonate To a solution of 3-(3-hydroxy-2-(hydroxymethyl)propyl)-6-methyl-1-(1-(4-(trifluoromethyl)phenyl)ethyl)-1H-pyrazolo[3,4-d]pyrimidin-4(5H)-one (70 mg, 0.2 mmol) in DCM (5 mL) at 0° C. was added p-toluenesulfonyl chloride (35.8 mg, 0.2 mmol) and pyridine (39 μL, 0.5 mmol). The reaction mixture was stirred at RT for 16 h whereupon the mixture was treated with brine (25 mL) and extracted with EtOAc (3×20 mL). The combined organic layers were washed with water (2×15 mL) and brine (2×15 mL), dried over $Na_2SO_4$, filtered, and concentrated under vacuum. The residue was purified by silica gel column chromatography (0-5% methanol in dichloromethane) to afford the title compound as an oil. MS=565.3 (+ESI).

Step 4. 6-Methyl-3-(oxetan-3-ylmethyl)-1-(1-(4-(trifluoromethyl)phenyl)ethyl)-1H-pyrazolo[3,4-d]pyrimidin-4(5H)-one)

To a solution of 3-hydroxy-2-((6-methyl-4-oxo-1-(1-(4-(trifluoromethyl)phenyl)ethyl)-4,5-dihydro-1H-pyrazolo[3,4-d]pyrimidin-3-yl)methyl)propyl 4-methylbenzenesulfonate (40 mg, 0.1 mmol) in DMF (5 mL) at 0° C. was added NaH (5.1 mg, 0.2 mmol). The mixture was heated to 60° C., stirred for 30 min, and was cooled to RT. The reaction mixture was then quenched with brine (10 mL) and extracted with EtOAc (2×10 mL). The combined organic layers were washed with water (1×10 mL), dried over $Na_2SO_4$, filtered, and concentrated under vacuum. The residue was purified by preparative HPLC (Xbridge C18, 38-42% acetonitrile in water (0.05% TFA)) to afford the title compound (Example 289) as a liquid. MS=393.2 (+ESI); $^1$H NMR (300 MHz, CDCl$_3$) δ: 7.60-7.52 (m, 4H), 6.20 (q, J=6.9 Hz, 1H), 5.53 (br, 1H), 4.90-4.84 (m, 1H), 4.65-4.45 (m, 1H), 3.85-3.79 (m, 1H), 3.75-3.68 (m, 1H), 3.30-3.17 (m, 1H), 3.10-2.95 (m, 1H), 2.71 (s, 3H), 2.55-2.50 (m, 1H), 2.00-1.92 (m, 3H).

EXAMPLES 290 and 291

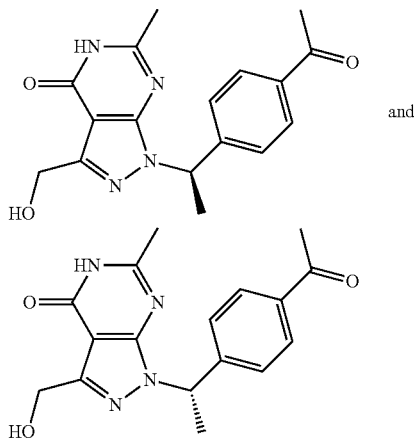

(R)- and (S)-1-(1-(4-Acetylphenyl)ethyl)-3-(hydroxymethyl)-6-methyl-1H-pyrazolo[3,4-d]pyrimidin-4(5H)-one (Scheme 48)

Step 1. 1-(4-(1-(5-(Benzyloxymethyl)-4-methoxy-2-methyl-7H-pyrrolo[3,4-d]pyrimidin-7-yl)ethyl)phenyl)ethanone The title compound was prepared using procedures similar to those described in step 5 of Examples 76 and 77 using 1-(4-(1-hydroxyethyl)phenyl)ethanone (*Tetrahedron Lett.* 1980, 21, 831-834) and 3-(benzyloxymethyl)-4-methoxy-6-methyl-1H-pyrazolo[3,4-d]pyrimidine to afford an oil. MS=431.1 (+ESI).

Step 2. 1-(1-(4-Acetylphenyl)ethyl)-3-(benzyloxymethyl)-6-methyl-1H-pyrazolo[3,4-d]pyrimidin-4(5H)-one The title compound was prepared using procedures similar to those described in step 4 of Examples 80 and 81 using 1-(4-(1-(5-(benzyloxymethyl)-4-methoxy-2-methyl-7H-pyrrolo[3,4-d]pyrimidin-7-yl)ethyl)phenyl)ethanone to afford a solid which was used in the next step without purification. MS=417.0 (+ESI).

Step 3. (R)- and (S)-1-(1-(4-Acetylphenyl)ethyl)-3-(hydroxymethyl)-6-methyl-1H-pyrazolo[3,4-d]pyrimidin-4(5H)-one The racemic title compound was prepared using procedures similar to those described in step 2 of Example 3 using 1-(1-(4-acetylphenyl)ethyl)-3-(benzyloxymethyl)-6-methyl-1H-pyrazolo[3,4-d]-pyrimidin-4(5H)-one and BBr$_3$ to afford a solid. The enantiopure title compounds were obtained by chiral preparative HPLC (Chiralpak IC, 30% EtOH in hexanes). The faster-eluting enantiomer of the title compound (Example 290) was obtained as a solid. MS=327.0 (+ESI). $^1$H NMR (400 MHz, CDCl$_3$) δ: 11.54 (br s, 1H), 7.90 (d, J=8.0 Hz, 2H), 7.46 (d, J=8.4 Hz, 2H), 6.07 (q, J=7.2 Hz, 1H), 4.90 (s, 2H), 2.57 (s, 3H), 2.55 (s, 3H), 1.95 (d, J=7.2 Hz, 3H). The slower-eluting enantiomer of the title compound (Example 291) was obtained as a solid. MS=327.0 (+ESI). $^1$H NMR (400 MHz, CDCl$_3$) δ: 11.54 (br s, 1H), 7.90 (d, J=8.0 Hz, 2H), 7.46 (d, J=8.4 Hz, 2H), 6.07 (q, J=7.2 Hz, 1H), 4.90 (s, 2H), 2.57 (s, 3H), 2.55 (s, 3H), 1.95 (d, J=7.2 Hz, 3H).

EXAMPLES 292 and 293

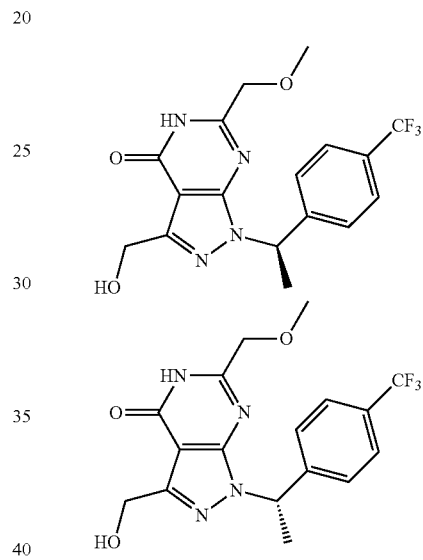

(R)- and (S)-3-(Hydroxymethyl)-6-(methoxymethyl)-1-(1-(4-(trifluoromethyl)phenyl)ethyl)-1H-pyrazolo[3,4-d]pyrimidin-4(5H)-one (Scheme 17)

Step 1. 3-((Benzyloxy)methyl)-6-(methoxymethyl)-1-(1-(4-(trifluoromethyl)phenyl)ethyl)-1H-pyrazolo[3,4-d]pyrimidin-4(5H)-one To a solution of 5-amino-3-((benzyloxy)methyl)-1-(1-(4-(trifluoromethyl)phenyl)ethyl)-1H-pyrazole-4-carboxamide (500 mg, 1.20 mmol) in dioxane (5 mL) at RT under N$_2$ added methoxyacetyl chloride (0.131 mL, 1.43 mmol). The reaction mixture was heated to 100° C., stirred for 12 h, and was cooled to RT. The reaction mixture was concentrated under reduced pressure and the resultant reside was purified by silica gel column chromatography (0-10% MeOH in DCM) to afford the title compound as a clear oil. MS=473.2 (M+H)$^+$.

Step 2. (R)- and (S)-3-(Hydroxymethyl)-6-(methoxymethyl)-1-(1-(4-(trifluoromethyl)phenyl) ethyl)-1H-pyrazolo[3,4-d]pyrimidin-4(5H)-one To a solution of 3-((benzyloxy)methyl)-6-(methoxymethyl)-1-(1-(4-(trifluoromethyl)phenyl)ethyl)-1H-pyrazolo

[3,4-d]pyrimidin-4(5H)-one (92 mg, 0.20 mmol) in MeOH (2 mL) under N$_2$ at RT added 20% Pd(OH)$_2$ (41 mg, 0.058 mmol) in one portion. The flask was evacuated, filled with H$_2$, and the mixture was stirred under a H$_2$ balloon for 2 h. The mixture purged to N$_2$ and filtered through a Celite™ pad washing the pad with MeOH (3×10 mL). The filtrate was concentrated under reduced pressure and the resulting residue was purified by reverse-phase chromatography (SureFire C18 column, 30-90% CH$_3$CN in H$_2$O (0.05% TFA)) to afford the racemic title compound. The enantiopure title compounds were obtained by chiral SFC chromatography (IC, 45% IPA (0.2% DEA/CO$_2$)). The faster eluting enantiomer of the title compound (Example 292) was isolated as a white solid. $^1$H NMR (CDCl$_3$, 500 MHz) δ: 7.60 (d, J=7.5 Hz, 2H), 7.51 (d, J=7.5 Hz, 2H), 6.01 (m, 1H), 4.91 (s, 2H), 4.48 (s, 2H), 3.62 (s, 3H), 1.99 (d, J=7.0 Hz, 3H). MS=382.9 (M+H)$^+$. The slower eluting enantiomer of the title compound (Example 293) was isolated as a white solid. $^1$H NMR (CDCl$_3$, 500 MHz) δ: 7.60 (d, J=7.5 Hz, 2H), 7.51 (d, J=7.5 Hz, 2H), 6.01 (m, 1H), 4.91 (s, 2H), 4.48 (s, 2H), 3.62 (s, 3H), 1.99 (d, J=7.0 Hz, 3H). MS=382.9 (M+H)$^+$.

TABLE 27

The following racemic compounds were prepared using procedures similar to those described in Examples 292 and 293 using the appropriate starting materials.

| Ex # | Structure | IUPAC Name | Exact Mass [M + H]+ |
|---|---|---|---|
| 294 | 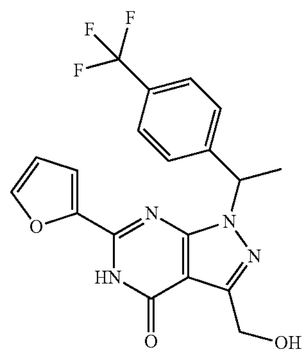 [SMILES: CC(c1ccc(C(F)(F)F)cc1)n1nc(CO)c2c(=O)[nH]c(-c3ccco3)nc21] | 6-Furan-2-yl-3-(hydroxymethyl)-1-{1-[4-(trifluoromethyl)phenyl]ethyl}-1,5-dihydro-4H-pyrazolo[3,4-d]pyrimidin-4-one | Calc'd 405.1, found 404.9 |
| 295 | 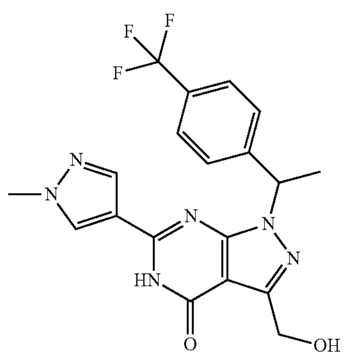 [SMILES: CC(c1ccc(C(F)(F)F)cc1)n1nc(CO)c2c(=O)[nH]c(-c3cnn(C)c3)nc21] | 3-(Hydroxymethyl)-6-(1-methyl-1H-pyrazol-4-yl)-1-{1-[4-(trifluoromethyl)phenyl]ethyl}-1,5-dihydro-4H-pyrazolo[3,4-d]pyrimidin-4-one | Calc'd 419.1, found 418.9 |
| 296 | 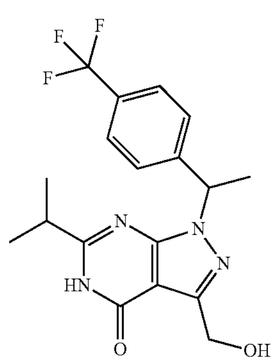 [SMILES: CC(C)c1nc2c(c(CO)nn2C(C)c2ccc(C(F)(F)F)cc2)c(=O)[nH]1] | 3-(Hydroxymethyl)-6-(1-methylethyl)-1-{1-[4-(trifluoromethyl)phenyl]ethyl}-1,5-dihydro-4H-pyrazolo[3,4-d]pyrimidin-4-one | Calc'd 381.2, found 381.0 |

TABLE 27-continued

The following racemic compounds were prepared using procedures similar to those described in Examples 292 and 293 using the appropriate starting materials.

| Ex # | Structure | IUPAC Name | Exact Mass [M + H]+ |
|---|---|---|---|
| 297 | 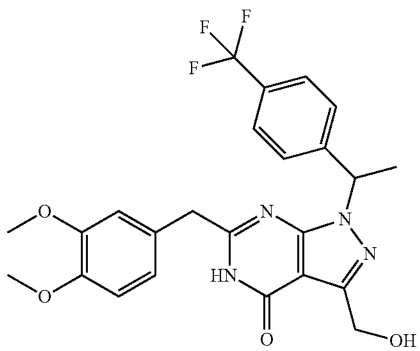 [SMILES: COc1ccc(Cc2nc3c(c(CO)nn3C(C)c3ccc(C(F)(F)F)cc3)c(=O)[nH]2)cc1OC] | 6-(3,4-Dimethoxybenzyl)-3-(hydroxymethyl)-1-{1-[4-(trifluoromethyl)phenyl]ethyl}-1,5-dihydro-4H-pyrazolo[3,4-d]pyrimidin-4-one | Calc'd 489.2, found 489.1 |
| 298 | 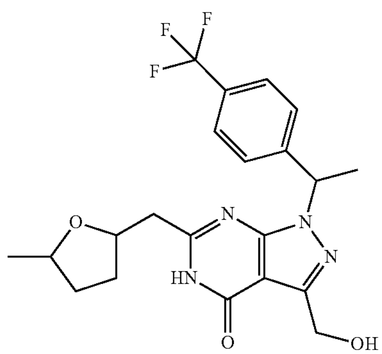 [SMILES: CC1CCC(Cc2nc3c(c(CO)nn3C(C)c3ccc(C(F)(F)F)cc3)c(=O)[nH]2)O1] | 3-(Hydroxymethyl)-6-[(5-methyltetrahydrofuran-2-yl)methyl]-1-{1-[4-(trifluoromethyl)phenyl]ethyl}-1,5-dihydro-4H-pyrazolo[3,4-d]pyrimidin-4-one | Calc'd 437.2, found: 437.0 |

TABLE 28

The following compounds were prepared using procedures similar to those described in Examples 292 and 293 using the appropriate starting materials. Racemic products were separated SFC using the chiral columns specified in the table. For those pairs of enantiomers, the faster-eluting isomer is listed first in this table.

| Ex # | Structure | IUPAC Name | Exact Mass [M + H]+ | Chiral column |
|---|---|---|---|---|
| 299 | 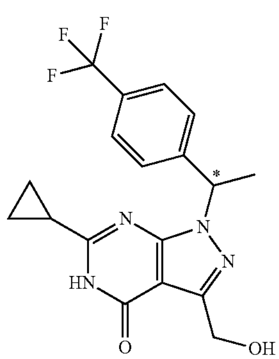 [SMILES: CC(c1ccc(C(F)(F)F)cc1)n1nc(CO)c2c(=O)[nH]c(C3CC3)nc21] | (R)- or (S)-6-Cyclopropyl-3-(hydroxymethyl)-1-{1-[4-(trifluoromethyl)phenyl]ethyl}-1,5-dihydro-4H-pyrazolo[3,4-d]pyrimidin-4-one | Calc'd 379.1, found 378.9 | OJ-H |

TABLE 28-continued

The following compounds were prepared using procedures similar to those described in Examples 292 and 293 using the appropriate starting materials. Racemic products were separated SFC using the chiral columns specified in the table. For those pairs of enantiomers, the faster-eluting isomer is listed first in this table.

| Ex # | Structure | IUPAC Name | Exact Mass [M + H]+ | Chiral column |
|---|---|---|---|---|
| 300 | 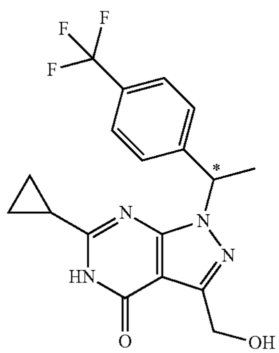 [SMILES: CC(c1ccc(C(F)(F)F)cc1)n1nc(CO)c2c(=O)[nH]c(C3CC3)nc21] | (S)- or (R)-6-Cyclopropyl-3-(hydroxymethyl)-1-{1-[4-(trifluoromethyl)phenyl]ethyl}-1,5-dihydro-4H-pyrazolo[3,4-d]pyrimidin-4-one | Calc'd 379.1, found 378.9 | OJ-H |
| 301 | 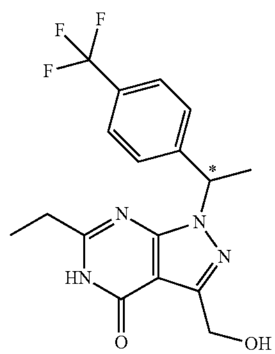 [SMILES: CCc1nc2c(c(CO)nn2C(C)c2ccc(C(F)(F)F)cc2)c(=O)[nH]1] | (R)- or (S)-6-Ethyl-3-(hydroxymethyl)-1-{1-[4-(trifluoromethyl)phenyl]ethyl}-1,5-dihydro-4H-pyrazolo[3,4-d]pyrimidin-4-one | Calc'd 367.1, found 366.97 | OJ |
| 302 | 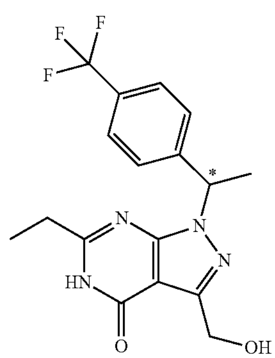 [SMILES: CCc1nc2c(c(CO)nn2C(C)c2ccc(C(F)(F)F)cc2)c(=O)[nH]1] | (S)- or (R)-6-Ethyl-3-(hydroxymethyl)-1-{1-[4-(trifluoromethyl)phenyl]ethyl}-1,5-dihydro-4H-pyrazolo[3,4-d]pyrimidin-4-one | Calc'd 367.1, found 366.97 | OJ |
| 303 | 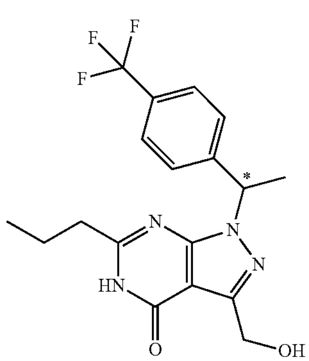 [SMILES: CCCc1nc2c(c(CO)nn2C(C)c2ccc(C(F)(F)F)cc2)c(=O)[nH]1] | (R)- or (S)-3-(Hydroxymethyl)-6-propyl-1-(1-(4-(trifluoromethyl)phenyl)ethyl)-1,5-dihydro-4H-pyrazolo[3,4-d]pyrimidin-4-one | Calc'd 381.2, found 380.9 | OJ-H |

TABLE 28-continued

The following compounds were prepared using procedures similar to those described in Examples 292 and 293 using the appropriate starting materials. Racemic products were separated SFC using the chiral columns specified in the table. For those pairs of enantiomers, the faster-eluting isomer is listed first in this table.

| Ex # | Structure | IUPAC Name | Exact Mass [M + H]+ | Chiral column |
|---|---|---|---|---|
| 304 | 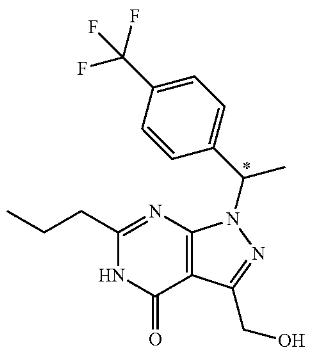 [SMILES: CCCc1nc2c(c(CO)nn2C(C)c2ccc(C(F)(F)F)cc2)c(=O)[nH]1] | (S)- or (R)-3-(Hydroxymethyl)-6-propyl-1-(1-(4-(trifluoromethyl)phenyl)ethyl)-1,5-dihydro-4H-pyrazolo[3,4-d]pyrimidin-4-one | Calc'd 381.2, found 380.9 | OJ-H |
| 305 | 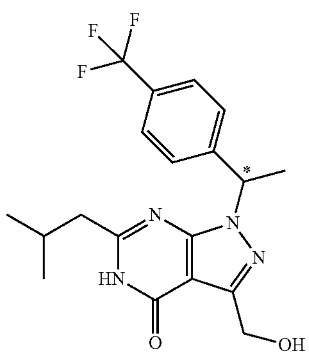 [SMILES: CC(C)Cc1nc2c(c(CO)nn2C(C)c2ccc(C(F)(F)F)cc2)c(=O)[nH]1] | (R)- or (S)-3-(Hydroxy-methyl)-6-isobutyl-1-(1-(4-(trifluoromethyl)phenyl)ethyl)-1,5-dihydro-4H-pyrazolo-[3,4-d]pyrimidin-4-one | Calc'd 395.2, found 394.9 | OJ-H |
| 306 | 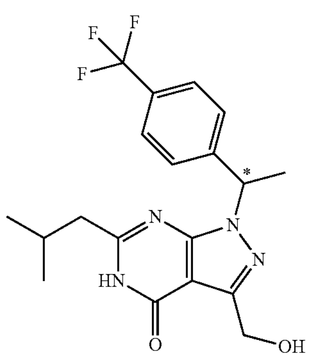 [SMILES: CC(C)Cc1nc2c(c(CO)nn2C(C)c2ccc(C(F)(F)F)cc2)c(=O)[nH]1] | (S)- or (R)-3-(Hydroxy-methyl)-6-isobutyl-1-(1-(4-(trifluoromethyl)phenyl)ethyl)-1,5-dihydro-4H-pyrazolo[3,4-d]pyrimidin-4-one | Calc'd 395.2, found 394.9 | OJ-H |
| 307 | 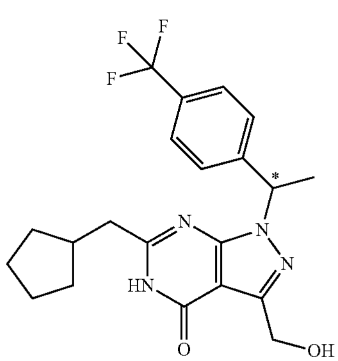 [SMILES: CC(c1ccc(C(F)(F)F)cc1)n1nc(CO)c2c(=O)[nH]c(CC3CCCC3)nc21] | (R)- or (S)-6-(Cyclopentyl-methyl)-3-(hydroxymethyl)-1-(1-(4-(trifluoromethyl)-phenyl)ethyl)-1,5-dihydro-4H-pyrazolo[3,4-d]pyrimidin-4-one | Calc'd 421.2, found 420.9 | OJ-H |

TABLE 28-continued

The following compounds were prepared using procedures similar to those described in Examples 292 and 293 using the appropriate starting materials. Racemic products were separated SFC using the chiral columns specified in the table. For those pairs of enantiomers, the faster-eluting isomer is listed first in this table.

| Ex # | Structure | IUPAC Name | Exact Mass [M + H]+ | Chiral column |
|---|---|---|---|---|
| 308 | 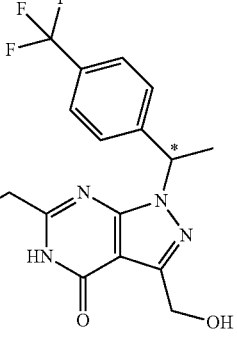 | (S)- or (R)-6-(Cyclopentyl-methyl)-3-(hydroxymethyl)-1-(1-(4-(trifluoromethyl)phenyl)ethyl)-1,5-dihydro-4H-pyrazolo[3,4-d]pyrimidin-4-one | Calc'd 421.2, found 420.9 | OJ-H |
| 309 | 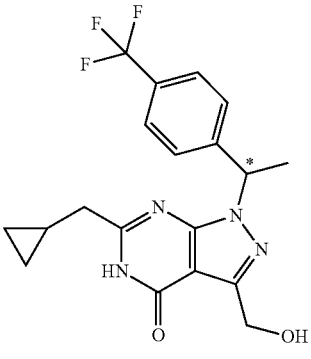 [SMILES: CC(c1ccc(C(F)(F)F)cc1)n1nc(CO)c2c(=O)[nH]c(CC3CC3)nc21] | (R)- or (S)-6-(Cyclopropyl-methyl)-3-(hydroxymethyl)-1-(1-(4-(trifluoromethyl)phenyl)ethyl)-1,5-dihydro-4H-pyrazolo[3,4-d]pyrimidin-4-one | Calc'd 393.2, found 392.9 | AD-H |
| 310 | 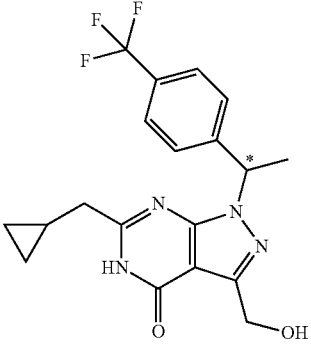 [SMILES: CC(c1ccc(C(F)(F)F)cc1)n1nc(CO)c2c(=O)[nH]c(CC3CC3)nc21] | (S)- or (R)-6-(Cyclopropyl-methyl)-3-(hydroxymethyl)-1-(1-(4-(trifluoromethyl)phenyl)ethyl)-1,5-dihydro-4H-pyrazolo[3,4-d]pyrimidin-4-one | Calc'd 393.2, found 392.9 | AD-H |
| 311 | 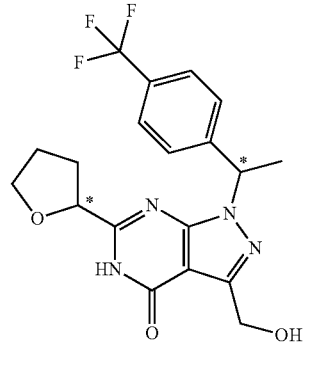 [SMILES: CC(c1ccc(C(F)(F)F)cc1)n1nc(CO)c2c(=O)[nH]c(C3CCCO3)nc21] | (R,R)- or (S,S)- or (R,S)- or (S,R)-3-(Hydroxymethyl)-6-(tetrahydrofuran-2-yl)-1-(1-(4-(trifluoromethyl)-phenyl)ethyl)-1,5-dihydro-4H-pyrazolo[3,4-d]pyrimidin-4-one | Calc'd 409.1, found: 409.2 | IA |

TABLE 28-continued

The following compounds were prepared using procedures similar to those described in Examples 292 and 293 using the appropriate starting materials. Racemic products were separated SFC using the chiral columns specified in the table. For those pairs of enantiomers, the faster-eluting isomer is listed first in this table.

| Ex # | Structure | IUPAC Name | Exact Mass [M + H]+ | Chiral column |
|---|---|---|---|---|
| 312 | 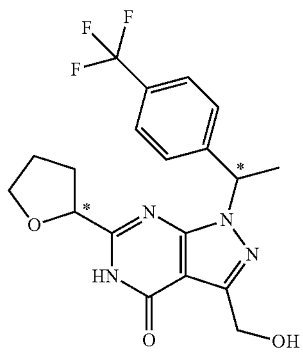 [SMILES: CC(c1ccc(C(F)(F)F)cc1)n1nc(CO)c2c(=O)[nH]c(C3CCCO3)nc21] | (S,S)- or (R,S)- or (S,R)- or (R,R)-3-(Hydroxymethyl)-6-(tetrahydrofuran-2-yl)-1-(1-(4-(trifluoromethyl)-phenyl)ethyl)-1,5-dihydro-4H-pyrazolo[3,4-d]pyrimidin-4-one | Calc'd 409.1, found: 409.2 | IA |
| 313 | 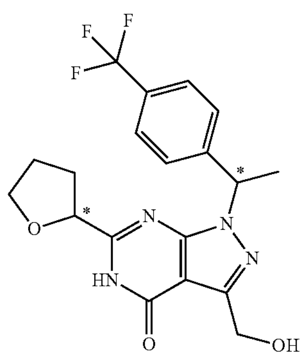 [SMILES: CC(c1ccc(C(F)(F)F)cc1)n1nc(CO)c2c(=O)[nH]c(C3CCCO3)nc21] | (R,S)- or (S,R)- or (R,R)- or (S,S)-3-(Hydroxymethyl)-6-(tetrahydrofuran-2-yl)-1-(1-(4-(trifluoromethyl)-phenyl)ethyl)-1,5-dihydro-4H-pyrazolo[3,4-d]pyrimidin-4-one | Calc'd 409.1, found: 409.2 | IA |
| 314 | 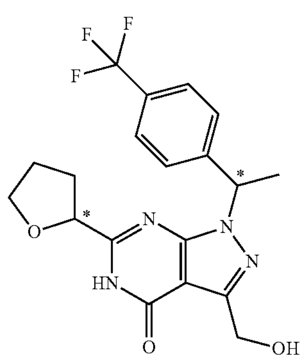 [SMILES: CC(c1ccc(C(F)(F)F)cc1)n1nc(CO)c2c(=O)[nH]c(C3CCCO3)nc21] | (S,R)- or (R,R)- or (S,S)- or (R,S)-3-(Hydroxymethyl)-6-(tetrahydrofuran-2-yl)-1-(1-(4-(trifluoromethyl)-phenyl)ethyl)-1,5-dihydro-4H-pyrazolo[3,4-d]pyrimidin-4-one | Calc'd 409.1, found: 408.9 | IA |
| 315 | 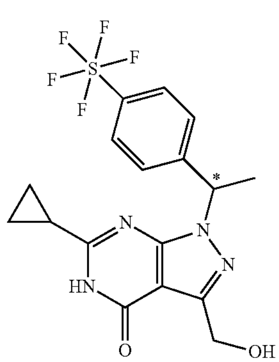 [SMILES: CC(c1ccc(S(F)(F)(F)(F)F)cc1)n1nc(CO)c2c(=O)[nH]c(C3CC3)nc21] | (R)- or (S)-6-Cyclopropyl-3-(hydroxymethyl)-1-{1-[4-(pentafluoro-sulfanyl)-phenyl]-ethyl}-1,5-dihydro-4H-pyrazolo[3,4-d]pyrimidin-4-one | Calc'd 437.1, found 436.9 | AS |

TABLE 28-continued

The following compounds were prepared using procedures similar to those described in Examples 292 and 293 using the appropriate starting materials. Racemic products were separated SFC using the chiral columns specified in the table. For those pairs of enantiomers, the faster-eluting isomer is listed first in this table.

| Ex # | Structure | IUPAC Name | Exact Mass [M + H]+ | Chiral column |
|---|---|---|---|---|
| 316 | 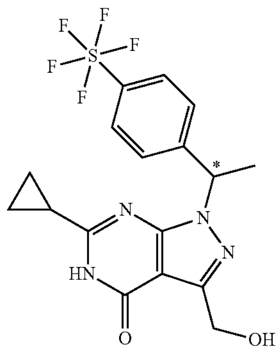 [SMILES: CC(c1ccc(S(F)(F)(F)(F)F)cc1)n1nc(CO)c2c(=O)[nH]c(C3CC3)nc21] | (S)- or (R)-6-Cyclopropyl-3-(hydroxymethyl)-1-{1-[4-(pentafluoro-sulfanyl)-phenyl]ethyl}-1,5-dihydro-4H-pyrazolo[3,4-d]pyrimidin-4-one | Calc'd 437.1, found 436.9 | AS |
| 317 | 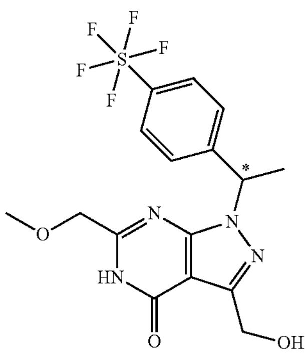 [SMILES: COCc1nc2c(c(CO)nn2C(C)c2ccc(S(F)(F)(F)(F)F)cc2)c(=O)[nH]1] | (R)- or (S)-3-(Hydroxy-methyl)-6-(methoxy-methyl)-1-{1-[4-(pentafluoro-sulfanyl)-phenyl]ethyl}-1,5-dihydro-4H-pyrazolo[3,4-d]pyrimidin-4-one | Calc'd 441.1, found 440.8 | AS |
| 318 | 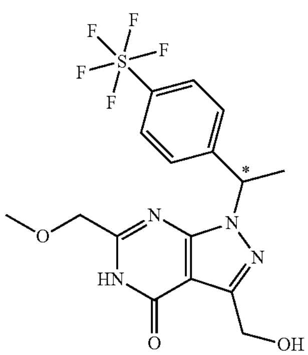 [SMILES: COCc1nc2c(c(CO)nn2C(C)c2ccc(S(F)(F)(F)(F)F)cc2)c(=O)[nH]1] | (S)- or (R)-3-(Hydroxymethyl)-6-(methoxymethyl)-1-{1-[4-(pentafluorosulfanyl)phenyl]ethyl}-1,5-dihydro-4H-pyrazolo[3,4-d]pyrimidin-4-one | Calc'd 441.1, found 440.8 | AS |

EXAMPLE 319

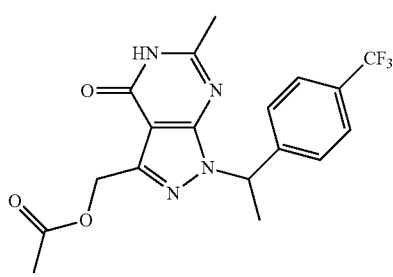 [SMILES: CC(=O)OCc1nn(C(C)c2ccc(C(F)(F)F)cc2)c2nc(C)[nH]c(=O)c12]

(6-Methyl-4-oxo-1-(1-(4-(trifluoromethyl)phenyl)ethyl)-4,5-dihydro-1H-pyrazolo[3,4-d]pyrimidin-3-yl)methyl acetate (Scheme 49)

Step 1. 5-Acetamido-3-((benzyloxy)methyl)-1-(1-(4-(trifluoromethyl)phenyl)ethyl)-1H-pyrazole-4-carboxamide To a solution of 5-amino-3-((benzyloxy)methyl)-1-(1-(4-(trifluoromethyl)phenyl)ethyl)-1H-pyrazole-4-carboxamide (1.2 g, 2.87 mmol) in dioxane (15 mL) at RT was added AcCl (0.306 ml, 4.30 mmol). The mixture was heated to 100° C., stirred for 4 h, and was recooled to RT. The reaction mixture was concentrated under reduced pressure and the resulting residue was purified by silica gel column chromatography (0-10% MeOH in $CH_2Cl_2$) to obtain the title compound as a solid. MS=461.3 $(M+H)^+$.

Step 2. 5-Acetamido-3-(hydroxymethyl)-1-(1-(4-(trifluoromethyl)phenyl)ethyl)-1H-pyrazole-4-carboxamide To a solution of 5-acetamido-3-((benzyloxy)methyl)-1-(1-(4-(trifluoromethyl)phenyl)ethyl)-1H-pyrazole-4-carboxamide (1.0 g, 2.3 mmol) in MeOH (20 mL) added 20% $Pd(OH)_2$ (0.95 g, 0.36 mmol) in one portion at RT. The reaction flask was evacuated, filled with $H_2$, and was stirred under a $H_2$ balloon for 4 h. The mixture was purged to $N_2$ and was filtered through a pad of Celite™. The pad was washed with MeOH (3×10 mL) and the resultant filtrated was concentrated under reduced pressure. The residue was purified by silica gel column chromatography (0-10% MeOH in $CH_2Cl_2$) to obtain the title compound as a solid. MS=371.2 $(M+H)^+$.

Step 3. (6-Methyl-4-oxo-1-(1-(4-(trifluoromethyl)phenyl)ethyl)-4,5-dihydro-1H-pyrazolo[3,4-d]pyrimidin-3-yl)methyl acetate To a solution of 5-acetamido-3-(hydroxymethyl)-1-(1-(4-(trifluoromethyl)phenyl)ethyl)-1H-pyrazole-4-carboxamide (150 mg, 0.41 mmol) in dioxane (1 mL) at RT was added acetyl chloride (0.3 ml, 0.41 mmol). The mixture was heated to 100° C. and was stirred for 12 h at this temperature. The mixture was cooled to RT and was concentrated under reduced pressure. The residue was purified by reverse-phase chromatography (SureFire C18 column, 30-90% $CH_3CN$ in water (0.05% TFA)) to afford the title compound (Example 319) as white solid. $^1H$ NMR ($CDCl_3$, 500 MHz) δ: 11.90 (br s, 1H), 7.61 (d, J=7.5 Hz, 2H), 7.53 (d, J=7.5 Hz, 2H), 6.10 (m, 1H), 5.41 (s, 1H), 2.56 (s, 3H), 2.19 (s, 3H), 1.99 (d, J=7.0 Hz, 3H). MS=394.9 $(M+H)^+$.

EXAMPLES 320 and 321

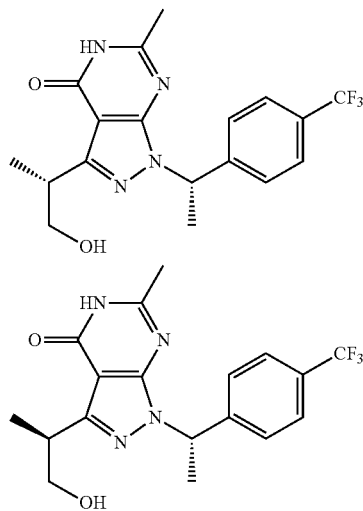

3-((R)-1-Hydroxypropan-2-yl)-6-methyl-1-((S)-1-(4-(trifluoromethyl)phenyl)ethyl)-1,5-dihydro-4H-pyrazolo[3,4-d]pyrimidin-4-one and 3-((S)-1-Hydroxypropan-2-yl)-6-methyl-1-((S)-1-(4-(trifluoromethyl)phenyl)ethyl)-1,5-dihydro-4H-pyrazolo[3,4-d]pyrimidin-4-one (Scheme 50)

Step 1. (S)-3-((Benzyloxy)methyl)-4-methoxy-6-methyl-1-(1-(4-(trifluoromethyl)phenyl)ethyl)-1H-pyrazolo[3,4-d]pyrimidine To a mixture of 3-((benzyloxy)methyl)-4-methoxy-6-methyl-1H-pyrazolo[3,4-d]pyrimidine (5.0 g, 17.6 mmol) from Preparative Example 123 in toluene (88 ml) under $N_2$ at RT was added (R)-1-(4-(trifluoromethyl)phenyl)ethanol (4.0 g, 21.1 mmol) to afford a white, heterogeneous mixture. $PPh_3$ (13.8 g, 53 mmol) was added to the mixture portionwise followed by dropwise addition of DIAD (10.3 mL, 53 mmol) over ~10 min. The resulting orange, homogenous mixture was stirred for 12 h at RT whereupon the resulting mixture was diluted with water (35 mL) and extracted with ethyl acetate (3×200 mL). The combined organic layers were washed with water (2×50 mL) and brine (3×50 mL). The organic layer was dried over $Na_2SO_4$, filtered, and concentrated under reduced pressure. The crude residue was purified by silica gel column chromatography (0-40% EtOAc in hexanes) to afford the title compound as an oil. MS=457.1 $(M+H)^+$.

Step 2. (S)-(4-Methoxy-6-methyl-1-(1-(4-(trifluoromethyl)phenyl)ethyl)-1H-pyrazolo[3,4-d]pyrimidin-3-yl)methanol To a round bottom flask charged with (S)-3-((benzyloxy)methyl)-4-methoxy-6-methyl-1-(1-(4-(trifluoromethyl)phenyl)ethyl)-1H-pyrazolo[3,4-d]pyrimidine (780 mg, 1.71 mmol) in MeOH/EtOAc (3.5 mL/3.5 mL) at RT was added 20% $Pd(OH)_2$ (0.36 g, 0.51 mmol) in a single portion. The flask was degassed under house vacuum and was filled with $N_2$ and this procedure was executed three additional times. The flask was degassed under house vacuum and was filled with $H_2$ (from a balloon) and this protocol was executed three additional times. The reaction mixture was stirred vigorously under $H_2$ for 3 h whereupon the mixture was purged with $N_2$ and was filtered through a pad of Celite™. The Celite™ pad was washed with MeOH (4×10 mL) and EtOAc (4×10 mL) and the resulting filtrate was concentrated under reduced pressure and placed under high vacuum. The crude material was purified by silica gel column chromatography (0-70% EtOAc in hexanes) to afford the title compound as a solid. MS=367.1 $(M+H)^+$.

Step 3. (S)-4-Methoxy-6-methyl-1-(1-(4-(trifluoromethyl)phenyl)ethyl)-1H-pyrazolo[3,4-d]pyrimidine-3-carbaldehyde To a solution of (S)-(4-methoxy-6-methyl-1-(1-(4-(trifluoromethyl)phenyl)ethyl)-1H-pyrazolo[3,4-d]pyrimidin-3-yl)methanol (0.52 g, 1.42 mmol) in $CH_2Cl_2$ (9.5 mL) at 0° C. was added Dess-Martin reagent (0.72 g, 1.70 mmol) to afford a homogenous mixture. The mixture was stirred at 0° C. for 3 h whereupon the mixture was diluted with $CH_2Cl_2$ (5 mL) and $Ca(OH)_2$ (~2 g) was added in one portion. The mixture was stirred for 1 h at RT whereupon the mixture was filtered through a pad of Celite™. The pad was washed with $CH_2Cl_2$ (3×15 mL) and the resulting filtrate was concentrated under reduced pressure to afford the title compound as a white solid. MS=365.1 (M+H)+.

Step 4. 1-(4-Methoxy-6-methyl-1-((S)-1-(4-(trifluoromethyl)phenyl)ethyl)-1H-pyrazolo[3,4-d]pyrimidin-3-yl)ethan-1-ol To a mixture of (S)-4-methoxy-6-methyl-1-(1-(4-(trifluoromethyl)phenyl)ethyl)-1H-pyrazolo[3,4-d]pyrimidine-3-carbaldehyde (0.50 g, 1.4 mmol) in THF (7 mL) at 0° C. was added a 3 M solution of MeMgBr in Et$_2$O (0.55 mL, 1.65 mmol) dropwise. The resulting mixture was stirred for 2 h at 0° C. whereupon the reaction mixture was treated with sat. aq. NH$_4$Cl (2 mL) and was diluted with EtOAc (7 mL). The layers were separated and the aqueous layer was extracted with EtOAc (3×10 mL). The organic layers were combined and were washed with brine (1×7 mL). The organic layer was dried over Na$_2$SO$_4$, filtered, and concentrated under reduced pressure to afford the title compound as a semisolid which was taken onto the next step without purification. MS=381.1 (M+H)+.

Step 5. (S)-1-(4-Methoxy-6-methyl-1-(1-(4-(trifluoromethyl)phenyl)ethyl)-1H-pyrazolo[3,4-d]pyrimidin-3-yl)ethan-1-one To a solution of 1-(4-methoxy-6-methyl-1-((S)-1-(4-(trifluoromethyl)phenyl)ethyl)-1H-pyrazolo[3,4-d]pyrimidin-3-yl)ethan-1-ol (0.51 g, 1.3 mmol) in CH$_2$Cl$_2$ (9 mL) at 0° C. was added Dess-Martin reagent (0.68 g, 1.61 mmol) in one portion. The mixture was stirred at 0° C. for 4 h whereupon the reaction mixture was diluted with CH$_2$Cl$_2$ (50 mL) and solid Ca(OH)$_2$ (~2 g) was added to the mixture. The mixture was stirred for 1 h at RT whereupon the mixture was filtered through a pad of Celite™. The pad was washed with CH$_2$Cl$_2$ (3×50 mL) and the resulting filtrate was concentrated under reduced pressure to afford the title compound as a solid which was taken onto the next step without purification. MS=379.0 (M+H)+.

Step 6. (S)-4-Methoxy-6-methyl-3-(prop-1-en-2-yl)-1-(1-(4-(trifluoromethyl)phenyl)ethyl)-1H-pyrazolo[3,4-d]pyrimidine To a mixture of methyltriphenylphosphonium bromide (0.71 g, 2.0 mmol) in THF (2.4 mL) under N$_2$ at RT was added t-BuOK (0.22 g, 2.0 mmol) portion-wise. The resulting mixture was stirred for 30 min at RT whereupon the mixture was cooled to 0° C. A solution of (S)-1-(4-methoxy-6-methyl-1-(1-(4-(trifluoromethyl)phenyl)ethyl)-1H-pyrazolo[3,4-d]pyrimidin-3-yl)ethan-1-one (0.25 g, 0.66 mmol) in THF (2 mL) was added dropwise over ~5 minutes. The mixture was allowed to warm to RT and was stirred for 12 h. The mixture was diluted with water (2 mL) and EtOAc (10 mL) and the layers were separated. The aqueous layer was extracted with EtOAc (2×10 mL) and the organic layers were combined. The organic layer was washed with brine (1×7 mL), dried over Na$_2$SO$_4$, filtered, and concentrated under reduced pressure. The crude residue was purified by silica gel column chromatography (0-35% EtOAc in hexanes) to afford the title compound as a solid. MS=377.1 (M+H)+.

Step 7. 2-(4-Methoxy-6-methyl-1-((S)-1-(4-(trifluoromethyl)phenyl)ethyl)-1H-pyrazolo[3,4-d]pyrimidin-3-yl)propan-1-ol To a mixture of (S)-4-methoxy-6-methyl-3-(prop-1-en-2-yl)-1-(1-(4-(trifluoromethyl)phenyl)ethyl)-1H-pyrazolo[3,4-d]pyrimidine (0.13 g, 0.35 mmol) in THF (1.2 mL) at 0° C. was added BH$_3$-DMS (49 µL, 0.52 mmol) dropwise over 1 min. The resulting mixture was allowed to warm to RT and stir for 5 h at RT. The mixture was opened to the air and EtOAc (2 mL) was added and the mixture was cooled to 0° C. A 30% H$_2$O$_2$ solution (0.60 mL, 5.9 mmol) was added dropwise followed by addition of 3 M NaOH (0.52 mL, 1.6 mmol) to afford a slightly heterogeneous mixture. The resulting mixture was stirred for 1 h at 0° C. whereupon the mixture was diluted with EtOAc (4 mL) and the layers were separated. The aqueous layer was extracted with EtOAc (3×3 mL) and the organic layers were combined. The organic layer was washed with sat. aq. NaHCO$_3$ (1×3 mL) and brine (1×3 mL) and was dried over Na$_2$SO$_4$. The organic layer was filtered, concentrated under reduced pressure, and placed under high vacuum. The crude material was purified by silica gel column chromatography (0-55% EtOAc in hexanes) to afford the title compound as a solid. MS=395.1 (M+H)+.

Step 8. 3-((R)-1-Hydroxypropan-2-yl)-6-methyl-1-((S)-1-(4-(trifluoromethyl)phenyl)ethyl)-1,5-dihydro-4H-pyrazolo[3,4-d]pyrimidin-4-one and 3-((S)-1-Hydroxypropan-2-yl)-6-methyl-1-((S)-1-(4-(trifluoromethyl)phenyl)ethyl)-15-dihydro-4H-pyrazolo[3,4-d]pyrimidin-4-one To a round bottom flask charged with 2-(4-methoxy-6-methyl-1-((S)-1-(4-(trifluoromethyl)phenyl)ethyl)-1H-pyrazolo[3,4-d]pyrimidin-3-yl)propan-1-ol (68 mg, 0.17 mmol) and a stir bar under N$_2$ at RT was added 4 N HCl in dioxane (0.86 mL, 3.5 mmol) to afford a homogenous solution. The mixture was affixed with a reflux condenser and was heated to 80° C. The mixture was stirred for 3 h at 80° C., cooled to RT, and was concentrated under reduced pressure. The resulting semisolid was taken up in CH$_2$Cl$_2$ (3 mL) and concentrated under reduced pressure and this protocol was repeated an additional four times to afford a white semisolid. The semisolid was purified by reverse-phase chromatography (SureFire C18 column, 10-90% CH$_3$CN in water (0.05% TFA)) to afford a diastereomeric mixture of title compound. The mixture of diastereomers was separated by chiral SFC chromatography (OJ, 10% MeOH (0.2% NH$_4$OH)/CO$_2$) into the individual diastereomers of the title compound. The faster-eluting diastereomer of the title compound (Example 320) was isolated as a solid. $^1$H NMR (CDCl$_3$, 500 MHz) δ: 7.60 (d, J=8.3 Hz, 2H), 7.50 (d, J=8.3 Hz, 2H), 6.10 (q, J=7.1 Hz, 1H), 3.99 (dd, J=7.2, 10.7 Hz, 1H), 3.80 (dd, J=6.7, 10.7 Hz, 1H), 3.32 (m, 1H), 2.42 (s, 3H), 1.94 (d, J=7.2 Hz, 3H), 1.38 (d, J=7.2 Hz, 3H). MS=381.1 (M+H)+. The slower-eluting diastereomer of the title compound (Example 321) was isolated as a solid. $^1$H NMR (CDCl$_3$, 500 MHz) δ: 7.60 (d, J=8.3 Hz, 2H), 7.50 (d, J=8.3 Hz, 2H), 6.10 (q, J=7.1 Hz, 1H), 3.99 (dd, J=7.2, 10.7 Hz, 1H), 3.80 (dd, J=6.7, 10.7 Hz, 1H), 3.32 (m, 1H), 2.42 (s, 3H), 1.94 (d, J=7.2 Hz, 3H), 1.38 (d, J=7.2 Hz, 3H). MS=381.1 (M+H)+.

EXAMPLE 322

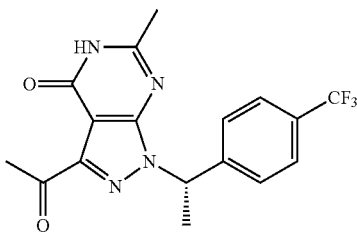 [SMILES: CC(=O)c1nn([C@@H](C)c2ccc(C(F)(F)F)cc2)c2nc(C)[nH]c(=O)c12]

(S)-3-Acetyl-6-methyl-1-(1-(4-(trifluoromethyl)phenyl)ethyl)-1,5-dihydro-4H-pyrazolo[3,4-d]pyrimidin-4-one (Scheme 51)

To a round bottom flask charged with (S)-1-(4-methoxy-6-methyl-1-(1-(4-(trifluoromethyl)phenyl)ethyl)-1H-pyrazolo[3,4-d]pyrimidin-3-yl)ethan-1-one (0.10 g, 0.26 mmol) from step 5 of Examples 320 and 321 and a stir bar at RT was added 4 M HCl in dioxane (1.3 mL, 5.3 mmol). The resulting mixture was heated to 80° C. in an oil bath and the mixture was stirred for 3 h at 80° C. The mixture was cooled to RT, concentrated under reduced pressure, and placed under high vacuum. The resulting semisolid was suspended in $CH_2Cl_2$ (3 mL) and the mixture was concentrated under reduced pressure. The crude residue was purified by silica gel column chromatography (0-100% EtOAc in hexanes) to afford the title compound (Example 322) as a solid. $^1$H NMR (CDCl$_3$, 500 MHz) δ: 11.81 (br s, 1H), 7.62 (d, J=8.3 Hz, 2H), 7.55 (d, J=8.3 Hz, 2H), 6.22 (q, J=7.1 Hz, 1H), 2.77 (s, 3H), 2.61 (s, 3H), 2.03 (d, J=7.1 Hz, 3H). MS=365.0 (M+H)+.

EXAMPLE 323

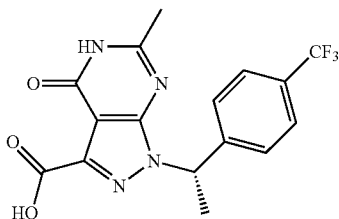 [SMILES: Cc1nc2c(c(C(=O)O)nn2[C@@H](C)c2ccc(C(F)(F)F)cc2)c(=O)[nH]1]

(S)-6-Methyl-4-oxo-1-(1-(4-(trifluoromethyl)phenyl)ethyl)-4,5-dihydro-1H-pyrazolo[3,4-d]pyrimidine-3-carboxylic acid (Scheme 52)

Step 1. (S)-6-Methyl-4-oxo-1-(1-(4-(trifluoromethyl)phenyl)ethyl)-4,5-dihydro-1H-pyrazolo[3,4-d]pyrimidine-3-carbaldehyde To a solution of (S)-3-(hydroxymethyl)-6-methyl-1-(1-(4-(trifluoromethyl)phenyl)ethyl)-1H-pyrazolo[3,4-d]pyrimidin-4(5H)-one (0.20 g, 0.57 mmol) in $CH_2Cl_2$ (5 mL) under $N_2$ was added Dess-Martin periodinane (0.72 g, 1.70 mmol) in one portion. The mixture was stirred at RT for 2 h whereupon the mixture was diluted with water (30 mE) and extracted with $CH_2Cl_2$ (3×50 mL). The organic layers were combined, dried over $Na_2SO_4$, filtered, and concentrated under reduced pressure. The residue was purified by silica gel column chromatography (0-100% EtOAc in hexanes) to obtain the title compound as a solid. MS=351.1 (M+H)+.

Step 2. (S)-6-Methyl-4-oxo-1-(1-(4-(trifluoromethyl)phenyl)ethyl)-4,5-dihydro-1H-pyrazolo[3,4-d]pyrimidine-3-carboxylic acid To a solution of (S)-6-methyl-4-oxo-1-(1-(4-(trifluoromethyl)phenyl)ethyl)-4,5-dihydro-1H-pyrazolo[3,4-d]pyrimidine-3-carbaldehyde (100 mg, 0.29 mmol) in $CH_2Cl_2$ (1.5 mL) at RT and EtOH (3 mL) added a solution of $AgNO_3$ (176 mg, 1.14 mmol) in water (2 mL). A 1M solution of NaOH (1.14 ml, 2.28 mmol) was added dropwise to the mixture which was stirred for 3 h at RT. The mixture was diluted with water (1 mL) and 1M HCl was added until the pH range was ~3-4. The mixture was extracted with $CH_2Cl_2$ (3×30 mL) and the organic layers were combined. The organic layer was dried over $MgSO_4$, filtered, and concentrated under reduced pressure. The residue was purified by reverse-phase HPLC chromatography (SureFire C18 column, 30-90% ACN in water (0.05% TFA)) to obtain the title compound (Example 323) as a solid. $^1$H NMR (CDCl$_3$, 500 MHz) δ: 7.61 (m, 4H), 6.20 (m, 1H), 2.60 (s, 3H), 2.04 (d, J=7.0 Hz, 3H). MS=367.1 (M+H)+.

EXAMPLES 324 and 325

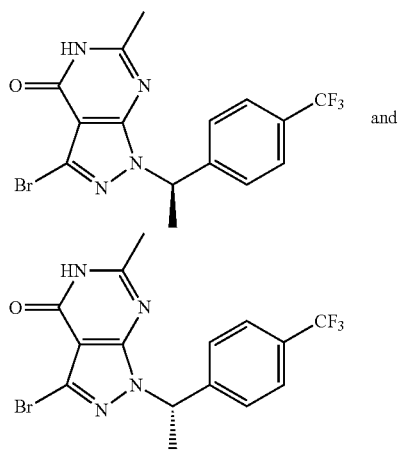

(R)- and (S)-3-Bromo-6-methyl-1-(1-(4-(trifluoromethyl)phenyl)ethyl)-1,5-dihydro-4H-pyrazolo[3,4-d]pyrimidin-4-one (Scheme 53)

To a solution of 3-bromo-6-methyl-1,5-dihydro-4H-pyrazolo[3,4-d]pyrimidin-4-one (0.20 g, 0.87 mmol) (*Tetrahedron* 1992, 48, 8089) in DMF (4.3 mL) at RT was added $Cs_2CO_3$ (0.34 g, 1.05 mmol) in one portion followed by addition of 1-(1-bromoethyl)-4-(trifluoromethyl)benzene (0.27 g, 1.05 mmol) to afford a heterogeneous mixture. The resulting mixture was stirred for 12 h at RT whereupon the mixture was diluted with EtOAc (15 mL). The organic layer was washed with water (2×3 mL) and brine (1×3 mL). The organic layer was dried over $Na_2SO_4$, filtered, and concentrated under reduced pressure. The crude oil was purified by silica gel column chromatography (0-85% EtOAc in hexanes) afford the racemic title compound as a solid. The enantiopure title compounds were obtained by chiral SFC chromatography (IC column, 15% IPA/CO$_2$). The faster-eluting enantiomer of the title compound (Example 324) was obtained as a solid. $^1$H NMR (CD$_3$OD, 500 MHz) δ: 7.64 (d, J=8.1 Hz, 2H), 7.53 (d, J=8.1 Hz, 2H), 6.13 (q, J=7.1 Hz, 1h), 4.60 (br s, 3H), 2.43 (s, 3H), 1.93 (d, J=7.2 Hz, 3H). MS=401.0/403.1 (M+H)$^+$. The slower-eluting enantiomer of the title compound (Example 325) was obtained as a solid. $^1$H NMR (CD$_3$OD, 500 MHz) δ: 7.64 (d, J=8.1 Hz, 2H), 7.53 (d, J=8.1 Hz, 2H), 6.13 (q, J=7.1 Hz, 1h), 4.60 (br s, 3H), 2.43 (s, 3H), 1.93 (d, J=7.2 Hz, 3H). MS=401.0/403.0 (M+H)$^+$.

EXAMPLE 326

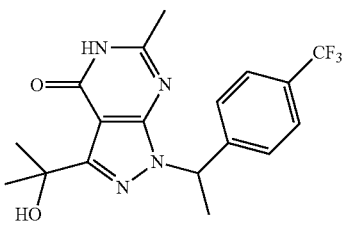 [SMILES: Cc1nc2c(c(C(C)(C)O)nn2C(C)c2ccc(C(F)(F)F)cc2)c(=O)[nH]1]

3-(1-Hydroxy-1-methylethyl)-6-methyl-1-{1-[4-(trifluoromethyl)phenyl]ethyl}-1,5-dihydro-4H-pyrazolo[3,4-d]pyrimidin-4-one (Scheme 54)

Step 1. 6-Methyl-4-oxo-1-{1-[4-(trifluoromethyl)phenyl]ethyl}-4,5-dihydro-1H-pyrazolo[3,4-d]pyrimidine-3-carboxylic acid To a solution of 6-methyl-4-oxo-1-(1-(4-(trifluoromethyl)phenyl)ethyl)-4,5-dihydro-1H-pyrazolo[3,4-d]pyrimidine-3-carbaldehyde (28 mg, 0.080 mmol) from Example 226 at RT was added sodium chlorite (18 mg, 0.16 mmol), KH$_2$PO$_4$ (44 mg, 0.32 mmol), followed by dropwise addition of 2-methyl-2-butene (8.5 mL, 0.80 mmol). t-BuOH (89 μL) and water (0.35 mL) were added to the mixture which was stirred for 30 min at RT whereupon it was cooled to 0° C. and treated with sat. aq. NH$_4$Cl. The resulting mixture was extracted with EtOAc (3×) and the organic layers were combined. The organic layer was washed with brine (1×), dried over Na$_2$SO$_4$, filtered, and the solvent was concentrated under reduced pressure to afford the title compound as a solid. MS=367.3 (M+H)$^+$.

Step 2. Methyl 6-methyl-4-oxo-1-(1-(4-(trifluoromethyl)phenyl)ethyl)-4,5-dihydro-1H-pyrazolo[3,4-d]pyrimidine-3-carboxylate To a solution of 6-methyl-4-oxo-1-{1-[4-(trifluoromethyl)phenyl]ethyl}-4,5-dihydro-1H-pyrazolo[3,4-d]pyrimidine-3-carboxylic acid (29 mg, 0.08 mmol) in CH$_2$Cl$_2$ (0.6 ml)/MeOH (0.20 ml) under N$_2$ was added a solution of trimethylsilyl diazomethane (2 M in THF, 0.040 ml, 0.080 mmol) dropwise and the resulting mixture was stirred for 10 min at RT. The mixture was concentrated under reduced pressure to afford the title compound as a solid which was used directly without purification. MS=381.3 (M+H)$^+$.

Step 3. 3-(1-Hydroxy-1-methylethyl)-6-methyl-1-{1-[4-(trifluoromethyl)phenyl]ethyl}-1,5-dihydro-4H-pyrazolo[3,4-d]pyrimidin-4-one To a solution of methyl 6-methyl-4-oxo-1-(1-(4-(trifluoromethyl)phenyl)ethyl)-4,5-dihydro-1H-pyrazolo[3,4-d]pyrimidine-3-carboxylate (30.4 mg, 0.08 mmol) in THF (0.27 ml) under N$_2$ at 0° C. was added a solution of MeMgBr (3 M in Et$_2$O, 67 μl, 0.20 mmol) dropwise and the resulting mixture was stirred for 10 min at 0° C. The mixture was quenched with sat. aq. NaHCO$_3$ followed by dilution with EtOAc and water. The layers were separated and the aqueous layer was extracted with EtOAc (3×) and the organic layers were combined. The organic layer was washed with brine (1×), dried over MgSO$_4$, filtered, concentrated under reduced pressure. The residue was purified by reverse-phase HPLC chromatography (0-95% MeCN/H$_2$O (0.1% TFA)) to afford the title compound (Example 326) as a solid. $^1$H NMR (500 MHz, CDCl$_3$): δ 12.16 (s, 1H); 7.57 (d, J=8.1 Hz, 2H); 7.49 (d, J=8.1 Hz, 2H); 6.04 (q, J=7.1 Hz, 1H); 5.61 (br s, 1H); 2.54 (s, 2H); 1.95 (d, J=7.1 Hz, 3H); 1.66 (d, J=7.5 Hz, 6H); MS=381.3 (M+H)$^+$.

EXAMPLE 327

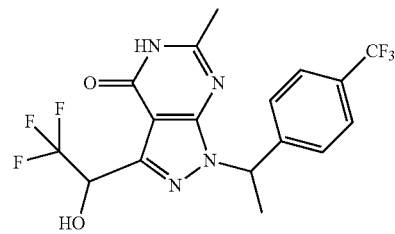 [SMILES: Cc1nc2c(c(C(O)C(F)(F)F)nn2C(C)c2ccc(C(F)(F)F)cc2)c(=O)[nH]1]

6-Methyl-3-(2,2,2-trifluoro-1-hydroxyethyl)-1-{1-[4-(trifluoromethyl)phenyl]ethyl}-1,5-dihydro-4H-pyrazolo[3,4-d]pyrimidin-4-one (Scheme 55)

To a solution of 6-methyl-4-oxo-1-(1-(4-(trifluoromethyl)phenyl)ethyl)-4,5-dihydro-1H-pyrazolo[3,4-d]pyrimidine-3-carbaldehyde (13 mg, 0.037 mmol) from Example 226 in THF (371 μl) at RT was added trimethyl(trifluoromethyl)silane (TMSCF$_3$) (89 μl, 0.045 mmol) followed by addition of a 1 M solution of TBAF in THF (1.9 μl, 1.9 μmol). The mixture was stirred for 12 h at RT whereupon an additional portion of TMSCF$_3$ (1 ml) and 1M TBAF in THF (25 uL) and the mixture was stirred for an additional 48 h. The mixture was treated with sat. aq. NaHCO$_3$ and was extracted with EtOAc (3×) combining the organic layers. The organic layer was washed with brine (1×), dried over MgSO$_4$, filtered, concentrated under reduced pressure. The residue was purified via reverse-phase HPLC chromatography (C18 column, 10-95% MeCN in H$_2$O (0.1% TFA)) to afford the title compound (Example 327) as a solid. $^1$H NMR (400 MHz, CDCl$_3$): δ 11.25 (s, 1H); 7.58 (dd, J=8.2, 3.6 Hz, 2H); 7.48 (dd, J=13.0, 8.1 Hz, 2H); 6.47 (dd, J=11.9, 7.1 Hz, 1H); 6.08-6.12 (m, 1H); 5.19-5.25 (m, 1H); 2.56 (d, J=4.3 Hz, 3H); 1.97 (d, J=7.1 Hz, 3H); MS=421.3 (M+H)$^+$.

EXAMPLE 328

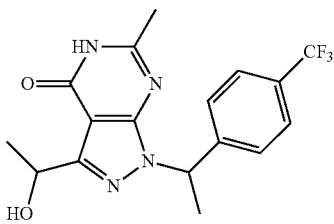 [SMILES: Cc1nc2c(c(C(C)O)nn2C(C)c2ccc(C(F)(F)F)cc2)c(=O)[nH]1]

3-(1-Hydroxyethyl)-6-methyl-1-{1-[4-(trifluoromethyl)phenyl]ethyl}-1,5-dihydro-4H-pyrazolo[3,4-d]pyrimidin-4-one (Scheme 35)

To a solution of 6-methyl-4-oxo-1-(1-(4-(trifluoromethyl)phenyl)ethyl)-4,5-dihydro-1H-pyrazolo[3,4-d]pyrimidine-3-carbaldehyde (13 mg, 0.037 mmol) from Example 248 in THF (124 μl) under $N_2$ at 0° C. was added a 3 M solution of MeMgBr in $Et_2O$ (19 μl, 0.056 mmol) dropwise. The reaction warmed to ambient temperature over 1 h. The reaction was quenched with MeOH, concentrated under reduced pressure, and the resultant residue was extracted into EtOAc. The organic layer was dried over $Na_2SO_4$, filtered, and concentrated under reduced pressure. The residue was purified by silica gel column chromatography (0-5% MeOH in $CH_2Cl_2$) to afford the title compound (Example 328) as a solid. $^1$H NMR ($CDCl_3$, 500 MHz) δ: 11.66 (br s, 1 H); 7.58 (d, J=8.3 Hz, 2 H); 7.50 (d, J=7.7 Hz, 2 H); 6.06 (d, J=7.9 Hz, 1 H); 5.12 (m, 1 H); 5.07 (m, 1 H); 2.55 (s, 3 H); 1.96 (d, J=7.0 Hz, 3 H); 1.62 (m, 3 H). MS=367.0 $(M+H)^+$.

EXAMPLE 329

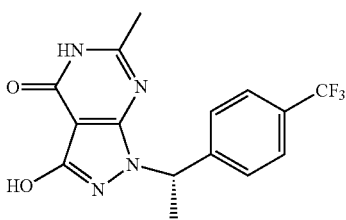 [SMILES: Cc1nc2c(c(O)nn2[C@@H](C)c2ccc(C(F)(F)F)cc2)c(=O)[nH]1]

(S)-3-Hydroxy-6-methyl-1-(1-(4-(trifluoromethyl)phenyl)ethyl)-1,5-dihydro-4H-pyrazolo[3,4-d]pyrimidin-4-one (Scheme 56)

Step 1. (S)-4-Methoxy-6-methyl-1-(1-(4-(trifluoromethyl)phenyl)ethyl)-1H-pyrazolo[3,4-d]pyrimidin-3-yl acetate To a mixture of (S)-1-(4-methoxy-6-methyl-1-(1-(4-(trifluoromethyl)phenyl)ethyl)-1H-pyrazolo[3,4-d]pyrimidin-3-yl)ethan-1-one (550 mg, 1.45 mmol) from step 5 of Examples 320 and 321 in $CH_2Cl_2$ (~3 mL) at RT under $N_2$ was added MCPBA (652 mg, 3.8 mmol) in one portion. The resulting mixture was cooled to 0° C. whereupon TFA (112 uL, 1.45 mmol) was added dropwise into the mixture and the flask was wrapped in foil. The mixture was allowed to warm to RT and stir for 12 h. The mixture was diluted with $CH_2Cl_2$ (25 ml) and was washed with 10% solution of sodium sulfite (1×7 mL), sat. aq. $K_2CO_3$ (1×7 mL), and water (1×7 mL). The organic layer was dried over $MgSO_4$, filtered, and concentrated under reduced pressure. The residue was purified by silica gel column chromatography (0-100% EtOAc in hexanes) to afford the title compound as a solid. MS=394.8. $(M+H)^+$.

Step 2. (S)-3-Hydroxy-6-methyl-1-(1-(4-(trifluoromethyl)phenyl)ethyl)-1,5-dihydro-4H-pyrazolo[3,4-d]pyrimidin-4-one To round bottom flask charged with (S)-4-methoxy-6-methyl-1-(1-(4-(trifluoromethyl)phenyl)ethyl)-1H-pyrazolo[3,4-d]pyrimidin-3-yl acetate (50 mg, 0.13 mmol) and a stir bar under $N_2$ at RT was added 4N HCl in dioxane (0.32 mL, 1.27 mmol). The mixture was heated to 80° C., stirred for 12 h, and recooled to RT. The mixture was concentrated under reduced pressure and the residue was purified by SFC chromatography (CN column, 20% MeOH(0.2% $NH_4OH$)/ $CO_2$) to afford the title compound (Example 329) as a solid. $^1$H NMR ($CD_3OD$, 500 MHz) δ: 7.65 (d, J=8.3 Hz, 2H), 7.44 (d, J=8.3 Hz, 2H), 5.66 (m, 1H), 4.59 (br s, 1H), 2.62 (s, 3H), 1.91 (d, J=6.9 Hz, 3H). MS=338.0 $(M+H)^+$.

EXAMPLE 330

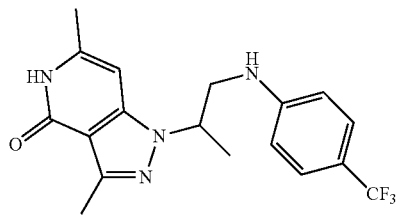 [SMILES: Cc1cc2c(c(C)nn2C(C)CNc2ccc(C(F)(F)F)cc2)c(=O)[nH]1]

3,6-Dimethyl-1-(1-(4-(trifluoromethyl)phenylamino)propan-2-yl)-1H-pyrazolo[3,4-d]pyrimidin-4(5H)-one (Scheme 57)

Step 1.
1-(4-(Trifluoromethyl)phenylamino)propan-2-one

To a solution of 4-(trifluoromethyl)benzenamine (10.0 g, 62.0 mmol) and TEA (1.72 mL, 0.124 mol) in ethanol (50 mL) at RT was added 1-bromopropan-2-one (8.40 g, 61.8 mmol). The reaction mixture was stirred for 5 h at RT and the mixture was diluted with water (100 mL) and extracted with EtOAc (3×100 mL). The combined organic layers were washed with brine (2×100 mL), dried over $Na_2SO_4$ and filtered. The filtrate was concentrated under reduced pressure and the residue was purified by silica gel column chromatography (16% ethyl acetate in petroleum ether) to afford the title compound as a solid. MS=218.0 (+ESI).

Step 2: tert-Butyl 2-(1-(4-(trifluoromethyl)phenylamino)propan-2-ylidene)hydrazinecarboxylate The title compound was prepared using procedures similar to those described in step 1 of Preparatory Example 50 using 1-(4-(trifluoromethyl)phenylamino)propan-2-one to afford a solid. MS=332.3 (+ESI).

Step 3. tert-Butyl-2-(1-(4-(trifluoromethyl)phenylamino)propan-2-yl)hydrazinecarboxylate The title compound was prepared using procedures similar to those described in step 2 of Preparatory Example 50 using tert-buty-2-(1-(4-(trifluoromethyl)phenylamino)propan-2-ylidene)hydrazinecarboxylate to afford a solid. MS=334.3 (+ESI).

Step 4. Hydrazinylpropyl)-4-(trifluoromethyl)benzenamine dihydrochloride

The title compound was prepared using procedures similar to those described in step 3 of Preparatory Example 50 using tert-butyl-2-(1-(4-(trifluoromethyl)phenylamino)propan-2-yl)hydrazinecarboxylate to afford an oil. MS=234.1 (+ESI).

Step 5. 5-Amino-3-methyl-1-(1-(4-(trifluoromethyl)phenylamino)propan-2-yl)-1H-pyrazole-4-carbonitrile The title compound was prepared using procedures similar to those described in step 4 of Preparatory Example 50 using N-(2-hydrazinylpropyl)-4-(trifluoromethyl)benzenamine dihydrochloride and 2-(1-ethoxyethylidene)malononitrile to afford a solid. MS=324.2 (+ESI).

Step 6. 5-Amino-3-methyl-1-(1-(4-(trifluoromethyl)phenylamino)propan-2-yl)-1H-pyrazole-4-carboxamide Hydrido(dimethylphosphinous acid-kP)[hydrogen bis(dimethylphosphinito-kP)]platinum(II) (85 mg, 0.2 mmol) (CAS #173416-05-2, STREM CHEMICALS) was added to a mixture of 5-amino-3-methyl-1-(1-(4-(trifluoromethyl)phenylamino)propan-2-yl)-1H-pyrazole-4-carbonitrile (0.56 g, 1.7 mmol) in THF and water (10:1, 4 mL total volume) at RT. The reaction mixture was stirred at 60° C. for 16 h and the resulting mixture was cooled to RT. The mixture was concentrated under reduced pressure to afford the title compound as a solid which was used in the next step directly without purification. MS=342.3 (+ESI).

Step 7. 3,6-Dimethyl-1-(1-(4-(trifluoromethyl)phenylamino)propan-2-yl)-1H-pyrazolo[3,4-d]pyrimidin-4(5H)-one The title compound was prepared using procedures similar to those described in step 1 of Example 1 using 5-amino-3-methyl-1-(1-(4-(trifluoromethyl)phenyl-amino)propan-2-yl)-1H-pyrazole-4-carboxamide to afford the title compound (Example 330) as a solid. MS=366.3 (+ESI). $^1$H NMR (300 MHz, CDCl$_3$) δ: 10.09 (br s, 1H), 7.35 (d, J=8.1 Hz, 2H), 6.54 (d, J=7.2 Hz, 2H), 5.11-5.02 (m, 1H), 3.70 (dd, J=8.7 Hz, 3.9 Hz, 1H), 3.52 (dd, J=13.8 Hz, 4.2 Hz, 1H), 2.57 (s, 3H), 2.42 (s, 3H), 1.59 (d, J=6.6 Hz, 3H).

EXAMPLE 331

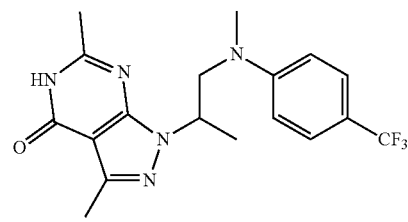 [SMILES: Cc1nc2c(c(C)nn2C(C)CN(C)c2ccc(C(F)(F)F)cc2)c(=O)[nH]1]

3,6-Dimethyl-1-(1-(methyl(4-(trifluoromethyl)phenyl)amino)propan-2-yl)-1H-pyrazolo[3,4-d]pyrimidin-4(5H)-one (Scheme 58)

To a mixture of 3,6-dimethyl-1-(1-((4-(trifluoromethyl)phenyl)amino)propan-2-yl)-1H-pyrazolo[3,4-d]pyrimidin-4(5H)-one (20 mg, 0.06 mmol) from Example 330 in methanol (1 mL) at RT was added sodium cyanoborohydride (6.88 mg, 0.1 mmol) at RT. Paraformaldehyde (8.22 mg, 0.3 mmol) was added to the mixture followed by glacial acetic acid (0.2 μL, 3.5 μmol). The reaction mixture was stirred at RT for 16 h, the solids were filtered, and the filtrate was concentrated under reduced pressure. The residue was purified by preparative HPLC (X Bridge RP C18, 30-45% ACN in water (0.1% NH$_4$HCO$_3$)) to afford the title compound (Example 331) as a solid. MS=380.3 (+ESI). $^1$H NMR (300 MHz, CDCl$_3$) δ: 10.43 (br s, 1H), 7.32 (d, J=8.7 Hz, 2H), 6.55 (d, J=8.7 Hz, 2H), 5.11 (q, J=6.9 Hz, 1H), 3.83 (dd, J=15.0 Hz, 9.0 Hz, 1H), 3.63 (dd, J=15.3 Hz, 4.8 Hz, 1H), 2.73 (s, 3H), 2.53 (s, 3H), 2.32 (s, 3H), 1.57 (d, J=6.9 Hz, 3H).

EXAMPLE 332

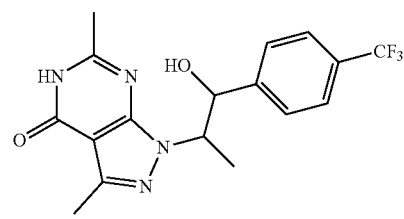 [SMILES: Cc1nc2c(c(C)nn2C(C)C(O)c2ccc(C(F)(F)F)cc2)c(=O)[nH]1]

1-(1-Hydroxy-1-(4-(trifluoromethyl)phenyl)propan-2-yl)-3,6-dimethyl-1H-pyrazolo[3,4-d]pyrimidin-4(5H)-one (Scheme 59)

Step 1. Benzyl 2-(1-tert-butoxy-1-oxopropan-2-yl)hydrazinecarboxylate

The title compound was prepared using procedures similar to those described in step 1 of Example 330 using benzyl hydrazinecarboxylate and tert-butyl 2-bromopropanoate to afford an oil. MS=295.2 (+ESI).

Step 2. tert-Butyl 2-hydrazinylpropanoate hydrochloride

A solution of benzyl 2-(1-tert-butoxy-1-oxopropan-2-yl)hydrazinecarboxylate (6.0 g, 20 mmol) in EtOAc (50 mL)

was purged with nitrogen 3 times whereupon 10% Pd on carbon (0.60 g) was added. The reaction mixture was purged with hydrogen three times and stirred under a hydrogen balloon for 16 h at RT. The resulting mixture was purged to nitrogen, filtered through a pad of Celite™, and the filtrate was concentrated under reduced pressure. The residue was dissolved in sat. HCl in EtOAc (20 mL) and the resulting solution was concentrated under reduced pressure to give the crude title compound as an oil. MS (+ESI) m/z=161.1 (+ESI).

Step 3. tert-Butyl 2-(5-amino-4-cyano-3-methyl-1H-pyrazol-1-yl)propanoate

The title compound was prepared using procedures similar to those described in step 4 of Preparatory Example 50 using tert-butyl 2-hydrazinylpropanoate hydrochloride to afford a solid. MS=251.1 (+ESI).

Step 4. tert-Butyl 2-(5-amino-4-carbamoyl-3-methyl-1H-pyrazol-1-yl)propanoate The title compound was prepared using procedures similar to those described in step 6 of Example 330 using tert-butyl 2-(5-amino-4-cyano-3-methyl-1H-pyrazol-1-yl)propanoate to afford a solid which was used in the next step directly without purification. MS=269.2 (+ESI).

Step 5. 2-(3,6-Dimethyl-4-oxo-4,5-dihydropyrazolo[3,4-d]pyrimidin-1-yl)propanoic acid The title compound was prepared using procedures similar to those described in step 1 of Example 1 using tert-butyl-2-(5-amino-4-carbamoyl-3-methyl-1H-pyrazol-1-yl)propanoate to afford a solid which was used in the next step directly without purification. MS=237.2 (+ESI).

Step 6. 2-(3,6-Dimethyl-4-oxo-4,5-dihydropyrazolo[3,4-d]pyrimidin-1-yl)-N-methoxy-N-methylpropanamide To a mixture of 2-(3,6-dimethyl-4-oxo-4,5-dihydro-1H-pyrazolo[3,4-d]pyrimidin-1-yl)propanoic acid (0.10 g, 0.4 mmol) in DMF (1 mL) was added N,O-dimethylhydroxylamine (38.8 mg, 0.635 mmol) followed by the addition of HATU (0.257 g, 0.7 mmol) and DIEA (0.164 g, 1.3 mmol). The reaction mixture was stirred for 1 h at 40° C. and the mixture was cooled to RT. The mixture was diluted with water (5 mL) and extracted with EtOAc (4×10 mL). The organic layers were combined and dried over anhydrous Na$_2$SO$_4$. The organic layer was filtered and concentrated under reduced pressure to afford the title compound as an oil which was used in the next step directly without purification. MS=280.2 (+ESI).

Step 7. 3,6-Dimethyl-1-(1-oxo-1-(4-(trifluoromethyl)phenyl)propan-2-yl)-1H-pyrazolo[3,4-d]pyrimidin-4(5H)-one The title compound was prepared using procedures similar to those described in Preparatory Example 20 using 2-(3,6-dimethyl-4-oxo-4,5-dihydropyrazolo[3,4-d]pyrimidin-1-yl)-N-methoxy-N-methylpropanamide to afford a solid. MS=365.2 (+ESI).

Step 8. 1-(1-Hydroxy-1-(4-(trifluoromethyl)phenyl)propan-2-yl)-3,6-dimethyl-1H-pyrazolo[3,4-d]pyrimidin-4(5H)-one The title compound was prepared using 3,6-dimethyl-1-(1-oxo-1-(4-(trifluoromethyl)phenyl)propan-2-yl)-1H-pyrazolo[3,4-d]pyrimidin-4(5H)-one using procedures similar to those described in Preparatory Example 82 afford the title compound (Example 332) as a solid. MS=367.1(+ESI). $^1$H NMR (300 MHz, CD$_3$OD): δ 7.68 (d, J=8.0 Hz, 2H), 7.58 (d, J=8.0 Hz, 2H), 5.09 (d, J=7.2 Hz, 1H), 5.04-4.97 (m, 1H), 2.56 (s, 3H), 2.41 (s, 3H), 1.34 (d, J=6.8 Hz, 3H).

EXAMPLE 333

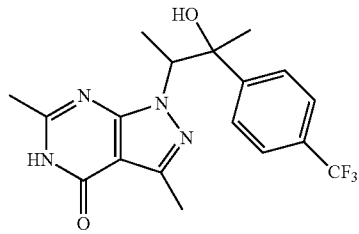 [SMILES: Cc1nc2c(c(C)nn2C(C)C(C)(O)c2ccc(C(F)(F)F)cc2)c(=O)[nH]1]

1-(3-Hydroxy-3-(4-(trifluoromethyl)phenyl)butan-2-yl)-3,6-dimethyl-1H-pyrazolo[3,4-d]pyrimidin-4(5H)-one (Scheme 60)

The title compound was prepared using procedures similar to those described in step 3 of Preparatory Example 102 using 3,6-dimethyl-1-(1-oxo-1-(4-(trifluoromethyl)phenyl)propan-2-yl)-1H-pyrazolo[3,4-d]pyrimidin-4(5H)-one prepared from step 7 of Example 332 to afford the title compound (Example 333) as a solid. MS=381.1 (+ESI). $^1$H NMR (400 MHz, CD$_3$OD) δ: 7.64 (d, J=8.4 Hz, 2H), 7.59 (d, J=8.8 Hz, 2H), 5.04 (q, J=6.8 Hz, 1H), 2.57 (s, 3H), 2.37 (s, 3H), 1.39 (s, 3H), 1.38 (d, J=6.8 Hz, 3H).

EXAMPLE 334

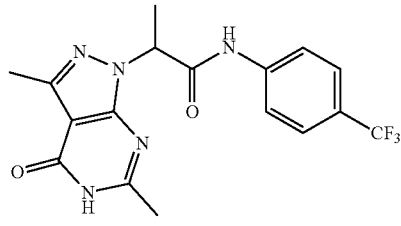 [SMILES: Cc1nc2c(c(C)nn2C(C)C(=O)Nc2ccc(C(F)(F)F)cc2)c(=O)[nH]1]

2-(3,6-Dimethyl-4-oxo-4,5-dihydropyrazolo[3,4-d]pyrimidin-1-yl)-N-(4-(trifluoromethyl)phenyl)propanamide (Scheme 61)

Step 1. tert-Butyl 2-(1-oxo-1-(4-(trifluoromethyl)phenylamino)propan-2-yl)hydrazinecarboxylate The title compound was prepared using procedures similar to those described in step 1 of Example 330 using 2-bromo-N-(4(trifluoromethyl)phenyl) propanamide (Nippon Kagaku Zasshi, 1958, 79, 889, 892; Chem. Abstr., 1960, 4430) and tert-butyl hydrazinecarboxylate to afford a solid. ¹H NMR (400 MHz, CDCl₃): δ 9.96 (br s, 1H), 7.84 (d, J=8.4 Hz, 2H), 7.58 (d, J=8.4 Hz, 2H), 6.37 (br s, 1H), 3.70-3.60 (m, 1H), 1.44 (s, 12H).

Step 2. 2-Hydrazinyl-N-(4-(trifluoromethyl)phenyl) propanamide hydrochloride

The title compound was prepared using procedures similar to those described in step 3 of Preparatory Example 50 using tert-butyl 2-(1-oxo-1-(4-(trifluoromethyl)phenylamino) propan-2-yl)hydrazinecarboxylate to afford a solid. MS=248.0 (+ESI).

Step 3. 2-(5-Amino-4-cyano-3-methyl-1H-pyrazol-1-yl)-N-(4-(trifluoromethyl)phenyl)propanamide The title compound was prepared using procedures similar to those described in step 4 of Preparatory Example 50 using 2-hydrazinyl-N-(4-(trifluoromethyl)phenyl)propanamidehydrochloride and 2-(1-ethoxyethylidene)malononitrile to afford a solid. MS=338.1 (+ESI).

Step 4. 5-Amino-3-methyl-1-(1-oxo-1-(4-(trifluoromethyl)phenylamino)propan-2-yl)-1H-pyrazole-4-carboxamide The title compound was prepared using procedures similar to those described in step 5 of Preparatory Example 50 using 2-(5-amino-4-cyano-3-methyl-1H-pyrazol-1-yl)-N-(4-(trifluoromethyl)phenyl)propanamide to afford a solid. MS=356.1 (+ESI).

Step 5. 3-(Benzyloxymethyl)-6-hydroxy-1-(2-methyl-1-(4-(trifluoromethyl)phenyl)propyl)-1H-pyrazolo[3,4-d]pyrimidin-4(5H)-one The title compound was prepared using procedures similar to those described in step 1 of Example 1 using 5-amino-3-methyl-1-(1-oxo-1-(4-(trifluoromethyl)phenylamino)propan-2-yl)-1H-pyrazole-4-carboxamide to afford the title compound (Example 334) as a solid. MS=380.0 (+ESI). ¹H NMR (300 MHz, DMSO-d₆): δ 12.02 (s, 1H), 10.43 (s, 1H), 7.78 (d, J=8.4 Hz, 2H), 7.68 (d, J=8.4 Hz, 2H), 5.44 (q, J=7.2 Hz, 1H), 2.42 (s, 3H), 2.33 (s, 3H), 1.74 (d, J=7.2 Hz, 3H).

EXAMPLE 335

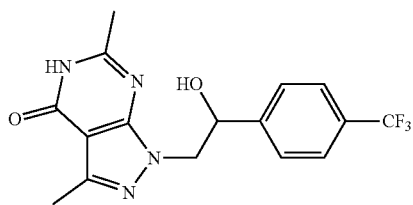 [SMILES: Cc1nc2c(c(C)nn2CC(O)c2ccc(C(F)(F)F)cc2)c(=O)[nH]1]

1-(2-Hydroxy-2-(4-(trifluoromethyl)phenyl)ethyl)-3,6-dimethyl-1H-pyrazolo[3,4-d]pyrimidin-4(5H)-one (Scheme 62)

Step 1. tert-Butyl 2-(2-oxo-2-(4-(trifluoromethyl)phenyl)ethyl)hydrazinecarboxylate The title compound was prepared using procedures similar to those described in step 1 of Example 330 using to 2-bromo-1-(4-(trifluoromethyl)phenyl)ethanone and tert-butyl hydrazinecarboxylate to afford an oil. MS=319.1 (+ESI).

Step 2. tert-Butyl 2-(2-hydroxy-2-(4-(trifluoromethyl)phenyl)ethyl)hydrazinecarboxylate The title compound was prepared using procedures similar to those described in Preparatory Example 82 using tert-butyl 2-(2-oxo-2-(4-(trifluoromethyl)phenyl)ethyl)hydrazinecarboxylate to afford a solid which was used directly in next step without purification. MS=321.2 (+ESI).

Step 3. 2-Hydrazinyl-1-(4-(trifluoromethyl)phenyl)ethanol dihydrochloride

The title compound was prepared using procedures similar to those described in step 3 of Preparatory Example 50 using tert-butyl 2-(2-hydroxy-2-(4-(trifluoromethyl)phenyl)ethyl)hydrazinecarboxylate to afford the title compound as a solid. MS=221.0 (+ESI).

Step 4. 5-Amino-1-(2-hydroxy-2-(4-(trifluoromethyl)phenyl)ethyl)-3-methyl-1H-pyrazole-4-carbonitrile The title compound was prepared using procedures similar to those described in step 4 of Preparatory Example 50 using 2-hydrazinyl-1-(4-(trifluoromethyl)phenyl)ethanol dihydrochloride to afford a solid. MS=311.2 (+ESI).

Step 5. 5-Amino-1-(2-hydroxy-2-(4-(trifluoromethyl)phenyl)ethyl)-3-methyl-1H-pyrazole-4-carboxamide The title compound was prepared using procedures similar to those described in step 5 of Preparatory Example 50 using 5-amino-1-(2-hydroxy-2-(4-(trifluoromethyl)phenyl)ethyl)-3-methyl-1H-pyrazole-4-carbonitrile to afford a solid. MS=329.0 (+ESI).

Step 6. 1-(2-Hydroxy-2-(4-(trifluoromethyl)phenyl)ethyl)-3,6-dimethyl-1H-pyrazolo[3,4-d]pyrimidin-4(5H)-one The title compound was prepared using procedures similar to those described in step 1 of Example 2 using 5-amino-1-(2-hydroxy-2-(4-(trifluoromethyl)phenyl)ethyl)-3-methyl-1H-pyrazole-4-carboxamide to afford the title compound (Example 335) as a solid. MS=353.2 (+ESI). ¹H NMR (400 MHz, CD₃OD): δ 7.63 (d, J=8.1 Hz, 2H), 7.52 (d, J=8.1 Hz, 2H), 5.25-5.21 (m, 1H), 4.53-4.48 (m, 1H), 4.36-4.29 (m, 1H), 2.52 (s, 3H), 2.35 (s, 3H).

EXAMPLE 336

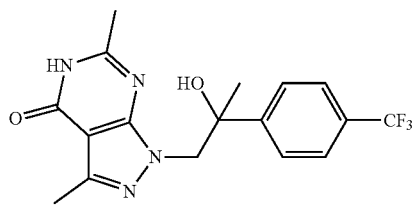 [SMILES: Cc1nc2c(c(C)nn2CC(C)(O)c2ccc(C(F)(F)F)cc2)c(=O)[nH]1]

1-(2-Hydroxy-2-(4-(trifluormethyl)phenyl)propyl)-3,6-dimethyl-1H-pyrazolo[4-d]pyrimidin-4(5H)-one (Scheme 62)

Step 1. 3,6-Dimethyl-1-(2-oxo-2-(4-(trifluoromethyl)phenyl)ethyl)-1H-pyrazolo[3,4-d]pyrimidin-4(5H)-one The title compound was prepared using procedures similar to those described in step 1 of Examples 175 and 176 using 1-(2-hydroxy-2-(4-(trifluoromethyl)phenyl)-ethyl)-3,6-dimethyl-1H-pyrazolo[3,4-d]pyrimidin-4(5H)-one to afford a solid. MS=351.2 (+ESI).

Step 2. (RS)-1-(2-Hydroxy-2-(4-(trifluoromethyl)phenyl)propyl)-3,6-dimethyl-H-pyrazolo[3,4-d]pyrimidin-4(5H)-one The title compound was prepared using procedures similar to those described in step 3 of Preparatory Example 102 using 3,6-dimethyl-1-(2-oxo-2-(4-(trifluoromethyl)phenyl)ethyl)-1H-pyrazolo[3,4-d]pyrimidin-4(5H)-one and methylmagnesium bromide to afford the title compound (Example 336) as a solid. MS=367.2 (+ESI). $^1$H NMR (400 MHz, DMSO-$d_6$): δ 11.82 (br s, 1H), 7.58 (d, J=8.6 Hz, 2H), 7.51 (d, J=8.6 Hz, 2H), 5.62 (s, 1H), 4.33 (s, 2H), 2.38 (s, 3H), 2.16 (s, 3H), 1.55 (s, 3H).

EXAMPLE 337

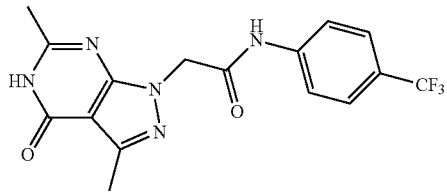 [SMILES: Cc1nc2c(c(C)nn2CC(=O)Nc2ccc(C(F)(F)F)cc2)c(=O)[nH]1]

2-(3,6-Dimethyl-4-oxo-45-dihydropyrazolo[3,4-d]pyrimidin-1-yl)-N-(4-(trifluoromethyl)phenyl)acetamide (Scheme 63)

Step 1. Ethyl 2-(5-amino-4-cyano-3-methyl-1H-pyrazol-1-yl)acetate

The title compound was prepared using procedures similar to those described in step 4 of Preparatory Example 50 using ethyl 2-hydrazinylacetate hydrochloride and 2-(1-ethoxyethylidene)malononitrile to afford a solid. MS=209.1 (+ESI).

Step 2. 2-(5-Amino-4-carbamoyl-3-methyl-1H-pyrazol-1-yl)acetic acid

The title compound was prepared using procedures similar to those described in step 5 of Preparatory Example 50 using ethyl 2-(5-amino-4-cyano-3-methyl-1H-pyrazol-1-yl) acetate to afford a solid. $^1$H NMR (300 MHz, DMSO-$d_6$) δ: 13.02 (br s, 1H), 6.59 (br s, 2H), 4.61 (s, 2H), 2.05 (s, 3H).

Step 3. 5-Amino-3-methyl-1-(2-oxo-2-((4-(trifluoromethyl)phenyl)amino)ethyl)-1H-pyrazole-4-carboxamide The title compound was prepared using procedures similar to those described in step 6 of Example 330 using 4-(trifluoromethyl)aniline and 2-(5-amino-4-carbamoyl-3-methyl-1H-pyrazol-1-yl) acetic acid to afford a solid. MS (+ESI) m/z=342.2 (+ESI).

Step 4. 2-(3,6-Dimethyl-4-oxo-4,5-dihydro-1H-pyrazolo[3,4-d]pyrimidin-1-yl)-N-(4-(trifluoromethyl)phenyl)acetamide The title compound was prepared using procedures similar to those described in step 1 of Example 1 using 5-amino-3-methyl-1-(2-oxo-2-((4-(trifluoromethyl)phenyl)amino)ethyl)-1H-pyrazole-4-carboxamide to afford the title compound (Example 337) as a solid. MS=366.1 (+ESI). $^1$H NMR (400 MHz, DMSO-$d_6$): δ 12.05 (br s, 1H), 10.74 (br s, 1H), 7.78 (d, J=8.4 Hz, 2H), 7.70 (d, J=8.8 Hz, 2H), 5.07 (s, 2H), 2.41 (s, 3H), 2.33 (s, 3H).

TABLE 29

The following compounds were prepared using procedures similar to those described in step 1 of Example 1 using the appropriate starting materials.

| Ex# | Structure | IUPAC Name | Exact Mass [M + H]+ |
|---|---|---|---|
| 338 | 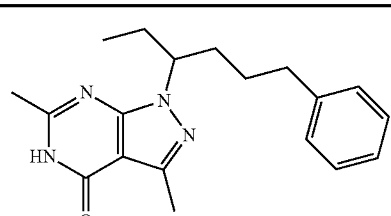 | 1-(1-ethyl-4-phenylbutyl)-3,6-dimethyl-1,5-dihydro-4H-pyrazolo[3,4-d]pyrimidin-4-one | Calc'd 325.2, found 325.4 |

TABLE 29-continued

The following compounds were prepared using procedures similar to those described in step 1 of Example 1 using the appropriate starting materials.

| Ex# | Structure | IUPAC Name | Exact Mass [M + H]+ |
|---|---|---|---|
| 339 | 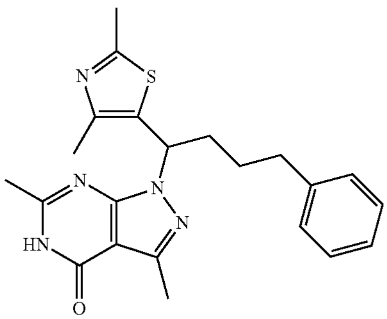 [SMILES: Cc1nc2c(c(C)nn2C(CCCc2ccccc2)c2sc(C)nc2C)c(=O)[nH]1] | 1-[1-(2,4-dimethyl-1,3-thiazol-5-yl)-4-phenylbutyl]-3,6-dimethyl-1,5-dihydro-4H-pyrazolo[3,4-d]pyrimidin-4-one | Calc'd 408.2, found 408.2 |

TABLE 30

The following compounds were made using procedures similar to those described for the preparation of Examples 262 and 263 shown in Scheme 39 except using the appropriate 6-substituted starting materials prepared according to Scheme 18. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 340 | 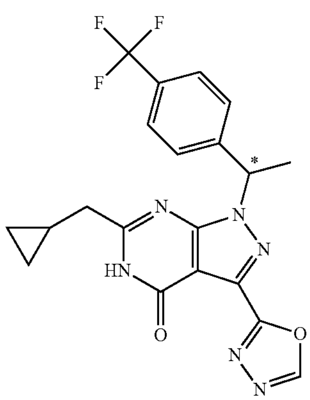 [SMILES: CC(c1ccc(C(F)(F)F)cc1)n1nc(-c2nnco2)c2c(=O)[nH]c(CC3CC3)nc21] | (R)- or (S)-6-(Cyclopropylmethyl)-3-(1,3,4-oxadiazol-2-yl)-1-(1-(4-(trifluoromethyl)phenyl)ethyl)-1,5-dihydro-4H-pyrazolo[3,4-d]pyrimidin-4-one | Calc'd 431.1, found 431.1. | Chiralpak IA |
| 341 | 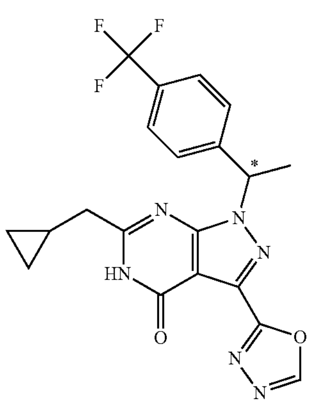 [SMILES: CC(c1ccc(C(F)(F)F)cc1)n1nc(-c2nnco2)c2c(=O)[nH]c(CC3CC3)nc21] | (S)- or (R)-6-(Cyclopropylmethyl)-3-(1,3,4-oxadiazol-2-yl)-1-(1-(4-(trifluoromethyl)phenyl)ethyl)-1,5-dihydro-4H-pyrazolo[3,4-d]pyrimidin-4-one | Calc'd 431.1, found 431.1. | Chiralpak IA |

TABLE 30-continued

The following compounds were made using procedures similar to those described for the preparation of Examples 262 and 263 shown in Scheme 39 except using the appropriate 6-substituted starting materials prepared according to Scheme 18. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 342 | 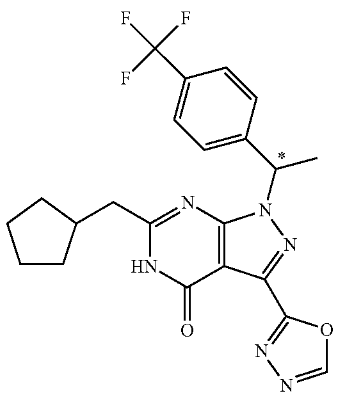 [SMILES: CC(c1ccc(C(F)(F)F)cc1)n1nc(-c2nnco2)c2c(=O)[nH]c(CC3CCCC3)nc21] | (R) or (S)-6-(Cyclopentylmethyl)-3-(1,3,4-oxadiazol-2-yl)-1-(1-(4-(trifluoromethyl)phenyl)ethyl)-1,5-dihydro-4H-pyrazolo[3,4-d]pyrimidin-4-one | Calc'd 459.2, found 459.2. | Chiralpak IC |
| 343 | 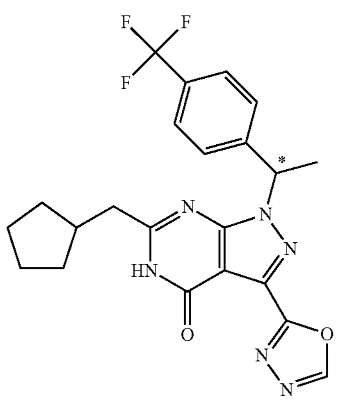 [SMILES: CC(c1ccc(C(F)(F)F)cc1)n1nc(-c2nnco2)c2c(=O)[nH]c(CC3CCCC3)nc21] | (S) or (R)-6-(Cyclopentylmethyl)-3-(1,3,4-oxadiazol-2-yl)-1-(1-(4-(trifluoromethyl)phenyl)ethyl)-1,5-dihydro-4H-pyrazolo[3,4-d]pyrimidin-4-one | Calc'd 459.2, found 459.2. | Chiralpak IC |
| 344 | 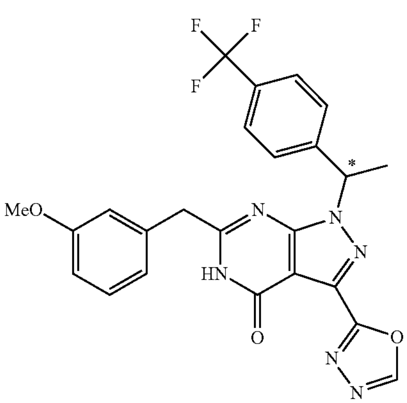 [SMILES: COc1cccc(Cc2nc3c(c(-c4nnco4)nn3C(C)c3ccc(C(F)(F)F)cc3)c(=O)[nH]2)c1] | (R)- or (S)-6-(3-Methoxybenzyl)-3-(1,3,4-oxadiazol-2-yl)-1-(1-(4-(trifluoromethyl)phenyl)ethyl)-1,5-dihydro-4H-pyrazolo[3,4-d]pyrimidin-4-one | Calc'd 497.2, found 497.2 | AD-H |

TABLE 30-continued

The following compounds were made using procedures similar to those described for the preparation of Examples 262 and 263 shown in Scheme 39 except using the appropriate 6-substituted starting materials prepared according to Scheme 18. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 345 | 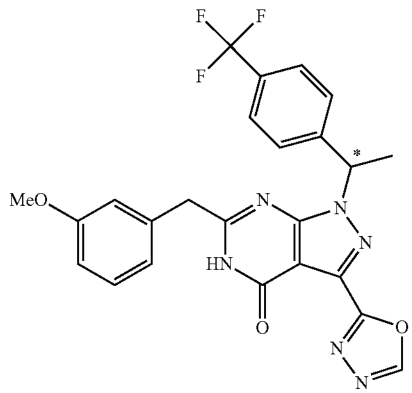 [SMILES: COc1cccc(Cc2nc3c(c(-c4nnco4)nn3C(C)c3ccc(C(F)(F)F)cc3)c(=O)[nH]2)c1] | (S)- or (R)-6-(3-Methoxybenzyl)-3-(1,3,4-oxadiazol-2-yl)-1-(1-(4-(trifluoromethyl)phenyl)ethyl)-1,5-dihydro-4H-pyrazolo[3,4-d]pyrimidin-4-one | Calc'd 497.2, found 497.2 | AD-H |

TABLE 31

The following compounds were made using procedures similar to those described for the preparation of Examples 251-253 shown in Scheme 34 except using the appropriate 6-substituted carboxaldehyde starting materials prepared according to Schemes 18 and 34. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 346 | 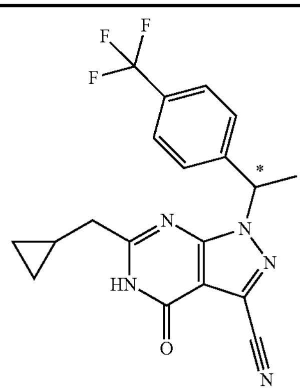 | (R)-or (S)-6-(Cyclopropylmethyl)-4-oxo-1-{1-[4-(trifluoromethyl)phenyl]ethyl}-4,5-dihydro-1H-pyrazolo[3,4-d]pyrimidine-3-carbonitrile | Calc'd 388.1, found 388.2 | OJ-H |
| 347 | 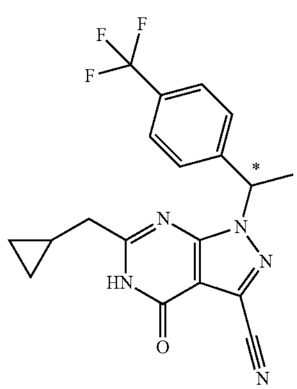 [SMILES: CC(c1ccc(C(F)(F)F)cc1)n1nc(C#N)c2c(=O)[nH]c(CC3CC3)nc21] | (S)-or (R)-6-(Cyclopropylmethyl)-4-oxo-1-{1-[4-(trifluoromethyl)phenyl]ethyl}-4,5-dihydro-1H-pyrazolo[3,4-d]pyrimidine-3-carbonitrile | Calc'd 388.1, found 388.2 | OJ-H |

TABLE 31-continued

The following compounds were made using procedures similar to those described for the preparation of Examples 251-253 shown in Scheme 34 except using the appropriate 6-substituted carboxaldehyde starting materials prepared according to Schemes 18 and 34. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 348 | 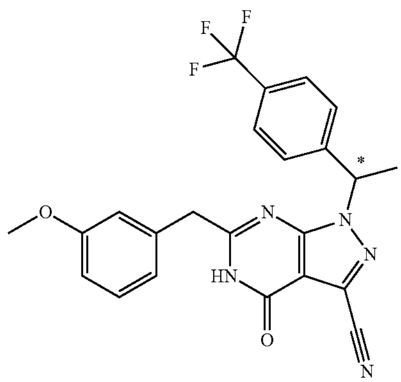 [SMILES: COc1cccc(Cc2nc3c(c(C#N)nn3C(C)c3ccc(C(F)(F)F)cc3)c(=O)[nH]2)c1] | (R)-or (S)-6-(3-Methoxybenzyl)-4-oxo-1-{1-[4-(trifluoromethyl)phenyl]ethyl}-4,5-dihydro-1H-pyrazolo[3,4-d]pyrimidine-3-carbonitrile | Calc'd 454.1, found 454.0 | Lux-4 |
| 349 | 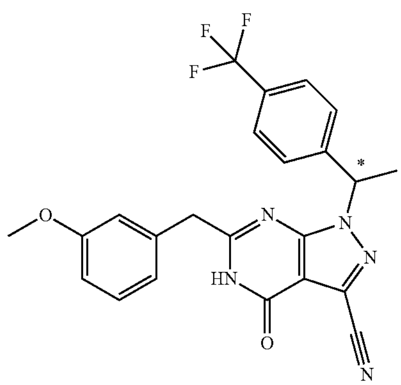 [SMILES: COc1cccc(Cc2nc3c(c(C#N)nn3C(C)c3ccc(C(F)(F)F)cc3)c(=O)[nH]2)c1] | (S)-or (R)-6-(3-Methoxybenzyl)-4-oxo-1-{1-[4-(trifluoromethyl)phenyl]ethyl}-4,5-dihydro-1H-pyrazolo[3,4-d]pyrimidine-3-carbonitrile | Calc'd 454.1, found 454.0 | Lux-4 |
| 350 | 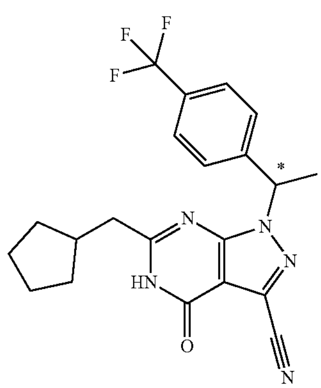 [SMILES: CC(c1ccc(C(F)(F)F)cc1)n1nc(C#N)c2c(=O)[nH]c(CC3CCCC3)nc21] | (R)-or (S)-6-(Cyclopentylmethyl)-4-oxo-1-{1-[4-(trifluoromethyl)phenyl]ethyl}-4,5-dihydro-1H-pyrazolo[3,4-d]pyrimidine-3-carbonitrile | Calc'd 416.2, found 416.0 | Lux-4 |

TABLE 31-continued

The following compounds were made using procedures similar to those described for the preparation of Examples 251-253 shown in Scheme 34 except using the appropriate 6-substituted carboxaldehyde starting materials prepared according to Schemes 18 and 34. Racemic products were separated using chiral columns specified in the table. For those pairs of enantiomers, the faster-eluting isomer is always listed first in this table.

| Ex # | Structure | IUPAC Name | Exact Mass [M + H]+ | Chiral column |
|---|---|---|---|---|
| 351 | 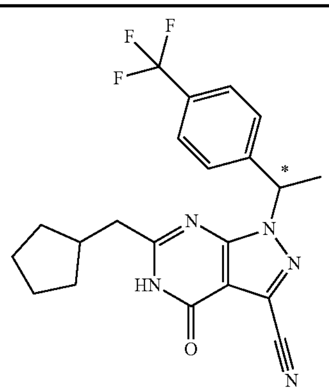 | (S)- or (R)-6-(Cyclopentylmethyl)-4-oxo-1-{1-[4-(trifluoromethyl)phenyl]ethyl}-4,5-dihydro-1H-pyrazolo[3,4-d]pyrimidine-3-carbonitrile | Calc'd 416.2, found 416.0 | Lux-4 |

Assay

The activity of the compounds in accordance with the present invention as PDE2 inhibitors may be readily determined using a fluorescence polarization (FP) methodology (Huang, W., et al., J. Biomol Screen, 2002, 7: 215). In particular, the compounds of the following examples had activity in reference assays by exhibiting the ability to inhibit the hydrolysis of the phosphate ester bond of a cyclic nucleotide. Any compound exhibiting a Ki (inhibitory constant) of about 50 μM or below would be considered a PDE2 inhibitor as defined herein.

The PDE2 inhibitory activity of the compounds of the present invention was determined in accordance with the following experimental method. Rhesus PDE2A3 was amplified from rhesus macaque brain cDNA (Biochain Institute, Hayward, Calif.) using primers based on human PDE2A sequence (accession NM_002599.3) where the forward primer containing a Kozak consensus was 5'-gccac-catggggcaggcatgtggc-3' and the reverse primer was 5'-tcactcagcatcaaggctgca-3'. Amplification with Easy-A High-Fidelity PCR cloning enzyme (Stratagene, La Jolla, Calif.) was 95° C. for 2 minutes followed by thirty three cycles of 95° C. for 40 seconds, 52° C. for 30 seconds, and 72° C. for 2 minutes 48 seconds. Final extension was 72° C. for 7 minutes. The PCR product was TA cloned into pcDNA3.3-TOPO (Invitrogen, Carlsbad, Calif.) according to standard protocol. A consensus sequence was developed from multiple clones and then deposited into GenBank (EU812167). AD293 cells (Stratagene, La Jolla, Calif.) with 70-80% confluency were transiently transfected with rhesus PDE2A3/pcDNA3.3-TOPO using Lipofectamine 2000 according to manufacturer specifications (Invitrogen, Carlsbad, Calif.). Cells were harvested 48 hours post-transfection and lysed by sonication (setting 3, 10×5 sec pulses) in a buffer containing 20 mM HEPES pH 7.4, 1 mM EDTA and Complete Protease Inhibitor Cocktail Tablets (Roche, Indianapolis, Ind.). Lysate was collected by centrifugation at 75,000×g for 20 minutes at 4° C. and supernatant utilized for evaluation of PDE2 activity. The fluorescence polarization assay for cyclic nucleotide phosphodiesterases was performed using an IMAP® FP kit supplied by Molecular Devices, Sunnyvale, Calif. (product #R8139). IMAP® technology has been applied previously to examine the effects of phosphodiesterase inhibitors (Huang, W., et al., J. Biomol Screen, 2002, 7: 215). Assays were performed at room temperature in 384-well microtiter plates with an incubation volume of 20.2 μL. Solutions of test compounds were prepared in DMSO and serially diluted with DMSO to yield 8 μL of each of 10 solutions differing by 3-fold in concentration, at 32 serial dilutions per plate. 100% inhibition is determined using a known PDE2 inhibitor, which can be any compound that is present at 5,000 times its Ki value in the assay described below, such as Bay 60-7550 (Ki—0.2 nM) at 1 μM concentration for 100% inhibition. Bay 60-7550 was obtained from Axxora via Fisher Scientific (cat# ALX-270-421-M025/cat# NC9314773). Put another way, any compound with Ki of ~0.2 to about 2 nM could be used at 1 to 10 μM. 0% of inhibition is determined by using DMSO (1% final concentrations).

A Labcyte Echo 555 (Labcyte, Sunnyvale, Calif.) is used to dispense 200 nL from each well of the titration plate to the 384 well assay plate. Ten microliters of a solution of enzyme (1/2000 final dilution from aliquots; sufficient to produce 20% substrate conversion) was added to the assay plate. Next 10 uL of a separate solution of the substrate FAM-labeled cAMP (50 nM final concentration product # R7506 from Molecular Devices) and the activator cGMP (1 uM final concentration), prepared in the assay buffer (10 mM Tris HCl, pH 7.2, 10 mM MgCl$_2$, 0.05% NaN$_3$ 0.01% Tween-20, and 1 mM DTT) was added to the assay plate and shaken to mix. The reaction is allowed to proceed at room temperature for 60 minutes. A binding solution is then made from the kit components, comprised of 80% Solution A, 20% Solution B and binding reagent at a volume of 1/600 the total binding solution. The enzymatic reaction is stopped by addition of 60 μL of the binding solution to each well of the assay plates and the plates are sealed and shaken for 30 seconds. The plate was incubated at room temperature for at least one hour prior to determining the fluorescence polarization (FP). The parallel and perpendicular fluorescence of each well of the plate was measured using a Tecan Genios Pro plate reader (Tecan, Switzerland) or Perkin Elmer EnVision™ plate reader (Waltham, Mass.). Fluorescence polarization (mP) was calculated from the parallel (S) and perpendicular (P) fluorescence of each sample well and the analogous values for the median control well, containing only substrate (So and Po), using the following equation:

Polarization($mP$)=1000*($S/So-P/Po$)/($S/So+P/Po$).

Dose-inhibition profiles for each compound were characterized by fitting the mP data to a four-parameter equation given below. The apparent inhibition constant ($K_I$), the maximum inhibition at the low plateau relative to "100% Inhibition Control" (Imax; e.g. 1=>same as this control), the minimum inhibition at the high plateau relative to the "0% Inhibition Control" (Imin, e.g. 0=>same as the no drug control) and the Hill slope (nH) are determined by a non-linear least squares fitting of the mP values as a function of dose of the compound using an in-house software based on the procedures described by Mosser et al., JALA, 2003, 8: 54-63, using the following equation:

$$mP = \frac{(0\%\ mP - 100\%\ mP)(I\max - I\min)}{1 + \left[\frac{[Drug]}{\left(10^{-pK_I}\left(1 + \frac{[Substrate]}{K_M}\right)\right)}\right]^{nH}} +$$

$$100\%\ mP + (0\%\ mP - 100\%\ mP)(1 - I\max)$$

The median signal of the "0% inhibition controls" (0% mP) and the median signal of the "100% inhibition controls" (100% mP) are constants determined from the controls located in columns 1-2 and 23-24 of each assay plate. An apparent ($K_M$) for FAM-labeled cAMP of ~10 uM was used.

Selectivity for PDE2, as compared to other PDE families, was assessed using the IMAP® technology. Human PDE10A2 enzyme was prepared from cytosolic fractions of transiently transfected HEK cells. All other PDE's were GST Tag human enzyme expressed in insect cells and were obtained from BPS Bioscience (San Diego, Calif.): PDE1A (Cat#60010), human PDE2A1 (Cat#60020), PDE3A (Cat#60030), PDE4A1A (Cat#60040), PDE5A1 (Cat#60050), PDE6C (Cat#60060), PDE7A (Cat#60070), PDE8A1 (Cat#60080), PDE9A2 (Cat#60090), PDE11A4 (Cat#60110).

Assays for PDE 1 through 11 were performed in parallel at room temperature in 384-well microtiter plates with an incubation volume of 20.2 µL. Solutions of test compounds were prepared in DMSO and serially diluted with DMSO to yield 30 µL of each of ten solutions differing by 3-fold in concentration, at 32 serial dilutions per plate. 100% inhibition was determined by adding buffer in place of the enzyme and 0% inhibition is determined by using DMSO (1% final concentrations). A Labcyte POD 810 (Labcyte, Sunnyvale, Calif.) was used to dispense 200 nL from each well of the titration plate to make eleven copies of the assay plate for each titration, one copy for each PDE enzyme. A solution of each enzyme (dilution from aliquots, sufficient to produce 20% substrate conversion) and a separate solution of FAM-labeled cAMP or FAM-labeled cGMP from Molecular Devices (Sunnyvale, Calif., product # R7506 or cGMP#R7508), at a final concentration of 50 nM were made in the assay buffer (10 mM Tris HCl, pH 7.2, 10 mM MgCl$_2$, 0.05% NaN$_3$ 0.01% Tween-20, and 1 mM DTT). Note that the substrate for PDE2 is 50 nM FAM cAMP containing 1000 nM of cGMP. The enzyme and the substrate were then added to the assay plates in two consecutive additions of 10 µL and then shaken to mix. The reaction was allowed to proceed at room temperature for 60 minutes. A binding solution was then made from the kit components, comprised of 80% Solution A, 20% Solution B and binding reagent at a volume of 1/600 the total binding solution. The enzymatic reaction was stopped by addition of 60 µL of the binding solution to each well of the assay plate. The plates were sealed and shaken for 10 seconds. The plates were incubated at room temperature for one hour, then the parallel and perpendicular fluorescence was measured using a Tecan Genios Pro plate reader (Tecan, Switzerland). The apparent inhibition constants for the compounds against all 11 PDE's was determined from the parallel and perpendicular fluorescent readings as described for PDE10 FP assay using the following apparent $K_M$ values for each enzyme and substrate combination: PDE1A (FAM cGMP) 70 nM, human PDE2A1 (FAM cAMP) 10,000 nM, PDE3A (FAM cAMP) 50 nM, PDE4A1A (FAM cAMP) 1500 nM, PDE5A1 (FAM cGMP) 400 nM, PDE6C (FAM cGMP) 700 nM, PDE7A (FAM cAMP) 150 nM, PDE8A1 (FAM cAMP) 50 nM, PDE9A2 (FAM cGMP) 60 nM, PDE10A2 (FAM cAMP) 150 nM, PDE11A4 (FAM cAMP) 1000 nM. The intrinsic PDE2 inhibitory activity of a compound which may be used in accordance with the present invention may be determined by these assays.

The compounds of the following examples had activity in inhibiting the human PDE2 enzyme in the aforementioned assays with a Ki of less than about 50 µM. Many of compounds within the present invention had activity in inhibiting the human PDE2 enzyme in the aforementioned assays, with a Ki of less than about 1 µM, preferably less than or about 0.1 µM. Additional data is provided in the following Examples. Such a result is indicative of the intrinsic activity of the compounds in use as inhibitors of the PDE2 enzyme. In general, one of ordinary skill in the art would appreciate that a substance is considered to effectively inhibit PDE2 activity if it has a Ki of less than or about 1 µM, preferably less than or about 0.1 µM. The present invention also includes compounds within the generic scope of the invention which possess activity as inhibitors of other phosphodiesterase enzymes.

In the following tables representative data for the compounds of formula I as PDE2 inhibitors as determined by the foregoing assays and as conducted in laboratory (Lab) A or B are shown. The PDE2 Ki is a measure of the ability of the test compound to inhibit the action of the PDE2 enzyme.

TABLE 32

| | PDE2 Ki's | | | |
|---|---|---|---|---|
| Ex # | Rhesus PDE2 Ki (nM) Lab A | Rhesus PDE2 Ki (nM) Lab B | Human PDE2 Ki (nM) Lab A | Human PDE2 Ki (nM) Lab B |
| 1 | 4.1 | 7.2 | 1.8 | 5.3 |
| 2 | 26 | 30 | 18 | 28 |
| 3 | 1.8 | 5.6 | ND | 3.7 |
| 4 | 3.8 | 7.1 | 4.6 | 5.9 |
| 5 | 0.62 | 1.0 | 0.56 | 0.74 |
| 6 | 1.6 | 3.5 | ND | 3.1 |
| 7 | 19 | ND | 11 | 17 |
| 8 | 192 | ND | 100 | 105 |
| 9 | 54 | 56 | 27 | 60 |
| 10 | 39 | 103 | ND | 50 |
| 11 | 0.85 | 2.0 | ND | 1.9 |
| 12 | 278 | 514 | ND | 205 |
| 13 | 1.3 | 3.0 | ND | 1.7 |
| 14 | ND | ND | ND | 2.4 |

TABLE 32-continued

PDE2 Ki's

| Ex # | Rhesus PDE2 Ki (nM) Lab A | Rhesus PDE2 Ki (nM) Lab B | Human PDE2 Ki (nM) Lab A | Human PDE2 Ki (nM) Lab B |
|---|---|---|---|---|
| 15 | ND | ND | ND | 154 |
| 16 | ND | ND | ND | 81 |
| 17 | ND | 1.7 | ND | 2.1 |
| 18 | ND | ND | ND | ~2850 |
| 19 | ND | 1.9 | ND | 1.8 |
| 20 | ND | ND | ND | 305 |
| 21 | ND | 2.9 | ND | 3.5 |
| 22 | ND | ND | ND | 125 |
| 23 | ND | 1.7 | ND | 1.1 |
| 24 | ND | 1.9 | ND | 1.9 |
| 25 | ND | 160 | ND | ND |
| 26 | 216 | 456 | 130 | 236 |
| 27 | 2.0 | 2.1 | 1.4 | 3.4 |
| 28 | 0.75 | 2.2 | ND | 1.6 |
| 29 | 583 | ND | ND | ND |
| 30 | 6.6 | 11 | 4.6 | 12 |
| 31 | 65 | 128 | 43 | ND |
| 32 | 275 | 416 | ND | ND |
| 33 | 386 | 531 | ND | ND |
| 34 | 267 | ND | ND | ND |
| 35 | 164 | ND | 105 | ND |
| 36 | 443 | ND | 428 | ND |
| 37 | 23 | ND | 23 | ND |
| 38 | 58 | ND | 28 | ND |
| 39 | 147 | ND | 84 | ND |
| 40 | 340 | ND | 197 | ND |
| 41 | 64 | ND | 35 | ND |
| 42 | 58 | ND | 40 | ND |
| 43 | 257 | ND | 132 | ND |
| 44 | 4.8 | ND | 2.1 | ND |
| 45 | 26 | ND | 22 | ND |
| 46 | 7.1 | ND | 8.6 | ND |
| 47 | 18 | ND | 17 | ND |
| 48 | 36 | ND | 21 | ND |
| 49 | 9.0 | ND | 5.4 | ND |
| 50 | 62 | ND | 47 | ND |
| 51 | 79 | ND | 50 | ND |
| 52 | 28 | ND | 18 | ND |
| 53 | 29 | ND | 17 | ND |
| 54 | 32 | ND | 12 | ND |
| 55 | 421 | ND | ND | ND |
| 56 | ND | 6020 | ND | ND |
| 57 | ND | 69 | ND | 62 |
| 58 | ND | 1085 | ND | ND |
| 59 | ND | 22 | ND | 23 |
| 60 | ND | ND | ND | >2955 |
| 61 | ND | ND | ND | 55 |
| 62 | ND | ND | ND | 1098 |
| 63 | ND | ND | ND | 45 |
| 64 | ND | ND | ND | 274 |
| 65 | ND | ND | ND | 5.0 |
| 66 | ND | ND | ND | 327 |
| 67 | ND | ND | ND | 6.7 |
| 68 | ND | ND | ND | 8.6 |
| 69 | ND | ND | ND | 713 |
| 70 | ND | ND | ND | 159 |
| 71 | ND | ND | ND | 111 |
| 72 | ND | ND | ND | 570 |
| 73 | ND | ND | ND | 423 |
| 74 | ND | ND | ND | 258 |
| 75 | ND | ND | ND | 203 |
| 76 | ND | 330 | ND | ND |
| 77 | ND | 4.2 | ND | 3.3 |
| 78 | ND | 6.7 | ND | 4.9 |
| 79 | ND | ND | ND | 23 |
| 80 | ND | ND | ND | 624 |
| 81 | ND | ND | ND | 7.7 |
| 82 | ND | 289 | ND | ND |
| 83 | ND | 9.4 | ND | 7.6 |
| 84 | ND | 16 | ND | 11 |
| 85 | ND | 0.91 | ND | 0.89 |
| 86 | ND | 436 | ND | ND |
| 87 | ND | 3.2 | ND | 3.3 |
| 88 | ND | 51 | ND | 45 |
| 89 | ND | 0.48 | ND | 0.33 |
| 90 | ND | 90 | ND | 78 |
| 91 | ND | 1.0 | ND | 1.1 |
| 92 | ND | 10 | ND | 8.3 |
| 93 | ND | 1.9 | ND | 1.7 |
| 94 | ND | 18 | ND | 18 |
| 95 | ND | 2.1 | ND | 2.0 |
| 96 | ND | ND | ND | 16 |
| 97 | ND | ND | ND | 467 |
| 98 | ND | ND | ND | 591 |
| 99 | ND | ND | ND | 4.5 |
| 100 | ND | ND | ND | ~1669 |
| 101 | ND | ND | ND | 13 |
| 102 | ND | ND | ND | >2955 |
| 103 | ND | ND | ND | 19 |
| 104 | ND | ND | ND | 162 |
| 105 | ND | ND | ND | 1.9 |
| 106 | ND | ND | ND | 633 |
| 107 | ND | ND | ND | 4.5 |
| 108 | ND | ND | ND | ~1284 |
| 109 | ND | ND | ND | 1.9 |
| 110 | ND | ND | ND | 1070 |
| 111 | ND | ND | ND | 3.2 |
| 112 | ND | ND | ND | 88 |
| 113 | ND | ND | ND | 3.0 |
| 114 | ND | ND | ND | 1207 |
| 115 | ND | ND | ND | 7.2 |
| 116 | ND | ND | ND | 392 |
| 117 | ND | ND | ND | 1.1 |
| 118 | ND | ND | ND | 323 |
| 119 | ND | ND | ND | 2.7 |
| 120 | ND | ND | ND | 496 |
| 121 | ND | ND | ND | 2.8 |
| 122 | ND | ND | ND | 194 |
| 123 | ND | ND | ND | 2.6 |
| 124 | ND | ND | ND | 521 |
| 125 | ND | ND | ND | 26 |
| 126 | ND | 6.0 | ND | 5.7 |
| 127 | ND | 0.90 | ND | 0.98 |
| 128 | ND | 413 | ND | ND |
| 129 | ND | 6.9 | ND | 8.9 |
| 130 | ND | ND | ND | 2955 |
| 131 | ND | ND | ND | 57 |
| 132 | ND | 1.5 | ND | 1.1 |
| 133 | ND | ND | ND | 66 |
| 134 | ND | ND | ND | 51 |
| 135 | ND | ND | ND | 1.0 |
| 136 | ND | ND | ND | 5.0 |
| 137 | ND | ND | ND | 121 |
| 138 | ND | ND | ND | >2955 |
| 139 | ND | ND | ND | 5.6 |
| 140 | ND | ND | ND | 939 |
| 141 | ND | ND | ND | 12 |
| 142 | ND | ND | ND | 8.2 |
| 143 | ND | ND | ND | 193 |
| 144 | ND | ND | ND | 0.59 |
| 145 | ND | ND | ND | >2955 |
| 146 | ND | ND | ND | 58 |
| 147 | ND | ND | ND | >2955 |
| 148 | ND | ND | ND | 671 |
| 149 | ND | ND | ND | >2955 |
| 150 | ND | ND | ND | 158 |
| 151 | ND | ND | ND | 25 |
| 152 | ND | ND | ND | 1180 |
| 153 | ND | ND | ND | >2955 |
| 154 | ND | ND | ND | 18 |
| 155 | ND | ND | ND | ~1635 |
| 156 | ND | ND | ND | 8.5 |
| 157 | ND | 0.96 | ND | 1.1 |
| 158 | ND | 4.5 | ND | 3.1 |
| 159 | ND | 2.8 | ND | 2.0 |
| 160 | ND | 0.30 | ND | 0.36 |
| 161 | ND | ND | ND | 224 |
| 162 | ND | ND | ND | 1.8 |

TABLE 32-continued

PDE2 Ki's

| Ex # | Rhesus PDE2 Ki (nM) Lab A | Rhesus PDE2 Ki (nM) Lab B | Human PDE2 Ki (nM) Lab A | Human PDE2 Ki (nM) Lab B |
|---|---|---|---|---|
| 163 | ND | ND | ND | 9.5 |
| 164 | ND | ND | ND | 8.2 |
| 165 | ND | ND | ND | 6.3 |
| 166 | 6.7 | 7.9 | ~5.9 | 9.5 |
| 167 | ND | ND | ND | 256 |
| 168 | ND | ND | ND | 1.4 |
| 169 | ND | ND | ND | 18 |
| 170 | ND | ND | ND | 0.48 |
| 171 | ND | ND | ND | 43 |
| 172 | ND | ND | ND | 0.31 |
| 173 | ND | ND | ND | 4.6 |
| 174 | ND | ND | ND | 278 |
| 175 | ND | 419 | ND | ND |
| 176 | ND | 1.4 | ND | 1.3 |
| 177 | ND | ND | ND | 61 |
| 178 | ND | ND | ND | 0.72 |
| 179 | ND | ND | ND | 28 |
| 180 | ND | ND | ND | 0.55 |
| 181 | ND | ND | ND | 82 |
| 182 | ND | 1.2 | ND | 0.84 |
| 183 | ND | ND | ND | 547 |
| 184 | ND | ND | ND | 1.6 |
| 185 | ND | ND | ND | 303 |
| 186 | ND | ND | ND | 0.63 |
| 187 | ND | ND | ND | 231 |
| 188 | ND | ND | ND | 2.6 |
| 189 | ND | ND | ND | 330 |
| 190 | ND | ND | ND | 2.7 |
| 191 | ND | ND | ND | 268 |
| 192 | ND | ND | ND | 3.4 |
| 193 | ND | 1.2 | ND | 1.8 |
| 194 | ND | ND | ND | 14 |
| 195 | ND | ND | ND | ~1672 |
| 196 | ND | 28 | ND | 61 |
| 197 | ND | ~0.15 | ND | 0.23 |
| 198 | ND | 17 | ND | 21 |
| 199 | ND | 210 | ND | ND |
| 200 | ND | 2.4 | ND | 2.0 |
| 201 | 1.4 | 4.1 | ND | 2.6 |
| 202 | ND | 3.1 | ND | 2.9 |
| 203 | ~12 | 12 | 8.3 | 17 |
| 204 | 4.0 | ND | 2.7 | ND |
| 205 | ND | 3.2 | ND | 3.4 |
| 206 | 41 | 123 | ND | 83 |
| 207 | 0.46 | 0.84 | ND | 1.1 |
| 208 | ND | 149 | ND | ND |
| 209 | ND | 1.0 | ND | 0.99 |
| 210 | ND | ND | ND | 75 |
| 211 | ND | 0.49 | ND | 0.65 |
| 212 | ND | 54 | ND | 43 |
| 213 | ND | 0.15 | ND | 0.19 |
| 214 | 179 | 318 | ND | 307 |
| 215 | 0.24 | 0.63 | ND | 0.48 |
| 216 | 19 | 41 | ND | 36 |
| 217 | 0.39 | 0.53 | ND | 0.70 |
| 218 | ND | 107 | ND | ND |
| 219 | ND | 0.87 | ND | 0.96 |
| 220 | ND | 189 | ND | ND |
| 221 | ND | 1.9 | ND | 1.3 |
| 222 | 0.17 | ~0.28 | <5.1 | 0.34 |
| 223 | 26 | ND | 12 | ND |
| 224 | ND | 0.94 | ND | 0.48 |
| 225 | ND | ND | ND | 4.6 |
| 226 | ND | 0.33 | ND | 0.32 |
| 227 | ND | ND | ND | 32 |
| 228 | ND | 0.50 | ND | 0.42 |
| 229 | ND | ND | ND | 2.0 |
| 230 | 2.3 | 3.4 | 1.5 | 3.6 |
| 231 | 0.87 | 1.2 | 0.39 | 0.97 |
| 232 | 0.47 | 0.85 | 0.27 | 0.70 |
| 233 | ND | 678 | ND | ND |
| 234 | ND | 15 | ND | 11 |
| 235 | ND | ND | ND | 25 |
| 236 | ND | ND | ND | 76 |
| 237 | ND | ND | ND | 2.5 |
| 238 | ND | ND | ND | 48 |
| 239 | ND | ND | ND | ~2819 |
| 240 | ND | ND | ND | 434 |
| 241 | ND | ND | ND | 610 |
| 242 | ND | ND | ND | 434 |
| 243 | ND | ND | ND | 808 |
| 244 | ND | ND | ND | 386 |
| 245 | ND | ND | ND | 72 |
| 246 | ND | ND | ND | 72 |
| 247 | ND | ND | ND | ~566.5 |
| 248 | ND | 53 | ND | 66 |
| 249 | ND | 245 | ND | ND |
| 250 | ND | 2.0 | ND | 1.9 |
| 251 | ND | 8.9 | ND | 7.2 |
| 252 | ND | 20 | ND | 16 |
| 253 | ND | 703 | ND | ND |
| 254 | ND | ND | ND | 452 |
| 255 | ND | 1.5 | ND | 1.6 |
| 256 | ND | ND | ND | 86 |
| 257 | ND | ND | ND | 115 |
| 258 | ND | ND | ND | 42 |
| 259 | ND | ND | ND | ~2118 |
| 260 | ND | ND | ND | 54 |
| 261 | ND | ND | ND | ~1797 |
| 262 | ND | ND | ND | 395 |
| 263 | ND | ND | ND | 0.88 |
| 264 | ND | ND | ND | 233 |
| 265 | ND | ND | ND | 375 |
| 266 | ND | ND | ND | 654 |
| 267 | ND | ND | ND | >2955 |
| 268 | ND | ND | ND | 311 |
| 269 | ND | ND | ND | ~1428 |
| 270 | ND | ND | ND | >2955 |
| 271 | ND | ND | ND | >2955 |
| 272 | ND | 1206 | ND | ND |
| 273 | ND | 757 | ND | ND |
| 274 | ND | ~14500 | ND | ND |
| 275 | ND | 987 | ND | ND |
| 276 | ND | ND | ND | ~1517 |
| 277 | ND | ND | ND | ~1297 |
| 278 | ND | 768 | ND | ND |
| 279 | ND | 24 | ND | 17 |
| 280 | ND | 71 | ND | 77 |
| 281 | ND | 1.9 | ND | 2.0 |
| 282 | ND | >2970 | ND | ND |
| 283 | ND | 387 | ND | ND |
| 284 | ND | 69 | ND | 64 |
| 285 | ND | 179 | ND | 111 |
| 286 | ND | 3.7 | ND | 2.0 |
| 287 | ND | ND | ND | 375 |
| 288 | ND | ND | ND | 350 |
| 289 | ND | ND | ND | 388 |
| 290 | ND | ND | ND | >2955 |
| 291 | ND | ND | ND | 104 |
| 292 | ND | 473 | ND | ND |
| 293 | ND | 3.6 | ND | 3.5 |
| 294 | ND | ~2589 | ND | ND |
| 295 | ND | >2970 | ND | ND |
| 296 | ND | 36 | ND | 39 |
| 297 | ND | ND | 0.72 | ND |
| 298 | ND | ND | ND | 62 |
| 299 | ND | ND | ND | 157 |
| 300 | ND | ND | ND | 2.8 |
| 301 | ND | ND | ND | 4.7 |
| 302 | ND | ND | ND | 116 |
| 303 | ND | ND | ND | 4.7 |
| 304 | ND | ND | ND | 263 |
| 305 | ND | ND | ND | 17 |
| 306 | ND | ND | ND | 568 |
| 307 | ND | ND | ND | 13 |
| 308 | ND | ND | ND | 329 |
| 309 | ND | ND | ND | 420 |
| 310 | ND | ND | ND | 11 |

TABLE 32-continued

PDE2 Ki's

| Ex # | Rhesus PDE2 Ki (nM) Lab A | Rhesus PDE2 Ki (nM) Lab B | Human PDE2 Ki (nM) Lab A | Human PDE2 Ki (nM) Lab B |
|---|---|---|---|---|
| 311 | ND | ND | ND | ~1209 |
| 312 | ND | ND | ND | ~1864 |
| 313 | ND | ND | ND | 22 |
| 314 | ND | ND | ND | 38 |
| 315 | ND | ND | ND | 3.3 |
| 316 | ND | ND | ND | 72 |
| 317 | ND | ND | ND | 150 |
| 318 | ND | ND | ND | 3.8 |
| 319 | ND | 283 | ND | ND |
| 320 | ND | ND | ND | 1.2 |
| 321 | ND | ND | ND | 33 |
| 322 | ND | ND | ND | 42 |
| 323 | ND | ND | ND | 798 |
| 324 | ND | ND | ND | 465 |
| 325 | ND | ND | ND | 3.7 |
| 326 | 134 | ND | 70 | ND |
| 327 | 93 | ND | 92 | ND |
| 328 | 22 | 33 | ~11 | 31 |
| 329 | ND | ND | ND | 2076 |
| 330 | ND | 2414 | ND | ND |
| 331 | ND | 1440 | ND | ND |
| 332 | ND | 8878 | ND | ND |
| 333 | ND | ~29050 | ND | ND |
| 334 | >1000 | ND | ND | ND |
| 335 | >1000 | ND | ND | ND |
| 336 | >1000 | 7662 | ND | ND |
| 337 | >1000 | ND | ND | ND |
| 338 | 113 | ND | 73 | ND |
| 339 | 292 | ND | ND | ND |
| 340 | ND | ND | ND | 2.2 |
| 341 | ND | ND | ND | 191 |
| 342 | ND | ND | ND | 2.5 |
| 343 | ND | ND | ND | 299 |
| 344 | ND | ND | ND | 26 |
| 345 | ND | ND | ND | 0.15 |
| 346 | ND | ND | ND | 34 |
| 347 | ND | ND | ND | 1030 |
| 348 | ND | ND | ND | 4.7 |
| 349 | ND | ND | ND | 373 |
| 350 | ND | ND | ND | 62 |
| 351 | ND | ND | ND | 1012 |

(ND = Not determined)

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound represented by structural formula I:

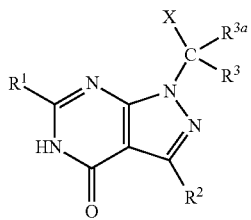

I or a pharmaceutically acceptable salt thereof, wherein:

X represents $ZC_{6-10}$aryl, said aryl optionally substituted with 1 to 3 groups of $R^a$;

Z represents a bond, —(CH2)$_n$-, —(C(O)NH—, —CH(OH)—, —C(CH$_3$)OH—, —(CH$_2$)$_n$NH—, or —(CH$_2$)$_n$NCH$_3$—;

$R^1$ represents $C_{1-6}$alkyl, (CH$_2$)$_{1-4}$OR, $C_{1-4}$haloalkyl, wherein said alkyl, are optionally substituted with 1 to 3 groups of $R^a$;

$R^2$ represents halo, $C_{1-6}$alkyl, (CH$_2$)$_n$OR, or $C_{1-4}$haloalkyl, said alkyl optionally substituted with 1 to 3 groups of $R^a$, $R^3$ and $R^{3a}$ independently represent hydrogen, $C_{1-6}$alkyl, or $C_{3-6}$ cycloalkyl, or $R^3$ and $R^{3a}$ can combine with the carbon atom to which they are attached to form a $C_{3-6}$cycloalkyl, said alkyl, and cycloalkyl, optionally substituted with 1 to 3 groups of $R^a$, R represents hydrogen or $C_{1-6}$alkyl, said alkyl optionally substituted with 1 to 3 groups of $R^a$, $R^a$ is selected from the group consisting of halo, CN, $C_{1-6}$alkyl, (CH$_2$)$_n$OR, (CH$_2$)$_n$C$_{1-4}$haloalkyl, O—C$_{1-4}$haloalkyl, SCF$_3$, SF$_5$, C$_{6-10}$aryl, C(O)N(CH$_3$)$_2$, NHOH, SO$_2$R, NR$_2$, OC(O)CH$_3$, NHC(O)CH$_3$, OCH$_2$C$_{6-10}$aryl, and C$_{3-6}$cycloalkyl, said cycloalkyl optionally substituted with 1 to 3 groups selected from $C_{1-6}$alkyl and $C_{1-4}$haloalkyl;

n represents 0, 1, 2, 3, or 4.

2. The compound according to claim 1 or a pharmaceutically acceptable salt thereof wherein Z is a bond.

3. The compound according claim 2 or a pharmaceutically acceptable salt thereof wherein X is optionally substituted phenyl.

4. The compound according to claim 1 or a pharmaceutically acceptable salt thereof wherein $R^1$ is selected from the group consisting of CH$_3$, (CH2)$_2$CH$_3$, CH$_2$(CH$_3$)$_2$, CH$_2$C(CH$_3$)$_3$, (CH$_2$)$_n$OCH$_3$, CH$_2$CH$_3$, CH(CH$_3$)$_2$, CH(CH$_3$)OH, (CH$_2$)$_2$OCH$_2$CH$_3$, CHF$_2$, CF$_3$, and CH$_2$F.

5. The compound according to claim 4 or a pharmaceutically acceptable salt thereof wherein $R^1$ is selected from the group consisting of CH$_3$, (CH2)$_2$CH$_3$, CH$_2$(CH$_3$)$_2$, CH$_2$C(CH$_3$)$_3$, (CH$_2$)$_n$OCH$_3$, CH$_2$CH$_3$, and CH(CH$_3$)$_2$.

6. The compound according to claim 1 or a pharmaceutically acceptable salt thereof wherein $R^2$ is selected from the group consisting of optionally substituted CH$_2$OH, CH$_3$, CH$_2$CN, CH(CH$_3$)OH, C(CH$_3$)$_2$OH, CH$_2$NHC(O)CH$_3$, CH$_2$C(CH$_3$)OH, CH$_2$OC(O)CH$_3$, CH$_2$SO$_2$CH$_3$, CH$_2$NHOH, CH$_2$F, CHF$_2$, (CH$_2$)$_n$CF$_3$, CH(CF$_3$)OH, CF$_2$CH$_2$OH, C(CH$_3$)CH$_2$OH, and CH$_2$oxetanyl.

7. The compound according to claim 6 or a pharmaceutically acceptable salt thereof wherein $R^2$ is selected from the group consisting of optionally substituted CH$_2$OH, CH$_3$, CH$_2$F, CHF$_2$, (CH$_2$)$_n$CF$_3$, and CF$_2$CH$_2$OH.

8. The compound according to claim 1 or a pharmaceutically acceptable salt thereof wherein each $R^3$ and $R^{3a}$ independently represents hydrogen, CH$_3$, CH(CH$_3$)$_2$, CH$_2$CH$_3$, CH$_2$OCH$_3$, C(CH$_3$)$_3$, CH$_2$CF$_3$, and optionally substituted cyclopropyl, cyclobutyl, cyclopentyl and cyclohexyl.

9. The compound according to claim 1 or a pharmaceutically acceptable salt thereof wherein one of $R^3$ and $R^{3a}$ is hydrogen and the other is selected from the group consisting of CH$_3$, CH(CH$_3$)$_2$, CH$_2$CH$_3$, CH2OCH3, C(CH$_3$)$_3$, CH$_2$CF$_3$, and optionally substituted cyclopropyl, cyclobutyl, cyclopentyl and cyclohexyl.

10. The compound according to claim 1 or a pharmaceutically acceptable salt thereof wherein one of $R^3$ and $R^{3a}$ is hydrogen and the other is CH$_3$, CH(CH$_3$)$_2$ or optionally substituted cyclopropyl.

11. The compound according to claim 1 or a pharmaceutically acceptable salt thereof wherein $R^3$ and $R^{3a}$ combine with the carbon atom to which they are attached to form oxetanyl, cyclopropyl, cyclobutyl, cyclopentyl or cyclohexyl.

12. The compound according to claim 1 or a pharmaceutically acceptable salt thereof represented by structural formula Ia:

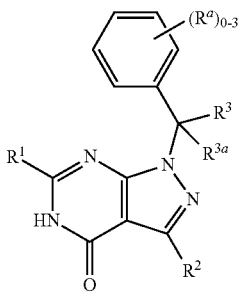

Ia wherein $R^1$, $R^2$, $R^3$, $R^{3a}$ and $R^a$ are as originally described.

13. The compound according claim 1 or a pharmaceutically acceptable salt thereof represented by structural formula Ib:

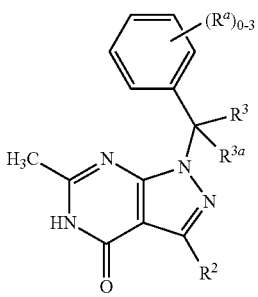

Ib or a pharmaceutically acceptable salt thereof wherein $R^2$ is selected from the group consisting of optionally substituted $CH_2OH$, $CH_3$, $CH_2CN$, $CH(CH_3)OH$, $C(CH_3)_2OH$, $CH_2NHC(O)CH_3$, $CH_2C(CH_3)OH$, $CH_2OC(O)CH_3$, $CH_2SO_2CH_3$, $CH_2NHOH$, and $CH_2OCH_2phenyl$, $CH_2F$, $CHF_2$, $(CH_2)_nCF_3$, $CF_2CH_2OH$, $C(CH_3)CH_2OH$, $CH(CF_3)$, and $CH_2oxetanyl$, $R^3$ and $R^{3a}$ independently represents hydrogen, $CH_3$, $CH(CH_3)_2$, $CH_2CH_3$, $CH_2OCH3$, $C(CH_3)_3$, $CH_2CF_3$, and optionally substituted cyclopropyl, cyclobutyl, cyclopentyl and cyclohexyl or $R^3$ and $R^{3a}$ combine with the carbon atom to which they are attached to form oxetanyl, cyclopropyl, cyclobutyl, cyclopentyl or cyclohexyl, and the $R^a$ on the phenyl ring of formula Ib is selected from fluorine, chlorine, iodine, bromine, $CH_3$, $CH(CH_3)_2$, $C(CH_3)_3$, $(CH_2)_nOCH_3$, $OC(CH_3)_2$, $C(CH_3)F_2$, $CF_2CF_3$, $CH_2F$, $CHF_2$, $CF_3$, $OCHF_2$, $OCF_3$, $SF_5$, and optionally substituted cyclopropyl.

14. The compound according to claim 13 or a pharmaceutically acceptable salt thereof wherein the invention of formula Ib is realized when $R^2$ is $CH_2OH$, $CH_2F$, $CHF_2$ or $CH_3$, one of $R^3$ and $R^{3a}$ is hydrogen and the other is selected from the group consisting of $CH_3$, $CH(CH_3)_2$, $CH_2CH_3$, $C(CH_3)_3$, $CH_2CF_3$, and cyclopropyl, or $R^3$ and $R^{3a}$ combine with the carbon atom to which they are attached to form an optionally substituted $C_{3-6}$cycloalkyl selected from cyclopropyl, cyclobutyl, cyclopentyl and cyclohexyl, and the $R^a$ on the phenyl ring of formula Ia is selected from fluorine, iodine, $CH_3$, $CH(CH_3)_2$, $C(CH_3)_3$, $(CH_2)_nOCH_3$, $OC(CH_3)_2$, $C(CH_3)F_2$, $CF_2CF_3$, $CH_2F$, $CHF_2$, $CF_3$, $OCHF_2$, $OCF_3$, $SF_5$, and cyclopropyl.

15. A compound which is:
1-(1-(3-Fluoro-4-(trifluoromethyl)phenyl)ethyl)-3-(hydroxymethyl)-6-methyl-1H-pyrazolo[3,4-d]pyrimidin-4(5H)-one,
3-(Hydroxymethyl)-6-methyl-1-(1-p-tolylethyl)-1H-pyrazolo[3,4-d]pyrimidin-4(5H)-one,
1-(1-(4-Cyclopropylphenyl)ethyl)-3-(hydroxymethyl)-6-methyl-1H-pyrazolo[3,4-d]pyrimidin-4(5H)-one,
3-(Hydroxymethyl)-6-methyl-1-(1-(4-(trifluoromethoxy)phenyl)ethyl)-1H-pyrazolo[3,4-d]pyrimidin-4(5H)-one,
3-(Hydroxymethyl)-6-methyl-1-(2-methyl-1-(4-(trifluoromethyl)phenyl)propyl)-1H-pyrazolo[3,4-d]pyrimidin-4(5H)-one,
3-(Hydroxymethyl)-6-methyl-1-(2,2,2-trifluoro-1-(4-(trifluoromethyl)phenyl)ethyl)-1H-pyrazolo[3,4-d]pyrimidin-4(5H)-one,
3-(Hydroxymethyl)-6-methyl-1-(1-(4-(trifluoromethyl)phenyl)ethyl)-1H-pyrazolo[3,4-d]pyrimidin-4(5H)-one,
3-(Hydroxymethyl)-6-methyl-1-[4-(trifluoromethyl)benzyl]-1,5-dihydro-4H-pyrazolo[3,4-d]pyrimidin-4-one,
3-(Hydroxymethyl)-6-methyl-1-{1-methyl-1-[4-(trifluoromethyl)phenyl]ethyl}-1,5-dihydro-4H-pyrazolo[3,4-d]pyrimidin-4-one,
(R)-1-(1-(3-Fluoro-4-(trifluoromethoxy)phenyl)ethyl)-3-(hydroxymethyl)-6-methyl-1H-pyrazolo[3,4-d]pyrimidin-4(5H)-one,
(S)-1-(1-(3-Fluoro-4-(trifluoromethoxy)phenyl)ethyl)-3-(hydroxymethyl)-6-methyl-1H-pyrazolo[3,4-d]pyrimidin-4(5H)-one,
(R)-1-(1-(3-Fluoro-4-(trifluoromethyl)phenyl)ethyl)-3-(hydroxymethyl)-6-methyl-1H-pyrazolo[3,4-d]pyrimidin-4(5H)-one,
(S)-1-(1-(3-Fluoro-4-(trifluoromethyl)phenyl)ethyl)-3-(hydroxymethyl)-6-methyl-1H-pyrazolo[3,4-d]pyrimidin-4(5H)-one,
(R)-1-((3-Fluoro-4-(trifluoromethyl)phenyl)(1-methylcyclopropyl)methyl)-3-(hydroxymethyl)-6-methyl-1H-pyrazolo[3,4-d]pyrimidin-4(5H)-one,
(S)-1-((3-Fluoro-4-(trifluoromethyl)phenyl)(1-methylcyclopropyl)methyl)-3-(hydroxymethyl)-6-methyl-1H-pyrazolo[3,4-d]pyrimidin-4(5H)-one,
(R)-1-(1-(2-Fluoro-4-(trifluoromethyl)phenyl)ethyl)-3-(hydroxymethyl)-6-methyl-1H-pyrazolo[3,4-d]pyrimidin-4(5H)-one,
(S)-1-(1-(2-Fluoro-4-(trifluoromethyl)phenyl)ethyl)-3-(hydroxymethyl)-6-methyl-1H-pyrazolo[3,4-d]pyrimidin-4(5H)-one,
(R)-1-(1-(2-Chloro-4-(trifluoromethyl)phenyl)ethyl)-3-(hydroxymethyl)-6-methyl-1H-pyrazolo[3,4-d]pyrimidin-4(5H)-one,
(S)-1-(1-(2-Chloro-4-(trifluoromethyl)phenyl)ethyl)-3-(hydroxymethyl)-6-methyl-1H-pyrazolo[3,4-d]pyrimidin-4(5H)-one,
(R)-1-(1-(4-(Difluoromethoxy)phenyl)ethyl)-3-(hydroxymethyl)-6-methyl-1H-pyrazolo[3,4-d]pyrimidin-4(5H)-one, (S)-1-(1-(4-(Difluoromethoxy)phenyl)ethyl)-3-(hydroxymethyl)-6-methyl-1H-pyrazolo[3,4-d]pyrimidin-4(5H)-one,
(R)-3-(Hydroxymethyl)-6-methyl-1-(1-(4-(trifluoromethylthio)phenyl)ethyl)-1H-pyrazolo[3,4-d]pyrimidin-4(5H)-one,
(S)-3-(Hydroxymethyl)-6-methyl-1-(1-(4-(trifluoromethylthio)phenyl)ethyl)-1H-pyrazolo[3,4-d]pyrimidin-4(5H)-one,
(R)-3-(Hydroxymethyl)-6-methyl-1-((1-methylcyclopropyl)(4-(trifluoromethyl)phenyl)methyl)-1H-pyrazolo[3,4-d]pyrimidin-4(5H)-one,
(S)-3-(Hydroxymethyl)-6-methyl-1-((1-methylcyclopropyl)(4-(trifluoromethyl)phenyl)methyl)-1H-pyrazolo[3,4-d]pyrimidin-4(5H)-one,
(R)-3-(Hydroxymethyl)-6-methyl-1-{1-[4-(trifluoromethyl)phenyl]ethyl}-1,5-dihydro-4H-pyrazolo[3,4-d]pyrimidin-4-one,
(S)-3-(Hydroxymethyl)-6-methyl-1-{1-[4-(trifluoromethyl)phenyl]ethyl}-1,5-dihydro-4H-pyrazolo[3,4-d]pyrimidin-4-one,
1-(Cyclopropyl(4-(trifluoromethyl)phenyl)methyl)-3-(hydroxymethyl)-6-methyl-1H-pyrazolo[3,4-d]pyrimidin-4(5H)-one,
6-(1-Hydroxyethyl)-3-methyl-1-(1-(4-(trifluoromethyl)phenyl)ethyl)-1H-pyrazolo[3,4-d]pyrimidin-4(5H)-one,
6-(3-Hydroxybenzyl)-3-methyl-1-(1-(4-(trifluoromethyl)phenyl)ethyl)-1H-pyrazolo[3,4-d]pyrimidin-4(5H)-one,
6-(2-Hydroxybenzyl)-3-methyl-1-(1-(4-(trifluoromethyl)phenyl)ethyl)-1H-pyrazolo[3,4-d]pyrimidin-4(5H)-one,
N,N-Dimethyl-3-(3-methyl-4-oxo-1-(1-(4-(trifluoromethyl)phenyl)ethyl)-4,5-dihydro-1H-pyrazolo[3,4-d]pyrimidin-6-yl)propanamide,
3-Methyl-6-(tetrahydrofuran-3-yl)-1-(1-(4-(trifluoromethyl)phenyl)ethyl)-1H-pyrazolo[3,4-d]pyrimidin-4(5H)-one,
6-(2-Methoxyethyl)-3-methyl-1-(1-(4-(trifluoromethyl)phenyl)ethyl)-1H-pyrazolo[3,4-d]pyrimidin-4(5H)-one,
6-(2-Ethoxyethyl)-3-methyl-1-(1-(4-(trifluoromethyl)phenyl)ethyl)-1H-pyrazolo[3,4-d]pyrimidin-4(5H)-one,
(R)-3,6-Dimethyl-1-(1-(4-(trifluoromethyl)phenyl)ethyl)-1,5-dihydro-4H-pyrazolo[3,4-d]pyrimidin-4-one,
(S)-3,6-Dimethyl-1-(1-(4-(trifluoromethyl)phenyl)ethyl)-1,5-dihydro-4H-pyrazolo[3,4-d]pyrimidin-4-one,
6-Ethyl-3-methyl-1-{1-[4-(trifluoromethyl)phenyl]ethyl}-1,5-dihydro-4H-pyrazolo[3,4-d]pyrimidin-4-one,
6-Cyclobutyl-3-methyl-1-{1-[4-(trifluoromethyl)phenyl]ethyl}-1,5-dihydro-4H-pyrazolo[3,4-d]pyrimidin-4-one,
6-Cyclopentyl-3-methyl-1-{1-[4-(trifluoromethyl)phenyl]ethyl}-1,5-dihydro-4H-pyrazolo[3,4-d]pyrimidin-4-one,
3-Methyl-6-propyl-1-{1-[4-(trifluoromethyl)phenyl]ethyl}-1,5-dihydro-4H-pyrazolo[3,4-d]pyrimidin-4-one,
6-Cyclopropyl-3-methyl-1-{1-[4-(trifluoromethyl)phenyl]ethyl}-1,5-dihydro-4H-pyrazolo[3,4-d]pyrimidin-4-one,
3-Methyl-6-(1-methylethyl)-1-{1-[4-(trifluoromethyl)phenyl]ethyl}-1,5-dihydro-4H-pyrazolo[3,4-d]pyrimidin-4-one,
6-(3,4-Dimethoxybenzyl)-3-methyl-1-{1-[4-(trifluoromethyl)phenyl]ethyl}-1,5-dihydro-4H-pyrazolo[3,4-d]pyrimidin-4-one,
6-(3-Methoxybenzyl)-3-methyl-1-{1-[4-(trifluoromethyl)phenyl]ethyl}-1,5-dihydro-4H-pyrazolo[3,4-d]pyrimidin-4-one,
6-(4-Methoxybenzyl)-3-methyl-1-{1-[4-(trifluoromethyl)phenyl]ethyl}-1,5-dihydro-4H-pyrazolo[3,4-d]pyrimidin-4-one,
6-(3-Methoxyphenyl)-3-methyl-1-{1-[4-(trifluoromethyl)phenyl]ethyl}-1,5-dihydro-4H-pyrazolo[3,4-d]pyrimidin-4-one,
6-(Methoxymethyl)-3-methyl-1-{1-[4-(trifluoromethyl)phenyl]ethyl}-1,5-dihydro-4H-pyrazolo[3,4-d]pyrimidin-4-one,
6-Furan-2-yl-3-methyl-1-{1-[4-(trifluoromethyl)phenyl]ethyl}-1,5-dihydro-4H-pyrazolo[3,4-d]pyrimidin-4-one,
3-Methyl-6-quinoxalin-2-yl-1-{1-[4-(trifluoromethyl)phenyl]ethyl}-1,5-dihydro-4H-pyrazolo[3,4-d]pyrimidin-4-one,
6-(Fluoromethyl)-3-methyl-1-{1-[4-(trifluoromethyl)phenyl]ethyl}-1,5-dihydro-4H-pyrazolo[3,4-d]pyrimidin-4-one,
3-Methyl-6-pyridin-2-yl-1-{1-[4-(trifluoromethyl)phenyl]ethyl}-1,5-dihydro-4H-pyrazolo[3,4-d]pyrimidin-4-one,
3-Methyl-6-(1-methyl-1H-pyrazol-4-yl)-1-{1-[4-(trifluoromethyl)phenyl]ethyl}-1,5-dihydro-4H-pyrazolo[3,4-d]pyrimidin-4-one,
6-(2,5-Dimethyl-1,3-oxazol-4-yl)-3-methyl-1-{1-[4-(trifluoromethyl)phenyl]ethyl}-1,5-dihydro-4H-pyrazolo[3,4-d]pyrimidin-4-one,
3-Methyl-6-(tetrahydro-2H-pyran-4-yl)-1-{1-[4-(trifluoromethyl)phenyl]ethyl}-1,5-dihydro-4H-pyrazolo[3,4-d]pyrimidin-4-one,
(R)-1-(2,2-Dimethyl-1-(4-(trifluoromethyl)phenyl)propyl)-6-methyl-3-(2,2,2-trifluoroethyl)-1H-pyrazolo[3,4-d]pyrimidin-4(5H)-one,
(S)-1-(2,2-Dimethyl-1-(4-(trifluoromethyl)phenyl)propyl)-6-methyl-3-(2,2,2-trifluoroethyl)-1H-pyrazolo[3,4-d]pyrimidin-4(5H)-one,
(R)-6-Methyl-1-((1-methylcyclopropyl)(4-(trifluoromethyl)phenyl)methyl)-3-(2,2,2-trifluoroethyl)-1H-pyrazolo[3,4-d]pyrimidin-4(5H)-one,
(S)-6-Methyl-1-((1-methylcyclopropyl)(4-(trifluoromethyl)phenyl)methyl)-3-(2,2,2-trifluoroethyl)-1H-pyrazolo[3,4-d]pyrimidin-4(5H)-one,
(R)-1-(1-(3-Fluoro-4-(trifluoromethyl)phenyl)-2,2-dimethylpropyl)-6-methyl-3-(2,2,2-trifluoroethyl)-1H-pyrazolo[3,4-d]pyrimidin-4(5H)-one,
(S)-1-(1-(3-Fluoro-4-(trifluoromethyl)phenyl)-2,2-dimethylpropyl)-6-methyl-3-(2,2,2-trifluoroethyl)-1H-pyrazolo[3,4-d]pyrimidin-4(5H)-one,
(R)-1-((3-Fluoro-4-(trifluoromethyl)phenyl)(1-methylcyclopropyl)methyl)-6-methyl-3-(2,2,2-trifluoroethyl)-1H-pyrazolo[3,4-d]pyrimidin-4(5H)-one,
(S)-1-((3-Fluoro-4-(trifluoromethyl)phenyl)(1-methylcyclopropyl)methyl)-6-methyl-3-(2,2,2-trifluoroethyl)-1H-pyrazolo[3,4-d]pyrimidin-4(5H)-one,
(R)-6-Methyl-3-(2,2,2-trifluoroethyl)-1-(1-(4-(trifluoromethyl)phenyl)ethyl)-1H-pyrazolo[3,4-d]pyrimidin-4(5H)-one, (S)-6-Methyl-3-(2,2,2-trifluoroethyl)-1-(1-(4-(trifluoromethyl)phenyl)ethyl)-1H-pyrazolo[3,4-d]pyrimidin-4(5H)-one,
(R)-6-Methyl-3-(2,2,2-trifluoroethyl)-1-(1-(4-(trifluoromethoxy)phenyl)ethyl)-1H-pyrazolo[3,4-d]pyrimidin-4(5H)-one,
(S)-6-Methyl-3-(2,2,2-trifluoroethyl)-1-(1-(4-(trifluoromethoxy)phenyl)ethyl)-1H-pyrazolo[3,4-d]pyrimidin-4(5H)-one,
(R)-6-Methyl-3-(trifluoromethyl)-1-(1-(4-(trifluoromethyl)phenyl)ethyl)-1H-pyrazolo[3,4-d]pyrimidin-4(5H)-one,
(S)-6-Methyl-3-(trifluoromethyl)-1-(1-(4-(trifluoromethyl)phenyl)ethyl)-1H-pyrazolo[3,4-d]pyrimidin-4(5H)-one,
(R, R)-6-Methyl-3-(-tetrahydrofuran-2-yl)-1-(-1-(4-(trifluoromethyl)phenyl)ethyl)-1H-pyrazolo[3,4-d]pyrimidin-4(5H)-one,
(R, S)-6-Methyl-3-(-tetrahydrofuran-2-yl)-1-(-1-(4-(trifluoromethyl)phenyl)ethyl)-1H-pyrazolo[3,4-d]pyrimidin-4(5H)-one,
(S, R)-6-Methyl-3-(-tetrahydrofuran-2-yl)-1-(-1-(4-(trifluoromethyl)phenyl)ethyl)-1H-pyrazolo[3,4-d]pyrimidin-4(5H)-one,
(S, S)-6-Methyl-3-(-tetrahydrofuran-2-yl)-1-(-1-(4-(trifluoromethyl)phenyl)ethyl)-1H-pyrazolo[3,4-d]pyrimidin-4(5H)-one,
(R)-3-(Furan-2-yl)-6-methyl-1-(1-(4-(trifluoromethyl)phenyl)ethyl)-1H-pyrazolo[3,4-d]pyrimidin-4(5H)-one,
(S)-3-(Furan-2-yl)-6-methyl-1-(1-(4-(trifluoromethyl)phenyl)ethyl)-1H-pyrazolo[3,4-d]pyrimidin-4(5H)-one,
(R)-3-(Hydroxymethyl)-6-methyl-1-(1-(4-(pentafluorothio)phenyl)ethyl)-1H-pyrazolo[3,4-d]pyrimidin-4(5H)-one,
(S)-3-(Hydroxymethyl)-6-methyl-1-(1-(4-(pentafluorothio)phenyl)ethyl)-1H-pyrazolo[3,4-d]pyrimidin-4(5H)-one,
3-(Hydroxymethyl)-6-methyl-1-(1-(4-(trifluoromethyl)phenyl)cyclobutyl)-1H-pyrazolo[3,4-d]pyrimidin-4(5H)-one,
3-(Hydroxymethyl)-6-methyl-1-(3-(4-(trifluoromethyl)phenyl)oxetan-3-yl)-1H-pyrazolo[3,4-d]pyrimidin-4(5H)-one,
(R)-3-(Hydroxymethyl)-6-methyl-1-(1-(4-(1-(trifluoromethyl)cyclopropyl)phenyl)ethyl)-1H-pyrazolo[3,4-d]pyrimidin-4(5H)-one,
(S)-3-(Hydroxymethyl)-6-methyl-1-(1-(4-(1-(trifluoromethyl)cyclopropyl)phenyl)ethyl)-1H-pyrazolo[3,4-d]pyrimidin-4(5H)-one,
(R)-1-(2,2-Dimethyl-1-(4-(trifluoromethyl)phenyl)-propyl)-3-(hydroxymethyl)-6-methyl-1H-pyrazolo[3,4-d]pyrimidin-4(5H)-one,
(S)-1-(2,2-Dimethyl-1-(4-(trifluoromethyl)phenyl)-propyl)-3-(hydroxymethyl)-6-methyl-1H-pyrazolo[3,4-d]pyrimidin-4(5H)-one,
(R)-3-(Hydroxymethyl)-6-methyl-1-(2-methyl-1-(4-(trifluoromethoxy)phenyl)propyl)-1H-pyrazolo[3,4-d]pyrimidin-4(5H)-one,
(S)-3-(Hydroxymethyl)-6-methyl-1-(2-methyl-1-(4-(trifluoromethoxy)phenyl)propyl)-1H-pyrazolo[3,4-d]pyrimidin-4(5H)-one,
(R)-1-(1-(3-Fluoro-4-(trifluoromethyl)phenyl)-2-methylpropyl)-3-(hydroxymethyl)-6-methyl-1H-pyrazolo[3,4-d]pyrimidin-4(5H)-one,
(S)-1-(1-(3-Fluoro-4-(trifluoromethyl)phenyl)-2-methylpropyl)-3-(hydroxymethyl)-6-methyl-1H-pyrazolo[3,4-d]pyrimidin-4(5H)-one,
(R)-1-((4-tert-Butylphenyl)(cyclopropyl)methyl)-3-(hydroxymethyl)-6-methyl-1H-pyrazolo[3,4-d]pyrimidin-4(5H)-one,
(S)-1-((4-tert-Butylphenyl)(cyclopropyl)methyl)-3-(hydroxymethyl)-6-methyl-1H-pyrazolo[3,4-d]pyrimidin-4(5H)-one,
(R)-1-(Cyclopropyl(3-fluoro-4-(trifluoromethyl)phenyl)methyl)-3-(hydroxymethyl)-6-methyl-1H-pyrazolo[3,4-d]pyrimidin-4(5H)-one,
(S)-1-(Cyclopropyl(3-fluoro-4-(trifluoromethyl)phenyl)methyl)-3-(hydroxymethyl)-6-methyl-1H-pyrazolo[3,4-d]pyrimidin-4(5H)-one,
(R)-1-(Cyclopropyl(3-fluoro-4-(trifluoromethoxy)phenyl)methyl)-3-(hydroxymethyl)-6-methyl-1H-pyrazolo[3,4-d]pyrimidin-4(5H)-one,
(S)-1-(Cyclopropyl(3-fluoro-4-(trifluoromethoxy)phenyl)methyl)-3-(hydroxymethyl)-6-methyl-1H-pyrazolo[3,4-d]pyrimidin-4(5H)-one,
(R)-1-(Cyclopropyl(4-(trifluoromethoxy)phenyl)methyl)-3-(hydroxymethyl)-6-methyl-1H-pyrazolo[3,4-d]pyrimidin-4(5H)-one,
(S)-1-(Cyclopropyl(4-(trifluoromethoxy)phenyl)methyl)-3-(hydroxymethyl)-6-methyl-1H-pyrazolo[3,4-d]pyrimidin-4(5H)-one,
(R)-3-(Hydroxymethyl)-6-methyl-1-(3,3,3-trifluoro-1-(4-(trifluoromethyl)phenyl)propyl)-1H-pyrazolo[3,4-d]pyrimidin-4(5H)-one,
(S)-3-(Hydroxymethyl)-6-methyl-1-(3,3,3-trifluoro-1-(4-(trifluoromethyl)phenyl)propyl)-1H-pyrazolo[3,4-d]pyrimidin-4(5H)-one,
(R)-3-(Hydroxymethyl)-6-methyl-1-(1-(4-(perfluoroethyl)phenyl)ethyl)-1H-pyrazolo[3,4-d]pyrimidin-4(5H)-one,
(S)-3-(Hydroxymethyl)-6-methyl-1-(1-(4-(perfluoroethyl)phenyl)ethyl)-1H-pyrazolo[3,4-d]pyrimidin-4(5H)-one,
(R)-3-(Hydroxymethyl)-1-(2-methoxy-1-(4-(trifluoromethyl)phenyl)ethyl)-6-methyl-1H-pyrazolo[3,4-d]pyrimidin-4(5H)-one,
(S)-3-(Hydroxymethyl)-1-(2-methoxy-1-(4-(trifluoromethyl)phenyl)ethyl)-6-methyl-1H-pyrazolo[3,4-d]pyrimidin-4(5H)-one,
(R)-3-(Hydroxymethyl)-6-methyl-1-(5-(trifluoromethyl)-2,3-dihydro-1H-inden-1-yl)-1H-pyrazolo[3,4-d]pyrimidin-4(5H)-one,
(S)-3-(Hydroxymethyl)-6-methyl-1-(5-(trifluoromethyl)-2, 3-dihydro-1H-inden-1-yl)-1H-pyrazolo[3,4-d]pyrimidin-4(5H)-one,
(R)-1-(1-(2-Fluoro-4-(trifluoromethoxy)phenyl)ethyl)-3-(hydroxymethyl)-6-methyl-1H-pyrazolo[3,4-d]pyrimidin-4(5H)-one,
(S)-1-(1-(2-Fluoro-4-(trifluoromethoxy)phenyl)ethyl)-3-(hydroxymethyl)-6-methyl-1H-pyrazolo[3,4-d]pyrimidin-4(5H)-one,
(R)-3-(Hydroxymethyl)-6-methyl-1-(1-(3-methyl-4-(trifluoromethyl)phenyl)ethyl)-1H-pyrazolo[3,4-d]pyrimidin-4(5H)-one,
(S)-3-(Hydroxymethyl)-6-methyl-1-(1-(3-methyl-4-(trifluoromethyl)phenyl)ethyl)-1H-pyrazolo[3,4-d]pyrimidin-4(5H)-one,
(R)-3-(Hydroxymethyl)-6-methyl-1-(1-(2-methyl-4-(trifluoromethyl)phenyl)ethyl)-1H-pyrazolo[3,4-d]pyrimidin-4(5H)-one, (S)-3-(Hydroxymethyl)-6-methyl-1-(1-(2-methyl-4-(trifluoromethyl)phenyl)ethyl)-1H-pyrazolo[3,4-d]pyrimidin-4(5H)-one,
(R)-1-(1-(4-(Difluoromethyl)phenyl)ethyl)-3-(hydroxymethyl)-6-methyl-1H-pyrazolo[3,4-d]pyrimidin-4(5H)-one,
(S)-1-(1-(4-(Difluoromethyl)phenyl)ethyl)-3-(hydroxymethyl)-6-methyl-1H-pyrazolo[3,4-d]pyrimidin-4(5H)-one,
(R)-1-(1-(4-(Difluoromethoxy)-3-fluorophenyl)ethyl)-3-(hydroxymethyl)-6-methyl-1H-pyrazolo[3,4-d]pyrimidin-4(5H)-one,
(S)-1-(1-(4-(Difluoromethoxy)-3-fluorophenyl)ethyl)-3-(hydroxymethyl)-6-methyl-1H-pyrazolo[3,4-d]pyrimidin-4(5H)-one,
(R)-1-(1-(2,2-Difluorobenzo[d][1,3]dioxol-5-yl)ethyl)-3-(hydroxymethyl)-6-methyl-1H-pyrazolo[3,4-d]pyrimidin-4(5H)-one,
(S)-1-(1-(2,2-Difluorobenzo[d][1,3]dioxol-5-yl)ethyl)-3-(hydroxymethyl)-6-methyl-1H-pyrazolo[3,4-d]pyrimidin-4(5H)-one,
(R)-1-(1-(4-(1,1-Difluoroethyl)phenyl)ethyl)-3-(hydroxymethyl)-6-methyl-1H-pyrazolo[3,4-d]pyrimidin-4(5H)-one,
(S)-1-(1-(4-(1,1-Difluoroethyl)phenyl)ethyl)-3-(hydroxymethyl)-6-methyl-1H-pyrazolo[3,4-d]pyrimidin-4(5H)-one,
(R)-1-(1-(4-(Difluoromethoxy)-2-fluorophenyl)ethyl)-3-(hydroxymethyl)-6-methyl-1H-pyrazolo[3,4-d]pyrimidin-4(5H)-one,
(S)-1-(1-(4-(Difluoromethoxy)-2-fluorophenyl)ethyl)-3-(hydroxymethyl)-6-methyl-1H-pyrazolo[3,4-d]pyrimidin-4(5H)-one,
(R)-3-(Hydroxymethyl)-6-methyl-1-(1-(4-(pentafluorothio)phenyl)ethyl)-1H-pyrazolo[3,4-d]pyrimidin-4(5H)-one,
(S)-3-(Hydroxymethyl)-6-methyl-1-(1-(4-(pentafluorothio)phenyl)ethyl)-1H-pyrazolo[3,4-d]pyrimidin-4(5H)-one,
(R)-3-(Hydroxymethyl)-6-methyl-1-(1-(4-(2,2,2-trifluoroethyl)phenyl)ethyl)-1H-pyrazolo[3,4-d]pyrimidin-4(5H)-one,
(S)-3-(Hydroxymethyl)-6-methyl-1-(1-(4-(2,2,2-trifluoroethyl)phenyl)ethyl)-1H-pyrazolo[3,4-d]pyrimidin-4(5H)-one,
(R)-3-(Hydroxymethyl)-6-methyl-1-((trans)-4-(trifluoromethyl)cyclohexyl)ethyl)-1H-pyrazolo[3,4-d]-pyrimidin-4(5H)-one,
(S)-3-(Hydroxymethyl)-6-methyl-1-((trans)-4-(trifluoromethyl)cyclohexyl)ethyl)-1H-pyrazolo[3,4-d]pyrimidin-4(5H)-one,
(R)-1-(1-(3-Fluoro-4-(trifluoromethoxy)phenyl)-2-methylpropyl)-3-(hydroxyl-methyl)-6-methyl-1H-pyrazolo-[3,4-d]pyrimidin-4(5H)-one,
(S)-1-(1-(3-Fluoro-4-(trifluoromethoxy)phenyl)-2-methylpropyl)-3-(hydroxymethyl)-6-methyl-1H-pyrazolo[3,4-d]pyrimidin-4(5H)-one,
(R)-1-(1-(3-Fluoro-4-(trifluoromethyl)phenyl)-2,2-dimethylpropyl)-3-(hydroxyl-methyl)-6-methyl-1H-pyrazolo-[3,4-d]pyrimidin-4(5H)-one,
(S)-1-(1-(3-Fluoro-4-(trifluoromethyl)phenyl)-2,2-dimethylpropyl)-3-(hydroxyl-methyl)-6-methyl-1H-pyrazolo-[3,4-d]pyrimidin-4(5H)-one,
(R)-3-(Hydroxymethyl)-6-methyl-1-(1-(6-(trifluoromethyl)pyridin-3-yl)ethyl)-1H-pyrazolo[3,4-d]pyrimidin-4(5H)-one,
(S)-3-(Hydroxymethyl)-6-methyl-1-(1-(6-(trifluoromethyl)pyridin-3-yl)ethyl)-1H-pyrazolo[3,4-d]pyrimidin-4(5H)-one,
(R)-3-(Hydroxymethyl)-6-methyl-1-(1-(4-(trifluoromethyl)phenyl)propyl)-1H-pyrazolo[3,4-d]pyrimidin-4(5H)-one,
(S)-3-(Hydroxymethyl)-6-methyl-1-(1-(4-(trifluoromethyl)phenyl)propyl)-1H-pyrazolo[3,4-d]pyrimidin-4(5H)-one,
(R)-3-(Hydroxymethyl)-6-methyl-1-(1-(4-(trifluoromethoxy)phenyl)propyl)-1H-pyrazolo[3,4-d]pyrimidin-4(5H)-one,
(S)-3-(Hydroxymethyl)-6-methyl-1-(1-(4-(trifluoromethoxy)phenyl)propyl)-1H-pyrazolo[3,4-d]pyrimidin-4(5H)-one,
(R)-1-(1-(2,6-Difluoro-4-(trifluoromethyl)phenyl)-ethyl)-3-(hydroxymethyl)-6-methyl-1H-pyrazolo[3,4-d]pyrimidin-4(5H)-one,
(S)-1-(1-(2,6-Difluoro-4-(trifluoromethyl)phenyl)-ethyl)-3-(hydroxymethyl)-6-methyl-1H-pyrazolo[3,4-d]pyrimidin-4(5H)-one,
(R)-3-(Hydroxymethyl)-1-(1-(3-iodo-4-(trifluoromethyl-)phenyl)ethyl)-6-methyl-1,5-dihydro-4H-pyrazolo[3,4-d]pyrimidin-4-one,
(S)-3-(Hydroxymethyl)-1-(1-(3-iodo-4-(trifluoromethyl-)phenyl)ethyl)-6-methyl-1,5-dihydro-4H-pyrazolo[3,4-d]pyrimidin-4-one,
(R)-3-(Hydroxymethyl)-1-(1-(2-iodo-4-(trifluoromethyl-)phenyl)ethyl)-6-methyl-1,5-dihydro-4H-pyrazolo[3,4-d]pyrimidin-4-one,
(S)-3-(Hydroxymethyl)-1-(1-(2-iodo-4-(trifluoromethyl-)phenyl)ethyl)-6-methyl-1,5-dihydro-4H-pyrazolo[3,4-d]pyrimidin-4-one,
3-(Hydroxymethyl)-6-methyl-1-(1-(4-(trifluoromethyl)phenyl)cyclopropyl)-1H-pyrazolo[3,4-d]pyrimidin-4(5H)-one,
(R)-3-(Hydroxymethyl)-6-methyl-1-(1-(4-(1-methylcyclopropyl)phenyl)ethyl)-1H-pyrazolo[3,4-d]pyrimidin-4(5H)-one,
(S)-3-(Hydroxymethyl)-6-methyl-1-(1-(4-(1-methylcyclopropyl)phenyl)ethyl)-1H-pyrazolo[3,4-d]pyrimidin-4(5H)-one,
(R)-3-(Hydroxymethyl)-6-methyl-1-(1-(6-(trifluoromethyl)pyridazin-3-yl)ethyl)-1H-pyrazolo[3,4-d]pyrimidin-4(5H)-one,
(S)-3-(Hydroxymethyl)-6-methyl-1-(1-(6-(trifluoromethyl)pyridazin-3-yl)ethyl)-1H-pyrazolo[3,4-d]pyrimidin-4(5H)-one,
(R)-3-(Hydroxymethyl)-6-methyl-1-(1-(1-(2,2,2-trifluoroethyl)-1H-1,2,4-triazol-3-yl)ethyl)-1H-pyrazolo[3,4-d]pyrimidin-4(5H)-one,
(S)-3-(Hydroxymethyl)-6-methyl-1-(1-(1-(2,2,2-trifluoroethyl)-1H-1,2,4-triazol-3-yl)ethyl)-1H-pyrazolo[3,4-d]pyrimidin-4(5H)-one,
(R)-3-(Hydroxymethyl)-6-methyl-1-(1-(1-(2,2,2-trifluoroethyl)-1H-pyrazol-4-yl)ethyl)-1H-pyrazolo[3,4-d]pyrimidin-4(5H)-one,
(S)-3-(Hydroxymethyl)-6-methyl-1-(1-(1-(2,2,2-trifluoroethyl)-1H-pyrazol-4-yl)ethyl)-1H-pyrazolo[3,4-d]pyrimidin-4(5H)-one,
(R)-3-(Hydroxymethyl)-6-methyl-1-(1-(5-(trifluoromethyl)pyridin-2-yl)ethyl)-1H-pyrazolo[3,4-d]pyrimidin-4(5H)-one,
(S)-3-(Hydroxymethyl)-6-methyl-1-(1-(5-(trifluoromethyl)pyridin-2-yl)ethyl)-1H-pyrazolo[3,4-d]pyrimidin-4(5H)-one, (R)-1-(1-(5-Chlorothiophen-2-yl)ethyl)-3-(hydroxymethyl)-6-methyl-1H-pyrazolo[3,4-d]pyrimidin-4(5H)-one,
(S)-1-(1-(5-Chlorothiophen-2-yl)ethyl)-3-(hydroxymethyl)-6-methyl-1H-pyrazolo[3,4-d]pyrimidin-4(5H)-one,
(R)-3-(Hydroxymethyl)-6-methyl-1-(1-(5-(trifluoromethyl)thiophen-2-yl)ethyl)-1H-pyrazolo[3,4-d]pyrimidin-4(5H)-one,
(S)-3-(Hydroxymethyl)-6-methyl-1-(1-(5-(trifluoromethyl)thiophen-2-yl)ethyl)-1H-pyrazolo[3,4-d]pyrimidin-4(5H)-one,
(S)-1-(1-(4-tert-Butylphenyl)ethyl)-3-(hydroxymethyl)-6-methyl-1H-pyrazolo[3,4-d]pyrimidin-4(5H)-one,
(S)-3-(Hydroxymethyl)-6-methyl-1-(1-(4-(trifluoromethoxy)phenyl)ethyl)-1H-pyrazolo[3,4-d]pyrimidin-4(5H)-one,
(S)-1-(1-(4-tert-Butylphenyl)-2-methylpropyl)-3-(hydroxymethyl)-6-methyl-1H-pyrazolo[3,4-d]pyrimidin-4(5H)-one,
(R)-1-(1-(4-tert-Butylphenyl)-2-methylpropyl)-3-(hydroxymethyl)-6-methyl-1H-pyrazolo[3,4-d]pyrimidin-4(5H)-one,
(S)-3-(Difluoromethyl)-6-methyl-1-(1-(4-(pentafluorothio)phenyl)ethyl)-1H-pyrazolo[3,4-d]pyrimidin-4(5H)-one,
(R)-3-(Difluoromethyl)-6-methyl-1-(1-(4-(pentafluorothio)phenyl)ethyl)-1H-pyrazolo[3,4-d]pyrimidin-4(5H)-one,
3-(Difluoromethyl)-6-methyl-1-(3-(4-(trifluoromethyl)phenyl)oxetan-3-yl)-1H-pyrazolo[3,4-d]pyrimidin-4(5H)-one,
3-(Difluoromethyl)-6-methyl-1-(1-(4-(1-(trifluoromethyl)cyclopropyl)phenyl)ethyl)-1H-pyrazolo[3,4-d]pyrimidin-4(5H)-one,
3-(Difluoromethyl)-6-methyl-1-(1-(4-(perfluoroethyl)phenyl)ethyl)-1H-pyrazolo[3,4-d]pyrimidin-4(5H)-one,
3-(Difluoromethyl)-6-methyl-1-{1-[4-(trifluoromethyl)phenyl]ethyl}-1,5-dihydro-4H-pyrazolo[3,4-d]pyrimidin-4-one,
(R)-3-(Difluoromethyl)-1-(1-(3-fluoro-4-(trifluoromethyl)phenyl)ethyl)-6-methyl-1H-pyrazolo[3,4-d]pyrimidin-4(5H)-one,
(S)-3-(Difluoromethyl)-1-(1-(3-fluoro-4-(trifluoromethyl)phenyl)ethyl)-6-methyl-1H-pyrazolo[3,4-d]pyrimidin-4(5H)-one,
(R)-3-(Difluoromethyl)-1-(1-(3-fluoro-4-(trifluoromethoxy)phenyl)ethyl)-6-methyl-1H-pyrazolo[3,4-d]pyrimidin-4(5H)-one,
(S)-3-(Difluoromethyl)-1-(1-(3-fluoro-4-(trifluoromethoxy)phenyl)ethyl)-6-methyl-1H-pyrazolo[3,4-d]pyrimidin-4(5H)-one,
(R)-3-(Difluoromethyl)-6-methyl-1-(2-methyl-1-(4-(trifluoromethyl)phenyl)propyl)-1H-pyrazolo[3,4-d]pyrimidin-4(5H)-one,
(S)-3-(Difluoromethyl)-6-methyl-1-(2-methyl-1-(4-(trifluoromethyl)phenyl)propyl)-1H-pyrazolo[3,4-d]pyrimidin-4(5H)-on,
(R)-3-(Difluoromethyl)-1-(2-methoxy-1-(4-(trifluoromethyl)phenyl)ethyl)-6-methyl-1H-pyrazolo[3,4-d]pyrimidin-4(5H)-one,
(S)-3-(Difluoromethyl)-1-(2-methoxy-1-(4-(trifluoromethyl)phenyl)ethyl)-6-methyl-1H-pyrazolo[3,4-d]pyrimidin-4(5H)-one,
(R)-3-(Difluoromethyl)-6-methyl-1-(1-(4-(trifluoromethyl)phenyl)ethyl)-1H-pyrazolo[3,4-d]pyrimidin-4(5H)-one,
(S)-3-(Difluoromethyl)-6-methyl-1-(1-(4-(trifluoromethyl)phenyl)ethyl)-1H-pyrazolo[3,4-d]pyrimidin-4(5H)-one,
(R)-3-(Difluoromethyl)-6-methyl-1-(1-(4-(trifluoromethoxy)phenyl)ethyl)-1H-pyrazolo[3,4-d]pyrimidin-4(5H)-one,
(S)-3-(Difluoromethyl)-6-methyl-1-(1-(4-(trifluoromethoxy)phenyl)ethyl)-1H-pyrazolo[3,4-d]pyrimidin-4(5H)-one,
(R)-3-(Difluoromethyl)-6-methyl-1-(1-(4-(trifluoromethylthio)phenyl)ethyl)-1H-pyrazolo[3,4-d]pyrimidin-4(5H)-one,
(S)-3-(Difluoromethyl)-6-methyl-1-(1-(4-(trifluoromethylthio)phenyl)ethyl)-1H-pyrazolo[3,4-d]pyrimidin-4(5H)-one,
(R)-1-(1-(4-(Difluoromethoxy)phenyl)ethyl)-3-(difluoromethyl)-6-methyl-1H-pyrazolo[3,4-d]pyrimidin-4(5H)-one,
(S)-1-(1-(4-(Difluoromethoxy)phenyl)ethyl)-3-(difluoromethyl)-6-methyl-1H-pyrazolo[3,4-d]pyrimidin-4(5H)-one,
(R)-1-(1-(2-Chloro-4-(trifluoromethyl)phenyl)ethyl)-3-(difluoromethyl)-6-methyl-1H-pyrazolo[3,4-d]pyrimidin-4(5H)-one,
(S)-1-(1-(2-Chloro-4-(trifluoro-methyl)phenyl)-ethyl)-3-(difluoromethyl)-6-methyl-1H-pyrazolo[3,4-d]pyrimidin-4(5H)-one,
(R)-3-(Difluoro-methyl)-1-(1-(2-fluoro-4-(trifluoromethyl)phenyl)-ethyl)-6-methyl-1H-pyrazolo[3,4-d]pyrimidin-4(5H)-one,
(S)-3-(Difluoro-methyl)-1-(1-(2-fluoro-4-(trifluoromethyl)phenyl)ethyl)-6-methyl-1H-pyrazolo[3,4-d]pyrimidin-4(5H)-one,
(R)-3-(Difluoromethyl)-6-(methoxymethyl)-1-{1-[4-(trifluoromethyl)phenyl]ethyl}-1,5-dihydro-4H-pyrazolo-[3,4-d]pyrimidin-4-one,
(S)-3-(Difluoro-methyl)-6-(methoxymethyl)-1-{1-[4-(trifluoromethyl)phenyl]ethyl}-1,5-dihydro-4H-pyrazolo-[3,4-d]pyrimidin-4-one,
(R)-3-(Difluoromethyl)-6-ethyl-1-(1-(4-(trifluoromethyl)phenyl)ethyl)-1,5-dihydro-4H-pyrazolo[3,4-d]pyrimidin-4-one,
(S)-3-(Difluoromethyl)-6-ethyl-1-(1-(4-(trifluoromethyl)-phenyl)ethyl)-1,5-dihydro-4H-pyrazolo[3,4-d]pyrimidin-4-one,
(R)-6-Cyclopropyl-3-(difluoromethyl)-1-(1-(4-(trifluoromethyl)phenyl)ethyl)-1,5-dihydro-4H-pyrazolo[3,4-d]pyrimidin-4-one,
(S)-6-Cyclopropyl-3-(difluoromethyl)-1-(1-(4-(trifluoromethyl)phenyl)ethyl)-1,5-dihydro-4H-pyrazolo[3,4-d]pyrimidin-4-one,
1-(Cyclopropyl(3-fluoro-4-(trifluoromethoxy)phenyl)methyl)-3-(difluoromethyl)-6-methyl-1H-pyrazolo[3,4-d]pyrimidin-4(5H)-one,
(R)-3-(Difluoromethyl)-6-methyl-1-(1-(6-(trifluoromethyl)pyridin-3-yl)ethyl)-1H-pyrazolo[3,4-d]pyrimidin-4(5H)-one,
(S)-3-(Difluoromethyl)-6-methyl-1-(1-(6-(trifluoromethyl)pyridin-3-yl)ethyl)-1H-pyrazolo[3,4-d]pyrimidin-4(5H)-one,
(R)-3-(Difluoromethyl)-6-(3,4-dimethoxybenzyl)-1-(1-(4-(trifluoromethyl)phenyl)ethyl)-1H-pyrazolo[3,4-d]pyrimidin-4(5H)-one, (S)-3-(Difluoromethyl)-6-(3,4-dimethoxybenzyl)-1-(1-(4-(trifluoromethyl)phenyl)ethyl)-1H-pyrazolo[3,4-d]pyrimidin-4(5H)-one,
3-(Difluoromethyl)-6-(3,4-dimethoxybenzoyl)-1-(1-(4-(trifluoromethyl)phenyl)ethyl)-1H-pyrazolo[3,4-d]pyrimidin-4(5H)-one,
(R)-3-(Fluoromethyl)-6-methyl-1-(1-(4-(pentafluorothio)phenyl)ethyl)-1H-pyrazolo[3,4-d]pyrimidin-4(5H)-one,
(S)-3-(Fluoromethyl)-6-methyl-1-(1-(4-(pentafluorothio)phenyl)ethyl)-1H-pyrazolo[3,4-d]pyrimidin-4(5H)-one,
3-(Fluoromethyl)-6-methyl-1-(2,2,2-trifluoro-1-(4-(trifluoromethyl)phenyl)-ethyl)-1H-pyrazolo[3,4-d]pyrimidin-4(5H)-one,
3-(Fluoromethyl)-6-methyl-1-(1-(4-(trifluoromethyl)phenyl)cyclobutyl)-1H-pyrazolo[3,4-d]pyrimidin-4(5H)-one,
3-(Fluoromethyl)-6-methyl-1-(1-p-tolylethyl)-1H-pyrazolo[3,4-d]pyrimidin-4(5H)-one,
3-(Fluoromethyl)-6-methyl-1-{1-[4-(trifluoromethyl)phenyl]ethyl}-1,5-dihydro-4H-pyrazolo[3,4-d]pyrimidin-4-one,
3-(Fluoromethyl)-6-(methoxymethyl)-1-{1-[4-(trifluoromethyl)phenyl]ethyl}-1,5-dihydro-4H-pyrazolo[3,4-d]pyrimidin-4-one,
(R)-3-(Fluoromethyl)-6-methyl-1-(1-(4-(trifluoromethoxy-)phenyl)ethyl)-1H-pyrazolo[3,4-d]pyrimidin-4(5H)-one,
(S)-3-(Fluoromethyl)-6-methyl-1-(1-(4-(trifluoromethoxy)phenyl)ethyl)-1H-pyrazolo[3,4-d]pyrimidin-4(5H)-one,
(R)-3-(Fluoromethyl)-6-methyl-1-((1-methylcyclopropyl)(4-(trifluoromethyl)phenyl)methyl)-1H-pyrazolo[3,4-d]pyrimidin-4(5H)-one,
(S)-3-(Fluoromethyl)-6-methyl-1-((1-methylcyclopropyl)(4-(trifluoromethyl)phenyl)methyl)-1H-pyrazolo[3,4-d]pyrimidin-4(5H)-one,
(R)-3-(Fluoromethyl)-6-methyl-1-(1-(4-(2,2,2-trifluoroethyl)phenyl)ethyl)-1H-pyrazolo[3,4-d]pyrimidin-4(5H)-one,
(S)-3-(Fluoromethyl)-6-methyl-1-(1-(4-(2,2,2-trifluoroethyl)phenyl)ethyl)-1H-pyrazolo[3,4-d]pyrimidin-4(5H)-one,
(R)-3-(Fluoromethyl)-6-methyl-1-(2-methyl-1-(4-(trifluoromethyl)phenyl)propyl)-1H-pyrazolo[3,4-d]pyrimidin-4(5H)-one,
(S)-3-(Fluoromethyl)-6-methyl-1-(2-methyl-1-(4-(trifluoromethyl)phenyl)propyl)-1H-pyrazolo[3,4-d]pyrimidin-4(5H)-one,
(R)-1-(1-(4-tert-Butylphenyl)ethyl)-3-(fluoromethyl)-6-methyl-1H-pyrazolo[3,4-d]pyrimidin-4(5H)-one,
(S)-1-(1-(4-tert-Butylphenyl)ethyl)-3-(fluoromethyl)-6-methyl-1H-pyrazolo[3,4-d]pyrimidin-4(5H)-one,
(R)-1-(1-(3-Fluoro-4-(trifluoromethoxy)phenyl)ethyl)-3-(fluoromethyl)-6-methyl-1H-pyrazolo[3,4-d]pyrimidin-4(5H)-one,
(S)-1-(1-(3-Fluoro-4-(trifluoromethoxy)phenyl)ethyl)-3-(fluoromethyl)-6-methyl-1H-pyrazolo[3,4-d]pyrimidin-4(5H)-one,
(R)-3-(Fluoromethyl)-6-(4-methoxybenzyl)-1-(1-(4-(trifluoromethyl)phenyl)ethyl)-1H-pyrazolo[3,4-d]pyrimidin-4(5H)-one,
(S)-3-(Fluoromethyl)-6-(4-methoxybenzyl)-1-(1-(4-(trifluoromethyl)phenyl)ethyl)-1H-pyrazolo[3,4-d]pyrimidin-4(5H)-one,
(R)-3-(Fluoromethyl)-6-(3-methoxybenzyl)-1-(1-(4-(trifluoromethyl)phenyl)ethyl)-1H-pyrazolo[3,4-d]pyrimidin-4(5H)-one,
(S)-3-(Fluoromethyl)-6-(3-methoxybenzyl)-1-(1-(4-(trifluoromethyl)phenyl)ethyl)-1H-pyrazolo[3,4-d]pyrimidin-4(5H)-one,
(R)-6-(3,4-Dimethoxybenzyl)-3-(fluoromethyl)-1-(1-(4-(trifluoromethyl)phenyl)ethyl)-1,5-dihydro-4H-pyrazolo[3,4-d]pyrimidin-4-one,
(S)-6-(3,4-Dimethoxybenzyl)-3-(fluoromethyl)-1-(1-(4-(trifluoromethyl)phenyl)ethyl)-1,5-dihydro-4H-pyrazolo[3,4-d]pyrimidin-4-one,
(R)-1-(Cyclopropyl(4-(trifluoromethoxy)phenyl)methyl)-3-(fluoromethyl)-6-methyl-1,5-dihydro-4H-pyrazolo[3,4-d]pyrimidin-4-one,
(S)-1-(Cyclopropyl(4-(trifluoromethoxy)phenyl)methyl)-3-(fluoromethyl)-6-methyl-1,5-dihydro-4H-pyrazolo[3,4-d]pyrimidin-4-one,
(R)-1-(Cyclopropyl(3-fluoro-4-(trifluoromethyl)phenyl)methyl)-3-(fluoromethyl)-6-methyl-1,5-dihydro-4H-pyrazolo[3,4-d]pyrimidin-4-one,
(S)-1-(Cyclopropyl(3-fluoro-4-(trifluoromethyl)phenyl)methyl)-3-(fluoromethyl)-6-methyl-1,5-dihydro-4H-pyrazolo[3,4-d]pyrimidin-4-one,
(R)-1-(Cyclopropyl(3-fluoro-4-(trifluoromethoxy)phenyl)methyl)-3-(fluoromethyl)-6-methyl-1,5-dihydro-4H-pyrazolo[3,4-d]pyrimidin-4-one,
(S)-1-(Cyclopropyl(3-fluoro-4-(trifluoromethoxy)phenyl)methyl)-3-(fluoromethyl)-6-methyl-1,5-dihydro-4H-pyrazolo[3,4-d]pyrimidin-4-one,
1-(1-(3-Fluoro-4-(trifluoromethyl)phenyl)ethyl)-3-(fluoromethyl)-6-methyl-1H-pyrazolo[3,4-d]pyrimidin-4(5H)-one,
1-(Cyclopropyl(4-(trifluoromethyl)phenyl)methyl)-3-(fluoromethyl)-6-methyl-1H-pyrazolo[3,4-d]pyrimidin-4(5H)-one,
3-(Chloromethyl)-1-(cyclopropyl(4-(trifluoromethyl)phenyl)methyl)-6-methyl-1H-pyrazolo[3,4-d]pyrimidin-4(5H)-one,
(R)-1-(2,2-Dimethyl-1-(4-(trifluoromethyl)phenyl)propyl)-3-(fluoromethyl)-6-methyl-1H-pyrazolo[3,4-d]pyrimidin-4(5H)-one,
(S)-1-(2,2-Dimethyl-1-(4-(trifluoromethyl)phenyl)propyl)-3-(fluoromethyl)-6-methyl-1H-pyrazolo[3,4-d]pyrimidin-4(5H)-one,
(R)-6-Methyl-3-(1H-pyrazol-5-yl)-1-(1-(4-(trifluoromethyl)phenyl)ethyl)-1H-pyrazolo[3,4-d]pyrimidin-4(5H)-one,
(S)-6-Methyl-3-(1H-pyrazol-5-yl)-1-(1-(4-(trifluoromethyl)phenyl)ethyl)-1H-pyrazolo[3,4-d]pyrimidin-4(5H)-one,
(R)-6-Methyl-3-(1H-pyrazol-4-yl)-1-(1-(4-(trifluoromethyl)phenyl)ethyl)-1H-pyrazolo[3,4-d]pyrimidin-4(5H)-one,
(S)-6-Methyl-3-(1H-pyrazol-4-yl)-1-(1-(4-(trifluoromethyl)phenyl)ethyl)-1H-pyrazolo[3,4-d]pyrimidin-4(5H)-one,
6-Methyl-3-((R)-3,3,3-trifluoro-2-hydroxypropyl)-1-((R)-1-(4-(trifluoromethyl)phenyl)ethyl)-1H-pyrazolo[3,4-d]pyrimidin-4(5H)-one,
6-Methyl-3-((S)-3,3,3-trifluoro-2-hydroxypropyl)-1-((S)-1-(4-(trifluoromethyl)phenyl)ethyl)-1H-pyrazolo[3,4-d]pyrimidin-4(5H)-one,
6-Methyl-3-((R)-3,3,3-trifluoro-2-hydroxypropyl)-1-((S)-1-(4-(trifluoromethyl)phenyl)ethyl)-1H-pyrazolo[3,4-d]pyrimidin-4(5H)-one, 6-Methyl-3-((S)-3,3,3-trifluoro-2-hydroxypropyl)-1-((R)-1-(4-(trifluoromethyl)phenyl)ethyl)-1H-pyrazolo[3,4-d]pyrimidin-4(5H)-one,
3-((R)-2-Hydroxypropyl)-6-methyl-1-((R)-1-(4-(trifluoromethyl)phenyl)ethyl)-1H-pyrazolo[3,4-d]pyrimidin-4(5H)-one,
3-((S)-2-hydroxypropyl)-6-methyl-1-((S)-1-(4-(trifluoromethyl)phenyl)ethyl)-1H-pyrazolo[3,4-d]pyrimidin-4(5H)-one,
3-((R)-2-hydroxypropyl)-6-methyl-1-((S)-1-(4-(trifluoromethyl)phenyl)ethyl)-1H-pyrazolo[3,4-d]pyrimidin-4(5H)-one,
3-((S)-2-hydroxypropyl)-6-methyl-1-((R)-1-(4-(trifluoromethyl)phenyl)ethyl)-1H-pyrazolo[3,4-d]pyrimidin-4(5H)-one,
3-(2-Hydroxy-2-methylpropyl)-6-methyl-1-(1-(4-(trifluoromethyl)phenyl)ethyl)-1H-pyrazolo[3,4-d]pyrimidin-4(5H)-one,
6-Methyl-4-oxo-1-(1-(4-(trifluoromethyl)phenyl)ethyl)-4,5-dihydro-1H-pyrazolo[3,4-d]pyrimidine-3-carbaldehyde,
(R)-3-(2-Hydroxyethyl)-6-methyl-1-(1-(4-(trifluoromethyl)phenyl)ethyl)-1H-pyrazolo[3,4-d]pyrimidin-4(5H)-one,
(S)-3-(2-Hydroxyethyl)-6-methyl-1-(1-(4-(trifluoromethyl)phenyl)ethyl)-1H-pyrazolo[3,4-d]pyrimidin-4(5H)-one,
(Z)-6-Methyl-4-oxo-1-(1-(4-(trifluoromethyl)phenyl)ethyl)-4,5-dihydro-1H-pyrazolo[3,4-d]pyrimidine-3-carbaldehyde oxime,
(S)-6-Methyl-4-oxo-1-(1-(4-(trifluoromethyl)phenyl)ethyl)-4,5-dihydro-1H-pyrazolo[3,4-d]pyrimidine-3-carbonitrile,
(S)-6-Methyl-4-oxo-1-(1-(4-(trifluoromethyl)phenyl)ethyl)-4,5-dihydro-1H-pyrazolo[3,4-d]pyrimidine-3-carbonitrile,
(R)-3-(1,1-Difluoro-2-hydroxyethyl)-6-methyl-1-(1-(4-(trifluoromethyl)phenyl)ethyl)-1H-pyrazolo[3,4-d]pyrimidin-4(5H)-one,
(S)-3-(1,1-Difluoro-2-hydroxyethyl)-6-methyl-1-(1-(4-(trifluoromethyl)phenyl)ethyl)-1H-pyrazolo[3,4-d]pyrimidin-4(5H)-one,
(R)-6-Methyl-4-oxo-1-(1-(4-(trifluoromethyl)phenyl)ethyl)-4,5-dihydro-1H-pyrazolo[3,4-d]pyrimidine-3-carboxamide,
(S)-6-Methyl-4-oxo-1-(1-(4-(trifluoromethyl)phenyl)ethyl)-4,5-dihydro-1H-pyrazolo[3,4-d]pyrimidine-3-carboxamide,
3-Amino-6-methyl-1-(1-(4-(trifluoromethyl)phenyl)ethyl)-1H-pyrazolo[3,4-d]pyrimidin-4(5H)-one,
(R)-N-(6-Methyl-4-oxo-1-(1-(4-(trifluoromethyl)phenyl)ethyl)-4,5-dihydro-1H-pyrazolo[3,4-d]pyrimidin-3-yl)acetamide,
(S)-N-(6-Methyl-4-oxo-1-(1-(4-(trifluoromethyl)phenyl)ethyl)-4,5-dihydro-1H-pyrazolo[3,4-d]pyrimidin-3-yl)acetamide,
N-(6-Methyl-4-oxo-1-(1-(4-(trifluoromethyl)phenyl)ethyl)-4,5-dihydro-1H-pyrazolo[3,4-d]pyrimidin-3-yl)methanesulfonamide,
(R)-6-Methyl-3-(1,3,4-oxadiazol-2-yl)-1-(1-(4-(trifluoromethyl)phenyl)ethyl)-1H-pyrazolo[3,4-d]pyrimidin-4(5H)-one,
(S)-6-Methyl-3-(1,3,4-oxadiazol-2-yl)-1-(1-(4-(trifluoromethyl)phenyl)ethyl)-1H-pyrazolo[3,4-d]pyrimidin-4(5H)-one,
(R)-N,6-Dimethyl-4-oxo-1-(1-(4-(trifluoromethyl)phenyl)ethyl)-4,5-dihydro-1H-pyrazolo[3,4-d]pyrimidine-3-carboxamide,
(S)-N,6-Dimethyl-4-oxo-1-(1-(4-(trifluoromethyl)phenyl)ethyl)-4,5-dihydro-1H-pyrazolo[3,4-d]pyrimidine-3-carboxamide,
(R)-N,N,6-Trimethyl-4-oxo-1-(1-(4-(trifluoromethyl)phenyl)ethyl)-4,5-dihydro-1H-pyrazolo[3,4-d]pyrimidine-3-carboxamide,
(S)-N,N,6-Trimethyl-4-oxo-1-(1-(4-(trifluoromethyl)phenyl)ethyl)-4,5-dihydro-1H-pyrazolo[3,4-d]pyrimidine-3-carboxamide,
(R)-6-Methyl-4-oxo-N-(2,2,2-trifluoroethyl)-1-(1-(4-(trifluoromethyl)phenyl)ethyl)-4,5-dihydro-1H-pyrazolo[3,4-d]pyrimidine-3-carboxamide,
(S)-6-Methyl-4-oxo-N-(2,2,2-trifluoroethyl)-1-(1-(4-(trifluoromethyl)phenyl)ethyl)-4,5-dihydro-1H-pyrazolo[3,4-d]pyrimidine-3-carboxamide,
(R)-6-Methyl-3-(morpholine-4-carbonyl)-1-(1-(4-(trifluoromethyl)phenyl)ethyl)-1H-pyrazolo[3,4-d]pyrimidin-4(5H)-one,
(S)-6-Methyl-3-(morpholine-4-carbonyl)-1-(1-(4-(trifluoromethyl)phenyl)ethyl)-1H-pyrazolo[3,4-d]pyrimidin-4(5H)-one,
(R)-6-Methyl-3-(methyl sulfonylmethyl)-1-(1-(4-(trifluoromethyl)phenyl)ethyl)-1H-pyrazolo[3,4-d]pyrimidin-4(5H)-one,
(S)-6-Methyl-3-(methyl sulfonylmethyl)-1-(1-(4-(trifluoromethyl)phenyl)ethyl)-1H-pyrazolo[3,4-d]pyrimidin-4(5H)-one,
(R)-3-(Aminomethyl)-6-methyl-1-(1-(4-(trifluoromethyl)phenyl)ethyl)-1H-pyrazolo[3,4-d]pyrimidin-4(5H)-one,
(S)-3-(Aminomethyl)-6-methyl-1-(1-(4-(trifluoromethyl)phenyl)ethyl)-1H-pyrazolo[3,4-d]pyrimidin-4(5H)-one,
(R)-N-((6-Methyl-4-oxo-1-(1-(4-(trifluoromethyl)phenyl)ethyl)-4,5-dihydro-1H-pyrazolo[3,4-d]pyrimidin-3-yl)methyl)acetamide,
(S)-N-((6-Methyl-4-oxo-1-(1-(4-(trifluoromethyl)phenyl)ethyl)-4,5-dihydro-1H-pyrazolo[3,4-d]pyrimidin-3-yl)methyl)acetamide,
(R)-3-(Methoxymethyl)-6-methyl-1-(1-(4-(trifluoromethyl)phenyl)ethyl)-1H-pyrazolo[3,4-d]pyrimidin-4(5H)-one,
(S)-3-(Methoxymethyl)-6-methyl-1-(1-(4-(trifluoromethyl)phenyl)ethyl)-1H-pyrazolo[3,4-d]pyrimidin-4(5H)-one,
(R)-2-(6-Methyl-4-oxo-1-(1-(4-(trifluoromethyl)phenyl)ethyl)-4,5-dihydro-1H-pyrazolo[3,4-d]pyrimidin-3-yl)acetonitrile,
(S)-2-(6-Methyl-4-oxo-1-(1-(4-(trifluoromethyl)phenyl)ethyl)-4,5-dihydro-1H-pyrazolo[3,4-d]pyrimidin-3-yl)acetonitrile,
3-(2-Aminoethyl)-6-methyl-1-(1-(4-(trifluoromethyl)phenyl)ethyl)-1H-pyrazolo[3,4-d]pyrimidin-4(5H)-one,
3-((Benzyloxy)methyl)-6-(difluoromethyl)-1-(1-(4-(trifluoromethyl)phenyl)ethyl)-1H-pyrazolo[3,4-d]pyrimidin-4(5H)-one,
6-(Difluoromethyl)-3-(hydroxymethyl)-1-(1-(4-(trifluoromethyl)phenyl)ethyl)-1H-pyrazolo[3,4-d]pyrimidin-4(5H)-one,
(R)-3-(2,2-Difluoroethyl)-6-methyl-1-(1-(4-(trifluoromethyl)phenyl)ethyl)-1H-pyrazolo[3,4-d]pyrimidin-4(5H)-one, (S)-3-(2,2-Difluoroethyl)-6-methyl-1-(1-(4-(trifluoromethyl)phenyl)ethyl)-1H-pyrazolo[3,4-d]pyrimidin-4(5H)-one,
(R)-6-Methyl-3-(2,2,2-trifluoroethoxy)-1-(1-(4-(trifluoromethyl)phenyl)ethyl)-1H-pyrazolo[3,4-d]pyrimidin-4(5H)-one,
and (S)-6-Methyl-3-(2,2,2-trifluoroethoxy)-1-(1-(4-(trifluoromethyl)phenyl)ethyl)-1H-pyrazolo[3,4-d]pyrimidin-4(5H)-one,
6-Methyl-3-(oxetan-3-ylmethyl)-1-(1-(4-(trifluoromethyl)phenyl)ethyl)-1H-pyrazolo[3,4-d]pyrimidin-4(5H)-one,
(R)-1-(1-(4-Acetylphenyl)ethyl)-3-(hydroxymethyl)-6-methyl-1H-pyrazolo[3,4-d]pyrimidin-4(5H)-one,
(S)-1-(1-(4-Acetylphenyl)ethyl)-3-(hydroxymethyl)-6-methyl-1H-pyrazolo[3,4-d]pyrimidin-4(5H)-one,
(R)-3-(Hydroxymethyl)-6-(methoxymethyl)-1-(1-(4-(trifluoromethyl)phenyl)ethyl)-1H-pyrazolo[3,4-d]pyrimidin-4(5H)-one,
(S)-3-(Hydroxymethyl)-6-(methoxymethyl)-1-(1-(4-(trifluoromethyl)phenyl)ethyl)-1H-pyrazolo[3,4-d]pyrimidin-4(5H)-one,
6-Furan-2-yl-3-(hydroxymethyl)-1-{1-[4-(trifluoromethyl)phenyl]ethyl}-1,5-dihydro-4H-pyrazolo[3,4-d]pyrimidin-4-one,
3-(Hydroxymethyl)-6-(1-methylethyl)-1-{1-[4-(trifluoromethyl)phenyl]ethyl}-1,5-dihydro-4H-pyrazolo[3,4-d]pyrimidin-4-one,
6-(3,4-Dimethoxybenzyl)-3-(hydroxymethyl)-1-{1-[4-(trifluoromethyl)phenyl]ethyl}-1,5-dihydro-4H-pyrazolo[3,4-d]pyrimidin-4-one,
3-(Hydroxymethyl)-6-[(5-methyltetrahydrofuran-2-yl)methyl]-1-{1-[4-(trifluoromethyl)phenyl]ethyl}-1,5-dihydro-4H-pyrazolo[3,4-d]pyrimidin-4-one,
(R)-6-Cyclopropyl-3-(hydroxymethyl)-1-{1-[4-(trifluoromethyl)phenyl]ethyl}-1,5-dihydro-4H-pyrazolo[3,4-d]pyrimidin-4-one,
(S)-6-Cyclopropyl-3-(hydroxymethyl)-1-{1-[4-(trifluoromethyl)phenyl]ethyl}-1,5-dihydro-4H-pyrazolo[3,4-d]pyrimidin-4-one,
(R)-6-Ethyl-3-(hydroxymethyl)-1-{1-[4-(trifluoromethyl)phenyl]ethyl}-1,5-dihydro-4H-pyrazolo[3,4-d]pyrimidin-4-one,
(S)-6-Ethyl-3-(hydroxymethyl)-1-{1-[4-(trifluoromethyl)phenyl]ethyl}-1,5-dihydro-4H-pyrazolo[3,4-d]pyrimidin-4-one,
(R)-3-(Hydroxymethyl)-6-propyl-1-(1-(4-(trifluoromethyl)phenyl)ethyl)-1,5-dihydro-4H-pyrazolo[3,4-d]pyrimidin-4-one,
(S)-3-(Hydroxymethyl)-6-propyl-1-(1-(4-(trifluoromethyl)phenyl)ethyl)-1,5-dihydro-4H-pyrazolo[3,4-d]pyrimidin-4-one,
(R)-3-(Hydroxy-methyl)-6-isobutyl-1-(1-(4-(trifluoromethyl)phenyl)ethyl)-1,5-dihydro-4H-pyrazolo-[3,4-d]pyrimidin-4-one,
(S)-3-(Hydroxy-methyl)-6-isobutyl-1-(1-(4-(trifluoromethyl)phenyl)ethyl)-1,5-dihydro-4H-pyrazolo[3,4-d]pyrimidin-4-one,
(R)-6-(Cyclopentyl-methyl)-3-(hydroxymethyl)-1-(1-(4-(trifluoromethyl)-phenyl)ethyl)-1,5-dihydro-4H-pyrazolo[3,4-d]pyrimidin-4-one,
(S)-6-(Cyclopentyl-methyl)-3-(hydroxymethyl)-1-(1-(4-(trifluoromethyl)phenyl)ethyl)-1,5-dihydro-4H-pyrazolo[3,4-d]pyrimidin-4-one,
(R)-6-(Cyclopropyl-methyl)-3-(hydroxymethyl)-1-(1-(4-(trifluoromethyl)phenyl)ethyl)-1,5-dihydro-4H-pyrazolo[3,4-d]pyrimidin-4-one,
(S)-6-(Cyclopropyl-methyl)-3-(hydroxymethyl)-1-(1-(4-(trifluoromethyl)phenyl)ethyl)-1,5-dihydro-4H-pyrazolo[3,4-d]pyrimidin-4-one,
(R,R)-3-(Hydroxymethyl)-6-(tetrahydrofuran-2-yl)-1-(1-(4-(trifluoromethyl)-phenyl)ethyl)-1,5-dihydro-4H-pyrazolo[3,4-d]pyrimidin-4-one,
(S,S)-3-(Hydroxymethyl)-6-(tetrahydrofuran-2-yl)-1-(1-(4-(trifluoromethyl-)phenyl)ethyl)-1,5-dihydro-4H-pyrazolo[3,4-d]pyrimidin-4-one,
(R,S)-3-(Hydroxymethyl)-6-(tetrahydrofuran-2-yl)-1-(1-(4-(trifluoromethyl)-phenyl)ethyl)-1,5-dihydro-4H-pyrazolo[3,4-d]pyrimidin-4-one,
(S,R)-3-(Hydroxymethyl)-6-(tetrahydrofuran-2-yl)-1-(1-(4-(trifluoromethyl)-phenyl)ethyl)-1,5-dihydro-4H-pyrazolo[3,4-d]pyrimidin-4-one,
(R)-6-Cyclopropyl-3-(hydroxymethyl)-1-{1-[4-(pentafluoro-sulfanyl)-phenyl]-ethyl}-1,5-dihydro-4H-pyrazolo[3,4-d]pyrimidin-4-one,
(S)-6-Cyclopropyl-3-(hydroxymethyl)-1-{1-[4-(pentafluoro-sulfanyl)-phenyl]ethyl}-1,5-dihydro-4H-pyrazolo[3,4-d]pyrimidin-4-one,
(R)-3-(Hydroxy-methyl)-6-(methoxy-methyl)-1-{1-[4-(pentafluoro-sulfanyl)-phenyl]ethyl}-1,5-dihydro-4H-pyrazolo[3,4-d]pyrimidin-4-one,
(S)-3-(Hydroxymethyl)-6-(methoxymethyl)-1-{1-[4-(pentafluorosulfanyl)phenyl]ethyl}-1,5-dihydro-4H-pyrazolo[3,4-d]pyrimidin-4-one,
(6-Methyl-4-oxo-1-(1-(4-(trifluoromethyl)phenyl)ethyl)-4,5-dihydro-1H-pyrazolo[3,4-d]pyrimidin-3-yl)methyl acetate,
3-((R)-1-Hydroxypropan-2-yl)-6-methyl-1-((S)-1-(4-(trifluoromethyl)phenyl)ethyl)-1,5-dihydro-4H-pyrazolo[3,4-d]pyrimidin-4-one,
3-((S)-1-Hydroxypropan-2-yl)-6-methyl-1-((S)-1-(4-(trifluoromethyl)phenyl)ethyl)-1,5-dihydro-4H-pyrazolo[3,4-d]pyrimidin-4-one,
(S)-3-Acetyl-6-methyl-1-(1-(4-(trifluoromethyl)phenyl)ethyl)-1,5-dihydro-4H-pyrazolo[3,4-d]pyrimidin-4-one,
(S)-6-Methyl-4-oxo-1-(1-(4-(trifluoromethyl)phenyl)ethyl)-4,5-dihydro-1H-pyrazolo[3,4-d]pyrimidine-3-carboxylic acid,
(R)-3-Bromo-6-methyl-1-(1-(4-(trifluoromethyl)phenyl)ethyl)-1,5-dihydro-4H-pyrazolo[3,4-d]pyrimidin-4-one,
(S)-3-Bromo-6-methyl-1-(1-(4-(trifluoromethyl)phenyl)ethyl)-1,5-dihydro-4H-pyrazolo[3,4-d]pyrimidin-4-one,
3-(1-Hydroxy-1-methylethyl)-6-methyl-1-{1-[4-(trifluoromethyl)phenyl]ethyl}-1,5-dihydro-4H-pyrazolo[3,4-d]pyrimidin-4-one,
6-Methyl-3-(2,2,2-trifluoro-1-hydroxyethyl)-1-{1-[4-(trifluoromethyl)phenyl]ethyl}-1,5-dihydro-4H-pyrazolo[3,4-d]pyrimidin-4-one,
3-(1-Hydroxyethyl)-6-methyl-1-{1-[4-(trifluoromethyl)phenyl]ethyl}-1,5-dihydro-4H-pyrazolo[3,4-d]pyrimidin-4-one,
(S)-3-Hydroxy-6-methyl-1-(1-(4-(trifluoromethyl)phenyl)ethyl)-1,5-dihydro-4H-pyrazolo[3,4-d]pyrimidin-4-one,
3,6-Dimethyl-1-(1-(4-(trifluoromethyl)phenylamino)propan-2-yl)-1H-pyrazolo[3,4-d]pyrimidin-4(5H)-one,
3,6-Dimethyl-1-(1-(methyl(4-(trifluoromethyl)phenyl)amino)propan-2-yl)-1H-pyrazolo[3,4-d]pyrimidin-4(5H)-one, 1-(1-Hydroxy-1-(4-(trifluoromethyl)phenyl)propan-2-yl)-3,6-dimethyl-1H-pyrazolo[3,4-d]pyrimidin-4(5H)-one,
2-(3,6-Dimethyl-4-oxo-4,5-dihydropyrazolo[3,4-d]pyrimidin-1-yl)-N-(4-(trifluoromethyl)phenyl)propanamide,
1-(2-Hydroxy-2-(4-(trifluoromethyl)phenyl)propyl)-3,6-dimethyl-1H-pyrazolo[3,4-d]pyrimidin-4(5H)-one,
1-(1-ethyl-4-phenylbutyl)-3,6-dimethyl-1,5-dihydro-4H-pyrazolo[3,4-d]pyrimidin-4-one,
1-[1-(2,4-dimethyl-1,3-thiazol-5-yl)-4-phenylbutyl]-3,6-dimethyl-1,5-dihydro-4H-pyrazolo[3,4-d]pyrimidin-4-one,
or a pharmaceutically acceptable salt thereof.

16. A pharmaceutical composition which comprises a pharmaceutically acceptable carrier and a compound of claim 1 or a pharmaceutically acceptable salt thereof.

17. A compound of claim 1 or a pharmaceutically acceptable salt thereof for use in medicine.

* * * * *

UNITED STATES PATENT AND TRADEMARK OFFICE
CERTIFICATE OF CORRECTION

PATENT NO. : 10,160,762 B2  
APPLICATION NO. : 15/574411  
DATED : December 25, 2018  
INVENTOR(S) : Dong Ming Shen et al.

Page 1 of 1

It is certified that error appears in the above-identified patent and that said Letters Patent is hereby corrected as shown below:

On the Title Page

In item (73), the Assignee field:  
Please replace:  
"MERCK SHARP & DOHME CORP., Rahway, NJ"  
With:  
--MERCK SHARP & DOHME CORP., Rahway, NJ (US); MSD R & D (China) Co. LTD., Shanghai (CN)--.

Signed and Sealed this  
Fourteenth Day of April, 2020

Andrei Iancu  
*Director of the United States Patent and Trademark Office*